US011952387B2

(12) United States Patent
Kinebuchi et al.

(10) Patent No.: US 11,952,387 B2
(45) Date of Patent: Apr. 9, 2024

(54) BICYCLIC HETEROAROMATIC RING DERIVATIVE

(71) Applicant: KYORIN PHARMACEUTICAL CO., LTD., Tokyo (JP)

(72) Inventors: Masahiko Kinebuchi, Tochigi (JP); Takekazu Kondou, Tochigi (JP); Koji Ochiai, Tochigi (JP); Yosuke Nishigaya, Tochigi (JP)

(73) Assignee: KYORIN PHARMACEUTICAL CO., LTD, Tokyo (JP)

( * ) Notice: Subject to any disclaimer, the term of this patent is extended or adjusted under 35 U.S.C. 154(b) by 589 days.

(21) Appl. No.: 15/734,655

(22) PCT Filed: Aug. 20, 2019

(86) PCT No.: PCT/JP2019/032335
§ 371 (c)(1),
(2) Date: Dec. 3, 2020

(87) PCT Pub. No.: WO2020/040104
PCT Pub. Date: Feb. 27, 2020

(65) Prior Publication Data
US 2022/0332730 A1    Oct. 20, 2022

(30) Foreign Application Priority Data
Aug. 21, 2018 (JP) ................................ 2018-154411

(51) Int. Cl.
*C07D 513/04* (2006.01)
*A61P 31/16* (2006.01)

(52) U.S. Cl.
CPC ............ *C07D 513/04* (2013.01); *A61P 31/16* (2018.01); *C07B 2200/05* (2013.01)

(58) Field of Classification Search
CPC ........ C07D 513/04; A61P 31/14; A61P 31/16; C07B 2200/05
See application file for complete search history.

(56) References Cited

U.S. PATENT DOCUMENTS

| | | | |
|---|---|---|---|
| 4,118,742 A | 10/1978 | Paget et al. | |
| 5,349,068 A | 9/1994 | Diana et al. | |
| 5,453,433 A | 9/1995 | Aldous et al. | |
| 5,464,848 A | 11/1995 | Diana et al. | |
| 5,567,719 A | 10/1996 | Aldous et al. | |
| 5,643,929 A | 7/1997 | Diana et al. | |
| 5,650,419 A | 7/1997 | Aldous et al. | |
| 5,750,527 A | 5/1998 | Aldous et al. | |
| 5,821,257 A | 10/1998 | Aldous et al. | |
| 2001/0031773 A1 | 10/2001 | Camden | |
| 2009/0036443 A1 | 2/2009 | Atenni et al. | |
| 2011/0130396 A1 | 6/2011 | Hoelzemann et al. | |
| 2012/0094996 A1 | 4/2012 | Pastor Fernandez et al. | |

FOREIGN PATENT DOCUMENTS

| | | |
|---|---|---|
| EP | 1 841 763 | 6/2010 |
| JP | 6-49066 | 2/1994 |
| JP | 7-503966 | 4/1995 |
| JP | 7-188017 | 7/1995 |
| JP | 10-500136 | 1/1998 |
| JP | 11-106340 | 4/1999 |
| JP | 2002-540156 | 11/2002 |
| JP | 2007-505091 | 3/2007 |
| JP | 2011-529456 | 12/2011 |
| JP | 2012-522759 | 9/2012 |
| WO | 93/17027 | 9/1993 |
| WO | 96/21667 | 7/1996 |
| WO | 2004/096797 | 11/2004 |
| WO | 2005/079735 | 9/2005 |
| WO | 2006/051270 | 5/2006 |
| WO | 2007/129044 | 11/2007 |
| WO | 2009/024585 | 2/2009 |
| WO | 2009/040552 | 4/2009 |
| WO | 2010/103130 | 9/2010 |
| WO | 2010/112874 | 10/2010 |
| WO | 2011/147753 | 12/2011 |
| WO | 2012/035423 | 3/2012 |
| WO | 2012/088438 | 6/2012 |
| WO | 2013/034738 | 3/2013 |
| WO | 2013/052845 | 4/2013 |
| WO | 2013/184755 | 12/2013 |
| WO | 2014/078813 | 5/2014 |
| WO | 2014/096423 | 6/2014 |
| WO | 2014/194127 | 12/2014 |
| WO | 2015/110491 | 7/2015 |
| WO | 2015/191988 | 12/2015 |
| WO | 2015/193167 | 12/2015 |
| WO | 2015/193168 | 12/2015 |
| WO | 2015/193169 | 12/2015 |

(Continued)

OTHER PUBLICATIONS

International Preliminary Report on Patentability dated Mar. 4, 2021 in International (PCT) Application No. PCT/JP2019/032335.
Scribner, Andrew et al., "Synthesis and biological activity of anitcoccidial agents: 5,6-Diarylimidazo[2, 1-*b*][1,3]thiazoles", Bioorganic & Medicinal Chemistry Letters, vol. 18, 2008, pp. 5263-5267.
Huang, Guoli et al., "Ligand-Free Copper-Catalyzed Regioselective C-2 Arylation of Imidazo[2,1-*b*]thiazoles", Organic Letters, 2011, vol. 13, No. 19, pp. 5224-5227.

(Continued)

*Primary Examiner* — Sarah Pihonak
(74) *Attorney, Agent, or Firm* — Wenderoth, Lind & Ponack, L.L.P.

(57) ABSTRACT

[Problem] To provide a compound having an antiviral action on a virus belonging to the picornavirus genus, specifically, a rhinovirus.

[Solution] Provided are a compound represented by general formula (1), a pharmaceutically acceptable salt thereof, or a hydrate thereof.

14 Claims, No Drawings
Specification includes a Sequence Listing.

(56) References Cited

FOREIGN PATENT DOCUMENTS

| WO | 2016/145032 | 9/2016 |
|---|---|---|
| WO | 2016/145045 | 9/2016 |
| WO | 2016/161268 | 10/2016 |
| WO | 2016/168510 | 10/2016 |
| WO | 2016/206999 | 12/2016 |
| WO | 2017/009773 | 1/2017 |
| WO | 2017/044889 | 3/2017 |
| WO | 2017/053192 | 3/2017 |
| WO | 2017/055305 | 4/2017 |
| WO | 2017/055306 | 4/2017 |
| WO | 2017/097871 | 6/2017 |
| WO | 2017/147526 | 8/2017 |
| WO | 2017/223414 | 12/2017 |
| WO | 2018/022868 | 2/2018 |

OTHER PUBLICATIONS

Schaar, Hilde M. van der et al., "A Novel, Broad-Spectrum Inhibitor of Enterovirus Replication That Targets Host Cell Factor Phosphatidylinositol 4-Kinase III β", Antimicrobial Agents and Chemotherapy, 2013, vol. 57, No. 10, pp. 4971-4981.

LaMarche, M. J. et al., "Anti-Hepatitis C Virus Activity and Toxicity of Type III Phosphatidylinositol-4-Kinase Beta Inhibitors", Antimicrobial Agents and Chemotherapy, Oct. 2012, vol. 56, No. 10, pp. 5149-5156.

Spickler, Catherine et al., "Phosphatidylinositol 4-Kinase III Beta is Essential for Replication of Human Rhinovirus and its Inhibition Causes a Lethal Phenotype In Vivo", Antimicrobial Agents and Chemotherapy, Jul. 2013, vol. 57, No. 7, pp. 3358-3368.

Keaney, Erin P. et al., "2-Alkyloxazoles as potent and selective PI4KIIIβ inhibitors demonstrating inhibition of HCV replication", Bioorganic & Medicinal Chemistry Letters, 2014, vol. 24, pp. 3714-3718.

Décor, Anne et al., "Design, synthesis and biological evaluation of novel aminothiazoles as antiviral compounds acting against human rhinovirus", Bioorganic & Medicinal Chemistry Letters, 2013, vol. 23, pp. 3841-3847.

Áála, Michal et al., "Purine analogs as phosphatidylinositol 4-kinase IIIβ inhibitors", Bioorganic & Medicinal Chemistry Letters, 2016, vol. 26, pp. 2706-2712.

Leivers, Anna L. et al., "Discovery of Selective Small Molecule Type III Phosphatidylinositol 4-Kinase Alpha (PI4KIIIα) Inhibitors as Anti Hepatitis C (HCV) Agents", Journal Medicinal Chemistry, 2014, vol. 57, pp. 2091-2106.

Arita, Minetaro et al., "Phosphatidylinositol 4-Kinase III Beta is a Target of Enviroxime-Like Compounds for Antipoliovirus Activity", Journal of Virology, Mar. 2011, vol. 85, No. 5, pp. 2364-2372.

Mejdrová, Ivana et al., "Highly Selective Phosphatidylinositol 4-Kinase IIIβ Inhibitors and Structural Insight into Their Mode of Action", Journal Medicinal Chemistry, 2015, vol. 58, pp. 3767-3793.

Rutaganira, Florentine U. et al., "Design and Structural Characterization of Potent and Selective Inhibitors of Phosphatidylinositol 4 Kinase IIIβ", Journal Medicinal Chemistry, 2016, vol. 59, pp. 1830-1839.

Mejdrová, Ivana et al., "Rational Design of Novel Highly Potent and Selective Phosphatidylinositol 4-Kinase IIIβ (PI4KB) Inhibitors as Broad-Spectrum Antiviral Agents and Tools for Chemical Biology", 2017, vol. 60, p. 100-118.

Noji, Satoru et al., "Concise SAR Exploration Based on the 'Head-to-Tail' Approach: Discovery of PI4KIIIα Inhibitors Bearing Diverse Scaffolds", ACS Medicinal Chemistry Letters, 2016, vol. 7, pp. 919-923.

Gadad, Andanappa K. et al., "Synthesis and biological evaluation of 2-trifluoromethyl/sulfonamido-5,6-diaryl substituted imidazo [2, 1-*b*]-1,3,4-thiadiazoles: A novel class of cyclooxygenase-2 inhibitors", Bioorganic & Medicinal Chemistry, 2008, vol. 16, pp. 276-283.

Mello, Chris et al., "Multiple Classes of Antiviral Agents Exhibit In Vitro Activity against Human Rhinovirus Type C", Antimicrobial Agents and Chemotherapy, Mar. 2014, vol. 58, No. 3, pp. 1546-1555.

Heinz, Beverly A. et al., "The Antiviral Compound Enviroxime Targets the 3A Coding Region of Rhinovirus and Poliovirus", Journal of Virology, Jul. 1995, vol. 69, No. 7, pp. 4189-4197.

Reghellin, V. et al., "NS5A Inhibitors Impair NS5A-Phosphatidylinositol 4-Kinase IIIα Complex Formation and Cause a Decrease of Phosphatidylinositol 4-Phosphate and Cholesterol Levels in Hepatitis C Virus-Associated Membranes", Antimicrobial Agents and Chemotherapy, Dec. 2014, vol. 58, No. 12, pp. 7128-7140.

Raubo, Piotr et al., "Discovery of potent, selective small molecule inhibitors of α-subtype of type III phosphatidylinositol-4-kinase (PI4KIIIα)", Bioorganic & Medicinal Chemistry Letters, 2015, vol. 25, pp. 3189-3193.

Bojjreddy, Naveen et al., "Pharmacological and Genetic Targeting of the PI4KA Enzyme Reveals its Important Role in Maintaining Plasma Membrane Phosphatidylinositol 4-Phosphate and Phosphatidylinositol 4,5-Bisphosphate Levels", The Journal of Biological Chemistry, Feb. 28, 2014, vol. 289, No. 9, pp. 6120-6132.

Humpolickova, Jana et al., "Fluorescent Inhibitors as Tools to Characterize Enzymes: Case Study of the Lipid Kinase Phosphatidylinositol 4-Kinase IIIβ (PI4KB)", Journal of Medicinal Chemistry, 2017, vol. 60, No. 1, pp. 119-127.

Waring, Michael J. et al., "Potent, selective small molecule inhibitors of type III phosphatidylinositol-4-kinase α- but not β-inhibit the phosphatidylinositol signaling cascade and cancer cell proliferation", Chem. Commun., 2014, vol. 50, pp. 5388-5390.

Kalgutkar, Amit S. et al., "Reactive Metabolite Trapping Studies on Imidazo- and 2-Methylimidazo[2,1-*b*]thiazole-Based Inverse Agonists of the Ghrelin Receptor", Drug Metabolism and Disposition, Jul. 2013, vol. 41, pp. 1375-1388.

Tassini, Sabrina et al., "Discovery of Multitarget Agents Active as Broad-Spectrum Antivirals and Correctors of Cystic Fibrosis Transmembrane Conductance Regulator for Associated Pulmonary Diseases", Journal of Medicinal Chemistry, 2017, vol. 60, No. 4, pp. 1400-1416.

Burke, John E. et al., "Structures of PI4KIIIβ complexes show simultaneous recruitment of Rab11 and its effectors", Science, May 30, 2014, vol. 344, Issue 6187, pp. 1035-1038.

Boura, Evzen et al., "Phosphatidylinositol 4-kinases: Function, structure, and inhibition", Experimental Cell Research, 2015, vol. 337, pp. 136-145.

International Search Report (ISR) dated Nov. 12, 2019 in International (PCT) Application No. PCT/JP2019/032335.

Angus M. MacLeod et al., "Identification of a Series of Compounds with Potent Antiviral Activity for the Treatment of Enterovirus Infections", ACS Medicinal Chemistry Letters, 4, pp. 585-589, 2013, cited in the specification.

SEQUENCE LISTING

<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: forward primer

<400> SEQUENCE: 1
ctagcctgcg tggc                                                         14

<210> SEQ ID NO 2
<211> LENGTH: 21
<212> TYPE: DNA
<213> ORGANISM: Artificial Sequence
<220> FEATURE:
<223> OTHER INFORMATION: reverse primer

<400> SEQUENCE: 2
gaaacacgga cacccaaagt a                                                 21

<210> SEQ ID NO 3
<211> LENGTH: 22
<212> TYPE: DNA
<213> ORGANISM: Artificial Sequence
<220> FEATURE:
<223> OTHER INFORMATION: probe

<400> SEQUENCE: 3
tcctccggcc cctgaatgcg gc                                                22

BICYCLIC HETEROAROMATIC RING DERIVATIVE

TECHNICAL FIELD

The present invention relates to a derivative of a bicyclic heteroaromatic ring having an anti-picornavirus action or a pharmaceutical composition comprising the derivative and pharmaceutical use thereof.

BACKGROUND ART

A picornavirus is one of RNA viruses belonging to the family Picornaviridae with a single positive-strand RNA genome. A picornavirus is composed of small (which corresponds to "pico") ribonucleic acid (which corresponds to "rna") and regular icosahedral capsid proteins. The family Picornaviridae is classified into the genera Enterovirus, Hepatovirus, Parechovirus, Kobuvirus, Cardiovirus, and the like, and many viruses included in this family are involved in human diseases.

Viral infections caused by the genus Enterovirus, for example enterovirus infection in children will result in acute airway inflammation, gastroenteritis, herpangina, hand-foot-and-mouth disease, viral exanthem, aseptic meningitis, acute encephalomyelitis, acute poliomyelitis (polio), myocarditis, hemorrhagic conjunctivitis, and the like. Rhinoviruses will cause common cold (cold symptoms) or exacerbation of asthma and chronic obstructive pulmonary disease, COPD. Among known viral infections caused by the genus Hepatovirus is hepatitis A infection caused by hepatitis A virus. Humanparechovirus infections caused by the genus Parechovirus will result in often symptoms of gastroenteritis (diarrhea, vomiting) and also signs of cold (cough, runny nose). Humanparechovirus infections are known to rarely cause myocarditis and aseptic meningitis. Aichiviruses, classified into the genus Kobuvirus, the family Picornaviridae, are known to be the causal virus of gastroenteritis.

Thus, viruses belonging to the family Picornaviridae are known to be a pathogen causing various diseases depending on their virus species.

On the other hand, therapeutic agents effective against infections of viruses belonging to the family Picornaviridae have not yet been developed. Pleconaril (3-(3,5-dimethyl-4-(3-(3-methylisoxazol-5-yl)propoxy)phenyl)-5-(trifluoromethyl)-1,2,4-oxazole) (Patent Literature 1) and enviroxime (2-amino-1-(isopropylsulfonyl)-6-benzimidazole phenyl ketone oxime) (Patent Literature 2) were reported to be a compound having an anti-picornavirus action. However, these compounds are not clinically used and are different in their structure from the compounds of the present invention.

Furthermore, antiviral agents known so far containing compounds having a bicyclic heteroaromatic ring skeleton include for example imidazopyrazines (Non Patent Literature 1), which are also different in their structure from the compounds of the present invention.

CITATION LIST

Patent Literature

[Patent Literature 1] JP H06-49066
[Patent Literature 2] U.S. Pat. No. 4,118,742

Non Patent Literature

[Non Patent Literature 1] ACS Med. Chem. Lett., 2013, 4, 585.

SUMMARY OF INVENTION

Technical Problem

Currently, as mentioned above, therapeutic agents effective against infections of viruses belonging to the family Picornaviridae have not yet been developed. The present invention aims to provide a compound having an antiviral action against viruses belonging to the family Picornaviridae, particularly rhinoviruses.

Solution to Problem

The inventors found as a result of their devoted research that bicyclic heteroaromatic ring compounds (which may be referred to as Compound (1) hereinafter) represented by General Formula (1) below has a potent anti-picornavirus action and has a successfully satisfying performance as a medicament, finally leading to completion of the present invention.

More specifically, the present invention is as follows:
[1] A compound represented by General Formula (1):

[Formula 1]

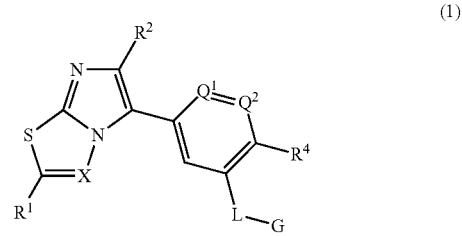

wherein
X represents N or CH;
$Q^1$ represents N or CH;
$Q^2$ represents N or $CR^3$;
L represents $—SO_2—$, $—SO_2C(R^8)_2—$, or $—SO_2NR^8—$;
$R^1$ represents H; a $C_1$-$C_6$ alkyl group, wherein the alkyl group is optionally substituted with one or more substituents selected from the group consisting of a halogen atom, a hydroxy group, a $C_1$-$C_6$ alkyl group, a $C_1$-$C_6$ alkoxy group, a halo$C_1$-$C_6$ alkyl group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, $—C(O)R^9$, and $—C(O)NR^{10}R^{11}$; a $C_3$-$C_6$ cycloalkyl group, wherein the cycloalkyl group is optionally substituted with one or more substituents selected from the group consisting of a halo$C_1$-$C_6$ alkyl group, a $C_1$-$C_6$ alkoxy group, a hydroxy group, and a cyano group; or a $C_2$-$C_6$ alkenyl group, wherein the alkenyl group is optionally substituted with one or more substituents selected from the group consisting of a halogen atom, a $C_1$-$C_6$ alkoxy group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, $—C(O)R^9$, and $—C(O)NR^{10}R^{11}$;

$R^2$ represents a $C_1$-$C_6$ alkyl group;

$R^3$ represents H; a $C_1$-$C_6$ alkyl group, wherein the alkyl group is optionally substituted with one or more substituents selected from the group consisting of a halogen atom, a hydroxy group, a $C_1$-$C_6$ alkoxy group, a halo$C_1$-$C_6$ alkyl group, a cyano group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)N$R^{10}R^{11}$; a hydroxy group; a $C_1$-$C_6$ alkoxy group; a halo$C_1$-$C_6$ alkyl group; a cyano group; a $C_3$-$C_{10}$ cycloalkyl group; a 3- to 10-membered heterocycloalkyl group; a $C_3$-$C_{10}$ cycloalkyloxy group; a 3- to 10-membered heterocycloalkyloxy group; —C(O)$R^9$; —C(O)N$R^{10}R^{11}$; or a halogen atom;

$R^4$ represents H, a halogen atom, a $C_1$-$C_6$ alkoxy group, a deuterated $C_1$-$C_6$ alkoxy group, a $C_1$-$C_6$ alkyl group, a halo$C_1$-$C_6$ alkyl group, a halo$C_1$-$C_6$alkoxy group, a hydroxy$C_1$-$C_6$ alkyl group, a hydroxy group, a cyano group, —C(O) $R^9$, —C(O) N$R^{10}R^{11}$, or N$R^{10}R^{11}$;

when $Q^2$ is $CR^3$, $R^3$ and $R^4$ may be joined together to form a ring;

G represents —$R^5$—$R^6$—$R^7$; a hydroxy$C_1$-$C_6$ alkyl group, wherein the hydroxy$C_1$-$C_6$ alkyl group is optionally substituted with $W^1$ and $W^2$, wherein $W^1$ and $W^2$ are each independently selected from the group consisting of H, a $C_1$-$C_6$ alkyl group, a deuterated $C_1$-$C_6$ alkyl group, a halo$C_1$-$C_6$ alkyl group, and a hydroxy$C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkyl group, wherein the $C_3$-$C_6$ cycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a $C_5$-$C_8$ bicycloalkyl group, wherein the $C_5$-$C_8$ bicycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a 3- to 10-membered heterocycloalkyl group, wherein the 3- to 10-membered heterocycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, —C(O) N($R^{13}$)$_2$, and an oxo group, and $W^3$ and $W^4$ may be joined together to form a ring; a $C_1$-$C_6$ alkyl group, wherein the $C_1$-$C_6$ alkyl group is optionally substituted with $W^5$ and $W^6$, wherein $W^5$ and $W^6$ are each independently selected from the group consisting of H, a cyano group, a hydroxy$C_1$-$C_6$ alkyl group, a $C_1$-$C_6$ alkyl group, a $C_1$-$C_6$ alkoxycarbonyl group, a carboxy group, and —C(O)N($R^{13}$)$_2$, and $W^5$ and $W^6$ may be joined together to form a ring; a phenyl group, wherein the phenyl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —N$R^{10}R^{11}$, —C(O) $R^9$, —C(O)N$R^{10}R^{11}$, a $C_1$-$C_6$ alkoxycarbonyl group, —SO$_2R^{12}$, and a $C_1$-$C_6$ alkoxy group; or a heteroaryl group, wherein the heteroaryl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —N$R^{10}R^{11}$, —C(O)$R^9$, —C(O)N$R^{10}R^{11}$, a $C_1$-$C_6$ alkoxycarbonyl group, —SO$_2R^{12}$, and a $C_1$-$C_6$ alkoxy group;

$R^5$ represents a hydroxy$C_1$-$C_6$ alkylene group, wherein the hydroxy$C_1$-$C_6$ alkylene group is optionally substituted with $W^1$ and $W^2$, wherein $W^1$ and $W^2$ are each independently selected from the group consisting of H, a $C_1$-$C_6$ alkyl group, a deuterated $C_1$-$C_6$ alkyl group, a halo$C_1$-$C_6$ alkyl group, and a hydroxy$C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkylene group, wherein the $C_3$-$C_6$ cycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a $C_5$-$C_8$ bicycloalkylene group, wherein the $C_5$-$C_8$ bicycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a 3- to 10-membered heterocycloalkylene group, wherein the 3- to 10-membered heterocycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_3$-$C_{10}$ cycloalkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, —C(O)N($R^{13}$)$_2$, and an oxo group, and $W^3$ and $W^4$ may be joined together to form a ring; a $C_1$-$C_6$ alkylene group, wherein the $C_1$-$C_6$ alkylene group is optionally substituted with $W^5$ and $W^6$, wherein $W^5$ and $W^6$ are each independently selected from the group consisting of H, a cyano group, a hydroxy$C_1$-$C_6$ alkyl group, a $C_1$-$C_6$ alkyl group, a $C_1$-$C_6$ alkoxycarbonyl group, a carboxy group, and —C(O)N($R^{13}$)$_2$, and $W^5$ and $W^6$ may be joined together to form a ring; a phenylene group, wherein the phenylene group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —N$R^{10}R^{11}$, —C(O)$R^9$, —C(O)N$R^{10}R^{11}$, a $C_1$-$C_6$ alkoxycarbonyl group, —SO$_2R^{12}$, and a $C_1$-$C_6$ alkoxy group; or a heteroarylene group, wherein the heteroarylene group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a haloC$_1$-C$_6$ alkyl group, a cyano group, a C$_3$-C$_{10}$ cycloalkyl group, a 3- to 10-membered heterocycloalkyl group, —NR$^{10}$R$^{11}$, —C(O)R$^9$, —C(O)NR$^{10}$R$^{11}$, a C$_1$-C$_6$ alkoxycarbonyl group, —SO$_2$R$^{12}$, and a C$_1$-C$_6$ alkoxy group;

R$^6$ represents a bond or a C$_3$-C$_6$ cycloalkylene group;
R$^7$ represents H or a hydroxy group;
each R$^8$ independently represents H or a C$_1$-C$_6$ alkyl group;
R$^9$ represents H, a hydroxy group, a C$_1$-C$_6$ alkyl group, a C$_1$-C$_6$ alkoxy group, or a C$_3$-C$_6$ cycloalkoxy group;
R$^{10}$ represents H or a C$_1$-C$_6$ alkyl group;
R$^{11}$ represents H or a C$_1$-C$_6$ alkyl group;
R$^{12}$ represents H or a C$_1$-C$_6$ alkyl group; and
each R$^{13}$ independently represents H, a C$_1$-C$_6$ alkyl group, or a hydroxyC$_1$-C$_6$ alkyl group.

[2] The compound according to [1], wherein in General Formula (1), Q$^1$ is CH, Q$^2$ is CR$^3$, and R$^3$ is H.

[3] The compound according to [1], wherein in General Formula (1), X is N.

[4] The compound according to [1] to [3], wherein in General Formula (1), R$^2$ is a methyl group.

[5] The compound according to [1] to [4], wherein in General Formula (1),
X represents N;
Q$^1$ represents CH;
Q$^2$ represents CR$^3$;
L represents —SO$_2$—;
R$^1$ represents a C$_1$-C$_6$ alkyl group, wherein the alkyl group is optionally substituted with one or more substituents selected from the group consisting of a halogen atom, a hydroxy group, a C$_1$-C$_6$ alkoxy group, a haloC$_1$-C$_6$ alkyl group, a cyano group, a 3- to 10-membered heterocycloalkyloxy group, —C(O)R$^9$, and —C(O)NR$^{10}$R$^{11}$;
R$^2$ represents a methyl group;
R$^3$ represents H;
R$^4$ represents a C$_1$-C$_6$ alkoxy group, a C$_1$-C$_6$ alkyl group, or a haloC$_1$-C$_6$ alkyl group; and
G represents a hydroxyC$_1$-C$_6$ alkyl group, wherein the hydroxyC$_1$-C$_6$ alkyl group is optionally substituted with W$^2$ and W$^2$, wherein W$^2$ and W$^2$ are each independently H or a C$_1$-C$_6$ alkyl group, and W$^2$ and W$^2$ may be joined together to form a ring, and the ring formed by W$^2$ and W$^2$ is optionally substituted with one or more halogen atoms.

[6] The compound according to [5], wherein in General Formula (1), R$^4$ is a C$_1$-C$_6$ alkoxy group.

[7] The compound according to [1] to [4], wherein in General Formula (1),
X represents N;
Q$^1$ represents CH;
Q$^2$ represents CR$^3$;
L represents —SO$_2$—, —SO$_2$NR$^8$—, or —SO$_2$C(R$^8$)$_2$—;
R$^2$ represents a C$_1$-C$_6$ alkyl group, wherein the alkyl group is optionally substituted with one or more hydroxy groups or C$_1$-C$_6$ alkoxy groups;
R$^2$ represents a methyl group;
R$^3$ represents H or a halogen atom;
R$^4$ represents a C$_1$-C$_6$ alkoxy group, a C$_1$-C$_6$ alkyl group, a haloC$_1$-C$_6$ alkyl group, or a haloC$_1$-C$_6$alkoxy group; and
G represents a hydroxyC$_1$-C$_6$ alkyl group, wherein the hydroxyC$_1$-C$_6$ alkyl group is optionally substituted with W$^2$ and W$^2$, wherein W$^2$ and W$^2$ are each independently H or a C$_1$-C$_6$ alkyl group, and W$^2$ and W$^2$ may be joined together to form a ring, and the ring formed by W$^2$ and W$^2$ is optionally substituted with one or more halogen atoms; a C$_3$-C$_6$ cycloalkyl group, wherein the C$_3$-C$_6$ cycloalkyl group is optionally substituted with W$^3$ and W$^4$, wherein W$^3$ and W$^4$ are each independently selected from the group consisting of H, a hydroxy group, a C$_1$-C$_6$ alkyl group, a C$_1$-C$_6$ acyl group, a hydroxyC$_1$-C$_6$ alkyl group, a C$_1$-C$_6$ alkoxycarbonyl group, and —SO$_2$R$^{12}$, and W$^3$ and W$^4$ may be joined together to form a ring; a 3- to 10-membered heterocycloalkyl group, wherein the 3- to 10-membered heterocycloalkyl group is optionally substituted with W$^3$ and W$^4$, wherein W$^3$ and W$^4$ are each independently selected from the group consisting of H, a hydroxy group, a C$_1$-C$_6$ alkyl group, a C$_1$-C$_6$ acyl group, a hydroxyC$_1$-C$_6$ alkyl group, a C$_1$-C$_6$ alkoxycarbonyl group, —SO$_2$R$^{12}$, and —C(O)N(R$^{13}$)$_2$, and W$^3$ and W$^4$ may be joined together to form a ring; a C$_1$-C$_6$ alkyl group, wherein the C$_1$-C$_6$ alkyl group is optionally substituted with W$^5$ and W$^6$, wherein W$^5$ and W$^6$ are each independently selected from the group consisting of H, a cyano group, a hydroxyC$_1$-C$_6$ alkyl group, a C$_1$-C$_6$ alkyl group, a C$_1$-C$_6$ alkoxycarbonyl group, a carboxy group, and —C(O)N(R$^{13}$)$_2$, and W$^5$ and W$^6$ may be joined together to form a ring; or a heteroaryl group, wherein the heteroaryl group is optionally substituted with one or more substituents selected from the group consisting of a halogen atom, a C$_1$-C$_6$ alkyl group, a hydroxyC$_1$-C$_6$ alkyl group, a C$_1$-C$_6$ acyl group, a carboxy group, a hydroxy group, a haloC$_1$-C$_6$ alkyl group, a cyano group, a C$_3$-C$_{10}$ cycloalkyl group, a 3- to 10-membered heterocycloalkyl group, —NR$^{10}$R$^{11}$, —C(O) R$^9$, —C(O) NR$^{10}$R$^{11}$, a C$_1$-C$_6$ alkoxycarbonyl group, —SO$_2$R$^{12}$, and a C$_1$-C$_6$ alkoxy group.

[8] The compound according to [1], wherein in General Formula (1),
X represents CH;
Q$^1$ represents N or CH;
Q$^2$ represents N or CR$^3$;
L represents —SO$_2$—, —SO$_2$NR$^8$—, or —SO$_2$C(R$^8$)$_2$—;
R$^1$ represents H; a C$_1$-C$_6$ alkyl group, wherein the alkyl group is optionally substituted with one or more substituents selected from the group consisting of a halogen atom, a hydroxy group, a C$_1$-C$_6$ alkoxy group, and a 3- to 10-membered heterocycloalkyloxy group; a C$_3$-C$_6$ cycloalkyl group, wherein the cycloalkyl group is optionally substituted with one or more substituents selected from the group consisting of a C$_1$-C$_6$ alkoxy group and a hydroxy group; or a C$_2$-C$_6$ alkenyl group;
R$^2$ represents a C$_1$-C$_6$ alkyl group;
R$^3$ represents H or a halogen atom;
R$^4$ represents a halogen atom, a C$_1$-C$_6$ alkoxy group, a C$_1$-C$_6$ alkyl group, a haloC$_1$-C$_6$ alkyl group, a haloC$_1$-C$_6$ alkoxy group, a cyano group, or NR$^{10}$R$^{11}$;
G represents a hydroxyC$_1$-C$_6$ alkyl group, wherein the hydroxyC$_1$-C$_6$ alkyl group is optionally substituted with W$^1$ and W$^2$, wherein W$^1$ and W$^2$ are each independently H or a C$_1$-C$_6$ alkyl group, and W$^1$ and W$^2$ may be joined together to form a ring, and the ring formed by W$^1$ and W$^2$ is optionally substituted with one or more halogen atoms; a C$_3$-C$_6$ cycloalkyl group, wherein the C$_3$-C$_6$ cycloalkyl group is optionally substituted with W$^3$ and W$^4$, wherein W$^3$ and W$^4$ are each independently H, a hydroxy group, or a C$_1$-C$_6$ alkoxy group, and W$^3$ and W$^4$ may be joined together to form a ring; a 3- to 10-membered heterocycloalkyl group; a phenyl group, wherein the phenyl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —$NR^{10}R^{11}$, —$C(O)R^9$, —$C(O)NR^{10}R^{11}$, a $C_1$-$C_6$ alkoxycarbonyl group, —$SO_2R^{12}$, and a $C_1$-$C_6$ alkoxy group; or a heteroaryl group, wherein the heteroaryl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —$NR^{10}R^{11}$, —$C(O)R^9$, —$C(O)NR^{10}R^{11}$, a $C_1$-$C_6$ alkoxycarbonyl group, —$SO_2R^{12}$, and a $C_1$-$C_6$ alkoxy group;

$R^8$ represents H or a $C_1$-$C_6$ alkyl group;

$R^{10}$ represents H or a $C_1$-$C_6$ alkyl group; and $R^{11}$ represents H or a $C_1$-$C_6$ alkyl group.

[9] The compound according to [8], wherein in General Formula (1), $Q^1$ is CH, and $Q^2$ is N.

[10] The compound according to claim 1, wherein the compound represented by General Formula (1) above is any one of the compounds listed in Tables 1 to 11.

TABLE 1

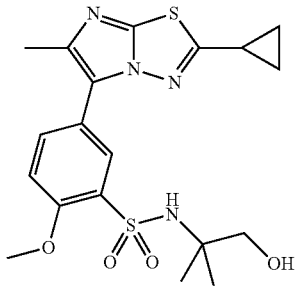

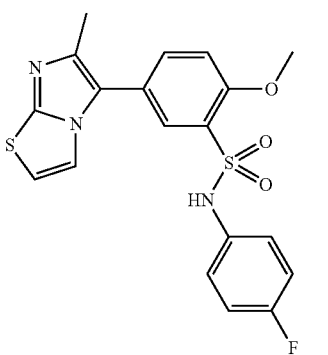 [SMILES: COc1ccc(-c2c(C)nc3sccn23)cc1S(=O)(=O)Nc1ccc(F)cc1]

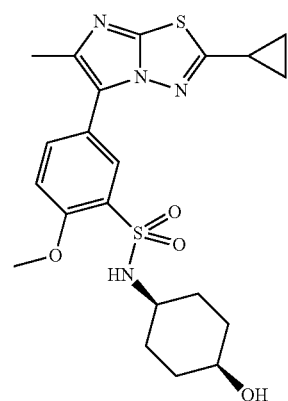

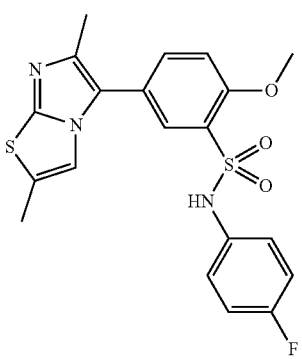 [SMILES: COc1ccc(-c2c(C)nc3sc(C)cn23)cc1S(=O)(=O)Nc1ccc(F)cc1]

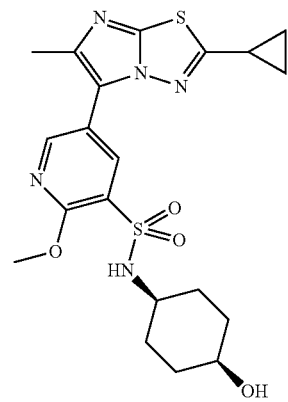 [SMILES: COc1ncc(-c2c(C)nc3sc(C4CC4)nn23)cc1S(=O)(=O)N[C@H]1CC[C@@H](O)CC1]

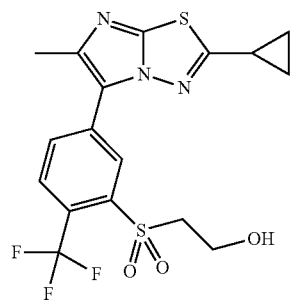 [SMILES: Cc1nc2sc(C3CC3)nn2c1-c1ccc(C(F)(F)F)c(S(=O)(=O)CCO)c1]

TABLE 1-continued
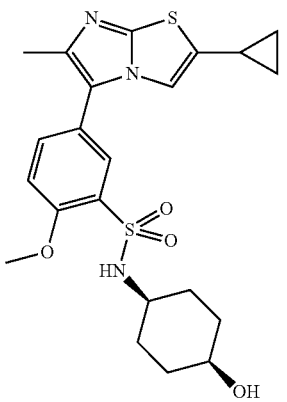
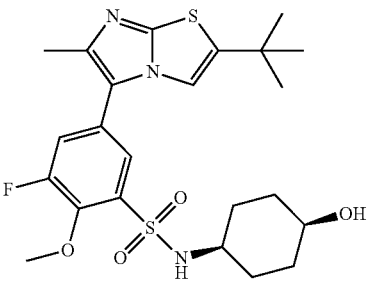
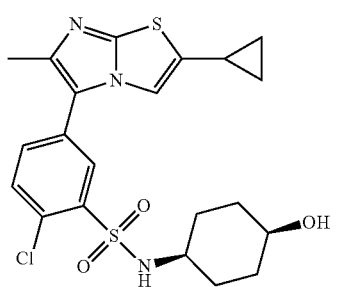 [SMILES: Cc1nc2sc(C3CC3)cn2c1-c1ccc(Cl)c(S(=O)(=O)N[C@H]2CC[C@@H](O)CC2)c1]
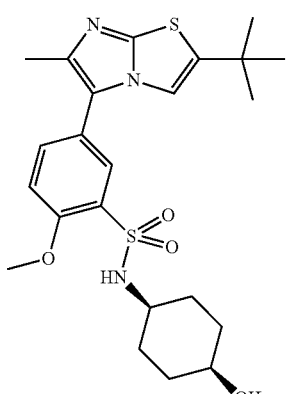
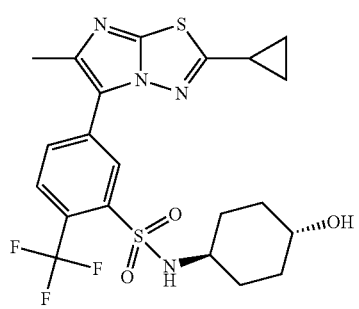 [SMILES: Cc1nc2sc(C3CC3)nn2c1-c1ccc(C(F)(F)F)c(S(=O)(=O)N[C@H]2CC[C@H](O)CC2)c1]
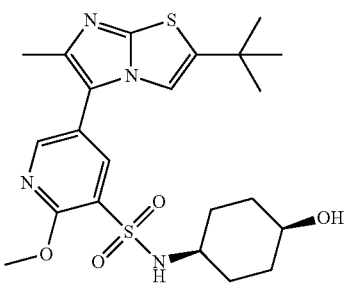
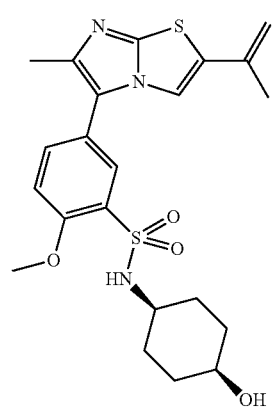 [SMILES: C=C(C)c1cn2c(-c3ccc(OC)c(S(=O)(=O)N[C@H]4CC[C@@H](O)CC4)c3)c(C)nc2s1]
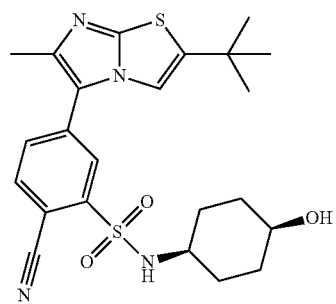 [SMILES: Cc1nc2sc(C(C)(C)C)cn2c1-c1ccc(C#N)c(S(=O)(=O)N[C@H]2CC[C@@H](O)CC2)c1]
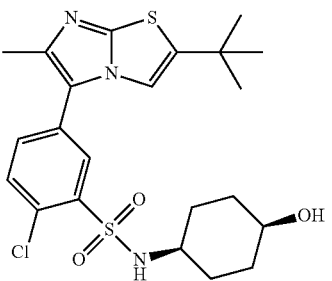 [SMILES: Cc1nc2sc(C(C)(C)C)cn2c1-c1ccc(Cl)c(S(=O)(=O)N[C@H]2CC[C@@H](O)CC2)c1]

TABLE 1-continued
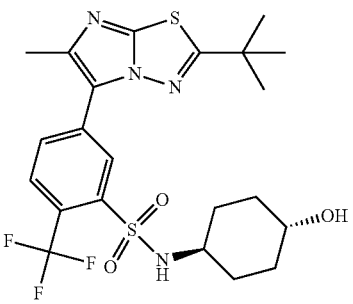
TABLE 2
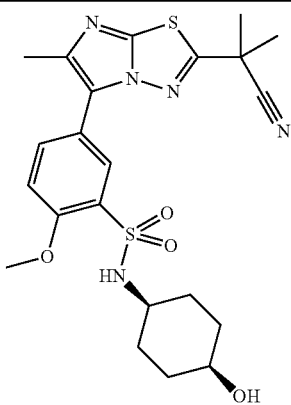
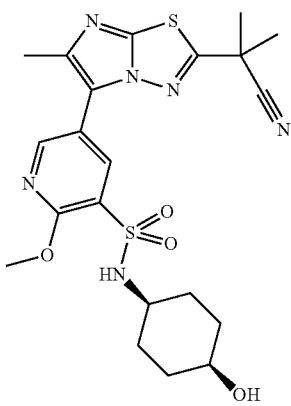 [SMILES: COc1ncc(-c2c(C)nc3sc(C(C)(C)C#N)nn23)cc1S(=O)(=O)N[C@H]1CC[C@@H](O)CC1]
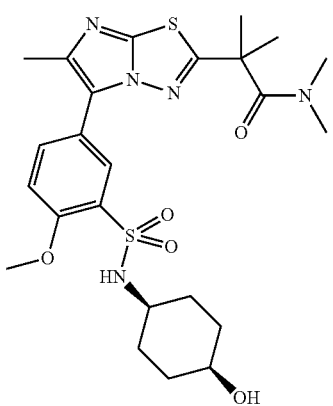
TABLE 2-continued
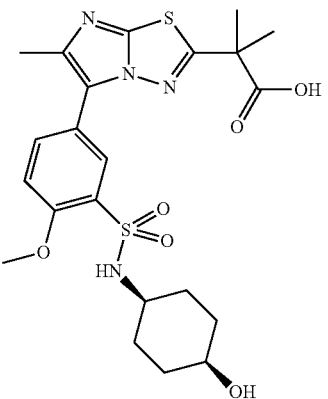 [SMILES: COc1ccc(-c2c(C)nc3sc(C(C)(C)C(=O)O)nn23)cc1S(=O)(=O)N[C@H]1CC[C@@H](O)CC1]
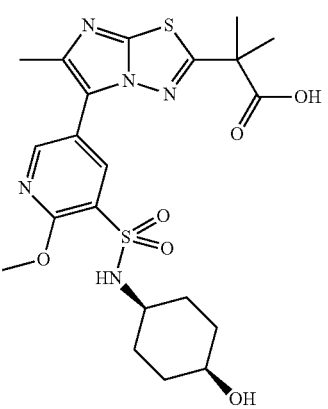
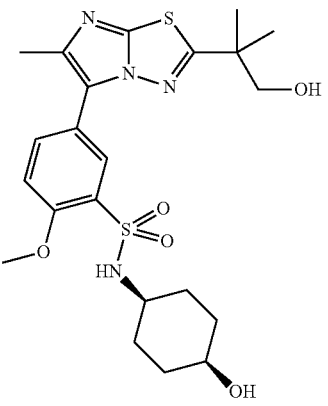 [SMILES: COc1ccc(-c2c(C)nc3sc(C(C)(C)CO)nn23)cc1S(=O)(=O)N[C@H]1CC[C@@H](O)CC1]
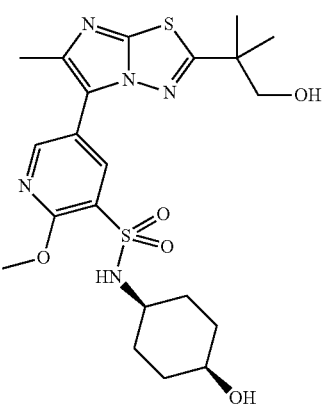 [SMILES: COc1ncc(-c2c(C)nc3sc(C(C)(C)CO)nn23)cc1S(=O)(=O)N[C@H]1CC[C@@H](O)CC1]

TABLE 2-continued
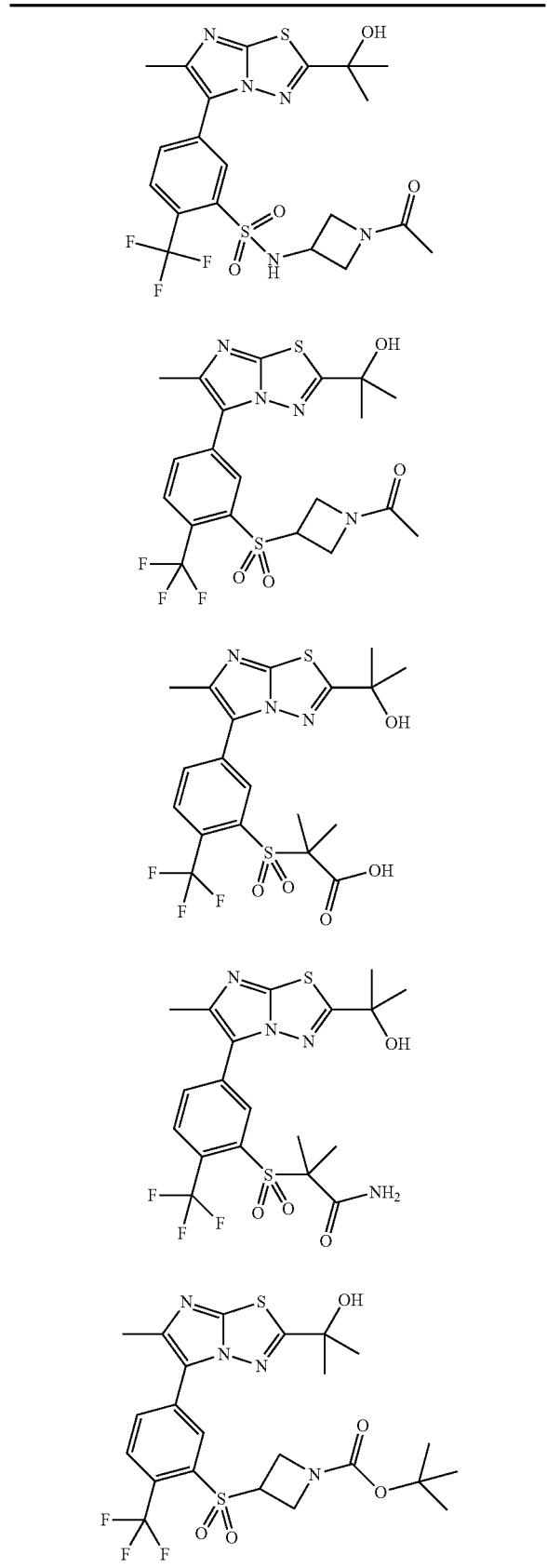
TABLE 2-continued
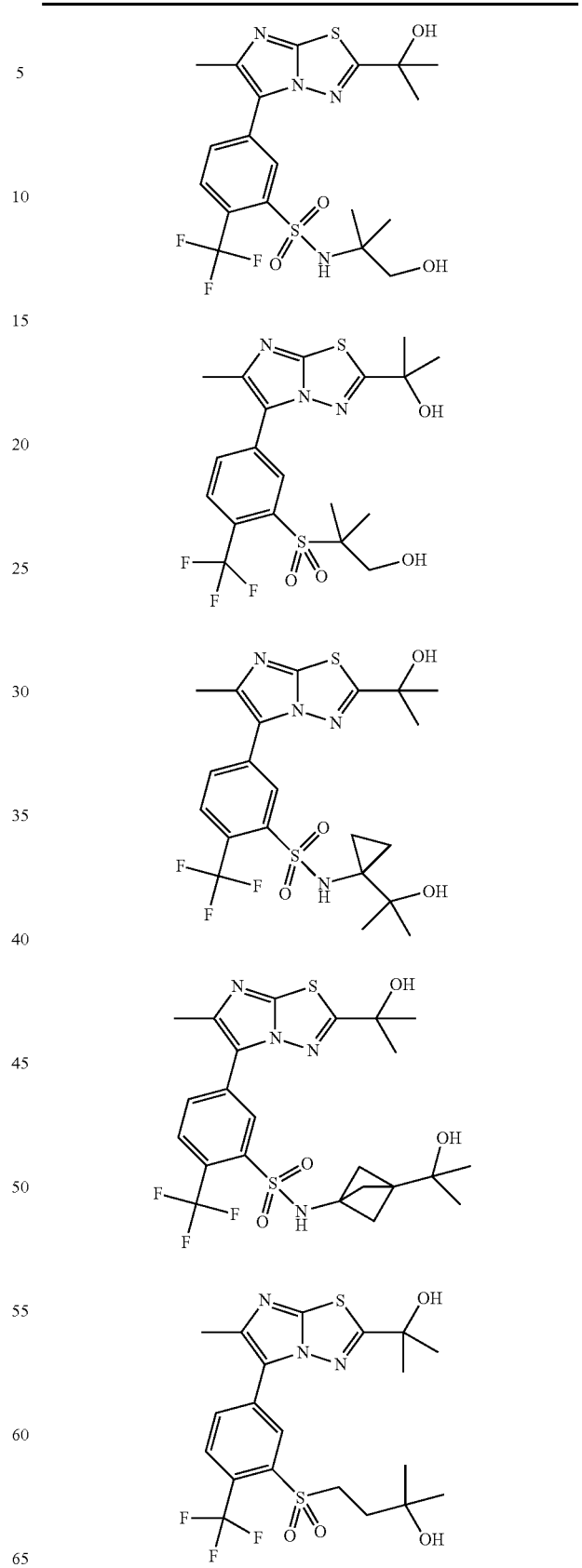

TABLE 2-continued
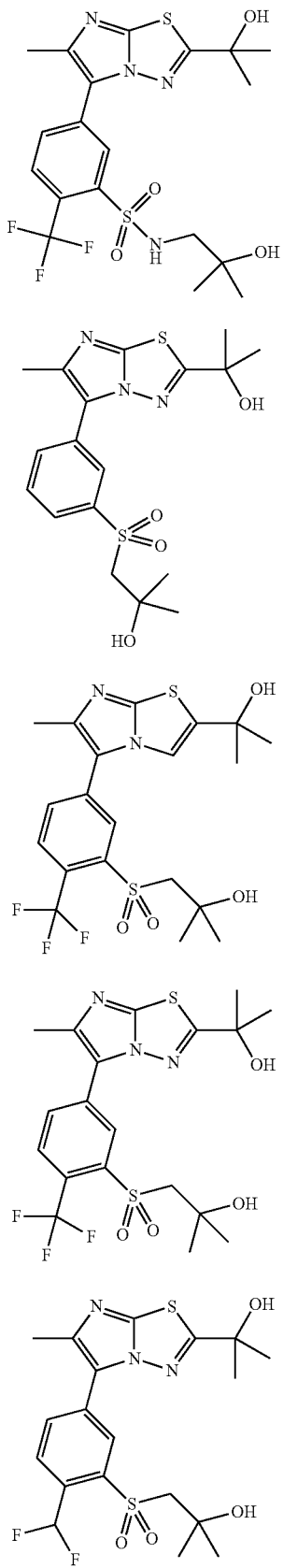
TABLE 2-continued
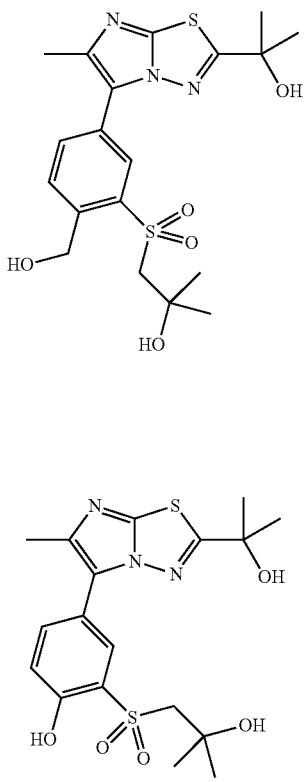
TABLE 3
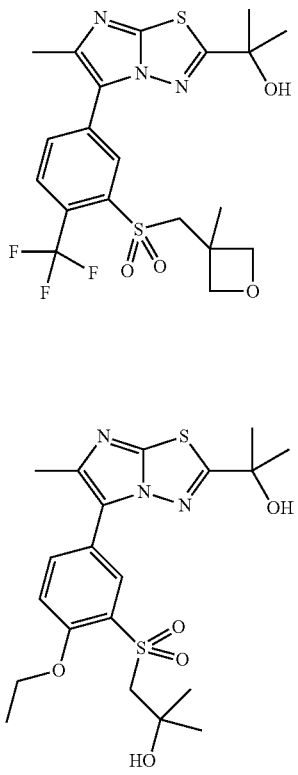

TABLE 3-continued
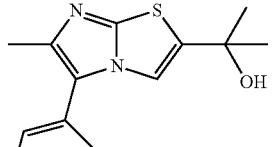
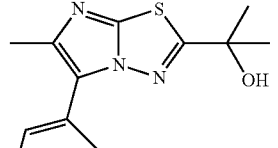
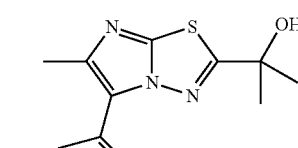
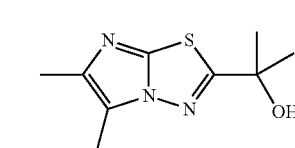
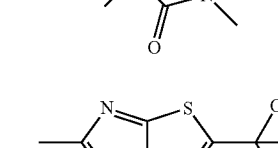
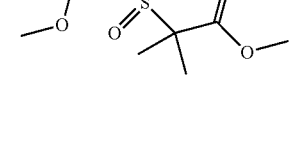
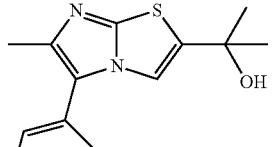
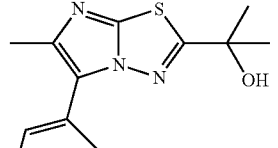
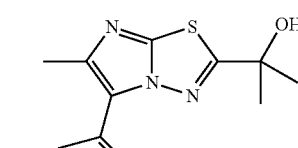
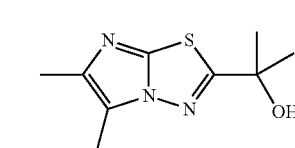

TABLE 3-continued
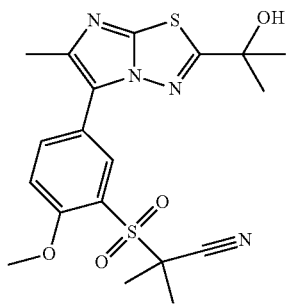 [SMILES: COc1ccc(-c2c(C)nc3sc(C(C)(C)O)nn23)cc1S(=O)(=O)C(C)(C)C#N]
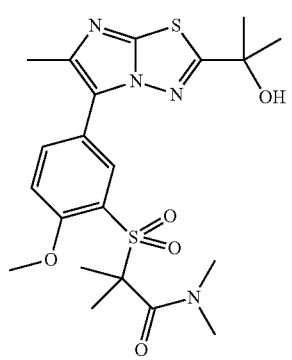 [SMILES: COc1ccc(-c2c(C)nc3sc(C(C)(C)O)nn23)cc1S(=O)(=O)C(C)(C)C(=O)N(C)C]
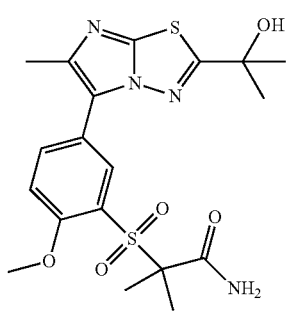 [SMILES: COc1ccc(-c2c(C)nc3sc(C(C)(C)O)nn23)cc1S(=O)(=O)C(C)(C)C(N)=O]
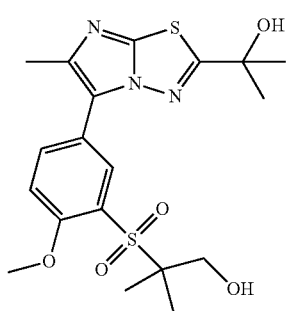 [SMILES: COc1ccc(-c2c(C)nc3sc(C(C)(C)O)nn23)cc1S(=O)(=O)C(C)(C)CO]
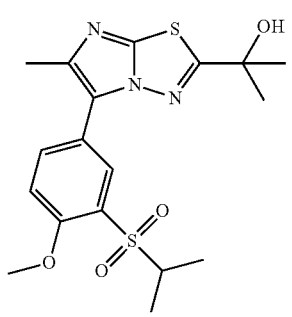 [SMILES: COc1ccc(-c2c(C)nc3sc(C(C)(C)O)nn23)cc1S(=O)(=O)C(C)C]
TABLE 3-continued
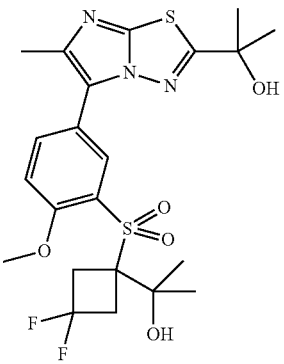 [SMILES: COc1ccc(-c2c(C)nc3sc(C(C)(C)O)nn23)cc1S(=O)(=O)C1(C(C)(C)O)CC(F)(F)C1]
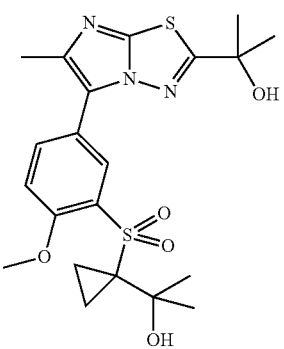 [SMILES: COc1ccc(-c2c(C)nc3sc(C(C)(C)O)nn23)cc1S(=O)(=O)C1(C(C)(C)O)CC1]
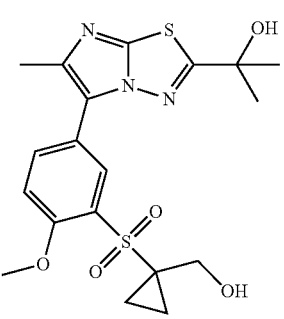 [SMILES: COc1ccc(-c2c(C)nc3sc(C(C)(C)O)nn23)cc1S(=O)(=O)C1(CO)CC1]
TABLE 4
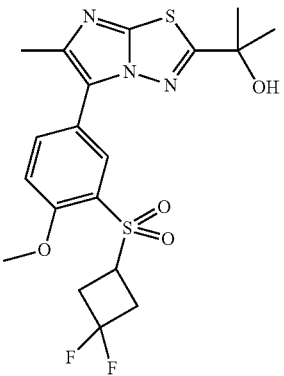 [SMILES: COc1ccc(-c2c(C)nc3sc(C(C)(C)O)nn23)cc1S(=O)(=O)C1CC(F)(F)C1]

TABLE 4-continued
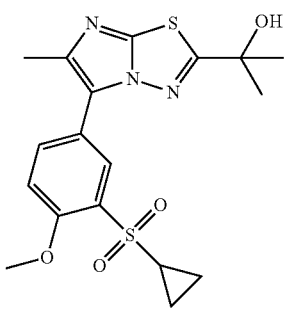 [SMILES: COc1ccc(-c2c(C)nc3sc(C(C)(C)O)nn23)cc1S(=O)(=O)C1CC1]
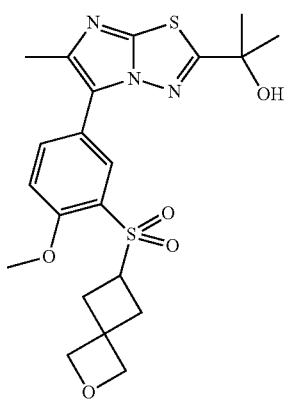 [SMILES: COc1ccc(-c2c(C)nc3sc(C(C)(C)O)nn23)cc1S(=O)(=O)C1CC2(COC2)C1]
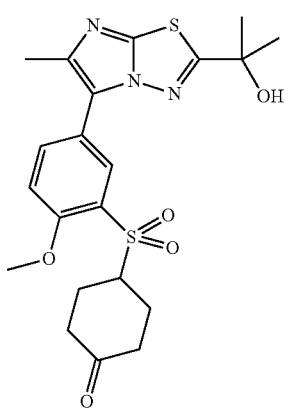 [SMILES: COc1ccc(-c2c(C)nc3sc(C(C)(C)O)nn23)cc1S(=O)(=O)C1CCC(=O)CC1]
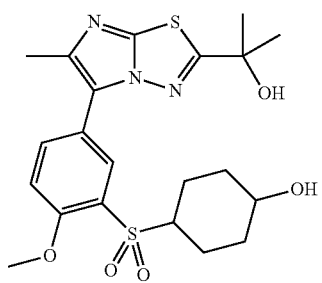 [SMILES: COc1ccc(-c2c(C)nc3sc(C(C)(C)O)nn23)cc1S(=O)(=O)C1CCC(O)CC1]
TABLE 4-continued
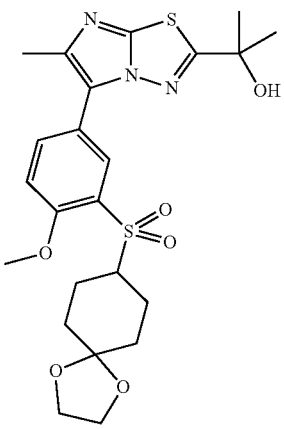 [SMILES: COc1ccc(-c2c(C)nc3sc(C(C)(C)O)nn23)cc1S(=O)(=O)C1CCC2(CC1)OCCO2]
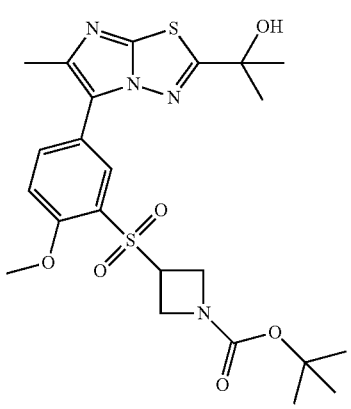 [SMILES: COc1ccc(-c2c(C)nc3sc(C(C)(C)O)nn23)cc1S(=O)(=O)C1CN(C(=O)OC(C)(C)C)C1]
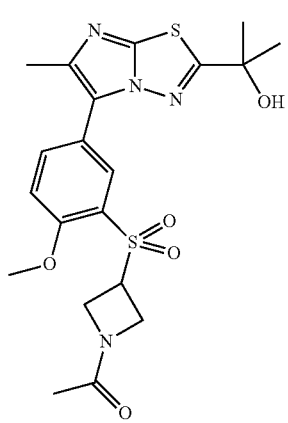 [SMILES: COc1ccc(-c2c(C)nc3sc(C(C)(C)O)nn23)cc1S(=O)(=O)C1CN(C(C)=O)C1]
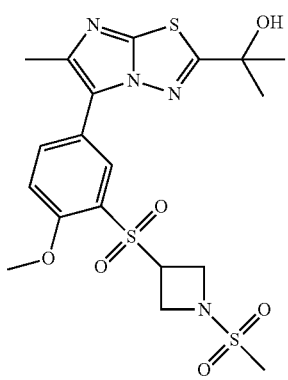 [SMILES: COc1ccc(-c2c(C)nc3sc(C(C)(C)O)nn23)cc1S(=O)(=O)C1CN(S(C)(=O)=O)C1]

TABLE 4-continued
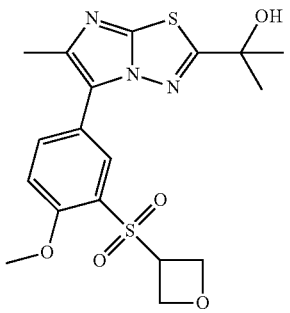 [SMILES: COc1ccc(-c2c(C)nc3sc(C(C)(C)O)nn23)cc1S(=O)(=O)C1COC1]
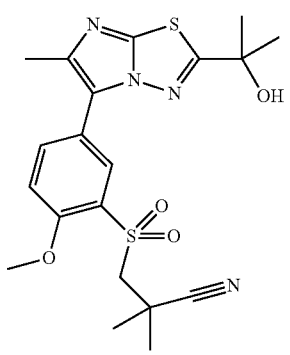 [SMILES: COc1ccc(-c2c(C)nc3sc(C(C)(C)O)nn23)cc1S(=O)(=O)CC(C)(C)C#N]
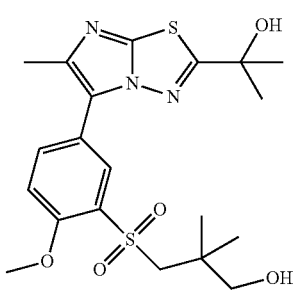 [SMILES: COc1ccc(-c2c(C)nc3sc(C(C)(C)O)nn23)cc1S(=O)(=O)CC(C)(C)CO]
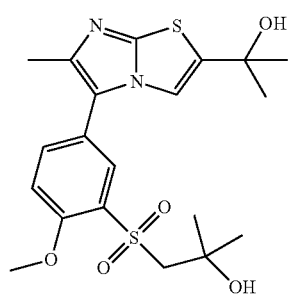 [SMILES: COc1ccc(-c2c(C)nc3sc(C(C)(C)O)cn23)cc1S(=O)(=O)CC(C)(C)O]
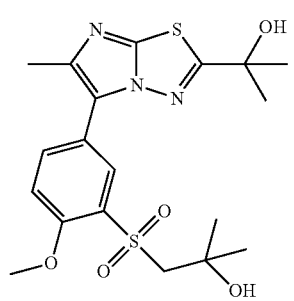 [SMILES: COc1ccc(-c2c(C)nc3sc(C(C)(C)O)nn23)cc1S(=O)(=O)CC(C)(C)O]
TABLE 4-continued
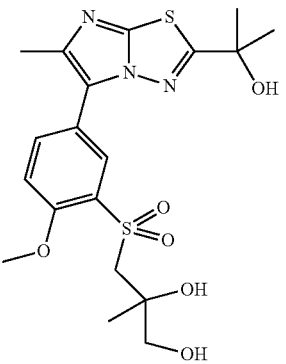 [SMILES: COc1ccc(-c2c(C)nc3sc(C(C)(C)O)nn23)cc1S(=O)(=O)CC(C)(O)CO]
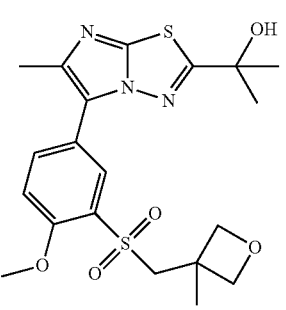 [SMILES: COc1ccc(-c2c(C)nc3sc(C(C)(C)O)nn23)cc1S(=O)(=O)CC1(C)COC1]
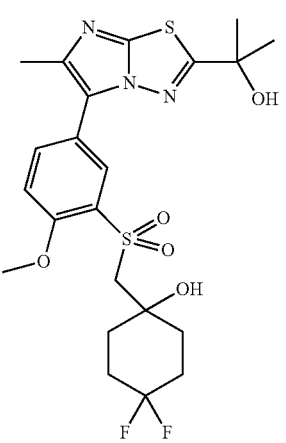 [SMILES: COc1ccc(-c2c(C)nc3sc(C(C)(C)O)nn23)cc1S(=O)(=O)CC1(O)CCC(F)(F)CC1]
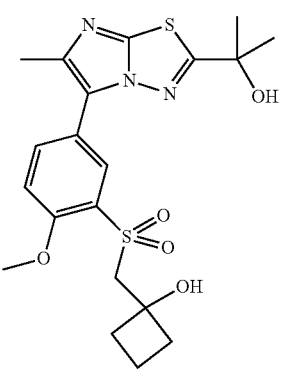 [SMILES: COc1ccc(-c2c(C)nc3sc(C(C)(C)O)nn23)cc1S(=O)(=O)CC1(O)CCC1]

TABLE 4-continued
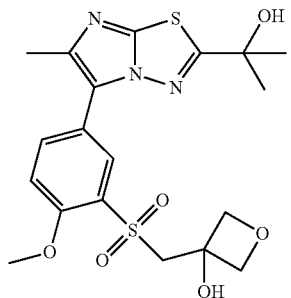 [SMILES: COc1ccc(-c2c(C)nc3sc(C(C)(C)O)nn23)cc1S(=O)(=O)CC1(O)COC1]
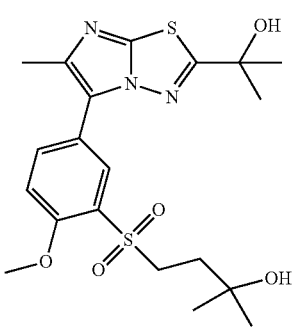 [SMILES: COc1ccc(-c2c(C)nc3sc(C(C)(C)O)nn23)cc1S(=O)(=O)CCC(C)(C)O]
TABLE 5
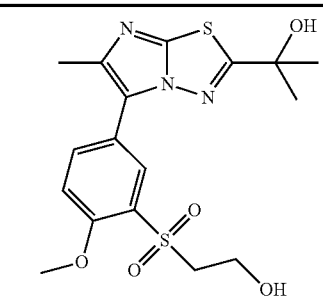
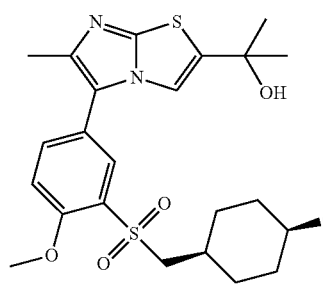
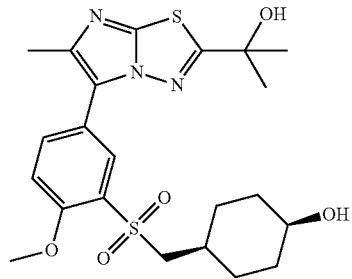 [SMILES: COc1ccc(-c2c(C)nc3sc(C(C)(C)O)nn23)cc1S(=O)(=O)C[C@H]1CC[C@@H](O)CC1]
TABLE 5-continued
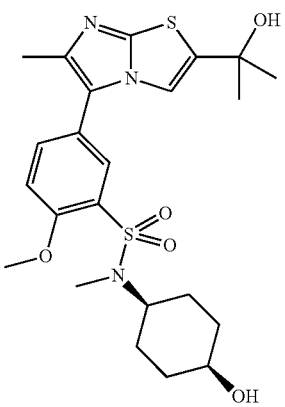 [SMILES: COc1ccc(-c2c(C)nc3sc(C(C)(C)O)cn23)cc1S(=O)(=O)N(C)[C@H]1CC[C@@H](O)CC1]
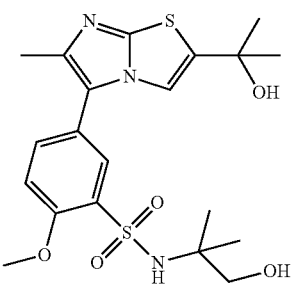 [SMILES: COc1ccc(-c2c(C)nc3sc(C(C)(C)O)cn23)cc1S(=O)(=O)NC(C)(C)CO]
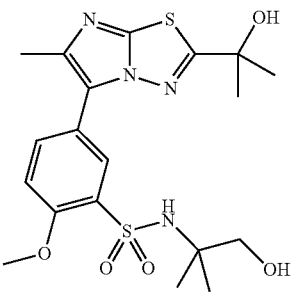 [SMILES: COc1ccc(-c2c(C)nc3sc(C(C)(C)O)nn23)cc1S(=O)(=O)NC(C)(C)CO]
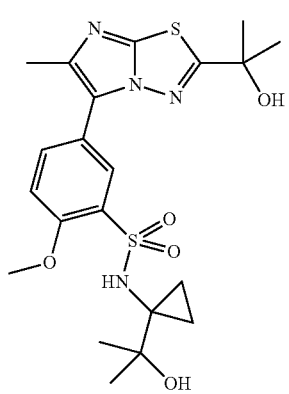 [SMILES: COc1ccc(-c2c(C)nc3sc(C(C)(C)O)nn23)cc1S(=O)(=O)NC1(C(C)(C)O)CC1]

TABLE 5-continued
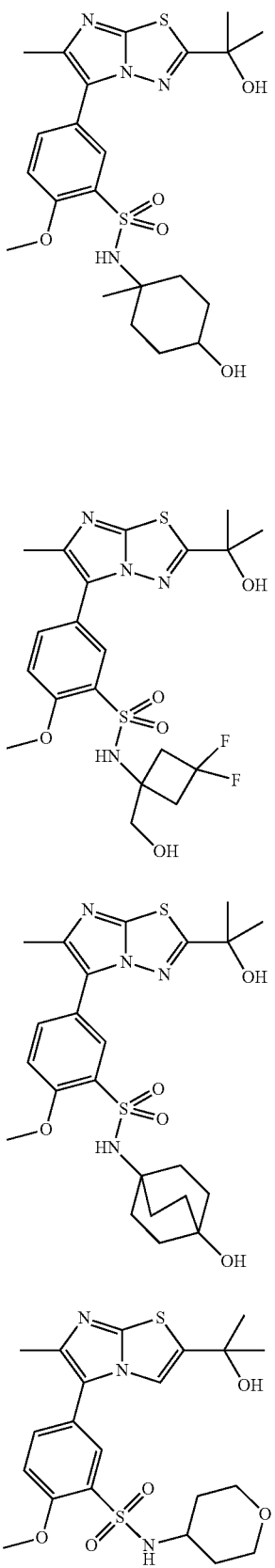
TABLE 5-continued
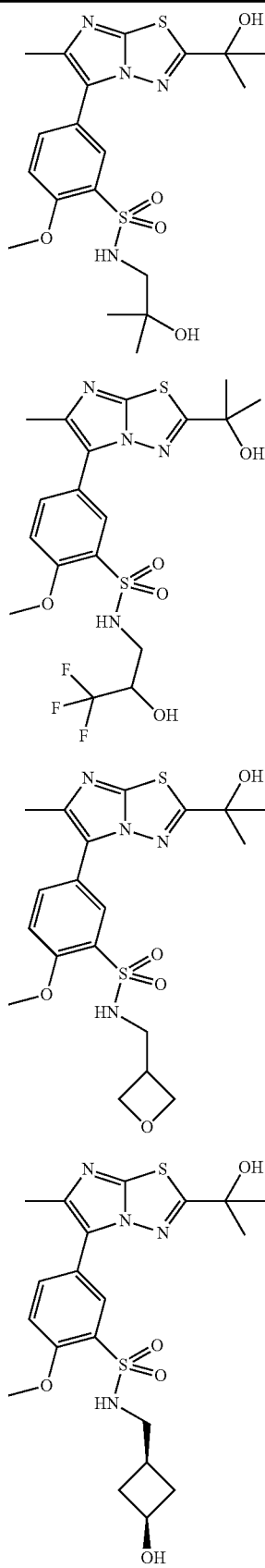

TABLE 5-continued
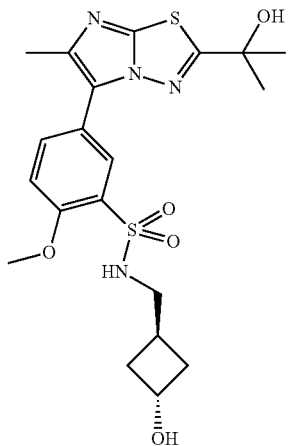 [SMILES: COc1ccc(-c2c(C)nc3sc(C(C)(C)O)nn23)cc1S(=O)(=O)NC[C@H]1C[C@H](O)C1]
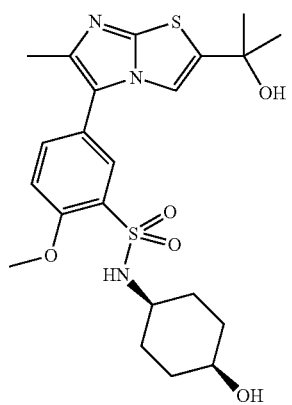 [SMILES: COc1ccc(-c2c(C)nc3sc(C(C)(C)O)cn23)cc1S(=O)(=O)N[C@H]1CC[C@@H](O)CC1]
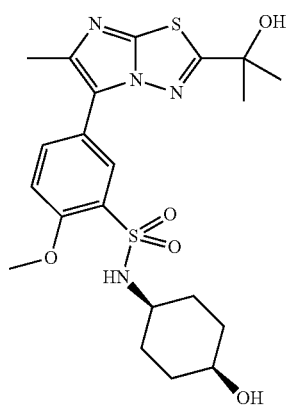 [SMILES: COc1ccc(-c2c(C)nc3sc(C(C)(C)O)nn23)cc1S(=O)(=O)N[C@H]1CC[C@@H](O)CC1]
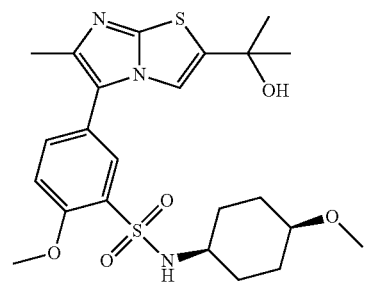
TABLE 5-continued
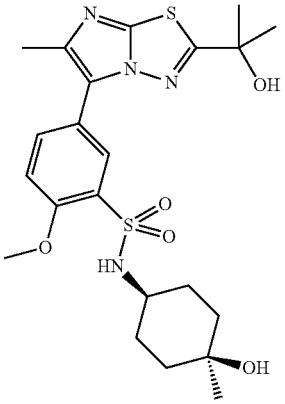 [SMILES: COc1ccc(-c2c(C)nc3sc(C(C)(C)O)nn23)cc1S(=O)(=O)N[C@H]1CC[C@@](C)(O)CC1]
TABLE 6
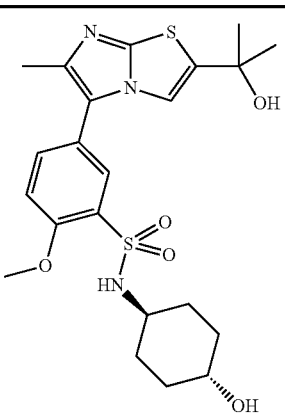
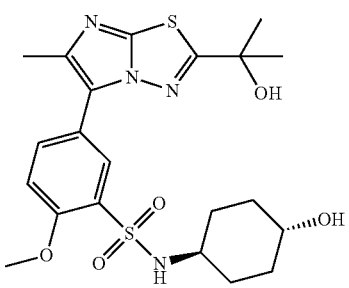
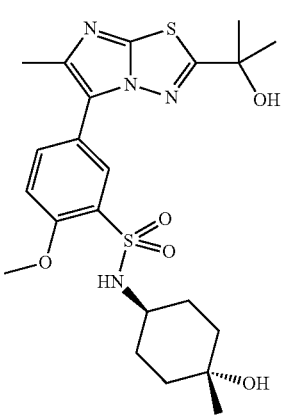 [SMILES: COc1ccc(-c2c(C)nc3sc(C(C)(C)O)nn23)cc1S(=O)(=O)N[C@H]1CC[C@](C)(O)CC1]

TABLE 6-continued
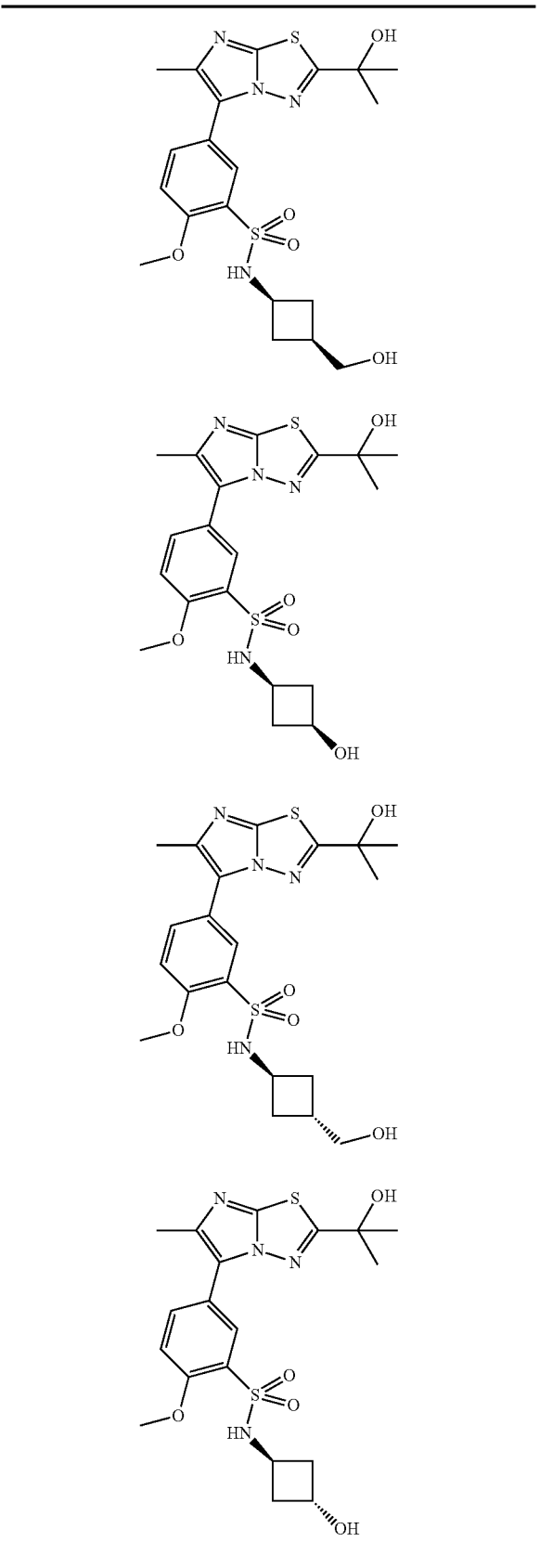
TABLE 6-continued
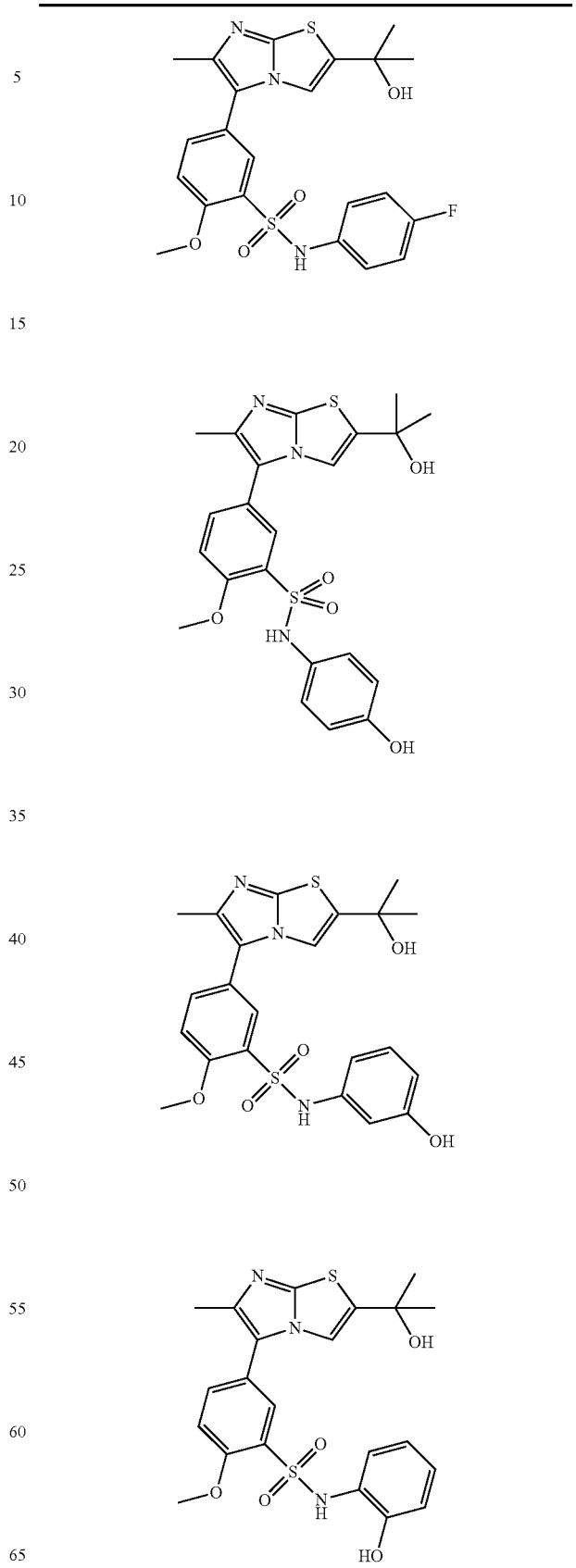

TABLE 6-continued
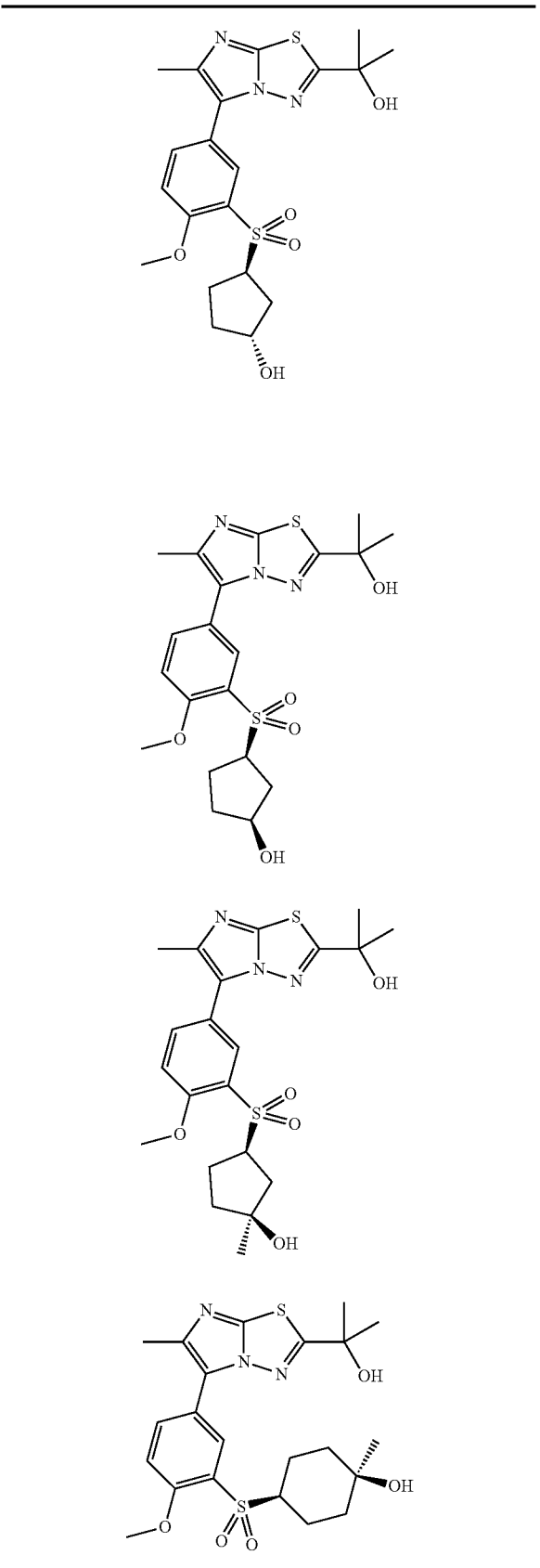
TABLE 6-continued
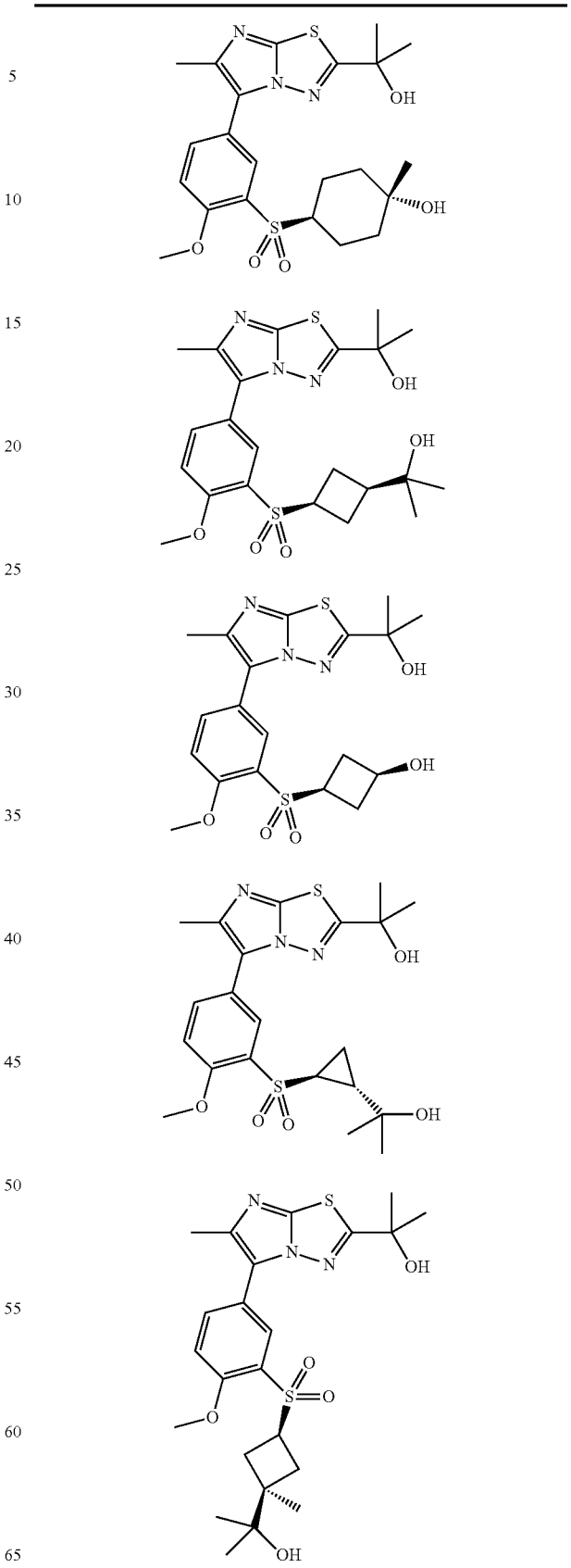

TABLE 7
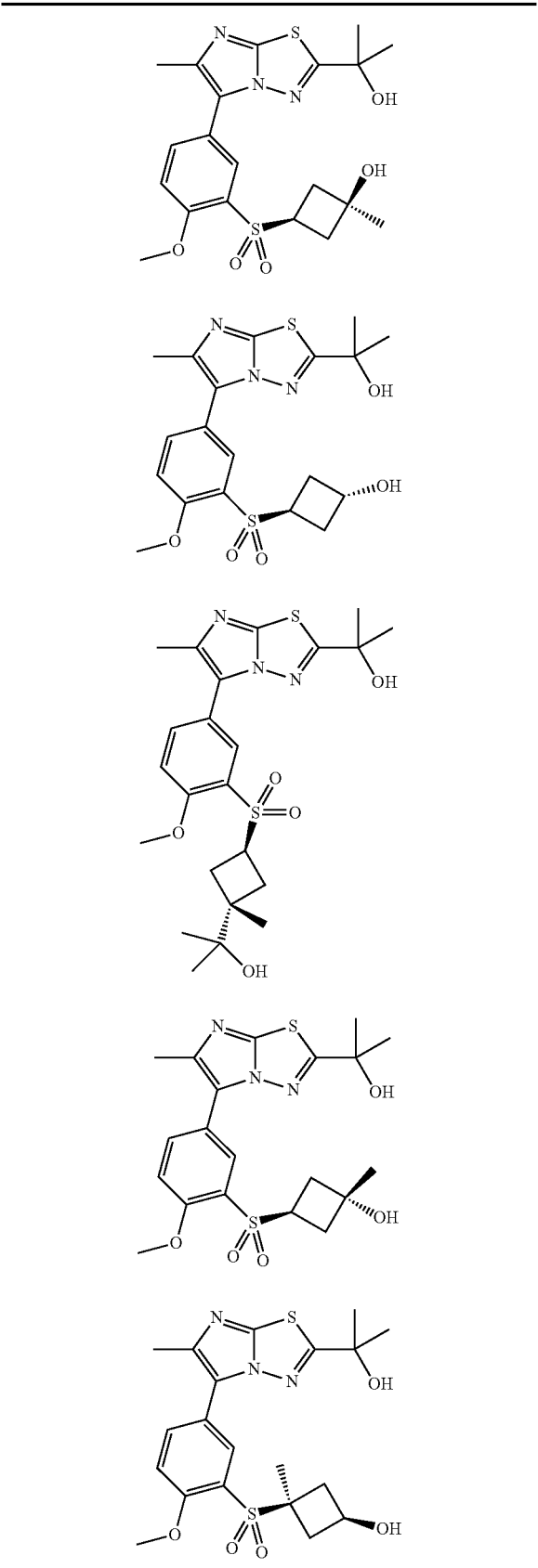
TABLE 7-continued
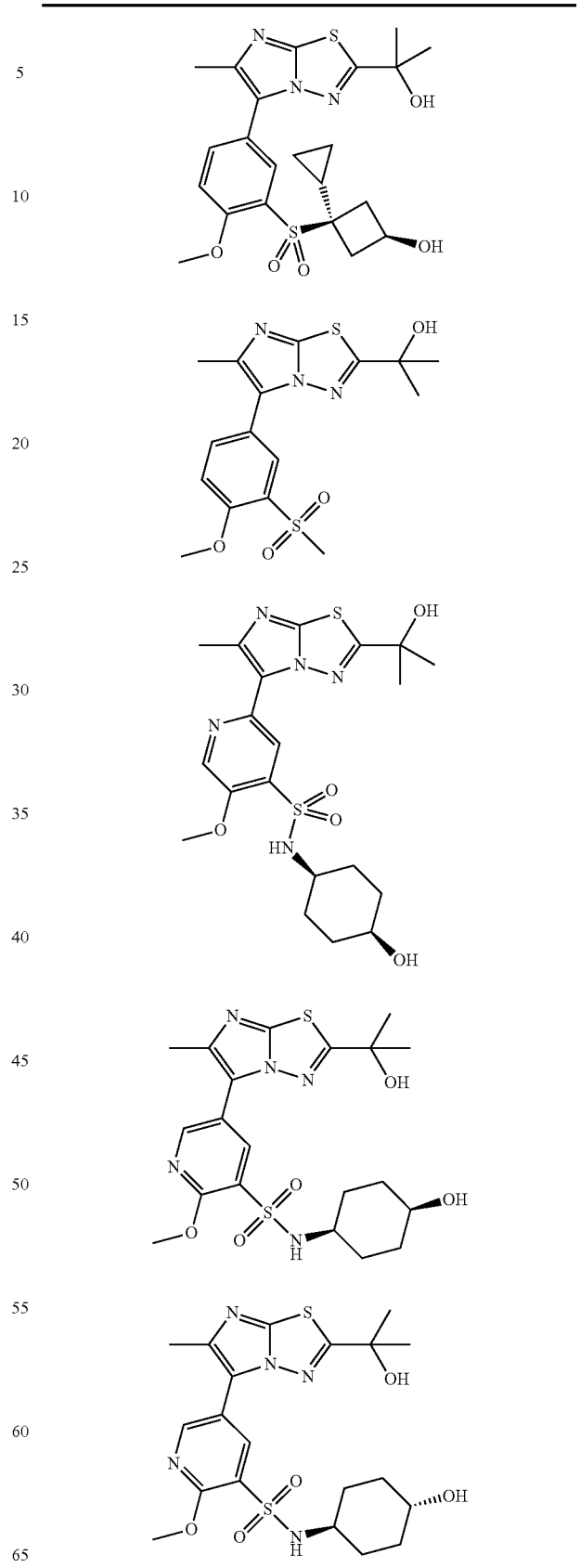

TABLE 7-continued
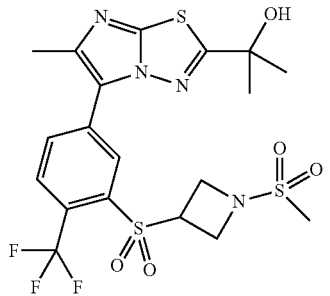 [SMILES: Cc1nc2sc(C(C)(C)O)nn2c1-c1ccc(C(F)(F)F)c(S(=O)(=O)C2CN(S(C)(=O)=O)C2)c1]
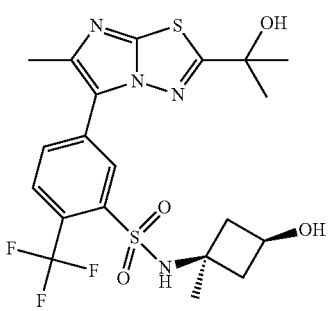 [SMILES: Cc1nc2sc(C(C)(C)O)nn2c1-c1ccc(C(F)(F)F)c(S(=O)(=O)N[C@]2(C)C[C@H](O)C2)c1]
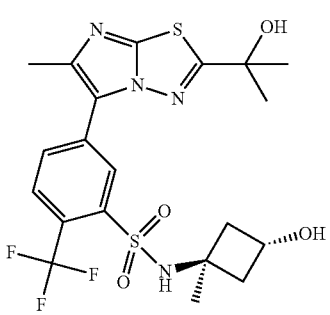 [SMILES: Cc1nc2sc(C(C)(C)O)nn2c1-c1ccc(C(F)(F)F)c(S(=O)(=O)N[C@]2(C)C[C@@H](O)C2)c1]
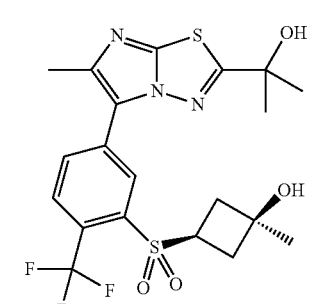
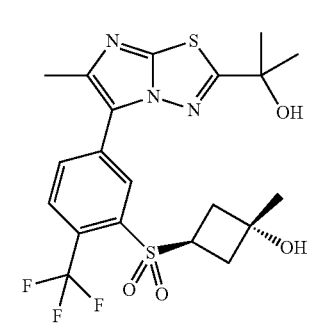 [SMILES: Cc1nc2sc(C(C)(C)O)nn2c1-c1ccc(C(F)(F)F)c(S(=O)(=O)[C@H]2C[C@](C)(O)C2)c1]
TABLE 7-continued
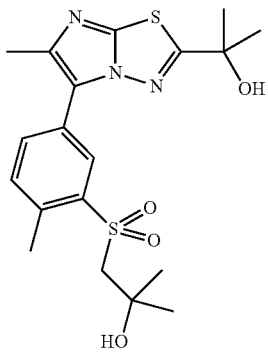 [SMILES: Cc1ccc(-c2c(C)nc3sc(C(C)(C)O)nn23)cc1S(=O)(=O)CC(C)(C)O]
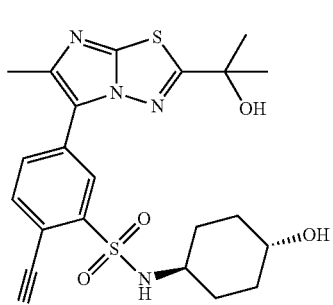
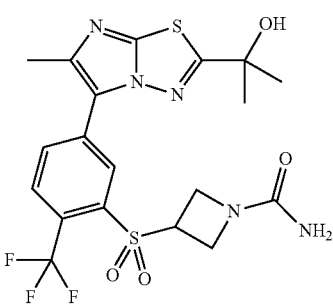 [SMILES: Cc1nc2sc(C(C)(C)O)nn2c1-c1ccc(C(F)(F)F)c(S(=O)(=O)C2CN(C(N)=O)C2)c1]
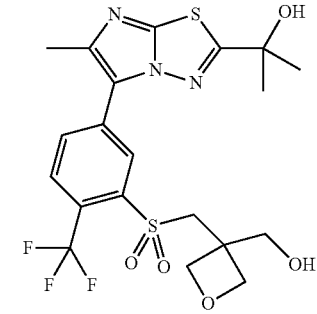 [SMILES: Cc1nc2sc(C(C)(C)O)nn2c1-c1ccc(C(F)(F)F)c(S(=O)(=O)CC2(CO)COC2)c1]
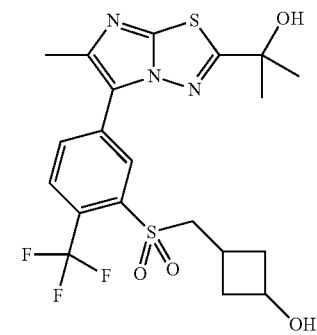 [SMILES: Cc1nc2sc(C(C)(C)O)nn2c1-c1ccc(C(F)(F)F)c(S(=O)(=O)CC2CC(O)C2)c1]

TABLE 7-continued
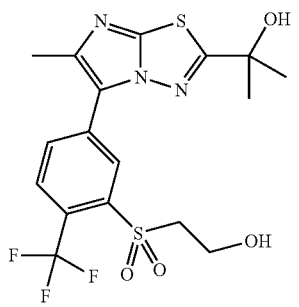 [SMILES: Cc1nc2sc(C(C)(C)O)nn2c1-c1ccc(C(F)(F)F)c(S(=O)(=O)CCO)c1]
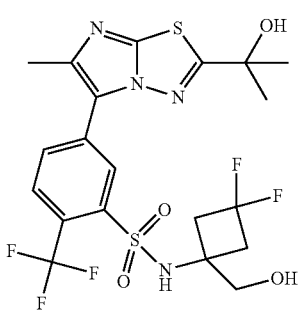 [SMILES: Cc1nc2sc(C(C)(C)O)nn2c1-c1ccc(C(F)(F)F)c(S(=O)(=O)NC2(CO)CC(F)(F)C2)c1]
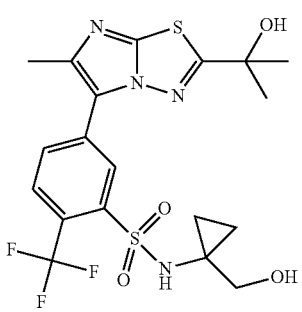 [SMILES: Cc1nc2sc(C(C)(C)O)nn2c1-c1ccc(C(F)(F)F)c(S(=O)(=O)NC2(CO)CC2)c1]
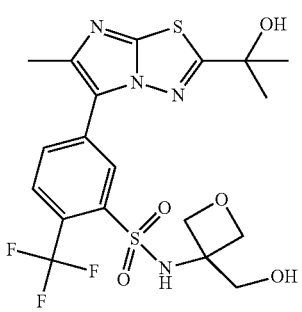 [SMILES: Cc1nc2sc(C(C)(C)O)nn2c1-c1ccc(C(F)(F)F)c(S(=O)(=O)NC2(CO)COC2)c1]
TABLE 8
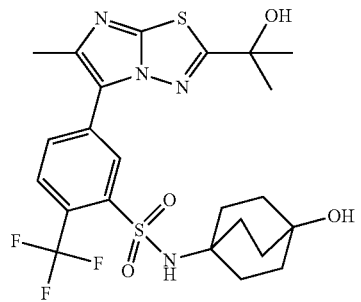 [SMILES: Cc1nc2sc(C(C)(C)O)nn2c1-c1ccc(C(F)(F)F)c(S(=O)(=O)NC23CCC(O)(CC2)CC3)c1]
TABLE 8-continued
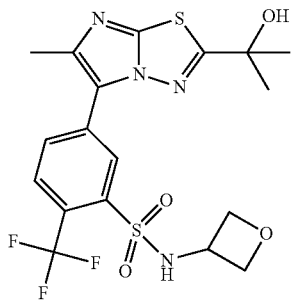 [SMILES: Cc1nc2sc(C(C)(C)O)nn2c1-c1ccc(C(F)(F)F)c(S(=O)(=O)NC2COC2)c1]
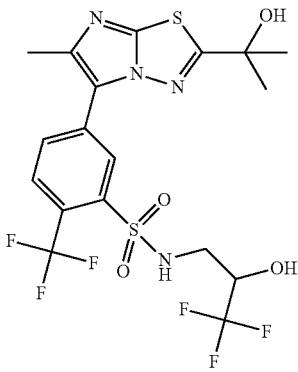 [SMILES: Cc1nc2sc(C(C)(C)O)nn2c1-c1ccc(C(F)(F)F)c(S(=O)(=O)NCC(O)C(F)(F)F)c1]
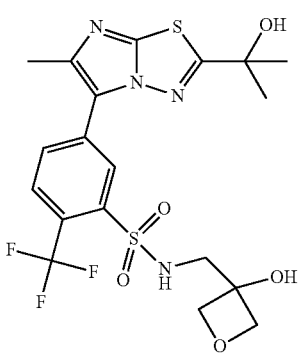 [SMILES: Cc1nc2sc(C(C)(C)O)nn2c1-c1ccc(C(F)(F)F)c(S(=O)(=O)NCC2(O)COC2)c1]
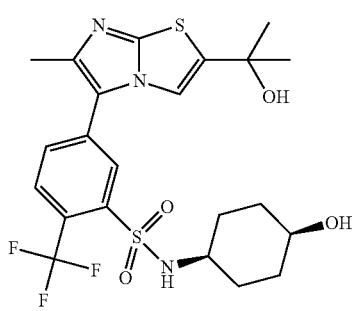 [SMILES: Cc1nc2sc(C(C)(C)O)cn2c1-c1ccc(C(F)(F)F)c(S(=O)(=O)N[C@H]2CC[C@@H](O)CC2)c1]
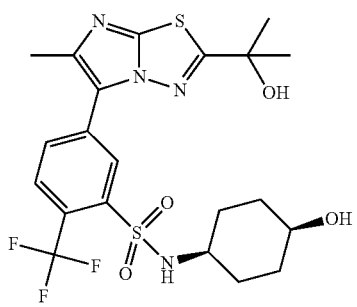 [SMILES: Cc1nc2sc(C(C)(C)O)nn2c1-c1ccc(C(F)(F)F)c(S(=O)(=O)N[C@H]2CC[C@@H](O)CC2)c1]

TABLE 8-continued

TABLE 8-continued
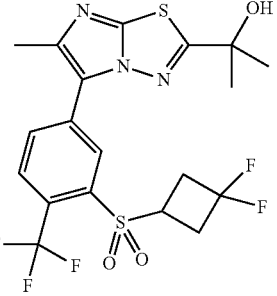
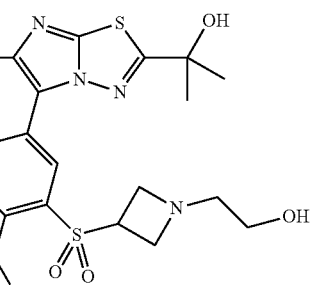
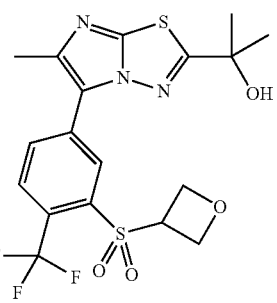
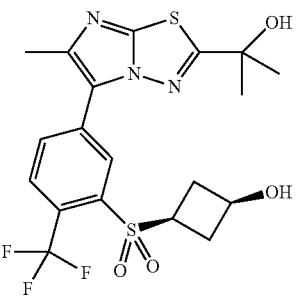 [SMILES: Cc1nc2sc(C(C)(C)O)nn2c1-c1ccc(C(F)(F)F)c(S(=O)(=O)[C@H]2C[C@@H](O)C2)c1]
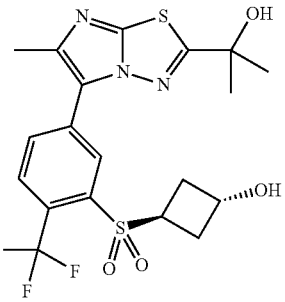
TABLE 8-continued
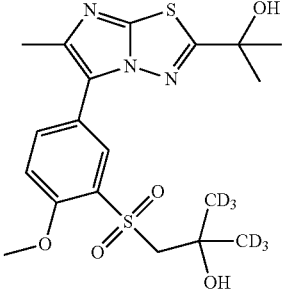 [SMILES: [2H]C([2H])([2H])C(O)(CS(=O)(=O)c1cc(-c2c(C)nc3sc(C(C)(C)O)nn23)ccc1OC)C([2H])([2H])[2H]]
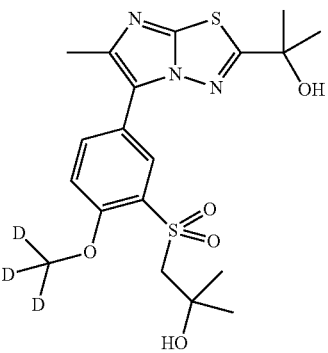 [SMILES: [2H]C([2H])([2H])Oc1ccc(-c2c(C)nc3sc(C(C)(C)O)nn23)cc1S(=O)(=O)CC(C)(C)O]
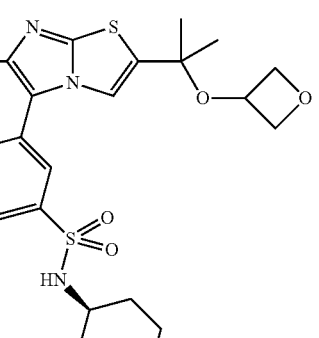
TABLE 9
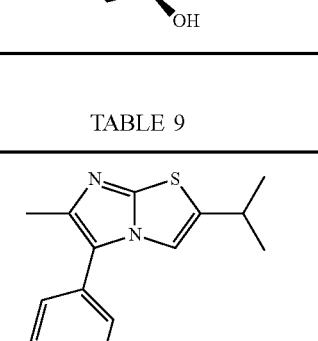

TABLE 9-continued
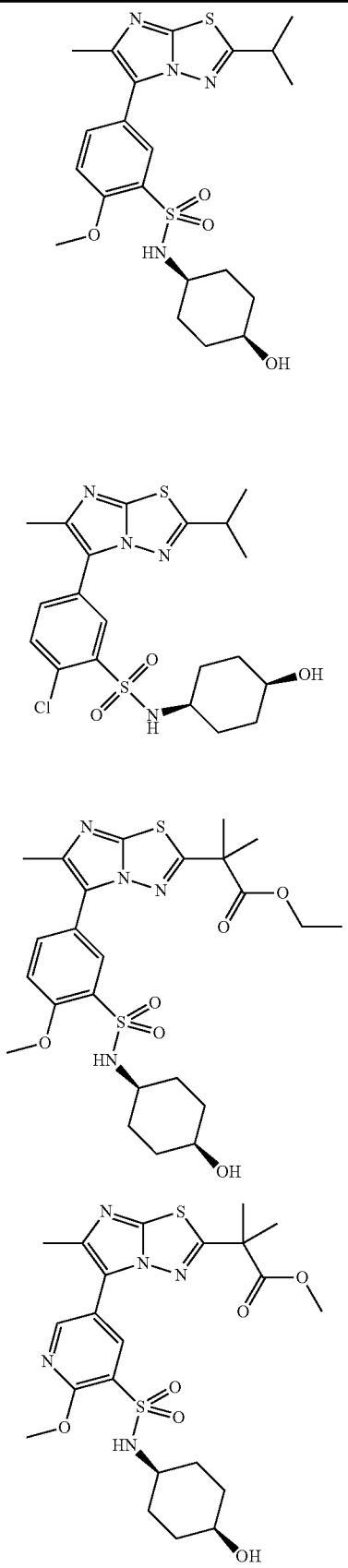
TABLE 9-continued
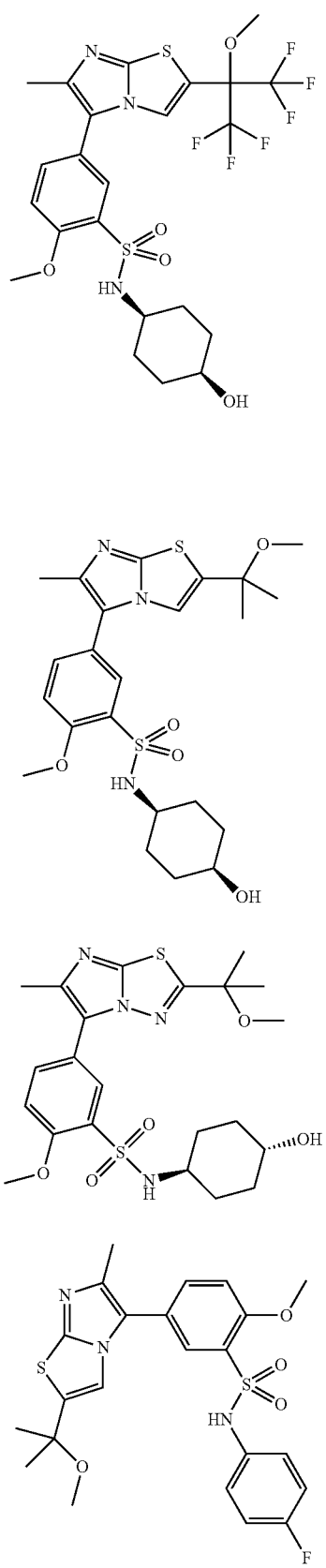

TABLE 9-continued
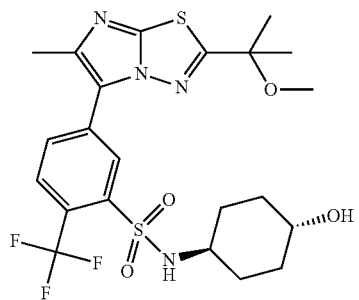 [SMILES: COC(C)(C)c1nn2c(-c3ccc(C(F)(F)F)c(S(=O)(=O)N[C@H]4CC[C@H](O)CC4)c3)c(C)nc2s1]
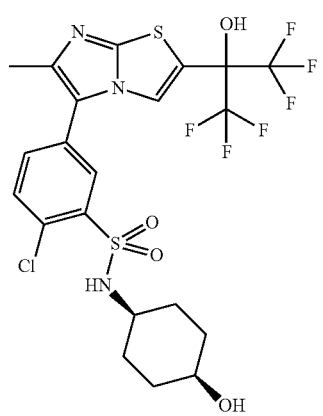 [SMILES: Cc1nc2sc(C(O)(C(F)(F)F)C(F)(F)F)cn2c1-c1ccc(Cl)c(S(=O)(=O)N[C@H]2CC[C@@H](O)CC2)c1]
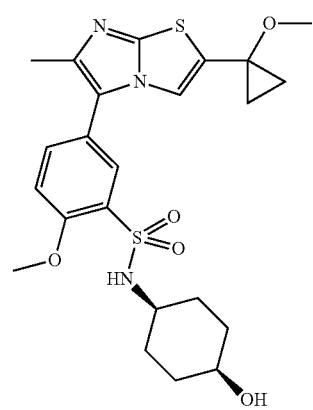
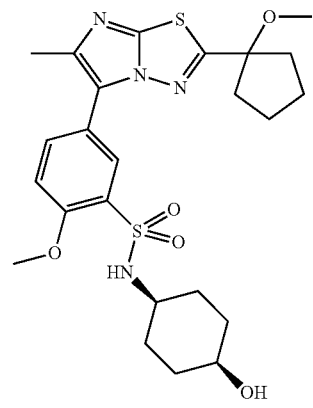
TABLE 9-continued
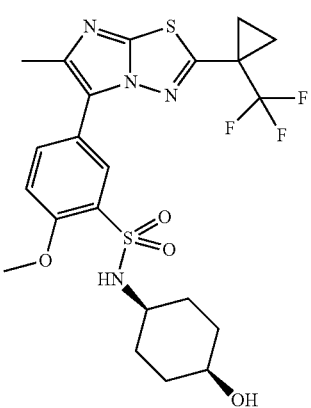 [SMILES: COc1ccc(-c2c(C)nc3sc(C4(C(F)(F)F)CC4)nn23)cc1S(=O)(=O)N[C@H]1CC[C@@H](O)CC1]
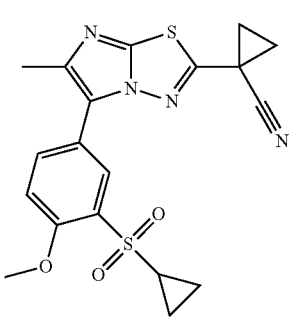 [SMILES: COc1ccc(-c2c(C)nc3sc(C4(C#N)CC4)nn23)cc1S(=O)(=O)C1CC1]
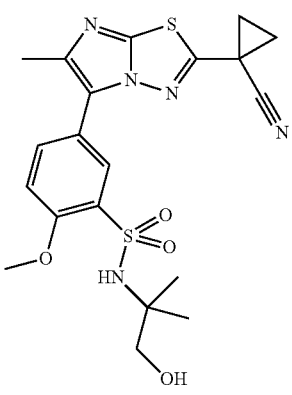 [SMILES: COc1ccc(-c2c(C)nc3sc(C4(C#N)CC4)nn23)cc1S(=O)(=O)NC(C)(C)CO]
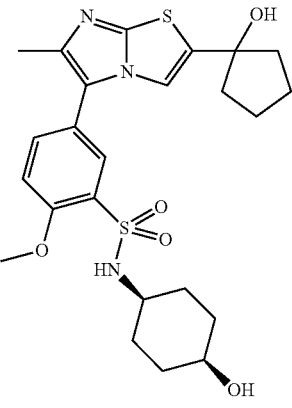 [SMILES: COc1ccc(-c2c(C)nc3sc(C4(O)CCCC4)cn23)cc1S(=O)(=O)N[C@H]1CC[C@@H](O)CC1]

TABLE 9-continued
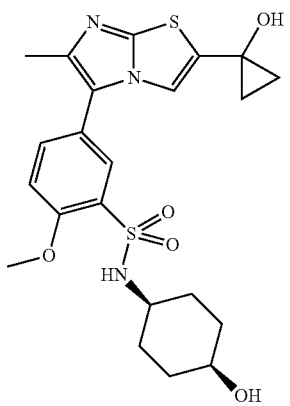 [SMILES: COc1ccc(-c2c(C)nc3sc(C4(O)CC4)cn23)cc1S(=O)(=O)N[C@H]1CC[C@@H](O)CC1]
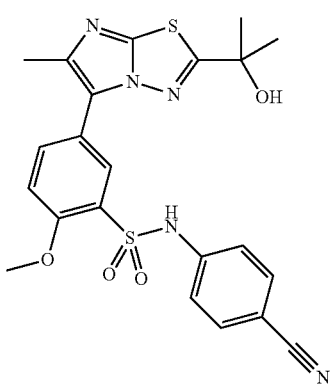 [SMILES: COc1ccc(-c2c(C)nc3sc(C(C)(C)O)nn23)cc1S(=O)(=O)Nc1ccc(C#N)cc1]
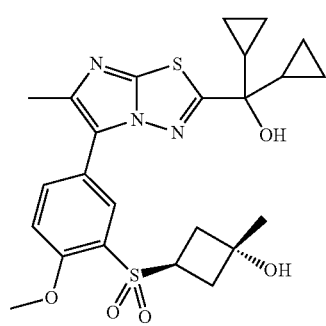 [SMILES: COc1ccc(-c2c(C)nc3sc(C(O)(C4CC4)C4CC4)nn23)cc1S(=O)(=O)[C@H]1C[C@](C)(O)C1]
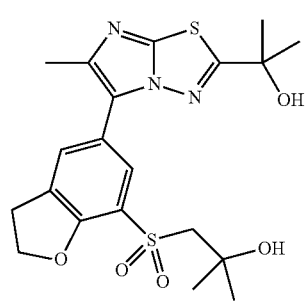 [SMILES: Cc1nc2sc(C(C)(C)O)nn2c1-c1cc2c(c(S(=O)(=O)CC(C)(C)O)c1)OCC2]
TABLE 9-continued
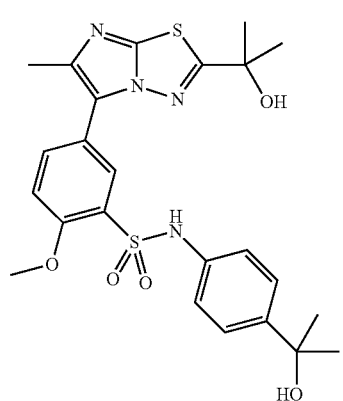 [SMILES: COc1ccc(-c2c(C)nc3sc(C(C)(C)O)nn23)cc1S(=O)(=O)Nc1ccc(C(C)(C)O)cc1]
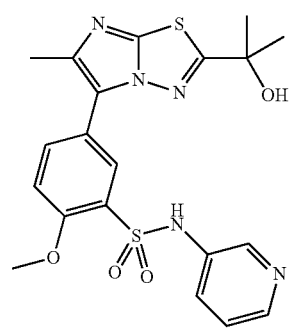 [SMILES: COc1ccc(-c2c(C)nc3sc(C(C)(C)O)nn23)cc1S(=O)(=O)Nc1cccnc1]
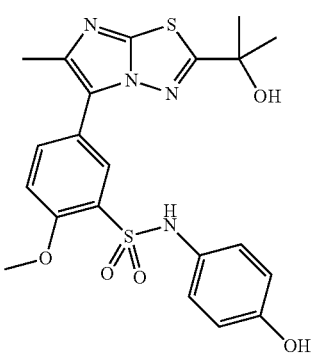 [SMILES: COc1ccc(-c2c(C)nc3sc(C(C)(C)O)nn23)cc1S(=O)(=O)Nc1ccc(O)cc1]
TABLE 10
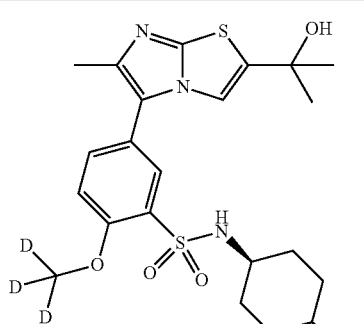

TABLE 10-continued
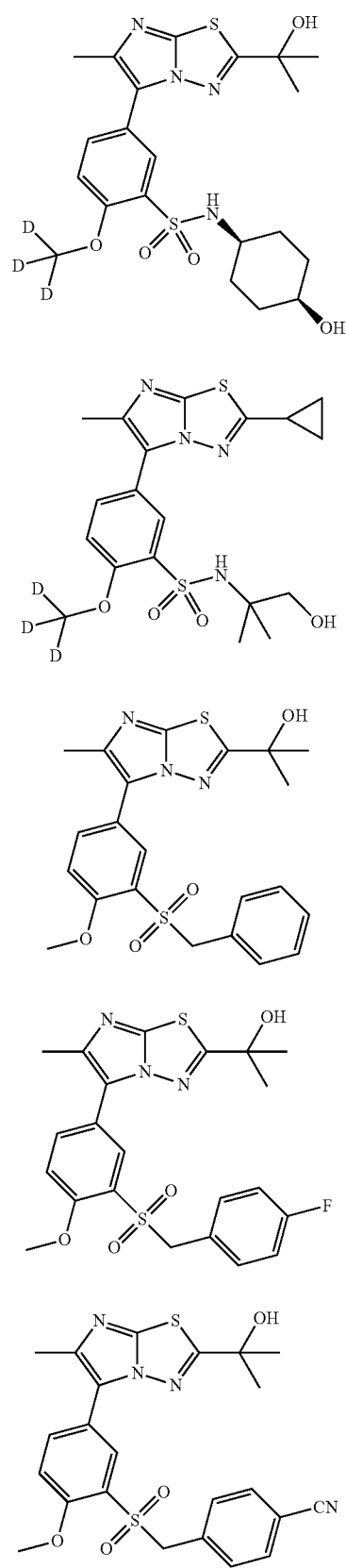
TABLE 10-continued
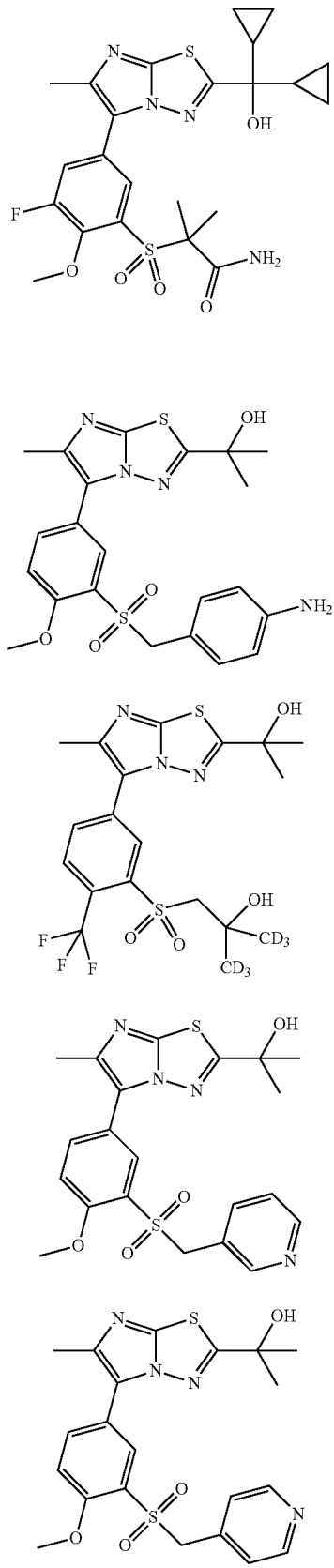

TABLE 10-continued
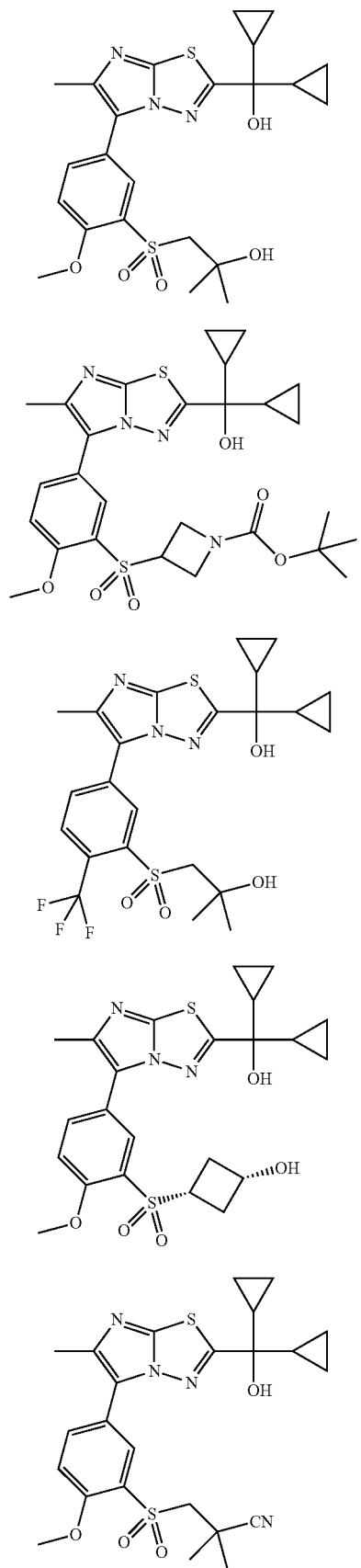
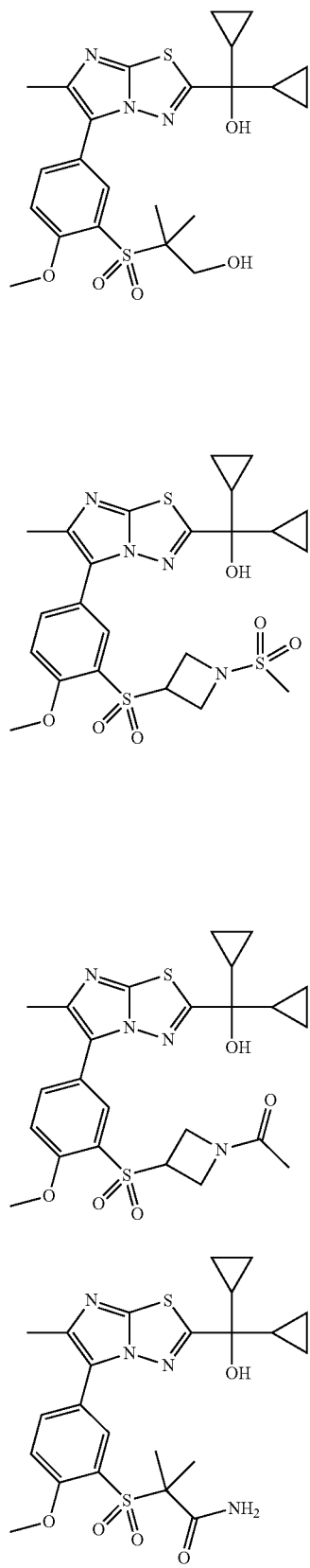

TABLE 10-continued
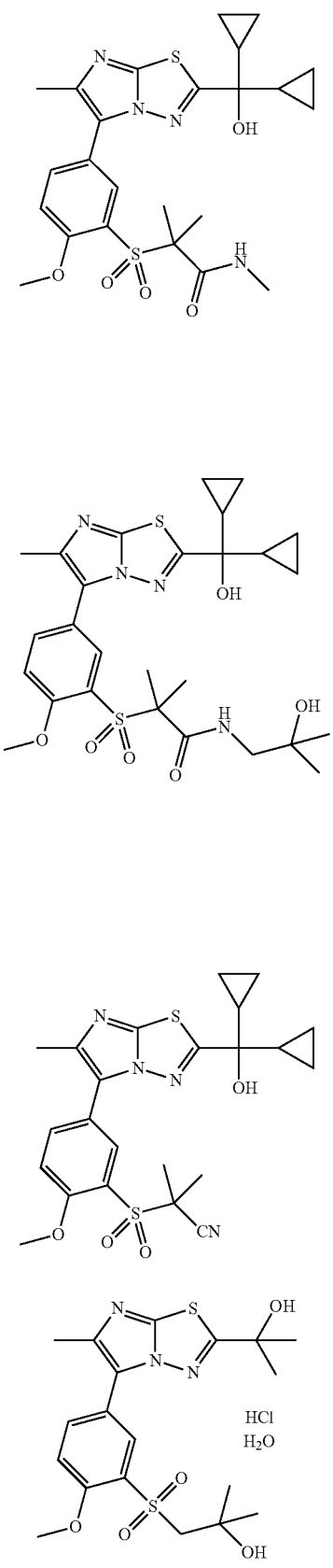
TABLE 11
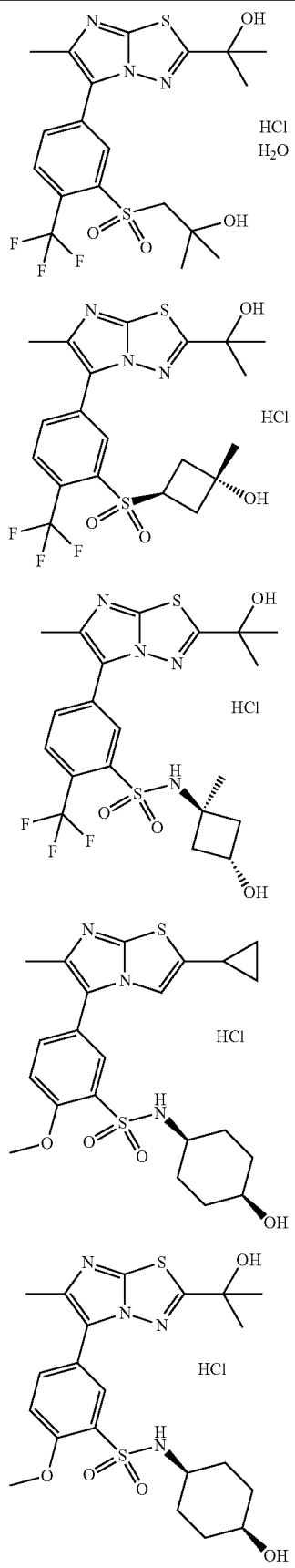

TABLE 11-continued

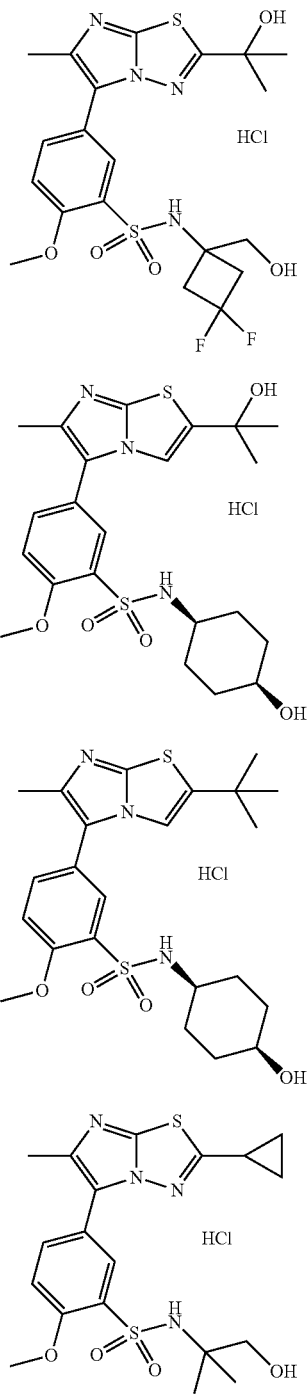

[11] A pharmacologically acceptable salt of the compound according to any one of [1] to [10] or a hydrate of the compound according to any one of [1] to [10] or a pharmacologically acceptable salt thereof.

[12] A medicament comprising the compound according to any one of [1] to [11] as an active ingredient.

[13] An antiviral agent against a virus belonging to the family Picornaviridae, comprising the compound according to any one of [1] to [11] as an active ingredient.

[14] A method for treating or preventing a viral infection caused by an enterovirus, a rhinovirus, or a coxsackievirus, comprising administering the compound according to any one of [1] to [11].

[15] Use of the compound according to any one of [1] to [11], for manufacturing a medicament for treating or preventing a viral infection caused by an enterovirus, a rhinovirus, or a coxsackievirus.

[16] A pharmaceutical composition comprising the compound according to any one of [1] to [11] and a pharmaceutically acceptable carrier, for use in the treatment or prevention of a viral infection caused by an enterovirus, a rhinovirus, or a coxsackievirus.

[17] A method for treating or preventing exacerbation of asthma or COPD, comprising administering the compound according to any one of [1] to [11].

[18] Use of the compound according to any one of [1] to [11] for manufacturing a medicament for treating or preventing exacerbation of asthma or COPD.

[19] A pharmaceutical composition comprising the compound according to any one of [1] to [11] and a pharmaceutically acceptable carrier, for use in the treatment or prevention of exacerbation of asthma or COPD.

Advantageous Effects of Invention

The present invention can provide compounds having an antiviral action against viruses belonging to the family Picornaviridae, particularly rhinovirus.

DESCRIPTION OF EMBODIMENTS

The terms as used herein will be now described.

The term "$C_n$-$C_m$" as used herein means the number of carbon atoms from n to m, wherein each of n and m is a natural number independent from each other, and m is larger than n. For example, "$C_1$-$C_6$" means from 1 to 6 carbon atoms.

The term "halogen atom" as used herein means a fluorine, chlorine, bromine, or iodine atom. Preferably, the halogen atom is a fluorine or chlorine atom.

The term "alkyl group" as used herein means a group in which one hydrogen atom is eliminated from a linear or branched, saturated aliphatic hydrocarbon. Examples of alkyl groups include, for example, methyl, ethyl, 1-propyl, isopropyl, 1-butyl, isobutyl, sec-butyl, t-butyl, 1-pentyl, isopentyl, neopentyl, 1-methylbutyl, 2-methylbutyl, 1,2-dimethylpropyl, 1-hexyl, and isohexyl groups.

The term "deuterated $C_1$-$C_6$ alkyl group" as used herein means the "alkyl group" as described above having from 1 to 6 carbon atoms, wherein any hydrogen atom is substituted with one or more deuterium atoms.

The term "alkylene group" as used herein refers to a bivalent group obtained by eliminating any one of hydrogen atoms from the "alkyl group" as described above. Specific examples include methanediyl, 1,1-ethanediyl, 1,2-ethanediyl, 1,1-propanediyl, 1,2-propanediyl, 1,3-propanediyl, 2,2-propanediyl, 1,4-butanediyl, 2-methyl-1,1-propanediyl, 2-methyl-1,2-propanediyl, 1,5-pentanediyl, 3-methyl-1,3-butanediyl, and 1,6-hexanediyl groups.

The term "hydroxy$C_1$-$C_6$ alkyl group" as used herein means the alkyl group as described above wherein one hydrogen atom of an alkyl group having from 1 to 6 carbon atoms is substituted with a hydroxy group. Examples of hydroxy$C_1$-$C_6$ alkyl groups include, for example, hydroxymethyl, 1-hydroxyethyl, 1-hydroxy-1,1-dimethylmethyl, 2-hydroxyethyl, 2-hydroxy-2-methylpropyl, and 3-hydroxypropyl groups.

The term "hydroxyC$_1$-C$_6$ alkylene group" as used herein refers to a bivalent group obtained by eliminating any one of hydrogen atoms from the "hydroxyC$_1$-C$_6$ alkyl group" as described above. Examples of hydroxyC$_1$-C$_6$ alkylene groups include, for example, hydroxymethylene, 1-hydroxyethylene, 1-hydroxy-1,1-dimethylmethylene, 2-hydroxyethylene, 2-hydroxy-2-methylpropylene, and 3-hydroxypropylene groups.

The term "alkoxy group" as used herein means a linear or branched alkyl group attached to an oxygen atom. Examples of alkoxy groups include, for example, methoxy, ethoxy, 1-propoxy, isopropoxy, isobutoxy, 1-butoxy, sec-butoxy, t-butoxy, 1-pentyloxy, and 1-hexyloxy groups.

The term "deuterated C$_1$-C$_6$ alkoxy group" as used herein means the "alkoxy group" as described above having from 1 to 6 carbon atoms, wherein any hydrogen atom is substituted with one or more deuterium atoms.

The term "cycloalkyl group" as used herein means a monocyclic or bicyclic saturated cycloaliphatic hydrocarbon group. Examples of cycloalkyl groups include, for example, cyclopropyl, cyclobutyl, cyclopentyl, cyclohexyl, spiroheptyl, spirooctyl, and octahydropentalenyl groups.

The term "cycloalkoxy group" as used herein means the "cycloalkyl group" as described above that is attached to an oxygen atom. Examples of cycloalkoxy groups include, for example, cyclopropyloxy, cyclobutyloxy, cyclopentyloxy, and cyclohexyloxy groups.

The term "cycloalkylene group" as used herein means a bivalent group obtained by eliminating any one of hydrogen atoms from the "cycloalkyl group" as described above. Examples of cycloalkylene groups include, for example, cyclopropylene, cyclobutylene, cyclopentylene, and cyclohexylene groups.

The term "alkenyl group" as used herein means a linear or branched hydrocarbon group having an unsaturated bond. Examples of alkenyl groups include vinyl, 1-propenyl, 2-propenyl, 2-methylethenyl, 1-butenyl, 2-butenyl, 3-butenyl, 1-pentenyl, 2-pentenyl, 3-pentenyl, 4-pentenyl, 3-methyl-1-butenyl, 3-methyl-2-butenyl, 3-methyl-3-butenyl, 1-hexenyl, 2-hexenyl, 3-hexenyl, 4-hexenyl, and 5-hexenyl groups.

The term "acyl group" as used herein means an acyl group derived from a linear or branched aliphatic carboxylic acid. Examples of acyl groups include, for example, formyl, acetyl, propanoyl, butanoyl, pentanoyl, and hexanoyl groups.

The term "alkoxycarbonyl group" as used herein means a linear or branched alkoxycarbonyl group. Examples of alkoxycarbonyl groups include, for example, methoxycarbonyl, ethoxycarbonyl, 1-propoxycarbonyl, isopropoxycarbonyl, isobutoxycarbonyl, 1-butoxycarbonyl, sec-butoxycarbonyl, t-butoxycarbonyl, 1-pentyloxycarbonyl, and 1-hexyloxycarbonyl groups.

The term "bicycloalkyl group" as used herein means a saturated cycloaliphatic hydrocarbon group having from 5 to 8 carbon atoms wherein two carbon atoms of cycloalkyl that are not adjacent to each other are crosslinked by C$_1$ or C$_2$. Examples of bicycloalkyl groups include, for example, bicyclo[1.1.1]pentyl, bicyclo[2.1.1]hexyl, bicyclo[2.2.1]heptyl, and bicyclo[2.2.2]octyl groups.

The term "bicycloalkylene group" as used herein refers to a bivalent group obtained by eliminating any one of hydrogen atoms from the "bicycloalkyl group" as described above. Specific examples of bicycloalkylene groups include bicyclo[1.1.1]pentylene, bicyclo[2.1.1]hexylene, bicyclo[2.2.1]heptylene, and bicyclo[2.2.2]octylene groups.

The term "3- to 10-membered heterocycloalkyl group" as used herein means a 3-, 4-, 5-, 6-, 7-, 8-, 9-, or 10-membered monocyclic, bicyclic, or tricyclic saturated heterocycloalkyl group having endocyclic heteroatoms from 1 to 4 independently selected from the group consisting of N, N-oxide, O, S, SO, and SO$_2$. Examples of 3- to 10-membered heterocycloalkyl groups include, for example, aziridinyl, oxiranyl, azetidinyl, oxetanyl, pyrrolidinyl, piperidinyl, piperazinyl, morpholinyl, thiomorpholinyl, thiazepanyl, diazepanyl, oxazocanyl, octahydroindolyl, decahydroquinolyl, azaspiroheptyl, oxaazaspiroheptyl, oxaazaspirooctyl, and oxaazaspirononyl groups.

The term "3- to 10-membered heterocycloalkyloxy group" as used herein means the "3- to 10-membered heterocycloalkyl group" as described above that is attached to an oxygen atom. Examples of 3- to 10-membered heterocycloalkyloxy groups include, for example, aziridinyloxy and azetidinyloxy groups.

The term "phenylene group" as used herein means a bivalent group obtained by eliminating any one of hydrogen atoms from a phenyl group.

The term "heteroaryl group" as used herein means a stable 5- to 14-membered heteroaryl group that is partially or fully unsaturated and has carbon atoms and 1, 2, 3, or 4 heteroatoms independently selected from the group consisting of N, O and S, wherein the nitrogen and sulfur atoms may be oxidized if desired. In other words, N→O and S(O)p may occur, wherein p is 1 or 2. A nitrogen atom may be substituted. In other words, a nitrogen atom may be N or NR, wherein R can be defined as H; —C(O) R$^9$; —C(O)NR$^{10}$R$^{11}$; or a C$_1$-C$_6$ alkyl group, wherein the alkyl group is optionally substituted with one or more substituents selected from the group consisting of a halogen atom, a hydroxy group, a C$_1$-C$_6$ alkoxy group, a haloC$_1$-C$_6$ alkyl group, a cyano group, a C$_3$-C$_{10}$ cycloalkyl group, a 3- to 10-membered heterocycloalkyl group, a C$_3$-C$_{10}$ cycloalkyloxy group, a 3- to 10-membered heterocycloalkyloxy group, —C(O)R$^9$, and —C(O)NR$^{10}$R$^{11}$. Examples of heteroaryl groups include, but not limited to, benzimidazolyl, benzofuranyl, benzothiofuranyl, benzothiophenyl, benzooxazolyl, benzoxazolinyl, benzthiazolyl, benztriazolyl, benztetrazolyl, benzisoxazolyl, benzoisothiazolyl, benzimidazolinyl, furanyl, imidazolidinyl, imidazolinyl, imidazolyl, 1H-indazolyl, imidazolopyridinyl, indolenyl, indolinyl, indolizinyl, indolyl, 3H-indolyl, isobenzofuranyl, isoindazolyl, isoindolinyl, isoindolyl, isoquinolinyl, isothiazolyl, isothiazolopyridinyl, isoxazolyl, isoxazolopyridinyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxyindolyl, pyrimidinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl groups.

The term "heteroarylene group" as used herein means a bivalent group obtained by eliminating any one of hydrogen atoms from a heteroaryl group The term "3- to 10-membered heterocycloalkylene group" as used herein means a bivalent group that is obtained by eliminating any one of hydrogen atoms from the "3- to 10-membered heterocycloalkyl group" as described above.

The term "3- to 10-membered heterocycloalkyloxy group" as used herein means the "3- to 10-membered heterocycloalkyl group" as described above that is attached to an oxygen atom. Examples of 3- to 10-membered heterocycloalkyloxy groups include the following functional groups:

[Formula 2]

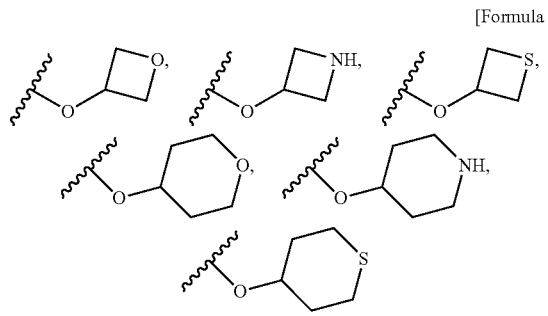

The term "haloC$_1$-C$_6$ alkyl group" as used herein means the alkyl group as described above having from 1 to 6 carbon atoms, wherein hydrogen atom(s) of the alkyl group is substituted with 1 to 8 halogen atoms which may be the same or different. Examples of haloC$_1$-C$_6$ alkyl groups include, for example, fluoromethyl, difluoromethyl, trifluoromethyl, 2-fluoroethyl, 2-chloroethyl, 2,2-difluoroethyl, 1,1-difluoroethyl, 1,2-difluoroethyl, 1-chloro-2-fluoroethyl, 2,2,2-trifluoroethyl, 1,1,2,2,2-pentafluoroethyl, 2,2,2-trichloroethyl, 3-fluoropropyl, 2-fluoropropyl, 1-fluoropropyl, 3,3-difluoropropyl, 2,2-difluoropropyl, 1,1-difluoropropyl, 4-fluorobutyl, 5-fluoropentyl, and 6-fluorohexyl groups.

The term "haloC$_1$-C$_6$alkoxy group" as used herein means the alkoxy group as described above, wherein hydrogen atom(s) of an alkyl group having from 1 to 6 carbon atoms is substituted with 1 to 8 halogen atoms which may be the same or different. Examples of haloC$_1$-C$_6$ alkoxy groups include, for example, monofluoromethoxy, difluoromethoxy, trifluoromethoxy, 2-chloroethoxy, 2-fluoroethoxy, 2,2-difluoroethoxy, 1,1-difluoroethoxy, 1,2-difluoroethoxy, 1-chloro-2-fluoroethoxy, 2,2,2-trifluoroethoxy, 1,1,2,2,2-pentafluoroethoxy, 2,2,2-trichloroethoxy, 3-fluoropropoxy, 2-fluoropropoxy, 1-fluoropropoxy, 3,3-difluoropropoxy, 2,2-difluoropropoxy, 1,1-difluoropropoxy, 4-fluorobutoxy, 5-fluoropentyloxy, and 6-fluorohexyloxy groups.

The term "phenylmethyl group" as used herein means a phenyl group directly attached to a methylene group.

The term "heteroarylmethyl group" as used herein means a group in which one hydrogen atom of a methyl group is substituted with the heteroaryl group as defined above.

Groups acceptable as a "substituent" in the "phenylmethyl group optionally having a substituent", "heteroarylmethyl group optionally having a substituent", "phenyl group optionally having a substituent", "heteroaryl group optionally having a substituent", "C$_1$-C$_6$ alkyl group optionally having a substituent", "deuterated C$_1$-C$_6$ alkyl group optionally having a substituent", "C$_2$-C$_6$ alkenyl group optionally having a substituent", "C$_3$-C$_6$ cycloalkyl group optionally having a substituent", "C$_5$-C$_8$ bicycloalkyl group optionally having a substituent", "3- to 10-membered heterocycloalkyl group optionally having a substituent", "hydroxyC$_1$-C$_6$ alkyl group optionally having a substituent", and "C$_3$-C$_5$ cycloalkylene group optionally having a substituent" as used herein are not particularly limited as long as they are commonly known. One or more substituents may exist, and examples of substituents include, for example, a halogen atom, amino, hydroxy, cyano, nitro, carboxy, C$_1$-C$_6$ acyl, C$_1$-C$_6$ alkyl, haloC$_1$-C$_6$ alkyl, hydroxyC$_1$-C$_6$ alkyl, C$_1$-C$_6$ alkoxy, haloC$_1$-C$_6$alkoxy, C$_1$-C$_6$ alkoxycarbonyl, C$_3$-C$_6$ cycloalkyl, 3- to 10-membered heterocycloalkyl, phenyl, heteroaryl, t-butyldimethylsilyloxy, and oxo groups.

The phrase "joined together to form a ring" as used herein means joining of two moieties obtained by eliminating any one hydrogen atom from each of two substituents that will form a ring. For example, when a methylene group has two substituents that will form a ring and the two substituents are a methyl group and a 1-hydroxyethyl group, the following cyclic structures will be formed:

[Formula 3]

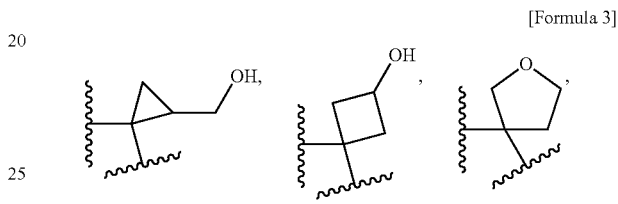

Embodiments of the present invention will be described in detail below.

In the description below, the definitions that have already described above are cited for functional groups in a general formula, and therefore, detailed description of the functional groups may be omitted. The definitions cited refer to ones explained in embodiments as described below.

Definitions for functional groups with the same symbol in the general formula are common in all general formulas having the same symbol as long as the definitions are not particularly mentioned.

The embodiments relate to a compound represented by General Formula (1) below or a pharmacologically acceptable salt thereof, or a hydrate thereof. These are also collectively referred to as compounds of the embodiments.

A compound represented by

[Formula 4]

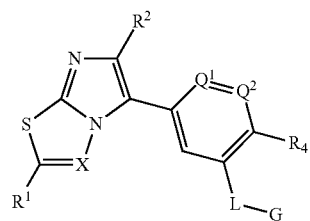

(1)

wherein
X represents N or CH;
Q$^1$ represents N or CH;
Q$^2$ represents N or CR$^3$;
L represents —SO$_2$—, —SO$_2$C(R$^8$)$_2$—, or —SO$_2$NR$^8$—;
R$^1$ represents H; a C$_1$-C$_6$ alkyl group, wherein the alkyl group is optionally substituted with one or more substituents selected from the group consisting of a halogen atom, a hydroxy group, a C$_1$-C$_6$ alkyl group, a C$_1$-C$_6$ alkoxy group, a haloC$_1$-C$_6$ alkyl group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)N$R^{10}R^{11}$; a $C_3$-$C_6$ cycloalkyl group, wherein the cycloalkyl group is optionally substituted with one or more substituents selected from the group consisting of a halo$C_1$-$C_6$ alkyl group, a $C_1$-$C_6$ alkoxy group, a hydroxy group, and a cyano group; or a $C_2$-$C_6$ alkenyl group, wherein the alkenyl group is optionally substituted with one or more substituents selected from the group consisting of a halogen atom, a $C_1$-$C_6$ alkoxy group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)N$R^{10}R^{11}$;

$R^2$ represents a $C_1$-$C_6$ alkyl group;

$R^3$ represents H; a $C_1$-$C_6$ alkyl group, wherein the alkyl group is optionally substituted with one or more substituents selected from the group consisting of a halogen atom, a hydroxy group, a $C_1$-$C_6$ alkoxy group, a halo$C_1$-$C_6$ alkyl group, a cyano group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)N$R^{10}R^{11}$; a hydroxy group; a $C_1$-$C_6$ alkoxy group; a halo$C_1$-$C_6$ alkyl group; a cyano group; a $C_3$-$C_{10}$ cycloalkyl group; a 3- to 10-membered heterocycloalkyl group; a $C_3$-$C_{10}$ cycloalkyloxy group; a 3- to 10-membered heterocycloalkyloxy group; —C(O)$R^9$; —C(O)N$R^{10}R^{11}$; or a halogen atom;

$R^4$ represents H, a halogen atom, a $C_1$-$C_6$ alkoxy group, a deuterated $C_1$-$C_6$ alkoxy group, a $C_1$-$C_6$ alkyl group, a halo$C_1$-$C_6$ alkyl group, a halo$C_1$-$C_6$ alkoxy group, a hydroxy$C_1$-$C_6$ alkyl group, a hydroxy group, a cyano group, —C(O) $R^9$, —C(O) N$R^{10}R^{11}$, or N$R^{10}R^{11}$;

when $Q^2$ is $CR^3$, $R^3$ and $R^4$ may be joined together to form a ring;

G represents —$R^5$—$R^6$—$R^7$; a hydroxy$C_1$-$C_6$ alkyl group, wherein the hydroxy$C_1$-$C_6$ alkyl group is optionally substituted with $W^1$ and $W^2$, wherein $W^1$ and $W^2$ are each independently selected from the group consisting of H, a $C_1$-$C_6$ alkyl group, a deuterated $C_1$-$C_6$ alkyl group, a halo$C_1$-$C_6$ alkyl group, and a hydroxy$C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkyl group, wherein the $C_3$-$C_6$ cycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a $C_5$-$C_8$ bicycloalkyl group, wherein the $C_5$-$C_8$ bicycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a 3- to 10-membered heterocycloalkyl group, wherein the 3- to 10-membered heterocycloalkyl group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, —C(O) N($R^{13}$)$_2$, and an oxo group, and $W^3$ and $W^4$ may be joined together to form a ring; a $C_1$-$C_6$ alkyl group, wherein the $C_1$-$C_6$ alkyl group is optionally substituted with $W^5$ and $W^6$, wherein $W^5$ and $W^6$ are each independently selected from the group consisting of H, a cyano group, a hydroxy$C_1$-$C_6$ alkyl group, a $C_1$-$C_6$ alkyl group, a $C_1$-$C_6$ alkoxycarbonyl group, a carboxy group, and —C(O)N($R^{13}$)$_2$, and $W^5$ and $W^6$ may be joined together to form a ring; a phenyl group, wherein the phenyl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —N$R^{10}R^{11}$, —C(O) $R^9$, —C(O)N$R^{10}R^{11}$, a $C_1$-$C_6$ alkoxycarbonyl group, —SO$_2R^{12}$, and a $C_1$-$C_6$ alkoxy group; or a heteroaryl group, wherein the heteroaryl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —N$R^{10}R^{11}$, —C(O) $R^9$, —C(O)N$R^{10}R^{11}$, a $C_1$-$C_6$ alkoxycarbonyl group, —SO$_2R^{12}$, and a $C_1$-$C_6$ alkoxy group;

$R^5$ represents a hydroxy$C_1$-$C_6$ alkylene group, wherein the hydroxy$C_1$-$C_6$ alkylene group is optionally substituted with $W^1$ and $W^2$, wherein $W^1$ and $W^2$ are each independently selected from the group consisting of H, a $C_1$-$C_6$ alkyl group, a deuterated $C_1$-$C_6$ alkyl group, a halo$C_1$-$C_6$ alkyl group, and a hydroxy$C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkylene group, wherein the $C_3$-$C_6$ cycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a $C_5$-$C_8$ bicycloalkylene group, wherein the $C_5$-$C_8$ bicycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, and an oxo group, and $W^3$ and $W^4$ may be joined together to form a ring; a 3- to 10-membered heterocycloalkylene group, wherein the 3- to 10-membered heterocycloalkylene group is optionally substituted with $W^3$ and $W^4$, wherein $W^3$ and $W^4$ are each independently selected from the group consisting of H, a halogen atom, a hydroxy group, a $C_1$-$C_6$ alkyl group, a $C_3$-$C_{10}$ cycloalkyl group, a $C_1$-$C_6$ acyl group, a hydroxy$C_1$-$C_6$ alkyl group, a $C_1$-$C_6$ alkoxy group, a $C_1$-$C_6$ alkoxycarbonyl group, —SO$_2R^{12}$, —C(O)N($R^{13}$)$_2$, and an oxo group, and $W^3$ and $W^4$ may be joined together to form a ring; a $C_1$-$C_6$ alkylene group, wherein the $C_1$-$C_6$ alkylene group is optionally substituted with $W^5$ and $W^6$, wherein $W^5$ and $W^6$ are each independently selected from the group consisting of H, a cyano group, a hydroxyC$_1$-C$_6$ alkyl group, a C$_1$-C$_6$ alkyl group, a C$_1$-C$_6$ alkoxycarbonyl group, a carboxy group, and —C(O)N(R$^{13}$)$_2$, and W$^5$ and W$^6$ may be joined together to form a ring; a phenylene group, wherein the phenylene group is optionally substituted with one or more substituents selected from the group consisting of a halogen atom, a C$_1$-C$_6$ alkyl group, a hydroxyC$_1$-C$_6$ alkyl group, a C$_1$-C$_6$ acyl group, a carboxy group, a hydroxy group, a haloC$_1$-C$_6$ alkyl group, a cyano group, a C$_3$-C$_{10}$ cycloalkyl group, a 3- to 10-membered heterocycloalkyl group, —NR$^{10}$R$^{11}$, —C(O)R$^9$, —C(O)NR$^{10}$R$^{11}$, a C$_1$-C$_6$ alkoxycarbonyl group, —SO$_2$R$^{12}$, and a C$_1$-C$_6$ alkoxy group; or a heteroarylene group, wherein the heteroarylene group is optionally substituted with one or more substituents selected from the group consisting of a halogen atom, a C$_1$-C$_6$ alkyl group, a hydroxyC$_1$-C$_6$ alkyl group, a C$_1$-C$_6$ acyl group, a carboxy group, a hydroxy group, a haloC$_1$-C$_6$ alkyl group, a cyano group, a C$_3$-C$_{10}$ cycloalkyl group, a 3- to 10-membered heterocycloalkyl group, —NR$^{10}$R$^{11}$, —C(O)R$^9$, —C(O)NR$^{10}$R$^{11}$, a C$_1$-C$_6$ alkoxycarbonyl group, —SO$_2$R$^{12}$, and a C$_1$-C$_6$ alkoxy group;

R$^6$ represents a bond or a C$_3$-C$_6$ cycloalkylene group;
R$^7$ represents H or a hydroxy group;
each R$^8$ independently represents H or a C$_1$-C$_6$ alkyl group;
R$^9$ represents H, a hydroxy group, a C$_1$-C$_6$ alkyl group, a C$_1$-C$_6$ alkoxy group, or a C$_3$-C$_6$ cycloalkoxy group;
R$^{10}$ represents H or a C$_1$-C$_6$ alkyl group;
R$^{11}$ represents H or a C$_1$-C$_6$ alkyl group;
R$^{12}$ represents H or a C$_1$-C$_6$ alkyl group; and
each R$^{13}$ independently represents H, a C$_1$-C$_6$ alkyl group, or a hydroxyC$_1$-C$_6$ alkyl group.

Preferred compounds of the embodiments include, for example, compounds listed in Tables 12 to 22 below.

TABLE 12

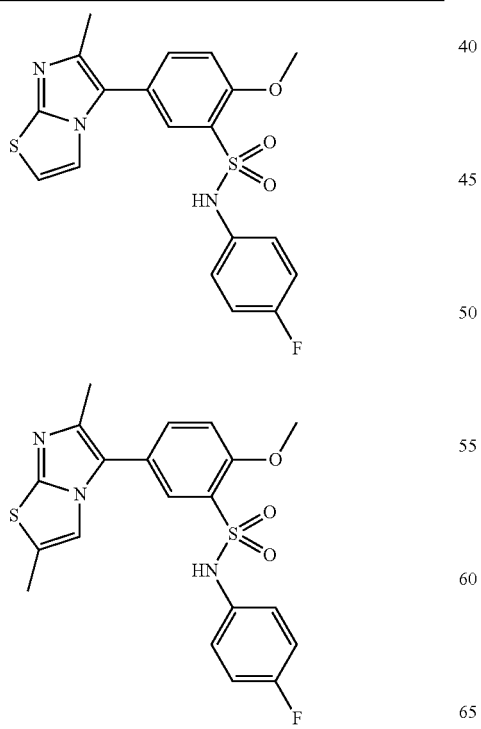

TABLE 12-continued

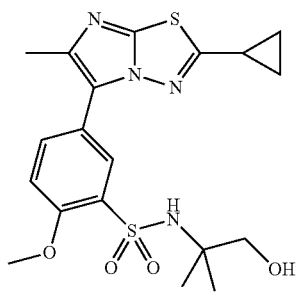 [SMILES: COc1ccc(-c2c(C)nc3sc(C4CC4)nn23)cc1S(=O)(=O)NC(C)(C)CO]

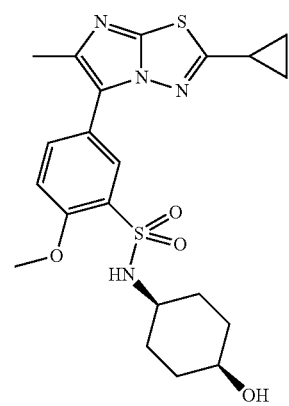 [SMILES: COc1ccc(-c2c(C)nc3sc(C4CC4)nn23)cc1S(=O)(=O)N[C@H]1CC[C@@H](O)CC1]

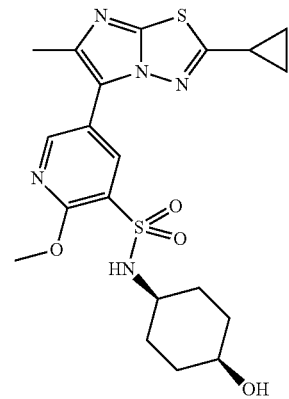 [SMILES: COc1ncc(-c2c(C)nc3sc(C4CC4)nn23)cc1S(=O)(=O)N[C@H]1CC[C@@H](O)CC1]

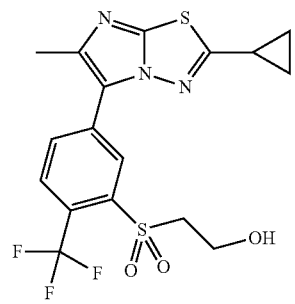 [SMILES: Cc1nc2sc(C3CC3)nn2c1-c1ccc(C(F)(F)F)c(S(=O)(=O)CCO)c1]

TABLE 12-continued
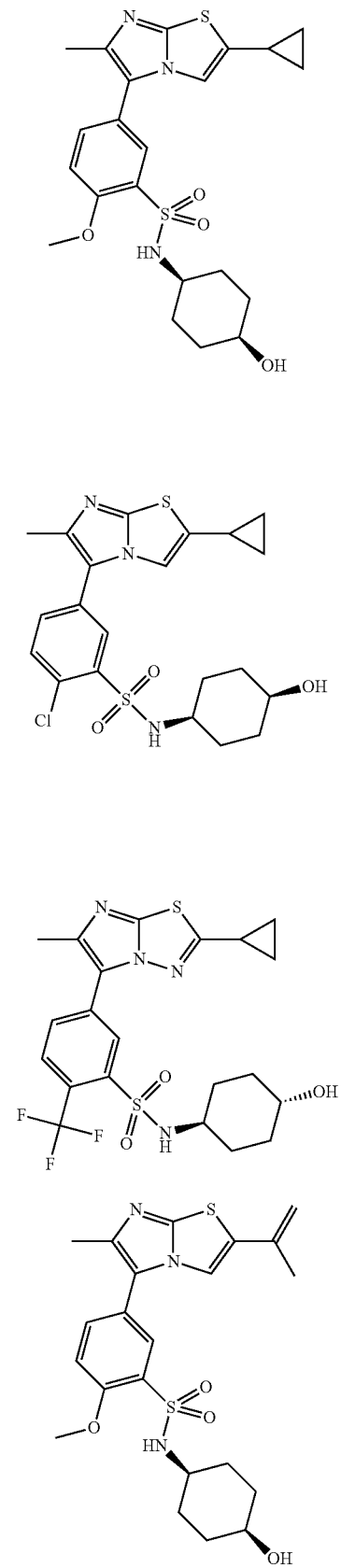
TABLE 12-continued
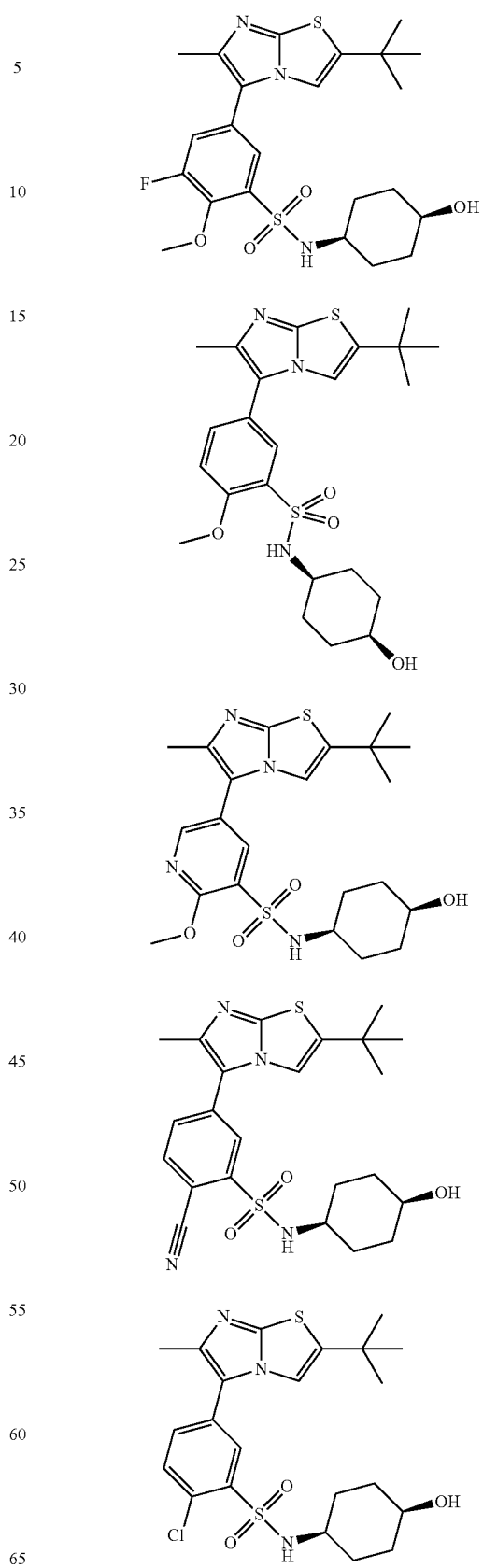

TABLE 12-continued
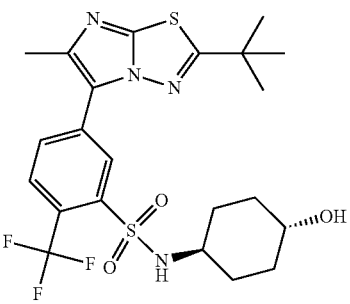 [SMILES: Cc1nc2sc(C(C)(C)C)nn2c1-c1ccc(C(F)(F)F)c(S(=O)(=O)N[C@H]2CC[C@H](O)CC2)c1]
TABLE 13
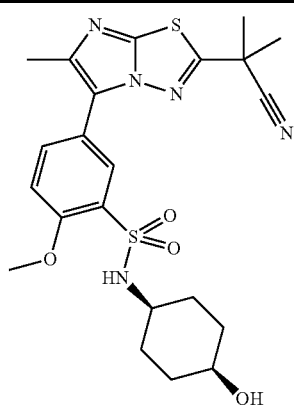
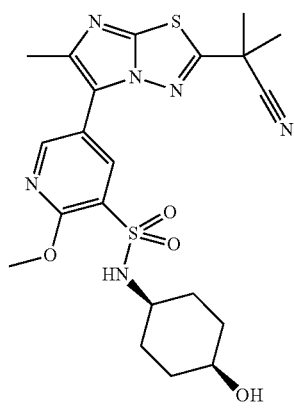
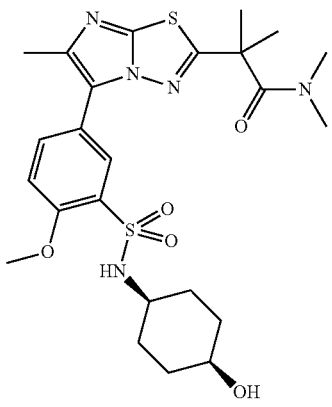
TABLE 13-continued
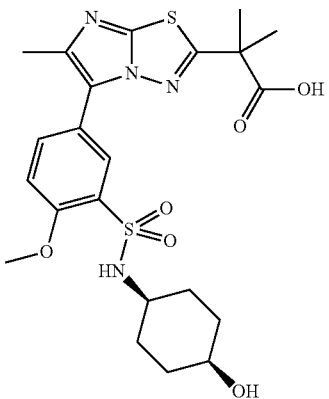 [SMILES: COc1ccc(-c2c(C)nc3sc(C(C)(C)C(=O)O)nn23)cc1S(=O)(=O)N[C@H]1CC[C@@H](O)CC1]
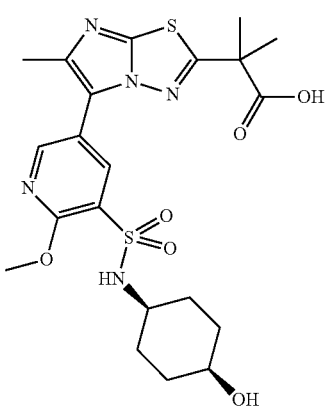 [SMILES: COc1ncc(-c2c(C)nc3sc(C(C)(C)C(=O)O)nn23)cc1S(=O)(=O)N[C@H]1CC[C@@H](O)CC1]
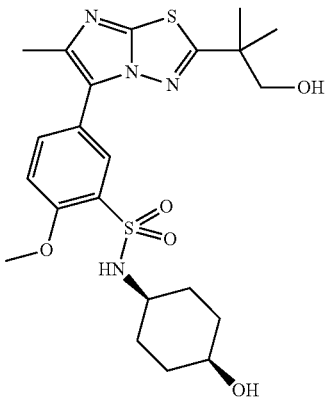 [SMILES: COc1ccc(-c2c(C)nc3sc(C(C)(C)CO)nn23)cc1S(=O)(=O)N[C@H]1CC[C@@H](O)CC1]
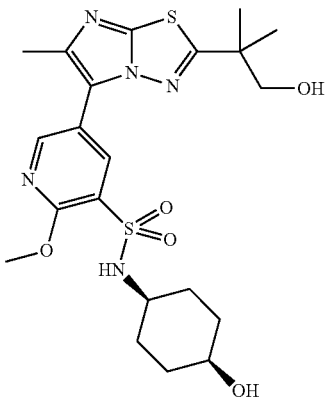

TABLE 13-continued
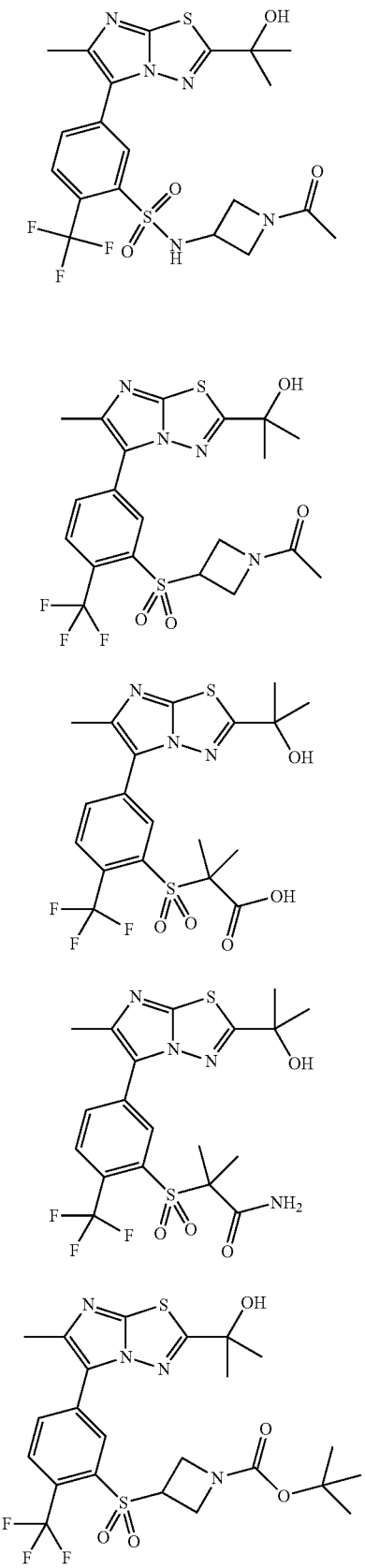
TABLE 13-continued
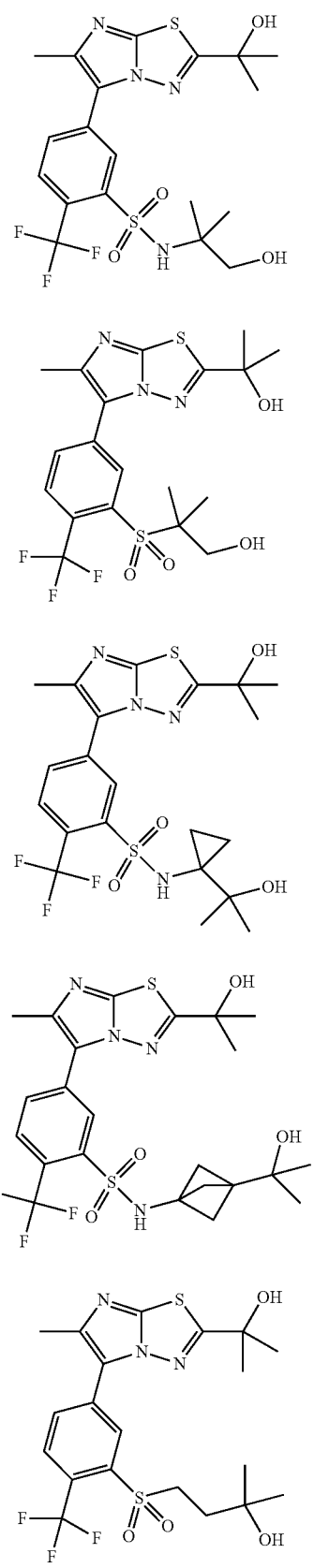

TABLE 13-continued
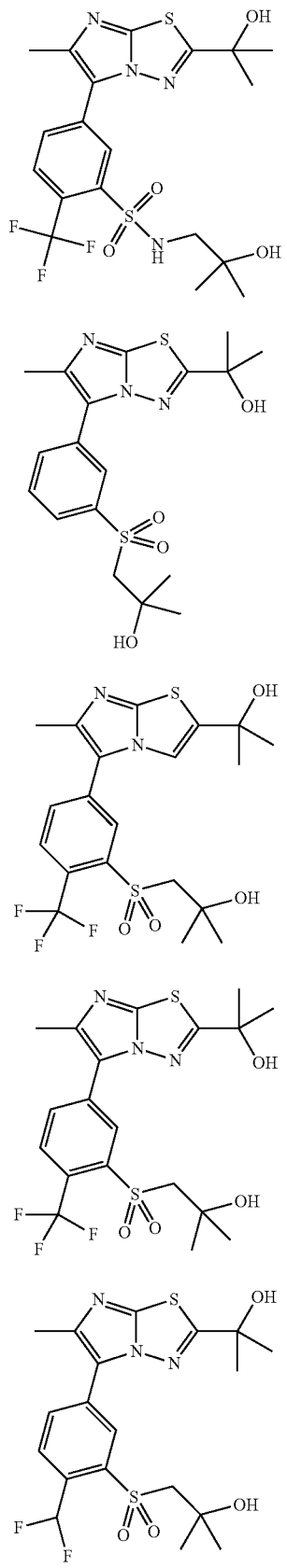
TABLE 13-continued

TABLE 14
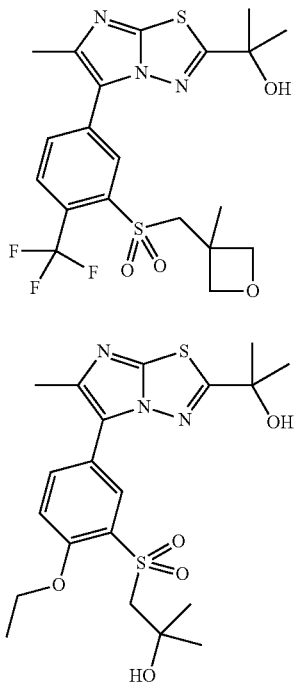

TABLE 14-continued
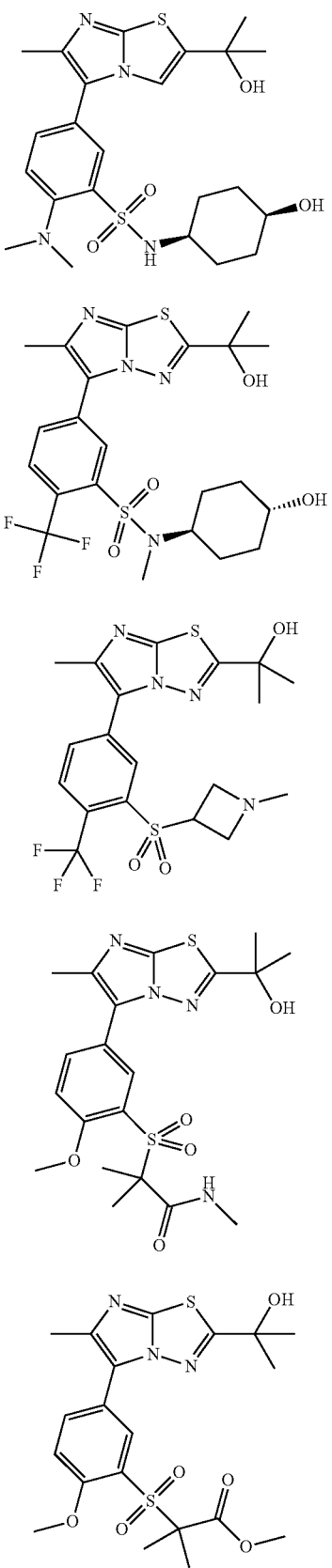
TABLE 14-continued
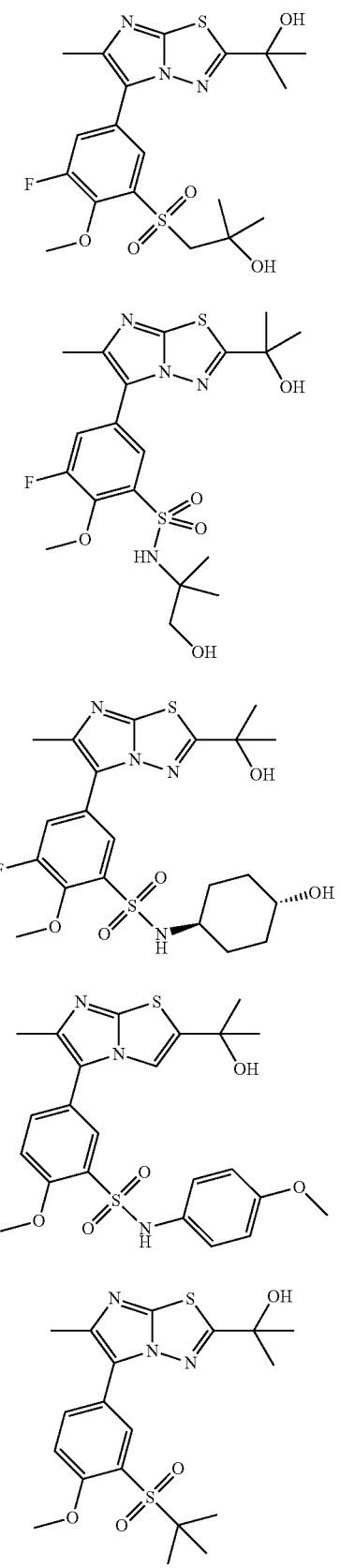

TABLE 14-continued
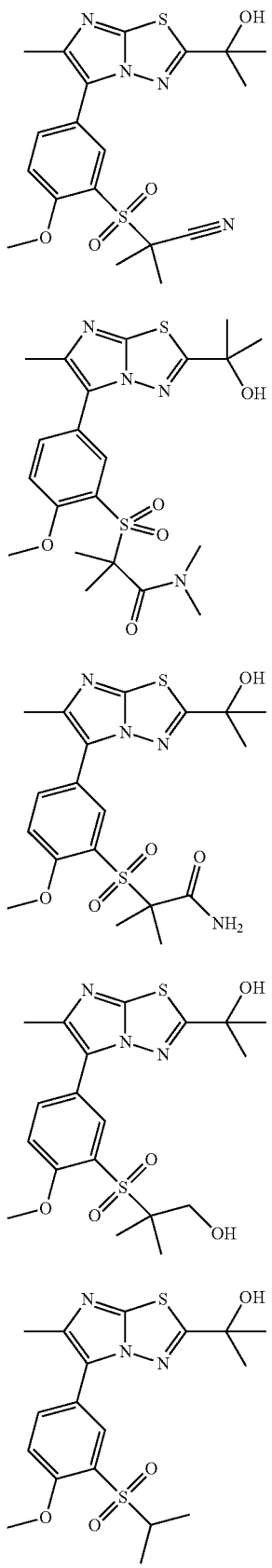
TABLE 14-continued
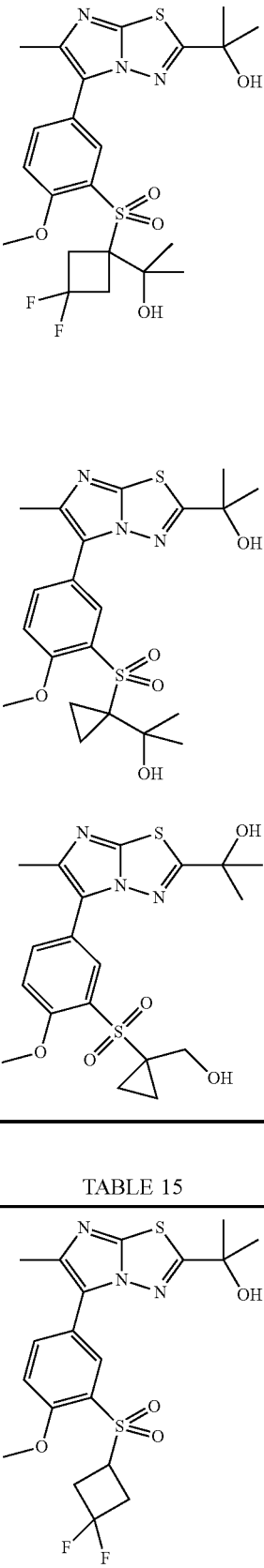
TABLE 15
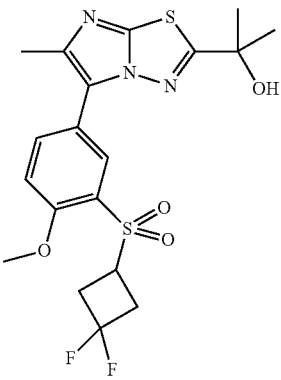 [SMILES: COc1ccc(-c2c(C)nc3sc(C(C)(C)O)nn23)cc1S(=O)(=O)C1CC(F)(F)C1]

TABLE 15-continued
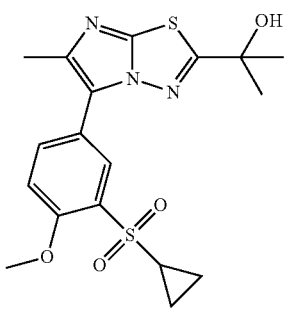 [SMILES: COc1ccc(-c2c(C)nc3sc(C(C)(C)O)nn23)cc1S(=O)(=O)C1CC1]
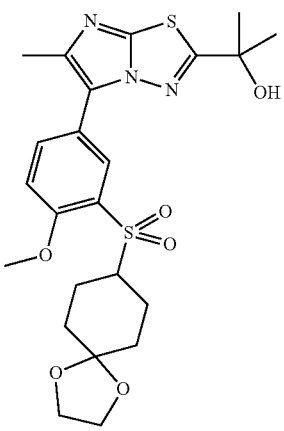
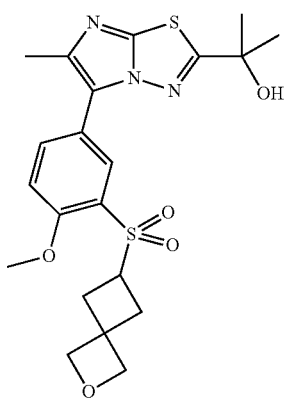 [SMILES: COc1ccc(-c2c(C)nc3sc(C(C)(C)O)nn23)cc1S(=O)(=O)C1CC2(COC2)C1]
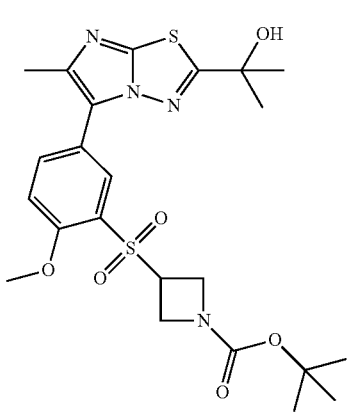
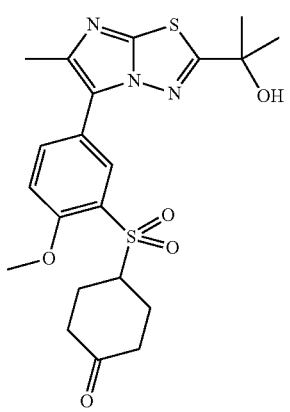 [SMILES: COc1ccc(-c2c(C)nc3sc(C(C)(C)O)nn23)cc1S(=O)(=O)C1CCC(=O)CC1]
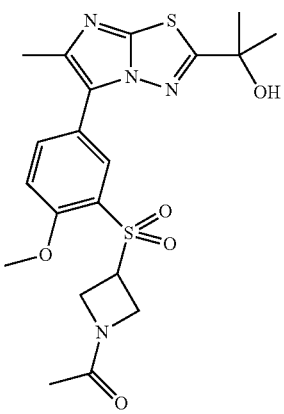
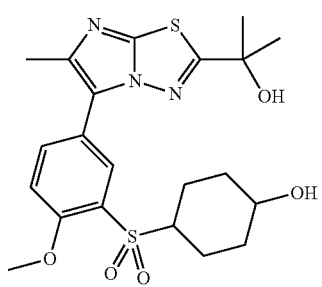 [SMILES: COc1ccc(-c2c(C)nc3sc(C(C)(C)O)nn23)cc1S(=O)(=O)C1CCC(O)CC1]
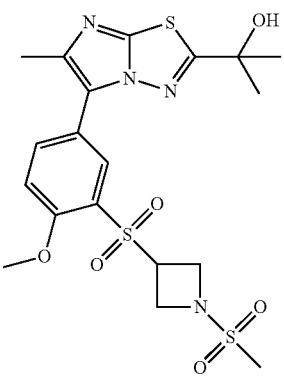 [SMILES: COc1ccc(-c2c(C)nc3sc(C(C)(C)O)nn23)cc1S(=O)(=O)C1CN(S(C)(=O)=O)C1]

TABLE 15-continued
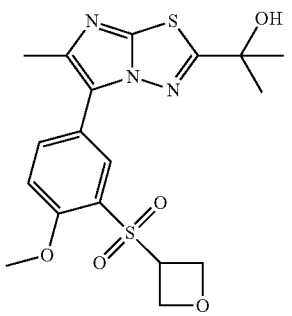 [SMILES: COc1ccc(-c2c(C)nc3sc(C(C)(C)O)nn23)cc1S(=O)(=O)C1COC1]
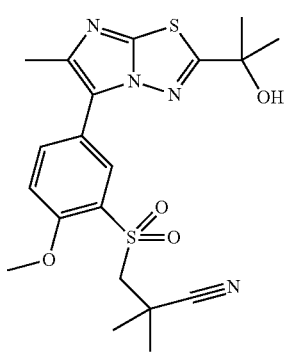 [SMILES: COc1ccc(-c2c(C)nc3sc(C(C)(C)O)nn23)cc1S(=O)(=O)CC(C)(C)C#N]
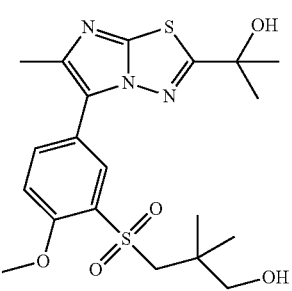 [SMILES: COc1ccc(-c2c(C)nc3sc(C(C)(C)O)nn23)cc1S(=O)(=O)CC(C)(C)CO]
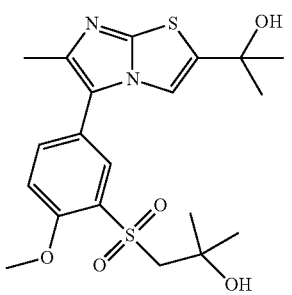 [SMILES: COc1ccc(-c2c(C)nc3sc(C(C)(C)O)cn23)cc1S(=O)(=O)CC(C)(C)O]
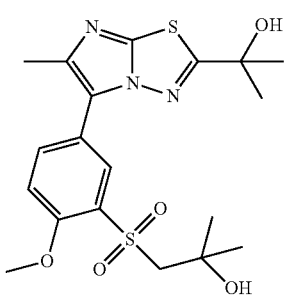 [SMILES: COc1ccc(-c2c(C)nc3sc(C(C)(C)O)nn23)cc1S(=O)(=O)CC(C)(C)O]
TABLE 15-continued
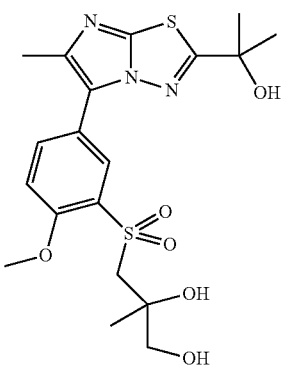 [SMILES: COc1ccc(-c2c(C)nc3sc(C(C)(C)O)nn23)cc1S(=O)(=O)CC(C)(O)CO]
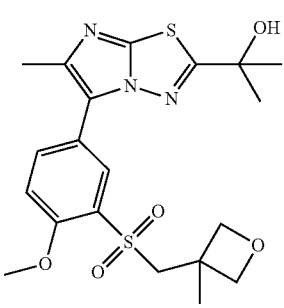 [SMILES: COc1ccc(-c2c(C)nc3sc(C(C)(C)O)nn23)cc1S(=O)(=O)CC1(C)COC1]
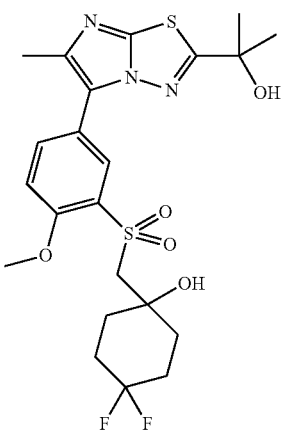 [SMILES: COc1ccc(-c2c(C)nc3sc(C(C)(C)O)nn23)cc1S(=O)(=O)CC1(O)CCC(F)(F)CC1]
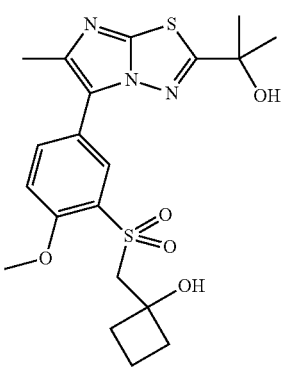 [SMILES: COc1ccc(-c2c(C)nc3sc(C(C)(C)O)nn23)cc1S(=O)(=O)CC1(O)CCC1]

TABLE 15-continued
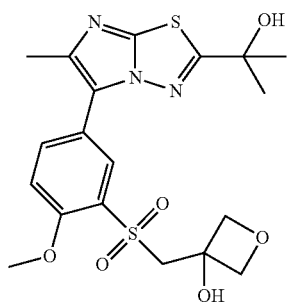 [SMILES: COc1ccc(-c2c(C)nc3sc(C(C)(C)O)nn23)cc1S(=O)(=O)CC1(O)COC1]
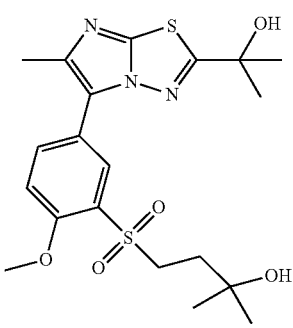 [SMILES: COc1ccc(-c2c(C)nc3sc(C(C)(C)O)nn23)cc1S(=O)(=O)CCC(C)(C)O]
TABLE 16
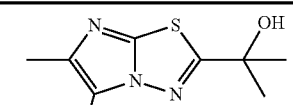
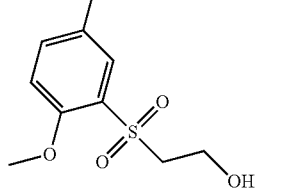
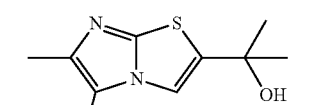
TABLE 16-continued
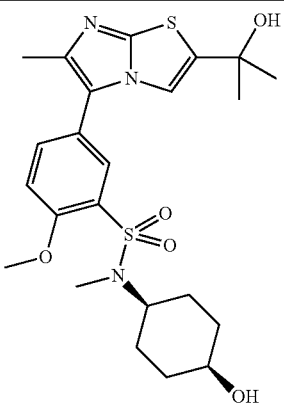
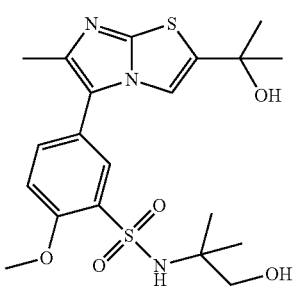 [SMILES: COc1ccc(-c2c(C)nc3sc(C(C)(C)O)cn23)cc1S(=O)(=O)NC(C)(C)CO]
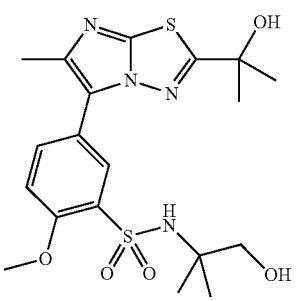 [SMILES: COc1ccc(-c2c(C)nc3sc(C(C)(C)O)nn23)cc1S(=O)(=O)NC(C)(C)CO]
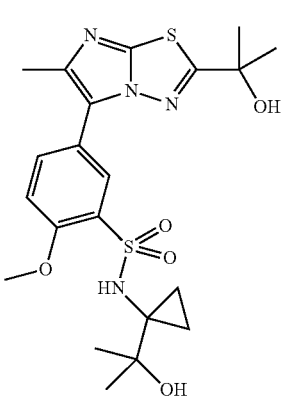 [SMILES: COc1ccc(-c2c(C)nc3sc(C(C)(C)O)nn23)cc1S(=O)(=O)NC1(C(C)(C)O)CC1]

TABLE 16-continued
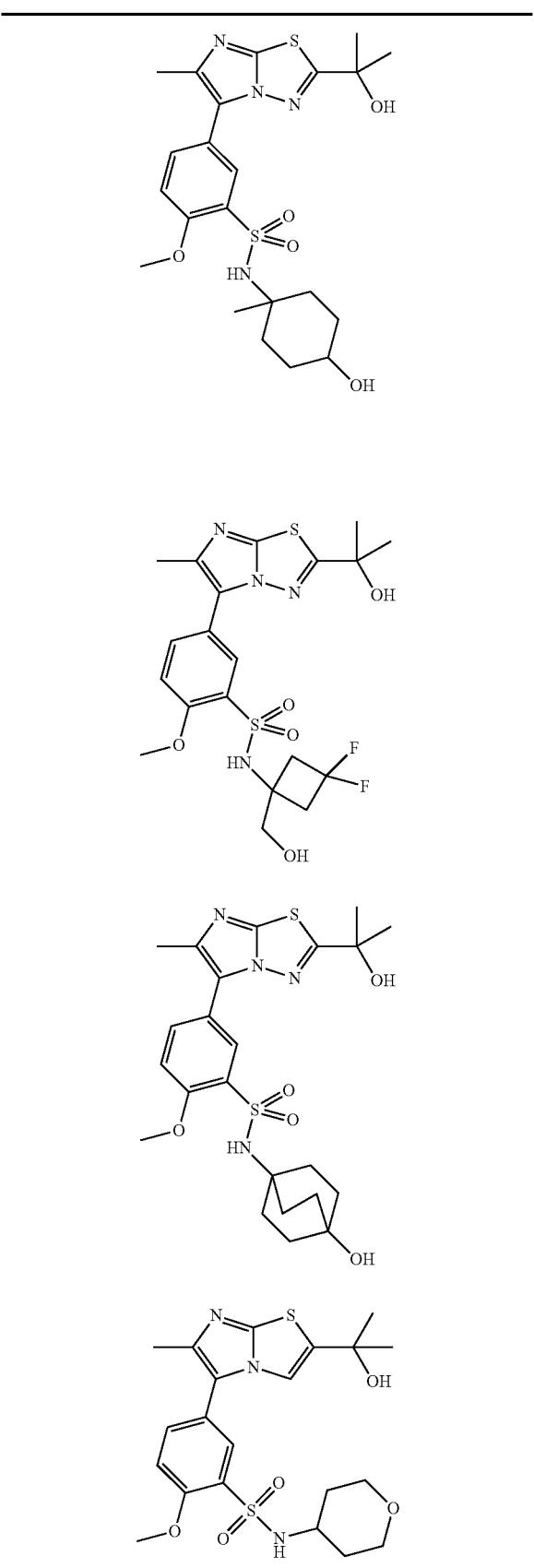
TABLE 16-continued
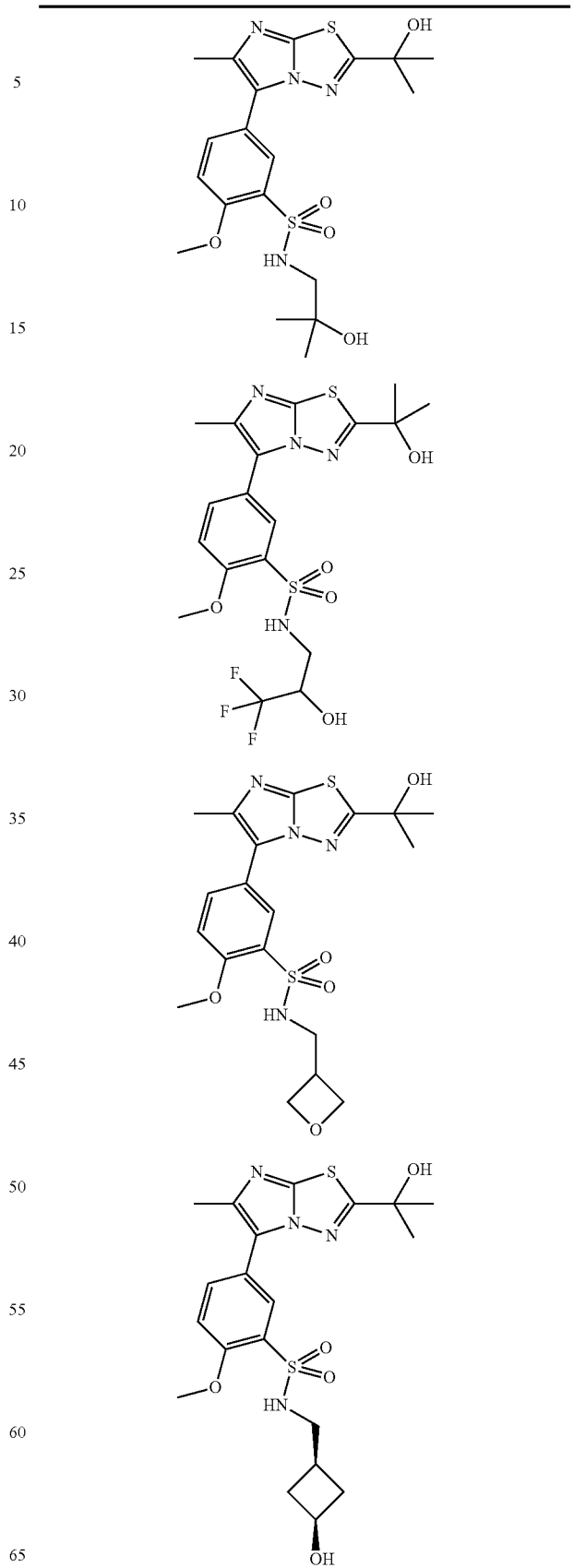

TABLE 16-continued
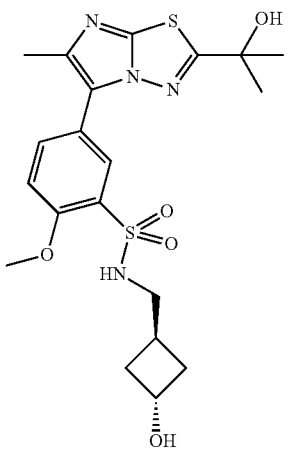 [SMILES: COc1ccc(-c2c(C)nc3sc(C(C)(C)O)nn23)cc1S(=O)(=O)NC[C@H]1C[C@H](O)C1]
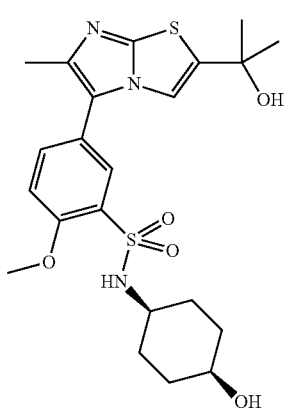 [SMILES: COc1ccc(-c2c(C)nc3sc(C(C)(C)O)cn23)cc1S(=O)(=O)N[C@H]1CC[C@@H](O)CC1]
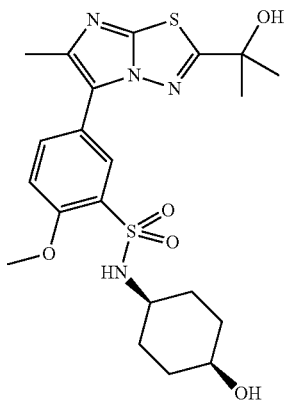 [SMILES: COc1ccc(-c2c(C)nc3sc(C(C)(C)O)nn23)cc1S(=O)(=O)N[C@H]1CC[C@@H](O)CC1]
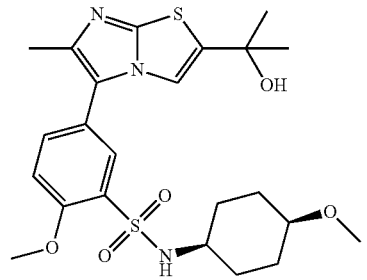
TABLE 16-continued
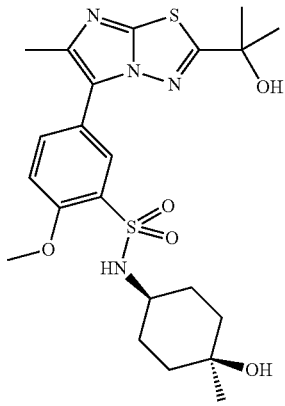 [SMILES: COc1ccc(-c2c(C)nc3sc(C(C)(C)O)nn23)cc1S(=O)(=O)N[C@H]1CC[C@@](C)(O)CC1]
TABLE 17
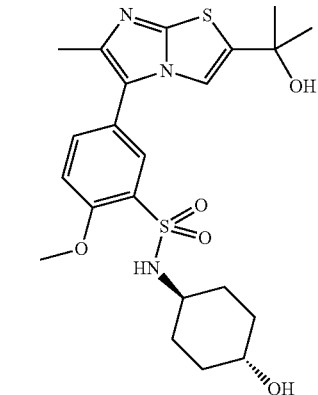 [SMILES: COc1ccc(-c2c(C)nc3sc(C(C)(C)O)cn23)cc1S(=O)(=O)N[C@H]1CC[C@H](O)CC1]
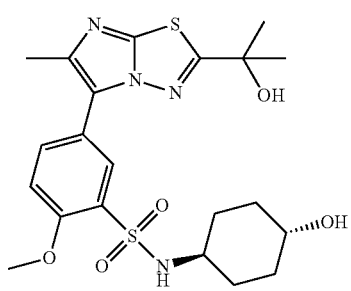
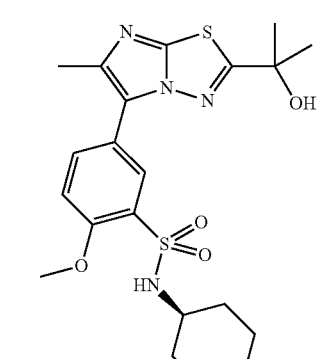

TABLE 17-continued
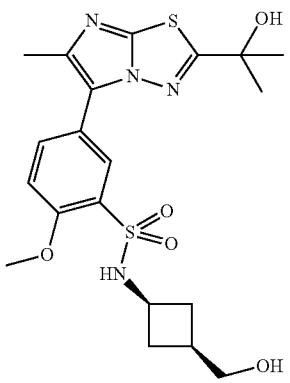 [SMILES: COc1ccc(-c2c(C)nc3sc(C(C)(C)O)nn23)cc1S(=O)(=O)N[C@H]1C[C@@H](CO)C1]
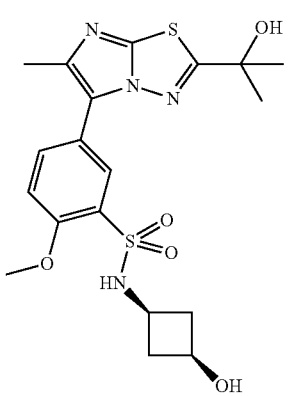 [SMILES: COc1ccc(-c2c(C)nc3sc(C(C)(C)O)nn23)cc1S(=O)(=O)N[C@H]1C[C@@H](O)C1]
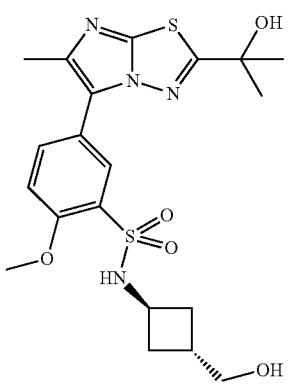 [SMILES: COc1ccc(-c2c(C)nc3sc(C(C)(C)O)nn23)cc1S(=O)(=O)N[C@H]1C[C@H](CO)C1]
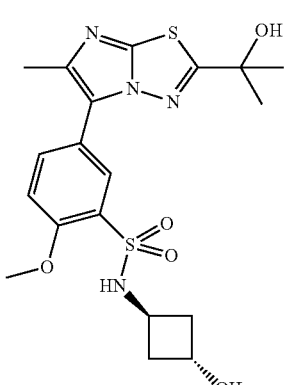
TABLE 17-continued
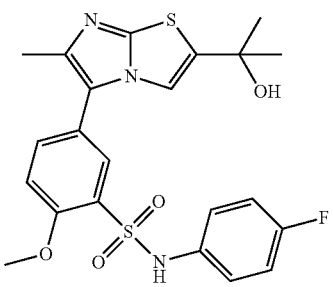 [SMILES: COc1ccc(-c2c(C)nc3sc(C(C)(C)O)cn23)cc1S(=O)(=O)Nc1ccc(F)cc1]
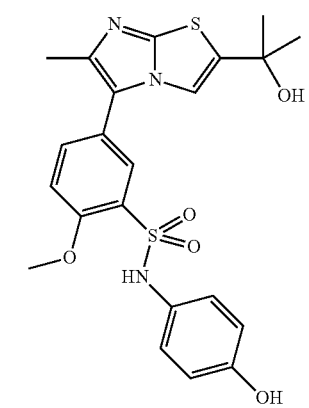 [SMILES: COc1ccc(-c2c(C)nc3sc(C(C)(C)O)cn23)cc1S(=O)(=O)Nc1ccc(O)cc1]
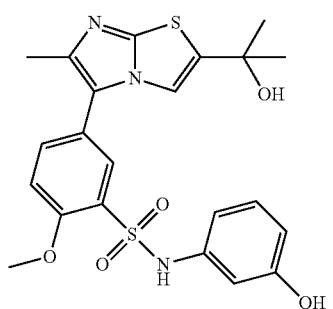 [SMILES: COc1ccc(-c2c(C)nc3sc(C(C)(C)O)cn23)cc1S(=O)(=O)Nc1cccc(O)c1]
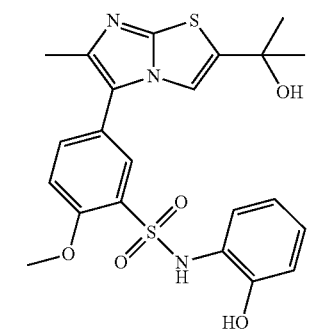 [SMILES: COc1ccc(-c2c(C)nc3sc(C(C)(C)O)cn23)cc1S(=O)(=O)Nc1ccccc1O]

TABLE 17-continued
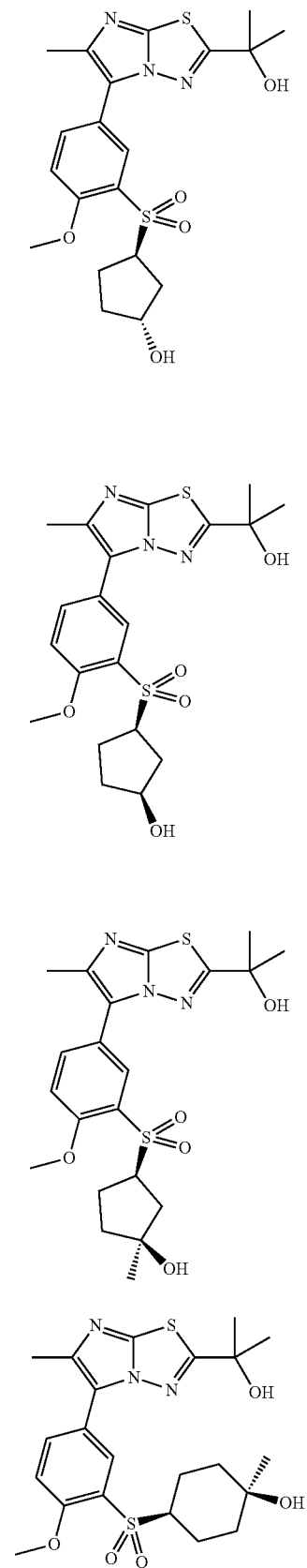
TABLE 17-continued
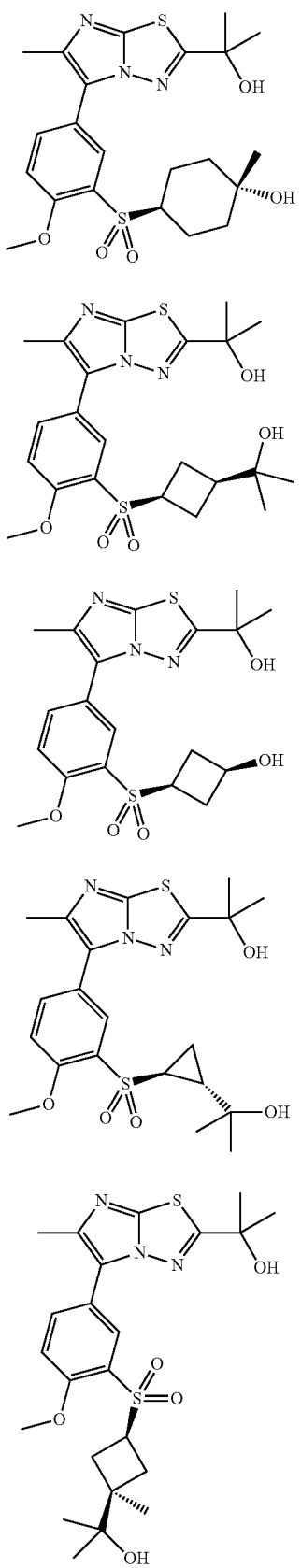

TABLE 18
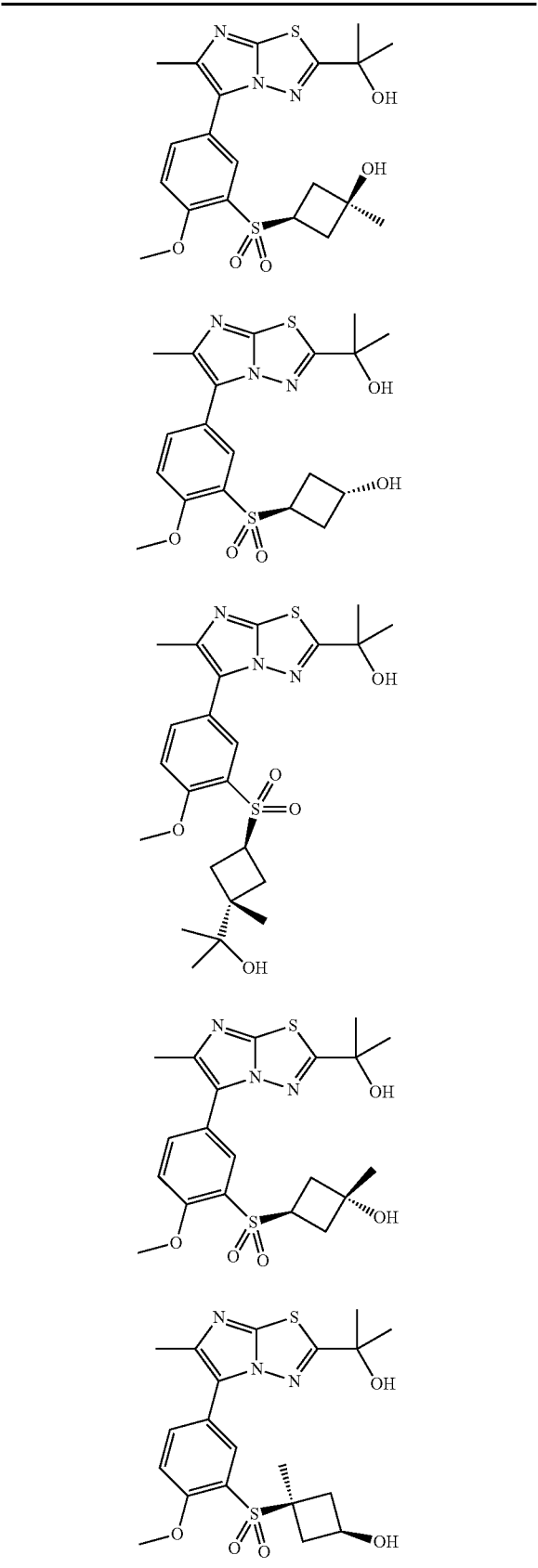
TABLE 18-continued
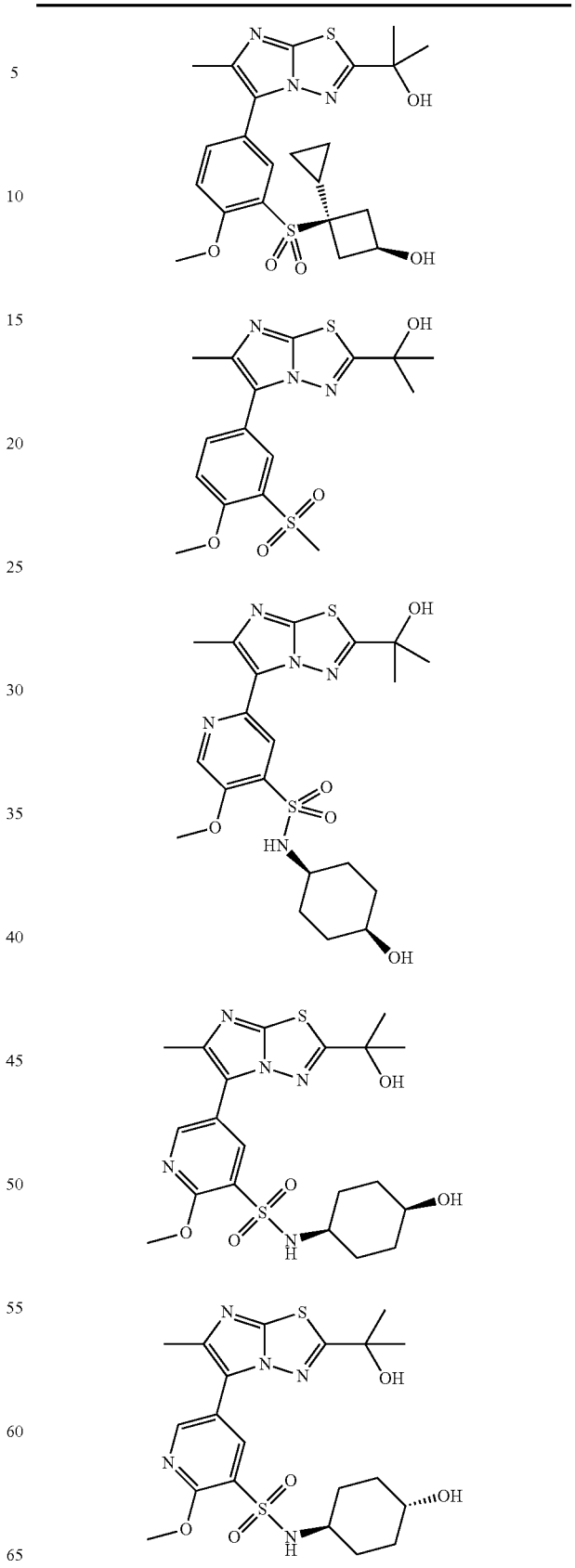

TABLE 18-continued
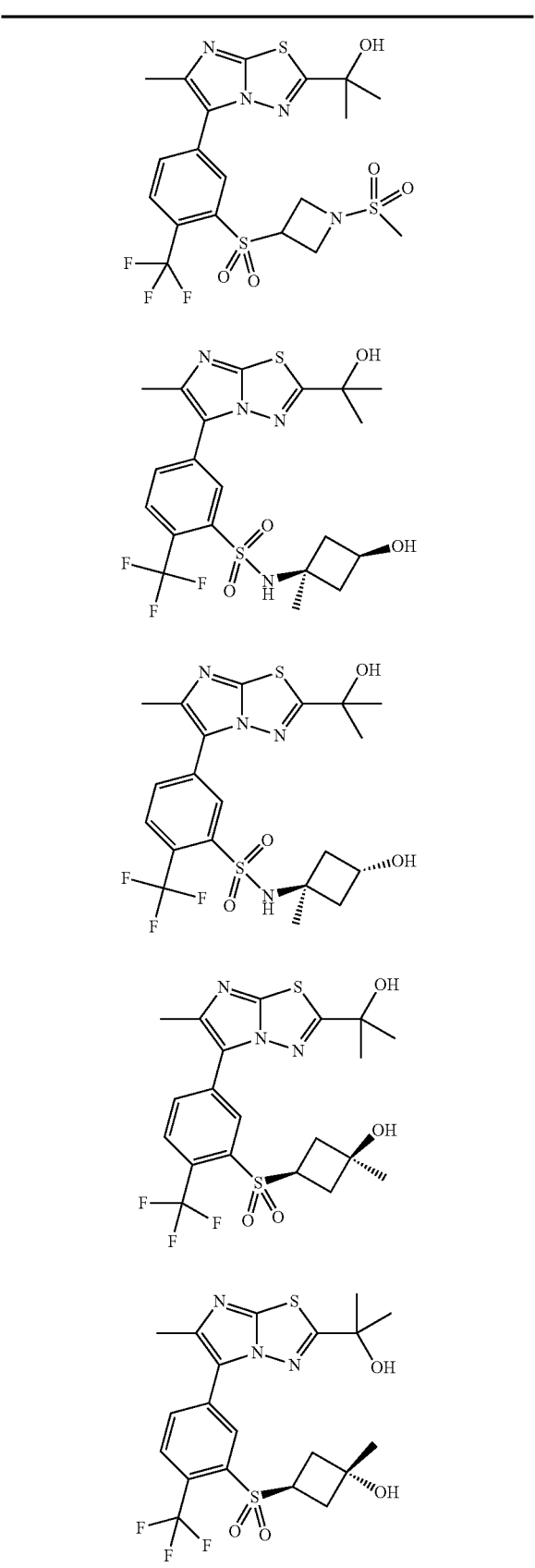
TABLE 18-continued
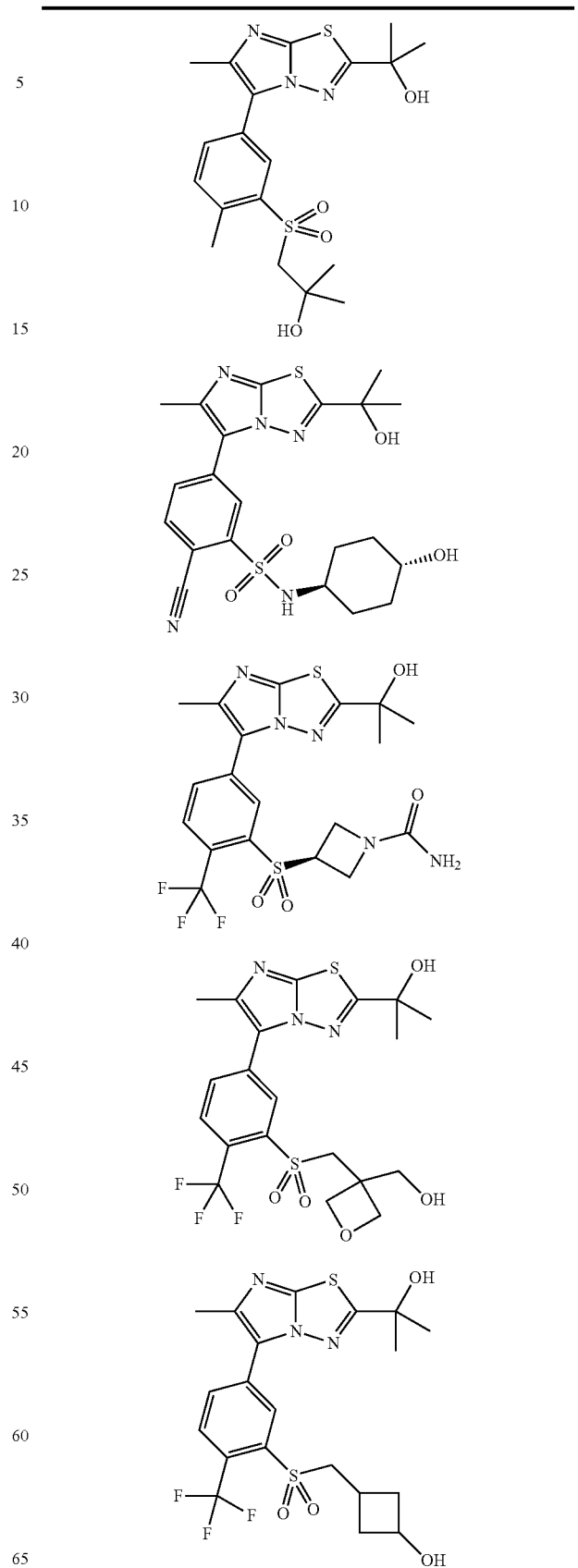

TABLE 18-continued
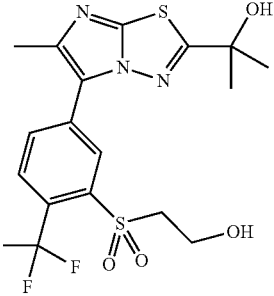
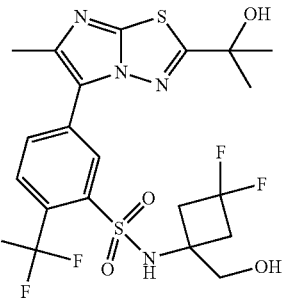
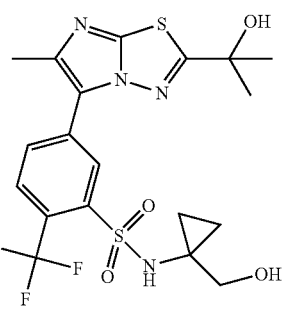
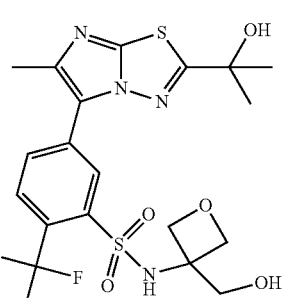
TABLE 19
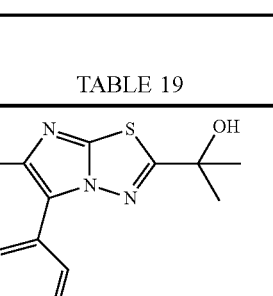
TABLE 19-continued
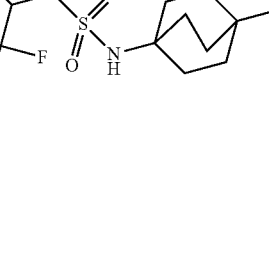
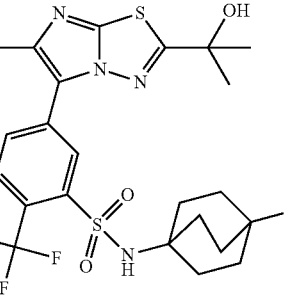
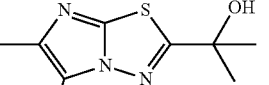
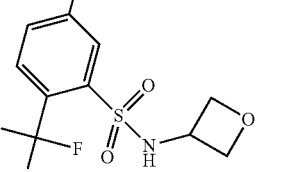

TABLE 19-continued
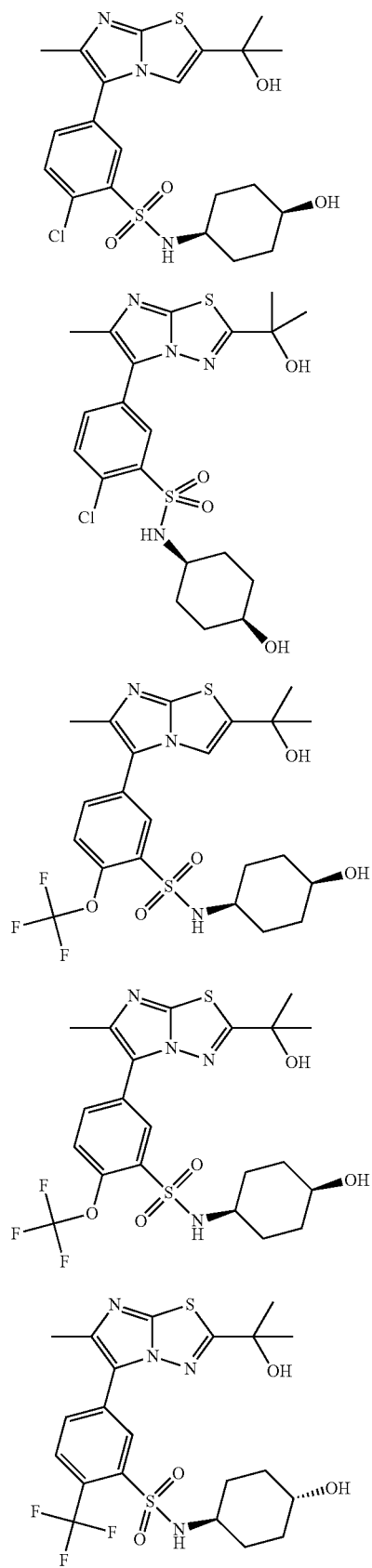
TABLE 19-continued
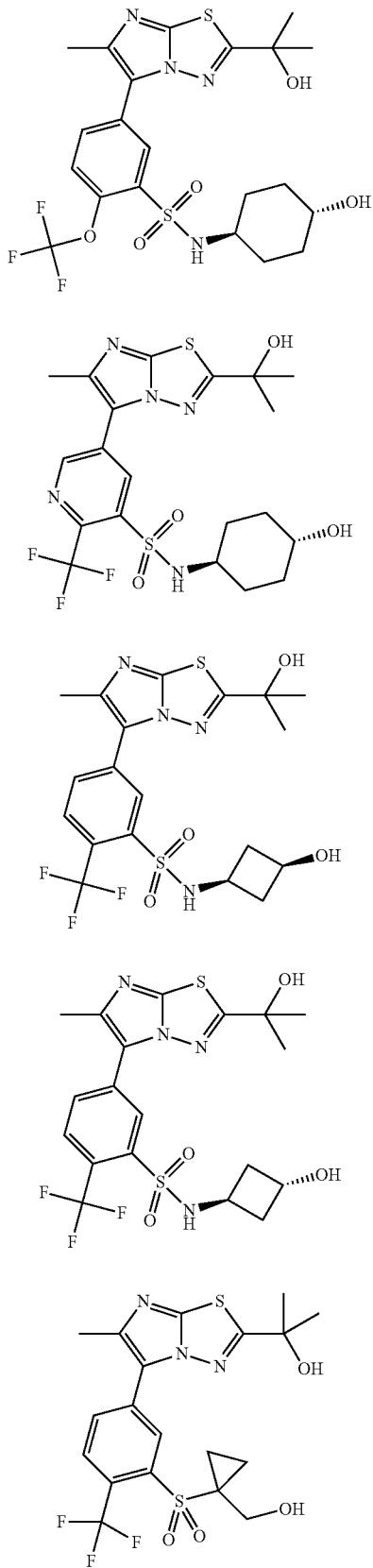

TABLE 19-continued
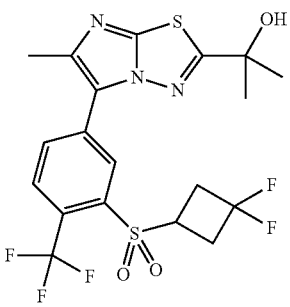 [SMILES: Cc1nc2sc(C(C)(C)O)nn2c1-c1ccc(C(F)(F)F)c(S(=O)(=O)C2CC(F)(F)C2)c1]
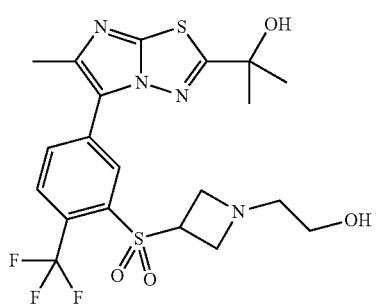 [SMILES: Cc1nc2sc(C(C)(C)O)nn2c1-c1ccc(C(F)(F)F)c(S(=O)(=O)C2CN(CCO)C2)c1]
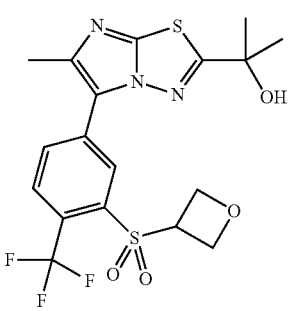 [SMILES: Cc1nc2sc(C(C)(C)O)nn2c1-c1ccc(C(F)(F)F)c(S(=O)(=O)C2COC2)c1]
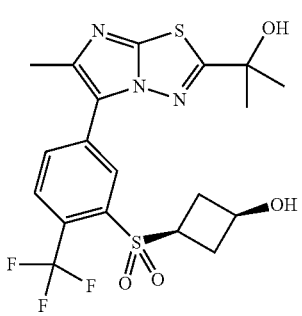 [SMILES: Cc1nc2sc(C(C)(C)O)nn2c1-c1ccc(C(F)(F)F)c(S(=O)(=O)[C@H]2C[C@@H](O)C2)c1]
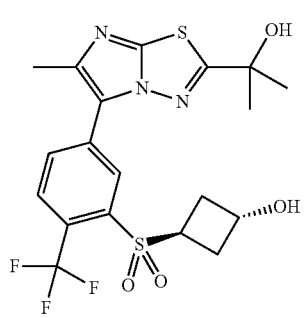 [SMILES: Cc1nc2sc(C(C)(C)O)nn2c1-c1ccc(C(F)(F)F)c(S(=O)(=O)[C@H]2C[C@H](O)C2)c1]
TABLE 19-continued
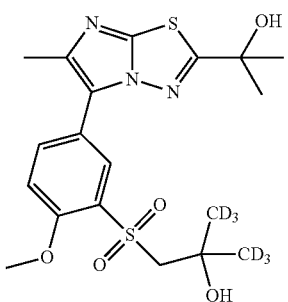 [SMILES: [2H]C([2H])([2H])C(O)(CS(=O)(=O)c1cc(-c2c(C)nc3sc(C(C)(C)O)nn23)ccc1OC)C([2H])([2H])[2H]]
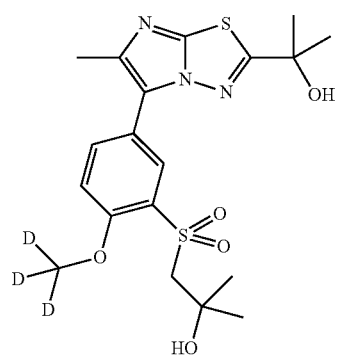 [SMILES: [2H]C([2H])([2H])Oc1ccc(-c2c(C)nc3sc(C(C)(C)O)nn23)cc1S(=O)(=O)CC(C)(C)O]
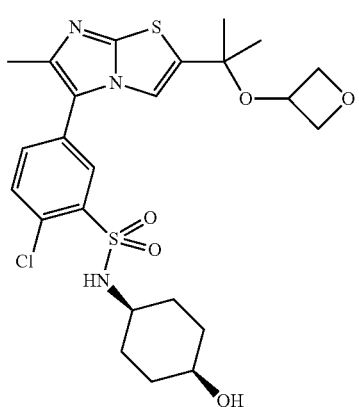 [SMILES: Cc1nc2sc(C(C)(C)OC3COC3)cn2c1-c1ccc(Cl)c(S(=O)(=O)N[C@H]2CC[C@@H](O)CC2)c1]
TABLE 20
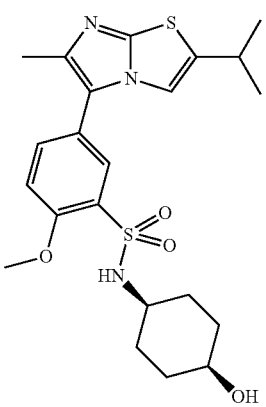 [SMILES: COc1ccc(-c2c(C)nc3sc(C(C)C)cn23)cc1S(=O)(=O)N[C@H]1CC[C@@H](O)CC1]

TABLE 20-continued
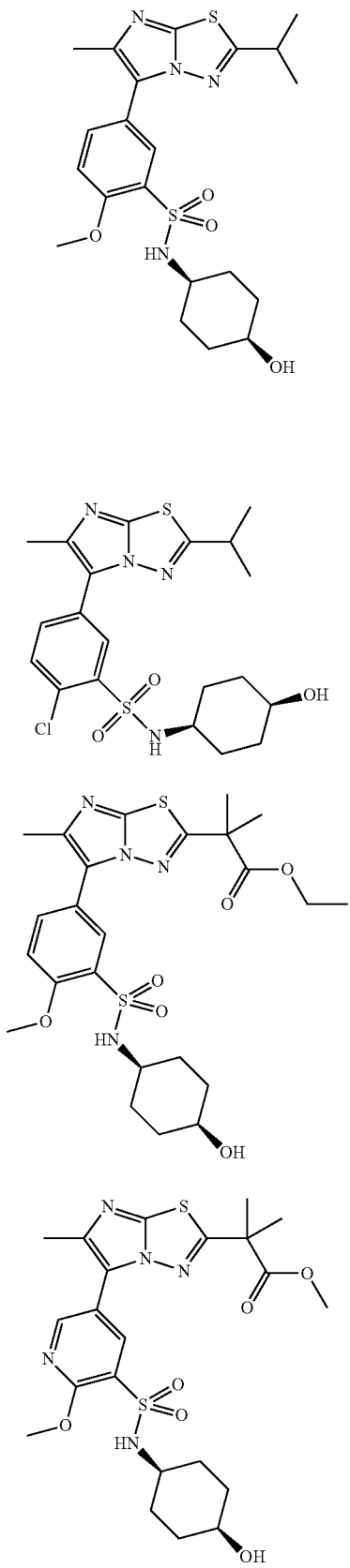
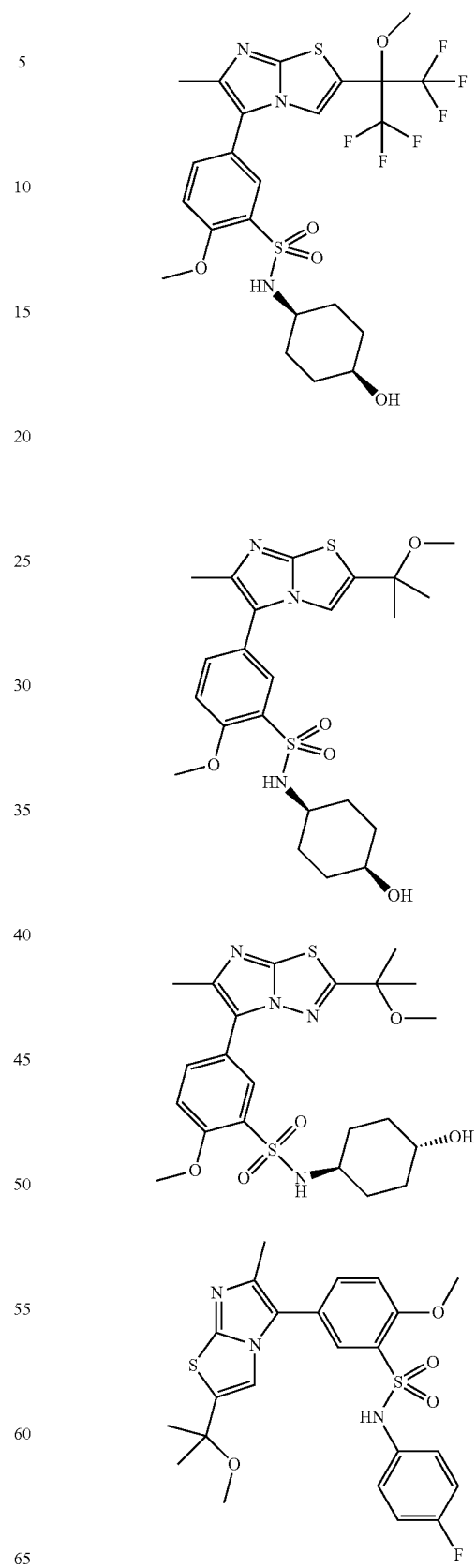

TABLE 20-continued
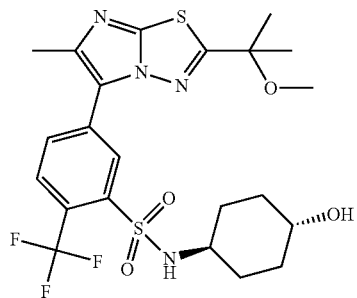 [SMILES: COC(C)(C)c1nn2c(-c3ccc(C(F)(F)F)c(S(=O)(=O)N[C@H]4CC[C@H](O)CC4)c3)c(C)nc2s1]
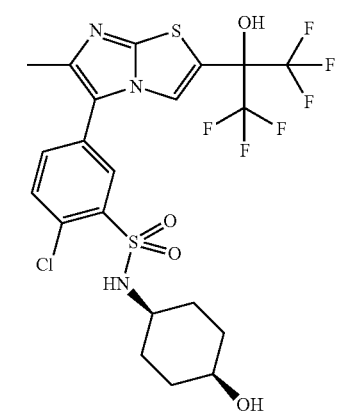 [SMILES: Cc1nc2sc(C(O)(C(F)(F)F)C(F)(F)F)cn2c1-c1ccc(Cl)c(S(=O)(=O)N[C@H]2CC[C@@H](O)CC2)c1]
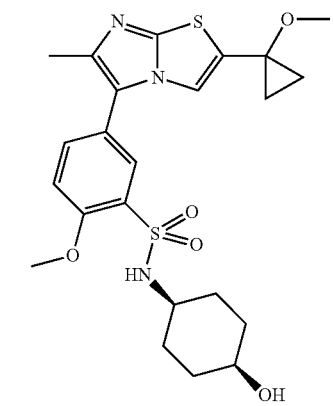
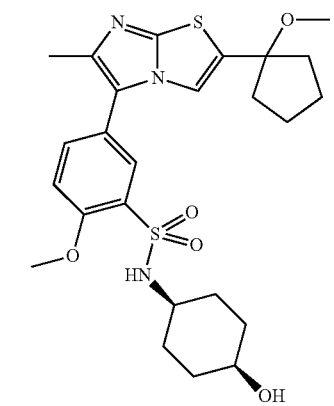
TABLE 20-continued
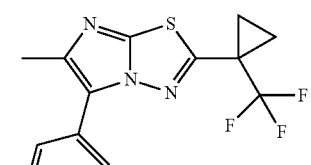
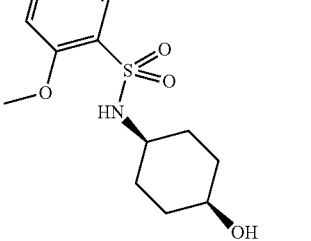
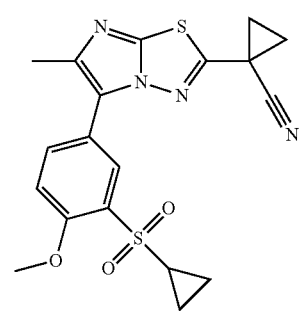 [SMILES: COc1ccc(-c2c(C)nc3sc(C4(C#N)CC4)nn23)cc1S(=O)(=O)C1CC1]
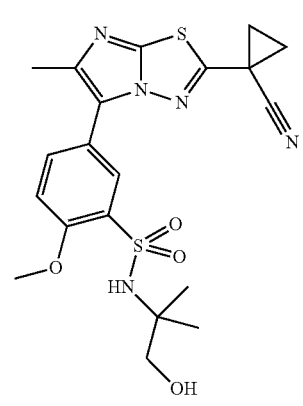 [SMILES: COc1ccc(-c2c(C)nc3sc(C4(C#N)CC4)nn23)cc1S(=O)(=O)NC(C)(C)CO]

TABLE 20-continued
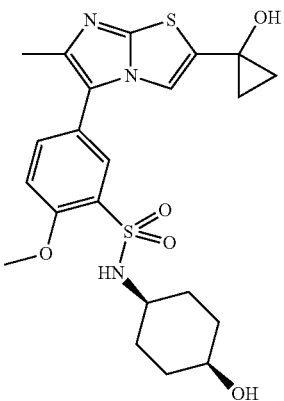 [SMILES: COc1ccc(-c2c(C)nc3sc(C4(O)CC4)cn23)cc1S(=O)(=O)N[C@H]1CC[C@@H](O)CC1]
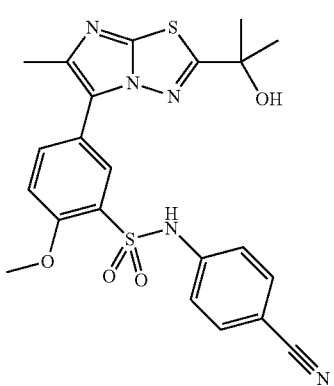 [SMILES: COc1ccc(-c2c(C)nc3sc(C(C)(C)O)nn23)cc1S(=O)(=O)Nc1ccc(C#N)cc1]
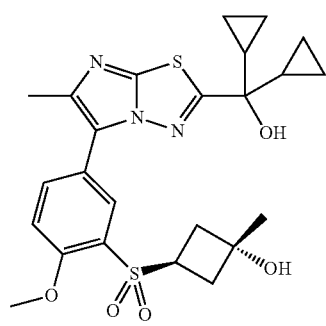 [SMILES: COc1ccc(-c2c(C)nc3sc(C(O)(C4CC4)C4CC4)nn23)cc1S(=O)(=O)[C@H]1C[C@](C)(O)C1]
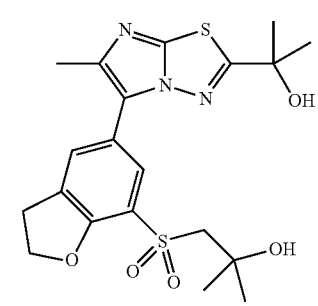 [SMILES: Cc1nc2sc(C(C)(C)O)nn2c1-c1cc2c(c(S(=O)(=O)CC(C)(C)O)c1)OCC2]
TABLE 20-continued
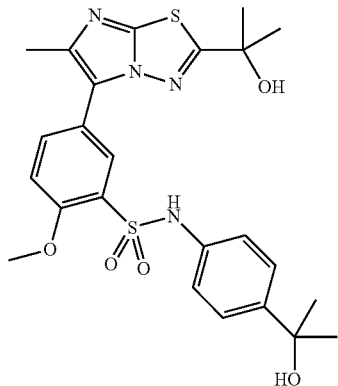 [SMILES: COc1ccc(-c2c(C)nc3sc(C(C)(C)O)nn23)cc1S(=O)(=O)Nc1ccc(C(C)(C)O)cc1]
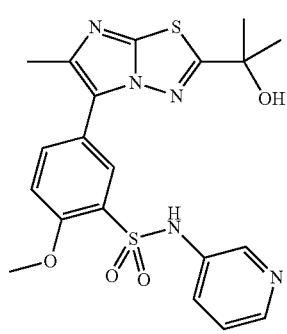 [SMILES: COc1ccc(-c2c(C)nc3sc(C(C)(C)O)nn23)cc1S(=O)(=O)Nc1cccnc1]
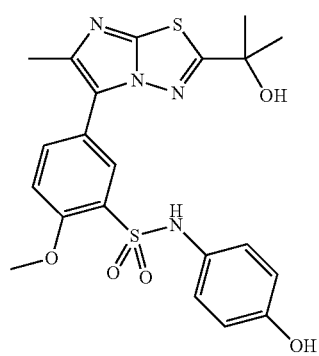 [SMILES: COc1ccc(-c2c(C)nc3sc(C(C)(C)O)nn23)cc1S(=O)(=O)Nc1ccc(O)cc1]
TABLE 21
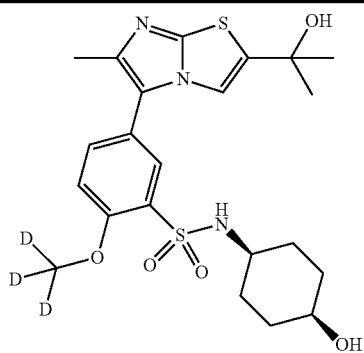

TABLE 21-continued
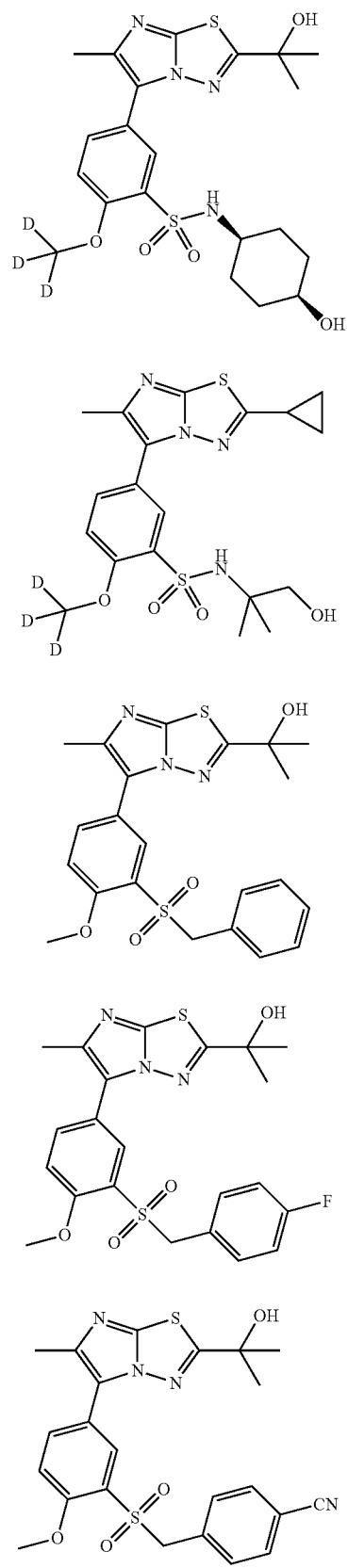
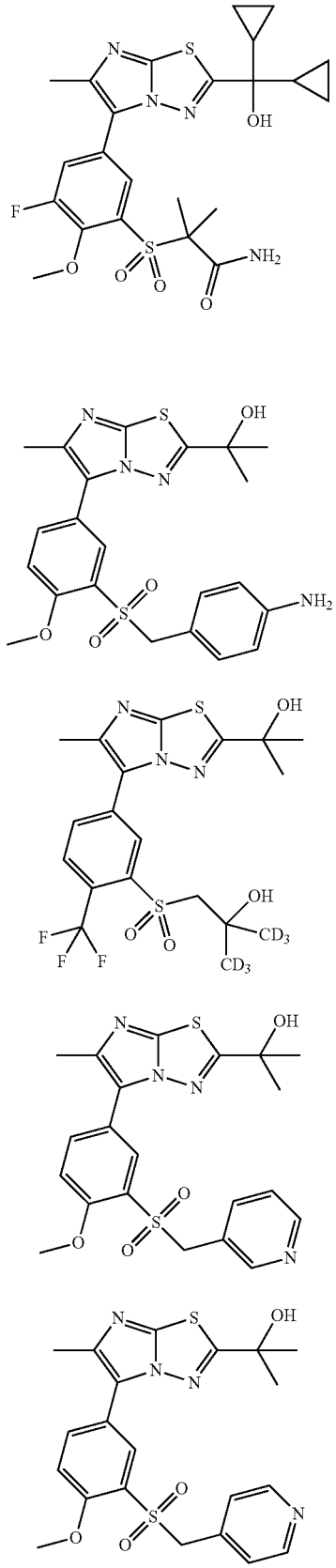

TABLE 21-continued
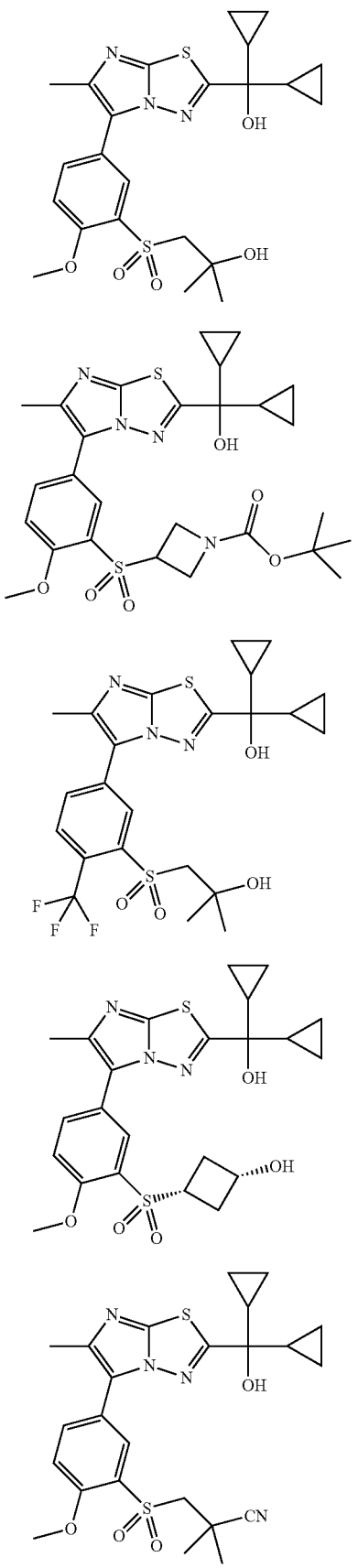
TABLE 21-continued
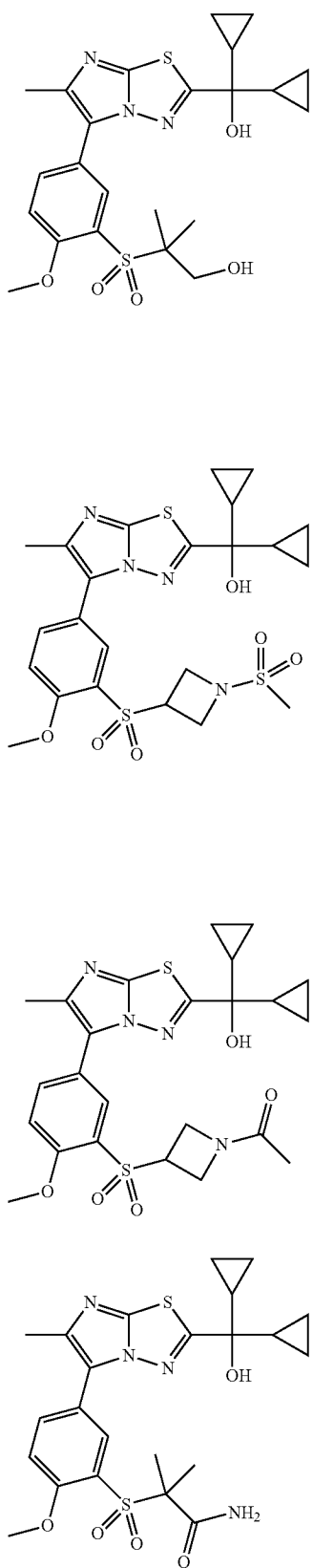

TABLE 21-continued
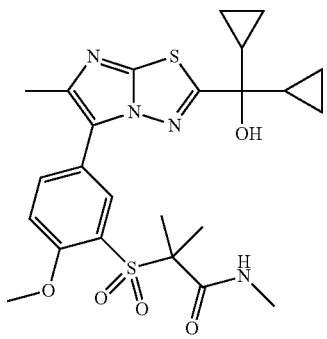 [SMILES: CNC(=O)C(C)(C)S(=O)(=O)c1cc(-c2c(C)nc3sc(C(O)(C4CC4)C4CC4)nn23)ccc1OC]
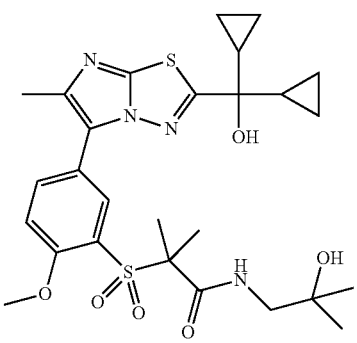 [SMILES: COc1ccc(-c2c(C)nc3sc(C(O)(C4CC4)C4CC4)nn23)cc1S(=O)(=O)C(C)(C)C(=O)NCC(C)(C)O]
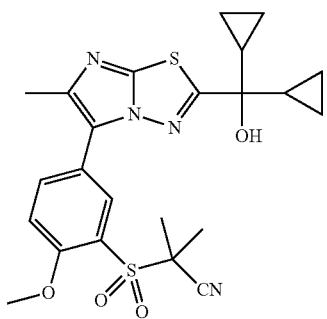 [SMILES: COc1ccc(-c2c(C)nc3sc(C(O)(C4CC4)C4CC4)nn23)cc1S(=O)(=O)C(C)(C)C#N]
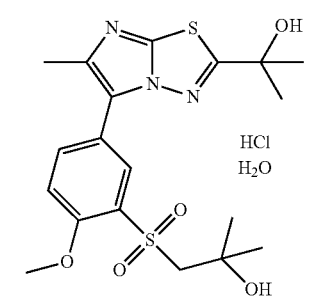 [SMILES: COc1ccc(-c2c(C)nc3sc(C(C)(C)O)nn23)cc1S(=O)(=O)CC(C)(C)O]
TABLE 22
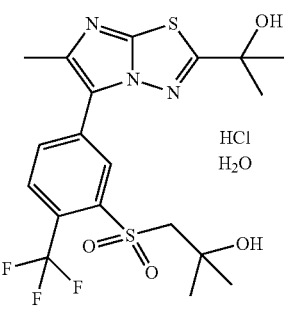 [SMILES: Cc1nc2sc(C(C)(C)O)nn2c1-c1ccc(C(F)(F)F)c(S(=O)(=O)CC(C)(C)O)c1]
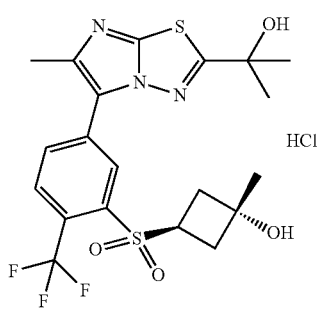 [SMILES: Cc1nc2sc(C(C)(C)O)nn2c1-c1ccc(C(F)(F)F)c(S(=O)(=O)[C@H]2C[C@](C)(O)C2)c1 ; Cl]
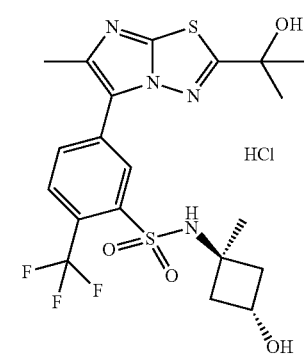 [SMILES: Cc1nc2sc(C(C)(C)O)nn2c1-c1ccc(C(F)(F)F)c(S(=O)(=O)N[C@]2(C)C[C@@H](O)C2)c1 ; Cl]
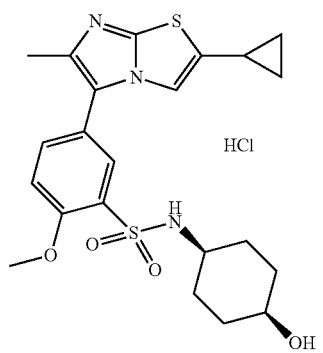 [SMILES: COc1ccc(-c2c(C)nc3sc(C4CC4)cn23)cc1S(=O)(=O)N[C@H]1CC[C@@H](O)CC1 ; Cl]

TABLE 22-continued

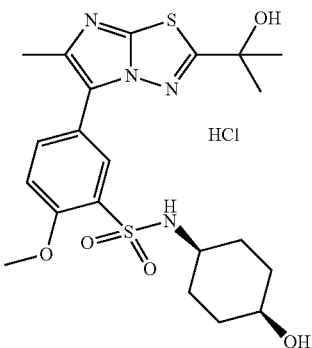 [SMILES: COc1ccc(-c2c(C)nc3sc(C(C)(C)O)nn23)cc1S(=O)(=O)N[C@H]1CC[C@@H](O)CC1 ; Cl]

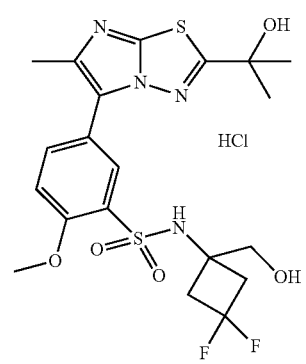 [SMILES: COc1ccc(-c2c(C)nc3sc(C(C)(C)O)nn23)cc1S(=O)(=O)NC1(CO)CC(F)(F)C1 ; Cl]

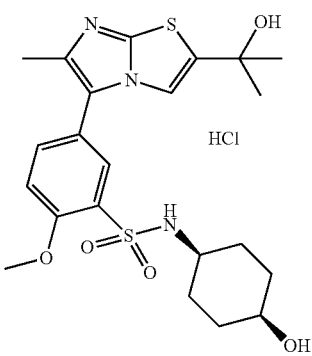 [SMILES: COc1ccc(-c2c(C)nc3sc(C(C)(C)O)cn23)cc1S(=O)(=O)N[C@H]1CC[C@@H](O)CC1 ; Cl]

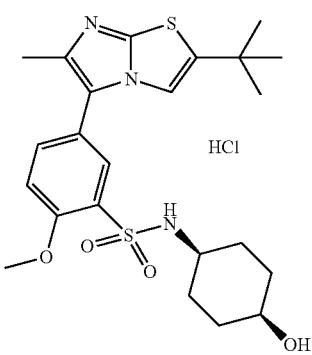 [SMILES: COc1ccc(-c2c(C)nc3sc(C(C)(C)C)cn23)cc1S(=O)(=O)N[C@H]1CC[C@@H](O)CC1 ; Cl]

TABLE 22-continued

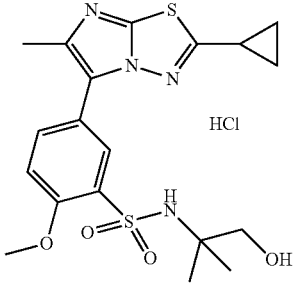 [SMILES: COc1ccc(-c2c(C)nc3sc(C4CC4)nn23)cc1S(=O)(=O)NC(C)(C)CO ; Cl]

The compounds of the embodiments include both a hydrate and solvate of Compound (1) or a pharmacologically acceptable salt thereof.

The Compound (1) can be converted into a pharmacologically acceptable salt thereof according to a conventional method where appropriate. Pharmacologically acceptable salts mean a salt with a pharmaceutically acceptable nontoxic base or acid (for example, inorganic or organic bases and inorganic or organic acids).

Salts derived from pharmaceutically acceptable nontoxic bases include salts prepared with inorganic bases, such as sodium, potassium, calcium, and magnesium salts, and salts with organic bases, such as piperidine, morpholine, pyrrolidine, arginine, and lysine.

Salts derived from pharmaceutically acceptable nontoxic acids include, for example, acid addition salts with mineral acids such as hydrochloric acid, hydrobromic acid, sulfuric acid, and nitric acid; and acid addition salts with organic acids such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

The compounds of the embodiments include a racemate as well as an optically active substance, stereoisomer, and rotamer.

When a compound of the embodiments is an optical isomer having one or more asymmetric carbon atoms, each of the asymmetric carbon atoms may have either an R or S configuration. The present invention includes any optical isomer and a mixture of optical isomers. Moreover, among a mixture of optically active substances, a racemate consisting of equal amounts of each optical isomer is also included in the scope of the present invention. When Compound (1) of the embodiments is a solid or crystal of its racemate, the racemate, a racemic mixture, and a racemic solid solution are also included in the scope of the present invention.

When the compounds of the embodiments have geometric isomers, the present invention includes any of the geometric isomers.

When the compounds of the embodiments have tautomers, the present invention includes any of the tautomers.

The compounds of the embodiments may be a compound labelled with an isotope (e.g., $^3$H, $^{14}$C, or $^{35}$S) or similar elements. These compounds are also included in the present invention.

Furthermore, the compounds of the embodiments may be a deuterated compound in which $^1$H is substituted with $^2$H (D). These compounds are also included in the present invention.

Preparations of the Compounds of the Embodiments

The compounds of the embodiments can be produced for example according to any of the method detailed in Synthetic Route A below or similar methods thereto and other methods described in literatures or similar methods thereto.

Synthetic Route A

[Formula 5]

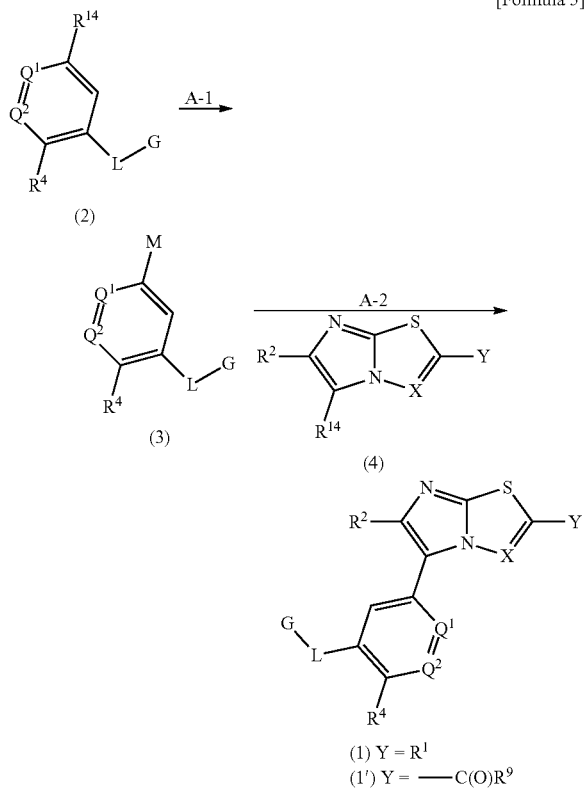

wherein

Y represents $R^1$ or —C(O)$R^9$;

each $R^{14}$ independently represents a bromine, iodine, or chlorine atom;

M represents —B(OH)$_2$, a $C_1$-$C_6$ trialkyltin group, or

[Formula 6]

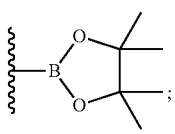

and $R^1$, $R^2$, $R^4$, $R^9$, G, $Q^1$, $Q^2$, X, and L are as defined in the General Formula (1).

Step A-1

A compound represented by General Formula (3) can be produced by converting $R^{14}$ of a compound represented by General Formula (2) into M.

When M of Compound (3) is —B(OH)$_2$ or the functional group depicted below, Step A-1 can be performed at a temperature ranging from room temperature to the reflux temperature by adding a base, such as potassium acetate, triethylamine, or N,N-diisopropylethylamine, and a boronating agent in the presence of a palladium catalyst such as [1,1'-bis(diphenylphosphino)ferrocene]palladium (II) dichloride (PdCl$_2$ (dppf)), [1,1'-bis(diphenylphosphino)ferrocene]palladium (II) dichloride methylene chloride complex (PdCl$_2$ (dppf)•CH$_2$Cl$_2$), tetrakis(triphenylphosphine)palladium (Pd(Ph$_3$P)$_4$), palladium acetate (Pd(OAc)$_2$), tris(dibenzylideneacetone)dipalladium (Pd$_2$(dba)$_3$), or (2-dicyclohexylphosphino-2',4',6'-triisopropylbiphenyl) aminobiphenyl palladium chloride (XPhos Pd G3) in a solvent such as 1,4-dioxane, dimethylsulfoxide, N,N-dimethylformamide, toluene, or benzene. Examples of the boronating agent that can be added include bis(pinacolato) diboron and pinacol borane.

[Formula 7]

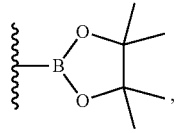

When M of Compound (3) is a $C_1$-$C_6$ trialkyltin group, Step A-1 can be performed, as reaction conditions, at a temperature ranging from room temperature to the reflux temperature by adding stannylating agents such as bis(trimethyltin) or bis(tributyltin) in the presence of a palladium catalyst such as [1,1'-bis(diphenylphosphino) ferrocene]palladium (II) dichloride (PdCl$_2$ (dppf)), tetrakis(triphenylphosphine)palladium (Pd(Ph$_3$P)$_4$), palladium acetate (Pd(OAc)$_2$), or tris(dibenzylideneacetone)dipalladium (Pd$_2$(dba)$_3$) in a solvent such as 1,4-dioxane, tetrahydrofuran, acetonitrile, toluene, or benzene.

Step A-2

A compound represented by General Formula (1) can be produced by coupling a compound represented by General Formula (4) to a compound represented by General Formula (3).

When M of Compound (3) is —B(OH)$_2$ or the functional group depicted below, a typical condition of the Suzuki-Miyaura coupling reaction can be applied to Step A-2. For example, Step A-2 can be performed at a temperature ranging from room temperature to the reflux temperature by adding a base such as potassium carbonate, sodium carbonate, cesium carbonate, sodium hydroxide, potassium hydroxide, tripotassium phosphate, cesium fluoride, triethylamine, or N,N-diisopropylethylamine and using as a catalyst palladium such as bis(triphenylphosphine)palladium (II) dichloride (PdCl$_2$(PPh$_3$)$_2$), [1,1'-bis(diphenylphosphino)ferrocene]palladium (II) dichloride methylene chloride complex (PdCl$_2$(dppf)•CH$_2$Cl$_2$), [1,1'-bis(diphenylphosphino) ferrocene]palladium (II) dichloride (PdCl$_2$(dppf)), tetrakis (triphenylphosphine)palladium (Pd(Ph$_3$P)$_4$), palladium acetate (Pd(OAc)$_2$), tris(dibenzylideneacetone)dipalladium (Pd$_2$(dba)$_3$), 2-dicyclohexylphosphino-2',4',6'-triisopropylbiphenyl)aminobiphenyl palladium chloride (XPhos Pd G3) in a solvent such as dimethylsulfoxide, N,N-dimethylformamide, 1,4-dioxane, toluene, tetrahydrofuran, 1,2-dimethoxyethane, methanol, ethanol, or water or a mixture thereof.

[Formula 8]

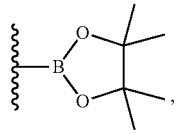

When M of Compound (3) is a $C_1$-$C_6$ trialkyltin group, a typical condition of Migita-Kosugi-Stille crosscoupling reaction can be applied to Step A-2. For example, Step A-2 can be performed at a temperature ranging from room temperature to the reflux temperature by adding preferably copper (I) iodide as an accelerant and using palladium catalyst such as tetrakis(triphenylphosphine)palladium (Pd (Ph₃P)₄), palladium acetate (Pd(OAc)₂), or tris(dibenzylideneacetone)dipalladium (Pd₂(dba)₃) in a solvent such as 1,4-dioxane, tetrahydrofuran, acetonitrile, or toluene. In some cases, the accelerant to be added may be lithium chloride.

When the Compound (4) is represented by Compound (4a) or (4c), the Compound (4a) or (4c) can be produced according to any of the method shown in Synthetic Route B or similar methods thereto and other methods described in literatures or similar methods thereto.

Synthetic Route B

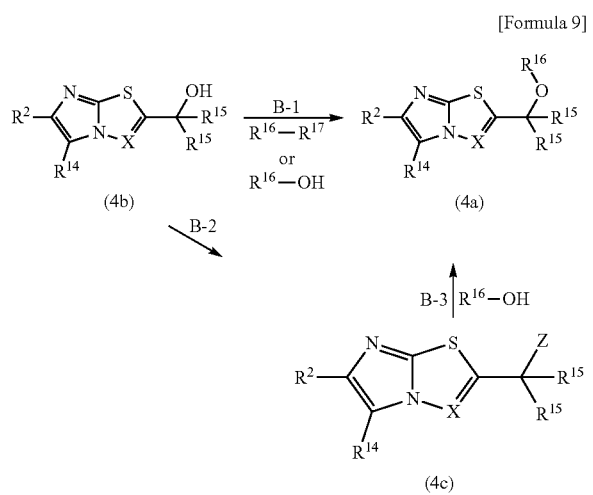

wherein

Z represents a fluorine, chlorine, bromine, or iodine atom; each $R^{15}$ independently represents a $C_1$-$C_6$ alkyl group, a deuterated $C_1$-$C_6$ alkyl group, a $C_3$-$C_{10}$ cycloalkyl group, or a 3- to 10-membered heterocycloalkyl group, and $R^{15}$ may be joined together to form a ring;

$R^{16}$ represents a $C_1$-$C_6$ alkyl group, a deuterated $C_1$-$C_6$ alkyl group, a $C_3$-$C_6$ cycloalkyl group, or a 3- to 10-membered heterocycloalkyl group;

$R^{17}$ represents a chlorine, bromine, or iodine atom, p-toluenesulfonate, methanesulfonate, or trifluoromethanesulfonate; and $R^{14}$, $R^2$, and X are as defined in the General Formula (4).

Step B-1

A compound represented by General Formula (4a) can be produced by alkylating the hydroxy group of a compound represented by General Formula (4b) with $R^{16}$-$R^{17}$.

A typical condition of $S_N2$ reaction can be applied to Step B-1. For example, Step B-1 can be performed at a temperature ranging from 0° C. to the reflux temperature by adding a base such as potassium carbonate, sodium carbonate, cesium carbonate, sodium hydride, sodium hydroxide, potassium hydroxide, tripotassium phosphate, cesium fluoride, triethylamine, or N,N-diisopropylethylamine and using an alkylating agent represented by $R^{16}$-$R^{17}$ such as an alkyl iodide, alkyl bromide, alkyl chloride, alkyl p-toluenesulfonate, alkyl methansulfonate, or alkyl trifluoromethanesulfonate, for example methyl iodide, 2-bromoethanol, or bromomethyl acetate in a solvent such as dimethylsulfoxide, N,N-dimethylformamide, N,N-dimethylacetamide, N-methyl-2-pyrrolidinone, 1,4-dioxane, tetrahydrofuran, or 1,2-dimethoxyethane. In some cases, an accelerant may be also added, wherein the accelerant includes sodium iodide, potassium iodide, tetra n-butylammonium iodide, sodium bromide, potassium bromide, and tetra n-butylammonium bromide.

When $R^{15}$ is trifluoromethyl or a similar group, in addition to the reaction condition mentioned above, a compound represented by General Formula (4a) can be also produced by alkylating the hydroxy group of a compound represented by General Formula (4b) with $R^{16}$—OH.

A typical condition of Mitsunobu reaction can be applied to Step B-1. For example, Step B-1 can be performed at a temperature ranging from 0° C. to the reflux temperature by using a phosphorus reagent such as triphenylphosphine, tributylphosphine, or trimethylphosphine and a diazo compound such as diisopropyl azodicarboxylate (DIAD), diethyl azodicarboxylate (DEAD), or 1,1'-azobis(N,N-dimethylformamide) and adding $R^{16}$—OH such as methanol in a solvent such as tetrahydrofuran, 1,4-dioxane, toluene, or benzene or under solvent free conditions.

Step B-2

A compound represented by General Formula (4c) can be produced by halogenating, preferably fluorinating the hydroxy group of a compound represented by General Formula (4b).

Step B-2 can be performed at a temperature ranging from −78° C. to the reflux temperature by adding a halogenation reagent to a solvent such as methylene chloride, chloroform, tetrahydrofuran, or 1,4-dioxane. When Z of Compound (4c) is a fluorine atom, the halogenation reagent that can be used includes N,N-diethylaminosulfur trifluoride (DAST) and bis(2-methoxyethyl)aminosulfur trifluoride.

Step B-3

A compound represented by General Formula (4a) can be also produced by allowing an alcohol represented by $R^{16}$—OH to act on a compound represented by General Formula (4c).

Step B-3 can be performed, as reaction conditions, at a temperature ranging from room temperature to the reflux temperature by adding an alcohol represented by $R^{16}$—OH such as 3-oxetanol in the absence of solvent or in a solvent such as tetrahydrofuran, 1,4-dioxane, acetonitrile, toluene, or benzene. In some cases, an acid or base can be also added, wherein the acid includes hydrochloric acid, hydrobromic acid, acetic acid, trifluoroacetic acid, and sulfuric acid, and the base includes potassium carbonate, sodium carbonate, cesium carbonate, sodium hydroxide, potassium hydroxide, tripotassium phosphate, cesium fluoride, triethylamine, and N,N-diisopropylethylamine.

The Compound (4) can be produced according to any of the method shown in Synthetic Route C or similar methods thereto and other methods described in literatures or similar methods thereto.

Synthetic Route C

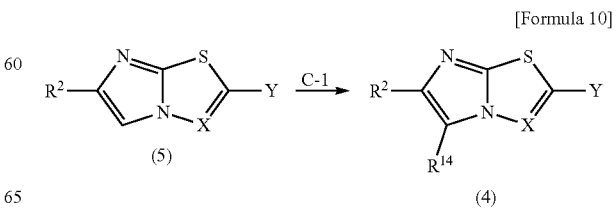

wherein
R$^{14}$ and Y are as defined in the Synthetic Route A; and
R$^2$ and X are as defined in the General Formula (1).

Step C-1

A compound represented by General Formula (4) can be produced by halogenating, preferably iodinating a compound represented by General Formula (5).

Step C-1 can be performed at a temperature of ranging from 0° C. to room temperature by adding a halogenating agent in a solvent such as acetonitrile, N,N-dimethylformamide, methanol, ethanol, methylene chloride, chloroform, acetic acid, or water. When R$^{14}$ of Compound (4) is an iodine atom, an iodinating agent can be added, wherein the iodinating agent includes N-iodosuccinimide, 1,3-diiodo-5,5-dimethylhydantoin, and iodine. When R$^{14}$ is a bromine atom, a brominating agent can be added, wherein the brominating agent includes N-bromosuccinimide, 1,3-dibromo-5,5-dimethylhydantoin, and bromine. In some cases, an acid such as acetic acid, trifluoroacetic acid, or sulfuric acid, iron (III) chloride or aluminum chloride, or a base such as sodium bicarbonate, potassium bicarbonate, potassium carbonate, sodium carbonate, or cesium carbonate can be also added.

When the Compound (5) is represented by Compound (5a), (5c), (5d), or (5e), the Compound (5) can be produced according to any of the method shown in Synthetic Route D or similar methods thereto and other methods described in literatures or similar methods thereto.

Synthetic Route D

[Formula 11]

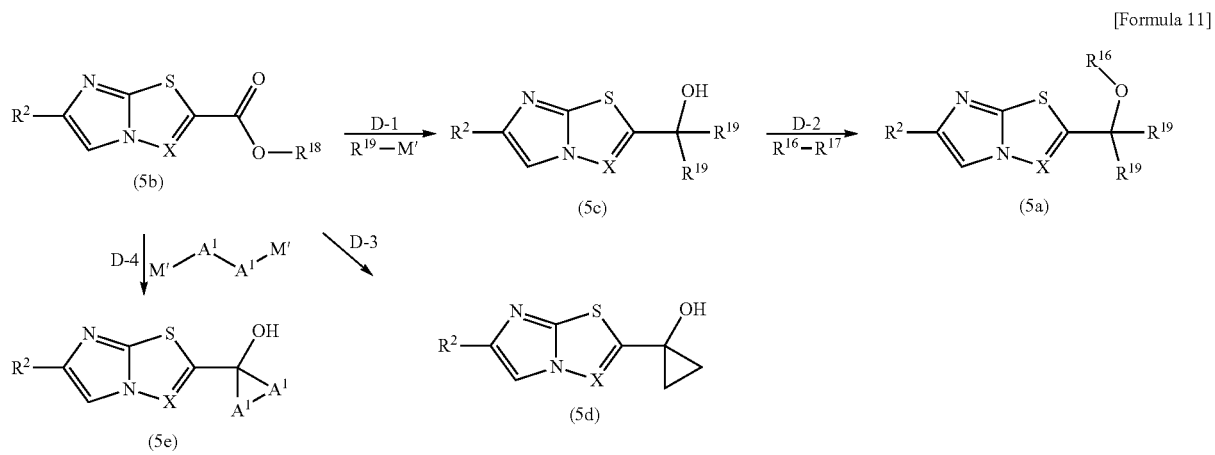

wherein M' represents —MgBr, —MgCl, —MgI, or a lithium atom;
each A$^1$ independently represents a C$_1$-C$_6$ alkylene, a deuterated C$_1$-C$_6$ alkylene, or a C$_3$-C$_6$ cycloalkylene group;
each of R$^{18}$ and R$^{19}$ independently represents a C$_1$-C$_6$ alkyl, C$_3$-C$_{10}$ cycloalkyl, or deuterated C$_1$-C$_6$ alkyl group; and
X, R$^2$, R$^{16}$, and R$^{17}$ are as defined in the Synthetic Route B.

Step D-1

A compound represented by General Formula (5c) can be produced by alkylating the ester moiety of a compound represented by General Formula (5b) with R$^{19}$-M'.

Step D-1 can be performed at a temperature ranging from −78° C. to the reflux temperature by adding an alkylating agent represented by R$^{19}$-M' such as an alkylmagnesium bromide, alkylmagnesium chloride, or alkyllithium, for example methylmagnesium bromide, methylmagnesium chloride, or cyclopropylmagnesium bromide to a solvent such as tetrahydrofuran, diethylether, t-butylmethyl ether, toluene, or hexane. In some cases, an alkyllithium or alkylmagnesium halide that is prepared just before use from an alkyl halide may be used as an alkylating agent.

Step D-2

A compound represented by General Formula (5a) can be produced by alkylating the hydroxy group of a compound represented by General Formula (5c) with R$^{16}$-R$^{17}$ according to a method similar to Step B-1.

Step D-3

A compound represented by General Formula (5d) can be produced by converting the ester moiety of a compound represented by General Formula (5b) with the Kulinkovich Reaction condition. A typical condition of the Kulinkovich Reaction can be used. For example, Step D-3 can be performed at a temperature ranging from −78° C. to the reflux temperature by adding a tetraalkoxy titanate, preferably tetraisopropyl orthotitanate, and an ethylmagnesium halide, preferably ethylmagnesium bromide in a solvent such as diethylether, tetrahydrofuran, or 1,4-dioxane.

Step D-4

In Synthetic Route D, a compound represented by General Formula (5e) can be produced by cyclizing the ester moiety of a compound represented by General Formula (5b) with M'-A$^1$-A$^1$M'.

Step D-4 can be performed, as reaction conditions, at a temperature ranging from −78° C. to the reflux temperature by adding a cyclizing agent represented by M'-A$^1$-A$^1$-M' in a solvent such as tetrahydrofuran, diethylether, t-butylmethyl ether, toluene, or hexane. In some cases, an alkylene dilithium or alkylene dimagnesium dihalide that is prepared just before use from an alkane dihalide may be also used as a cyclizing agent. For example, (butan-1,4-diyl)dimagnesium dibromide that is prepared just before use by allowing metal magnesium to act on 1,4-dibromobutane can be also used.

When the Compound (5) is represented by Compound (5f), (5g), or (5h), the Compound (5f), (5g), or (5h) can be produced according to any of the method shown in Synthetic Route E or similar methods thereto and other methods described in literatures or similar methods thereto.

Synthetic Route E

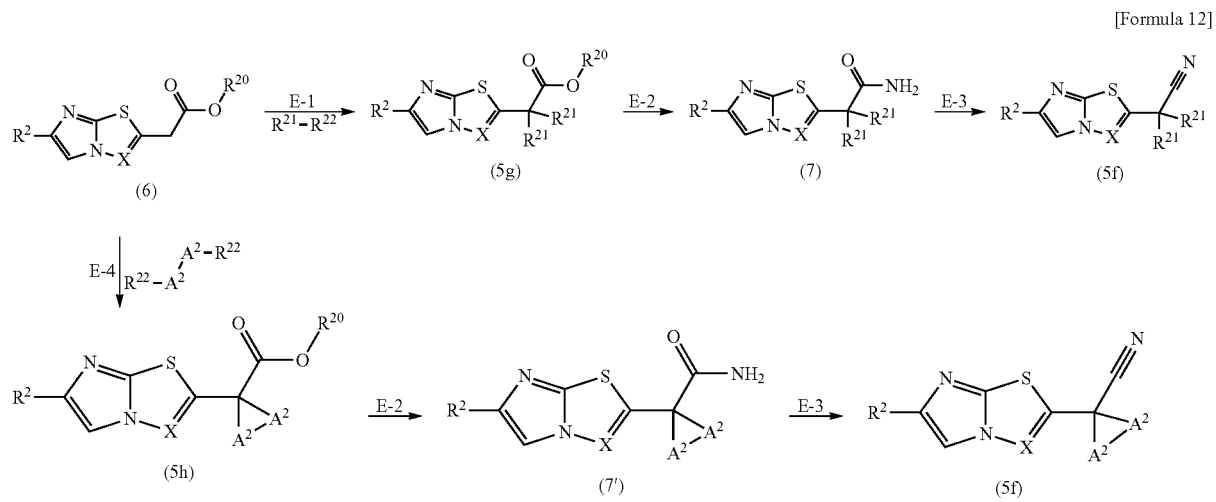

[Formula 12]

wherein
$R^{20}$ represents a $C_1$-$C_6$ alkyl, deuterated $C_1$-$C_6$ alkyl, or $C_3$-$C_6$ cycloalkyl group;
$R^{21}$ represents a $C_1$-$C_6$ alkyl, deuterated $C_1$-$C_6$ alkyl, or $C_3$-$C_6$ cycloalkyl group;
$R^{22}$ represents a chlorine, bromine, or iodine atom, p-toluenesulfonate, methanesulfonate, or trifluoromethanesulfonate;
each $A^2$ independently represents a $C_1$-$C_6$ alkylene or deuterated $C_1$-$C_6$ alkylene group; and
$R^2$ and X are as defined in the Synthetic Route D.

Step E-1
A compound represented by General Formula (5g) can be produced by alkylating a compound represented by General Formula (6) with $R^{21}$-$R^{22}$.

Step E-1 can be performed, as reaction conditions, at a temperature ranging from 0° C. to the reflux temperature by adding a base such as sodium hydride, potassium carbonate, sodium carbonate, cesium carbonate, sodium hydroxide, potassium hydroxide, tripotassium phosphate, cesium fluoride, triethylamine, or N,N-diisopropylethylamine and using an alkylating agent represented by $R^{21}$-$R^{22}$ such as an alkyl iodide, alkyl bromide, alkyl chloride, alkyl p-toluenesulfonate, alkyl methansulfonate, or alkyl trifluoromethanesulfonate, for example methyl iodide or 1,2-dibromoethane in a solvent such as dimethylsulfoxide, N,N-dimethylformamide, N,N-dimethylacetamide, N-methyl-2-pyrrolidinone, 1,4-dioxane, tetrahydrofuran, or 1,2-dimethoxyethane. In some cases, an accelerant may be also added, wherein the accelerant includes sodium iodide, potassium iodide, tetra n-butylammonium iodide, sodium bromide, potassium bromide, and tetra n-butylammonium bromide.

Step E-2
A compound represented by General Formula (7) can be produced by converting a compound represented by General Formula (5g) into a primary amide.

Step E-2 can be performed, as reaction conditions, at a temperature ranging from 0° C. to the reflux temperature by using ammonia or a solution such as methanol, ethanol, 1,4-dioxane, or water containing ammonia, ammonium chloride, ammonium acetate, ammonium formate, or the like in the absence of solvent or in a solvent such as methanol, ethanol, dimethylsulfoxide, N,N-dimethylformamide, 1,4-dioxane, tetrahydrofuran, or water. In some cases, a base may be also added, wherein the base includes potassium carbonate, sodium carbonate, cesium carbonate, sodium hydroxide, potassium hydroxide, tripotassium phosphate, cesium fluoride, triethylamine, and N,N-diisopropylethylamine.

Step E-3
A compound represented by General Formula (5f) can be produced by dehydrating the primary amide moiety of a compound represented by General Formula (7) to convert the moiety into a cyano group.

Step E-3 can be performed, as reaction conditions, at a temperature ranging from 0° C. to the reflux temperature by adding a base such as potassium carbonate, sodium carbonate, cesium carbonate, tripotassium phosphate, cesium fluoride, pyridine, triethylamine, or N,N-diisopropylethylamine and using trifluoroacetic anhydride, acetic anhydride, trifluoromethanesulfonic anhydride, p-toluenesulfonyl chloride, methanesulfonyl chloride, or the like in a solvent such as methylene chloride, 1,4-dioxane, tetrahydrofuran, or acetonitrile.

Step E-4
A compound represented by General Formula (5h) can be produced by cycloalkylating a compound represented by General Formula (6) with $R^{22}$-$A^2$-$A^2$-$R^{22}$.

Step E-4 can be performed, as reaction conditions, at a temperature ranging from 0° C. to the reflux temperature by adding a base such as sodium hydride, potassium carbonate, sodium carbonate, cesium carbonate, sodium hydroxide, potassium hydroxide, tripotassium phosphate, cesium fluoride, triethylamine, or N,N-diisopropylethylamine and using a cycloalkylating agent represented by $R^{22}$-$A^2$-$A^2$-$R^{22}$, such as 1,2-dibromoethane in a solvent such as dimethylsulfoxide, N,N-dimethylformamide, N,N-dimethylacetamide, N-methyl-2-pyrrolidinone, 1,4-dioxane, tetrahydrofuran, or 1,2-dimethoxyethane. In some cases, an accelerant may be also added, wherein the accelerant includes sodium iodide, potassium iodide, tetra n-butylammonium iodide, sodium bromide, potassium bromide, and tetra n-butylammonium bromide.

The Compound (5) can be produced according to any of the method shown in Synthetic Route F or similar methods thereto and other methods described in literatures or similar methods thereto.

Synthetic Route F

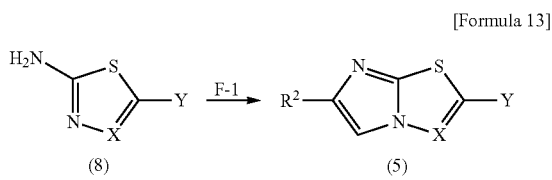

[Formula 13]

wherein
Y is as defined in the Synthetic Route A; and
$R^2$ and X are as defined in the General Formula (1).
Step F-1

A compound represented by General Formula (5) can be produced by mixing a compound represented by General Formula (8) with a suitable α-halocarbonyl compound.

When $R^2$ is a methyl group, Step F-1 can be performed at a temperature ranging from room temperature to the reflux temperature by using bromoacetone or chloroacetone as an α-halocarbonyl compound in a solvent such as ethanol, 2-propanol, acetonitrile, N,N-dimethylformamide, ethyl methyl ketone, acetone, toluene, or benzene. In some cases, an accelerant may be also added wherein the accelerant includes an acid such as hydrochloric acid, hydrobromic acid, acetic acid, trifluoroacetic acid, or sulfuric acid and a base such as potassium carbonate, sodium carbonate, cesium carbonate, sodium hydroxide, potassium hydroxide, tripotassium phosphate, cesium fluoride, triethylamine, or N,N-diisopropylethylamine. Optionally, sodium iodide, potassium iodide, tetra n-butylammonium iodide, sodium bromide, potassium bromide, tetra n-butylammonium bromide, and the like can be also added.

When the Compound (8) is represented by Compound (8a), the Compound (8a) can be produced according to any of the method shown in Synthetic Route G or similar methods thereto and other methods described in literatures or similar methods thereto.

Synthetic Route G

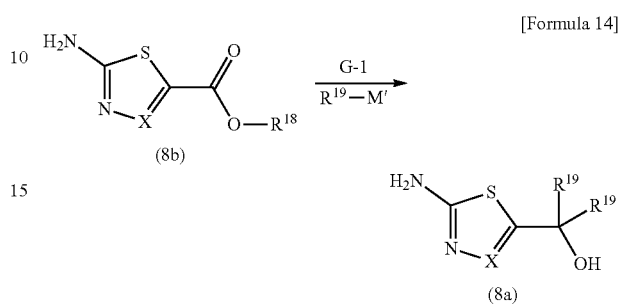

[Formula 14]

wherein $R^{18}$, $R^{19}$, M', and X are as defined in the Synthetic Route D.
Step G-1

A compound represented by General Formula (8a) can be produced by alkylating the ester moiety of a compound represented by General Formula (8b) with $R^{19}$-M'.

Step G-1 can be performed according to a method similar to Step D-1.

When the Compound (2) is represented by Compound (2a), (2c), (2d), (2e), (2f), or (2g), the Compound (2a), (2c), (2d), (2e), (2f), or (2g) can be produced according to any of the method shown in Synthetic Route H or similar methods thereto and other methods described in literatures or similar methods thereto.

Synthetic Route H

[Formula 15]

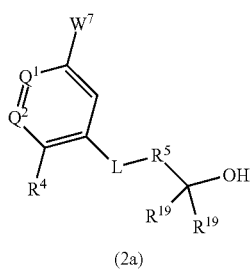

(2a)

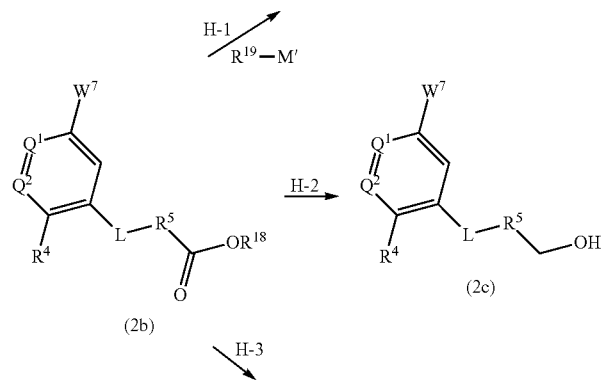

-continued

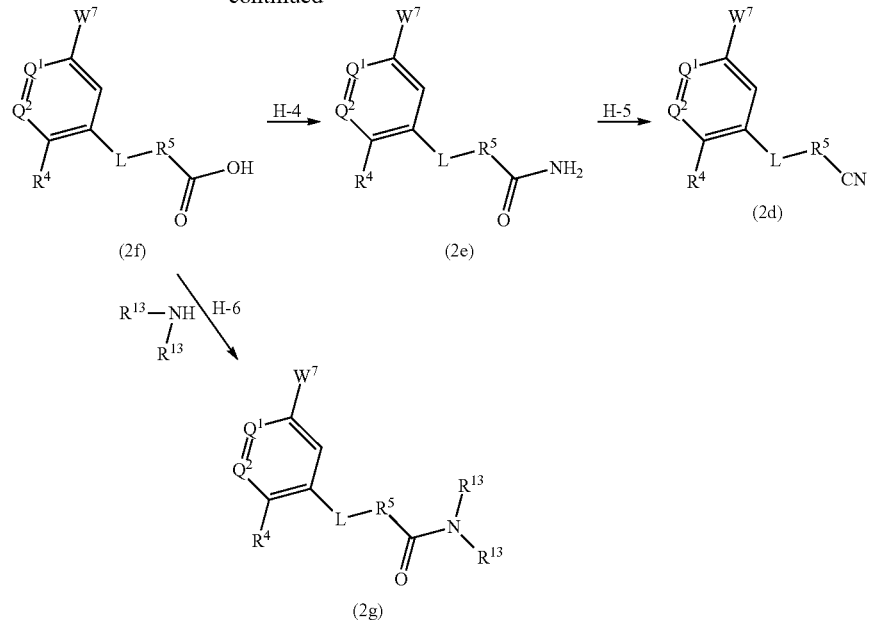

wherein

W⁷ represents a bromine, iodine, or chlorine atom, trifluoromethanesulfonate, or

[Formula 16]

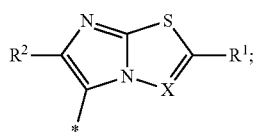

wherein $R^{18}$, $R^{19}$, M', and X are as defined in the Synthetic route D; and $R^1$, $R^2$, $Q^1$, $Q^2$, L, $R^4$, $R^5$, and $R^{13}$ are as defined in the General Formula (1).

Step H-1

A compound represented by General Formula (2a) can be produced by alkylating the ester moiety of a compound represented by General Formula (2b) with $R^{19}$-M'.

Step H-1 can be performed according to a method similar to Step D-1.

Step H-2

A compound represented by General Formula (2c) can be produced by reducing the ester moiety of a compound represented by General Formula (2b).

Step H-2 can be performed, as reaction conditions, at a temperature ranging from −78° C. to the reflux temperature by using a hydride reducing agent such as diisobutylaluminum hydride, lithium aluminum hydride, lithium borohydride, sodium borohydride, sodium bis(2-methoxyethoxy)aluminum hydride (Red-Al), or lithium tri(sec-butyl) borohydride in a solvent such as methanol, ethanol, tetrahydrofuran, diethylether, methylene chloride, toluene, benzene, or hexane or a mixture thereof.

Step H-3

A compound represented by General Formula (2f) can be produced by hydrolyzing the ester moiety of a compound represented by General Formula (2b).

Step H-3 can be performed, as reaction conditions, at a temperature ranging from −78° C. to the reflux temperature by using an alkali metal salt such as lithium hydroxide, sodium hydroxide, potassium hydroxide, potassium carbonate, sodium carbonate, or cesium carbonate in a solvent such as water, methanol, ethanol, 1-propanol, 2-propanol, tetrahydrofuran, or 1,4-dioxane or an aqueous mixture thereof.

Step H-4

A compound represented by General Formula (2e) can be produced by converting the carboxy group of a compound represented by General Formula (2f) into a primary amide.

Step H-4 can be performed, as reaction conditions, at a temperature ranging from 0° C. to room temperature, optionally at the reflux temperature by using a condensation agent such as 1-[bis(dimethylamino)methylene]-1H-1,2,3-triazolo[4,5-b]pyridinium-3-oxide hexafluorophosphate (HATU), 1-ethyl-3-(3-dimethylaminopropyl)carbodiimide (EDCI), or N,N'-dicyclohexylcarbodiimide (DCC) and adding ammonium chloride or ammonia in a solvent such as methanol, ethanol, 1,4-dioxane, or water as an ammonia source in a solvent such as N,N-dimethylformamide, N,N-dimethylacetamide, N-methyl-2-pyrrolidone, methylene chloride, acetonitrile, toluene, benzene, 1,4-dioxane, or tetrahydrofuran. A base such as triethylamine or N,N-diisopropylethylamine may also be optionally added. N,N-dimethylaminopyridine, pyridine, 1-hydroxibenzotriazole (HOBT), or 1-hydroxybenzotriazole (HOAt) may also be optionally added as an accelerant.

Step H-5

A compound represented by General Formula (2d) can be produced by dehydrating the primary amide moiety of a compound represented by General Formula (2e) to convert into a cyano group.

Step H-5 can be performed according to a method similar to Step E-3.

Step H-6

In Synthetic Route H, a compound represented by General Formula (2g) can be produced by amidating the carboxy group of a compound represented by General Formula (2f) with $R^{13}$—NH—$R^{13}$.

Step H-6 can be performed according to a method similar to Step H-4 by using 1-amino-2-methyl-2-propanol, or alternatively a primary amine, secondary amine represented by $R^{13}$—NH—$R^{13}$, or a salt thereof such as methylamine, dimethylamine, or their tetrahydrofuran solution, instead of the ammonia source.

When the Compound (2) is represented by Compound (2h), (2i), (2j), (2k), (2l), or (2m), the Compound (2h), (2i), (2j), (2k), (2l), or (2m) can be produced according to any of the method shown in Synthetic Route I or similar methods thereto and other methods described in literatures or similar methods thereto.

Synthetic Route I optionally at the reflux temperature by adding an acid such as trifluoroacetic acid, p-toluenesulfonic acid, sulfuric acid, hydrochloric acid, hydrobromic acid, boron trifluoride diethyl ether complex, boron tribromide, or aluminum chloride in a solvent such as methylene chloride, chloroform, 1,4-dioxane, tetrahydrofuran, toluene, benzene, or water.

Step I-2

A compound represented by General Formula (2h) can be produced by allowing $R^{16}$-$R^{17}$ to act on a compound represented by General Formula (2m).

Step I-2 can be performed by using $R^{16}$-$R^{17}$ according to a method similar to Step B-1.

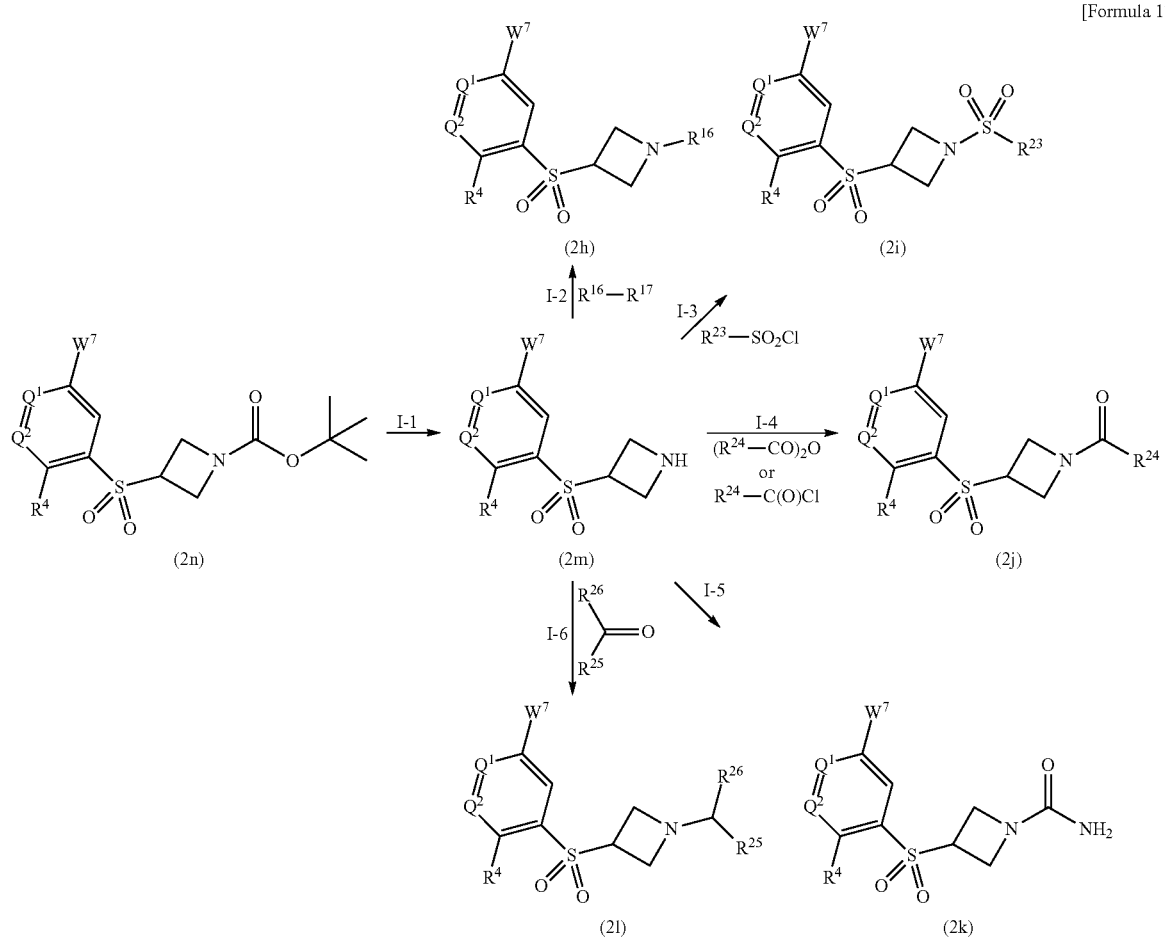

[Formula 17]

wherein
each of $R^{23}$ and $R^{24}$ represents a $C_1$-$C_6$ alkyl, deuterated $C_1$-$C_6$ alkyl, or $C_3$-$C_6$ cycloalkyl group;
each of $R^{25}$ and $R^{26}$ represents H, a $C_1$-$C_6$ alkyl, deuterated $C_1$-$C_6$ alkyl, $C_3$-$C_6$ cycloalkyl, or hydroxy$C_1$-$C_6$ alkyl group;
$R^{16}$ and $R^{17}$ are as defined in the Synthetic Route B; $W^7$ is as defined in the Synthetic Route H; and $Q^1$, $Q^2$, and $R^4$ are as defined in the General Formula (1).

Step I-1

A compound represented by General Formula (2m) can be produced by removing the t-butyloxycarbonyl group of a compound represented by General Formula (2n).

Step I-1 can be performed, as reaction conditions, at a temperature ranging from −78° C. to room temperature, Step I-3

A compound represented by General Formula (2i) can be produced by sulfonylating a compound represented by General Formula (2m) with $R^{23}$—$SO_2Cl$.

Step I-3 can be performed, as reaction conditions, at a temperature ranging from −78° C. to room temperature, optionally at the reflux temperature by preferably adding a base such as potassium carbonate, sodium carbonate, cesium carbonate, sodium hydroxide, potassium hydroxide, tripotassium phosphate, cesium fluoride, pyridine, N,N-dimethyl-4-aminopyridine, N-methylimidazole, triethylamine, or N,N-diisopropylethylamine and adding a sulfonylating agent represented by $R^{23}$—$SO_2Cl$ such as sulfonyl chloride, for example methanesulfonyl chloride in a solvent such as methylene chloride, chloroform, 1,4-dioxane, tetrahydrofuran, toluene, benzene, or water or a mixture thereof.

Step I-4

A compound represented by General Formula (2j) can be produced by acylating a compound represented by General Formula (2m) with ($R^{24}$—CO)$_2$O or $R^{24}$—C(O)Cl.

Step I-4 can be performed, as reaction conditions, at a temperature ranging from −78° C. to room temperature, optionally at the reflux temperature by preferably adding a base such as potassium carbonate, sodium carbonate, cesium carbonate, sodium hydroxide, potassium hydroxide, tripotassium phosphate, cesium fluoride, pyridine, N,N-dimethyl-4-aminopyridine, N-methylimidazole, triethylamine, or N,N-diisopropylethylamine and adding an acylating agent such as acyl chloride or carboxylic anhydride represented by ($R^{24}$—CO)$_2$O or $R^{24}$—C(O)Cl for example acetic anhydride in a solvent such as methylene chloride, chloroform, 1,4-dioxane, tetrahydrofuran, toluene, benzene, or water.

Step I-5

A compound represented by General Formula (2k) can be produced via urea formation with to a compound represented by General Formula (2m).

Step I-5 can be performed, as reaction conditions, at a temperature ranging from 0° C. to room temperature, optionally at the reflux temperature by adding a agent for urea formation such as trimethylsilyl isocyanate in a solvent such as methylene chloride, chloroform, 1,4-dioxane, tetrahydrofuran, toluene, benzene, or water. In some cases, a base can be also added, wherein the base includes potassium carbonate, sodium carbonate, cesium carbonate, sodium hydroxide, potassium hydroxide, tripotassium phosphate, cesium fluoride, pyridine, N,N-dimethyl-4-aminopyridine, N-methylimidazole, triethylamine, and N,N-diisopropylethylamine.

Step I-6

A compound represented by General Formula (2l) can be produced by reductively alkylating a compound represented by General Formula (2m) with $R^{25}$C(O)$R^{26}$.

Step I-6 can be performed, as reaction conditions, at a temperature ranging from −78° C. to room temperature, optionally at the reflux temperature by adding an aldehyde, ketone, or a similar compound represented by $R^{25}$C(O)$R^{26}$, for example aqueous formalin solution or glycolaldehyde dimer and adding a reducing agent such as sodium triacetoxyborohydride, sodium cyanoborohydride, sodium borohydride, lithium borohydride, borane dimethylsulfide complex, or lithium aluminum hydride in a solvent such as methylene chloride, chloroform, 1,4-dioxane, tetrahydrofuran, toluene, benzene, methanol, or ethanol. An accelerant may be optionally added, wherein the accelerant includes an acid such as trifluoroacetic acid, p-toluenesulfonic acid, boron trifluoride diethyl ether complex, boron tribromide, aluminum chloride, chlorotrimethylsilane, or tetraalkoxy titanate.

When the Compound (2) is represented by Compound (2o), (2p), (2q), or (2r), the Compound (2o), (2p), (2q), or (2r) can be produced according to any of the method shown in Synthetic Route J or similar methods thereto and other methods described in literatures or similar methods thereto.

Synthetic Route J

[Formula 18]

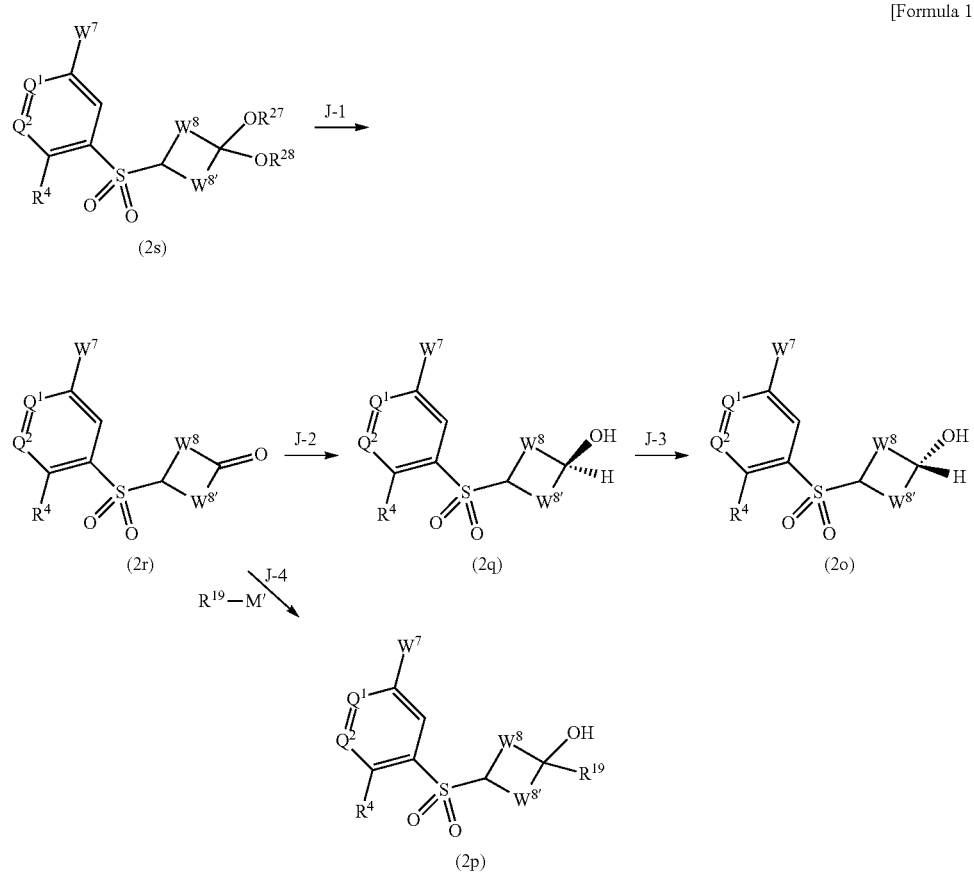

wherein
each of $W^8$ and $W^{8'}$ independently represents a $C_1$-$C_6$ alkylene group;
each of $R^{27}$ and $R^{28}$ is independently selected from the group consisting of H, a $C_1$-$C_6$ alkyl group, a deuterated $C_1$-$C_6$ alkyl group, and a $C_3$-$C_6$ cycloalkyl group, and $R^{27}$ and $R^{28}$ may be joined together to form a ring;
$R^{19}$ and M' are as defined in the Synthetic Route D; $W^7$ is as defined in the Synthetic Route H; and $Q^1$, $Q^2$, and $R^4$ are as defined in the General Formula (1).

Step J-1

A compound represented by General Formula (2r) can be produced by converting the acetal moiety of a compound represented by General Formula (2s), into the ketone moiety.

Step J-1 can be performed, as reaction conditions, at a temperature ranging from −78° C. to the reflux temperature by adding an acid such as trifluoroacetic acid, p-toluenesulfonic acid, sulfuric acid, hydrochloric acid, or hydrobromic acid, boron trifluoride diethyl ether complex, boron tribromide, or aluminum chloride in a solvent such as water, acetone, methylene chloride, chloroform, 1,4-dioxane, tetrahydrofuran, toluene, benzene, methanol, or ethanol.

Step J-2

A compound represented by General Formula (2q) can be produced by reducing the ketone moiety of a compound represented by General Formula (2r).

Step J-2 can be performed according to a method similar to Step H-2.

Step J-3

A compound represented by General Formula (2o) can be produced by reversing the stereochemistry of a hydroxy group of a compound represented by General Formula (2q) via the Mitsunobu reaction. More specifically, Step J-3 can be performed by introducing an O-acyl group using a typical Mitsunobu reaction in the first step and removing the introduced acyl group in the second step.

The Mitsunobu reaction in the first step can be performed, as reaction conditions, at a temperature ranging from 0° C. to the reflux temperature by using a phosphorus reagent such as triphenylphosphine, tributylphosphine, or trimethylphosphine and a diazo compound such as diisopropyl azodicarboxylate (DIAD), diethyl azodicarboxylate (DEAD), or 1,1'-azobis(N,N-dimethylformamide) and adding a carboxylic acid such as acetic acid or p-nitrobenzoic acid in a solvent such as tetrahydrofuran, 1,4-dioxane, toluene, or benzene or under solvent free conditions.

Removing the acyl group in the second step can be performed, as reaction conditions, at a temperature ranging from 0° C. to the reflux temperature by using an alkali metal salt such as potassium carbonate, sodium carbonate, lithium hydroxide, sodium hydroxide, or potassium hydroxide in a solvent such as water, methanol, ethanol, 1-propanol, 2-propanol, tetrahydrofuran, or 1,4-dioxane or a mixture thereof.

Step J-4

A compound represented by General Formula (2p) can be produced by alkylating the ketone group of a compound represented by General Formula (2r) with $R^{19}$-M'.

Step J-4 can be performed according to a method similar to Step D-1.

When the Compound (2) is represented by Compound (2t), the Compound (2t) can be produced according to any of the method shown in Synthetic Route K or similar methods thereto and other methods described in literatures or similar methods thereto.

Synthetic Route K

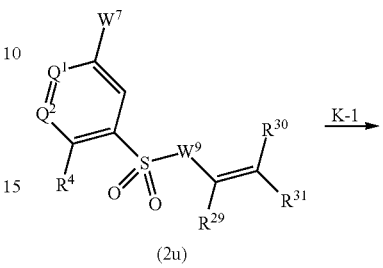

[Formula 19]

wherein
$W^9$ represents a $C_1$-$C_6$ alkylene group;
each of $R^{29}$, $R^{30}$, and $R^{32}$ is independently selected from H, a $C_1$-$C_6$ alkyl group, a deuterated $C_1$-$C_6$ alkyl group, and a $C_3$-$C_6$ cycloalkyl group; and
$W^7$ is as defined in the Synthetic Route H; and $Q^1$, $Q^2$, and $R^4$ are as defined in the General Formula (1).

A compound represented by General Formula (2t) can be produced by oxidizing a double bond of a compound represented by General Formula (2u) to produce a diol.

Step K-1 can be performed, as reaction conditions, at a temperature ranging from 0° C. to room temperature, optionally at the reflux temperature by adding an oxidizing agent such as osmium tetraoxide or ruthenium tetraoxide, and preferably allowing a reoxidizing agent such as N-methylmorpholine N-oxide, trimethylamine N-oxide, or t-butylhydroperoxide to coexist in a solvent such as water, tetrahydrofuran, acetone, t-butanol, or 1,4-dioxane or a mixture thereof. In some cases, an accelerant may be added, wherein the accelerant includes pyridine, 2,6-lutidine, and methanesulfonylamide.

When the Compound (2) is represented by Compound (2v), (2w), or (2x), the Compound (2v), (2w), or (2x) can be produced according to any of the method shown in Synthetic Route L or similar methods thereto and other methods described in literatures or similar methods thereto.

Synthetic Route L

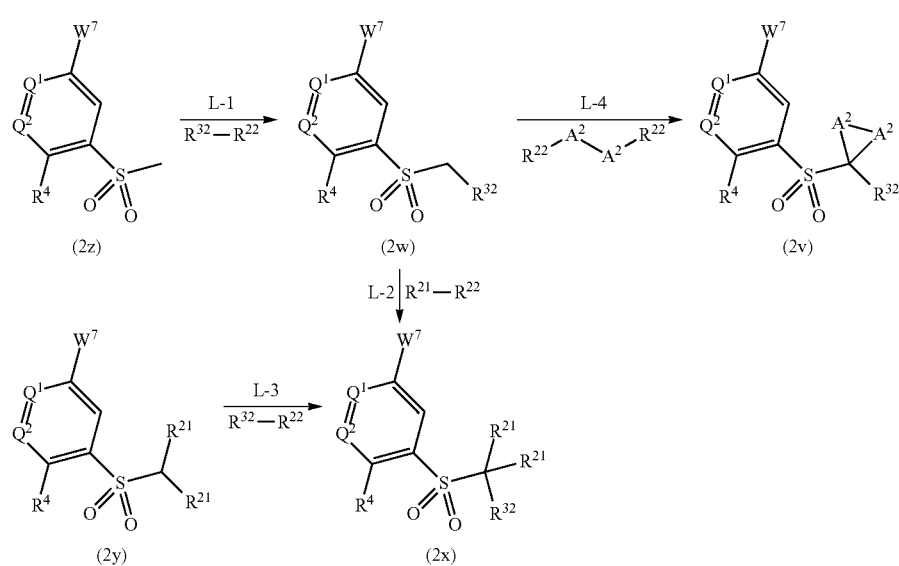

[Formula 20]

wherein
$R^{32}$ represents a $C_1$-$C_6$ alkyl, deuterated $C_1$-$C_6$ alkyl, $C_2$-$C_6$ alkenyl, $C_3$-$C_6$ cycloalkyl, or $C_1$-$C_6$ alkoxycarbonyl group;
$R^{21}$, $R^{22}$, and $A^2$ are as defined in the Synthetic Route E; $W^7$ is as defined in the Synthetic Route H; and $Q^1$, $Q^2$, and $R^4$ are as defined in the General Formula (1).

Step L-1
A compound represented by General Formula (2w) can be produced by alkylating a compound represented by General Formula (2z) with $R^{32}$-$R^{22}$.

Step L-1 can be performed, as reaction conditions, at a temperature ranging from −78° C. to room temperature, optionally at the reflux temperature by adding a base such as lithium diisopropylamide, lithium hexamethyldisilazide, sodium hexamethyldisilazide, potassium hexamethyldisilazide, n-butyllithium, sec-butyllithium, t-butyllithium, phenyllithium, potassium t-butoxide, sodium hydride, potassium hydride, sodium carbonate, potassium carbonate, cesium carbonate, or tripotassium phosphate and using an alkylating agent or an alkoxycarbonylating agent represented by $R^{32}$-$R^{22}$ such as an alkyl iodide, alkyl bromide, alkyl chloride, alkyl p-toluenesulfonate, alkyl methansulfonate, alkyl trifluoromethanesulfonate, or chloroformate, for example, methyl iodide, or 1-bromo-3-methyl-2-butene in a solvent such as tetrahydrofuran, diethylether, t-butylmethyl ether, N,N-dimethylformamide, toluene, or hexane.

Step L-2
A compound represented by General Formula (2x) can be produced by alkylating a compound represented by General Formula (2w) with $R^{21}$-$R^{22}$.

Step L-2 can be performed, for example, by using methyl iodide according to a method similar to Step L-1.

Step L-3
A compound represented by General Formula (2x) can be also produced by alkylating a compound represented by General Formula (2y) with $R^{32}$-$R^{22}$.

Step L-3 can be performed, for example, by using methyl iodide according to a method similar to Step L-1.

Step L-4
A compound represented by General Formula (2v) can be produced by cycloalkylating a compound represented by General Formula (2w) with $R^{22}$-$A^2$-$A^2$-$R^{22}$.

Step L-4 can be performed, for example, by using 1,2-dibromoethane according to a method similar to Step E-4.

When the Compound (2) is represented by Compound (2aa), the Compound (2aa) can be produced according to any of the method shown in Synthetic Route M or similar methods thereto and other methods described in literatures or similar methods thereto.

Synthetic Route M

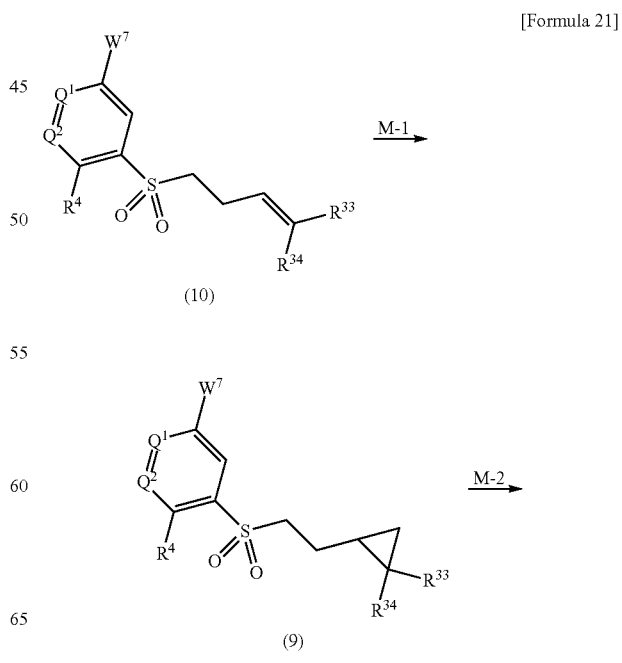

[Formula 21]

-continued

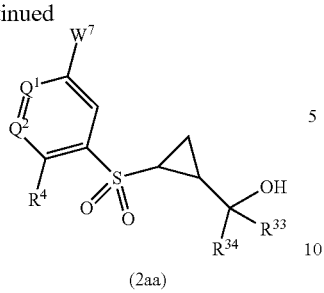

(2aa)

wherein
each of $R^{33}$ and $R^{34}$ independently represents a $C_1$-$C_6$ alkyl, deuterated $C_1$-$C_6$ alkyl, $C_2$-$C_6$ alkenyl, or $C_3$-$C_6$ cycloalkyl group;
$W^7$ is as defined in the Synthetic Route H; and $Q^1$, $Q^2$, and $R^4$ are as defined in the General Formula (1).

Step M-1

A compound represented by General Formula (9) can be produced by epoxidizing a double bond of a compound represented by General Formula (10).

Step M-1 can be performed, as reaction conditions, at a temperature ranging from −20° C. to the reflux temperature by adding an oxidizing agent such as 3-chloroperbenzoic acid, hydrogen peroxide aqueous solution, or dimethyldioxirane in a solvent such as methylene chloride, chloroform, N,N-dimethylformamide, 1,4-dioxane, tetrahydrofuran, 1,2-dimethoxyethane, or water. In some cases, a base may be also added, wherein the base includes sodium bicarbonate, potassium bicarbonate, sodium carbonate, potassium carbonate, sodium hydroxide, and potassium hydroxide.

Step M-2

A compound represented by General Formula (2aa) can be produced via intramolecular cyclopropanation of a compound represented by General Formula (9).

Step M-2 can be performed, as reaction conditions, at a temperature ranging from −78° C. to room temperature, optionally at the reflux temperature by adding a base such as lithium diisopropylamide, lithium hexamethyldisilazide, sodium hexamethyldisilazide, potassium hexamethyldisilazide, n-butyllithium, sec-butyllithium, t-butyl lithium, phenyllithium, sodium hydride, potassium hydride, sodium carbonate, potassium carbonate, cesium carbonate, or tripotassium phosphate in a solvent such as tetrahydrofuran, diethyl ether, t-butylmethyl ether, toluene, or hexane.

When the Compound (2) is represented by Compound (2ab), the Compound (2ab) can be produced according to any of the method shown in Synthetic Route N or similar methods thereto and other methods described in literatures or similar methods thereto.

Synthetic Route N

[Formula 22]

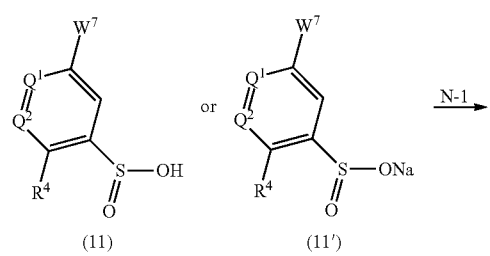

-continued

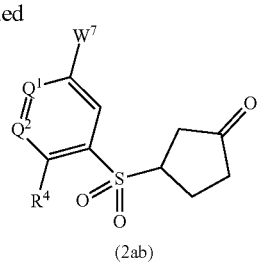

(2ab)

wherein $W^7$ is as defined in the Synthetic Route H; and $Q^1$, $Q^2$, and $R^4$ are as defined in the General Formula (1).

Step N-1

A compound represented by General Formula (2ab) can be produced by allowing 2-cyclopenten-1-one to act on a compound represented by General Formula (11) or (11').

Step N-1 can be performed, as reaction conditions, at a temperature ranging from room temperature to the reflux temperature by adding an acid such as hydrochloric acid, acetic acid, trifluoroacetic acid, sulfuric acid, hydrobromic acid, boron trifluoride diethyl ether complex, aluminum chloride, or trimethylsilyl chloride and allowing 2-cyclopenten-1-one to act thereon in a solvent such as tetrahydrofuran, 1,4-dioxane, acetonitrile, toluene, methylene chloride, chloroform, or water or a mixture thereof.

When the Compound (2) is represented by Compound (2ac), the Compound (2ac) can be produced according to any of the method shown in Synthetic Route O or similar methods thereto and other methods described in literatures or similar methods thereto.

Synthetic Route O

[Formula 23]

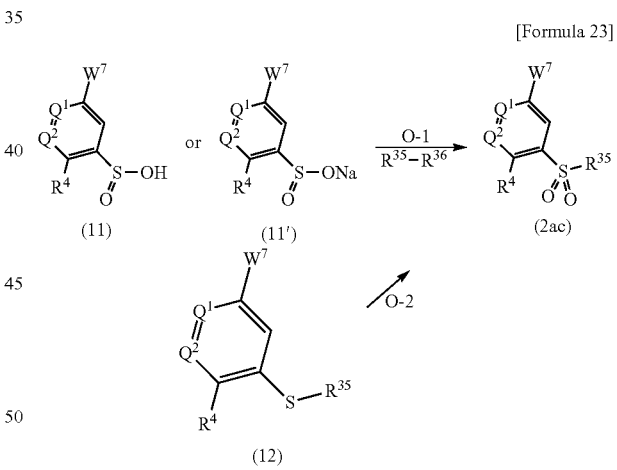

wherein
$R^{35}$ represents G, a hydroxy$C_1$-$C_6$ alkyl group optionally having a substituent, a $C_1$-$C_6$ alkyl group optionally having a substituent, a deuterated $C_1$-$C_6$ alkyl group optionally having a substituent, a $C_2$-$C_6$ alkenyl group optionally having a substituent, a $C_3$-$C_6$ cycloalkyl group optionally having a substituent, a $C_5$-$C_8$ bicycloalkyl group optionally having a substituent, a 3- to 10-membered heterocycloalkyl group optionally having a substituent, a phenyl group optionally having a substituent, a heteroaryl group optionally having a substituent, a phenylmethyl group optionally having a substituent, or a heteroarylmethyl group optionally having a substituent;

$R^{36}$ represents a chlorine, bromine, or iodine atom, p-toluenesulfonate, methanesulfonate, or trifluoromethanesulfonate;

$W^7$ is as defined in the Synthetic Route H; and $Q^1$, $Q^2$, $R^4$, and G are as defined in the General Formula (1).

Step O-1

A compound represented by General Formula (2ac) can be produced by alkylating a compound represented by General Formula (11) or (11') with $R^{35}$-$R^{36}$.

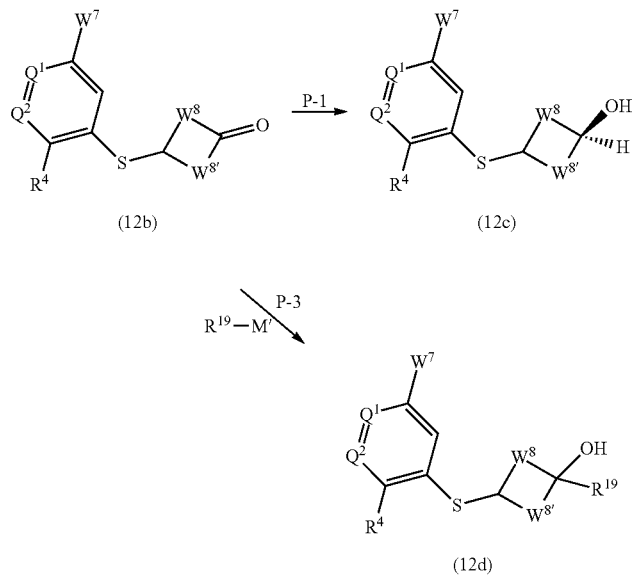
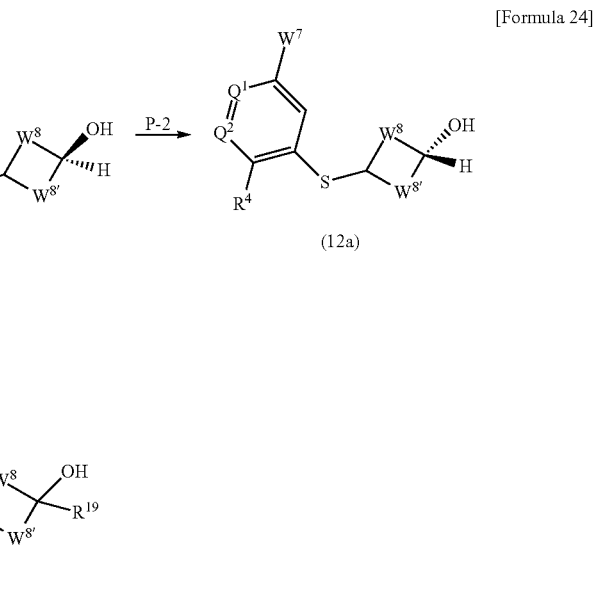

[Formula 24]

A typical condition of $S_N2$ reaction can be applied to Step O-1. For example, Step O-1 can be performed at a temperature ranging from 0° C. to the reflux temperature by optionally adding a base such as sodium hydride, potassium carbonate, sodium carbonate, cesium carbonate, sodium hydroxide, potassium hydroxide, tripotassium phosphate, cesium fluoride, triethylamine, or N,N-diisopropylethylamine and using an alkylating agent represented by $R^{35}$-$R^{36}$ such as an alkyl iodide, alkyl bromide, alkyl chloride, alkyl p-toluenesulfonate, alkyl methansulfonate, or alkyl trifluoromethanesulfonate, for example methyl iodide or bromomethyl acetate in a solvent such as dimethylsulfoxide, N,N-dimethylformamide, N,N-dimethylacetamide, N-methyl-2-pyrrolidinone, 1,4-dioxane, tetrahydrofuran, or 1,2-dimethoxyethane. In some cases, an accelerant may be also added, wherein the accelerant includes sodium iodide, potassium iodide, tetra n-butylammonium iodide, sodium bromide, potassium bromide, and tetra n-butylammonium bromide.

Step O-2

A compound represented by General Formula (2ac) can be also produced by oxidizing the sulfide moiety of a compound represented by General Formula (12).

For example, Step O-2 can be performed, as reaction conditions, at a temperature ranging from −20° C. to the reflux temperature by adding an oxidizing agent such as 3-chloroperbenzoic acid, magnesium monoperoxyphthalate hexahydrate, hydrogen peroxide aqueous solution, or sodium hypochlorite in a solvent such as methylene chloride, chloroform, N,N-dimethylformamide, 1,4-dioxane, tetrahydrofuran, 1,2-dimethoxyethane, or water. In some cases, a base may be added, wherein the base includes such as sodium bicarbonate, potassium bicarbonate, sodium carbonate, and potassium carbonate.

When the Compound (12) is represented by Compound (12a), (12c), or (12d), the Compound (12a), (12c), or (12d) can be produced according to any of the method shown in Synthetic Route P or similar methods thereto and other methods described in literatures or similar methods thereto.

Synthetic Route P wherein $W^8$, $W^{8'}$, $R^{19}$, and M' are as defined in the Synthetic Route J; $W^7$ is as defined in the Synthetic Route H; and $Q^1$, $Q^2$, and $R^4$ are as defined in the General Formula (1).

Step P-1

A compound represented by General Formula (12c) can be produced by reducing a compound represented by General Formula (12b).

Step P-1 can be performed according to a method similar to Step H-2.

Step P-2

A compound represented by General Formula (12a) can be produced by reversing the stereochemistry of the hydroxy group of a compound represented by General Formula (12c) via the Mitsunobu reaction.

Step P-2 can be performed according to a method similar to Step J-3.

Step P-3

A compound represented by General Formula (12d) can be produced by alkylating the ketone group of a compound represented by General Formula (12b) with $R^{19}$-M'.

Step P-3 can be performed according to a method similar to Step D-1.

The Compound (12) can be produced according to any of the method shown in Synthetic Route Q or similar methods thereto and other methods described in literatures or similar methods thereto.

Synthetic Route Q

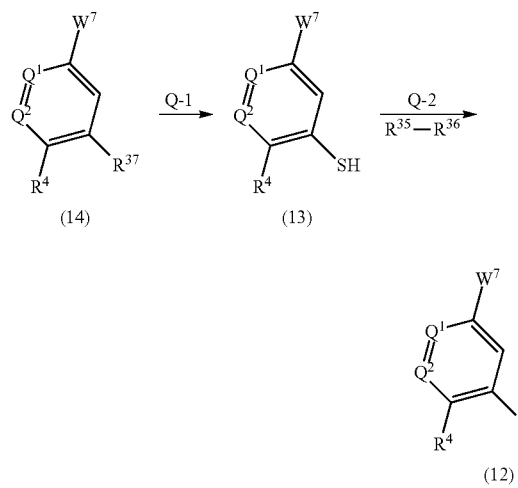

wherein $R^{37}$ represents a fluorine or chlorine atom;

$R^{35}$ and $R^{36}$ are as defined in the Synthetic Route O; $W^7$ is as defined in the Synthetic Route H; and $Q^1$, $Q^2$, and $R^4$ are as defined in the General Formula (1). A compound represented by General Formula (13) obtained from Step Q-1 can be used for Step Q-2 without purification to produce General Formula (12).

Step Q-1

A compound represented by General Formula (13) can be produced by thiolating a compound represented by General Formula (14).

Step Q-1 can be performed, as reaction conditions, at a temperature ranging from 0° C. to room temperature, optionally at the reflux temperature by adding sodium hydrogensulfide or sodium sulfide in a solvent such as N,N-dimethylformamide, N,N-dimethylacetamide, N-methyl-2-pyrrolidone, methylene chloride, 1,4-dioxane, or tetrahydrofuran. A base may be also optionally added, wherein the base includes sodium bicarbonate, potassium bicarbonate, sodium carbonate, potassium carbonate, triethylamine, and N,N-diisopropylethylamine. This reaction may also use thioacetic acid or thiourea instead of sodium hydrogensulfide and sodium sulfide as described above. In this case, an additional reaction may be required after this reaction, wherein the additional reaction is performed at a temperature ranging from 0° C. to the reflux temperature by using an alkali metal salt such as lithium hydroxide, sodium hydroxide, or potassium hydroxide in a solvent such as water, methanol, ethanol, 1-propanol, 2-propanol, tetrahydrofuran, or 1,4-dioxane or a mixture thereof.

Step Q-2

A compound represented by General Formula (12) can be produced by alkylating a compound represented by General Formula (13) with $R^{35}$-$R^{36}$.

Step Q-2 can be performed according to a method similar to Step O-1.

The Compound (11) or (11') or a compound represented by General Formula (20) can be produced according to any of the method shown in Synthetic Route R or similar methods thereto and other methods described in literatures or similar methods thereto.

Synthetic Route R

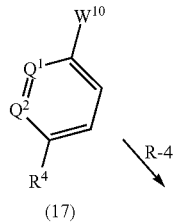

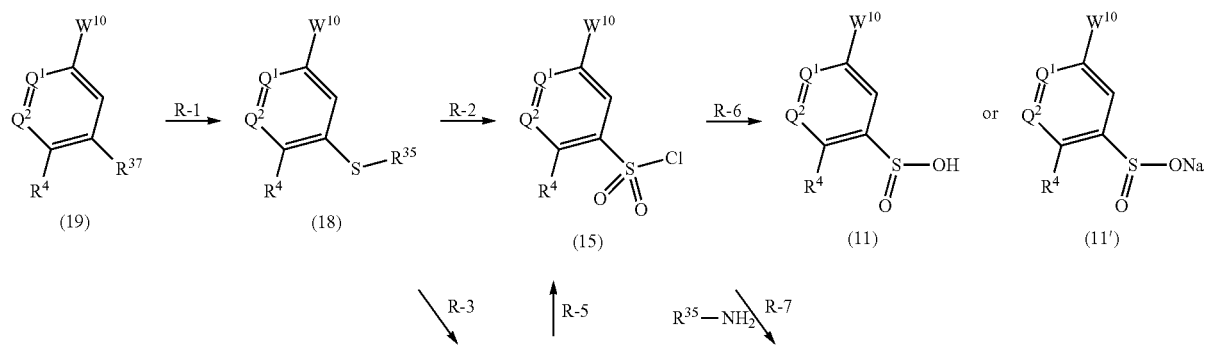

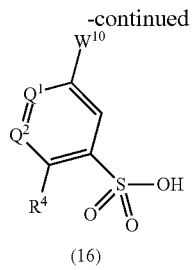

(16)

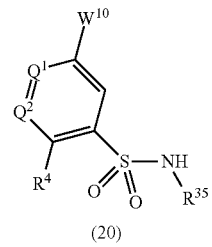

(20)

wherein $W^{10}$ represents a bromine, iodine, chlorine atom, trifluoromethanesulfonate, or

[Formula 27]

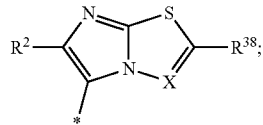

$R^{38}$ represents $R^1$ or —C(O)$R^9$;

$R^{35}$ and $R^{37}$ are as defined in the Synthetic Route Q; and $Q^2$, $Q^2$, X, $R^1$, $R^2$, $R^4$, and $R^9$ are as defined in the General Formula (1).

Step R-1

A compound represented by General Formula (18) can be produced by sulfidation of a compound represented by General Formula (19).

Step R-1 can be performed, as reaction conditions, at a temperature ranging from 0° C. to room temperature, optionally at the reflux temperature by adding a suitable sulfidation agent such as benzyl mercaptan or thioglycolic acid ester in a solvent such as N,N-dimethylformamide, N,N-dimethylacetamide, N-methyl-2-pyrrolidone, methylene chloride, 1,4-dioxane, or tetrahydrofuran. A base may be also optionally added, wherein the base includes sodium hydride, sodium bicarbonate, potassium bicarbonate, sodium carbonate, potassium carbonate, triethylamine, and N,N-diisopropylethylamine.

Step R-2

When $R^{35}$ of a compound represented by General Formula (18) is a benzyl group, a compound represented by General Formula (15) can be produced by converting the thiobenzyl group into a sulfonyl chloride group.

Step R-2 can be performed at a temperature ranging from −78° C. to the reflux temperature by adding N-chlorosuccinimide, 1,3-dichloro-5,5-dimethylimidazolidin-2,4-dione, sulfuryl chloride, chlorine gas, or the like to a solvent such as methylene chloride, chloroform, acetonitrile, 1,4-dioxane, tetrahydrofuran, water, acetic acid, or sulfuric acid or a mixture thereof.

Step R-3

When $R^{35}$ of a compound represented by General Formula (18) is a benzyl group, a compound represented by General Formula (16) can be produced by converting the thiobenzyl group into a sulfonic acid.

Step R-3 can be performed according to a method similar to Step R-2.

Step R-4

A compound represented by General Formula (15) can be produced by chlorosulfonylating a compound represented by General Formula (17).

Step R-4 can be performed, as reaction conditions, at a temperature ranging from −78° C. to the reflux temperature by using a reagent for chlorosulfonylation such as chlorosulfuric acid in a solvent such as methylene chloride or chloroform or under a solvent free conditions.

Step R-5

In Synthetic Route R, a compound represented by General Formula (15) can be produced by converting the sulfonic acid moiety of a compound represented by General Formula (16) into a sulfonyl chloride group.

Step R-5 can be performed, as reaction conditions, at a temperature ranging from −78° C. to the reflux temperature by adding thionyl chloride, oxalyl chloride, phosphorus oxychloride, triphosgene, or phosphorous pentachloride in a solvent such as methylene chloride, chloroform, acetonitrile, 1,4-dioxane, or tetrahydrofuran. Optionally, N,N-dimethylformamide may be added as an accelerant.

Step R-6

A compound represented by General Formula (11) or (11') can be produced by converting the sulfonyl chloride moiety of a compound represented by General Formula (15) into a sulfinic acid or a salt thereof.

For example, Step R-6 can be performed, as reaction conditions, at a temperature ranging from room temperature to the reflux temperature by adding a base such as potassium carbonate, sodium carbonate, cesium carbonate, sodium hydroxide, potassium hydroxide, tripotassium phosphate, sodium bicarbonate, or potassium bicarbonate in combination with a reducing agent in a solvent such as water, N,N-dimethylformamide, tetrahydrofuran, 1,4-dioxane, diethylether, toluene, or benzene. The reducing agent that can be used includes sodium sulfite, zinc, tin(II) chloride, sodium borohydride, lithium aluminum hydride, sodium iodide, and potassium iodide.

Step R-7

A compound represented by General Formula (20) can be produced by allowing an amine represented by $R^{35}$—$NH_2$ or a hydrochloride thereof to act on a compound represented by General Formula (15).

Step R-7 can be performed, as reaction conditions, at a temperature ranging from −78° C. to the reflux temperature by optionally adding a base such as potassium carbonate, sodium carbonate, cesium carbonate, sodium hydroxide, potassium hydroxide, tripotassium phosphate, sodium bicarbonate, potassium bicarbonate, pyridine, triethylamine, or N,N-diisopropylethylamine in a solvent such as methylene chloride, chloroform, tetrahydrofuran, 1,4-dioxane, acetonitrile, water, or pyridine or a mixture thereof. Examples of amines represented by $R^{35}$—$NH_2$ or a hydrochloride thereof include cis-4-aminocyclohexanol hydrochloride and p-aminophenol.

When the Compound (2) is represented by Compound (2ad), the Compound (2ad) can be produced according to any of the method shown in Synthetic Route S or similar methods thereto and other methods described in literatures or similar methods thereto.

Synthetic Route S

[Formula 28]

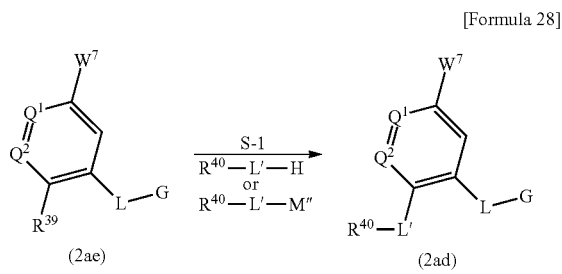

wherein
L' represents —O— or —NR$^{41}$—;
R$^{39}$ represents a fluorine or chlorine atom;
each of R$^{40}$ and R$^{41}$ independently represents a $C_1$-$C_6$ alkyl group or a deuterated $C_1$-$C_6$ alkyl group;
M" represents lithium, sodium, or potassium;
W$^7$ is as defined in the Synthetic route H; and Q$^1$, Q$^2$, G, and L are as defined in the General Formula (1).

Step S-1

A compound represented by General Formula (2ad) can be produced by substituting a compound represented by General Formula (2ae) with -L'-R$^{40}$.

A typical condition of nucleophilic aromatic substitution reaction can be applied to Step S-1. For example, Step S-1 can be performed at a temperature ranging from 0° C. to the reflux temperature, optionally under microwave irradiation by optionally adding a base such as potassium carbonate, sodium carbonate, cesium carbonate, sodium hydroxide, potassium hydroxide, tripotassium phosphate, cesium fluoride, triethylamine, or N,N-diisopropylethylamine and using a reagent represented by R$^{40}$-L'-H or R$^{40}$-L'-M", for example methanol, ethanol, sodium methoxide, or sodium ethoxide for an alkoxy group, and for example ammonia, methylamine, dimethylamine, or a salt thereof, or a solution thereof such as in methanol, ethanol, 1,4-dioxane, tetrahydrofuran, or water for an amino group in a solvent such as dimethylsulfoxide, N,N-dimethylformamide, N,N-dimethylacetamide, N-methyl-2-pyrrolidinone, 1,4-dioxane, tetrahydrofuran, 1,2-dimethoxyethane, methylene chloride, or methanol. In some cases, an accelerant may be also added, wherein the accelerant includes tetra n-butylammonium fluoride or an acid such as hydrochloric acid, acetic acid, trifluoroacetic acid, sulfuric acid, p-toluenesulfonic acid, hydrobromic acid, boron trifluoride diethyl ether complex, and aluminum chloride.

When the Compound (2) is represented by Compound (2af), the Compound (2af) can be produced according to any of the method shown in Synthetic Route T or similar methods thereto and other methods described in literatures or similar methods thereto.

Synthetic Route T

[Formula 29]

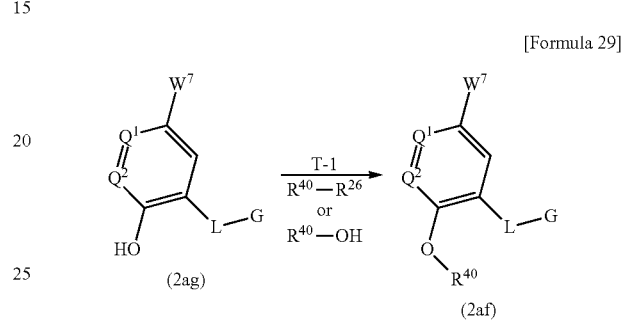

wherein R$^{36}$ is as defined in the Synthetic Route O; R$^{40}$ is as defined in the Synthetic Route S; W$^7$ is as defined in the Synthetic Route H; and Q$^1$, Q$^2$, G, and L are as defined in the General Formula (1).

Step T-1

A compound represented by General Formula (2af) can be produced by alkylating the hydroxy group of a compound represented by General Formula (2ag) with R$^{40}$—OH or R$^{40}$-R$^{36}$.

Step T-1 can be performed according to a method similar to Step B-1 via any of $S_N2$ reaction or Mitsunobu reaction as described above.

When the Compound (1) is represented by Compound (1a) or (1b), the Compound (1a) or (1b) can be produced according to any of the method shown in Synthetic Route U or similar methods thereto and other methods described in literatures or similar methods thereto.

Synthetic Route U

[Formula 30]

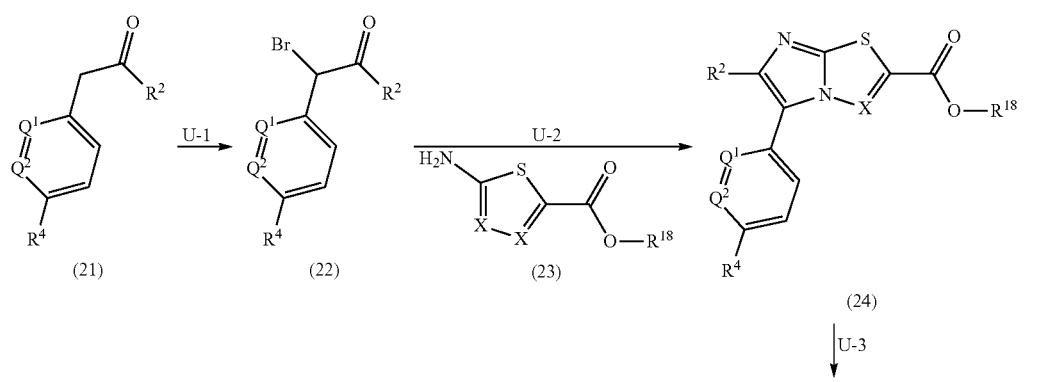

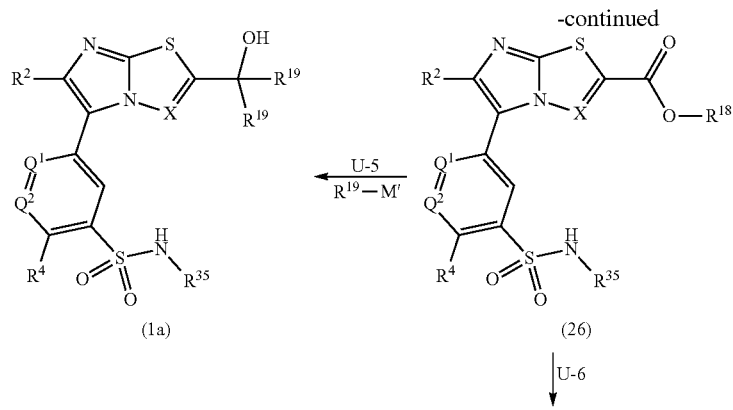
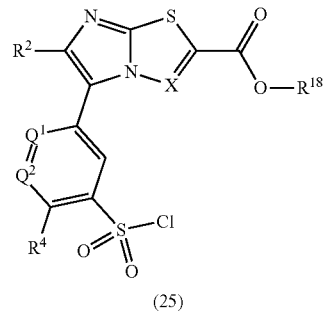

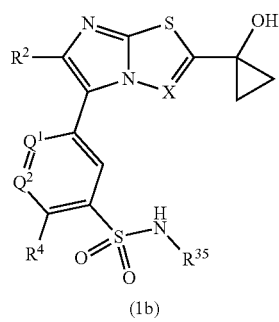

wherein $R^{18}$, $R^{19}$, and M' are as defined in the Synthetic Route D; $R^{35}$ is as defined in the Synthetic Route Q; and $Q^1$, $Q^2$, $R^2$, $R^4$, and X are as defined in the General Formula (1).

Step U-1

A compound represented by General Formula (22) can be produced by brominating a compound represented by General Formula (21).

Step U-1 can be performed, as reaction conditions, at a temperature ranging from −78° C. to the reflux temperature by adding a brominating agent such as bromine, N-bromosuccinimide, trimethylphenylammonium tribromide, or pyridinium bromide perbromide in a solvent such as diethylether, tetrahydrofuran, benzene, 1,4-dioxane, methylene chloride, chloroform, acetonitrile, or acetic acid.

Step U-2

A compound represented by General Formula (24) can be produced by allowing a compound represented by General Formula (23) to act on a compound represented by General Formula (22).

Step U-2 can be performed at a temperature ranging from room temperature to the reflux temperature in a solvent such as ethanol, 2-propanol, acetonitrile, N,N-dimethylformamide, ethyl methyl ketone, or acetone. In some cases, an acid such as hydrochloric acid, hydrobromic acid, acetic acid, trifluoroacetic acid, or sulfuric acid and a base such as potassium carbonate, sodium carbonate, cesium carbonate, sodium hydroxide, potassium hydroxide, tripotassium phosphate, cesium fluoride, triethylamine, or N,N-diisopropylethylamine can be also added as an accelerant.

Step U-3

A compound represented by General Formula (25) can be produced by chlorosulfonylating a compound represented by General Formula (24).

Step U-3 can be performed according to a method similar to Step R-4.

Step U-4

A compound represented by General Formula (26) can be produced by allowing an amine represented by $R^{35}$—$NH_2$ or a hydrochloride thereof to act on a compound represented by General Formula (25).

Step U-4 can be performed according to a method similar to Step R-7.

Step U-5 A compound represented by General Formula (1a) can be produced by alkylating of an ester moiety of a compound represented by General Formula (26) with $R^{19}$-M'.

Step U-5 can be performed according to a method similar to Step D-1.

Step U-6

A compound represented by General Formula (1b) can be produced by converting the ester moiety of a compound represented by General Formula (26) with the Kulinkovich Reaction condition.

Step U-6 can be performed according to a method similar to Step D-3.

When the Compound (1) is represented by Compound (1c), the Compound (1c) can be produced according to any of the method shown in Synthetic Route V or similar methods thereto and other methods described in literatures or similar methods thereto.

Synthetic Route V

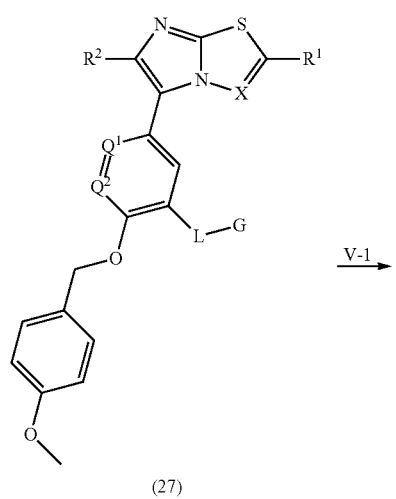

(27)

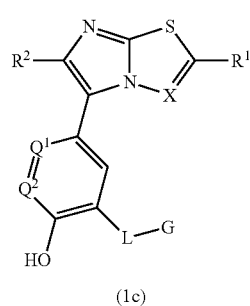

(1c)

wherein $Q^1$, $Q^2$, $R^1$, $R^2$, G, L, and X are as defined in the General Formula (1).

Step V-1

A compound represented by General Formula (1c) can be produced by removing a p-methoxybenzyl group of a compound represented by General Formula (27).

Step V-1 can be performed, as reaction conditions, at a temperature ranging from −78° C. to room temperature, optionally at the reflux temperature by adding an acid such as trifluoroacetic acid, p-toluenesulfonic acid, sulfuric acid, hydrochloric acid, hydrobromic acid, boron trifluoride diethyl ether complex, boron tribromide, or aluminum chloride in a solvent such as methylene chloride, chloroform, 1,4-dioxane, tetrahydrofuran, toluene, benzene, or water. Optionally, anisole, pentamethylbenzene, dimethyl sulfide, or the like may be added.

When the Compound (1) is represented by Compound (1e), the Compound (1e) can be produced according to any of the method shown in Synthetic Route W or similar methods thereto and other methods described in literatures or similar methods thereto.

Synthetic Route W

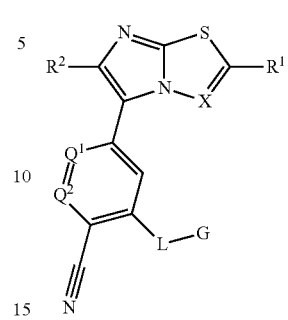

(1d)

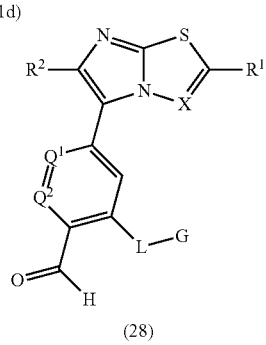

(28)

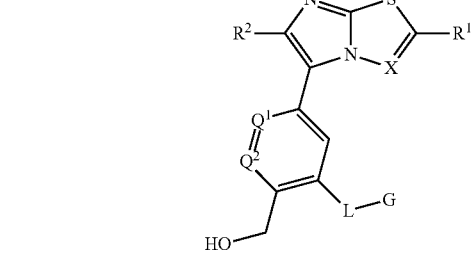

(1e)

wherein $Q^1$, $Q^2$, $R^1$, $R^2$, G, L, and X are as defined in the General Formula (1).

Step W-1

A compound represented by General Formula (28) can be produced by reducing the cyano group of a compound represented by General Formula (1d) into an aldehyde group.

Step W-1 can be performed, as reaction conditions, at a temperature ranging from −78° C. to room temperature, optionally at the reflux temperature by using a hydride reducing agent such as diisobutylaluminum hydride, lithium aluminum hydride, sodium bis(2-methoxyethoxy)aluminum hydride (Red-Al), or lithium tri(sec-butyl)borohydride in a solvent such as tetrahydrofuran, diethyl ether, methylene chloride, toluene, benzene, or hexane.

Step W-2

A compound represented by General Formula (1e) can be produced by reducing the aldehyde group of a compound represented by General Formula (28) into a hydroxymethyl group.

Step W-2 can be performed according to a method similar to Step H-2.

When the Compound (1) is represented by Compound (1g), (1h), or (1i), the Compound (1g), (1h), or (1i) can be produced according to any of the method shown in Synthetic Route X or similar methods thereto and other methods described in literatures or similar methods thereto.

Synthetic Route X

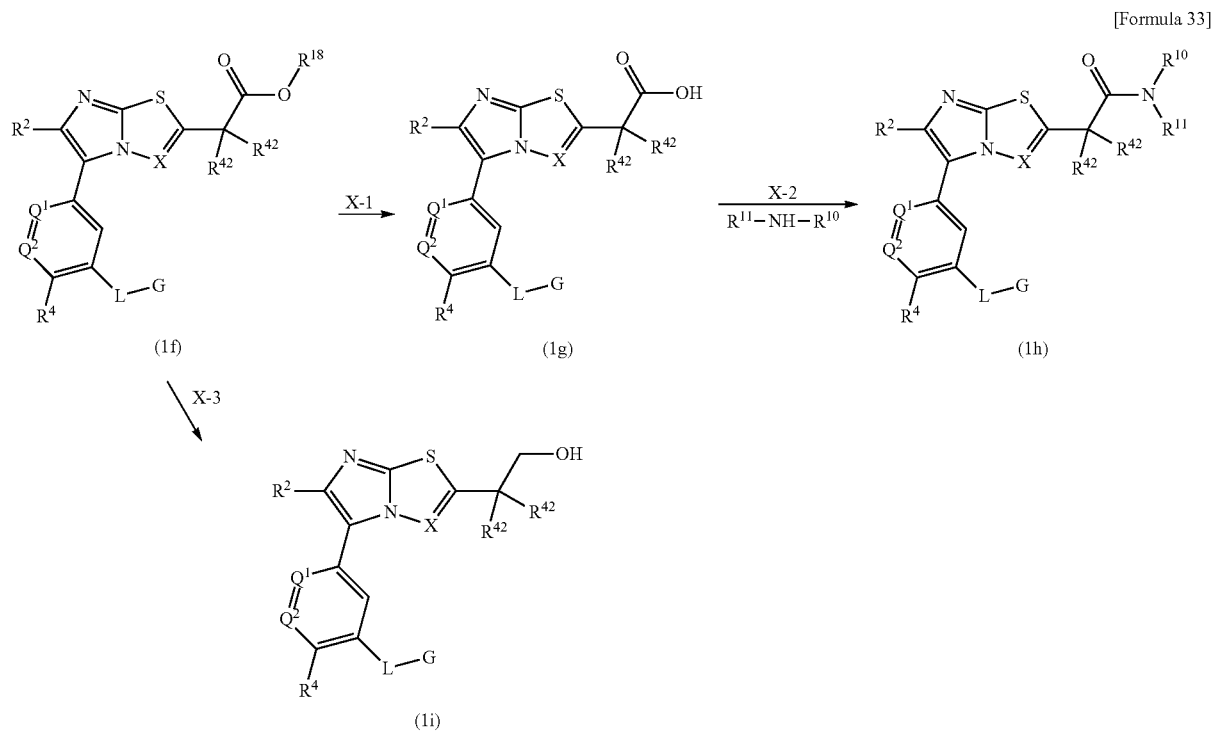

wherein each $R^{42}$ independently represents H or a $C_1$-$C_5$ alkyl group;

$R^{18}$ is as defined in the Synthetic Route D; and $Q^1$, $Q^2$, $R^2$, $R^4$, G, $R^{10}$, $R^{11}$, L, and X are as defined in the General Formula (1).

Step X-1

A compound represented by General Formula (1g) can be produced by hydrolyzing the ester moiety of a compound represented by General Formula (1f).

Step X-1 can be performed according to a method similar to Step H-3.

Step X-2

A compound represented by General Formula (1h) can be produced by amidating the carboxy group of a compound represented by General Formula (1g) with $R^{10}$—NH—$R^{11}$.

Step X-2 can be performed according to a method similar to Step H-4 using a primary amine, secondary amine represented by $R^{10}$—NH—$R^{11}$, or a salt thereof, for example a solution of dimethylamine in tetrahydrofuran in addition of the ammonia source described in Step H-4.

Step X-3

A compound represented by General Formula (1i) can be produced by reducing the ester moiety of a compound represented by General Formula (1f).

Step X-3 can be performed according to a method similar to Step H-2.

When the Compound (1) is represented by Compound (1k), the Compound (1k) can be produced according to any of the method shown in Synthetic Route Y or similar methods thereto and other methods described in literatures or similar methods thereto.

Synthetic Route Y

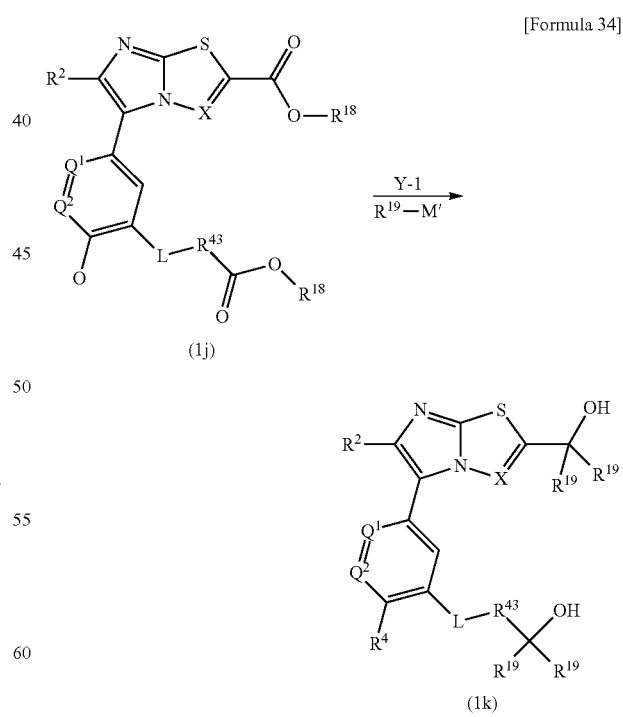

wherein $R^{43}$ represents a $C_1$-$C_5$ alkylene group or a $C_3$-$C_5$ cycloalkylene group optionally having a substituent;

$R^{18}$, $R^{19}$, and M' are as defined in the Synthetic Route D; each $R^{18}$ can be independently selected; and $R^4$, $Q^1$, $Q^2$, $R^2$, L, and X are as defined in the General Formula (1).

Step Y-1

A compound represented by General Formula (1k) can be produced by alkylating two ester moieties of a compound represented by General Formula (1j) with $R^{19}$-M'.

Step Y-1 can be performed according to a method similar to Step D-1.

When the Compound (1) or (2) is represented by Compound (1l) or (2ah), the Compound (1l) or (2ah) can be produced according to any of the method shown in Synthetic Route Z or similar methods thereto and other methods described in literatures or similar methods thereto.

Synthetic Route Z

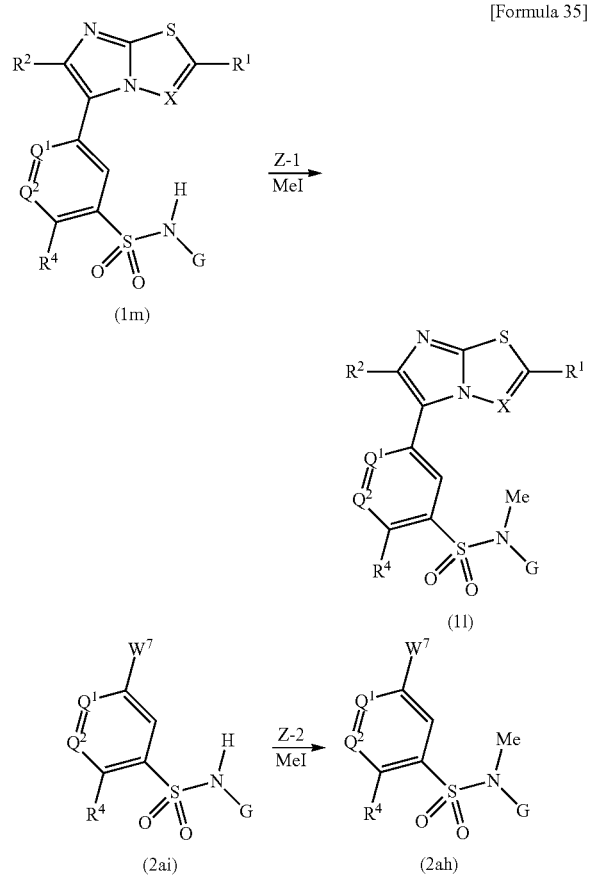

wherein $W^7$ is as defined in the Synthetic Route H; and $Q^1$, $Q^2$, $R^1$, $R^2$, $R^4$, G, and X are as defined in the General Formula (1).

Step Z-1

A compound represented by General Formula (1l) can be produced by N-methylating a compound represented by General Formula (1m).

Step Z-1 can be performed according to a method similar to Step B-1 using methyl iodide.

Step Z-2

A compound represented by General Formula (2ah) can be produced by N-methylating a compound represented by General Formula (2ai).

Step Z-2 can be performed according to a method similar to Step B-1 using methyl iodide.

Alkylating agents described in this production method such as an alkyl iodide, alkyl bromide, alkyl chloride, alkyl p-toluenesulfonate, alkyl methansulfonate, and alkyl trifluoromethanesulfonate can be produced according to any of methods described in literatures or similar methods thereto except easily available reagents. For example, the following compound represented by General Formula (33) can be produced according to Synthetic Route AA.

Synthetic Route AA

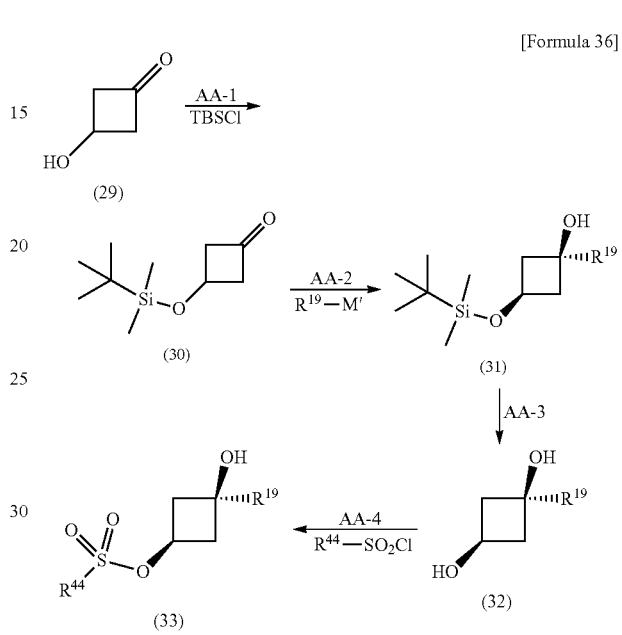

wherein $R^{44}$ represents a $C_1$-$C_6$ alkyl group or a phenyl group optionally having a substituent; and $R^{19}$ and M' are as defined in the Synthetic Route D.

Step AA-1

A compound represented by General Formula (30) can be produced by converting the hydroxy group of a compound represented by General Formula (29) into a t-butyldimethylsilyloxy group.

A typical condition of silylation can be applied to Step AA-1. For example, Step AA-1 can be performed, as reaction conditions, at a temperature ranging from 0° C. to the reflux temperature by adding a base such as potassium carbonate, sodium carbonate, cesium carbonate, sodium hydroxide, potassium hydroxide, tripotassium phosphate, cesium fluoride, imidazole, pyridine, triethylamine, or N,N-diisopropylethylamine and using t-butyl dimethylchlorosilane (TBSCl) in a solvent such as N,N-dimethylformamide, N,N-dimethylacetamide, N-methyl-2-pyrrolidinone, 1,4-dioxane, tetrahydrofuran, or 1,2-dimethoxyethane. In some cases, an accelerant may be also added, wherein the accelerant includes sodium iodide, potassium iodide, tetra n-butylammonium iodide, sodium bromide, potassium bromide, tetra n-butylammonium bromide, and silver nitrate.

Step AA-2

A compound represented by General Formula (31) can be produced by alkylating the ketone group of a compound represented by General Formula (30) with $R^{19}$-M'.

Step AA-2 can be performed according to a method similar to Step D-1.

Step AA-3

A compound represented by General Formula (32) can be produced by removing the t-butyldimethylsilyl group of a compound represented by General Formula (31).

Step AA-3 can be performed, as reaction conditions, at a temperature ranging from −78° C. to the reflux temperature by adding tetra-n-butylammonium fluoride, cesium fluoride, tris(dimethylamino)sulfonium difluorotrimethylsilicate (TASF) or an acid such as trifluoroacetic acid, p-toluenesulfonic acid, sulfuric acid, hydrochloric acid, hydrobromic acid, boron trifluoride diethyl ether complex, boron tribromide, or aluminum chloride in a solvent such as water, acetone, methylene chloride, chloroform, 1,4-dioxane, tetrahydrofuran, toluene, benzene, methanol, or ethanol or a mixture thereof.

Step AA-4

A compound represented by General Formula (33) can be produced by sulfonylating a hydroxy group of a compound represented by General Formula (32) with $R^{44}$—$SO_2Cl$.

Step AA-4 can be performed, as reaction conditions, at a temperature ranging from −78° C. to the reflux temperature by adding a base such as potassium carbonate, sodium carbonate, cesium carbonate, sodium hydroxide, potassium hydroxide, tripotassium phosphate, cesium fluoride, pyridine, N,N-dimethyl-4-aminopyridine, N-methylimidazole, triethylamine, or N,N-diisopropylethylamine and adding a sulfonylating agent represented by $R^{44}$—$SO_2Cl$ such as an alkylsulfonyl chloride or an alkylsulfonic anhydride, for example p-toluenesulfonyl chloride in a solvent such as methylene chloride, chloroform, 1,4-dioxane, tetrahydrofuran, toluene, benzene, or water.

When the Compound (12) is represented by Compound (12e), the Compound (12e) can be produced according to any of the method shown in Synthetic Route AB or similar methods thereto and other methods described in literatures or similar methods thereto.

Synthetic Route AB

[Formula 37]

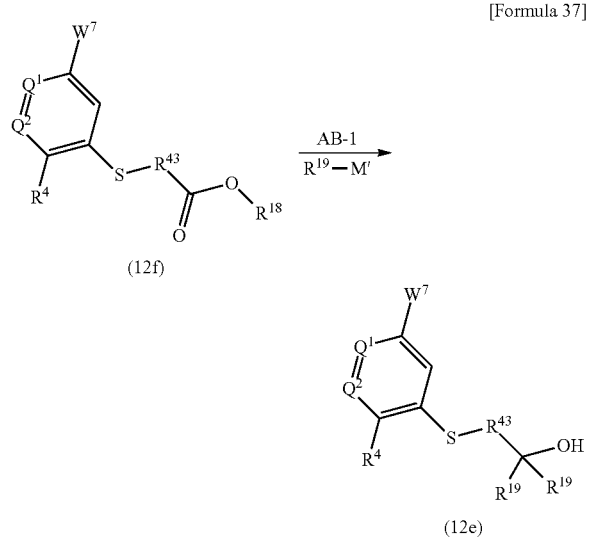

wherein
$R^{18}$, $R^{19}$, and M' are as defined in the Synthetic Route D; $W^7$ is as defined in the Synthetic Route H; $R^{43}$ is as defined in the Synthetic Route Y; and $R^4$, $Q^1$, and $Q^2$ are as defined in the General Formula (1).

Step AB-1

A compound represented by General Formula (12e) can be produced by alkylating the ester moiety of a compound represented by General Formula (12f) with $R^{19}$-M'.

Step AB-1 can be performed according to a method similar to Step D-1.

When the Compound (1) is represented by Compound (1n), the Compound (1n) can be produced according to any of the method shown in Synthetic Route AC or similar methods thereto and other methods described in literatures or similar methods thereto.

Synthetic Route AC

[Formula 38]

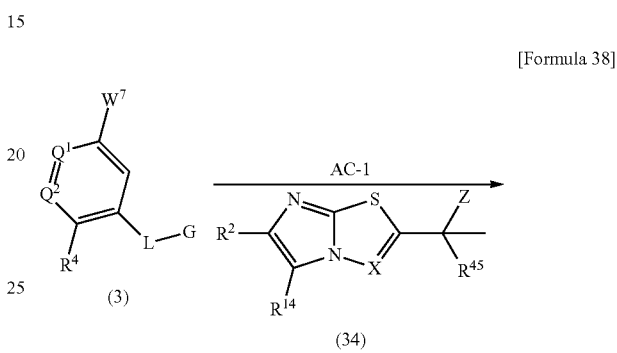

wherein $R^{45}$ represents a $C_1$-$C_6$ alkyl group;

M is as defined in the Synthetic Route A; $R^{14}$ and Z are as defined in the Synthetic Route B; and L, X, $Q^1$, $Q^2$, $R^2$, $R^4$, and G are as defined in the General Formula (1).

Step AC-1

A compound represented by General Formula (1n) can be produced via a coupling reaction between a compound represented by General Formula (3) and a compound represented by General Formula (34).

Step AC-1 can be performed according to a method similar to Step A-2.

When the Compound (2) is represented by Compound (2ak), the Compound (2ak) can be produced according to any of the method shown in Synthetic Route AD or similar methods thereto and other methods described in literatures or similar methods thereto.

Synthetic Route AD

[Formula 39]

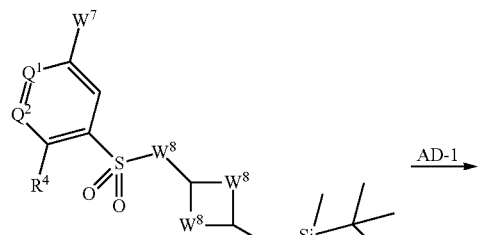

wherein W⁷ is as defined in the Synthetic Route H; W⁸ is as defined in the Synthetic Route J; and $Q^1$, $Q^2$, and $R^4$ are as defined in the General Formula (1).

Step AD-1

A compound represented by General Formula (2ak) can be produced by removing the t-butyldimethylsilyl group of a compound represented by General Formula (2aj).

Step AD-1 can be performed according to a method similar to Step AA-3.

Alkylating agents described in this production method such as an alkyl iodide, alkyl bromide, alkyl chloride, alkyl p-toluenesulfonate, alkyl methansulfonate, or alkyl trifluoromethanesulfonate can be produced according to methods described in literatures or similar methods thereto except easily available reagents. For example, the following compound represented by General Formula (35) can be produced according to Synthetic Route AE.

Synthetic Route AE

[Formula 40]

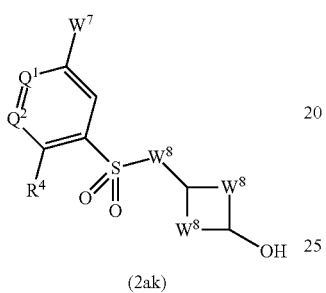

wherein each $W^{11}$ independently represents a bond or a $C_1$-$C_6$ alkylene group;

each of $W^{12}$ and $W^{13}$ is independently selected from H, a halogen atom, a $C_1$-$C_6$ alkyl group, a $C_1$-$C_6$alkoxy group, a $C_1$-$C_6$alkoxycarbonyl group, and t-butyldimethylsilyloxy group, and $W^{12}$ and $W^{13}$ may be joined together to form a ring, provided that two $W^{11}$ present in the ring does not concurrently represent a bond.

Step AE-1

A compound represented by General Formula (35) can be produced by sulfonylating the hydroxy group of a compound represented by General Formula (36) with p-toluenesulfonyl chloride.

Step AE-1 can be performed according to a method similar to Step AA-4.

When the Compound (5g) is represented by Compound (5i), the Compound (5i) can be produced according to any of the method shown in Synthetic Route AF or similar methods thereto and other methods described in literatures or similar methods thereto.

Synthetic Route AF

[Formula 41]

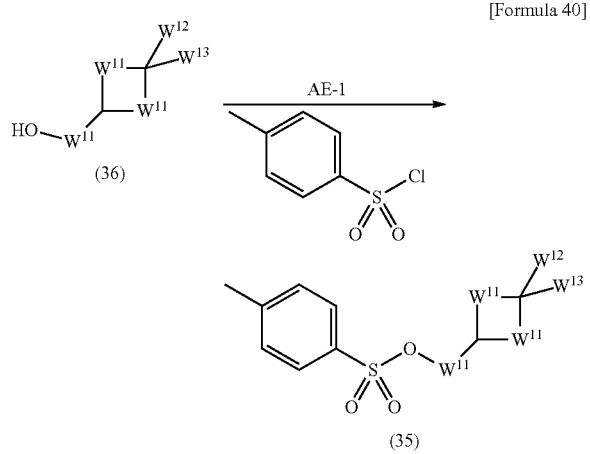

wherein $R^{46}$ represents a $C_1$-$C_5$ alkyl group;

$R^{21}$ is as defined in the Synthetic Route E; and $R^2$ and X are as defined in the General Formula (1).

Step AF-1

A compound represented by General Formula (5i) can be produced by methyl-esterifying the ester moiety of a compound represented by General Formula (5j).

Step AF-1 can be performed, as reaction conditions, at a temperature ranging from 0° C. to the reflux temperature by adding ammonia in methanol in the absence of solvent or in a solvent such as methanol, methylene chloride, 1,4-dioxane, tetrahydrofuran, toluene, benzene, or water. When methanol is used as a solvent, this reaction can be also performed at a temperature ranging from −78° C. to the reflux temperature by adding an acid such as trifluoroacetic acid, p-toluenesulfonic acid, sulfuric acid, hydrochloric acid, hydrobromic acid, boron trifluoride diethyl ether complex, boron tribromide, or aluminum chloride.

When the Compound (2) is represented by Compound (2al), the Compound (2al) can be produced according to any of the method shown in Synthetic Route AG or similar methods thereto and other methods described in literatures or similar methods thereto.

Synthetic Route AG

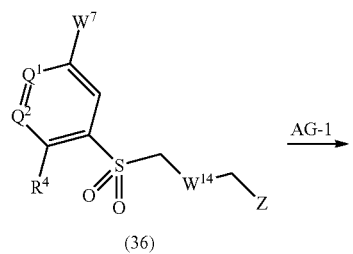

wherein
W$^{14}$ represents a C$_1$-C$_4$ alkylene group;
Z is as defined in the Synthetic Route B; W$^7$ is as defined in the Synthetic Route H; and Q$^1$, Q$^2$, and R$^4$ are as defined in the General Formula (1).

Step AG-1

In Synthetic Route AG, a compound represented by General Formula (2al) can be produced by intramolecularly alkylating a compound represented by General Formula (36).

Step AG-1 can be performed according to a method similar to Step M-2.

When the Compound (2) is represented by Compound (2 am), the Compound (2 am) can be produced according to any of the method shown in Synthetic Route AH or similar methods thereto and other methods described in literatures or similar methods thereto.

Synthetic Route AH

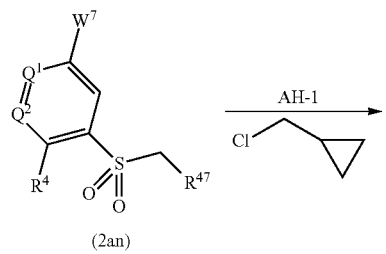

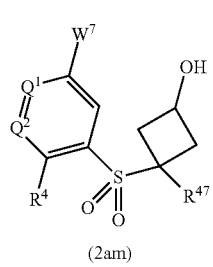

wherein
R$^{47}$ represents a C$_1$-C$_5$ alkyl or C$_3$-C$_6$ cycloalkyl group;
W$^7$ is as defined in the Synthetic Route H; and Q$^1$, Q$^2$, and R$^4$ are as defined in the General Formula (1).

Step AH-1

A compound represented by General Formula (2 am) can be produced by allowing epichlorohydrin to act on a compound represented by General Formula (2an).

Step AH-1 can be performed according to a method similar to Step M-2 using epichlorohydrin.

When the Compound (2) is represented by Compound (2ao), the Compound (2ao) can be produced according to any of the method shown in Synthetic Route AI or similar methods thereto and other methods described in literatures or similar methods thereto.

Synthetic Route AI

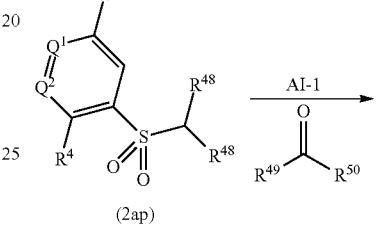

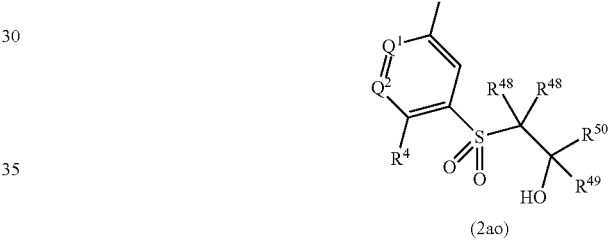

wherein
each R$^{48}$ independently represents H, a C$_1$-C$_6$ alkyl group optionally having a substituent, a hydroxyC$_1$-C$_6$ alkyl group optionally having a substituent, or a C$_3$-C$_6$ cycloalkyl group optionally having a substituent, and two R$^{48}$ may be joined together to form a ring;
each of R$^{49}$ and R$^{50}$ independently represents H, a C$_1$-C$_6$ alkyl group optionally having a substituent, a deuterated C$_1$-C$_6$ alkyl group, a haloC$_1$-C$_6$ alkyl group, or a hydroxyC$_1$-C$_6$ alkyl group optionally having a substituent, and R$^{49}$ and R$^{50}$ may be joined together to form a ring; and
W$^7$ is as defined in the Synthetic Route H; and Q$^1$, Q$^2$, and R$^4$ are as defined in the General Formula (1).

Step AI-1

A compound represented by General Formula (2ao) can be produced by hydroxyalkylation of a compound represented by General Formula (2ap) with R$^{49}$C(O)R$^{50}$.

Step AI-1 can be performed, as reaction conditions, at a temperature ranging from −78° C. to room temperature, optionally at the reflux temperature by adding a base such as lithium diisopropylamide, lithium hexamethyldisilazide, sodium hexamethyldisilazide, potassium hexamethyldisilazide, n-butyllithium, sec-butyllithium, t-butyl lithium, phenyllithium, potassium t-butoxide, sodium hydride, potassium hydride, sodium carbonate, potassium carbonate, cesium carbonate, or tripotassium phosphate and using an aldehyde or ketone represented by R$^{49}$C(O)R$^{50}$, for example acetone, cyclobutanone, 4,4-difluorocyclohexanone, 3-oxetanone, or deuterated acetone in a solvent such as tetrahydrofuran, diethyl ether, t-butyl methyl ether, N,N-dimethylformamide, toluene, or hexane.

When the Compound (2) is represented by Compound (2aq), the Compound (2aq) can be produced according to any of the method shown in Synthetic Route AJ or similar methods thereto and other methods described in literatures or similar methods thereto.

Synthetic Route AJ

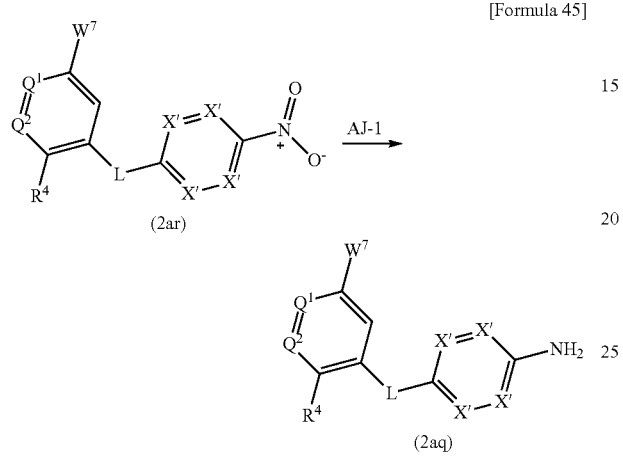

[Formula 45]

(2ar)

(2aq)

wherein each X' independently represents N or CH; and $Q^1$, $Q^2$, $R^4$, and L are as defined in the General Formula (1).

Step AJ-1

A compound represented by General Formula (2aq) can be produced by reducing the nitro group of a compound represented by General Formula (2ar) into an amino group.

Step AJ-1 can be performed under typical conditions of reducing nitro groups. For example, Step AJ-1 can be performed at a temperature ranging from 0° C. to room temperature, optionally at the reflux temperature by using iron powder, zinc powder, tin(II) chloride, tin metal, indium metal, samarium metal, Raney nickel, formic acid, sodium borohydride, nickel borohydride, cobalt borohydride, lithium aluminum hydride, sodium dithionite, sodium sulfide, sodium hydrogensulfide, or hydrazine in a solvent such as methanol, ethanol, isopropylalcohol, 1,4-dioxane, 1,2-dimethoxyethane, acetic acid, ethyl acetate, water, tetrahydrofuran, diethylether, t-butyl methyl ether, N,N-dimethylformamide, toluene, or hexane or a mixture thereof. In some cases, this reaction may be performed by adding an acid such as ammonium chloride, hydrochloric acid, acetic acid, trifluoroacetic acid, and sulfuric acid, or a base such as potassium carbonate, sodium carbonate, cesium carbonate, sodium hydroxide, potassium hydroxide, tripotassium phosphate, sodium bicarbonate, potassium bicarbonate, pyridine, triethylamine, or N,N-diisopropylethylamine. Alternatively, this reaction may be performed via reduction with a catalyst such as palladium on carbon, rhodium on carbon, platinum on carbon, or platinum oxide in a solvent such as methanol, ethanol, isopropylalcohol, 1,4-dioxane, 1,2-dimethoxyethane, acetic acid, ethyl acetate, water, tetrahydrofuran, t-butyl methyl ether, N,N-dimethylformamide, or toluene or a mixture thereof under a hydrogen atmosphere.

When the compound of the embodiments is represented by Compound (1-salt), the Compound (1-salt) can be produced according to any of the method shown in Synthetic Route AK or similar methods thereto and other methods described in literatures or similar methods thereto.

Synthetic Route AK

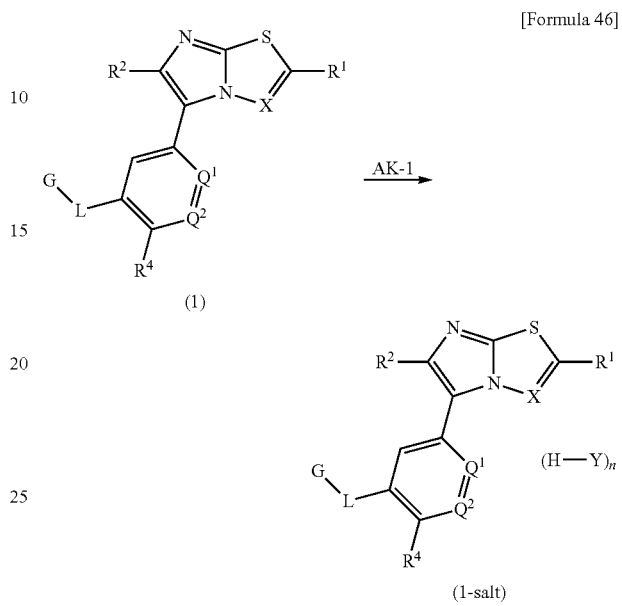

[Formula 46]

(1)

(1-salt)

wherein $R^1$, $R^2$, $Q^1$, $Q^2$, $R^4$, L, G, and X are as defined in the General Formula (1). H—Y represents hydrogen chloride, hydrogen bromide, sulfuric acid, nitric acid, phosphoric acid, formic acid, acetic acid, maleic acid, fumaric acid, succinic acid, lactic acid, malic acid, tartaric acid, citric acid, methanesulfonic acid, p-toluenesulfonic acid, salicylic acid, stearic acid, or palmitic acid, and n is from ⅓ to 3.

Step AK-1

A compound represented by General Formula (1-salt) can be produced by converting a compound represented by General Formula (1) into a corresponding salt.

A typical condition of salt formation can be used. For example, Step AK-1 can be performed at a temperature ranging from 0° C. to the reflux temperature by mixing hydrochloric acid, hydrobromic acid, sulfuric acid, nitric acid, phosphoric acid, formic acid, acetic acid, maleic acid, fumaric acid, succinic acid, lactic acid, malic acid, tartaric acid, citric acid, methanesulfonic acid, p-toluenesulfonic acid, salicylic acid, stearic acid, or palmitic acid with General Formula (1) in a solvent such as methanol, ethanol, 2-propanol, water, acetonitrile, diethyl ether, tetrahydrofuran, 1,4-dioxane, 1,2-dimethoxyethane, ethyl acetate, ethyl methyl ketone, acetone, toluene, or benzene or in the absence of a solvent. Hydrogen chloride or hydrogen bromide gas, or a solution of hydrogen chloride or hydrogen bromide in ethyl acetate, 1,4-dioxane, methanol, ethanol, 2-propanol, diethyl ether, or acetic acid can be also used instead of hydrochloric acid or hydrobromic acid.

The synthetic routes described above are exemplary methods for producing the compounds of the embodiments. The compounds of the embodiments can be produced according to any of methods described above or similar methods thereto and other methods described in literatures or similar methods thereto. These production methods can be variously modified into schemes as easily understood by those skilled in the art.

If functional groups require protecting groups due to their nature, the protecting groups can be utilized by a proper combination of introduction and removal of the protecting groups according to conventional methods. Types and methods of introduction and removal of protecting groups can be found in, for example, Theodra W. Green & Peter G. M. Wuts, ed., "Greene's Protective Groups in Organic Synthesis", fourth edition, Wiley-Interscience, 2006.

Intermediates to be used for producing the compounds of the embodiments can be optionally isolated and purified using techniques of isolation and purification well known to those skilled in the art, including solvent extraction, crystallization, recrystallization, chromatography, and preparative high-performance liquid chromatography. Intermediates may be also directly used as a crude product in the next step without isolation or purification.

The term "antiviral action" as used in the embodiments means suppression of viral replication. The term "antipicornavirus action" as used in the embodiments means replication suppression of viruses belonging to the family Picornaviridae.

Viruses belonging to the family Picornaviridae are single strand RNA viruses which utilize protein synthesis function of host cells to synthesize their viral proteins.

Viruses belonging to the family Picornaviridae are further classified into the genera Enterovirus, Hepatovirus, Parechovirus, Kobuvirus, Cardiovirus, Aphtovirus, Aquamavirus, Avihepatovirus, Cosavirus, Dicipivirus, Erbovirus, Salivirus, Sapelovirus, Senecavirus, Teschovirus, Tremovirus, and the like.

Viruses included in the genus Enterovirus include enteroviruses, rhinoviruses, and coxsackieviruses.

Viruses included in the genus Hepatovirus include hepatitis A virus.

The compounds of the embodiments exhibit a strong antiviral action particularly against viruses included in the genus Enterovirus.

The compounds of the embodiments exhibit a strong antiviral action particularly against enteroviruses, coxsackieviruses, or rhinoviruses.

The compounds of the embodiments strongly suppress replication of picornaviruses, for example. Consequently, the compounds of the embodiments are useful for a therapeutic or prophylactic agent against picornavirus infection, particularly viral infections caused by enteroviruses, coxsackieviruses, and rhinoviruses. More preferably, the compounds of the embodiments are useful for a therapeutic or prophylactic agent against rhinovirus infections.

A medicament containing a compound of the embodiment as an active ingredient can be also used as a therapeutic or prophylactic agent against, for example, exacerbation of asthma or COPD caused by infection of respiratory viruses.

A medicament containing a compound of the embodiment as an active ingredient can be formulated into different dosage forms depending on its use. Such dosage forms include, for example, a powder, granule, fine granule, dry syrup, tablet, capsule, injection, solution, ointment, suppository, patch, and sublingual tablet.

The medicaments can be used to formulate a pharmaceutical composition comprising a compound of the embodiments, as an active ingredient, and a pharmaceutically acceptable additive using known techniques suitable for their dosage form. Examples of additives contained in the pharmaceutical compositions include an excipient, disintegrator, binder, lubricant, diluent, buffering agent, tonicity agent, preservative, wetting agent, emulsifying agent, dispersing agent, stabilizing agent, and dissolution aid. The pharmaceutical compositions can be formulated by appropriately mixing or diluting the compounds of the embodiments with an additive or dissolving the compounds in an additive.

The medicaments according to the embodiments can be administered systemically or locally via the oral or parenteral route (such as nasal, pulmonary, intravenous, intrarectal, subcutaneous, intramuscular, and transcutaneous routes).

EXAMPLES

The present invention will be now described in detail with reference to Test Examples, Examples, and Reference Examples. Novel compounds are also included in source compounds to be used for production of Compound (1), and therefore, exemplary methods of producing the source compounds are also described in the Reference Examples. The present invention is not limited to the compounds described in the Examples below, but may be varied without departing from the scope of the present invention.

Among the symbols used in each of the Reference Examples, Examples, and Tables, $^1$H-NMR means a spectrum determined by proton nuclear magnetic resonance spectroscopy. $CDCl_3$ means chloroform-d while DMSO-$d_6$ means dimethylsulfoxide-$d_6$. MS (ESI$^+$) and MS (ESI$^-$) means mass spectrometry spectral data determined by electrospray ionization; MS (FI$^+$) means mass spectrometry spectral data determined by field ionization; MS (FD$^+$) means mass spectrometry spectral data determined by field desorption ionization; MS (EI$^+$) means mass spectrometry spectral data determined by electron ionization; and MS (CI$^+$) means mass spectrometry spectral data determined by chemical ionization. Room temperature means a temperature from 1 to 30° C.

Reference Example 1-1

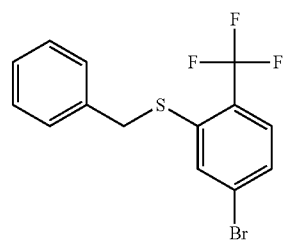

[Formula 47]

Benzyl mercaptan (2.41 mL) was dissolved in N,N-dimethylformamide (40 mL) under an argon atmosphere, and 55% sodium hydride (943 mg) was then added to the mixture with ice cooling. The mixture was stirred at 0° C. for 10 minutes, allowed to rise in temperature, and then stirred at room temperature for 10 minutes (Reaction Solution 1). Subsequently, 4-bromo-2-fluoro-1-trifluoromethylbenzene (5.00 g) was dissolved in N,N-dimethylformamide (53 mL) and cooled in ice (Reaction Solution 2). Reaction Solution 1 was added slowly dropwise to Reaction Solution 2 with ice cooling, and the mixture was stirred at the same temperature for 30 minutes. Saturated aqueous ammonium chloride solution (100 mL) and water (100 mL) were then added, and the mixture was extracted with ethyl acetate (200 mL). The organic layer was washed with saturated brine (100 mL), dried over anhydrous sodium sulfate, and then filtered to remove insoluble residues. The solvent was distilled away under reduced pressure, and the residue was then dissolved in the mixture of hexane:dichloromethane=2:1 (30 mL) and purified by silica gel column chromatography (hexane:ethyl acetate=98:2 to 90:10) to give the title compound (6.11 g).

$^1$H-NMR (400 MHz, CDCl$_3$) δ: 4.16 (2H, s), 7.25-7.34 (5H, m), 7.36-7.41 (1H, m), 7.46-7.51 (2H, m). MS (ESI$^-$): 345 [M−H]$^-$.

Reference Examples 1-2 to 1-5

A suitable compound of General Formula (19) was used to perform reactions according to any of methods similar to Reference Example 1-1, the method described in Step R-1 or similar methods thereto, and other methods described in literatures or similar methods thereto to give the compounds of Reference Examples 1-2 to 1-5 shown below.

TABLE 23

| Reference Example | Structure | Instrumental Data |
|---|---|---|
| 1-2 | 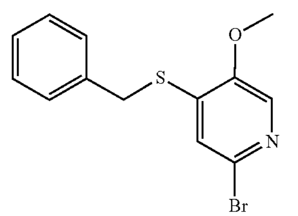 [SMILES: COc1cnc(Br)cc1SCc1ccccc1] | $^1$H-NMR (400 MHz, CDCl$_3$) δ: 3.94 (3H, s), 4.14 (2H, s), 7.19 (1H, s), 7.30-7.41 (5H, m), 7.81 (1H, s). MS (EI$^+$): 309 [M]$^+$ |
| 1-3 | 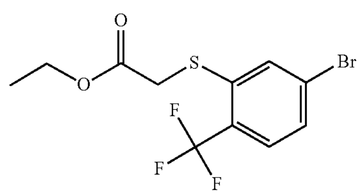 [SMILES: CCOC(=O)CSc1cc(Br)ccc1C(F)(F)F] | $^1$H-NMR (400 MHz, CDCl$_3$) δ: 1.26 (3H, t, J = 7.3 Hz), 3.68 (2H, s), 4.20 (2H, q, J = 7.3 Hz), 7.47 (1H, d, J = 8.5 Hz), 7.52 (1H, d, J = 8.5 Hz), 7.74 (1H, s). MS (ESI$^-$): 341 [M − H]$^-$ |
| 1-4 | 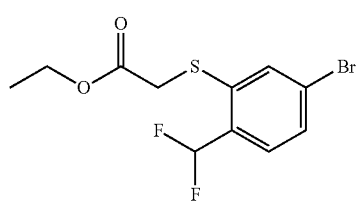 [SMILES: CCOC(=O)CSc1cc(Br)ccc1C(F)F] | $^1$H-NMR (400 MHz, CDCl$_3$) δ: 1.23 (3H, t, J = 7.3 Hz), 3.62 (2H, s), 4.16 (2H, dd, J = 14.1, 7.3 Hz), 7.10 (1H, t, J = 55.3 Hz), 7.53-7.54 (2H, m), 7.73-7.74 (1H, m). MS (ESI$^-$): 323 [M − H]$^-$ |
| 1-5 | 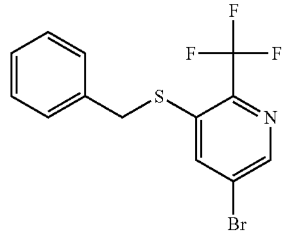 [SMILES: FC(F)(F)c1ncc(Br)cc1SCc1ccccc1] | $^1$H-NMR (400 MHz, CDCl$_3$) δ: 4.17 (2H, s), 7.27-7.38 (5H, m), 7.77 (1H, d, J = 1.8 Hz), 8.48 (1H, d, J = 1.8 Hz). MS (ESI$^+$): 348 [M + H]$^+$ |

Reference Example 2

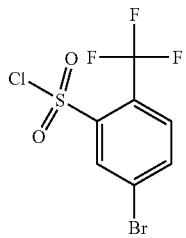

[Formula 48]

The compound obtained in Reference Example 1-1 (6.11 g) was suspended in acetic acid (43.5 mL) and water (14.5 mL), and N-chlorosuccinimide (7.05 g) was then added to the mixture with ice cooling. The mixture was stirred at room temperature for 2 hours followed by addition of water (100 mL), and the mixture was extracted with ethyl acetate (100 mL). The organic layer was washed with saturated brine (100 mL), dried over anhydrous sodium sulfate, and then filtered to remove insoluble residues. The solvent was distilled away under reduced pressure, and the residue was then dissolved in the mixture of hexane:dichloromethane=1:1 (30 mL) and purified by silica gel column chromatography (hexane:ethyl acetate=98:2 to 80:20) to give the title compound (4.96 g).

$^1$H-NMR (400 MHz, CDCl$_3$) δ: 7.84 (1H, d, J=8.5 Hz), 7.98-8.03 (1H, m), 8.48 (1H, d, J=1.8 Hz).

Reference Example 3

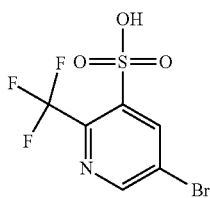

[Formula 49]

The compound obtained in Reference Example 1-5 (213 mg) was suspended in acetic acid (4.6 mL) and water (1.8 mL), and N-chlorosuccinimide (245 mg, 1.84 mmol) was then added to the mixture with ice cooling. The mixture was stirred at room temperature for 1 hour and then stirred at 50° C. for 1 hour. Water (10 mL) was added to the mixture at room temperature, and the mixture was left to stand. The solvent was distilled away under reduced pressure, and the residue was then dissolved in water (8 mL) and purified by reversed-phase silica gel column chromatography (water:acetonitrile=80:20) to give the title compound (138.4 mg).

$^1$H-NMR (400 MHz, DMSO-d$_6$) δ: 8.53 (1H, d, J=2.1 Hz), 8.84 (1H, d, J=2.1 Hz). MS (ESI$^-$): 304 [M–H]$^-$.

Reference Example 4-1

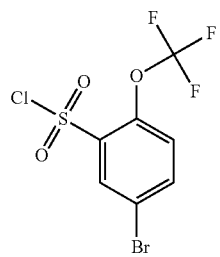

[Formula 50]

1-bromo-4-(trifluoromethoxy)benzene (2.0 mL) was dissolved in chlorosulfuric acid (13.0 mL), and the solution was stirred at room temperature for 2.5 hours. The reaction mixture was slowly poured into ice (100 g) at room temperature, and the vessel was washed with water (20 mL). Water (20 mL) was added to the mixture, and the mixture was extracted with dichloromethane (100 mL). The organic layer was washed with saturated brine (75 mL), dried over anhydrous sodium sulfate, and filtered to remove insoluble residues. The solvent was distilled away under reduced pressure to give the title compound (2.91 g).

$^1$H-NMR (400 MHz, CDCl$_3$) δ: 7.39-7.43 (1H, m), 7.88-7.93 (1H, m), 8.23 (1H, d, J=2.4 Hz).

Reference Examples 4-2 to 4-3

A suitable compound of General Formula (17) was used to perform reactions according to any of methods similar to Reference Example 4-1, the method described in Step R-4 or similar methods thereto, and other methods described in literatures or similar methods thereto to give the compounds of Reference Examples 4-2 to 4-3 shown below.

TABLE 24

| | | |
|---|---|---|
| 4-2 | 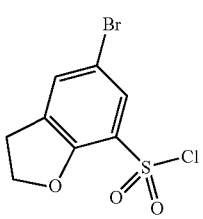 [SMILES: O=S(=O)(Cl)c1cc(Br)cc2c1OCC2] | $^1$H-NMR (400 MHz, CDCl$_3$) δ: 3.38 (2H, t, J = 8.9 Hz), 4.94 (2H, t, J = 8.9 Hz), 7.62-7.64 (1H, m), 7.81-7.82 (1H, m). |

TABLE 24-continued

| | | |
|---|---|---|
| 4-3 | 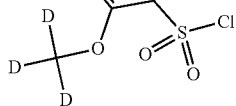 | $^1$H-NMR (400 MHz, DMSO-$d_6$) δ: 6.94 (1H, d, J = 8.6 Hz), 7.46 (1H, dd, J = 8.6, 2.4 Hz), 7.76 (1H, d, J = 2.4 Hz). MS (CI$^+$): 287 [M]$^+$ |

Reference Example 5-1

[Formula 51]

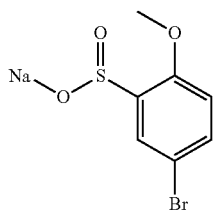

Sodium sulfite (1.42 g) and sodium bicarbonate (948 mg) were dissolved in water (17.0 mL), and heated with stirring at 70° C. A solution of 5-bromo-2-methoxybenzenesulfonyl chloride (2.00 g) in 1,4-dioxane (17.0 mL) was added dropwise over 10 minutes to the mixture, and the mixture was stirred at 70° C. for 2.5 hours. The solvent and similar materials were distilled away under reduced pressure, and the residue was dissolved in water (15 mL) and purified by reversed-phase silica gel column chromatography (water:acetonitrile=100:0 to 80:20) to give the title compound (1.89 g).

$^1$H-NMR (400 MHz, DMSO-$d_6$) δ: 3.72 (3H, s), 6.82 (1H, d, J=8.5 Hz), 7.30 (1H, dd, J=8.5, 2.4 Hz), 7.60 (1H, t, J=2.4 Hz). MS (ESI$^-$): 249 [M–H]$^-$.

Reference Examples 5-2 to 5-4

A suitable compound of General Formula (15) was used to perform reactions according to any of methods similar to Reference Example 5-1, the method described in Step R-6 or similar methods thereto, and other methods described in literatures or similar methods thereto to give the compounds of Reference Examples 5-2 to 5-4 shown below.

TABLE 25

| | | |
|---|---|---|
| 5-2 | 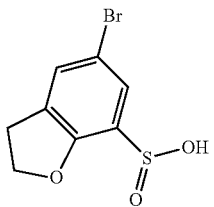 [SMILES: O=S(O)c1cc(Br)cc2c1OCC2] | $^1$H-NMR (400 MHz, DMSO-$d_6$) δ: 3.23 (2H, t, J = 8.6 Hz), 4.67 (2H, t, J = 8.9 Hz), 7.43-7.44 (1H, m), 7.58-7.59 (1H, m). MS (ESI$^-$): 261 [M − H]$^-$. |
| 5-3 | 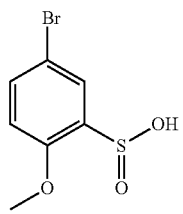 | $^1$H-NMR (400 MHz, DMSO-$d_6$) δ: 3.86 (3H, s), 7.14 (1H, dd, J = 6.7, 3.0 Hz), 7.68-7.72 (2H, m). |
| 5-4 | 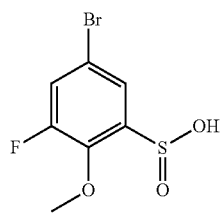 | $^1$H-NMR (400 MHz, DMSO-$d_6$) δ: 3.93 (3H, s), 7.53-7.56 (1H, m), 7.85 (1H, dd, J =10.9, 2.4 Hz). MS (ESI$^-$): 267 [M − H]$^-$. |

Reference Example 6-1

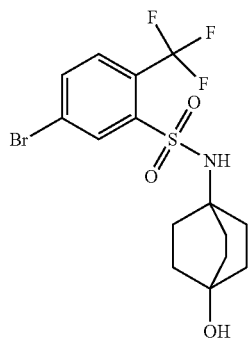

4-aminobicyclo[2.2.2]octan-1-ol hydrochloride (100 mg) was suspended in tetrahydrofuran (2.3 mL), and 2 mol/L aqueous sodium hydroxide solution (0.705 mL) and the compound obtained in Reference Example 2 (152 mg) were added to the mixture. The mixture was stirred at room temperature for 1 hour. 1 mol/L hydrochloric acid (1.41 mL) and water (10 mL) were added to the reaction mixture, and the mixture was extracted with ethyl acetate (10 mL). The organic layer was washed with saturated brine (10 mL), dried over anhydrous sodium sulfate, and then filtered to remove insoluble residues. The solvent was distilled away under reduced pressure, and the residue was then dissolved in dichloromethane and purified by silica gel column chromatography (hexane:ethyl acetate=84:16 to 0:100) to give the title compound (108 mg).

$^1$H-NMR (400 MHz, CDCl$_3$) δ: 1.16 (1H, s), 1.67-1.75 (6H, m), 1.84-1.93 (6H, m), 4.60 (1H, s), 7.69 (1H, d, J=8.5 Hz), 7.79-7.83 (1H, m), 8.41 (1H, d, J=1.8 Hz). MS (ESI$^-$): 426 [M−H]$^-$.

Reference Examples 6-2 to 6-43

A suitable amine derivative and a suitable compound of General Formula (15) were used to perform reactions according to any of methods similar to Reference Example 6-1 and the method described in Step R-7 or similar methods thereto to give the compounds of Reference Examples 6-2 to 6-43 shown below.

TABLE 26

| Reference Example | Structure | Instrumental Data |
|---|---|---|
| 6-2 | 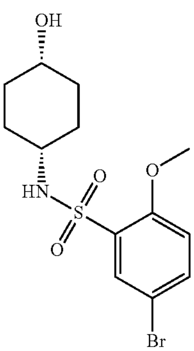 [SMILES: COc1ccc(Br)cc1S(=O)(=O)N[C@H]1CC[C@@H](O)CC1] | $^1$H-NMR (400 MHz, CDCl$_3$) δ: 1.45-1.67 (9H, m), 3.25 (1H, br), 3.83 (1H, br s), 3.98 (3H, s), 4.91-4.95 (1H, m), 6.92 (1H, d, J = 9.1 Hz), 7.63 (1H, dd, J = 9.1, 2.4 Hz), 8.04 (1H, d, J = 2.4 Hz). |
| 6-3 | 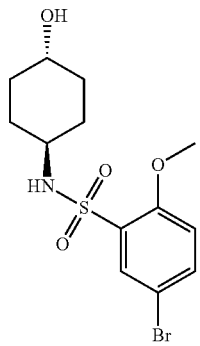 [SMILES: COc1ccc(Br)cc1S(=O)(=O)N[C@H]1CC[C@H](O)CC1] | $^1$H-NMR (400 MHz, DMSO-d$_6$) δ: 1.03-1.12 (2H, m), 1.15-1.27 (2H, m), 1.53-1.56 (2H, m), 1.69-1.72 (2H, m), 2.92-2.99 (1H, m), 3.24-3.30 (1H, m), 3.90 (3H, s), 4.48 (1H, d, J = 4.2 Hz), 7.20 (1H, d, J = 9.1 Hz), 7.42 (1H, d, J = 9.1 Hz), 7.76-7.79 (2H, m). MS (ESI$^+$): 364 [M + H]$^+$ |

TABLE 26-continued

| Reference Example | Structure | Instrumental Data |
|---|---|---|
| 6-4 | 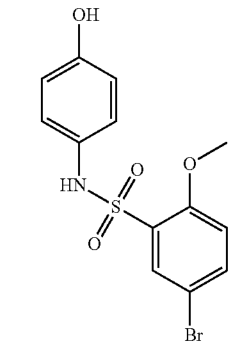 [SMILES: COc1ccc(Br)cc1S(=O)(=O)Nc1ccc(O)cc1] | $^1$H-NMR (400 MHz, DMSO-d$_6$) δ: 3.92 (3H, s), 8.57-6.61 (2H, m), 6.84-6.87 (2H, m), 7.17 (1H, d, J = 8.6 Hz), 7.64 (1H, d, J = 2.4 Hz), 7.73 (1H, dd, J = 8.6, 2.4 Hz), 9.30 (1H, s), 9.60 (1H, s). |
| 6-5 | 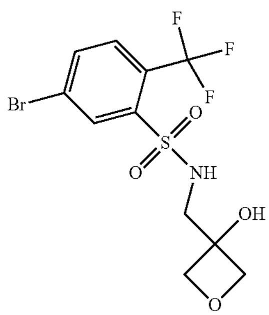 [SMILES: O=S(=O)(NCC1(O)COC1)c1cc(Br)ccc1C(F)(F)F] | $^1$H-NMR (400 MHz, CDCl$_3$) δ: 2.81 (1H, s), 3.39 (2H, d, J = 6.3 Hz), 4.48 (2H, d, J = 7.8 Hz), 4.57 (2H, d, J = 7.8 Hz), 5.22 (1H, t, J = 6.3 Hz), 7.76 (1H, d, J = 8.5 Hz), 7.84-7.89 (1H, m), 8.39 (1H, d, J = 1.8 Hz). MS (ESI$^-$): 388 [M − H]$^-$ |
| 6-6 | 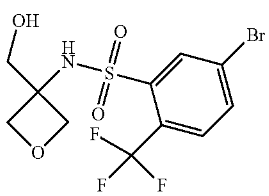 [SMILES: O=S(=O)(NC1(CO)COC1)c1cc(Br)ccc1C(F)(F)F] | $^1$H-NMR (400 MHz, CDCl$_3$) δ: 4.06 (2H, s), 4.39 (2H, d, J = 7.3 Hz), 4.69 (2H, d, J = 7.3 Hz), 5.42 (1H, s), 7.75 (1H, d, J = 8.5 Hz), 7.85-7.89 (1H, m), 8.38 (1H, d, J = 2.1 Hz). MS (ESI$^-$): 388 [M − H]$^-$ |
| 6-7 | 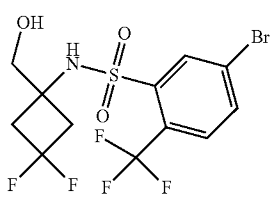 [SMILES: O=S(=O)(NC1(CO)CC(F)(F)C1)c1cc(Br)ccc1C(F)(F)F] | $^1$H-NMR (400 MHz, CDCl$_3$) δ: 1.97 (1H, t, J = 4.8 Hz), 2.63-2.83 (4H, m), 3.76 (2H, d, J = 4.8 Hz), 5.40 (1H, s), 7.75 (1H, d, J = 8.2 Hz), 7.84-7.89 (1H, m), 8.38 (1H, d, J = 1.8 Hz). MS (ESI$^-$): 422 [M − H]$^-$ |

TABLE 27

| Reference Example | Structure | Instrumental Data |
|---|---|---|
| 6-8 | 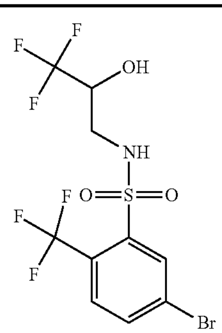 | $^1$H-NMR (400 MHz, CDCl$_3$) δ: 2.96 (1H, d, J = 3.6 Hz), 3.12-3.21 (1H, m), 3.41-3.50 (1H, m), 4.12-4.22 (1H, m), 5.18-5.25 (1H, m), 7.76 (1H, d, J = 8.2 Hz), 7.85-7.89 (1H, m), 8.37 (1H, d, J = 1.8 Hz). MS (ESI$^-$): 414 [M − H]$^-$ |

TABLE 27-continued

| Reference Example | Structure | Instrumental Data |
|---|---|---|
| 6-9 | 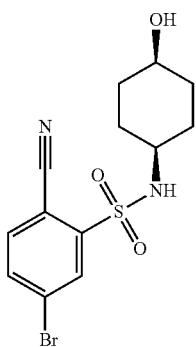 [SMILES: N#Cc1ccc(Br)cc1S(=O)(=O)N[C@H]1CC[C@@H](O)CC1] | $^1$H-NMR (400 MHz, CDCl$_3$) δ: 1.53-1.78 (8H, m), 3.31-3.40 (1H, m), 3.85-3.90 (1H, m), 5.15 (1H, d, J = 7.9 Hz), 7.70 (1H, d, J = 8.1 Hz), 7.82 (1H, dd, J = 8.1, 2.1 Hz), 8.30 (1H, d, J = 2.1 Hz).<br>MS (ESI$^-$): 357 [M − H]$^-$ |
| 6-10 | 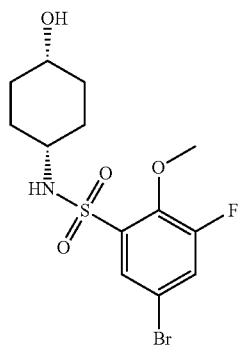 [SMILES: COc1c(F)cc(Br)cc1S(=O)(=O)N[C@H]1CC[C@@H](O)CC1] | $^1$H-NMR (400 MHz, CDCl$_3$) δ: 1.23-1.28 (1H, m), 1.51-1.88 (8H, m), 3.21-3.30 (1H, m), 3.81-3.87 (1H, m), 4.08 (3H, d, J = 1.8 Hz), 4.90 (1H, d, J = 7.6 Hz), 7.47 (1H, dd, J = 10.6, 2.4 Hz), 7.82 (1H, dd, J = 2.4, 1.5 Hz).<br>MS (ESI$^+$): 382 [M + H]$^+$ |
| 6-11 | 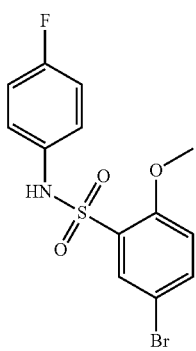 [SMILES: COc1ccc(Br)cc1S(=O)(=O)Nc1ccc(F)cc1] | $^1$H-NMR (400 MHz, CDCl$_3$) δ: 4.04 (3H, s), 6.87 (1H, s), 6.90-6.96 (3H, m), 7.01-7.07 (2H, m), 7.60 (1H, dd, J = 8.8, 2.4 Hz), 7.87 (1H, d, J = 2.7 Hz).<br>MS (ESI$^-$): 358 [M − H]$^-$ |
| 6-12 | 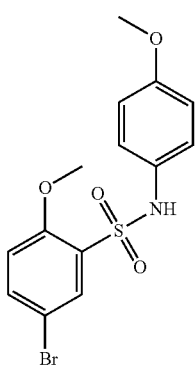 [SMILES: COc1ccc(NS(=O)(=O)c2cc(Br)ccc2OC)cc1] | $^1$H-NMR (400 MHz, DMSO-d$_6$) δ: 3.65 (3H, s), 3.91 (3H, s), 6.77-6.81 (2H, m), 6.96-7.01 (2H, m), 7.17 (1H, d, J = 8.8 Hz), 7.67 (1H, d, J = 2.7 Hz), 7.74 (1H, dd, J = 8.8, 2.4 Hz), 9.78 (1H, s).<br>MS (ESI$^-$): 370 [M − H]$^-$ |

TABLE 27-continued

| Reference Example | Structure | Instrumental Data |
|---|---|---|
| 6-13 | 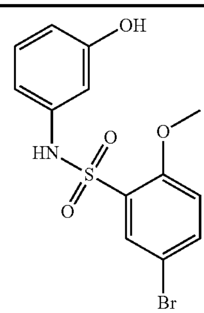 | $^1$H-NMR (400 MHz, DMSO-d$_6$) δ: 3.88 (3H, s), 6.37 (1H, dd, J = 8.2, 1.8 Hz), 6.50 (1H, dd, J = 7.9, 1.2 Hz), 6.55 (1H, t, J = 2.1 Hz), 6.97 (1H, t, J = 8.0 Hz), 7.16 (1H, d, J = 8.8 Hz), 7.74 (1H, dd, J = 8.8, 2.7 Hz), 7.77 (1H, d, J = 2.7 Hz), 9.43 (1H, S), 10.03 (1H, s).<br>MS (ESI$^-$): 356 [M − H]$^-$ |

TABLE 28

| Reference Example | Structure | Instrumental Data |
|---|---|---|
| 6-14 | 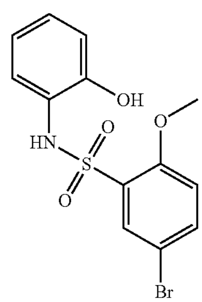 [SMILES: COc1ccc(Br)cc1S(=O)(=O)Nc1ccccc1O] | $^1$H-NMR (400 MHz, DMSO-d$_6$) δ: 3.87 (3 H, s), 6.69 (1H, td, J = 7.8, 1.5 Hz), 6.74 (1H, dd, J = 7.8, 1.5 Hz), 6.93 (1H, td, J = 7.8, 1.5 Hz), 7.13 (1H, dd, J = 7.8, 1.5 Hz), 7.19 (1H, d, J = 9.0 Hz), 7.69 (1H, d, J = 2.7 Hz), 7.75 (1H, dd, J = 9.0, 2.7 Hz), 8.75 (1H, br s), 9.68 (1H, br s).<br>MS (ESI$^-$): 356 [M − H]$^-$ |
| 6-15 | 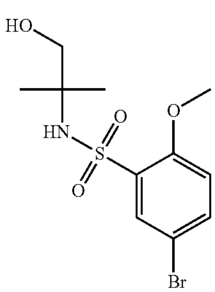 [SMILES: COc1ccc(Br)cc1S(=O)(=O)NC(C)(C)CO] | $^1$H-NMR (400 MHz, CDCl$_3$) δ: 1.13 (6H, s), 2.12 (1H, t. J = 6.3 Hz), 3.46 (2H, d, J = 6.3 Hz), 3.99 (3H, s), 5.21 (1H, s), 6.92 (1H, d, J = 8.8 Hz), 7.63 (1H, dd, J = 8.8, 2.4 Hz), 8.04 (1H, d, J = 2.4 Hz).<br>MS (ESI$^-$): 336 [M − H]$^-$ |
| 6-16 | 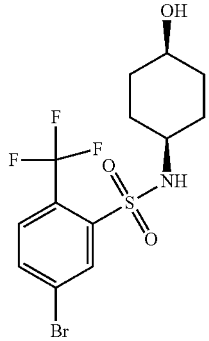 [SMILES: O=S(=O)(N[C@H]1CC[C@@H](O)CC1)c1cc(Br)ccc1C(F)(F)F] | $^1$H-NMR (400 MHz, CDCl$_3$) δ: 1.21-1.31 (1H, m), 1.50-1.72 (8H, m), 3.27-3.40 (1H, m), 3.83-3.90 (1H, m), 4.71 (1H, d, J = 7.9 Hz), 7.73 (1H, d, J = 8.5 Hz), 7.80-7.85 (1H, m), 8.40 (1H, d, J = 1.8 Hz).<br>MS (ESI$^-$): 400 [M − H]$^-$ |

TABLE 28-continued

| Reference Example | Structure | Instrumental Data |
|---|---|---|
| 6-17 | 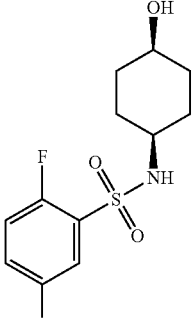 | $^1$H-NMR (400 MHz, CDCl$_3$) δ: 1.28 (1H, br s), 1.57-1.71 (8H, m), 3.29-3.38 (1H, m), 3.84-3.90 (1H, m), 4.78 (1H, d, J = 7.3 Hz), 7.11 (1H, t, J = 9.1 Hz), 7.65-7.69 (1H, m), 8.04 (1H, dd, J = 6.4, 2.4 Hz). MS (ESI$^-$): 350 [M − H]$^-$ |
| 6-18 | 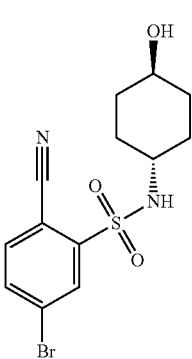 [SMILES: N#Cc1ccc(Br)cc1S(=O)(=O)N[C@H]1CC[C@H](O)CC1] | $^1$H-NMR (400 MHz, CDCl$_3$) δ: 1.29-1.43 (5H, m), 1.86-1.99 (4H, m), 3.19-3.30 (1H, m), 3.56-3.67 (1H, m), 5.00 (1H, d, J = 7.6 Hz), 7.70 (1H, d, J = 8.2 Hz), 7.83 (1H, dd, J = 8.2, 2.0 Hz), 8.31 (1H, d, J = 2.0 Hz). MS (ESI$^-$): 357 [M − H]$^-$ |
| 6-19 | 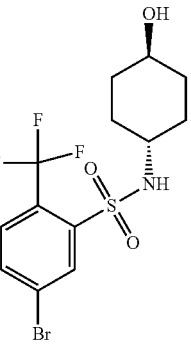 | $^1$H-NMR (400 MHz, CDCl$_3$) δ: 1.19-1.41 (5H, m), 1.83-1.96 (4H, m), 3.17-3.29 (1H, m), 3.53-3.63 (1H, m), 4.56 (1H, d, J = 7.6 Hz), 7.73 (1H, d, J = 8.5 Hz), 7.81-7.86 (1H, m), 8.41 (1H, d, J = 1.8 Hz). MS (ESI$^-$): 400 [M − H]$^-$ |

TABLE 29

| Reference Example | Structure | Instrumental Data |
|---|---|---|
| 6-20 | 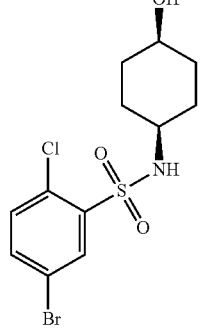 | $^1$H-NMR (400 MHz, DMSO-d$_6$) δ: 1.27-1.39 (4H, m), 1.48-1.67 (4H, m), 3.01-3.13 (1H, m), 3.57-3.64 (1H, m), 4.34 (1H, d, J = 2.7 Hz), 7.63 (1H, d, J = 8.5 Hz), 7.85 (1H, dd, J = 8.5, 2.6 Hz), 8.06 (1H, d, J = 2.6 Hz), 8.08 (1H, d, J = 7.6 Hz). MS (ESI$^-$): 366 [M − H]$^-$ |

TABLE 29-continued

| Reference Example | Structure | Instrumental Data |
|---|---|---|
| 6-21 | 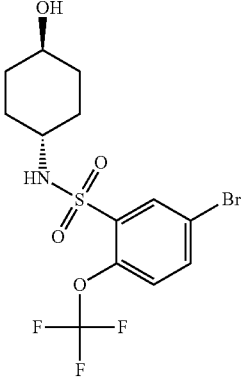 [SMILES: O=S(=O)(N[C@H]1CC[C@H](O)CC1)c1cc(Br)ccc1OC(F)(F)F] | $^1$H-NMR (400 MHz, CDCl$_3$) δ: 1.21-1.37 (4H, m), 1.40 (1H, d, J = 3.6 Hz), 1.83-1.97 (4H, m), 3.17-3.27 (1H, m), 3.54-3.63 (1H, m), 4.56 (1H, d, J = 7.6 Hz), 7.26-7.30 (1H, m), 7.73 (1H, dd, J = 8.8, 2.4 Hz), 8.18 (1H, d, J = 2.4 Hz).<br>MS (ESI$^-$): 416 [M − H]$^-$ |
| 6-22 | 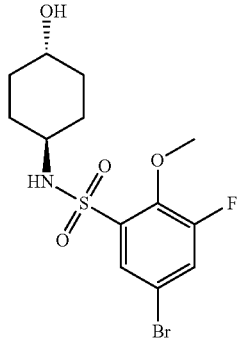 [SMILES: COc1c(F)cc(Br)cc1S(=O)(=O)N[C@H]1CC[C@H](O)CC1] | $^1$H-NMR (400 MHz, CDCl$_3$) δ: 1.21-1.33 (4H, m), 1.35 (1H, d, J = 3.9 Hz), 1.81-1.96 (4H, m), 3.10-3.19 (1H, m), 3.52-3.62 (1H, m), 4.06 (3H, d, J = 1.8 Hz), 4.77 (1H, d, J = 7.3 Hz), 7.48 (1H, dt, J = 13.0, 2.4 Hz), 7.82 (1H, dd, J = 2.4, 1.5 Hz).<br>MS (ESI$^-$): 380 [M − H]$^-$ |
| 6-23 | 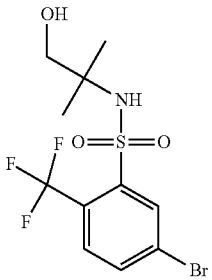 | $^1$H-NMR (400 MHz, CDCl$_3$) δ: 1.20 (6H, s), 2.00 (1H, t, J = 5.7 Hz), 3.51 (2H, d, J = 5.7 Hz), 5.07 (1H, s), 7.71 (1H, d, J = 8.6 Hz), 7.79-7.84 (1H, m), 8.43 (1H, d, J = 2.1 Hz).<br>MS (ESI$^-$): 374 [M − H]$^-$ |
| 6-24 | 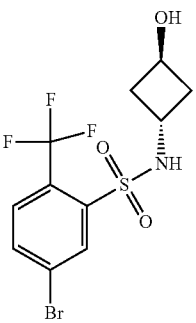 [SMILES: O=S(=O)(N[C@H]1C[C@H](O)C1)c1cc(Br)ccc1C(F)(F)F] | $^1$H-NMR (400 MHz, CDCl$_3$) δ: 2.14-2.26 (4H, m), 3.99-4.09 (1H, m), 4.42-4.49 (1H, m), 4.84 (1H, d, J = 7.0 Hz), 7.73 (1H, d, J = 8.3 Hz), 7.84 (1H, dd, J = 8.3, 1.5 Hz), 8.38 (1H, d, J = 1.5 Hz).<br>MS (ESI$^-$): 372 [M − H]$^-$ |

TABLE 30

| Reference Example | Structure | Instrumental Data |
|---|---|---|
| 6-25 | 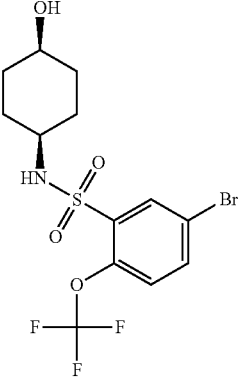 [SMILES: O=S(=O)(N[C@H]1CC[C@@H](O)CC1)c1cc(Br)ccc1OC(F)(F)F] | $^1$H-NMR (400 MHz, DMSO-d$_6$) δ: 1.29-1.41 (4H, m), 1.50-1.69 (4H, m), 3.09-3.21 (1H, m), 3.58-3.08 (1H, m), 4.35 (1H, d, J = 2.7 Hz), 7.52-7.56 (1H, m), 7.95 (1H, dd, J = 8.8, 2.7 Hz), 8.04 (1H, d, J = 2.7 Hz), 8.06 (1H, br s). MS (ESI$^-$): 416 [M − H]$^-$ |
| 6-26 | 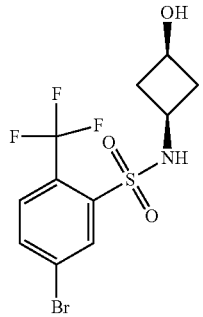 [SMILES: O=S(=O)(N[C@H]1C[C@@H](O)C1)c1cc(Br)ccc1C(F)(F)F] | $^1$H-NMR (400 MHz, CDCl$_3$) δ: 1.69-1.81 (3H, m), 2.56-2.65 (2H, m), 3.37-3.50 (1H, m), 3.94-4.04 (1H, m), 4.86 (1H, d, J = 8.5 Hz), 7.73 (1H, d, J = 8.2 Hz), 7.81-7.86 (1H, m), 8.36 (1H, d, J = 1.8 Hz). MS (ESI$^-$): 372 [M − H]$^-$ |
| 6-27 | 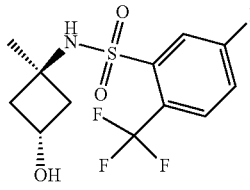 | $^1$H-NMR (400 MHz, CDCl$_3$) δ: 1.43 (3H, s), 1.71 (1H, d, J = 4.5 Hz), 1.93-2.01 (2H, m), 2.58-2.68 (2H, m), 4.31-4.40 (1H, m), 4.83 (1H, s), 7.71 (1H, d, J = 8.5 Hz), 7.80-7.84 (1H, m), 8.41 (1H, d, J = 1.8 Hz). MS (ESI$^-$): 386 [M − H]$^-$ |
| 6-28 | 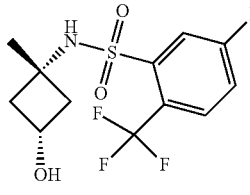 | $^1$H-NMR (400 MHz, CDCl$_3$) δ: 1.34 (3H, s), 1.76 (1H, d, J = 6.4 Hz), 2.10-2.18 (2H, m), 2.41-2.49 (2H, m), 4.09-4.18 (1H, m), 4.95 (1H, s), 7.72 (1H, d, J = 8.2 Hz), 7.80-7.84 (1H, m), 8.40 (1H, d, J = 1.8 Hz). MS (ESI$^-$): 386 [M − H]$^-$ |
| 6-29 | 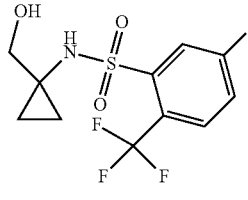 | $^1$H-NMR (400 MHz, CDCl$_3$) δ: 0.72-0.76 (2H, m), 0.78-0.83 (2H, m), 2.00 (1H, t, J = 5.7 Hz), 3.49 (2H, d, J = 5.7 Hz), 5.51 (1H, s), 7.72 (1H, d, J = 8.5 Hz), 7.82-7.86 (1H, m), 8.43 (1H, d, J = 2.1 Hz). MS (ESI$^-$): 372 [M − H]$^-$ |

TABLE 30-continued

| Reference Example | Structure | Instrumental Data |
|---|---|---|
| 6-30 | 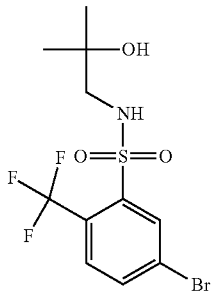 [SMILES: CC(C)(O)CNS(=O)(=O)c1cc(Br)ccc1C(F)(F)F] | $^1$H-NMR (400 MHz, CDCl$_3$) δ: 1.26 (6H, s), 1.46 (1H, s), 2.94 (2H, d, J = 6.1 Hz), 5.13 (1H, t, J = 6.1 Hz), 7.74 (1H, d, J = 8.5 Hz), 7.81-7.85 (1H, m), 8.35 (1H, d, J = 1.8 Hz). MS (ESI$^-$): 374 [M − H]$^-$ |
| 6-31 | 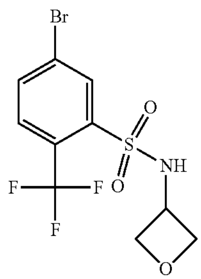 [SMILES: O=S(=O)(NC1COC1)c1cc(Br)ccc1C(F)(F)F] | $^1$H-NMR (400 MHz, CDCl$_3$) δ: 4.46 (2H, t, J = 6.8 Hz), 4.52-4.63 (1H, m), 4.75 (2H, t, J = 7.3 Hz), 5.33-5.44 (1H, m), 7.74 (1H, d, J = 8.2 Hz), 7.84-7.89 (1H, m), 8.33 (1H, d, J = 1.8 Hz). MS (ESI$^-$): 358 [M − H]$^-$ |

TABLE 31

| Reference Example | Structure | Instrumental Data |
|---|---|---|
| 6-32 | 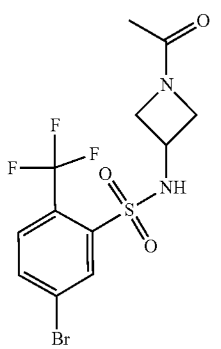 [SMILES: CC(=O)N1CC(NS(=O)(=O)c2cc(Br)ccc2C(F)(F)F)C1] | $^1$H-NMR (400 MHz, CDCl$_3$) δ: 1.85 (3H, s), 3.68 (1H, dd, J = 10.4, 5.3 Hz), 3.99 (1H, dd, J = 9.1, 5.1 Hz), 4.14 (1H, t, J = 9.2 Hz), 4.19-4.28 (1H, m), 4.36 (1H, t, J = 8.3 Hz), 5.54 (1H, d, J = 7.9 Hz), 7.76 (1H, d, J = 8.2 Hz), 7.85-7.89 (1H, m), 8.34 (1H, d, J = 2.1 Hz). MS (ESI$^+$): 401 [M + H]$^+$ |
| 6-33 | 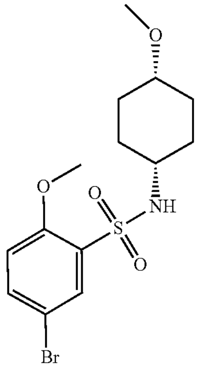 [SMILES: COc1ccc(Br)cc1S(=O)(=O)N[C@H]1CC[C@@H](OC)CC1] | $^1$H-NMR (400 MHz, DMSO-d$_6$) δ: 1.27-1.38 (4H, m), 1.39-1.51 (2H, m), 1.64-1.74 (2H, m), 2.99-3.10 (1H, m), 3.15 (3H, s), 3.17-3.22 (1H, m), 3.90 (3H, s), 7.20 (1H, d, J = 8.8 Hz), 7.46 (1H, d, J = 7.6 Hz), 7.75-7.80 (2H, m). MS (ESI$^+$): 378 [M + H]$^+$ |

TABLE 31-continued

| Reference Example | Structure | Instrumental Data |
|---|---|---|
| 6-34 | 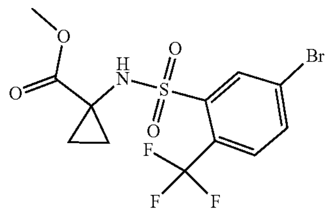 [SMILES: COC(=O)C1(NS(=O)(=O)c2cc(Br)ccc2C(F)(F)F)CC1] | $^1$H-NMR (400 MHz, CDCl$_3$) δ: 1.49 (2H, t, J = 3.0 Hz), 1.52 (2H, t, J = 3.0 Hz), 3.37 (3H, 8), 5.67 (1H, s), 7.75 (1H, d, J = 8.5 Hz), 7.81-7.85 (1H, m), 8.30 (1H, d, J = 1.8 Hz).<br>MS (ESI$^+$): 400 [M − H]$^−$ |
| 6-35 | 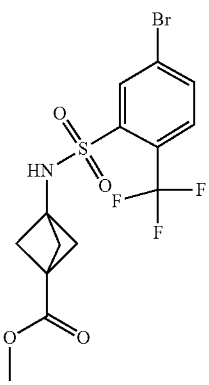 [SMILES: COC(=O)C12CC(NS(=O)(=O)c3cc(Br)ccc3C(F)(F)F)(C1)C2] | $^1$H-NMR (400 MHz, CDCl$_3$) δ: 2.18 (6H, s), 3.66 (3H, s), 5.42 (1H, s), 7.73 (1H, d, J = 8.5 Hz), 7.83-7.88 (1H, m), 8.41 (1H, d, J = 1.8 Hz).<br>MS (ESI$^+$): 426 [M − H]$^−$ |
| 6-36 | 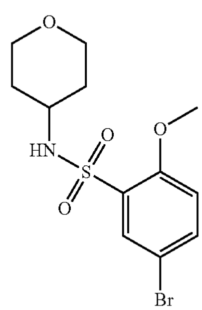 [SMILES: COc1ccc(Br)cc1S(=O)(=O)NC1CCOCC1] | $^1$H-NMR (400 MHz, CDCl$_3$) δ: 1.41-1.51 (2H, m), 1.68-1.74 (2H, m), 3.32-3.38 (3H, m), 3.82-3.88 (2H, m), 3.98 (3H, s), 4.89 (1H, d, J = 7.3 Hz), 6.93 (1H, d, J = 9.1 Hz), 7.64 (1H, dd, J = 9.1, 2.4 Hz), 8.04 (1H, d, J = 2.4 Hz).<br>MS (FD$^+$): 349 [M + H]$^+$ |
| 6-37 | 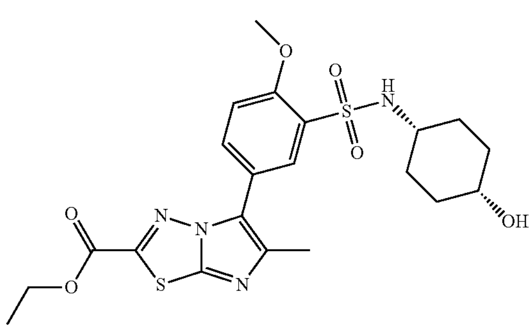 [SMILES: CCOC(=O)c1nn2c(-c3ccc(OC)c(S(=O)(=O)N[C@H]4CC[C@@H](O)CC4)c3)c(C)nc2s1] | $^1$H-NMR (400 MHz, CDCl$_3$) δ: 1.32 (1H, br), 1.46 (3H, t, J = 7.3 Hz), 1.54-1.67 (8H, m), 2.55 (3H, s), 3.27 (1H, br), 3.82 (1H, br), 4.06 (3H, s), 4.52 (2H, q, J = 7.1 Hz), 4.96 (1H, d, J = 7.3 Hz), 7.19 (1H, d, J = 9.1 Hz), 7.96 (1H, dd, J = 8.5, 2.4 Hz), 8.18 (1H, d, J = 2.4 Hz).<br>MS (ESI$^+$): 495 [M + H]$^+$ |

TABLE 32

| Reference Example | Structure | Instrumental Data |
|---|---|---|
| 6-38 | 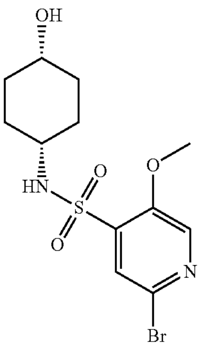 [SMILES: COc1cnc(Br)cc1S(=O)(=O)N[C@H]1CC[C@@H](O)CC1] | $^1$H-NMR (400 MHz, CDCl$_3$) δ: 1.27 (1H, br), 1.56-1.62 (8H, m), 3.31 (1H, br), 3.88 (1H, br), 4.09 (3H, s), 4.91 (1H, d, J = 7.9 Hz), 7.92 (1H, s), 8.24 (1H, s). MS (ESI$^+$): 365 [M + H]$^+$ |
| 6-39 | 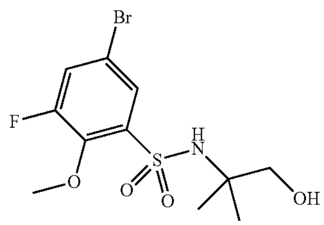 [SMILES: COc1c(F)cc(Br)cc1S(=O)(=O)NC(C)(C)CO] | $^1$H-NMR (400 MHz, CDCl$_3$) δ: 1.16 (6H, s), 2.12 (1H, t, J = 6.4 Hz), 3.49 (2H, t, J = 6.1 Hz), 3.96 (3H, s), 5.34 (1H, s), 7.44 (1H, d, J = 10.3 Hz), 7.77 (1H, d, J = 8.5 Hz). |
| 6-40 | 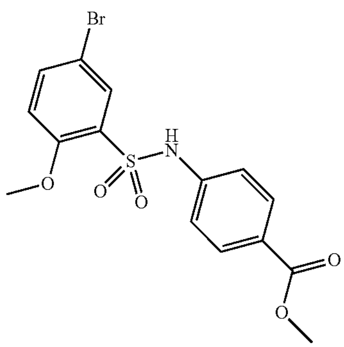 [SMILES: COC(=O)c1ccc(NS(=O)(=O)c2cc(Br)ccc2OC)cc1] | $^1$H-NMR (400 MHz, CDCl$_3$) δ: 3.87 (3H, s), 4.00 (3H, s), 6.87 (1H, d, J = 8.6 Hz), 7.05 (1H, s), 7.10-7.14 (2H, m), 7.59 (1H, dd, J = 9.2, 2.4 Hz), 7.89-7.93 (2H, m), 7.99 (1H, d, J = 2.4 Hz). |
| 6-41 | 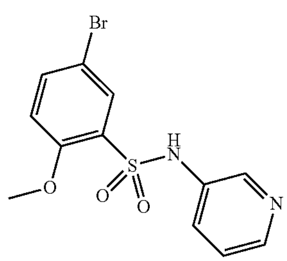 [SMILES: COc1ccc(Br)cc1S(=O)(=O)Nc1cccnc1] | $^1$H-NMR (400 MHz, DMSO-d$_6$) δ: 3.85 (3H, s), 7.17 (1H, d, J = 9.2 Hz), 7.26-7.29 (1H, m), 7.48-7.51 (1H, m), 7.76-7.78 (1H, m), 7.81 (1H, d, J = 2.4 Hz), 8.23 (1H, dd, J = 4.9, 1.2 Hz), 8.30 (1H. d. J = 1.8 Hz), 10.43 (1H, s). MS (ESI$^+$): 343 [M + H]$^+$ |
| 6-42 | 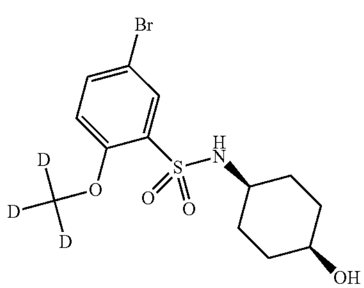 [SMILES: [2H]C([2H])([2H])Oc1ccc(Br)cc1S(=O)(=O)N[C@H]1CC[C@@H](O)CC1] | $^1$H-NMR (400 MHz, DMSO-d$_6$) δ: 1.24-1.38 (4H, m), 1.47-1.62 (4H, m), 2.97-3.07 (1H, m), 3.56-3.62 (1H, m), 4.31 (1H. d. J = 3.1 Hz), 7.19 (1H, d, J = 8.6 Hz), 7.41 (1H, d, J = 7.3 Hz), 7.75-7.79 (2H, m). MS (ESI$^+$): 367 [M + H]$^+$ |

TABLE 32-continued

| Reference Example | Structure | Instrumental Data |
|---|---|---|
| 6-43 | ![structure] | $^1$H-NMR (400 MHz, DMSO-d$_6$) δ: 0.98 (6H, s), 3.16 (2H, d, J = 5.5 Hz), 4.90 (1H, t, J = 5.5 Hz), 6.79 (1H, s), 7.21 (1H, d, J = 8.6 Hz), 7.77 (1H, dd, J = 8.6, 2.4 Hz), 7.80 (1H, d, J = 2.4 Hz). MS (ESI$^+$): 341 [M + H]$^+$ |

Reference Example 7

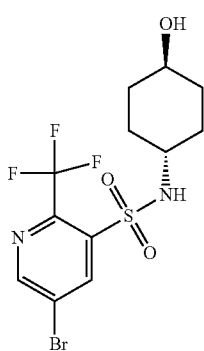

[Formula 53]

The compound obtained in Reference Example 3 (123 mg) was dissolved in dichloromethane (2.0 mL) under an argon atmosphere, and oxalyl chloride (0.103 mL) and N,N-dimethylformamide (0.020 mL) were added to the mixture. The mixture was stirred at room temperature for 5 hours. An additional portion of oxalyl chloride (0.0515 mL) was added to the mixture, and the mixture was stirred for 15 minutes. The solvent was then distilled away under reduced pressure. Toluene (2 mL) was added to the residue, and the solvent was then distilled away under reduced pressure. The resulting residue was used in the next step without purification.

Trans-4-aminocyclohexanol (69.2 mg) was dissolved in dichloromethane (2.0 mL) followed by addition of N,N-diisopropylethylamine (0.136 mL), and a solution of the previously obtained residue in dichloromethane (2.0 mL) was then added slowly dropwise to the mixture. After stirring for 5 minutes, water (20 mL) was added, and the mixture was extracted twice with ethyl acetate (20 mL). The combined organic layer was washed with saturated brine (10 mL), dried over anhydrous sodium sulfate, and then filtered to remove insoluble residues. The solvent was distilled away under reduced pressure, and the residue was then dissolved in dichloromethane (4 mL) and purified by silica gel column chromatography (hexane:ethyl acetate=92:8 to 0:100) to give the title compound (65.6 mg).

$^1$H-NMR (400 MHz, CDCl$_3$) δ: 1.23-1.39 (4H, m), 1.41 (1H, d, J=4.2 Hz), 1.84-1.98 (4H, m), 3.20-3.33 (1H, m), 3.55-3.65 (1H, m), 4.72 (1H, d, J=7.6 Hz), 8.70 (1H, d, J=1.8 Hz), 8.90 (1H, d, J=1.8 Hz). MS (ESI$^-$): 401 [M–H]$^-$.

Reference Example 8-1

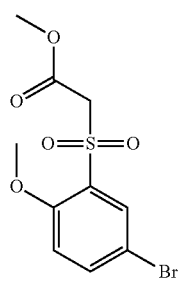

[Formula 54]

The compound obtained in Reference Example 5-1 (1.00 g) was suspended in N,N-dimethylformamide (12.2 mL) under an argon atmosphere, and methyl bromoacetate (0.675 mL) was added. The mixture was stirred at room temperature for 8.5 hours and left to stand for 14.5 hours. After stirring for additional 3 hours, water (20 mL) was added to the mixture, and the mixture was extracted with ethyl acetate (20 mL). The organic layer was washed with saturated brine (10 mL), dried over anhydrous sodium sulfate, and then filtered to remove insoluble residues. The solvent was distilled away under reduced pressure, and the residue was then dissolved in dichloromethane (8 mL) and purified by silica gel column chromatography (hexane:ethyl acetate=84:16 to 0:100) to give the title compound (871 mg).

$^1$H-NMR (400 MHz, CDCl$_3$) δ: 3.70 (3H, s), 4.00 (3H, s), 4.38 (2H, s), 6.96 (1H, d, J=8.8 Hz), 7.72 (1H, dd, J=8.8, 2.7 Hz), 8.06 (1H, d, J=2.7 Hz). MS (ESI$^+$): 323 [M+H]$^+$.

Reference Examples 8-2 to 8-16

A suitable compound of General Formula (11) or (11') was used to perform reactions according to any of methods similar to Reference Example 8-1 and the method described in Step O-1 or similar methods thereto to give the compounds of Reference Examples 8-2 to 8-16 shown below.

TABLE 33

| Reference Example | Structure | Instrumental Data |
|---|---|---|
| 8-2 | (3-bromo-5-fluoro-2-methoxyphenyl methyl sulfone) | ¹H-NMR (400MHz, CDCl₃) δ: 3.24 (3H, s), 4.09 (3H, d, J = 2.1 Hz), 7.54 (1H, dd, J = 10.4, 2.3 Hz), 7.88 (1H, dd, J = 2.3, 1.7 Hz). MS (ESI⁺): 282 [M]⁺ |
| 8-3 | (5-bromo-2-methoxyphenyl ethyl sulfone) | ¹H-NMR (400 MHz, CDCl₃) δ: 1.26 (3H, t, J = 7.4 Hz), 3.37 (2H, q, J = 7.4 Hz), 3.97 (3H, 6), 6.94 (1H, d, J = 9.1 Hz), 7.69 (1H, dd, J = 9.1, 2.4 Hz), 8.07 (1H, s). MS (FI⁺): 278 [M]⁺ |
| 8-4 | (5-bromo-2-methoxyphenyl cyclopropylmethyl sulfone) | ¹H-NMR (400 MHz, CDCl₃) δ: 0.18-0.24 (2H, m), 0.52-0.59 (2H, m), 0.93-1.04 (1H, m), 3.27 (2H, d, J = 7.3 Hz), 3.96 (3H, s), 6.93 (1H, d, J = 8.8 Hz), 7.69 (1H, dd, J = 8.8, 2.6 Hz), 8.12 (1H, d, J = 2.6 Hz). MS (ESI⁺): 305 [M + H]⁺ |
| 8-5 | (5-bromo-2-methoxyphenyl 3-hydroxy-3-methylbutyl sulfone) | ¹H-NMR (400 MHz, CDCl₃) δ: 1.24 (6H, s), 1.41 (1H, s), 1.80-1.87 (2H, m), 3.47-3.54 (2H, m), 3.98 (3H, s), 6.95 (1H, d, J = 8.8 Hz), 7.69 (1H, dd, J = 8.8, 2.5 Hz), 8.06 (1H, d, J = 2.5 Hz). MS (ESI⁺): 337 [M + H]⁺ |
| 8-6 | (5-bromo-2-methoxyphenyl methyl sulfone) | ¹H-NMR (400 MHz, CDCl₃) δ: 3.22 (3H, s), 4.00 (3H, s), 6.95 (1H, d, J = 8.8 Hz), 7.69 (1H, dd, J = 8.8, 2.6 Hz), 8.10 (1H, d, J = 2.6 Hz). |
| 8-7 | (5-bromo-2-methoxyphenyl 3-chloropropyl sulfone) | ¹H-NMR (400 MHz, CDCl₃) δ: 2.16-2.24 (2H, m), 3.54 (2H, t, J = 7.6 Hz), 3.84 (2H, t, J = 6.2 Hz), 3.99 (3H, s), 6.96 (1H, d, J = 8.8 Hz), 7.70 (1H, dd, J = 8.8, 2.4 Hz), 8.07 (1H, d, J = 2.4 Hz). MS (ESI⁺): 327 [M + H]⁺ |

TABLE 33-continued

| Reference Example | Structure | Instrumental Data |
|---|---|---|
| 8-8 | 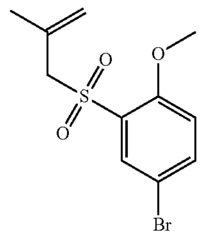 [SMILES: C=C(C)CS(=O)(=O)c1cc(Br)ccc1OC] | $^1$H-NMR (400 MHz, CDCl$_3$) δ: 1.87 (3H, s), 3.99 (3H, s), 4.04 (2H, s), 4.81 (1H, s), 5.01-5.02 (1H, m), 6.93 (1H, d, J = 9.1 Hz), 7.68 (1H, dd, J = 9.1, 2.7 Hz), 8.03 (1H, d, J = 2.7 Hz).<br>MS (ESI$^+$): 305 [M + H]$^+$ |

TABLE 34

| Reference Example | Structure | Instrumental Data |
|---|---|---|
| 8-9 | 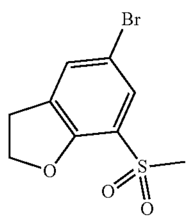 | $^1$H-NMR (400 MHz, CDCl$_3$) δ: 3.19 (3H, s), 3.32 (2H, t, J = 8.9 Hz), 4.84 (2H, t, J = 8.9 Hz), 7.54-7.55 (1H, m), 7.805-7.808 (1H, m).<br>MS (FI$^+$): 276 [M]$^+$. |
| 8-10 | 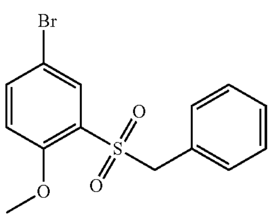 [SMILES: COc1ccc(Br)cc1S(=O)(=O)Cc1ccccc1] | $^1$H-NMR (400 MHz, CDCl$_3$) δ: 4.04 (3H, s), 4.58 (2H, s), 6.94 (1H, d, J = 9.1 Hz), 7.18-7.22 (2H, m), 7.24-7.33 (3H, m), 7.63 (1H, dd, J = 9.1, 2.4 Hz), 7.80 (1H, d, J = 2.4 Hz).<br>MS (EI$^+$): 340 [M]$^+$ |
| 8-11 | 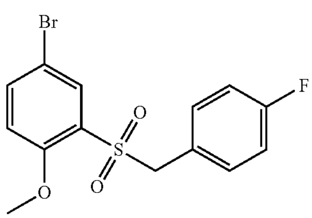 [SMILES: COc1ccc(Br)cc1S(=O)(=O)Cc1ccc(F)cc1] | $^1$H-NMR (400 MHz, CDCl$_3$) δ: 4.04 (3H, s), 4.55 (2H, s), 6.93-7.01 (3H, m), 7.16-7.22 (2H, m), 7.65 (1H, dd, J = 8.8, 2.7 Hz), 7.82 (1H, d, J = 2.4 Hz).<br>MS (EI$^+$): 358 [M]$^+$ |
| 8-12 | 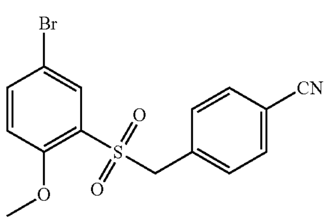 [SMILES: COc1ccc(Br)cc1S(=O)(=O)Cc1ccc(C#N)cc1] | $^1$H-NMR (400 MHz, CDCl$_3$) δ: 4.05 (3H, s), 4.62 (2H, s), 6.97 (1H, d, J = 9.1 Hz), 7.36 (2H, d, J = 7.9 Hz), 7.60 (2H, d, J = 7.9 Hz), 7.68 (1H, dd, J = 9.1, 2.4 Hz), 7.82 (1H, d, J = 2.4 Hz).<br>MS (FI$^+$): 365 [M]$^+$ |
| 8-13 | 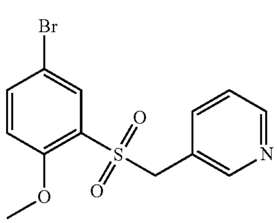 [SMILES: COc1ccc(Br)cc1S(=O)(=O)Cc1cccnc1] | $^1$H-NMR (400 MHz, CDCl$_3$) δ: 4.05 (3H, s), 4.59 (2H, s), 6.96 (1H, d, J = 9.1 Hz), 7.25-7.29 (1H, m), 7.66 (1H, dd, J = 8.8, 2.7 Hz), 7.69 (1H, dt, J = 7.9, 1.8 Hz), 7.80 (1H, d, J = 2.4 Hz), 8.34 (1H, d, J = 1.8 Hz), 8.55 (1H, dd, J = 4.8, 1.2 Hz).<br>MS (FI$^+$): 341 [M]$^+$ |

TABLE 34-continued

| Reference Example | Structure | Instrumental Data |
|---|---|---|
| 8-14 | 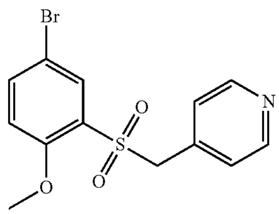 [SMILES: COc1ccc(Br)cc1S(=O)(=O)Cc1ccncc1] | $^1$H-NMR (400 MHz, CDCl$_3$) δ: 4.05 (3H, s), 4.57 (2H, s), 6.96 (1H, d, J = 8.6 Hz), 7.17 (2H, dd, J = 4.3, 1.8 Hz), 7.68 (1H, dd, J = 9.2, 2.4 Hz), 7.83 (1H, d, J = 2.4 Hz), 8.55 (2H, dd, J = 4.3, 1.8 Hz). MS (ESI$^+$): 342 [M + H]$^+$ |
| 8-15 | 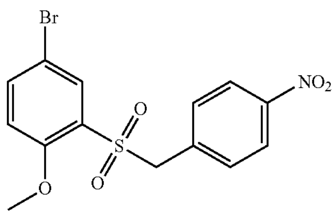 [SMILES: COc1ccc(Br)cc1S(=O)(=O)Cc1ccc([N+](=O)[O-])cc1] | $^1$H-NMR (400 MHz, CDCl$_3$) δ: 4.07 (3H, s), 4.68 (2H, s), 6.98 (1H, d, J = 8.5 Hz), 7.41-7.45 (2H, m), 7.69 (1H, dd, J = 9.1, 2.4 Hz), 7.83 (1H, d, J = 2.4 Hz), 8.14-8.18 (2H, m). MS (ESI$^-$): 384 [M − H]$^-$ |
| 8-16 | 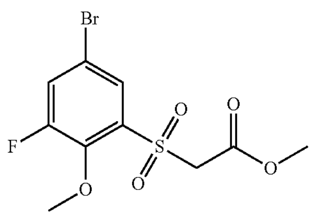 [SMILES: COC(=O)CS(=O)(=O)c1cc(Br)cc(F)c1OC] | $^1$H-NMR (400 MHz, CDCl$_3$) δ: 3.71 (3H, s), 4.10 (3H, d, J = 1.8 Hz), 4.40 (2H, s), 7.56 (1H, dd, J =10.8, 2.1 Hz), 7.84-7.87 (1H, m). MS (ESI$^-$): 339 [M − H]$^-$ |

Reference Example 9-1

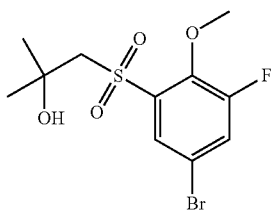

[Formula 55]

The compound obtained in Reference Example 8-2 (286 mg) was dissolved in tetrahydrofuran (5.1 mL) under an argon atmosphere and cooled to 0° C. followed by addition of a solution of 1.08 mol/L lithium diisopropylamide in tetrahydrofuran-hexane (1.12 mL). The reaction was stirred at 0° C. for 30 minutes followed by addition of acetone (0.112 mL), and the reaction was stirred at the same temperature for 1 hour. Saturated aqueous ammonium chloride solution (6 mL) and water (6 mL) were added to the mixture, and the mixture was then extracted with ethyl acetate (10 mL). The organic layer was washed with saturated brine (10 mL), dried over anhydrous sodium sulfate, and filtered to remove insoluble residues. The solvent was distilled away under reduced pressure, and the residue was then dissolved in dichloromethane (3 mL) and purified by silica gel column chromatography (hexane:ethyl acetate=95:5 to 60:40) to give the title compound (220 mg).

$^1$H-NMR (400 MHz, CDCl$_3$) δ: 1.42 (6H, s), 3.42 (1H, s), 3.58 (2H, s), 4.08 (3H, d, J=1.8 Hz), 7.54 (1H, dd, J=10.4, 2.3 Hz), 7.86 (1H, dd, J=2.3, 1.5 Hz). MS (ESI$^+$): 341 [M+H]$^+$.

Reference Examples 9-2 to 9-15

A suitable compound of General Formula (2ap) was used to perform reactions according to any of methods similar to Reference Example 9-1 and the method described in Step AI-1 or similar methods thereto to give the compounds of Reference Examples 9-2 to 9-15 shown below.

TABLE 35

| Reference Example | Structure | Instrumental Data |
|---|---|---|
| 9-2 | 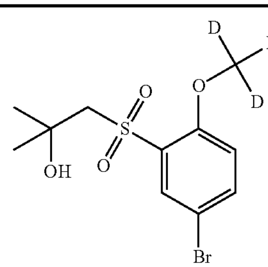 | $^1$H-NMR (400 MHz, CDCl$_3$) δ: 1.42 (6H, s), 3.54 (2H, s), 3.63 (1H, s), 6.95 (1H, d, J = 8.8 Hz), 7.69 (1H, dd, J = 8.8, 2.1 Hz), 8.06 (1H, d, J = 2.1 Hz). MS (CI$^+$): 325 [M]$^+$ |

TABLE 35-continued

| Reference Example | Structure | Instrumental Data |
|---|---|---|
| 9-3 | 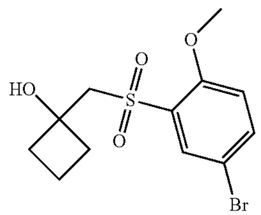 [SMILES: COc1ccc(Br)cc1S(=O)(=O)CC1(O)CCC1] | $^1$H-NMR (400 MHz, CDCl$_3$) δ: 1.63-2.38 (6H, m), 3.70 (2H, s), 3.85 (1H, s), 4.01 (3H, s), 6.96 (1H, d, J = 9.2 Hz), 7.68-7.70 (1H, m), 8.06 (1H, d. J = 2.4 Hz). MS (ESI$^+$): 317 [M − OH]$^+$ |
| 9-4 | 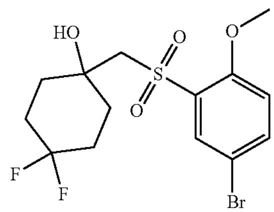 | $^1$H-NMR (400 MHz, CDCl$_3$) δ: 1.70-1.77 (2H, m), 1.90-2.28 (6H, m), 3.53 (2H, s), 3.72 (1H, s), 4.00 (3H, s), 6.96 (1H, d, J = 8.9 Hz), 7.71 (1H, dd, J = 8.9, 2.4 Hz), 8.06 (1H, d, J = 2.4 Hz). MS (ESI$^−$): 443 [M + HCOO]$^−$ |

TABLE 36

| Reference Example | Structure | Instrumental Data |
|---|---|---|
| 9-5 | | $^1$H-NMR (400 MHz, CDCl$_3$) δ: 1.20-1.23 (8H, m), 1.69 (2H, dd, J = 7.0, 5.1 Hz), 2.56 (1H, s), 3.94 (3H, s), 6.90 (1H, d, J = 9.1 Hz), 7.66 (1H, dd, J = 9.1, 2.4 Hz), 8.14 (1H, d, J = 2.4 Hz). MS (CI$^+$): 331 [M − OH]$^+$ |
| 9-6 | 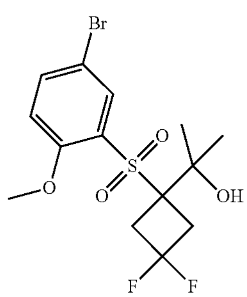 [SMILES: COc1ccc(Br)cc1S(=O)(=O)C1(C(C)(C)O)CC(F)(F)C1] | $^1$H-NMR (400 MHz, CDCl$_3$) δ: 1.44 (6H, s), 2.84 (1H, s), 3.01-3.11 (2H, m), 3.33-3.44 (2H, m), 3.95 (3H, s), 6.96 (1H, d, J = 8.8 Hz), 7.73 (1H, dd, J = 8.8, 2.4 Hz), 8.08 (1H, d, J = 2.4 Hz). MS (CI$^+$): 381 [M − OH]$^+$ |
| 9-7 | 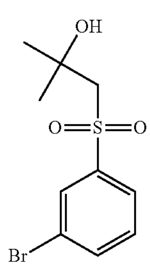 | $^1$H-NMR (400 MHz, CDCl$_3$) δ: 1.47 (6H, s), 3.32 (2H, s), 3.52 (1H, s), 7.48 (1H, d, J = 7.9 Hz), 7.80 (1H, d, J = 6.7 Hz), 7.87 (1H, d, J = 7.3 Hz), 8.08 (1H, s). MS (ESI$^+$): 315 [M + Na]$^+$ |

TABLE 36-continued

| Reference Example | Structure | Instrumental Data |
|---|---|---|
| 9-8 | 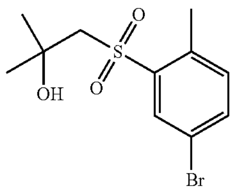 [SMILES: Cc1ccc(Br)cc1S(=O)(=O)CC(C)(C)O] | $^1$H-NMR (400 MHz, CDCl$_3$) δ: 1.48 (6H, s), 2.66 (3H, s), 3.31 (2H, s), 3.83 (1H, s), 7.23 (1H, d, J = 8.1 Hz), 7.65 (1H, dd, J = 8.1, 2.3 Hz), 8.15 (1H, d, J = 2.3 Hz).<br>MS (ESI$^+$): 329 [M + Na]$^+$ |
| 9-9 | 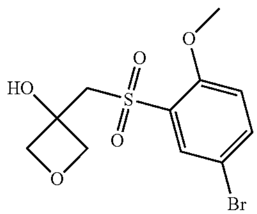 [SMILES: COc1ccc(Br)cc1S(=O)(=O)CC1(O)COC1] | $^1$H-NMR (400 MHz, CDCl$_3$) δ: 3.94 (2H, s), 4.02 (3H, s), 4.12 (1H, s), 4.61 (2H, d, J = 7.6 Hz), 4.70 (2H, d, J = 7.6 Hz), 6.98 (1H, d, J = 8.8 Hz), 7.74 (1H, dd, J = 8.8, 2.4 Hz), 8.04 (1H, d, J = 2.4 Hz).<br>MS (ESI$^+$): 337 [M + H]$^+$ |
| 9-10 | 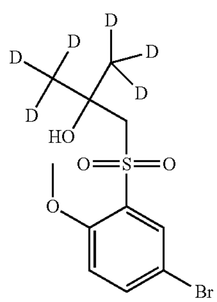 [SMILES: [2H]C([2H])([2H])C(O)(CS(=O)(=O)c1cc(Br)ccc1OC)C([2H])([2H])[2H]] | $^1$H-NMR (400 MHz, CDCl$_3$) δ: 3.53 (2H, s), 3.60 (1H, s), 3.99 (3H, s), 6.95 (1H, d, J = 8.9 Hz), 7.70 (1H, dd, J = 8.9, 2.4 Hz), 8.07 (1H, d, J = 2.4 Hz).<br>MS (EI$^+$): 328 [M]$^+$ |
| 9-11 | 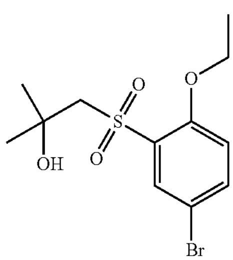 [SMILES: CCOc1ccc(Br)cc1S(=O)(=O)CC(C)(C)O] | $^1$H-NMR (400 MHz, CDCl$_3$) δ: 1.43 (6H, s), 1.52 (3H, t, J = 7.1 Hz), 3.57 (2H, s), 3.66 (1H, s), 4.21 (2H, q, J = 7.1 Hz), 6.92 (1H, d, J = 8.8 Hz), 7.66 (1H, dd, J = 8.8, 2.4 Hz), 8.06 (1H, d, J = 2.4 Hz).<br>MS (CI$^+$): 336 [M]$^+$ |
| 9-12 | 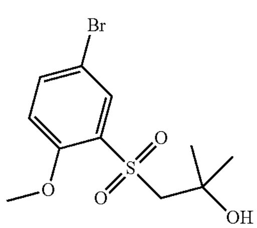 [SMILES: COc1ccc(Br)cc1S(=O)(=O)CC(C)(C)O] | $^1$H-NMR (400 MHz, CDCl$_3$) δ: 1.43 (6H, s), 3.54 (2H, s), 3.62 (1H, s), 3.99 (3H, s), 6.95 (1H, d, J = 8.8 Hz), 7.70 (1H, dd, J = 8.8, 2.6 Hz), 8.07 (1H, d, J = 2.6 Hz).<br>MS (ESI$^+$): 323 [M + H]$^+$ |

TABLE 37

| Reference Example | Structure | Instrumental Data |
|---|---|---|
| 9-13 | 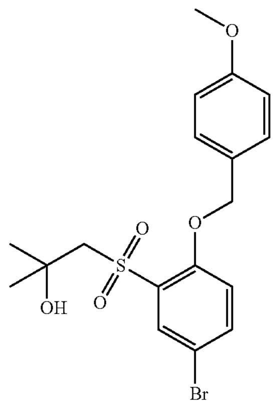 [SMILES: COc1ccc(COc2ccc(Br)cc2S(=O)(=O)CC(C)(C)O)cc1] | $^1$H-NMR (400 MHz, CDCl$_3$) δ: 1.34 (6H, s), 3.50 (1H, s), 3.51 (2H, s), 3.82 (3H, s), 5.18 (2H, s), 6.92 (2H, d, J = 8.8 Hz), 6.99 (1H, d, J = 9.0 Hz), 7.40 (2H, d, J = 8.8 Hz), 7.65 (1H, dd, J = 9.0, 2.6 Hz), 8.08 (1H, d, J = 2.6 Hz). MS (ESI$^-$): 427 [M − H]$^-$ |
| 9-14 | 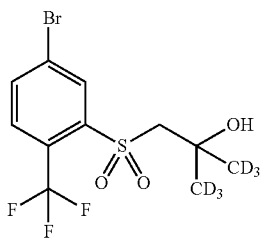 [SMILES: [2H]C([2H])([2H])C(O)(CS(=O)(=O)c1cc(Br)ccc1C(F)(F)F)C([2H])([2H])[2H]] | $^1$H-NMR (400 MHz, CDCl$_3$) δ: 3.40 (1H, s), 3.44 (2H, s), 7.77 (1H, d, J = 8.5 Hz), 7.90-7.94 (1H, m), 8.42 (1H, d, J = 1.8 Hz). MS (EI$^+$): 366 [M]$^+$ |
| 9-15 | 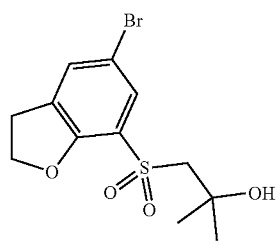 [SMILES: CC(C)(O)CS(=O)(=O)c1cc(Br)cc2c1OCC2] | $^1$H-NMR (400 MHz, CDCl$_3$) δ: 1.43 (6H, s), 3.31 (2H, t, J = 8.9 Hz), 3.49 (2H, s), 3.52 (1H, s), 4.83 (2H, t, J = 8.9 Hz), 7.53-7.54 (1H, m), 7.75-7.77 (1H, m). MS (FI$^+$): 334 [M]$^+$ |

Reference Example 10

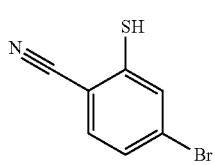

[Formula 56]

To a solution of 4-bromo-2-fluorobenzonitrile (1.07 g) in N,N-dimethylformamide (5.4 mL) was added sodium hydrogensulfide n-hydrate (65% purity, 461 mg) at 0° C., and the mixture was stirred at room temperature for 17 hours under an argon atmosphere. To the reaction mixture was added 1 mol/L hydrochloric acid at 0° C., and the mixture was extracted with ethyl acetate. The solvent in the organic layer was distilled away under reduced pressure, and the residue was purified by silica gel column chromatography (hexane:ethyl acetate=4:1) to give the title compound (467 mg).

$^1$H-NMR (400 MHz, CDCl$_3$) δ: 4.13 (1H, s), 7.37 (1H, dd, J=7.9, 1.8 Hz), 7.45 (1H, d, J=7.9 Hz), 7.59 (1H, d, J=1.8 Hz). MS (EI$^+$): 213 [M]$^+$.

Reference Example 11-1

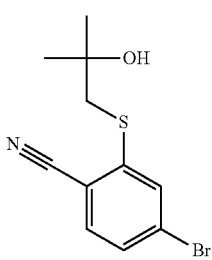

[Formula 57]

To a solution of the compound obtained in Reference Example 10 (467 mg) and 1-chloro-2-methyl-2-propanol (0.335 mL) in N,N-dimethylformamide (44 mL) was added potassium carbonate (602 mg) at 0° C. The mixture was stirred at room temperature for 6 hours under an argon atmosphere. The reaction was purified by silica gel column chromatography (hexane:ethyl acetate=2:1) to give the title compound (557 mg).

$^1$H-NMR (400 MHz, CDCl$_3$) δ: 1.38 (6H, s), 1.94 (1H, s), 3.19 (2H, s), 7.40 (1H, dd, J=8.5, 1.8 Hz), 7.46 (1H, d, J=8.5 Hz), 7.68 (1H, d, J=1.8 Hz). MS (ESI$^-$): 268 [M–OH]$^+$.

Reference Examples 11-2 to 11-18

A suitable compound of General Formula (13) was used to perform reactions according to any of methods similar to Reference Example 11-1 and the method described in Step Q-2 or similar methods thereto to give the compounds of Reference Examples 11-2 to 11-18 shown below.

TABLE 38

| Reference Example | Structure | Instrumental Data |
|---|---|---|
| 11-2 | 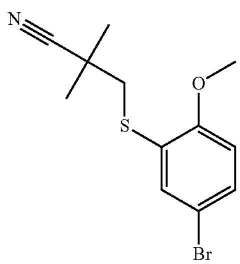 [SMILES: COc1ccc(Br)cc1SCC(C)(C)C#N] | $^1$H-NMR (400 MHz, CDCl$_3$) δ: 1.46 (6H, s), 3.08 (2H, s), 3.89 (3H, s), 6.76 (1H, d, J = 8.6 Hz), 7.34 (1H, dd, J = 8.6, 2.4 Hz), 7.50 (1H, d, J = 2.4 Hz). MS (CI$^+$): 300 [M + H]$^+$ |
| 11-3 | 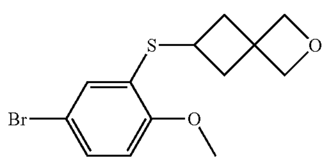 [SMILES: COc1ccc(Br)cc1SC1CC2(COC2)C1] | $^1$H-NMR (400 MHz, CDCl$_3$) δ: 2.24-2.29 (2H, m), 2.78-2.84 (2H, m), 3.62-3.69 (1H, m), 3.85 (3H, s), 4.68 (2H, s), 4.72 (2H, s), 6.69 (1H, d, J = 8.8 Hz), 7.08 (1H, d, J = 2.4 Hz), 7.24 (1H, dd, J = 8.8, 2.4 Hz). MS (ESI$^+$): 315 [M + H]$^+$ |
| 11-4 | 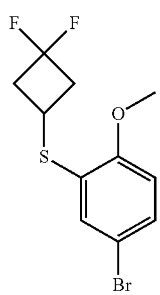 [SMILES: COc1ccc(Br)cc1SC1CC(F)(F)C1] | $^1$H-NMR (400 MHz, CDCl$_3$) δ: 2.55-2.67 (2H, m), 3.03-3.14 (2H, m), 3.61-3.71 (1H, m), 3.87 (3H, s), 6.73 (1H, d, J = 8.8 Hz), 7.20 (1H, d, J = 2.4 Hz), 7.30 (1H, dd, J = 8.8, 2.4 Hz). MS (CI$^+$): 309 [M + H]$^+$ |
| 11-5 | 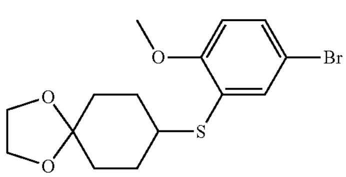 [SMILES: COc1ccc(Br)cc1SC1CCC2(CC1)OCCO2] | $^1$H-NMR (400 MHz, CDCl$_3$) δ: 1.56-1.62 (2H, m), 1.67-1.76 (2H, m), 1.83-1.89 (2H, m), 1.95-2.01 (2H, m), 3.25-3.32 (1H, m), 3.86 (3H, s), 3.94 (4H, s), 6.73 (1H, d, J = 8.5 Hz), 7.31 (1H, dd, J = 8.5, 2.4 Hz), 7.43 (1H, d, J = 2.4 Hz). MS (CI$^+$): 358 [M + H]$^+$ |

TABLE 39

| Reference Example | Structure | Instrumental Data |
|---|---|---|
| 11-6 | 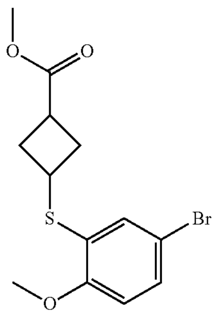 [SMILES: COC(=O)C1CC(Sc2cc(Br)ccc2OC)C1] | $^1$H-NMR (400 MHz, CDCl$_3$) δ: 2.35-2.43 (2H, m), 2.70-2.77 (2H, m), 3.06-3.15 (1H, m), 3.68 (3H, s), 3.72-3.80 (1H, m), 3.85 (3H, s), 6.70 (1H, d, J = 8.5 Hz), 7.21 (1H, d, J = 2.1 Hz), 7.25 (1H, dd, J = 8.5, 2.1 Hz).<br>MS (ESI$^+$): 331 [M + H]$^+$ |
| 11-7 | 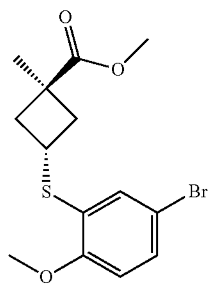 [SMILES: COc1ccc(Br)cc1S[C@H]1C[C@](C)(C(=O)OC)C1] | $^1$H-NMR (400 MHz, CDCl$_3$) δ: 1.46 (3H, s), 2.01-2.06 (2H, m), 3.02-3.08 (2H, m), 3.75 (3H, s), 3.82-3.89 (4H, m), 6.89 (1H, d, J = 8.5 Hz), 7.10 (1H, d, J = 2.1 Hz), 7.24 (1H, dd, J = 8.5, 2.1 Hz).<br>MS (FI$^+$): 344 [M]$^+$ |
| 11-8 | 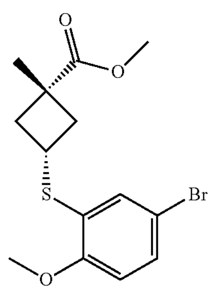 [SMILES: COc1ccc(Br)cc1S[C@H]1C[C@@](C)(C(=O)OC)C1] | $^1$H-NMR (400 MHz, CDCl$_3$) δ: 1.48 (3H, s), 2.38-2.44 (2H, m), 2.55-2.80 (2H, m), 3.68 (3H, s), 3.79-3.87 (4H, m), 6.70 (1H, d, J = 8.5 Hz), 7.16 (1H, d, J = 2.4 Hz), 7.25 (1H, dd, J = 8.5, 2.4 Hz).<br>MS (FI$^+$): 344 [M]$^+$ |
| 11-9 | 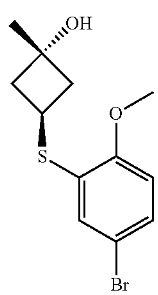 [SMILES: COc1ccc(Br)cc1S[C@H]1C[C@](C)(O)C1] | $^1$H-NMR (400 MHz, CDCl$_3$) δ: 1.50 (3H, s), 1.70 (1H, s), 2.13-2.18 (2H, m), 2.65-2.72 (2H, m), 3.86 (3H, s), 3.88-3.95 (1H, m), 6.89 (1H, d, J = 8.8 Hz), 7.08 (1H, d, J = 2.3 Hz), 7.23 (1H, dd, J = 8.8, 2.3 Hz).<br>MS (FI$^+$): 302 [M]$^+$ |
| 11-10 | 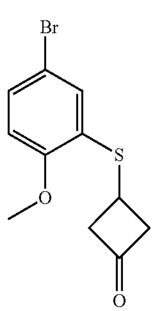 | $^1$H-NMR (400 MHz, CDCl$_3$) δ: 3.07-3.14 (2H, m), 3.56-3.63 (2H, m), 3.88 (3H, s), 3.94-4.01 (1H, m), 6.75 (1H, d, J = 8.8 Hz), 7.25 (1H, d, J = 2.4 Hz), 7.32 (1H, dd, J = 8.8, 2.4 Hz). |

TABLE 39-continued

| Reference Example | Structure | Instrumental Data |
| --- | --- | --- |
| 11-11 | 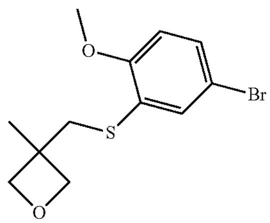 [SMILES: COc1ccc(Br)cc1SCC1(C)COC1] | ¹H-NMR (400 MHz, CDCl₃) δ: 1.45 (3H, s), 3.22 (2H, s), 3.89 (3H, s), 4.39 (2H, d, J = 5.9 Hz), 4.52 (2H, d, J = 5.9 Hz), 6.72 (1H, d, J = 8.6 Hz), 7.29 (1H, dd, J = 8.6, 2.3 Hz), 7.37 (1H, d, J = 2.3 Hz).<br>MS (ESI⁺): 303 [M + H]⁺ |
| 11-12 | 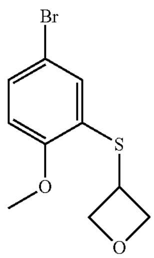 | ¹H-NMR (400 MHz, CDCl₃) δ: 3.86 (3H, s), 4.39-4.47 (1H, m), 4.66 (2H, t, J = 7.0 Hz), 6.05 (2H, t, J = 7.0 Hz), 6.73 (1H, d, J = 8.6 Hz), 7.12 (1H, d, J = 2.4 Hz), 7.30 (1H, dd, J = 8.6, 2.4 Hz).<br>MS (EI⁺): 274 [M]⁺ |

TABLE 40

| Reference Example | Structure | Instrumental DataI |
| --- | --- | --- |
| 11-13 | 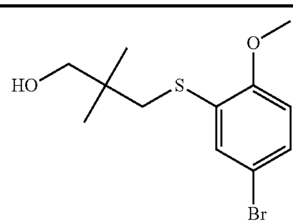 | ¹H-NMR (400 MHz, CDCl₃) δ: 1.05 (6H, s), 1.76 (1H, t, J = 6.2 Hz), 2.88 (2H, s), 3.50 (2H, d, J = 6.2 Hz), 3.88 (3H, s), 6.71 (1H, d, J = 8.6 Hz). 7.26 (1H, dd, J = 8.6, 2.2 Hz), 7.38 (1H, d, J = 2.2 Hz).<br>MS (ESI⁺): 305 [M + H]⁺ |
| 11-14 | 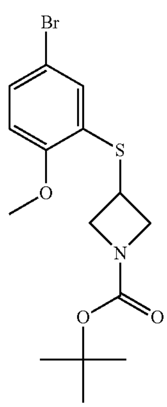 [SMILES: COc1ccc(Br)cc1SC1CN(C(=O)OC(C)(C)C)C1] | ¹H-NMR (400 MHz, CDCl₃) δ: 1.44 (9H, s), 3.84-3.90 (5H, m), 3.95-4.02 (1H, m), 4.35 (2H, dd, J = 8.9, 7.7 Hz), 6.73 (1H, d, J = 8.8 Hz), 7.13 (1H, d, J = 2.4 Hz), 7.30 (1H, dd, J = 8.8, 2.4 Hz).<br>MS (ESI⁺): 374 [M + H]⁺ |
| 11-15 | 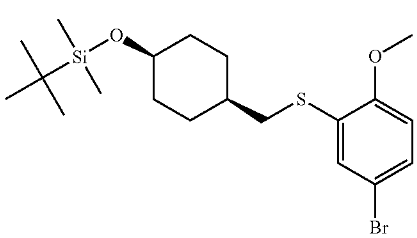 [SMILES: COc1ccc(Br)cc1SC[C@H]1CC[C@@H](O[Si](C)(C)C(C)(C)C)CC1] | ¹H-NMR (400 MHz, CDCl₃) δ: 0.03 (6H, s), 0.89 (8H, s), 1.38-1.49 (2H, m), 1.50-1.70 (7H, m), 2.79 (2H, d, J = 5.8 Hz), 3.87 (3H, s), 3.91-3.96 (1H, m), 6.69 (1H, d, J = 8.7 Hz), 7.22 (1H, dd, J = 8.7, 2.3 Hz), 7.25 (1H, d, J = 2.3 Hz).<br>MS (ESI⁺): 444 [M]⁺ |

TABLE 40-continued

| Reference Example | Structure | Instrumental Data |
|---|---|---|
| 11-16 | (HO-CH2CH2-S-(2-methoxy-5-bromophenyl)) | $^1$H-NMR (400 MHz, CDCl$_3$) δ: 2.27 (1H, t, J = 6.1 Hz), 3.07 (2H, t, J = 6.1 Hz), 3.71 (2H, q, J = 6.1 Hz), 3.88 (3H, s), 6.75 (1H, d, J = 8.5 Hz), 7.34 (1H, dd, J = 8.5, 2.4 Hz), 7.47 (1H, d, J = 2.4 Hz). MS (ESI$^+$): 245 [M − OH]$^+$ |
| 11-17 | (HO-C(CH3)2-CH2-S-(2-methoxy-5-bromophenyl)) | $^1$H-NMR (400 MHz, CDCl$_3$) δ: 1.32 (6H, s), 2.40 (1H, s), 3.04 (2H, s), 3.89 (3H, s), 6.73 (1H, d, J = 8.7 Hz), 7.30 (1H, dd, J = 8.7, 2.4 Hz), 7.48 (1H, d, J = 2.4 Hz). MS (ESI$^+$): 273 [M − OH]$^+$ |
| 11-18 | (iPr-S-(2-methoxy-5-bromophenyl)) | $^1$H-NMR (400 MHz, CDCl$_3$) δ: 1.31 (6H, d, J = 6.7 Hz), 3.42-3.54 (1H, m), 3.86 (3H, s), 6.72 (1H, d, J = 8.6 Hz), 7.29 (1H, dd, J = 8.6, 2.4 Hz), 7.41 (1H, d, J = 2.4 Hz). MS (EI$^+$): 260 [M]$^+$ |

Reference Examples 12-1 to 12-12

A suitable compound of General Formula (13) synthesized in reactions using a suitable compound of General Formula (14) according to any of methods similar to Reference Example 10 and the method described in Step Q-1 or similar methods thereto was directly used as a crude product to perform reactions according to any of methods similar to Reference Example 11-1 and the method described in Step Q-2 or similar methods thereto to give the compounds of Reference Examples 12-1 to 12-12 shown below.

TABLE 41

| Reference Example | Structure | Instrumental Data |
|---|---|---|
| 12-1 | (cyclobutane with HO, CH3, and S-aryl-CF3, Br substituents) | $^1$H-NMR (400 MHz, CDCl$_3$) δ: 1.51 (3H, s), 1.68 (1H, s), 2.16-2.21 (2H, m), 2.69-2.75 (2H, m), 3.96-4.04 (1H, m), 7.31 (1H, s), 7.34 (1H, d, J = 8.5 Hz), 7.46 (1H, d, J = 8.5 Hz). MS (FI$^+$): 340 [M]$^+$ |

TABLE 41-continued

| Reference Example | Structure | Instrumental Data |
|---|---|---|
| 12-2 | 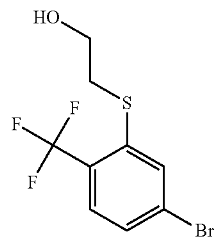 [SMILES: OCCSc1cc(Br)ccc1C(F)(F)F] | ¹H-NMR (400 MHz, CDCl₃) δ: 1.97 (1H, t, J = 6.1 Hz), 3.20 (2H, t, J = 6.1 Hz), 3.81 (2H, dd, J = 12.1, 6.1 Hz), 7.44 (1H, d, J = 8.5 Hz), 7.51 (1H, d, J = 8.5 Hz), 7.68 (1H, s). MS (CI⁺): 300 [M]⁺ |
| 12-3 | 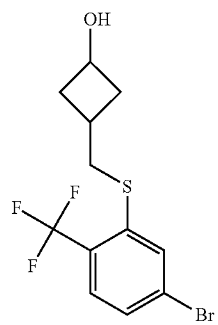 [SMILES: OC1CC(CSc2cc(Br)ccc2C(F)(F)F)C1] | ¹H-NMR (400 MHz, CDCl₃) δ: 1.62-1.70 (2H, m), 1.78 (1H, br), 2.00-2.08 (1H, m), 2.51-2.58 (2H, m), 3.06 (2H, d, J = 7.3 Hz), 4.11-4.18 (1H, m), 7.38 (1H, d, J = 8.5 Hz), 7.47 (1H, d, J = 8.5 Hz), 7.54 (1H, s). MS (ESI⁺): 340 [M]⁺ |
| 12-4 | 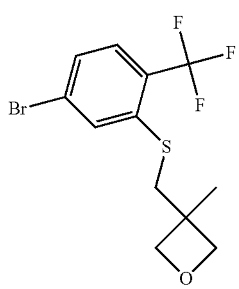 [SMILES: CC1(CSc2cc(Br)ccc2C(F)(F)F)COC1] | ¹H-NMR (400 MHz, CDCl₃) δ: 1.44 (3H, s), 3.34 (2H, s), 4.42 (2H, d, J = 6.1 Hz), 4.51 (2H, d, J = 6.1 Hz), 7.43 (1H, dd, J = 8.5, 1.2 Hz), 7.50 (1H, d, J = 8.5 Hz), 7.64 (1H, d, J = 1.2 Hz). MS (ESI⁺): 341 [M + H]⁺ |
| 12-5 | 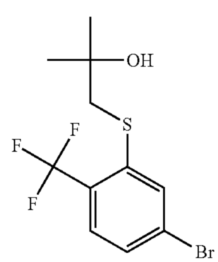 [SMILES: CC(C)(O)CSc1cc(Br)ccc1C(F)(F)F] | ¹H-NMR (400 MHz, CDCl₃) δ: 1.35 (6H, s), 2.04 (1H, s), 3.17 (2H, s), 7.41 (1H, dd, J = 7.9, 1.5 Hz), 7.49 (1H, d, J = 7.9 Hz), 7.71 (1H, d, J = 1.5 Hz). MS (EI⁺): 328 [M]⁺ |
| 12-6 | 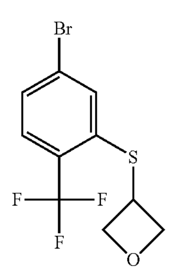 | ¹H-NMR (400 MHz, CDCl₃) δ: 4.49-4.56 (1H, m), 4.69 (2H, t, J = 7.0 Hz), 5.10 (2H, t, J = 7.0 Hz), 7.20 (1H, d, J = 1.2 Hz), 7.43 (1H, dd, J = 8.5, 1.2 Hz), 7.52 (1H, d, J = 8.5 Hz). MS (EI⁺): 312 [M]⁺ |

TABLE 41-continued

| Reference Example | Structure | Instrumental Data |
|---|---|---|
| 12-7 | 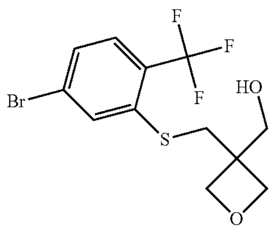 [SMILES: OCC1(CSc2cc(Br)ccc2C(F)(F)F)COC1] | $^1$H-NMR (400 MHz, CDCl$_3$) δ: 1.74 (1H, t, J = 4.8 Hz), 3.46 (2H, s), 3.99 (2H, d, J = 4.2 Hz), 4.50 (4H, dd, J = 7.9, 6.7 Hz), 7.43 (1H, d, J = 8.5 Hz), 7.50 (1H, d, J = 8.5 Hz), 7.71 (1H, s). MS (ESI$^+$): 357 [M + H]$^+$ |

TABLE 42

| Reference Example | Structure | Instrumental Data |
|---|---|---|
| 12-8 | 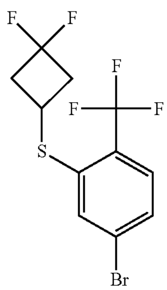 [SMILES: FC1(F)CC(Sc2cc(Br)ccc2C(F)(F)F)C1] | $^1$H-NMR (400 MHz, CDCl$_3$) δ: 2.61-2.74 (2H, m), 3.09-3.20 (2H, m), 3.69-3.74 (1H, m), 7.40 (1H, s), 7.43 (1H, d, J = 8.5 Hz), 7.52 (1H, d, J = 8.5 Hz). MS (EI$^+$): 346 [M]$^+$ |
| 12-9 | 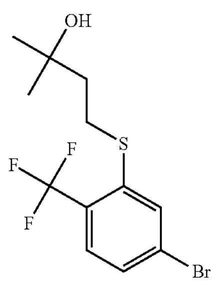 [SMILES: CC(C)(O)CCSc1cc(Br)ccc1C(F)(F)F] | $^1$H-NMR (400 MHz, CDCl$_3$) δ: 1.27-1.31 (7H, m), 1.82-1.86 (2H, m), 3.07-3.11 (2H, m), 7.37 (1H, d, J = 8.5 Hz), 7.48 (1H, d, J = 8.5 Hz), 7.58 (1H, s). MS (ESI$^+$): 325 [M − OH]$^+$ |
| 12-10 | 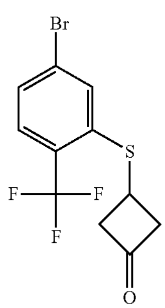 [SMILES: O=C1CC(Sc2cc(Br)ccc2C(F)(F)F)C1] | $^1$H-NMR (400 MHz, CDCl$_3$) δ: 3.14-3.20 (2H, m), 3.63-3.70 (2H, m), 3.99-4.06 (1H, m), 7.43-7.46 (2H, m), 7.53 (1H, d, J = 8.6 Hz). MS (ESI$^+$): 325 [M + H]$^+$ |

TABLE 42-continued

| Reference Example | Structure | Instrumental Data |
|---|---|---|
| 12-11 | 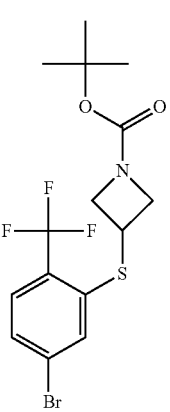 | $^1$H-NMR (400 MHz, CDCl$_3$) δ: 1.45 (9H, s), 3.90-3.94 (2H, m), 4.04-4.10 (1H, m), 4.39-4.43 (2H, m), 7.25 (1H, s), 7.42 (1H, d, J = 8.5 Hz), 7.51 (1H, d, J = 8.5 Hz). MS (ESI$^+$): 412 [M + H]$^+$ |
| 12-12 | 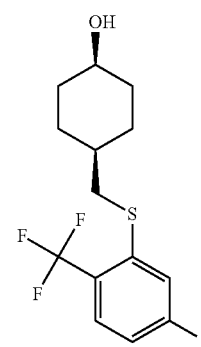 | $^1$H-NMR (400 MHz, CDCl$_3$) δ: 1.23-1.31 (1H, m), 1.53-1.77 (8H, m), 2.91 (2H, d, J = 6.1 Hz), 4.01 (1H, s), 7.36 (1H, d, J = 8.5 Hz), 7.47 (1H, d, J = 8.5 Hz), 7.52 (1H, s). MS (ESI$^+$): 368 [M]$^+$ |

Reference Example 13-1

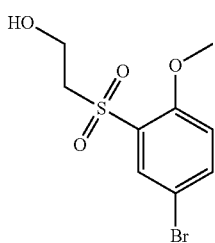

[Formula 58]

The compound obtained in Reference Example 11-16 (178 mg) was dissolved in dichloromethane (3.4 mL) under an argon atmosphere, and 3-chloroperbenzoic acid (423 mg) was added to the mixture. The mixture was stirred at room temperature for 1.5 hours. Saturated aqueous sodium thiosulfate solution (10 mL), saturated aqueous sodium bicarbonate solution (10 mL), and water (5 mL) were added to the solution, and the mixture was then extracted with ethyl acetate (20 mL). The organic layer was washed with saturated brine (10 mL), dried over anhydrous sodium sulfate, and then filtered to remove insoluble residues. The solvent was distilled away under reduced pressure, and the residue was then dissolved in dichloromethane (6 mL) and purified by silica gel column chromatography (hexane:ethyl acetate=84:16 to 0:100) to give the title compound (183.3 mg).

$^1$H-NMR (400 MHz, CDCl$_3$): δ 2.64 (1H, t, J=6.5 Hz), 3.58-3.62 (2H, m), 3.98 (3H, s), 3.99-4.04 (2H, m), 6.96 (1H, d, J=8.8 Hz), 7.72 (1H, dd, J=8.8, 2.7 Hz), 8.09 (1H, d, J=2.7 Hz). MS (ESI$^-$): 295 [M+H]$^+$.

Reference Examples 13-2 to 13-34

A suitable compound of General Formula (12) was used to perform reactions according to any of methods similar to Reference Example 13-1 and the method described in Step O-2 or similar methods thereto to give the compounds of Reference Examples 13-2 to 13-34 shown below.

TABLE 43

| Reference Example | Structure | Instrumental Data |
|---|---|---|
| 13-2 | 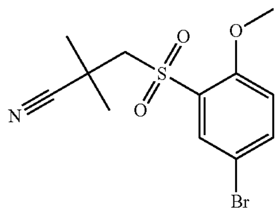 [SMILES: COc1ccc(Br)cc1S(=O)(=O)CC(C)(C)C#N] | $^1$H-NMR (400 MHz, CDCl$_3$) δ: 1.60 (6H, s), 3.56 (2H, s), 4.01 (3H, s), 6.97 (1H, d, J = 9.2 Hz), 7.73 (1H, dd, J = 9.2, 2.4 Hz), 8.10 (1H, d, J = 2.4 Hz).<br>MS (ESI$^+$): 332 [M + H]$^+$ |
| 13-3 | 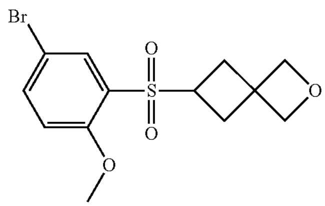 [SMILES: COc1ccc(Br)cc1S(=O)(=O)C1CC2(COC2)C1] | $^1$H-NMR (400 MHz, CDCl$_3$) δ: 2.48-2.54 (2H, m), 2.70-2.75 (2H, m), 3.94 (3H, s), 4.00-4.08 (1H, m), 4.66 (2H, s), 4.71 (2H, s), 6.92 (1H, d, J = 8.8 Hz), 7.68 (1H, dd, J = 8.8, 2.7 Hz), 8.05 (1H, d, J = 2.7 Hz).<br>MS (ESI$^+$): 347 [M + H]$^+$ |
| 13-4 | 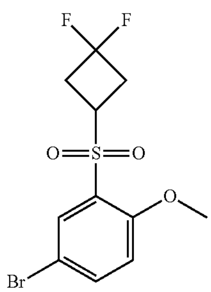 [SMILES: COc1ccc(Br)cc1S(=O)(=O)C1CC(F)(F)C1] | $^1$H-NMR (400 MHz, CDCl$_3$) δ: 2.75-2.85 (2H, m), 3.06-3.22 (2H, m), 3.98 (3H, s), 4.01-4.11 (1H, m), 6.95 (1H, d, J = 9.0 Hz), 7.71 (1H, dd, J = 9.0, 2.6 Hz), 8.07 (1H, d, J =2.6 Hz).<br>MS (CI$^+$): 341 [M + H]$^+$ |
| 13-5 | 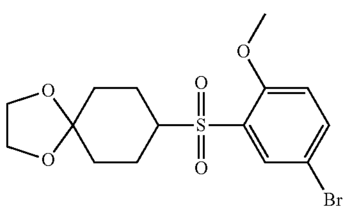 [SMILES: COc1ccc(Br)cc1S(=O)(=O)C1CCC2(CC1)OCCO2] | $^1$H-NMR (400 MHz, CDCl$_3$) δ: 1.49-1.57 (2H, m), 1.87-1.97 (6H, m), 3.35-3.46 (1H, m), 3.93 (4H, s), 3.97 (3H, s), 6.94 (1H, d, J = 9.1 Hz), 7.68 (1H, dd, J = 9.1, 2.4 Hz), 8.05 (1H, d, J = 2.4 Hz).<br>MS (CI$^+$): 391 [M + H]$^+$ |

TABLE 44

| Reference Example | Structure | Instrumental Data |
|---|---|---|
| 13-6 | 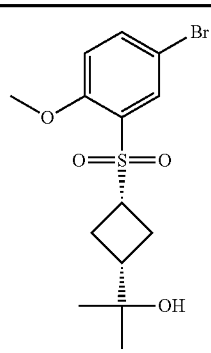 | $^1$H-NMR (400 MHz, CDCl$_3$) δ: 1.13 (6H, s), 2.04-2.14 (2H, m), 2.26-2.35 (1H, m), 2.45-2.53 (2H, m), 3.96 (3H, s), 4.03-4.15 (1H, m), 6.91 (1H, d, J = 8.8 Hz), 7.66 (1H, dd, J = 8.8, 2.4 Hz), 8.08 (1H, d, J = 2.4 Hz).<br>MS (FI$^+$): 362 [M]$^+$ |

TABLE 44-continued

| Reference Example | Structure | Instrumental Data |
|---|---|---|
| 13-7 | 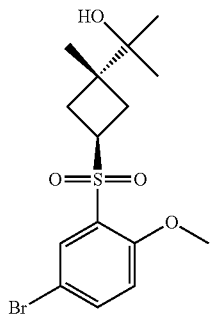 [SMILES: COc1ccc(Br)cc1S(=O)(=O)[C@H]1C[C@](C)(C(C)(C)O)C1] | $^1$H-NMR (400 MHz, CDCl$_3$) δ: 1.14 (6H, s), 1.21 (3H, s), 1.29 (1H, s), 2.15-2.21 (2H, m), 2.42-2.48 (2H, m), 3.93 (3H, s), 4.07-4.16 (1H, m), 6.89 (1H, d, J = 9.1 Hz), 7.64 (1H, dd, J = 9.1, 2.6 Hz), 8.09 (1H, d, J = 2.6 Hz).<br>MS (FI$^+$): 376 [M]$^+$ |
| 13-8 | 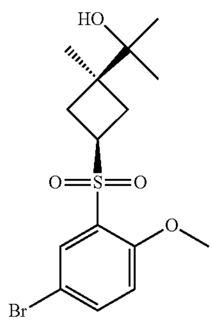 [SMILES: COc1ccc(Br)cc1S(=O)(=O)[C@H]1C[C@@](C)(C(C)(C)O)C1] | $^1$H-NMR (400 MHz, CDCl$_3$) δ: 1.10 (6H, s), 1.21 (3H, s), 1.68-1.74 (2H, m), 1.79 (1H, s), 2.77-2.82 (2H, m), 3.97 (3H, s), 4.10-4.19 (1H, m), 6.91 (1H, d, J = 8.6 Hz), 7.65 (1H, dd, J = 8.8, 2.4 Hz), 8.09 (1H, d, J = 2.4 Hz).<br>MS (FI$^+$): 376 [M]$^+$ |
| 13-9 | 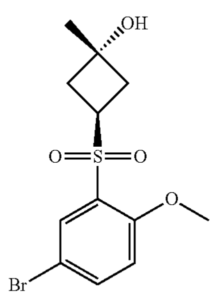 [SMILES: COc1ccc(Br)cc1S(=O)(=O)[C@H]1C[C@](C)(O)C1] | $^1$H-NMR (400 MHz, CDCl$_3$) δ: 1.48 (3H, s), 1.71 (1H, s), 2.26-2.32 (2H, m), 2.57-2.63 (2H, m), 3.95 (3H, s), 4.32-4.41 (1H, m), 6.91 (1H, d, J = 8.8 Hz), 7.67 (1H, dd, J = 8.8, 2.4 Hz), 8.06 (1H, d, J = 2.4 Hz).<br>MS (FI$^+$): 334 [M]$^+$ |
| 13-10 | 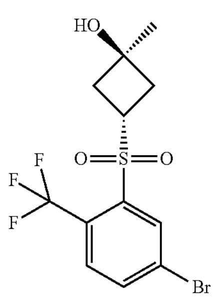 [SMILES: C[C@]1(O)C[C@H](S(=O)(=O)c2cc(Br)ccc2C(F)(F)F)C1] | $^1$H-NMR (400 MHz, CDCl$_3$) δ: 1.50 (3H, s), 1.66 (1H, s), 2.28-2.34 (2H, m), 2.61-2.67 (2H, m), 4.18-4.27 (1H, m), 7.77 (1H, d, J = 8.5 Hz), 7.89 (1H, d, J = 8.5 Hz), 8.33 (1H, s).<br>MS (FI$^+$): 372 [M]$^+$ |
| 13-11 | 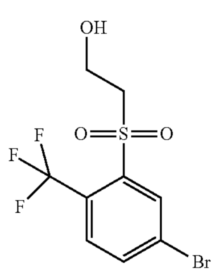 [SMILES: O=S(=O)(CCO)c1cc(Br)ccc1C(F)(F)F] | $^1$H-NMR (400 MHz, CDCl$_3$) δ: 2.50-2.59 (1H, m), 3.53-3.56 (2H, m), 4.10-4.15 (2H, m), 7.78 (1H, d, J = 8.6 Hz), 7.93 (1H, dd, J = 8.6, 1.2 Hz), 8.42 (1H, d, J = 1.8 Hz).<br>MS (CI$^+$): 333 [M + H]$^+$ |

TABLE 45

| Reference Example | Structure | Instrumental Data |
|---|---|---|
| 13-12 | 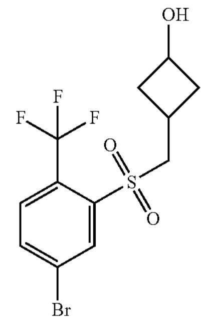 [SMILES: O=S(=O)(CC1CC(O)C1)c1cc(Br)ccc1C(F)(F)F] | ¹H-NMR (400 MHz, CDCl₃) δ: 1.65-1.73 (2H, m), 1.84 (1H, s), 2.25-2.33 (1H, m), 2.49-2.56 (2H, m), 3.40 (2H, d, J = 7.3 Hz), 4.17-4.24 (1H, m), 7.77 (1H, d, J = 8.8 Hz), 7.91 (1H, d, J = 8.8 Hz), 8.38 (1H, d, J = 1.8 Hz).<br>MS (ESI⁺): 373 [M + H]⁺ |
| 13-13 | 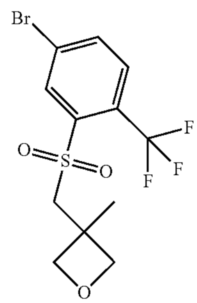 [SMILES: CC1(CS(=O)(=O)c2cc(Br)ccc2C(F)(F)F)COC1] | ¹H-NMR (400 MHz, CDCl₃) δ: 1.75 (3H, s), 3.63 (2H, s), 4.48 (2H, d, J = 6.4 Hz), 4.69 (2H, d, J = 6.4 Hz), 7.79 (1H, d, J = 8.6 Hz), 7.93 (1H, dd, J = 8.6, 1.5 Hz), 8.41 (1H, d, J = 1.5 Hz).<br>MS (ESI⁺): 373 [M + H]⁺ |
| 13-14 | 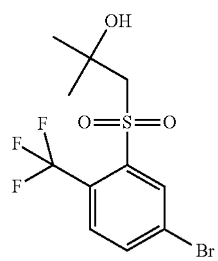 [SMILES: CC(C)(O)CS(=O)(=O)c1cc(Br)ccc1C(F)(F)F] | ¹H-NMR (400 MHz, CDCl₃) δ: 1.51 (6H, s), 3.43 (1H, s), 3.45 (2H, s), 7.77 (1H, d, J = 8.6 Hz), 7.92 (1H, dd, J = 8.6, 1.5 Hz), 8.42 (1H, d, J = 1.5 Hz).<br>MS (ESI⁺): 361 [M + H]⁺ |
| 13-15 | 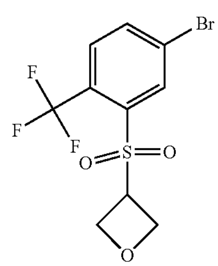 [SMILES: O=S(=O)(c1cc(Br)ccc1C(F)(F)F)C1COC1] | ¹H-NMR (400 MHz, CDCl₃) δ: 4.71-4.78 (1H, m), 4.83 (2H, t, J = 7.0 Hz), 5.03 (2H, t, J = 7.0 Hz), 7.79 (1H, d, J = 8.6 Hz), 7.94 (1H, dd, J = 8.6, 1.5 Hz), 8.44 (1H, d, J = 1.5 Hz).<br>MS (EI⁺): 345 [M + H]⁺ |
| 13-16 | 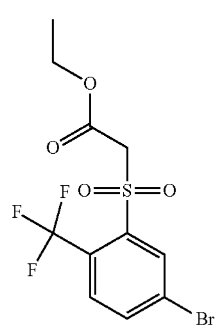 [SMILES: CCOC(=O)CS(=O)(=O)c1cc(Br)ccc1C(F)(F)F] | ¹H-NMR (400 MHz, CDCl₃) δ: 1.22 (3H, t, J = 7.1 Hz), 4.17 (2H, q, J = 7.1 Hz), 4.31 (2H, s), 7.79 (1H, d, J = 8.5 Hz), 7.94 (1H, d, J = 8.5 Hz), 8.42 (1H, d, J = 1.8 Hz).<br>MS (ESI⁻): 373 [M − H]⁻ |

TABLE 45-continued

| Reference Example | Structure | Instrumental Data |
| --- | --- | --- |
| 13-17 | 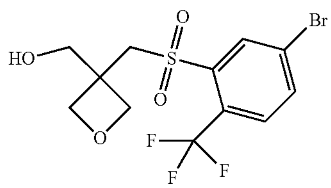 [SMILES: O=S(=O)(CC1(CO)COC1)c1cc(Br)ccc1C(F)(F)F] | ¹H-NMR (400 MHz, CDCl₃) δ: 2.42 (1H, s), 3.76 (2H, s), 4.31 (2H, s), 4.54 (2H, d, J = 6.7 Hz), 4.67 (2H, d, J = 6.7 Hz), 7.80 (1H, d, J = 8.5 Hz), 7.95 (1H, d, J = 8.5 Hz), 8.41 (1H, s).<br>MS (ESI⁺): 389 [M + H]⁺ |

TABLE 46

| Reference Example | Structure | Instrumental Data |
| --- | --- | --- |
| 13-18 | 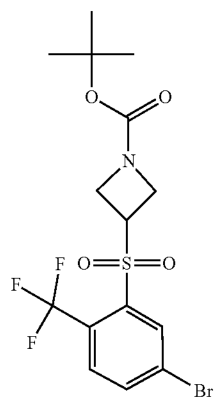 [SMILES: CC(C)(C)OC(=O)N1CC(S(=O)(=O)c2cc(Br)ccc2C(F)(F)F)C1] | ¹H-NMR (400 MHz, CDCl₃) δ: 1.46 (9H, s), 4.07-4.15 (2H, m), 4.24-4.33 (3H, m), 7.80 (1H, d, J = 8.6 Hz), 7.94 (1H, d, J = 8.6 Hz), 8.43 (1H, d, J = 1.8 Hz).<br>MS (ESI⁺): 444 [M + H]⁺ |
| 13-19 | 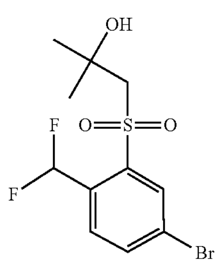 | ¹H-NMR (400 MHz, CDCl₃) δ: 1.49 (6H, s), 3.28 (1H, s), 3.39 (2H, s), 7.55 (1H, t, J = 55.0 Hz), 7.77 (1H, d, J = 8.3 Hz), 7.90 (1H, dd, J = 8.3, 1.8 Hz), 8.23 (1H, s).<br>MS (ESI⁻): 387 [M + HCOO]⁻ |
| 13-20 | 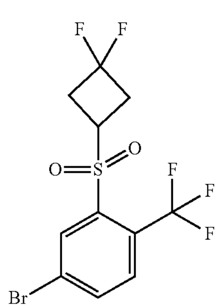 [SMILES: O=S(=O)(c1cc(Br)ccc1C(F)(F)F)C1CC(F)(F)C1] | ¹H-NMR (400 MHz, CDCl₃) δ: 2.79-2.89 (2H, m), 3.10-3.23 (2H, m), 3.91-3.96 (1H, m), 7.81 (1H, d, J = 8.5 Hz), 7.95 (1H, d, J = 8.5 Hz), 8.36 (1H, s).<br>MS (EI⁺): 378 [M]⁺ |

TABLE 46-continued

| Reference Example | Structure | Instrumental Data |
|---|---|---|
| 13-21 | 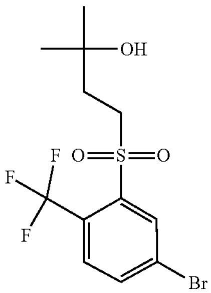 [SMILES: CC(C)(O)CCS(=O)(=O)c1cc(Br)ccc1C(F)(F)F] | $^1$H-NMR (400 MHz, CDCl$_3$) δ: 1.26 (6H, s), 1.30 (1H, s), 1.94-1.98 (2H, m), 3.40-3.44 (2H, m), 7.78 (1H, d, J = 7.9 Hz), 7.91 (1H, d, 3 = 7.9 Hz), 8.41 (1H, s).<br>MS (ESI$^+$): 375 [M + H]$^+$ |
| 13-22 | 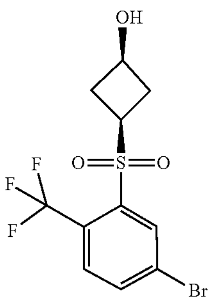 [SMILES: O=S(=O)(c1cc(Br)ccc1C(F)(F)F)[C@H]1C[C@@H](O)C1] | $^1$H-NMR (400 MHz, CDCl$_3$) δ: 2.14 (1H, d, J = 8.5 Hz), 2.44-2.51 (2H, m), 2.59-2.66 (2H, m), 3.62-3.70 (1H, m), 4.18-4.27 (1H, m), 7.77 (1H, d, J = 8.5 Hz), 7.90 (1H, d, J = 8.5 Hz), 8.35 (1H, s).<br>MS (EI$^+$): 341 [M − OH]$^+$ |
| 13-23 | 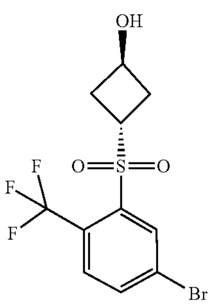 [SMILES: O=S(=O)(c1cc(Br)ccc1C(F)(F)F)[C@H]1C[C@H](O)C1] | $^1$H-NMR (400 MHz, CDCl$_3$) δ: 1.97 (1H, d, J = 4.8 Hz), 2.30-2.38 (2H, m), 2.81-2.88 (2H, m), 4.04-4.11 (1H, m), 4.69-4.77 (1H, m), 7.78 (1H, d, J = 8.5 Hz), 7.90 (1H, d, J = 8.5 Hz), 8.38 (1H, s).<br>MS (EI$^+$): 359 [M + H]$^+$ |

TABLE 47

| Reference Example | Structure | Instrumental Data |
|---|---|---|
| 13-24 | 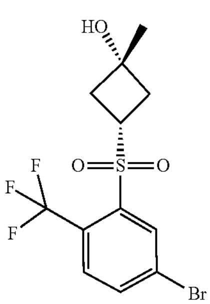 [SMILES: C[C@]1(O)C[C@@H](S(=O)(=O)c2cc(Br)ccc2C(F)(F)F)C1] | $^1$H-NMR (400 MHz, CDCl$_3$) δ: 1.38 (3H, s), 2.37-2.44 (3H, m), 2.58-2.63 (2H, m), 3.69-3.77 (1H, m), 7.77 (1H, d, J = 8.5 Hz), 7.90 (1H, d, J = 8.5 Hz), 8.35 (1H, d, J = 1.8 Hz).<br>MS (EI$^+$): 355 [M − OH]$^+$ |

TABLE 47-continued

| Reference Example | Structure | Instrumental Data |
|---|---|---|
| 13-25 | 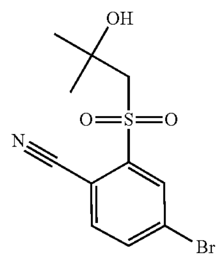 | ¹H-NMR (400 MHz, CDCl₃) δ: 1.50 (6H, s), 2.95 (1H, s), 3.58 (2H, s), 7.75 (1H, d, J = 7.9 Hz), 7.91 (1H, dd, J = 7.9, 1.8 Hz), 8.32 (1H, d, J = 1.8 Hz).<br>MS (ESI⁻): 362 [M + HCOO]⁻ |
| 13-26 | 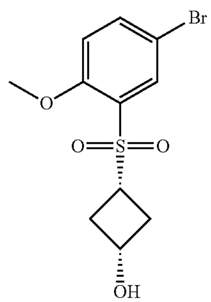 [SMILES: COc1ccc(Br)cc1S(=O)(=O)[C@H]1C[C@@H](O)C1] | ¹H-NMR (400 MHz, CDCl₃) δ: 2.40-2.47 (3H, m), 2.59-2.66 (2H, m), 3.79-3.87 (1H, m), 3.95 (3H, s), 4.20-4.26 (1H, m), 6.92 (1H, d, J = 9.1 Hz), 7.68 (1H, dd, J = 9.1, 2.4 Hz), 8.07 (1H, d, J = 2.4 Hz).<br>MS (CI⁺): 321 [M + H]⁺ |
| 13-27 | 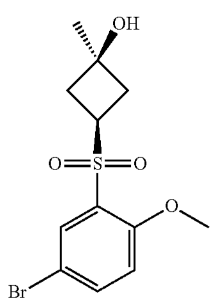 [SMILES: COc1ccc(Br)cc1S(=O)(=O)[C@H]1C[C@@](C)(O)C1] | ¹H-NMR (400 MHz, CDCl₃) δ: 1.38 (3H, s), 2.35-2.41 (2H, m), 2.53-2.59 (2H, m), 2.90 (1H, br), 3.85-3.92 (1H, m), 3.96 (3H, s), 6.91 (1H, d, J = 9.1 Hz), 7.68 (1H, dd, J = 9.1, 2.4 Hz), 8.06 (1H, d, J = 2.4 Hz).<br>MS (ESI⁺): 335 [M + H]⁺ |
| 13-28 | 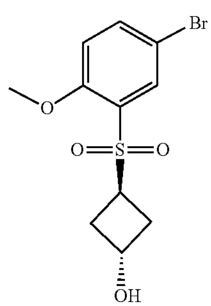 [SMILES: COc1ccc(Br)cc1S(=O)(=O)[C@H]1C[C@H](O)C1] | ¹H-NMR (400 MHz, CDCl₃) δ: 1.95 (1H, d, J = 4.9 Hz), 2.27-2.34 (2H, m), 2.76-2.82 (2H, m), 3.95 (3H, s), 4.17-4.24 (1H, m), 4.66-4.74 (1H, m), 6.92 (1H, d, J = 8.6 Hz), 7.68 (1H, dd, J = 8.6, 2.4 Hz), 8.09 (1H, d, J = 2.4 Hz).<br>MS (CI⁺): 321 [M + H]⁺ |
| 13-29 | 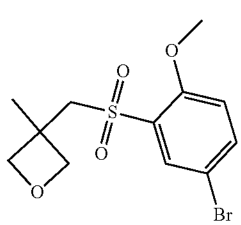 [SMILES: COc1ccc(Br)cc1S(=O)(=O)CC1(C)COC1] | ¹H-NMR (400 MHz, CDCl₃) δ: 1.64 (3H, s), 3.73 (2H, s), 4.01 (3H, s), 4.43 (2H, d, J = 6.4 Hz), 4.68 (2H, d, J = 6.4 Hz), 6.96 (1H, d, J = 8.9 Hz), 7.70 (1H, dd, J = 8.9, 2.5 Hz), 8.05 (1H, d, J = 2.5 Hz).<br>MS (ESI⁺): 335 [M + H]⁺ |

TABLE 47-continued

| Reference Example | Structure | Instrumental Data |
|---|---|---|
| 13-30 | 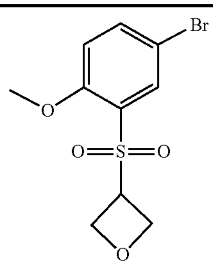 | $^1$H-NMR (400 MHz, CDCl$_3$) δ: 3.94 (3H, s), 4.73-4.84 (3H, m), 5.00-5.09 (2H, m), 6.93 (1H, d, J = 8.8 Hz), 7.70 (1H, dd, J = 8.8, 2.4 Hz), 8.12 (1H, d, J = 2.4 Hz).<br>MS (EI$^+$): 306 [M]$^+$ |

TABLE 48

| Reference Example | Structure | Instrumental Data |
|---|---|---|
| 13-31 | 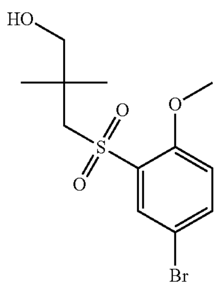 [SMILES: COc1ccc(Br)cc1S(=O)(=O)CC(C)(C)CO] | $^1$H-NMR (400 MHz, CDCl$_3$) δ: 1.14 (6H, s), 2.58 (1H, t, J = 7.1 Hz), 3.36 (2H, s), 3.63 (2H, d, J = 7.1 Hz), 3.89 (3H, s), 6.94 (1H, d, J = 8.8 Hz), 7.69 (1H, dd, J = 8.8, 2.4 Hz), 8.06 (1H, d, J = 2.4 Hz).<br>MS (EI$^+$): 336 [M]$^+$ |
| 13-32 | 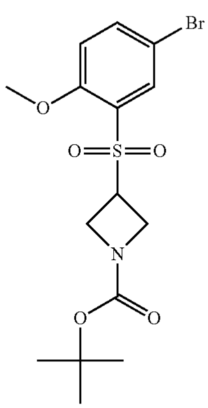 | $^1$H-NMR (400 MHz, CDCl$_3$) δ: 1.44 (9H, s), 3.96 (3H, s), 4.09 (2H, t, J = 8.8 Hz), 4.26-4.40 (3H, m), 6.94 (1H, d, J = 8.9 Hz), 7.71 (1H, dd, J = 8.9, 2.5 Hz), 8.11 (1H, d, J = 2.5 Hz).<br>MS (ESI$^+$): 406 [M + H]$^+$ |
| 13-33 | 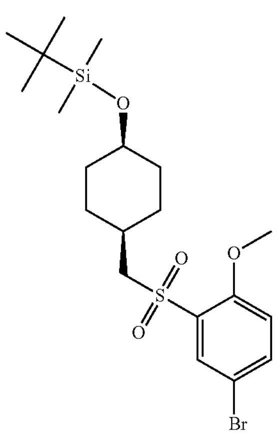 [SMILES: COc1ccc(Br)cc1S(=O)(=O)C[C@H]1CC[C@@H](O[Si](C)(C)C(C)(C)C)CC1] | $^1$H-NMR (400 MHz, CDCl$_3$) δ: 0.02 (6H, s), 0.87 (9H, s), 1.42-1.52 (2H, m), 1.53-1.63 (6H, m), 1.99-2.08 (1H, m), 3.27 (2H, d, J = 6.1 Hz), 3.87-3.92 (1H, m), 3.98 (3H, s), 6.93 (1H, d, J = 8.8 Hz), 7.67 (1H, dd, J = 8.8, 2.4 Hz), 8.08 (1H, d, J = 2.4 Hz).<br>MS (ESI$^+$): 477 [M + H]$^+$ |

TABLE 48-continued

| Reference Example | Structure | Instrumental Data |
|---|---|---|
| 13-34 | 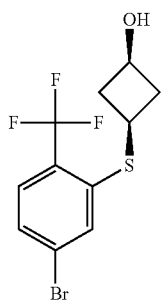 | $^1$H-NMR (400 MHz, CDCl$_3$) δ: 1.30 (6H, d, J = 7.0 Hz), 3.64-3.75 (1H, m), 3.96 (3H, s), 6.93 (1H, d, J = 8.8 Hz), 7.68 (1H, dd, J = 8.8, 2.6 Hz), 8.07 (1H, d, J = 2.6 Hz). MS (EI$^+$): 292 [M]$^+$ |

Reference Example 14-1

[Formula 59]

To a solution of the compound obtained in Reference Example 12-10 (590 mg) in methanol (9 mL) was added sodium borohydride (68.6 mg) at 0° C. The mixture was stirred at room temperature for 1 hour under an argon atmosphere. Saturated aqueous sodium bicarbonate solution was added to the reaction mixture, and the mixture was extracted with ethyl acetate. The solvent in the organic layer was distilled away under reduced pressure, and the residue was purified by silica gel column chromatography (hexane: ethyl acetate=2:1) to give the title compound (539 mg).

$^1$H-NMR (400 MHz, CDCl$_3$) δ: 1.90 (1H, d, J=6.7 Hz), 2.06-2.14 (2H, m), 2.93-2.99 (2H, m), 3.33-3.41 (1H, m), 4.25-4.34 (1H, m), 7.37 (1H, d, J=8.6 Hz), 7.40 (1H, s), 7.47 (1H, d, J=8.6 Hz). MS (EI$^+$): 326 [M]$^+$.

Reference Example 14-2

A suitable compound of General Formula (12b) was used to perform reactions according to any of methods similar to Reference Example 14-1 and the method described in Step P-1 or similar methods thereto to give the compound of Reference Example 14-2 shown below.

TABLE 49

| Reference Example | Structure | Instrumental Data |
|---|---|---|
| 14-2 | Br | $^1$H-NMR (400 MHz, CDCl$_3$) δ: 1.85 (1H, d, J = 7.3 Hz), 2.00-2.08 (2H, m), 2.88-2.96 (2H, m), 3.26-3.35 (1H, m), 3.86 (3H, s), 4.22-4.31 (1H, m), 6.70 (1H, d, J = 8.5 Hz), 7.19 (1H, d, J = 2.4 Hz), 7.25 (1H, dd, J = 8.5, 2.4 Hz). MS (ESI$^+$): 289 [M + H]$^+$ |

Reference Example 15-1

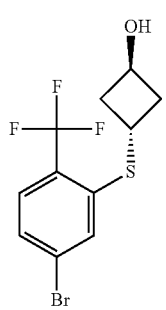

[Formula 60]

To a solution of the compound obtained in Reference Example 14-1 (285 mg), 4-nitrobenzoic acid (174 mg), and triphenylphosphine (275 mg) in tetrahydrofuran (4.4 mL) was added diisopropyl azodicarboxylate (0.175 mL) at 0° C. The mixture was stirred at room temperature for 0.5 hours under an argon atmosphere. The solvent in the reaction mixture was distilled away under reduced pressure, and the residue was purified by silica gel column chromatography (hexane:ethyl acetate=4:1). The resulting residue was dissolved in methanol (8.7 mL). Potassium carbonate (361 mg) was added to the reaction mixture at room temperature, and the mixture was stirred at room temperature for 1 hour. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (hexane: ethyl acetate=3:1) to give the title compound (250 mg).

$^1$H-NMR (400 MHz, CDCl$_3$) δ: 1.89 (1H, d, J=4.9 Hz), 2.40-2.46 (2H, m), 2.52-2.60 (2H, m), 3.91-3.96 (1H, m), 4.67-4.71 (1H, m), 7.29 (1H, s), 7.36 (1H, d, J=8.3 Hz), 7.47 (1H, d, J=8.3 Hz). MS (EI$^+$): 326 [M]$^+$.

Reference Example 15-2

A suitable compound of General Formula (12c) was used to perform reactions according to any of methods similar to Reference Example 15-1 and the method described in Step P-2 or similar methods thereto to give the compounds of Reference Example 15-2 shown below.

TABLE 50

| Reference Example | Structure | Instrumental Data |
|---|---|---|
| 15-2 | 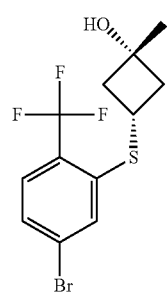 | $^1$H-NMR (400 MHz, CDCl$_3$) δ: 1.81 (1H, d, J = 4.8 Hz), 2.38-2.44 (2H, m), 2.49-2.56 (2H, m), 3.81-3.86 (1H, m), 3.86 (3H, s), 4.63-4.70 (1H, m), 6.70 (1H, d, J = 8.5 Hz), 7.06 (1H, d, J = 2.4 Hz), 7.23 (1H, dd, J = 8.5, 2.4 Hz). MS (CI$^+$): 289 [M + H]$^+$ |

TABLE 51

| Reference Example | Structure | Instrumental Data |
|---|---|---|
| 16-2 | 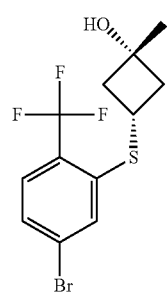 | $^1$H-NMR (400 MHz, CDCl$_3$) δ: 1.44 (3H, s), 2.00 (1H, br), 2.13-2.23 (2H, m), 2.64-2.70 (2H, m), 3.34-3.42 (1H, m), 3.85 (3H, s), 6.70 (1H, d, J = 9.0 Hz), 7.15 (1H, d, J = 2.3 Hz), 7.24 (1H, dd, J = 9.0, 2.3 Hz). MS (ESI$^+$): 303 [M + H]$^+$ |

Reference Example 16-1

[Formula 61]

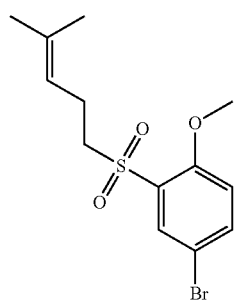

To a solution of the compound obtained in Reference Example 12-10 (543 mg) in tetrahydrofuran (9.0 mL) was added methylmagnesium bromide (0.95 mol/L in diethylether, 2.1 mL) at −78° C. The mixture was stirred at the same temperature for 1 hour under an argon atmosphere and then at 0° C. for 1 hour. Subsequently, saturated aqueous ammonium chloride solution was added to the reaction mixture, and the mixture was extracted with ethyl acetate. The solvent in the organic layer was distilled away under reduced pressure, and the residue was purified by silica gel column chromatography (hexane:ethyl acetate=4:1) to give the title compound (220 mg).

$^1$H-NMR (400 MHz, CDCl$_3$) δ: 1.46 (3H, s), 1.91 (1H, s), 2.24 (2H, t, J=10.7 Hz), 2.68-2.73 (2H, m), 3.40-3.48 (1H, m), 7.36-7.38 (2H, m), 7.47 (1H, d, J=9.2 Hz). MS (EI$^+$): 340 [M]$^+$.

Reference Example 16-2

A suitable compound of General Formula (12b) was used to perform reactions according to any of methods similar to Reference Example 16-1 and the method described in Step P-3 or similar methods thereto to give the compounds of Reference Example 16-2 shown below.

Reference Example 17

[Formula 62]

To a solution of the compound obtained in Reference Example 8-6 (111 mg) in tetrahydrofuran (4.2 mL) was added lithium bis(trimethylsilyl)amide (1.0 mol/L in tetrahydrofuran, 0.545 mL) at 0° C. The mixture was stirred at 0° C. for 5 minutes under an argon atmosphere. To the reaction mixture was added 1-bromo-3-methyl-2-butene (0.0580 mL) at 0° C., and the mixture was stirred at 0° C. for 3 hours. Saturated aqueous ammonium chloride solution was added to the reaction mixture, and the mixture was extracted with ethyl acetate. The solvent in the organic layer was distilled away under reduced pressure, and the residue was purified by silica gel column chromatography (hexane:ethyl acetate=3:1) to give the title compound (53.6 mg).

$^1$H-NMR (400 MHz, CDCl$_3$) δ: 1.55 (3H, s), 1.60 (3H, s), 2.38 (2H, q, J=7.7 Hz), 3.33-3.36 (2H, m), 3.97 (3H, s), 4.93-4.98 (1H, m), 6.93 (1H, d, J=8.8 Hz), 7.67 (1H, dd, J=8.8, 2.4 Hz), 8.06 (1H, d, J=2.4 Hz).

Reference Example 18-1

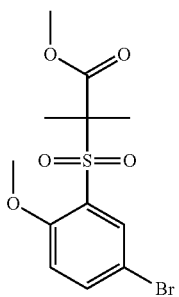

The compound obtained in Reference Example 8-1 (500 mg) was dissolved in N,N-dimethylformamide (7.7 mL) under an argon atmosphere, and iodomethane (0.482 ml) and potassium carbonate (855 mg) were added. The mixture was stirred at 60° C. for 6.5 hours, and then left to stand at room temperature for 16 hours and 40 minutes. The reaction mixture was poured into saturated aqueous ammonium chloride solution (20 mL) and water (10 mL) at room temperature, and then the vessel was washed with ethyl acetate (20 mL) and water (10 mL). An additional portion of ethyl acetate (20 mL) was added to the mixture, and the organic layer was extracted. The organic layer was washed with saturated brine (20 mL), dried over anhydrous sodium sulfate, and filtered to remove insoluble residues. The solvent was distilled away under reduced pressure, and the residue was then dissolved in dichloromethane (6 mL) and purified by silica gel column chromatography (hexane:ethyl acetate=88:12 to 0:100) to give the title compound (535.1 mg).

$^1$H-NMR (400 MHz, CDCl$_3$) δ: 1.64 (6H, s), 3.72 (3H, s), 3.89 (3H, s), 6.92 (1H, d, J=8.9 Hz), 7.69 (1H, dd, J=8.9, 2.4 Hz), 7.99 (1H, d, J=2.4 Hz). MS (ESI$^+$): 351 [M+H]$^+$

Reference Examples 18-2 to 18-3

A suitable compound of General Formula (2w) was used to perform reactions according to any of methods similar to Reference Example 18-1 and the method described in Step L-2 or similar methods thereto to give the compounds of Reference Examples 18-2 to 18-3 shown below.

TABLE 52

| Reference Example | Structure | Instrumental Data |
|---|---|---|
| 18-2 | 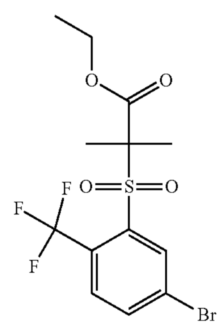 | $^1$H-NMR (400 MHz, CDCl$_3$) δ: 1.22 (3H, t, J = 7.2 Hz), 1.67 (6H, s), 4.15 (2H, q, J = 7.2 Hz), 7.79 (1H, d, J = 8.5 Hz), 7.91 (1H, d, J = 8.5 Hz), 8.23 (1H, d, J = 1.8 Hz). MS (EI$^+$) 403 [M + H]$^+$ |
| 18-3 | 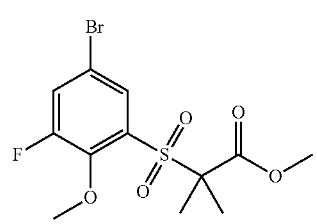 [SMILES: COC(=O)C(C)(C)S(=O)(=O)c1cc(Br)cc(F)c1OC] | $^1$H-NMR (400 MHz, CDCl$_3$) δ: 1.64 (6H, s), 3.73 (3H, s), 3.96 (3H, d, J = 1.8 Hz), 7.55 (1H, dd, J = 10.3, 2.4 Hz), 7.77-7.79 (1H, m). MS (ESI$^+$): 369 [M + H]$^+$ |

Reference Example 19

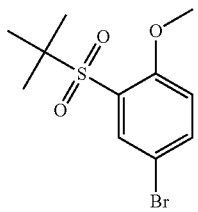

[Formula 64]

The compound obtained in Reference Example 13-34 (100 mg) was dissolved in tetrahydrofuran (3.4 mL) under an argon atmosphere, and 1.13 mol/L lithium diisopropylamide in tetrahydrofuran (0.362 ml) was added dropwise to the mixture with ice cooling. The mixture was then stirred for 20 minutes. Iodomethane (0.0319 ml) was added to the mixture, and the mixture was stirred at the same temperature for 10 minutes. Saturated aqueous ammonium chloride solution (5 mL) and water (5 mL) were then added to the mixture, and the mixture was extracted with ethyl acetate (10 mL). The organic layer was washed with saturated brine (10 mL), dried over anhydrous sodium sulfate, and filtered to remove insoluble residues. The solvent was distilled away under reduced pressure, and the residue was then dissolved in dichloromethane (3 mL) and purified by silica gel column chromatography (hexane:ethyl acetate=92:8 to 34:66) to give the title compound (83.0 mg).

$^1$H-NMR (400 MHz, CDCl$_3$) δ: 1.37 (9H, s), 3.91 (3H, s), 6.94 (1H, d, J=9.0 Hz), 7.68 (1H, dd, J=9.0, 2.7 Hz), 8.02 (1H, d, J=2.7 Hz). MS (ESI$^+$): 307 [M+H]$^+$.

Reference Example 20-1

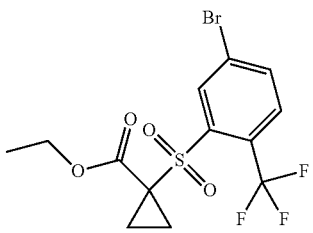

[Formula 65]

To a solution of the compound obtained in Reference Example 13-16 (215 mg) and 1,2-dibromoethane (0.0593 mL) in N,N-dimethylformamide (11 mL) was added potassium carbonate (238 mg) at 0° C. The mixture was stirred at room temperature for 2.5 hours under an argon atmosphere, and then at 60° C. for 9.5 hours. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (hexane:ethyl acetate=4:1) to give the title compound (206 mg).

$^1$H-NMR (400 MHz, CDCl$_3$) δ: 1.03 (3H, t, J=7.0 Hz), 1.86 (2H, q, J=4.5 Hz), 2.11 (2H, q, J=4.5 Hz), 4.04 (2H, q, J=7.1 Hz), 7.74 (1H, d, J=8.6 Hz), 7.88 (1H, dd, J=7.6, 1.5 Hz), 8.61 (1H, d, J=1.8 Hz).

Reference Example 20-2

A suitable compound of General Formula (2w) was used to perform reactions according to any of methods similar to Reference Example 20-1 and the method described in Step L-4 or similar methods thereto to give the compounds of Reference Example 20-2 shown below.

TABLE 53

| Reference Example | Structure | Instrumental Data |
|---|---|---|
| 20-2 | 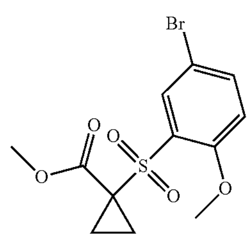 [SMILES: COC(=O)C1(S(=O)(=O)c2cc(Br)ccc2OC)CC1] | $^1$H-NMR (400 MHz, CDCl$_3$) δ: 1.75 (2H. dd, J = 8.4, 4.7 Hz), 2.10 (2H, dd, J = 8.4, 4.7 Hz), 3.59 (3H, s), 3.91 (3H, s), 6.90 (1H, d, J = 8.9 Hz), 7.66 (1H, dd, J = 8.9, 2.5 Hz), 8.24 (1H, d, J = 2.5 Hz). MS (ESI$^+$): 349 [M + H]$^+$ |

Reference Example 21-1

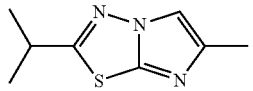

To a solution of 5-isopropyl-1,3,4-thiadiazole-2-amine (600 mg) in ethanol (4.2 mL) was added bromoacetone (0.352 mL) at room temperature. The mixture was heated to reflux under an argon atmosphere for 8 hours. The solvent in the reaction mixture was distilled away under reduced pressure followed by addition of saturated aqueous sodium bicarbonate solution, and the mixture was extracted with ethyl acetate. The solvent in the organic layer was distilled away under reduced pressure, and the residue was purified by silica gel column chromatography (hexane:ethyl acetate=9:1) to give the title compound (659 mg).

$^1$H-NMR (400 MHz, CDCl$_3$) δ: 1.42 (6H, d, J=6.7 Hz), 2.35 (3H, d, J=1.2 Hz), 3.23-3.30 (1H, m), 7.40-7.41 (1H, m). MS (EI$^+$): 181 [M]$^+$.

Reference Examples 21-2 to 21-14

A suitable compound of General Formula (8) was used to perform reactions according to any of methods similar to Reference Example 21-1 and the method described in Step F-1 or similar methods thereto to give the compounds of Reference Examples 21-2 to 21-14 shown below.

TABLE 54

| Reference Example | Structure | Instrumental Data |
|---|---|---|
| 21-2 | 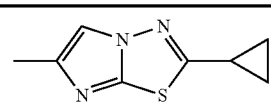 | $^1$H-NMR (400 MHz, CDCl$_3$) δ: 1.06-1.23 (4H, m), 2.16-2.23 (1H, m), 2.33 (3H, s), 7.37 (1H, d, J = 1.2 Hz). MS (EI$^+$): 179 [M]$^+$ |
| 21-3 | 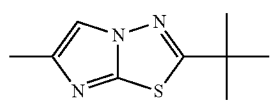 | $^1$H-NMR (400 MHz, CDCl$_3$) δ: 1.45 (9H, s), 2.35 (3H, d, J = 1.2 Hz), 7.40 (1H, s). MS (ESI$^+$): 196 [M + H]$^+$ |
| 21-4 | 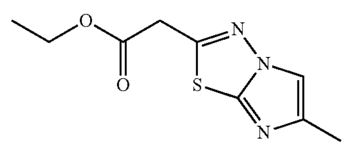 | $^1$H-NMR (400 MHz, CDCl$_3$) δ: 1.31 (3H, t, J = 7.3 Hz), 2.36 (3H, s), 4.01 (2H, s), 4.26 (2H, q, J = 7.3 Hz), 7.45 (1H, d, J = 1.2 Hz). MS (ESI$^+$): 226 [M + H]$^+$ |
| 21-5 | 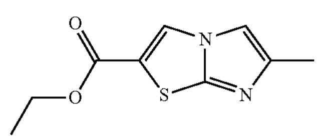 | $^1$H-NMR (400 MHz, CDCl$_3$) δ: 1.38 (3H, t, J = 7.3 Hz), 2.36 (3H, s), 4.38 (2H, q, J = 7.3 Hz), 7.22 (1H, s), 8.06 (1H, s). |
| 21-6 | 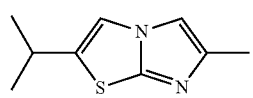 | $^1$H-NMR (400 MHz, CDCl$_3$) δ: 1.32 (6H, d, J = 6.7 Hz), 2.32 (3H, s), 3.00-3.07 (1H, m), 7.03 (1H, d, J = 1.2 Hz), 7.06 (1H, s). MS (ESI$^+$): 181 [M + H]$^+$ |
| 21-7 | 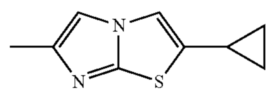 | $^1$H-NMR (400 MHz, CDCl$_3$) δ: 0.71-0.75 (2H, m), 0.95-1.00 (2H, m), 1.90-1.97 (1H, m), 2.31 (3H, s), 7.04 (1H, d, J = 1.2 Hz), 7.05 (1H, d, J = 1.2 Hz). MS (ESI$^+$): 179 [M + H]$^+$ |
| 21-8 | 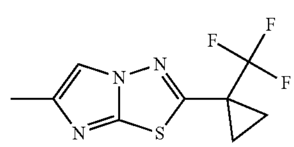 [SMILES: Cc1cn2nc(C3(C(F)(F)F)CC3)sc2n1] | $^1$H-NMR (400 MHz, CDCl$_3$) δ: 1.52-1.59 (4H, m), 2.36 (3H, d, J = 1.2 Hz), 7.45 (1H, s). |
| 21-9 | 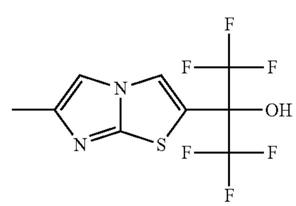 [SMILES: Cc1cn2cc(C(O)(C(F)(F)F)C(F)(F)F)sc2n1] | $^1$H-NMR (400 MHz, DMSO-d$_6$) δ: 2.23 (3H, s), 7.49 (1H, s), 8.23 (1H, s), 9.74 (1H, br s). MS (ESI$^+$): 305 [M + H]$^+$ |
| 21-10 | 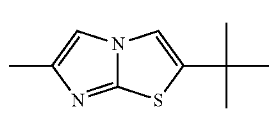 | $^1$H-NMR (400 MHz, CDCl$_3$) δ: 1.36 (9H, s), 2.32 (3H, s), 7.02 (1H, s), 7.05 (1H, s). MS (ESI$^+$): 195 [M + H]$^+$ |

TABLE 54-continued

| Reference Example | Structure | Instrumental Data |
|---|---|---|
| 21-11 | 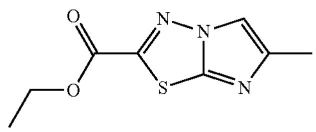 | ¹H-NMR (400 MHz, CDCl₃) δ: 1.47 (3H, t, J = 7.2 Hz), 2.40 (3H, d, J = 0.9 Hz), 4.53 (2H, q, J = 7.2 Hz), 7.60 (1H, d, J = 0.9 Hz). MS (ESI⁺): 212 [M + H]⁺ |
| 21-12 | 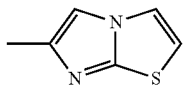 | ¹H-NMR (400 MHz, CDCl₃) δ: 2.35 (3H, d, J = 1.2 Hz), 6.74 (1H, d, J = 4.3 Hz), 7.20 (1H, s), 7.33 (1H, d, J = 4.3 Hz). |
| 21-13 | 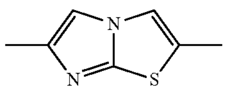 | ¹H-NMR (400 MHz, CDCl₃) δ: 2.32 (3H, s), 2.38 (3H, d, J = 1.2 Hz), 7.03 (1H, d, J = 1.2 Hz), 7.07 (1H, s). |
| 21-14 | 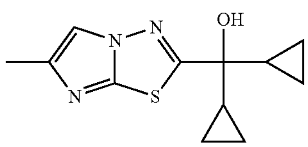 [SMILES: Cc1cn2nc(C(O)(C3CC3)C3CC3)sc2n1] | ¹H-NMR (400 MHz, CDCl₃) δ: 0.45-0.51 (2H, m), 0.58-0.67 (6H, m), 1.31-1.38 (2H, m), 2.35 (1H, s), 2.36 (3H, d, J = 1.2 Hz), 7.43 (1H, d, J = 1.2 Hz). MS (ESI⁺): 250 [M + H]⁺ |

Reference Example 22-1

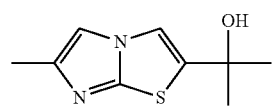

[Formula 67]

To a solution of the compound obtained in Reference Example 21-5 (116 mg) in tetrahydrofuran (5.5 mL) was added dropwise methylmagnesium chloride (3.0 mol/L in tetrahydrofuran, 0.552 mL) with ice cooling. The mixture was stirred at room temperature for 8 hours under an argon atmosphere. Saturated aqueous ammonium chloride solution was added to the reaction mixture with ice cooling, and the mixture was extracted with ethyl acetate. The solvent in the organic layer was distilled away under reduced pressure, and the residue was purified by silica gel column chromatography (ethyl acetate) to give the title compound (57.7 mg).

¹H-NMR (400 MHz, CDCl₃) δ: 1.65 (6H, s), 2.15 (1H, s), 2.33 (3H, s), 7.08 (1H, s), 7.22 (1H, s). MS (ESI⁺): 197 [M+H]⁺.

Reference Example 22-2

A suitable compound of General Formula (5b) was used to perform reactions according to any of methods similar to Reference Example 22-1 and the method described in Step D-1 or similar methods thereto to give the compounds of Reference Example 22-2 shown below.

TABLE 55

| Reference Example | Structure | Instrumental Data |
|---|---|---|
| 22-2 | 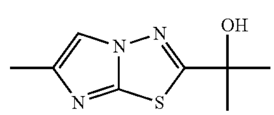 | ¹H-NMR (400 MHz, CDCl₃) δ: 1.71 (6H, s), 2.35 (3H, d, J = 1.1 Hz), 3.28 (1H, s), 7.40 (1H, d, J = 1.1 Hz). MS (ESI⁺): 198 [M + H]⁺ |

Reference Example 23

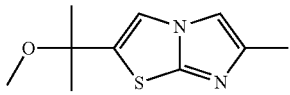

[Formula 68]

To a solution of the compound obtained in Reference Example 22-1 (18.0 mg) and methyl iodide (0.00860 mL) in N,N-dimethylformamide (0.4 mL) was added 60% sodium hydride (4.4 mg) with ice cooling. The mixture was stirred at room temperature for 1 hour under an argon atmosphere. Saturated aqueous ammonium chloride solution was added to the reaction mixture, and the mixture was extracted with ethyl acetate. The solvent in the organic layer was distilled away under reduced pressure, and the residue was purified by silica gel column chromatography (hexane:ethyl acetate=1:4) to give the title compound (16.7 mg).

$^1$H-NMR (400 MHz, CDCl$_3$) δ: 1.58 (6H, s), 2.33 (3H, s), 3.18 (3H, s), 7.09 (1H, s), 7.17 (1H, s).

Reference Example 24

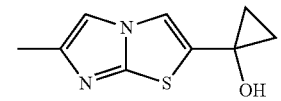

[Formula 69]

To a solution of the compound obtained in Reference Example 21-5 (500 mg) in tetrahydrofuran (12 mL) was added dropwise tetraisopropyl orthotitanate (0.418 mL) with ice cooling, and the mixture was stirred at the same temperature for 30 minutes under an argon atmosphere and then stirred at room temperature for 10 minutes. Ethylmagnesium bromide (1.0 mol/L in tetrahydrofuran, 7.14 mL) was added dropwise to the reaction mixture at room temperature over 1 hour, and the mixture was stirred at room temperature for 3 days under an argon atmosphere. Saturated aqueous ammonium chloride solution was added to the reaction mixture, and the mixture was extracted with ethyl acetate. The solvent in the organic layer was distilled away under reduced pressure, and the residue was purified by silica gel column chromatography (hexane:ethyl acetate=1:1) to give the title compound (61.0 mg).

$^1$H-NMR (400 MHz, CDCl$_3$) δ: 1.05 (2H, dd, J=7.6, 5.8 Hz), 1.30 (2H, dd, J=7.9, 5.4 Hz), 2.33 (3H, t, J=1.8 Hz), 2.87 (1H, s), 7.08 (1H, d, J=1.2 Hz), 7.23 (1H, s).

Reference Example 25

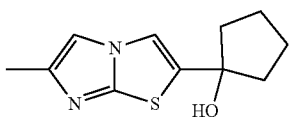

[Formula 70]

To a suspension of magnesium (wire, 77.5 mg) in tetrahydrofuran (3.4 mL) was added dropwise 1,4-dibromobutane (0.197 mL) with ice cooling. The mixture was stirred at room temperature for 1 hour under an argon atmosphere. The compound obtained in Reference Example 21-5 (100 mg) was added to the reaction mixture with ice cooling, and the mixture was stirred at 0° C. for 40 minutes under an argon atmosphere and then stirred at room temperature for 10 minutes. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (ethyl acetate) to give the title compound (98.3 mg).

$^1$H-NMR (400 MHz, CDCl$_3$) δ: 1.80-2.05 (9H, m), 2.33 (3H, s), 7.08 (1H, d, J=1.2 Hz), 7.26 (1H, s). MS (ESI$^+$): 223 [M+H]$^+$.

Reference Example 26-1

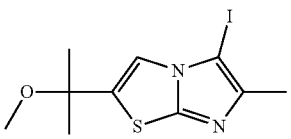

[Formula 71]

To a solution of the compound obtained in Reference Example 23 (63.9 mg) in acetonitrile (1.5 mL) was added N-iodosuccinimide (68.4 mg) with ice cooling. The mixture was stirred at room temperature for 30 minutes under an argon atmosphere. Saturated aqueous sodium bicarbonate solution and saturated aqueous sodium thiosulfate solution were added to the reaction, and the mixture was extracted with ethyl acetate. The solvent in the organic layer was distilled away under reduced pressure, and the residue was purified by silica gel column chromatography (hexane:ethyl acetate=2:1) to give the title compound (83.8 mg).

$^1$H-NMR (400 MHz, CDCl$_3$) δ: 1.60 (6H, s), 2.33 (3H, s), 3.19 (3H, s), 7.09 (1H, s). MS (ESI$^+$): 337 [M+H]$^+$.

Reference Examples 26-2 to 26-21

A suitable compound of General Formula (5) was used to perform reactions according to any of methods similar to Reference Example 26-1 and the method described in Step C-1 or similar methods thereto to give the compounds of Reference Examples 26-2 to 26-21 shown below.

TABLE 56

| Reference Example | Structure | Instrumental Data |
|---|---|---|
| 26-2 | 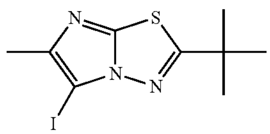 | 1H-NMR (400 MHz, CDCl₃) δ: 1.47 (9H, s), 2.35 (3H, s).<br>MS (ESI⁺): 322 [M + H]⁺ |
| 26-3 | 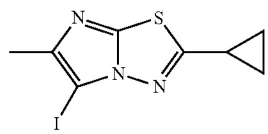 | ¹H-NMR (400 MHz, CDCl₃) δ: 1.10-1.26 (4H, m), 2.24-2.31 (1H, m), 2.34 (3H, s).<br>MS (EI⁺): 305 [M]⁺ |
| 26-4 | 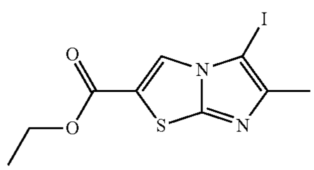 | ¹H-NMR (400 MHz, CDCl₃) δ: 1.40 (3H, t, J = 7.3 Hz), 2.37 (3H, s), 4.40 (2H, q, J = 7.3 Hz), 7.99 (1H, s). |
| 26-5 | 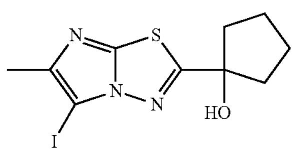 [SMILES: Cc1nc2sc(C3(O)CCCC3)nn2c1I] | ¹H-NMR (400 MHz, CDCl₃) δ: 1.84-2.06 (9H, m), 2.33 (3H, s), 7.21 (1H, s).<br>MS (ESI⁺): 349 [M + H]⁺ |
| 26-6 | 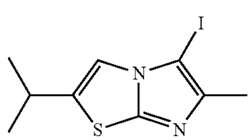 | ¹H-NMR (400 MHz, CDCl₃) δ: 1.34 (6H, d, J = 6.7 Hz), 2.32 (3H, s), 3.04-3.11 (1H, m), 6.99 (1H, d, J = 1.2 Hz).<br>MS (ESI⁺): 307 [M + H]⁺ |
| 26-7 | 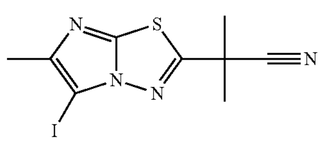 | ¹H-NMR (400 MHz, CDCl₃) δ: 1.92 (6H, s), 2.38 (3H, s).<br>MS (ESI⁺): 333 [M + H]⁺ |
| 26-8 | 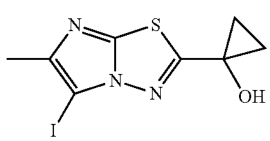 | ¹H-NMR (400 MHz, CDCl₃) δ: 1.01-1.05 (2H, m), 1.30-1.34 (2H, m), 1.68 (1H, s), 2.30 (3H, d, J = 1.2 Hz), 7.12 (1H, d, J = 1.8 Hz).<br>MS (ESI⁺): 321 [M + H]⁺ |
| 26-9 | 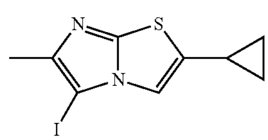 | ¹H-NMR (400 MHz, CDCl₃) δ: 0.75-0.79 (2H, m), 0.99-1.03 (2H, m), 1.93-1.99 (1H, m), 2.31 (3H, s), 7.01 (1H, d, J = 1.2 Hz).<br>MS (ESI⁺): 305 [M + H]⁺ |
| 26-10 | 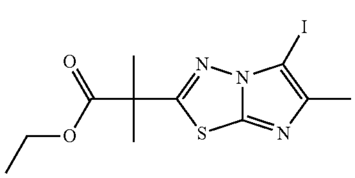 [SMILES: CCOC(=O)C(C)(C)c1nn2c(I)c(C)nc2s1] | ¹H-NMR (400 MHz, CDCl₃) δ: 1.28 (3H, t, J = 7.2 Hz), 1.74 (6H, s), 2.36 (3H, s), 4.23 (2H, q, J = 7.2 Hz).<br>MS (ESI⁺): 380 [M + H]⁺ |

TABLE 57

| Reference Example | Structure | Instrumental Data |
|---|---|---|
| 26-11 | 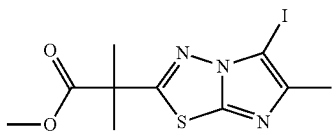 | $^1$H-NMR (400 MHz, CDCl$_3$) δ: 1.75 (6H, s), 2.36 (3H, s), 3.76 (3H, s).<br>MS (ESI$^+$): 366 [M + H]$^+$ |
| 26-12 | 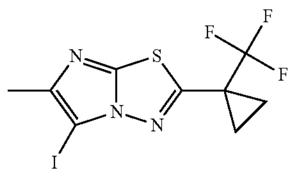 [SMILES: Cc1nc2sc(C3(C(F)(F)F)CC3)nn2c1I] | $^1$H-NMR (400 MHz, CDCl$_3$) δ: 1.61-1.63 (4H, m), 2.37 (3H, s).<br>MS (ESI$^+$): 374 [M + H]$^+$ |
| 26-13 | 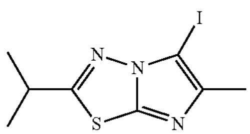 | $^1$H-NMR (400 MHz, CDCl$_3$) δ: 1.43 (6H, d, J = 6.7 Hz), 2.35 (3H, s), 3.31-3.38 (1H, m).<br>MS (EI$^+$): 307 [M]$^+$ |
| 26-14 | 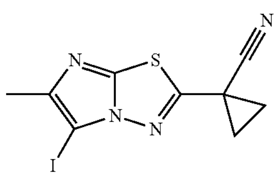 | $^1$H-NMR (400 MHz, CDCl$_3$) δ: 1.98 (4H, q, J = 3.4 Hz), 2.36 (3H, s).<br>MS (ESI$^+$): 331 [M + H]$^+$ |
| 26-15 | 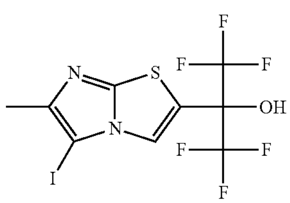 [SMILES: Cc1nc2sc(C(O)(C(F)(F)F)C(F)(F)F)cn2c1I] | $^1$H-NMR (400 MHz, DMSO-d$_6$) δ: 2.24 (3H, s), 7.83 (1H, s), 9.84 (1H, s).<br>MS (ESI$^+$): 431 [M + H]$^+$ |
| 26-16 | 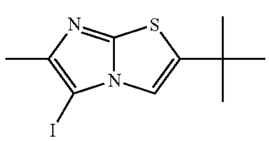 | $^1$H-NMR (400 MHz, CDCl$_3$) δ: 1.38 (9H, s), 2.32 (3H, s), 6.96 (1H, s).<br>MS (ESI$^+$): 321 [M + H]$^+$ |
| 26-17 | 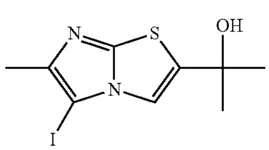 | $^1$H-NMR (400 MHz, CDCl$_3$) δ: 1.67 (6H, s), 2.32 (3H, s), 7.15 (1H, s). |
| 28-18 | 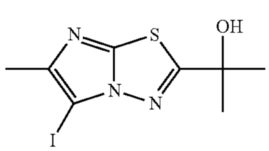 | $^1$H-NMR (400 MHZ, CDCl$_3$) δ: 1.74 (6H, s), 2.36 (3H, s), 2.94 (1H, s).<br>MS (ESI$^+$): 324 [M + H]$^+$ |
| 26-19 | 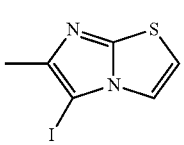 | $^1$H-NMR (400 MHz, DMSO-d$_6$) δ: 2.22 (3H, s), 7.31 (1H, d, J = 4.2 Hz), 7.71 (1H, d, J = 4.2 Hz).<br>MS (EI$^+$): 284 [M]$^+$ |

TABLE 57-continued

| Reference Example | Structure | Instrumental Data |
|---|---|---|
| 26-20 | 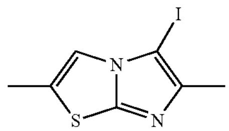 | $^1$H-NMR (400 MHz, DMSO-$d_6$) δ: 2.19 (3H, s), 2.40 (3H, d, J = 1.2 Hz), 7.52 (1H, d, J = 1.2 Hz). MS (EI$^+$): 278 [M]$^+$ |
| 26-21 | 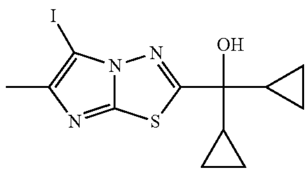 [SMILES: Cc1nc2sc(C(O)(C3CC3)C3CC3)nn2c1I] | $^1$H-NMR (400 MHz, DMSO-$d_6$) δ: 0.47-0.52 (2H, m), 0.57-0.70 (6H, m), 1.35-1.42 (2H, m), 2.358 (1H, s), 2.363 (3H, s). MS (ESI$^+$): 376 [M + H]$^+$ |

Reference Example 27-1

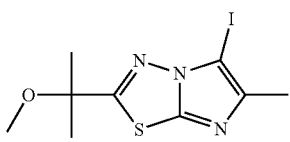

[Formula 72]

The compound obtained in Reference Example 26-18 (300 mg) was dissolved in N,N-dimethylformamide (3.1 mL) under an argon atmosphere, and iodomethane (0.0867 ml) was added. 55% sodium hydride (48.6 mg) was added to the solution with ice cooling, and the mixture was stirred at the same temperature for 40 minutes. Saturated aqueous ammonium chloride solution (5 mL) and water (10 mL) were added to the reaction mixture, and the mixture was stirred for 35 minutes. The resultant product was then collected by filtration, and the product was washed with water and then dried at 70° C. under reduced pressure to give the title compound (309.8 mg).

$^1$H-NMR (400 MHz, CDCl$_3$) δ: 1.67 (6H, s), 2.36 (3H, s), 3.28 (3H, s). MS (ESI$^+$): 338 [M+H]$^+$.

Reference Examples 27-2 to 27-3

A suitable compound of General Formula (4b) was used to perform reactions according to any of methods similar to Reference Example 27-1 and the method described in Step B-1 or similar methods thereto to give the compounds of Reference Examples 27-2 to 27-3 shown below.

TABLE 58

| Reference Example | Structure | Instrumental Data |
|---|---|---|
| 27-2 | 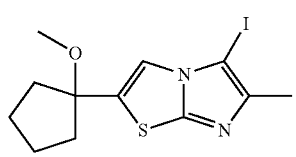 [SMILES: COC1(c2cn3c(I)c(C)nc3s2)CCCC1] | $^1$H-NMR (400 MHz, CDCl$_3$) δ: 1.73-1.93 (6H, m), 2.13-2.20 (2H, m), 2.33 (3H, s), 3.14 (3H, s), 7.11 (1H, s). MS (ESI$^+$): 363 [M + H]$^+$ |
| 27-3 | 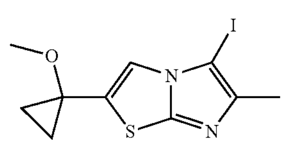 | $^1$H-NMR (400 MHz, CDCl$_3$) δ: 1.03 (2H, dd, J = 7.9, 5.4 Hz), 1.25 (2H, dd, J = 7.3, 5.4 Hz), 2.33 (3H, s), 3.31 (3H, s), 7.14 (1H, s). |

Reference Example 28

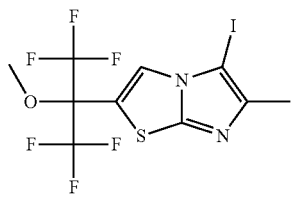

[Formula 73]

To a solution of the compound obtained in Reference Example 26-15 (35.4 mg), triphenylphosphine (25.9 mg), and methanol (0.0132 mL) in tetrahydrofuran (0.4 mL) was added diisopropyl azodicarboxylate (0.0194 mL) with ice cooling. The mixture was stirred at room temperature for 2 hours under an argon atmosphere. The solvent in the reaction mixture was distilled away under reduced pressure, and the residue was purified by silica gel column chromatography (hexane:ethyl acetate=2:1) to give the title compound (21.4 mg).

$^1$H-NMR (400 MHz, CDCl$_3$) δ: 2.36 (3H, s), 3.69 (3H, s), 7.46 (1H, s). MS (EI$^+$): 444 [M]$^+$.

Reference Example 29

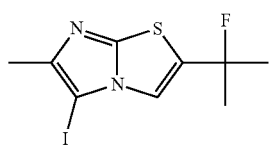

[Formula 74]

To a solution of the compound obtained in Reference Example 26-17 (61.0 mg) in methylene chloride (0.9 mL) was added (diethylamino)sulfur trifluoride (0.0297 mL) with ice cooling. The mixture was stirred at room temperature for 2 hours under an argon atmosphere. Saturated aqueous sodium bicarbonate solution was added to the reaction mixture with ice cooling, and the mixture was extracted with methylene chloride. The solvent in the organic layer was distilled away under reduced pressure, and the residue was purified by silica gel column chromatography (hexane:ethyl acetate=4:1) to give the title compound (44.2 mg).

$^1$H-NMR (400 MHz, CDCl$_3$) δ: 1.77 (3H, s), 1.83 (3H, s), 2.34 (3H, s), 7.23 (1H, d, J=1.8 Hz). MS (ESI$^+$): 325 [M+H]$^+$.

Reference Example 30

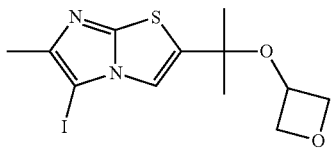

[Formula 75]

To a solution of the compound obtained in Reference Example 29 (56.7 mg) in 1,4-dioxane (0.1 mL) was added 3-oxetanol (64.8 mg) at room temperature. The mixture was stirred at 80° C. for 1 hour under an argon atmosphere and then stirred at 110° C. for 1 hour. The reaction mixture was purified by silica gel column chromatography (hexane:ethyl acetate=1:1) to give the title compound (17.1 mg).

$^1$H-NMR (400 MHz, CDCl$_3$) δ: 1.56 (6H, s), 2.33 (3H, s), 4.59-4.69 (5H, m), 7.08 (1H, s). MS (ESI$^+$): 379 [M+H]$^+$.

Reference Example 31-1

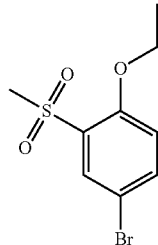

[Formula 76]

To a solution of 4-bromo-2-(methylsulfonyl)phenol (51.5 mg) and ethyl iodide (0.0197 mL) in N,N-dimethylformamide (0.6 mL) was added potassium carbonate (42.4 mg) at 0° C. The mixture was stirred at room temperature for 4 hours under an argon atmosphere. The reaction mixture was purified by silica gel column chromatography (hexane:ethyl acetate=2:1) to give the title compound (38.2 mg).

$^1$H-NMR (400 MHz, CDCl$_3$) δ: 1.52 (3H, t, J=7.0 Hz), 3.23 (3H, s), 4.21 (2H, q, J=6.9 Hz), 6.92 (1H, d, J=8.5 Hz), 7.66 (1H, dd, J=9.1, 2.4 Hz), 8.09 (1H, d, J=2.4 Hz).

Reference Example 31-2

A suitable compound of General Formula (2ag) was used to perform reactions according to any of methods similar to Reference Example 31-1 and the method described in Step T-1 or similar methods thereto to give the compounds of Reference Example 31-2 shown below.

TABLE 59

| Reference Example | Structure | Instrumental Data |
|---|---|---|
| 31-2 | 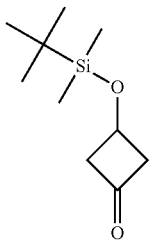 | $^1$H-NMR (400 MHz, CDCl$_3$) δ: 3.22 (3H, s), 6.95 (1H, d, J = 9.1 Hz), 7.69 (1H, dd, J = 9.1, 2.4 Hz), 8.10 (1H, d, J = 2.4 Hz). MS (ESI$^+$): 268 [M + H]$^+$ |

Reference Example 32

[Formula 77]

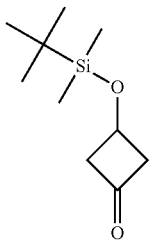

To a solution of 3-hydroxycyclobutan-1-one (220 mg) in N,N-dimethylformamide (2.6 mL) were added imidazole (261 mg) and t-butyl dimethylchlorosilane (463 mg) at 0° C. The mixture was stirred at room temperature for 18 hours under an argon atmosphere. Methanol (0.5 mL) was added to the reaction mixture, and the mixture was stirred at room temperature for 30 minutes. The solvent in the reaction mixture was distilled away under reduced pressure, and the residue was purified by silica gel column chromatography (hexane:ethyl acetate=4:1) to give the title compound (428 mg).

$^1$H-NMR (400 MHz, CDCl$_3$) δ: 0.09 (6H, s), 0.91 (9H, s), 3.04-3.12 (2H, m), 3.20-3.28 (2H, m), 4.58-4.63 (1H, m). MS (ESI$^+$): 201 [M+H]$^+$.

Reference Example 33

[Formula 78]

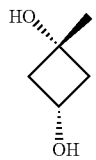

To a solution of the compound obtained in Reference Example 32 (428 mg) in tetrahydrofuran (11 mL) was added methylmagnesium chloride (3 mol/L in tetrahydrofuran, 0.853 mL) at −78° C. The mixture was stirred at the same temperature for 40 minutes under an argon atmosphere. Methylmagnesium chloride (3 mol/L in tetrahydrofuran, 0.213 mL) was added to the mixture, and the mixture was gradually allowed to rise in temperature to −20° C., and stirred at the same temperature for 10 minutes. Saturated aqueous ammonium chloride solution was added to the reaction mixture at −20° C., and the mixture was extracted with ethyl acetate. The solvent in the organic layer was distilled away under reduced pressure, and p-toluenesulfonic acid monohydrate (81.0 mg) was added to a solution of the residue in methylene chloride (10 mL) at 0° C. The mixture was stirred at room temperature for 2 hours under an argon atmosphere. P-toluenesulfonic acid monohydrate (81.0 mg) was added to the reaction mixture at room temperature, and the mixture was stirred at the same temperature for 16 hours. Saturated aqueous sodium bicarbonate solution was added to the reaction mixture, and the mixture was extracted with chloroform/methanol (5:1). The solvent in the organic layer was distilled away under reduced pressure, and the residue was purified by silica gel column chromatography (ethyl acetate:methanol=9:1) to give the title compound (139 mg).

$^1$H-NMR (400 MHz, CDCl$_3$) δ: 1.32 (3H, s), 1.71 (1H, d, J=5.4 Hz), 1.74 (1H, s), 2.02-2.06 (2H, m), 2.48-2.55 (2H, m), 3.96-4.04 (1H, m). MS (FI$^+$): 103 [M+H]$^+$.

Reference Example 34

[Formula 79]

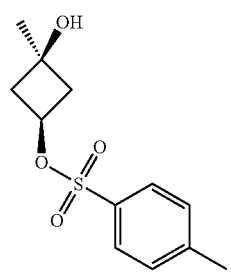

To a solution of the compound obtained in Reference Example 33 (139 mg) in methylene chloride (3.4 mL) were added pyridine (0.215 mL) and p-toluenesulfonyl chloride (259 mg) at room temperature. The mixture was stirred at 0° C. for 1.5 hours under an argon atmosphere and then stirred at room temperature for 21 hours. The solvent in the reaction mixture was distilled away under reduced pressure, and the residue was purified by silica gel column chromatography (hexane:ethyl acetate=1:1) to give the title compound (283 mg).

$^1$H-NMR (400 MHz, CDCl$_3$) δ: 1.29 (3H, s), 1.72 (1H, s), 2.23-2.28 (2H, m), 2.40-2.44 (2H, m), 2.45 (3H, s), 4.47-4.54 (1H, m), 7.34 (2H, d, J=7.9 Hz), 7.78 (2H, d, J=7.9 Hz). MS (FI$^+$): 257 [M+H]$^+$.

Reference Example 35

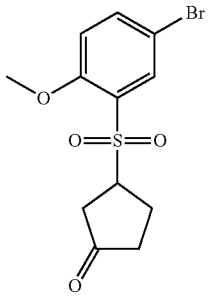

[Formula 80]

To a suspension of 5-bromo-2-methoxybenzene sulfinic acid (107 mg) in water (0.22 mL) were added cyclopentenone (35.0 mg) and 1 mol/L hydrochloric acid (0.43 mL) at room temperature. The mixture was stirred at room temperature for 7 hours under an argon atmosphere. To the reaction mixture was added 10 mL of water, and the product was collected by filtration to give the title compound (129 mg).

$^1$H-NMR (400 MHz, CDCl$_3$) δ: 2.27-2.70 (6H, m), 3.99 (3H, s), 4.25-4.33 (1H, m), 6.97 (1H, d, J=9.1 Hz), 7.72 (1H, dd, J=9.1, 2.4 Hz), 8.07 (1H, d, J=2.4 Hz).

Reference Example 36

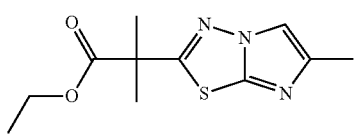

[Formula 81]

To a solution of the compound obtained in Reference Example 21-4 (345 mg) and methyl iodide (0.286 mL) in N,N-dimethylformamide (3 mL) was added 60% sodium hydride (153 mg) at 0° C. The mixture was stirred at room temperature for 2 hours under an argon atmosphere. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (hexane:ethyl acetate=3:1) to give the title compound (229 mg).

$^1$H-NMR (400 MHz, CDCl$_3$) δ: 1.26 (3H, t, J=7.1 Hz), 1.71 (6H, s), 2.36 (3H, d, J=1.2 Hz), 4.21 (2H, q, J=7.1 Hz), 7.44 (1H, s). MS (ESI$^+$): 254 [M+H]$^+$.

Reference Example 37-1

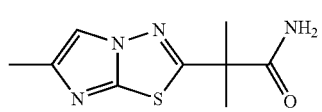

[Formula 82]

A pressure-resistant vessel was charged with the compound obtained in Reference Example 36 (141 mg), and ammonia (7.0 mol/L in methanol, 1 mL) was added to the vessel at room temperature. The vessel was then sealed, and the content was heated at 70° C. for 5.5 hours and then stirred at 110° C. for 3 hours. The solvent in the reaction mixture was distilled away under reduced pressure, and the residue was purified by silica gel column chromatography (ethyl acetate) to give the title compound (55.5 mg).

$^1$H-NMR (400 MHz, CDCl$_3$) δ: 1.74 (6H, s), 2.36 (3H, d, J=1.2 Hz), 5.36 (1H, br s), 6.03 (1H, br s), 7.45 (1H, d, J=1.2 Hz). MS (ESI$^+$): 225 [M+H]$^+$.

Reference Example 37-2

A suitable compound of General Formula (5g) was used to perform reactions according to any of methods similar to Reference Example 37-1 and the method described in Step E-2 or similar methods thereto to give the compound of Reference Example 37-2 listed in Table 51.

TABLE 60

| Reference Example | Structure | Instrumental Data |
|---|---|---|
| 37-2 | 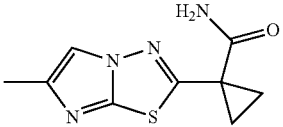 | $^1$H-NMR (400 MHz, CDCl$_3$) δ: 1.45 (2H, q, J = 4.0 Hz), 1.95 (2H, q, J = 4.0 Hz), 2.36 (3H, s), 3.38-3.65 (1H, m), 5.48-5.70 (1H, m), 7.44 (1H, s). |

Reference Example 38-1

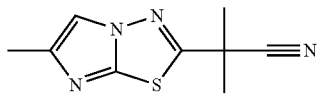

[Formula 83]

To a solution of the compound obtained in Reference Example 37-1 (55.5 mg) in methylene chloride (2.5 mL) were added N,N-diisopropylethylamine (0.210 mL) and trifluoroacetic anhydride (0.0865 mL) at 0° C. The mixture was stirred at 0° C. for 1 hour under an argon atmosphere and then at room temperature for 1 hour. Saturated aqueous sodium bicarbonate solution was added to the reaction mixture, and the mixture was extracted with ethyl acetate. The solvent in the organic layer was distilled away under reduced pressure, and the residue was purified by silica gel column chromatography (hexane:ethyl acetate=2:1) to give the title compound (39.8 mg).

$^1$H-NMR (400 MHz, CDCl$_3$) δ: 1.89 (6H, s), 2.37 (3H, d, J=1.2 Hz), 7.49 (1H, s). MS (ESI$^+$): 207 [M+H]$^+$.

Reference Example 38-2

A suitable compound of General Formula (7) was used to perform reactions according to any of methods similar to Reference Example 38-1 and the method described in Step E-3 or similar methods thereto to give the compounds of Reference Example 38-2 listed in Table 52.

TABLE 61

| Reference Example | Structure | Instrumental Data |
|---|---|---|
| 38-2 | 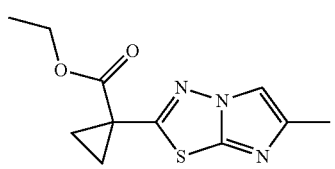 | $^1$H-NMR (400 MHz, CDCl$_3$) δ: 1.86-1.90 (2H, m), 1.93-1.97 (2H, m), 2.35 (3H, d, J = 1.2 Hz), 7.42 (1H, d, J = 1.2 Hz). MS (ESI$^+$): 205 [M + H]$^+$ |

Reference Example 39

[Formula 84]

To a solution of the compound obtained in Reference Example 21-4 (3.50 g) and 1,2-dibromoethane (1.60 mL) in N,N-dimethylformamide (31 mL) was added 60% sodium hydride (1.49 g) at 0° C. The mixture was stirred at room temperature for 4 hours under an argon atmosphere. 1,2-Dibromoethane (0.543 mL) and 60% sodium hydride (496 mg) were added to the mixture at 0° C., and the mixture was stirred at room temperature for 1.5 hours. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (hexane:ethyl acetate=2:1) to give the title compound (645 mg).

$^1$H-NMR (400 MHz, CDCl$_3$) δ: 1.29 (3H, t, J=7.2 Hz), 1.78-1.81 (2H, m), 1.88-1.91 (2H, m), 2.35 (3H, d, J=1.2 Hz), 4.25 (2H, q, J=7.2 Hz), 7.36 (1H, d, J=1.2 Hz). MS (ESI$^+$): 252 [M+H]$^+$.

Reference Example 40

[Formula 85]

To a mixture of the compound obtained in Reference Example 8-8 (132 mg) in tetrahydrofuran (3 mL) and water (1 mL) were added N-methylmorpholine N-oxide (76.1 mg) and osmium tetraoxide (2.5% in 2-methyl-2-propanol, 0.0881 mL) at room temperature. The mixture was stirred at room temperature for 19 hours. Saturated aqueous sodium bicarbonate solution and 10% aqueous sodium sulfate solution were added to the reaction mixture at 0° C., and the mixture was extracted with ethyl acetate. The solvent in the organic layer was distilled away under reduced pressure, and the residue was purified by silica gel column chromatography (ethyl acetate) to give the title compound (160 mg).

$^1$H-NMR (400 MHz, CDCl$_3$) δ: 1.41 (3H, s), 2.52-2.58 (1H, m), 3.53 (1H, d, J=14.5 Hz), 3.58-3.66 (2H, m), 3.71 (1H, d, J=14.5 Hz), 3.73 (1H, s), 3.99 (3H, s), 6.96 (1H, d, J=9.0 Hz), 7.71 (1H, dd, J=9.0, 2.6 Hz), 8.05 (1H, d, J=2.6 Hz). MS (ESI$^+$): 339 [M+H]$^+$.

Reference Example 41

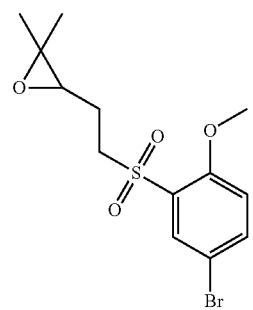

[Formula 86]

To a solution of the compound obtained in Reference Example 17 (53.6 mg) in methylene chloride (1.6 mL) was added 3-chloroperbenzoic acid (70% pure, 43.7 mg) at 0° C. The mixture was stirred at room temperature for 1 hour under an argon atmosphere. Saturated aqueous sodium bicarbonate solution and saturated aqueous sodium thiosulfate solution were added to the reaction mixture, and the mixture was extracted with methylene chloride. The solvent in the organic layer was distilled away under reduced pressure, and the residue was purified by silica gel column chromatography (hexane:ethyl acetate=1:1) to give the title compound (45.9 mg).

$^1$H-NMR (400 MHz, CDCl$_3$) δ: 1.25 (3H, s), 1.30 (3H, s), 1.80-1.89 (1H, m), 2.04-2.13 (1H, m), 2.79 (1H, dd, J=7.9, 4.8 Hz), 3.42-3.59 (2H, m), 3.98 (3H, s), 6.95 (1H, d, J=9.0 Hz), 7.70 (1H, dd, J=9.0, 2.6 Hz), 8.08 (1H, d, J=2.6 Hz). MS (FI$^+$): 348 [M]$^+$.

Reference Example 42

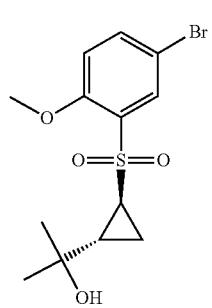

[Formula 87]

To a solution of the compound obtained in Reference Example 41 (45.9 mg) in tetrahydrofuran (1.3 mL) was added lithium bis(trimethylsilyl)amide (1.0 mol/L in tetrahydrofuran, 0.157 mL) at 0° C. The mixture was stirred at 0° C. for 40 minutes under an argon atmosphere. Saturated aqueous ammonium chloride solution was added to the reaction mixture, and the mixture was extracted with ethyl acetate. The solvent in the organic layer was distilled away under reduced pressure, and the residue was purified by silica gel column chromatography (ethyl acetate) to give the title compound (39.0 mg).

$^1$H-NMR (400 MHz, CDCl$_3$) δ: 1.10 (1H, s), 1.14-1.19 (4H, m), 1.26 (3H, s), 1.36-1.41 (1H, m), 1.74-1.79 (1H, m), 2.98-3.03 (1H, m), 3.99 (3H, s), 6.94 (1H, d, J=9.0 Hz), 7.66 (1H, dd, J=9.0, 2.6 Hz), 7.98 (1H, d, J=2.6 Hz). MS (FI$^+$): 348 [M]$^+$.

Reference Example 43-1

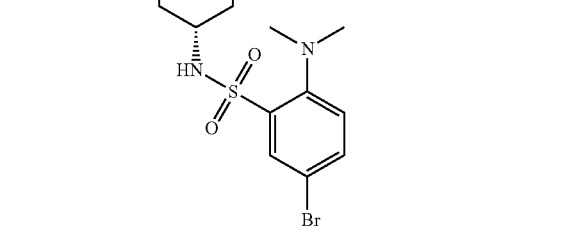

[Formula 88]

The compound obtained in Reference Example 6-17 (50.0 mg) was dissolved in 2 mol/L dimethylamine in tetrahydrofuran (1.4 mL), and the solution was stirred at 150° C. for 1 hour under microwave irradiation. The solvent was distilled away under reduced pressure, and the residue was then dissolved in dichloromethane (2 mL) and purified by silica gel column chromatography (hexane:ethyl acetate=84:16 to 0:100) to give the title compound (48.3 mg).

$^1$H-NMR (400 MHz, CDCl$_3$) δ: 1.22 (1H, d, J=3.0 Hz), 1.45-1.70 (8H, m), 2.77 (6H, s), 3.14-3.26 (1H, m), 3.79-3.88 (1H, m), 6.03 (1H, d, J=7.0 Hz), 7.28 (1H, d, J=8.5 Hz), 7.65 (1H, dd, J=8.5, 2.4 Hz), 8.12 (1H, d, J=2.4 Hz). MS (ESI$^+$): 377 [M+H]$^+$.

Reference Examples 43-2 to 43-3

A suitable compound of General Formula (20) obtained in reactions using a suitable compound of General Formula (15) according to any of methods similar to Reference Example 6-1 and the method described in Step R-7 or similar methods thereto was used to perform reactions according to any of methods similar to Reference Example 43-1 and the method described in Step S-1 or similar methods thereto to give the compounds of Reference Examples 43-2 to 43-3 shown below.

TABLE 62

| Reference Example | Structure | Instrumental Data |
|---|---|---|
| 43-2 | 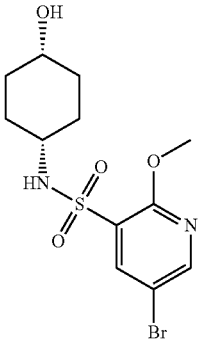 | $^1$H-NMR (400 MHz, DMSO-$d_6$) δ: 1.25-1.42 (4H, m), 1.47-1.64 (4H, m), 3.03-3.14 (1H, m), 3.57-3.64 (1H, m), 3.99 (3H, s), 4.33 (1H, d, J = 2.7 Hz), 7.78 (1H, d, J = 6.7 Hz), 8.17 (1H, d, J = 2.4 Hz), 8.54 (1H, d, J = 2.4 Hz). MS (ESI$^+$): 365 [M + H]$^+$ |
| 43-3 | 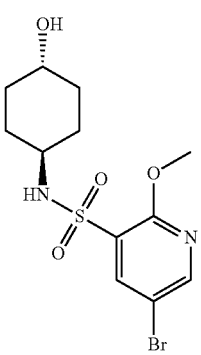 [SMILES: COc1ncc(Br)cc1S(=O)(=O)N[C@H]1CC[C@H](O)CC1] | $^1$H-NMR (400 MHz, CDCl$_3$) δ: 1.20-1.36 (4H, m), 1.38 (1H, d, J = 3.9 Hz), 1.81-1.88 (2H, m), 1.89-1.97 (2H, m), 3.07-3.19 (1H, m), 3.53-3.64 (1H, m), 4.09 (3H, s), 4.83 (1H, d, J = 7.3 Hz), 8.29 (1H, d, J = 2.4 Hz), 8.38 (1H, d, J = 2.4 Hz). MS (ESI$^+$): 365 [M + H]$^+$ |

Reference Example 44

[Formula 89]

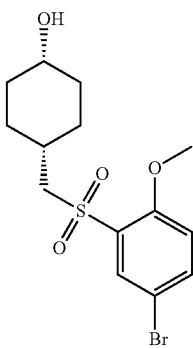

The compound obtained in Reference Example 13-33 (603 mg) was dissolved in 2 mol/L hydrogen chloride in ethanol (4.2 mL), and the solution was stirred at room temperature for 5 hours. The reaction mixture was poured into a mixture of saturated aqueous sodium bicarbonate solution (20 mL) and water (10 mL), and the resulting mixture was extracted with ethyl acetate (20 mL). The organic layer was washed with saturated brine (10 mL), dried over anhydrous sodium sulfate, and filtered to remove insoluble residues. The solvent was distilled away under reduced pressure, and the residue was then dissolved in dichloromethane (4 mL) and purified by silica gel column chromatography (hexane:ethyl acetate=84:16 to 0:100) to give the title compound (422.7 mg).

$^1$H-NMR (400 MHz, CDCl$_3$) δ: 1.21-1.30 (1H, m), 1.49-1.68 (8H, m), 2.06-2.15 (1H, m), 3.30 (2H, d, J=6.1 Hz), 3.93-4.02 (4H, m), 6.94 (1H, d, J=8.8 Hz), 7.68 (1H, dd, J=8.8, 2.4 Hz), 8.08 (1H, d, J=2.4 Hz). MS (ESI$^+$): 363 [M+H]$^+$.

Reference Example 45-1

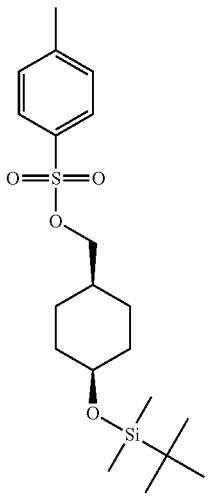

Cis-4-(t-butyldimethylsiloxy)cyclohexanemethanol (500 mg) was dissolved in dichloromethane (6.8 mL), and N,N-diisopropylethylamine (0.428 mL) and p-toluenesulfonyl chloride (409 mg) were added to the mixture. The mixture was stirred at room temperature for 3 hours. N,N,N',N'-tetramethylethylenediamine (0.0308 mL) was added to the mixture, and the mixture was stirred for 4 hours and then left to stand for 15 hours. After stirring for additional 2.5 hours, N,N,N',N'-tetramethylethylenediamine (0.0308 mL), diisopropylethylamine (0.285 mL), and p-toluenesulfonyl chloride (175 mg) were added to the mixture, and the resulting mixture was stirred for 4.5 hours. Water (5 mL) was added to the reaction mixture, and the mixture was stirred for 1 hour. Saturated aqueous ammonium chloride solution (5 mL) and water (10 mL) were then added to the mixture, and the mixture was extracted with ethyl acetate (20 mL). The organic layer was washed with saturated brine (20 mL), dried over anhydrous sodium sulfate, and then filtered to remove insoluble residues. The solvent was distilled away under reduced pressure, and the residue was then dissolved in dichloromethane (6 mL) and purified by silica gel column chromatography (hexane:ethyl acetate=95:5 to 60:40) to give the title compound (806 mg).

$^1$H-NMR (400 MHz, CDCl$_3$) δ: 0.00 (6H, s), 0.85 (9H, s), 1.32-1.46 (6H, m), 1.56-1.72 (3H, m), 2.45 (3H, s), 3.84 (2H, d, J=7.0 Hz), 3.89-3.94 (1H, m), 7.34 (2H, d, J=8.2 Hz), 7.79 (2H, d, J=8.2 Hz). MS (ESI$^+$): 399 [M+H]$^+$.

Reference Examples 45-2 to 45-4

A suitable compound of General Formula (36) was used to perform reactions according to any of methods similar to Reference Example 45-1 and the method described in Step AE-1 or similar methods thereto to give the compounds of Reference Examples 45-2 to 45-4 shown below.

TABLE 63

| Reference Example | Structure | Instrumental Data |
|---|---|---|
| 45-2 | ![structure] | $^1$H-NMR (400 MHz, CDCl$_3$) δ: 2.47 (3H, s), 2.69-2.82 (2H, m), 2.86-2.96 (2H, m), 4.70-4.77 (1H, m), 7.37 (2H, d, J = 8.3 Hz), 7.79 (2H, d, J = 8.3 Hz). MS (CI$^+$): 263 [M + H]$^+$ |
| 45-3 | ![structure] | $^1$H-NMR (400 MHz, CDCl$_3$) δ: 1.52-1.58 (2H, m), 1.75-1.90 (6H, m), 2.45 (3H, s), 3.87-3.95 (4H, m), 4.62-4.66 (1H, m), 7.33 (2H, d, J = 8.5 Hz), 7.80 (2H, d, J = 8.5 Hz). MS (CI$^+$): 140 [M − OSO$_2$PhMe]$^+$ |
| 45-4 | ![structure] | $^1$H-NMR (400 MHz, CDCl$_3$) δ: 1.33 (3/2H, s), 1.38 (3/2H, s), 2.08-2.13 (1H, m), 2.17-2.22 (1H, m), 2.45 (3H, s), 2.56-2.62 (1H, m), 2.71-2.76 (1H, m), 3.679 (3/2H, s), 3.685 (3/2H, s), 4.85-4.93 (1H, m), 7.34 (2H, d, J = 8.2 Hz), 7.78 (2H, d, J = 8.2 Hz). MS (FI$^+$): 299 [M]$^+$ |

Reference Example 46

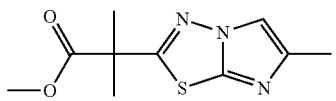

[Formula 91]

A pressure-resistant vessel was charged with the compound obtained in Reference Example 36 (141 mg), and ammonia (7.0 mol/L in methanol, 1 mL) was added to the vessel at room temperature. The vessel was then sealed, and the content was heated at 70° C. for 5.5 hours and then heated at 110° C. for 3 hours. The solvent in the reaction mixture was distilled away under reduced pressure, and the residue was purified by silica gel column chromatography (ethyl acetate) to give the title compound (72.9 mg).

$^1$H-NMR (400 MHz, CDCl$_3$) δ: 1.75 (6H, s), 2.38 (3H, s), 3.78 (3H, s), 7.46 (1H, s). MS (FI$^+$): 239 [M]$^+$.

Reference Example 47

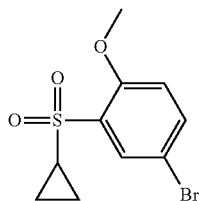

[Formula 92]

The compound obtained in Reference Example 8-7 (221 mg) was dissolved in tetrahydrofuran (6.7 mL) under an argon atmosphere and then cooled to −78° C., and 1 mol/L potassium hexamethyldisilazide in tetrahydrofuran (1.01 mL) was added to the mixture dropwise. The mixture was stirred for 1 hour. After cooling to 0° C., saturated aqueous ammonium chloride solution (10 mL) and water (10 mL) were added. The mixture was extracted with ethyl acetate (10 mL). The organic layer was washed with saturated brine (10 mL), dried over anhydrous sodium sulfate, and filtered to remove insoluble residues. The solvent was distilled away under reduced pressure, and the residue was then dissolved in dichloromethane (6 mL) and purified by silica gel column chromatography (hexane:ethyl acetate=88:12 to 0:100) to give the title compound (178 mg).

$^1$H-NMR (400 MHz, CDCl$_3$) δ: 0.98-1.04 (2H, m), 1.29-1.35 (2H, m), 2.92-3.00 (1H, m), 3.99 (3H, s), 6.95 (1H, d, J=8.8 Hz), 7.66 (1H, dd, J=8.8, 2.7 Hz), 7.99 (1H, d, J=2.7 Hz). MS (ESI$^+$): 291 [M+H]$^+$.

Reference Example 48-1

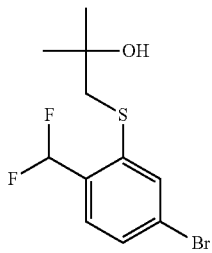

[Formula 93]

To a solution of the compound obtained in Reference Example 1-4 (1.15 g) in tetrahydrofuran (18 mL) was added methylmagnesium bromide (0.98 mol/L in diethylether, 10.8 mL) at 0° C. The mixture was stirred at room temperature for 1 hour under an argon atmosphere. Saturated aqueous ammonium chloride solution was added to the reaction mixture, and the mixture was extracted with ethyl acetate. The solvent in the organic layer was distilled away under reduced pressure, and the residue was purified by silica gel column chromatography (hexane:ethyl acetate=4:1) to give the title compound (601 mg).

$^1$H-NMR (400 MHz, CDCl$_3$) δ: 1.34 (6H, s), 2.01 (1H, s), 3.11 (2H, s), 7.06 (1H, t, J=55.0 Hz), 7.44-7.50 (2H, m), 7.69 (1H, d, J=1.2 Hz).

Reference Examples 48-2 to 48-4

A suitable compound of General Formula (12f) was used to perform reactions according to any of methods similar to Reference Example 48-1 and the method described in Step AB-1 or similar methods thereto to give the compounds of Reference Examples 48-2 to 48-4 shown below.

TABLE 64

| Reference Example | Structure | Instrumental Data |
| --- | --- | --- |
| 48-2 | ![structure] | $^1$H-NMR (400 MHz, CDCl$_3$) δ: 1.12 (6H, s), 1.98-2.05 (2H, m), 2.31-2.40 (1H, m), 2.44-2.51 (2H, m), 3.62-3.70 (1H, m), 3.85 (3H, s), 6.69 (1H, d, J = 8.6 Hz), 7.19 (1H, d, J = 2.4 Hz), 7.22 (1H, dd, J = 8.6, 2.4 Hz). MS (FI$^+$): 330 [M]$^+$ |

TABLE 64-continued

| Reference Example | Structure | Instrumental Data |
|---|---|---|
| 48-3 | HO, methylcyclobutyl-S-(2-methoxy-5-bromophenyl) structure | $^1$H-NMR (400 MHz, CDCl$_3$) δ: 1.16 (6H, s), 1.26 (3H, s), 1.36 (1H, s), 1.75 (2H, dd, J = 14.1, 6.1 Hz), 2.89 (2H, dd, J = 14.1, 9.2 Hz), 3.66-3.74 (1H, m), 3.86 (3H, s), 6.68 (1H, d, J = 8.6 Hz), 7.04 (1H, d, J = 2.4 Hz), 7.20 (1H, dd, J = 8.6, 2.4 Hz). MS (FI$^+$): 344 [M]$^+$ |
| 48-4 | HO, methylcyclobutyl-S-(2-methoxy-5-bromophenyl) structure (stereoisomer) | $^1$H-NMR (400 MHz, CDCl$_3$) δ: 1.09 (6H, s), 1.26 (3H, s), 1.40 (1H, s), 2.07-2.12 (2H, m), 2.32-2.37 (2H, m), 3.75-3.81 (1H, m), 3.84 (3H, s), 6.67 (1H, d, J = 8.8 Hz), 7.14 (1H, d, J = 2.0 Hz), 7.21 (1H, dd, J = 8.8, 2.0 Hz). MS (FI$^+$): 344 [M]$^+$ |

Reference Example 49-1

[Formula 94]

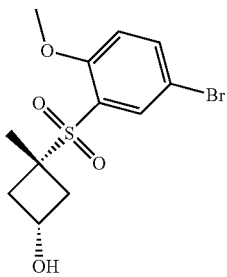

To a solution of the compound obtained in Reference Example 8-3 (81.3 mg) in tetrahydrofuran (2.5 mL) was added lithium diisopropylamide (1.1 mol/L in hexane/tetrahydrofuran, 0.635 mL) at −78° C. The mixture was stirred at −78° C. for 5 minutes under an argon atmosphere. Epichlorohydrin (0.0350 mL) was added to the reaction mixture at −78° C., and the mixture was allowed to rise in temperature to room temperature over 2 hours and stirred at room temperature for 26 hours. Saturated aqueous ammonium chloride solution was added to the reaction mixture at 0° C., and the mixture was extracted with ethyl acetate. The solvent in the organic layer was distilled away under reduced pressure, and the residue was purified by silica gel column chromatography (hexane:ethyl acetate=1:2) to give the title compound (69.0 mg).

$^1$H-NMR (400 MHz, CDCl$_3$) δ: 1.31 (3H, s), 2.20 (1H, d, J=8.6 Hz), 2.39-2.44 (2H, m), 2.86-2.91 (2H, m), 3.90 (3H, s), 4.28-4.37 (1H, m), 6.90 (1H, d, J=8.6 Hz), 7.67 (1H, dd, J=8.9, 2.8 Hz), 8.06 (1H, d, J=2.4 Hz). MS (FI$^+$): 334 [M]$^+$.

Reference Example 49-2

A suitable compound of General Formula (2an) was used to perform reactions according to any of methods similar to Reference Example 49-1 and the method described in Step AH-1 or similar methods thereto to give the compounds of Reference Example 49-2 shown below.

TABLE 65

| Reference Example | Structure | Instrumental Data |
|---|---|---|
| 49-2 | HO-cyclobutyl(cyclopropyl)-SO$_2$-(2-methoxy-5-bromophenyl) structure | $^1$H-NMR (400 MHz, CDCl$_3$) δ: 0.19 (2H, q, J = 5.5 Hz), 0.36-0.41 (2H, m), 0.85-0.91 (1H, m), 2.24-2.29 (2H, m), 2.34 (1H, d, J = 9.2 Hz), 2.80-2.85 (2H, m), 3.89 (3H, s), 4.12-4.21 (1H, m), 6.88 (1H, d, J = 8.9 Hz), 7.65 (1H, dd, J = 8.9, 2.4 Hz), 8.09 (1H, d, J = 2.4 Hz). MS (ESI$^+$): 361 [M + H]$^+$ |

Reference Example 50-1

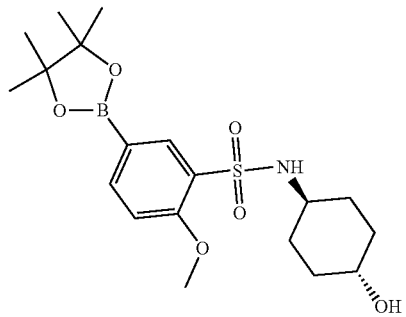

The compound obtained in Reference Example 6-3 (500 mg), bis(pinacolato)diboron (418 mg), potassium acetate (404 mg), and [1,1'-bis(diphenylphosphino) ferrocene]palladium (II) dichloride dichloromethane adduct (112 mg) were dissolved in 1,4-dioxane (6.9 mL) under an argon atmosphere, degassed, and then stirred at 90° C. for 2.5 hours. The reaction mixture was diluted with ethyl acetate (10 mL) at room temperature, and insoluble materials were then filtered off with Celite and washed with ethyl acetate (30 mL). The solvent in the filtrate was distilled away under reduced pressure, and the residue was then dissolved in dichloromethane (8 mL) and purified by silica gel column chromatography (hexane:ethyl acetate=25:75 to 0:100) to give the title compound (535 mg).

$^1$H-NMR (400 MHz, CDCl$_3$) δ: 1.19-1.30 (4H, m), 1.35 (12H, s), 1.78-1.93 (4H, m), 3.04-3.15 (1H, m), 3.51-3.62 (1H, m), 4.00 (3H, s), 4.73 (1H, d, J=7.0 Hz), 7.01 (1H, d, J=8.3 Hz), 7.97 (1H, dd, J=8.3, 1.5 Hz), 8.36 (1H, d, J=1.5 Hz).

Reference Examples 50-2 to 50-7

A suitable compound of General Formula (2) was used to perform reactions according to any of methods similar to Reference Example 50-1 and the method described in Step A-1 or similar methods thereto to give the compounds of Reference Examples 50-2 to 50-7 shown below.

TABLE 66

| Reference Example | Structure | Instrumental Data |
|---|---|---|
| 50-2 | 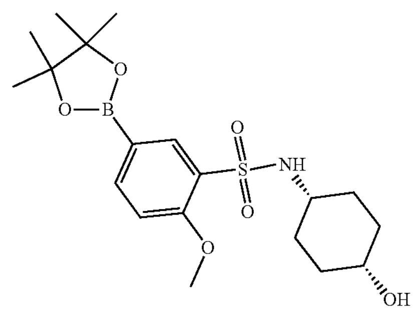 [SMILES: COc1ccc(B2OC(C)(C)C(C)(C)O2)cc1S(=O)(=O)N[C@H]1CC[C@@H](O)CC1] | $^1$H-NMR (400 MHz, CDCl$_3$) δ: 1.34(12H, s), 1.50-1.73 (9H, m), 3.24 (1H, br), 3.79 (1H, br), 4.00 (3H, s), 4.89 (1H, d, J = 7.3 Hz), 7.01 (1H, d, J = 8.6 Hz), 7.96 (1H, dd, J = 8.0, 1.2 Hz), 8.36 (1H, d, J = 1.2 Hz) |
| 50-3 | 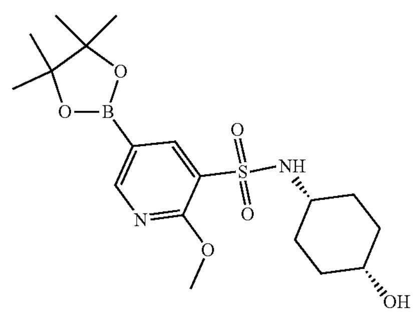 [SMILES: COc1ncc(B2OC(C)(C)C(C)(C)O2)cc1S(=O)(=O)N[C@H]1CC[C@@H](O)CC1] | $^1$H-NMR (400 MHz, CDCl$_3$) δ: 1.35 (12H, s), 1.49-1.67 (8H, m), 3.18-3.27 (1H, m), 3.79-3.86 (1H, m), 4.13 (3H, s), 4.93 (1H, d, J = 7.6 Hz), 8.53 (1H, d, J = 1.8 Hz), 8.66 (1H, d, J = 1.8 Hz). MS (ESI$^+$): 413 [M + H]$^+$ |
| 50-4 | 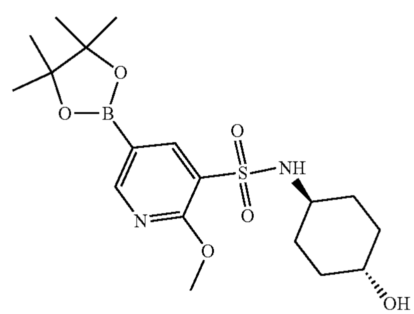 [SMILES: COc1ncc(B2OC(C)(C)C(C)(C)O2)cc1S(=O)(=O)N[C@H]1CC[C@H](O)CC1] | $^1$H-NMR (400 MHz, CDCl$_3$) δ; 1.17-1.29 (5H, m), 1.35 (12H, s), 1.79-1.94 (4H, m), 3.04-3.15 (1H, m), 3.52-3.62 (1H, m), 4.13 (3H, s), 4.77 (1H, d, J = 7.3 Hz), 8.54 (1H, d, J = 1.8 Hz), 8.67 (1H, d, J = 1.8 Hz). MS (ESI$^+$): 413 [M + H]$^+$ |

TABLE 66-continued

| Reference Example | Structure | Instrumental Data |
|---|---|---|
| 50-5 | 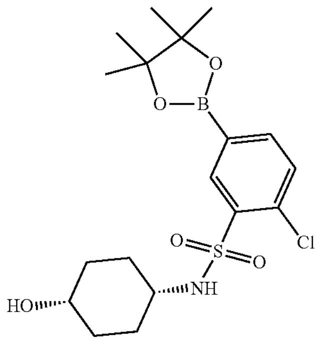 [SMILES: CC1(C)OB(c2ccc(Cl)c(S(=O)(=O)N[C@H]3CC[C@@H](O)CC3)c2)OC1(C)C] | $^1$H-NMR (400 MHz, CDCl$_3$) δ: 1.23-1.25 (1H, m), 1.35 (12H, s), 1.50-1.71 (8H, m), 3.21-3.31 (1H, m), 3.77-3.84 (1H, m), 4.99 (1H, d, J = 7.6 Hz), 7.52 (1H, d, J = 7.9 Hz), 7.89 (1H, dd, J = 7.9, 1.5 Hz), 8.51 (1H, d, J = 1.5 Hz). |
| 50-6 | 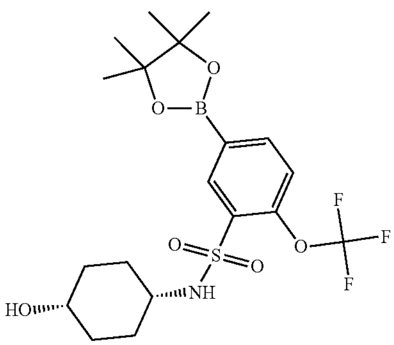 [SMILES: CC1(C)OB(c2ccc(OC(F)(F)F)c(S(=O)(=O)N[C@H]3CC[C@@H](O)CC3)c2)OC1(C)C] | $^1$H-NMR (400 MHz, CDCl$_3$) δ: 1.25-1.28 (1H, m), 1.35 (12H, s), 1.52-1.71 (8H, m), 3.24-3.35 (1H, m), 3.81-3.87 (1H, m), 4.66 (1H, d, J = 7.6 Hz), 7.34-7.39 (1H, m), 8.01 (1H, dd, J = 8.3, 1.7 Hz), 8.45 (1H, d, J = 1.7 Hz). |
| 50-7 | 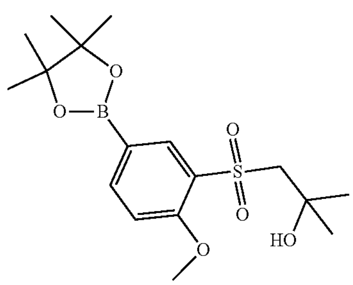 [SMILES: COc1ccc(B2OC(C)(C)C(C)(C)O2)cc1S(=O)(=O)CC(C)(C)O] | $^1$H-NMR (400 MHz, CDCl$_3$) δ: 1.34 (12H, s), 1.41 (6H, s), 3.53 (2H, s), 3.85 (1H, s), 4.02 (3H, s), 7.03 (1H, d, J = 7.9 Hz), 8.02 (1H, dd, J = 8.5, 1.8 Hz), 8.40 (1H, d, J = 1.2 Hz). MS (FI$^+$): 370 [M]$^+$ |

Example 1-1

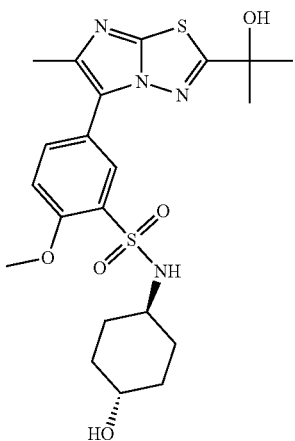

[Formula 96]

The compound obtained in Reference Example 26-18 (50.0 mg), the compound obtained in Reference Example 50-1 (76.4 mg), and [1,1'-bis(diphenylphosphino)ferrocene]palladium (II) dichloride dichloromethane adduct (12.6 mg) were dissolved in dimethylsulfoxide (1.6 mL) under an argon atmosphere, and then 2 mol/L aqueous sodium carbonate solution (0.232 mL) was added to the mixture. The mixture was degassed and then stirred at 80° C. for 1 hour. Saturated aqueous ammonium chloride solution (5 mL) and water (5 mL) were added to the mixture at room temperature, and the mixture was extracted with ethyl acetate (10 mL). The organic layer was washed with saturated brine (10 mL), dried over anhydrous sodium sulfate, and filtered to remove insoluble residues. The solvent was distilled away under reduced pressure, and the residue was then dissolved in dichloromethane (2 mL) and purified by silica gel column chromatography (ethyl acetate:methanol=98:2 to 80:20) to give the title compound (42.5 mg).

$^1$H-NMR (400 MHz, DMSO-d$_6$) δ: 0.98-1.10 (2H, m), 1.17-1.29 (2H, m), 1.55-1.62 (8H, m), 1.67-1.75 (2H, m), 2.40 (3H, s), 2.92-3.02 (1H, m), 3.22-3.32 (1H, m), 3.95 (3H, s), 4.48 (1H, d, J=4.3 Hz), 6.47 (1H, s), 7.31 (1H, d, J=6.4 Hz), 7.37 (1H, d, J=8.8 Hz), 7.89 (1H, dd, J=8.8, 2.4 Hz), 8.10 (1H, d, J=2.4 Hz). MS (ESI$^+$): 481 [M+H]$^+$.

Examples 1-2 to 1-53

Suitable compounds of General Formula (3) and General Formula (4) were used to perform reactions according to any of methods similar to Example 1-1 and the method described in Step A-2 or similar methods thereto to give the compounds of Examples 1-2 to 1-53 shown below.

TABLE 67

| Example | Structure | Instrumental Data |
|---|---|---|
| 1-2 | 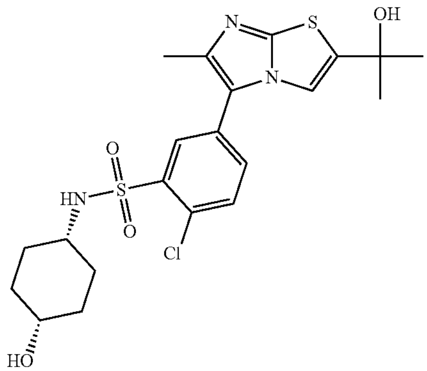 [SMILES: Cc1nc2sc(C(C)(C)O)cn2c1-c1ccc(Cl)c(S(=O)(=O)N[C@H]2CC[C@@H](O)CC2)c1] | $^1$H-NMR (400 MHz, DMSO-$d_6$) δ: 1.29-1.42 (4H, m), 1.48-1.58 (8H, m), 1.59-1.71 (2H, m), 2.32 (3H, s), 3.06-3.18 (1H, m), 3.56-3.63 (1H, m), 4.35 (1H, d, J = 3.0 Hz), 5.79 (1H, s), 7.67 (1H, s), 7.72-7.78 (2H, m), 7.94-8.00 (2H, m). MS (ESI$^+$): 484 [M + H]$^+$ |
| 1-3 | 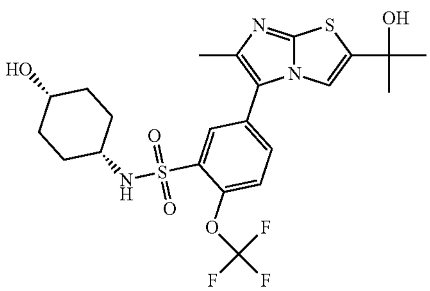 [SMILES: Cc1nc2sc(C(C)(C)O)cn2c1-c1ccc(OC(F)(F)F)c(S(=O)(=O)N[C@H]2CC[C@@H](O)CC2)c1] | $^1$H-NMR (400 MHz, DMSO-$d_6$) δ: 1.31-1.44 (4H, m), 1.49-1.70 (10H, m), 2.32 (3H, s), 3.16-3.26 (1H, m), 3.60-3.65 (1H, m), 4.36 (1H, d, J = 2.4 Hz), 5.80 (1H, s), 7.64-7.69 (1H, m), 7.70 (1H, s), 7.85 (1H, dd, J = 8.5, 1.8 Hz), 7.91 (1H, d, J = 2.4 Hz), 7.99-8.05 (1H, m). MS (ESI$^+$): 534 [M + H]$^+$ |
| 1-4 | 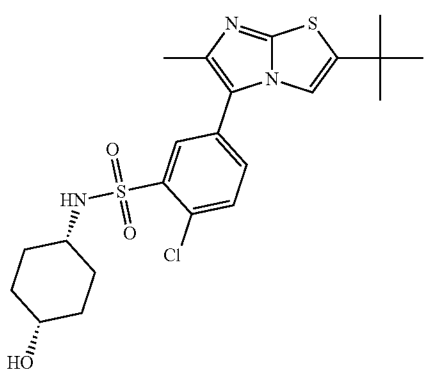 [SMILES: Cc1nc2sc(C(C)(C)C)cn2c1-c1ccc(Cl)c(S(=O)(=O)N[C@H]2CC[C@@H](O)CC2)c1] | $^1$H-NMR (400 MHz, DMSO-$d_6$) δ: 1.30-1.39 (13H, m), 1.49-1.58 (2H, m), 1.59-1.70 (2H, m), 2.31 (3H, s), 3.06-3.16 (1H, m), 3.57-3.62 (1H, m), 4.35 (1H, d, J = 3.0 Hz), 7.55 (1H, s), 7.75-7.77 (2H, m), 7.95-7.99 (2H, m). MS (ESI$^+$): 482 [M + H]$^+$ |
| 1-5 | 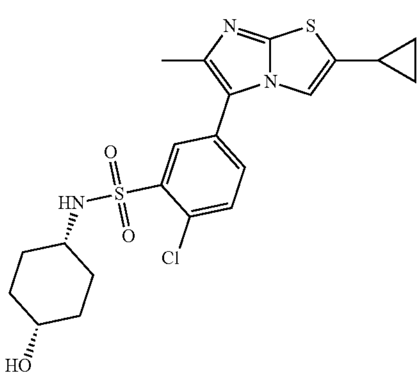 [SMILES: Cc1nc2sc(C3CC3)cn2c1-c1ccc(Cl)c(S(=O)(=O)N[C@H]2CC[C@@H](O)CC2)c1] | $^1$H-NMR (400 MHz, DMSO-$d_6$) δ: 0.75-0.81 (2H, m), 0.95-1.01 (2H, m), 1.29-1.42 (4H, m), 1.49-1.58 (2H, m), 1.59-1.70 (2H, m), 2.05-2.13 (1H, m), 2.31 (3H, s), 3.08-3.18 (1H, m), 3.57-3.64 (1H, m), 4.35 (1H, d, J = 3.0 Hz), 7.70 (1H, d, J = 0.9 Hz), 7.73-7.76 (2H, m), 7.95 (1H, t, J = 1.4 Hz), 7.98 (1H, d, J = 4.8 Hz). MS (ESI$^+$): 466 [M + H]$^+$ |

TABLE 67-continued

| Example | Structure | Instrumental Data |
|---|---|---|
| 1-6 | 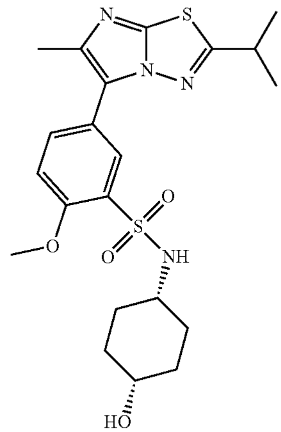 [SMILES: COc1ccc(-c2c(C)nc3sc(C(C)C)nn23)cc1S(=O)(=O)N[C@H]1CC[C@@H](O)CC1] | $^1$H-NMR (400 MHz, CDCl$_3$) δ: 1.27 (1H, d, J = 3.0 Hz), 1.44 (6H, d, J = 6.7 Hz), 1.54-1.66 (8H, m), 2.52 (3H, s), 3.26-3.36 (2H, m), 3.81 (1H, br), 4.04 (3H, s), 4.94 (1H, d, J = 7.3 Hz), 7.15 (1H, d, J = 8.5 Hz), 7.91 (1H, dd, J = 8.5, 2.4 Hz), 8.29 (1H, d, J = 2.4 Hz). MS (ESI$^+$): 465 [M + H]$^+$ |
| 1-7 | 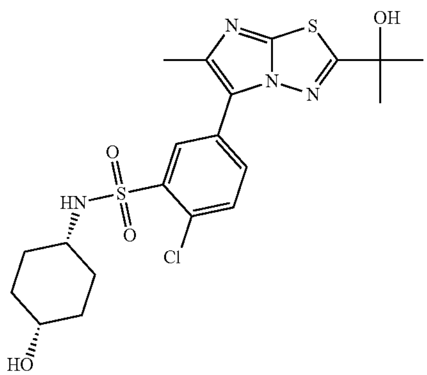 [SMILES: Cc1nc2sc(C(C)(C)O)nn2c1-c1ccc(Cl)c(S(=O)(=O)N[C@H]2CC[C@@H](O)CC2)c1] | $^1$H-NMR (400 MHz, CDCl$_3$) δ: 1.26 (1H, d, J = 3.0 Hz), 1.51-1.71 (8H, m), 1.76 (6H, s), 2.44 (1H, s), 2.57 (3H, s), 3.26-3.33 (1H, m), 3.80-3.84 (1H, m), 5.02 (1H, d, J = 7.3 Hz), 7.61 (1H, d, J = 8.5 Hz), 7.87 (1H, dd, J = 8.2, 2.1 Hz), 8.56 (1H, d, J = 2.4 Hz). MS (ESI$^+$): 485 [M + H]+ |

TABLE 68

| Example | Structure | Instrumental Data |
|---|---|---|
| 1-8 | 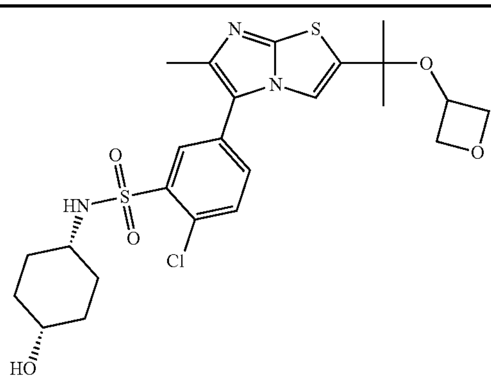 | $^1$H-NMR (400 MHz, CDCl$_3$) δ: 1.15 (1H, d, J = 6.1 Hz), 1.56-1.76 (14H, m), 2.45 (3H, s), 3.28-3.35 (1H, m), 3.83-3.88 (1H, m), 4.61-4.71 (5H, m), 5.05 (1H, d, J = 7.3 Hz), 7.24 (1H, s), 7.56 (1H, dd, J = 8.2, 2.1 Hz), 7.66 (1H, d, J = 7.9 Hz), 8.18 (1H, d, J = 1.8 Hz). MS (ESI$^+$): 540 [M + H]$^+$ |
| 1-9 | 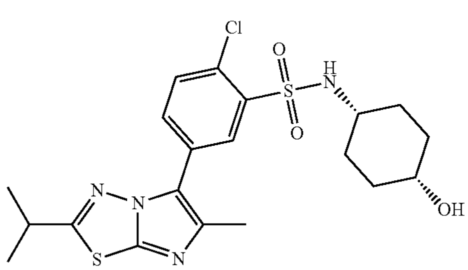 [SMILES: Cc1nc2sc(C(C)C)nn2c1-c1ccc(Cl)c(S(=O)(=O)N[C@H]2CC[C@@H](O)CC2)c1] | $^1$H-NMR (400 MHz, DMSO-d$_6$) δ: 1.25-1.43 (10H, m), 1.49-1.58 (2H, m), 1.58-1.70 (2H, m), 2.46 (3H, s), 3.02-3.13 (1H, m), 3.37-3.46 (1H, m), 3.56-3.62 (1H, m), 4.34 (1H, d, J = 2.4 Hz), 7.79 (1H, d, J = 8.5 Hz), 7.93 (1H, dd, J = 8.5, 1.8 Hz), 7.96 (1H, d, J = 6.1 Hz), 8.42 (1H, d, J = 1.8 |

TABLE 68-continued
| Example | Structure | Instrumental Data |
|---|---|---|
| | | Hz). MS (ESI⁺): 469 [M + H]⁺ |
| 1-10 | 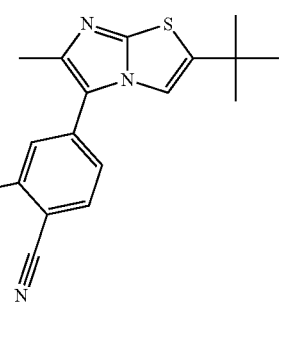 | ¹H-NMR (400 MHz, DMSO-d₆) δ: 1.33-1.47 (13H, m), 1.50-1.70 (4H, m), 2.38 (3H, s), 3.21-3.30 (1H, m), 3.59-3.65 (1H, m), 4.37 (1H, d, J = 2.7 Hz), 7.66 (1H, s), 7.93 (1H, dd, J = 8.2, 1.8 Hz), 8.01 (1H, d, J = 1.8 Hz), 8.15 (1H, d, J = 8.2 Hz), 8.24 (1H, s). MS (ESI⁺): 473 [M + H]⁺ |
| 1-11 | 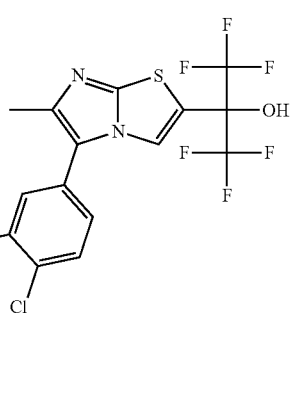 | ¹H-NMR (400 MHz, CDCl₃) δ: 1.61-1.73 (8H, m), 2.45 (3H, s), 3.28-3.33 (1H, m), 3.85-3.90 (1H, m), 5.03 (1H, d, J = 6.7 Hz), 7.55 (1H, dd, J = 8.2, 2.1 Hz), 7.66-7.69 (2H, m), 8.17 (1H, d, J = 2.4 Hz). MS (ESI⁺): 592 [M + H]⁺ |
| 1-12 | 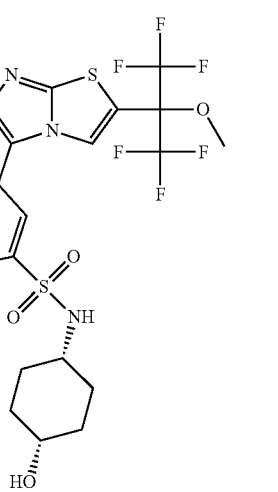 | ¹H-NMR (400 MHz, CDCl₃) δ: 1.28 (1H, d, J = 3.6 Hz), 1.51-1.67 (8H, m), 2.41 (3H, s), 3.30 (1H, br), 3.69 (3H, s), 3.84 (1H, br), 4.07 (3H, s), 4.94 (1H, d, J = 7.3 Hz), 7.20 (1H, d, J = 8.5 Hz), 7.52 (1H, s), 7.57 (1H, dd, J = 8.5, 2.4 Hz), 7.99 (1H, d, J = 2.4 Hz). MS (ESI⁺): 602 [M + H]⁺ |

TABLE 68-continued

| Example | Structure | Instrumental Data |
|---------|-----------|-------------------|
| 1-13 | 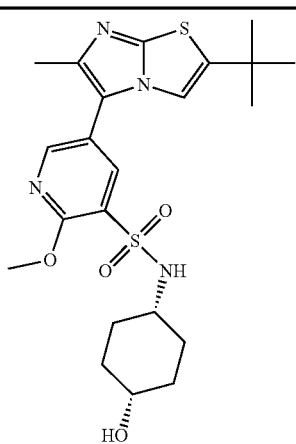 | $^1$H-NMR (400 MHz, DMSO-d$_6$) δ: 1.29-1.41 (13H, m), 1.49-1.68 (4H, m), 2.25 (3H, s), 3.10-3.20 (1H, m), 3.58-3.64 (1H, m), 4.06 (3H, s), 4.34 (1H, d, J = 3.0 Hz), 7.55 (1H, s), 7.70 (1H, q, J = 7.1 Hz), 8.07 (1H, d, J = 2.4 Hz), 8.56 (1H, d, J = 2.4 Hz). MS (ESI$^+$): 479 [M + H]$^+$ |

TABLE 69

| Example | Structure | Instrumental Data |
|---------|-----------|-------------------|
| 1-14 | 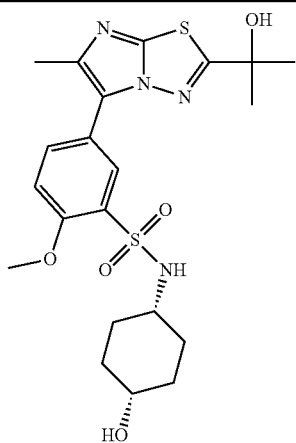 | $^1$H-NMR (400 MHz, CDCl$_3$) δ: 1.29 (1H, br), 1.56-1.65 (8H, m), 1.75 (6H, s), 2.53 (3H, s), 2.58 (1H, s), 3.28 (1H, br), 3.81 (1H, br), 4.05 (3H, s), 4.95 (1H, d, J = 7.3 Hz), 7.15 (1H, d, J = 8.5 Hz), 7.87 (1H, dd, J = 8.5, 2.4 Hz), 8.31 (1H, d, J = 2.4 Hz). MS (ESI$^+$): 481 [M + H]$^+$ |
| 1-15 | 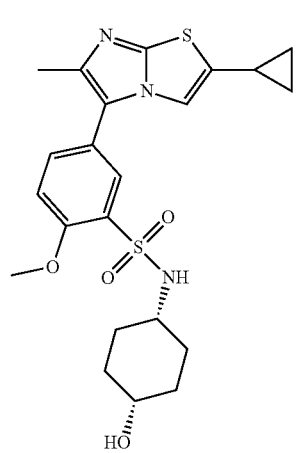 [SMILES: COc1ccc(-c2c(C)nc3sc(C4CC4)cn23)cc1S(=O)(=O)N[C@H]1CC[C@@H](O)CC1] | $^1$H-NMR (400 MHz, CDCl$_3$) δ: 1.11-1.28 (5H, m), 1.54-1.66 (8H, m), 2.23-2.30 (1H, m), 2.50 (3H, s), 3.28 (1H, br), 3.82 (1H, br), 4.04 (3H, s), 4.94 (1H, d, J = 7.3 Hz), 7.14 (1H, d, J = 9.1 Hz), 7.88 (1H, dd, J = 8.5, 2.4 Hz), 8.26 (1H, d, J = 2.4 Hz). MS (ESI$^+$): 463 [M + H]$^+$ |

TABLE 69-continued
| Example | Structure | Instrumental Data |
|---|---|---|
| 1-16 | 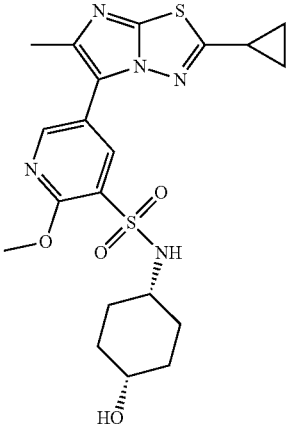 [SMILES: COc1ncc(-c2c(C)nc3sc(C4CC4)nn23)cc1S(=O)(=O)N[C@H]1CC[C@@H](O)CC1] | ¹H-NMR (400 MHz, CDCl₃) δ: 1.12-1.28 (5H, m), 1.53-1.69 (8H, m), 2.23-2.29 (1H, m), 2.51 (3H, s), 3.29 (1H, br), 3.84 (1H, br), 4.17 (3H, s), 4.98 (1H, d, J = 7.3 Hz), 8.55 (1H, d, J = 1.8 Hz), 8.67 (1H, d, J = 2.4 Hz). MS (ESI⁺): 464 [M + H]⁺ |
| 1-17 | 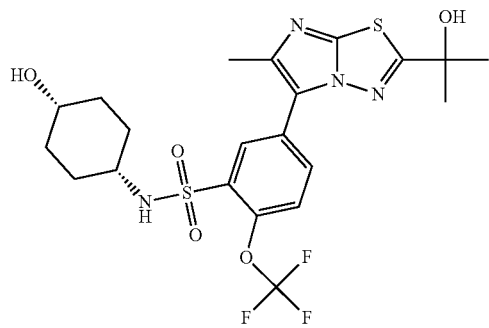 [SMILES: Cc1nc2sc(C(C)(C)O)nn2c1-c1ccc(OC(F)(F)F)c(S(=O)(=O)N[C@H]2CC[C@@H](O)CC2)c1] | ¹H-NMR (400 MHz, DMSO-d₆) δ: 1.27-1.42 (4H, m), 1.51-1.69 (10H, m), 2.46 (3H, s), 3.11-3.22 (1H, m), 3.59-3.65 (1H, m), 4.35 (1H, d, J = 2.7 Hz), 6.52 (1H, s), 7.68-7.73 (1H, m), 7.98 (1H, br s), 8.05 (1H, dd, J = 8.6, 2.4 Hz), 8.32 (1H, d, J = 2.4 Hz). MS (ESI⁺): 535 [M + H]⁺ |
| 1-18 | 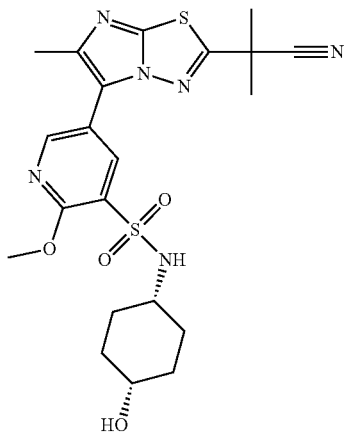 [SMILES: COc1ncc(-c2c(C)nc3sc(C(C)(C)C#N)nn23)cc1S(=O)(=O)N[C@H]1CC[C@@H](O)CC1] | ¹H-NMR (400 MHz, CDCl₃) δ: 1.27 (1H, d, J = 3.6 Hz), 1.55-1.68 (8H, m), 1.93 (6H, s), 2.55 (3H, s), 3.31 (1H, br), 3.65 (1H, br), 4.18 (3H, s), 4.98 (1H, d, J = 7.3 Hz), 8.55 (1H, d, J = 2.4 Hz), 8.68 (1H, d, J = 2.4 Hz). MS (ESI⁺): 491 [M + H]⁺ |
| 1-19 | 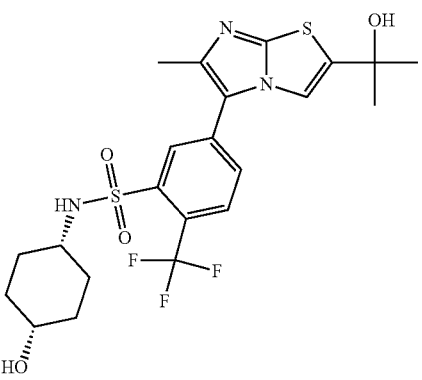 [SMILES: Cc1nc2sc(C(C)(C)O)cn2c1-c1ccc(C(F)(F)F)c(S(=O)(=O)N[C@H]2CC[C@@H](O)CC2)c1] | ¹H-NMR (400 MHz, DMSO-d₆) δ: 1.31-1.46 (4H, m), 1.48-1.59 (8H, m), 1.59-1.72 (2H, m), 2.38 (3H, s), 3.15-3.23 (1H, m), 3.57-3.65 (1H, m), 4.36 (1H, d, J = 3.0 Hz), 5.82 (1H, s), 7.76 (1H, s), 7.91 (1H, d, J = 8.2 Hz), 8.04 (1H, d, J = 8.5 Hz), 8.07 (1H, d, J = 6.1 Hz), 8.13 (1H, d, J = 1.5 Hz). MS (ESI⁺): 518 [M + H]⁺ |

TABLE 70

| Example | Structure | Instrumental Data |
|---|---|---|
| 1-20 | 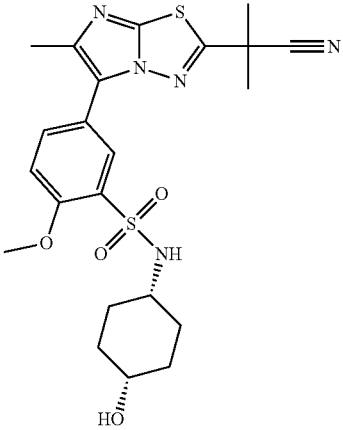 [SMILES: COc1ccc(-c2c(C)nc3sc(C(C)(C)C#N)nn23)cc1S(=O)(=O)N[C@H]1CC[C@@H](O)CC1] | $^1$H-NMR (400 MHz, CDCl$_3$) δ: 1.25-1.27 (1H, br m), 1.54-1.66 (8H, m), 1.93 (6H, s), 2.54 (3H, s), 3.29 (1H, br), 3.82 (1H, br), 4.05 (3H, s), 4.94 (1H, d, J = 7.9 Hz), 7.17 (1H, d, J = 9.1 Hz), 7.89 (1H, dd, J = 8.5, 2.4 Hz), 8.29 (1H, d, J = 2.4 Hz). MS (ESI$^-$): 488 [M – H]$^-$ |
| 1-21 | 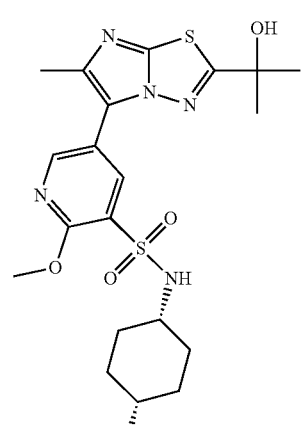 | $^1$H-NMR (400 MHz, DMSO-d$_6$) δ: 1.28-1.39 (4H, m), 1.50-1.67 (10H, m), 2.42 (3H, s), 3.07-3.16 (1H, m), 3.57-3.63 (1H, m), 4.06 (3H, s), 4.33 (1H, d, J = 2.7 Hz), 6.49 (1H, s), 7.71 (1H, d, J = 6.4 Hz), 8.43 (1H, d, J = 2.4 Hz), 8.70 (1H, d, J = 2.4 Hz). MS (ESI$^+$): 482 [M + H]$^+$ |
| 1-22 | 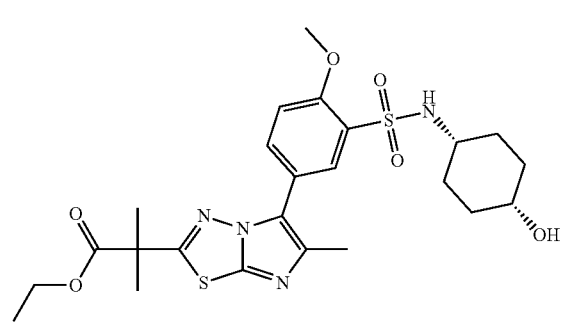 [SMILES: CCOC(=O)C(C)(C)c1nn2c(-c3ccc(OC)c(S(=O)(=O)N[C@H]4CC[C@@H](O)CC4)c3)c(C)nc2s1] | $^1$H-NMR (400 MHz, CDCl$_3$) δ: 1.25-1.29 (4H, m), 1.55-1.65 (8H, m), 1.75 (6H, s), 2.53 (3H, s), 3.28 (1H, br), 3.82 (1H, br), 4.05 (3H, s), 4.23 (2H, q, J = 7.1 Hz), 4.93 (1H, d, J = 7.3 Hz), 7.14 (1H, d, J = 9.1 Hz), 7.89 (1H, dd, J = 9.1, 2.4 Hz), 8.32 (1H, d, J = 2.4 Hz). MS (ESI$^+$): 537 [M + H]$^+$ |
| 1-23 | 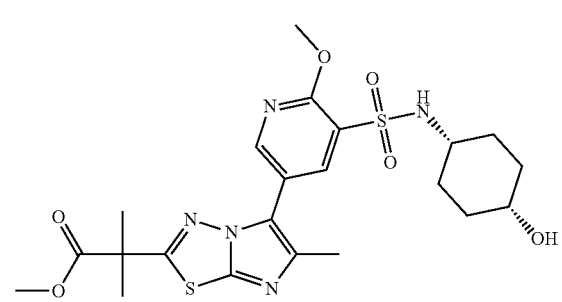 [SMILES: COC(=O)C(C)(C)c1nn2c(-c3cnc(OC)c(S(=O)(=O)N[C@H]4CC[C@@H](O)CC4)c3)c(C)nc2s1] | $^1$H-NMR (400 MHz, CDCl$_3$) δ: 1.26 (1H, br), 1.55-1.68 (8H, m), 1.75 (6H, s), 2.54 (3H, s), 3.30 (1H, br), 3.77 (3H, s), 3.85 (1H, br), 4.17 (3H, s), 4.97 (1H, d, J = 7.3 Hz), 8.59 (1H, d, J = 2.4 Hz), 8.68 (1H, d, J = 2.4 Hz). MS (ESI$^+$): 524 [M + H]$^+$ |

TABLE 70-continued

| Example | Structure | Instrumental Data |
|---------|-----------|-------------------|
| 1-24 | 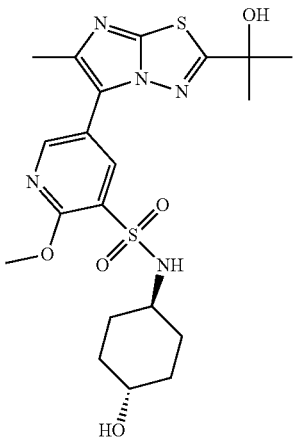 [SMILES: COc1ncc(-c2c(C)nc3sc(C(C)(C)O)nn23)cc1S(=O)(=O)N[C@H]1CC[C@H](O)CC1] | ¹H-NMR (400 MHz, DMSO-d$_6$) δ: 1.00-1.13 (2H, m), 1.18-1.32 (2H, m), 1.56-1.65 (8H, m), 1.68-1.77 (2H, m), 2.43 (3H, s), 2.99-3.11 (1H, m), 3.22-3.36 (1H, m), 4.05 (3H, s), 4.51 (1H, d, J = 4.2 Hz), 6.50 (1H, s), 7.70 (1H, br s), 8.44 (1H, d, J = 2.4 Hz), 8.70 (1H, d, J = 2.4 Hz). MS (ESI$^+$) 482 [M + H]$^+$ |
| 1-25 | 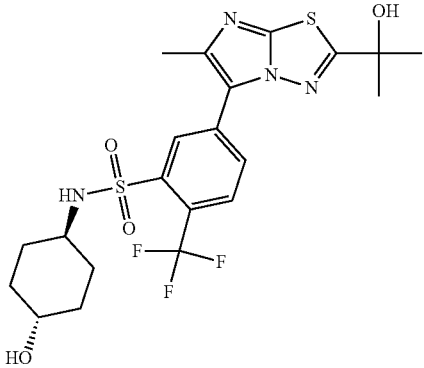 [SMILES: Cc1nc2sc(C(C)(C)O)nn2c1-c1ccc(C(F)(F)F)c(S(=O)(=O)N[C@H]2CC[C@H](O)CC2)c1] | ¹H-NMR (400 MHz, DMSO-d$_6$) δ: 1.00-1.12 (2H, m), 1.22-1.34 (2H, m), 1.58-1.66 (8H, m), 1.68-1.75 (2H, m), 2.52 (3H, s), 3.03-3.12 (1H, m), 3.23-3.31 (1H, m), 4.51 (1H, d, J = 4.2 Hz), 6.56 (1H, s), 7.92 (1H, s), 8.08 (1H, d, J = 8.2 Hz), 8.10-8.14 (1H, m), 8.57 (1H, d, J = 1.5 Hz). MS (ESI$^+$): 519 [M + H]$^+$ |

TABLE 71

| Example | Structure | Instrumental Data |
|---------|-----------|-------------------|
| 1-26 | 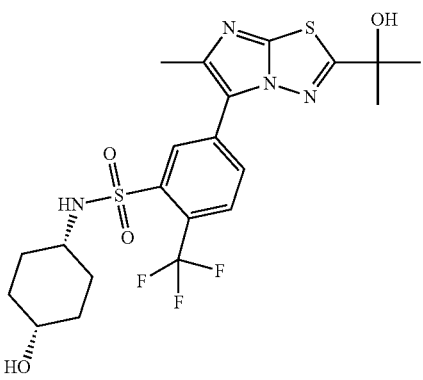 [SMILES: Cc1nc2sc(C(C)(C)O)nn2c1-c1ccc(C(F)(F)F)c(S(=O)(=O)N[C@H]2CC[C@@H](O)CC2)c1] | ¹H-NMR (400 MHz, DMSO-d$_6$) δ: 1.27-1.41 (4H, m), 1.49-1.58 (2H, m), 1.58-1.70 (8H, m), 2.52 (3H, s), 3.09-3.18 (1H, m), 3.57-3.63 (1H, m), 4.34 (1H, d, J = 3.0 Hz), 6.55 (1H, s), 7.98 (1H, d, J = 6.7 Hz), 8.08 (1H, d, J = 8.5 Hz), 8.13 (1H, dd, J = 8.5, 1.5 Hz), 8.55 (1H, d, J = 1.5 Hz). MS (ESI$^+$) 519 [M + H]$^+$ |

TABLE 71-continued

| Example | Structure | Instrumental Data |
|---|---|---|
| 1-27 | 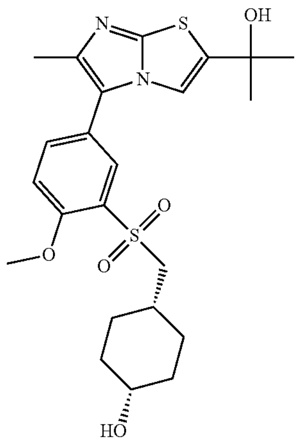 [SMILES: COc1ccc(-c2c(C)nc3sc(C(C)(C)O)cn23)cc1S(=O)(=O)C[C@H]1CC[C@@H](O)CC1] | ¹H-NMR (400 MHz, DMSO-d₆) δ: 1.33-1.55 (14H, m), 1.80-1.89 (1H, m), 2.27 (3H, s), 3.37 (2H, d, J = 6.4 Hz), 3.62-3.68 (1H, m), 4.01 (3H, s), 4.33 (1H, d, J = 3.1 Hz), 5.76 (1H, s), 7.45 (1H, d, J = 8.5 Hz), 7.53 (1H, s), 7.77 (1H, d, J = 2.2 Hz), 7.83 (1H, dd, J = 8.5, 2.2 Hz). MS (ESI⁺) 479 [M + H]⁺ |
| 1-28 | 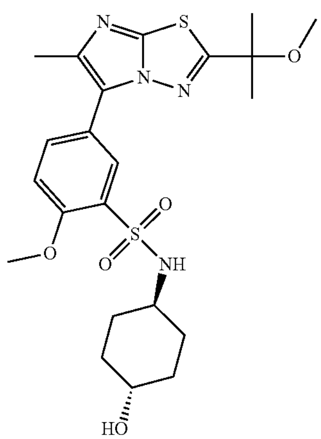 | ¹H-NMR (400 MHz, DMSO-d₆) δ: 0.98-1.10 (2H, m), 1.17-1.29 (2H, m), 1.54-1.64 (8H, m), 1.67-1.75 (2H, m), 2.41 (3H, s), 2.92-3.03 (1H, m), 3.23 (3H, s), 3.24-3.31 (1H, m), 3.96 (3H, s), 4.48 (1H, d, J = 4.2 Hz), 7.32 (1H, d, J = 7.3 Hz), 7.37 (1H, d, J = 8.8 Hz), 7.91 (1H, dd, J = 8.5, 2.4 Hz), 8.13 (1H, d, J = 2.4 Hz). MS (ESI⁺) 495 [M + H]⁺ |
| 1-29 | 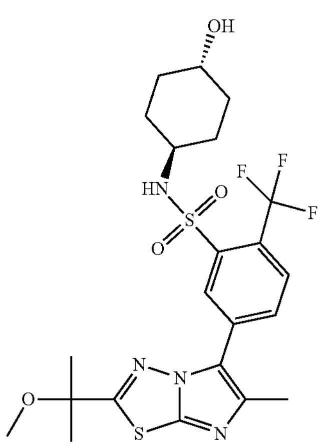 [SMILES: COC(C)(C)c1nn2c(-c3ccc(C(F)(F)F)c(S(=O)(=O)N[C@H]4CC[C@H](O)CC4)c3)c(C)nc2s1] | ¹H-NMR (400 MHz, DMSO-d₆) δ: 1.00-1.12 (2H, m), 1.22-1.35 (2H, m), 1.59-1.67 (8H, m), 1.68-1.76 (2H, m), 2.53 (3H, s), 3.03-3.13 (1H, m), 3.23-3.32 (4H, m), 4.51 (1H, d, J = 4.2 Hz), 7.92 (1H, s), 8.09 (1H, d, J = 8.2 Hz), 8.12-8.17 (1H, m), 8.59 (1H, d, J = 1.5 Hz). MS (ESI⁺): 533 [M + H]⁺ |

TABLE 71-continued
| Example | Structure | Instrumental Data |
|---|---|---|
| 1-30 | 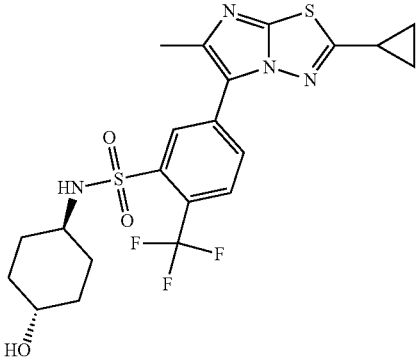 [SMILES: Cc1nc2sc(C3CC3)nn2c1-c1ccc(C(F)(F)F)c(S(=O)(=O)N[C@H]2CC[C@H](O)CC2)c1] | ¹H-NMR (400 MHz, DMSO-$d_6$) δ: 1.01-1.17 (4H, m), 1.22-1.36 (4H, m), 1.61-1.77 (4H, m), 2.47-2.56 (4H, m), 3.03-3.14 (1H, m), 3.23-3.35 (1H, m), 4.51 (1H, d, J = 4.2 Hz), 7.95 (1H, d, J = 6.4 Hz), 8.07 (1H, d, J = 8.5 Hz), 8.08-8.13 (1H, m), 8.54 (1H, d, J = 1.2 Hz). MS (ESI⁺): 501 [M + H]⁺ |
| 1-31 | 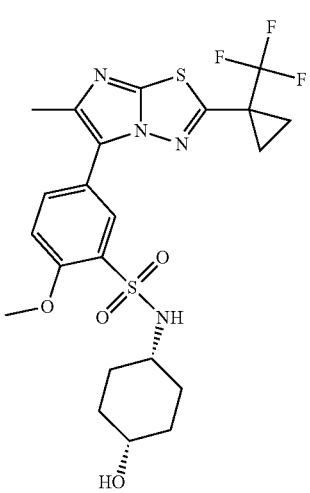 [SMILES: COc1ccc(-c2c(C)nc3sc(C4(C(F)(F)F)CC4)nn23)cc1S(=O)(=O)N[C@H]1CC[C@@H](O)CC1] | ¹H-NMR (400 MHz, CDCl₃) δ: 1.26 (1H, br s), 1.53-1.68 (12H, m), 2.53 (3H, s), 3.25-3.31 (1H, m), 3.79-3.84 (1H, m), 4.05 (3H, s), 4.93 (1H, d, J = 7.9 Hz), 7.16 (1H, d, J = 8.5 Hz), 7.86 (1H, dd, J = 8.5, 2.4 Hz), 8.27 (1H, d, J = 2.4 Hz). MS (ESI⁺): 531 [M + H]⁺ |
TABLE 72
| Example | Structure | Instrumental Data |
|---|---|---|
| 1-32 | 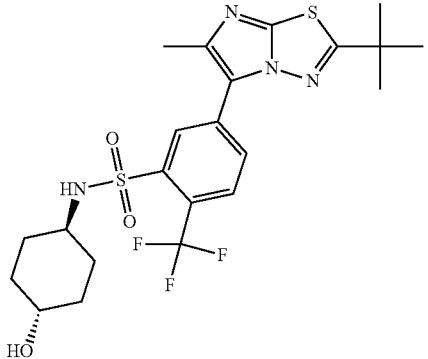 [SMILES: Cc1nc2sc(C(C)(C)C)nn2c1-c1ccc(C(F)(F)F)c(S(=O)(=O)N[C@H]2CC[C@H](O)CC2)c1] | ¹H-NMR (400 MHz, DMSO-$d_6$) δ: 0.99-1.11 (2H, m), 1.21-1.33 (2H, m), 1.48 (9H, s), 1.57-1.65 (2H, m), 1.67-1.76 (2H, m), 2.53 (3H, s), 3.03-3.13 (1H, m), 3.22-3.31 (1H, m), 4.50 (1H, d, J = 4.2 Hz), 7.87 (1H, s), 8.08 (1H, d, J = 8.5 Hz), 8.11-8.16 (1H, m), 8.63 (1H, d, J = 1.5 Hz). MS (ESI⁺): 517 [M + H]⁺ |

TABLE 72-continued
| Example | Structure | Instrumental Data |
| --- | --- | --- |
| 1-33 | 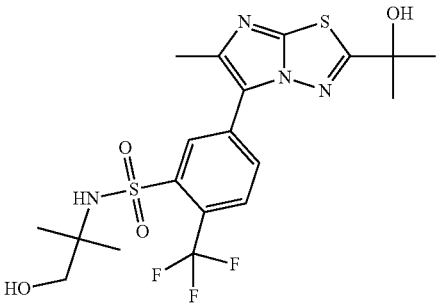 [SMILES: Cc1nc2sc(C(C)(C)O)nn2c1-c1ccc(C(F)(F)F)c(S(=O)(=O)NC(C)(C)CO)c1] | ¹H-NMR (400 MHz, DMSO-d₆) δ: 1.13 (6H, s), 1.61 (6H, s), 2.52 (3H, s), 3.29 (2H, s), 4.91 (1H, br s), 6.55 (1H, br s), 7.45 (1H, s), 8.06 (1H, d, J = 8.5 Hz), 8.09-8.13 (1H, m), 8.66 (1H, d, J = 1.5 Hz). MS (ESI⁺): 493 [M + H]⁺ |
| 1-34 | 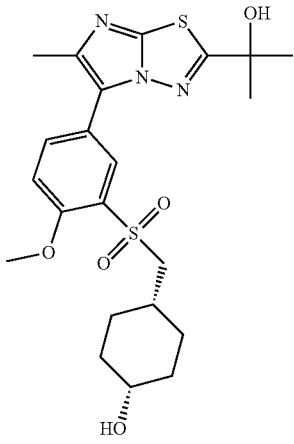 [SMILES: COc1ccc(-c2c(C)nc3sc(C(C)(C)O)nn23)cc1S(=O)(=O)C[C@H]1CC[C@@H](O)CC1] | ¹H-NMR (400 MHz, DMSO-d₆) δ: 1.32-1.52 (8H, m), 1.58 (6H, s), 1.75-1.87 (1H, m), 2.41 (3H, s), 3.36 (2H, d, J = 6.4 Hz), 3.61-3.66 (1H, m), 4.01 (3H, s), 4.32 (1H, d, J = 3.3 Hz), 6.47 (1H, s), 7.46 (1H, d, J = 8.8 Hz), 7.99 (1H, dd, J = 8.8, 2.4 Hz), 8.16 (1H, d, J = 2.4 Hz). MS (ESI⁺): 480 [M + H]⁺ |
| 1-35 | 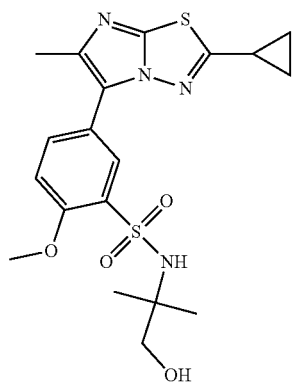 [SMILES: COc1ccc(-c2c(C)nc3sc(C4CC4)nn23)cc1S(=O)(=O)NC(C)(C)CO] | ¹H-NMR (400 MHz, CDCl₃) δ: 1.11-1.26 (10H, m), 2.21-2.27 (2H, m), 2.49 (3H, s), 3.49 (2H, d, J = 6.1 Hz), 4.05 (3H, s), 5.15 (1H, s), 7.14 (1H, d, J = 8.5 Hz), 7.86 (1H, dd, J = 8.5, 2.1 Hz), 8.27 (1H, d, J = 2.1 Hz). MS (ESI⁺): 437 [M + H]⁺ |
| 1-36 | 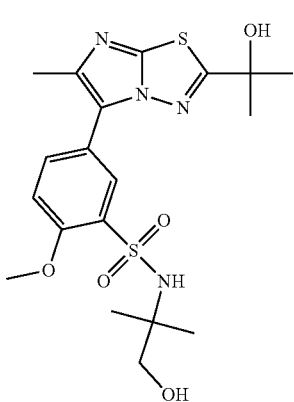 [SMILES: COc1ccc(-c2c(C)nc3sc(C(C)(C)O)nn23)cc1S(=O)(=O)NC(C)(C)CO] | ¹H-NMR (400 MHz, CDCl₃) δ: 1.15 (6H, s), 1.74 (6H, s), 2.34 (1H, s), 2.52 (3H, s), 2.59 (1H, s), 3.50 (2H, d, J = 6.7 Hz), 4.06 (3H, s), 5.13 (1H, s), 7.15 (1H, d, J = 8.5 Hz), 7.84 (1H, dd, J = 8.5, 2.4 Hz), 8.33 (1H, d, J = 2.4 Hz). MS (ESI⁺): 455 [M + H]⁺ |

TABLE 72-continued

| Example | Structure | Instrumental Data |
|---|---|---|
| 1-37 | 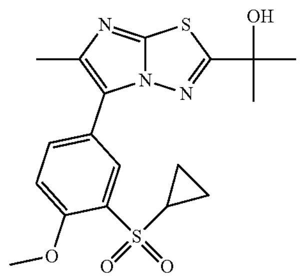 [SMILES: COc1ccc(-c2c(C)nc3sc(C(C)(C)O)nn23)cc1S(=O)(=O)C1CC1] | ¹H-NMR (400 MHz, DMSO-d₆) δ: 1.02-1.12 (4H, m), 1.58 (6H, s), 2.41 (3H, s), 3.03-3.12 (1H, m), 4.02 (3H, s), 6.46 (1H, s), 7.48 (1H, d, J = 8.7 Hz), 7.98 (1H, dd, J = 8.7, 2.2 Hz), 8.08 (1H, d, J = 2.2 Hz). MS (ESI⁺): 408 [M + H]⁺ |

TABLE 73

| Example | Structure | Instrumental Data |
|---|---|---|
| 1-38 | 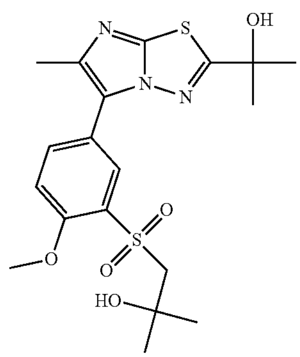 [SMILES: COc1ccc(-c2c(C)nc3sc(C(C)(C)O)nn23)cc1S(=O)(=O)CC(C)(C)O] | ¹H-NMR (400 MHz, DMSO-d₆) δ: 1.24 (6H, s), 1.58 (6H, s), 2.41 (3H, s), 3.56 (2H, s), 4.01 (3H, s), 4.80 (1H, s), 6.47 (1H, s), 7.44 (1H, d, J = 9.0 Hz), 7.97 (1H, dd, J = 9.0, 2.3 Hz), 8.16 (1H, d, J = 2.3 Hz). MS (ESI⁺): 440 [M + H]⁺ |
| 1-39 | 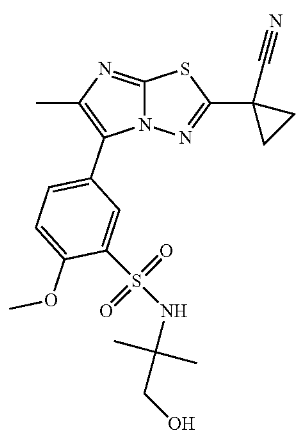 [SMILES: COc1ccc(-c2c(C)nc3sc(C4(C#N)CC4)nn23)cc1S(=O)(=O)NC(C)(C)CO] | ¹H-NMR (400 MHz, CDCl₃) δ: 1.15 (6H, s), 1.94-1.98 (4H, m), 2.24 (1H, t, J = 6.4 Hz), 2.51 (3H, s), 3.48 (2H, d, J = 6.1 Hz), 4.06 (3H, s), 5.16 (1H, s), 7.15 (1H, d, J = 8.7 Hz), 7.78 (1H, dd, J = 8.7, 2.3 Hz), 8.26 (1H, d, J = 2.3 Hz). MS (ESI+): 462 [M + H]+ |
| 1-40 | 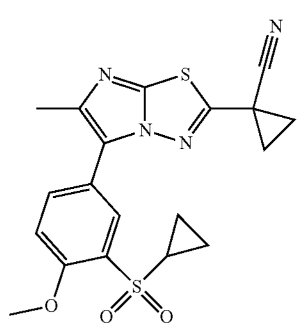 [SMILES: COc1ccc(-c2c(C)nc3sc(C4(C#N)CC4)nn23)cc1S(=O)(=O)C1CC1] | ¹H-NMR (400 MHz, DMSO-d₆) δ: 1.02-1.09 (4H, m), 1.89 (2H, dd, J = 8.5, 5.1 Hz), 2.12 (2H, dd, J = 8.5, 5.1 Hz), 2.41 (3H, s), 3.03-3.12 (1H, m), 4.02 (3H, s), 7.48 (1H, d, J = 8.7 Hz), 7.97 (1H, dd, J = 8.7, 2.4 Hz), 8.03 (1H, d, J = 2.4 Hz). MS (ESI⁺): 415 [M + H]⁺ |

TABLE 73-continued
| Example | Structure | Instrumental Data |
|---|---|---|
| 1-41 | 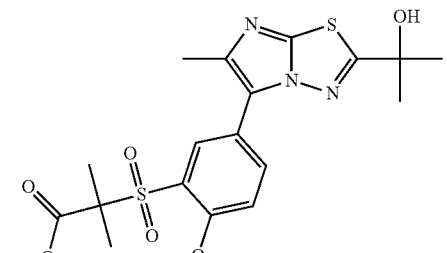 | $^1$H-NMR (400 MHz, DMSO-$d_6$) δ: 1.54 (6H, s), 1.58 (6H, s), 2.42 (3H, s), 3.62 (3H, s), 3.91 (3H, s), 6.48 (1H, s), 7.44 (1H, d, J = 8.9 Hz), 8.02 (1H, dd, J = 8.9, 2 4 Hz), 8.10 (1H, d, J = 2.4 Hz). MS (ESI$^+$): 468 [M + H]$^+$ |
| 1-42 | 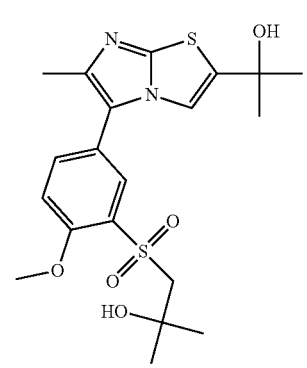 [SMILES: COc1ccc(-c2c(C)nc3sc(C(C)(C)O)cn23)cc1S(=O)(=O)CC(C)(C)O] | $^1$H-NMR (400 MHz, DMSO-$d_6$) δ: 1.26 (6H, s), 1.51 (6H, s), 2.28 (3H, s), 3.56 (2H, s), 4.01 (3H, s), 4.80 (1H, s), 5.75 (1H, s), 7.42 (1H, d, J = 8.5 Hz), 7.52 (1H, s), 7.77 (1H, d, J = 2.4 Hz), 7.80 (1H, dd, J = 8.5, 2.4 Hz). MS (ESI$^+$): 439 [M + H]$^+$ |
| 1-43 | 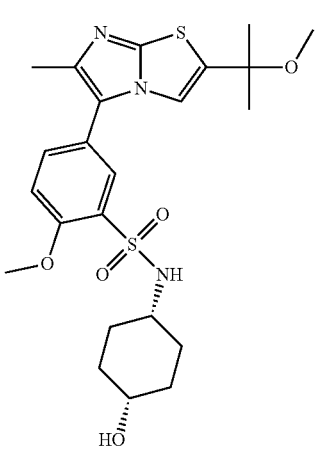 | $^1$H-NMR (400 MHz, CDCl$_3$) δ: 1.32 (1H, d, J = 3.6 Hz), 1.56-1.63 (14H, m), 2.39 (3H, s), 3.19 (3H, s), 3.30 (1H, br), 3.83 (1H, br), 4.06 (3H, s), 4.95 (1H, d, J = 7.3 Hz), 7.16 (2H, t, J = 4.2 Hz), 7.58 (1H, dd, J = 8.5, 2.4 Hz), 7.99 (1H, d, J = 1.8 Hz). MS (ESI$^+$): 494 [M + H]$^+$ |

TABLE 74
| Example | Structure | Instrumental Data |
|---|---|---|
| 1-44 | 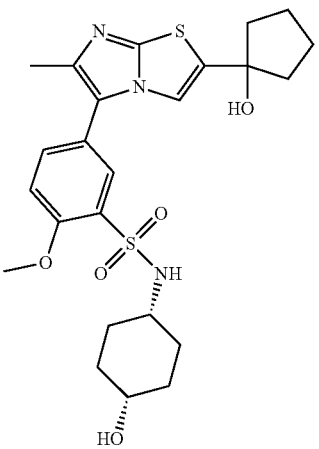 [SMILES: COc1ccc(-c2c(C)nc3sc(C4(O)CCCC4)cn23)cc1S(=O)(=O)N[C@H]1CC[C@@H](O)CC1] | ¹H-NMR (400 MHz, CDCl₃) δ: 1.31 (1H, d, J = 3.7 Hz), 1.53-1.67 (8H, m), 1.82-2.05 (8H, m), 2.39 (3H, s), 3.29 (1H, br), 3.83 (1H, br), 4.05 (3H, s), 4.95 (1H, d, J = 7.3 Hz), 7.15 (1H, d, J = 8.6 Hz), 7.30 (1H, s), 7.57 (1H, dd, J = 8.6, 2.4 Hz), 7.98 (1H, d, J = 2.4 Hz). MS (ESI⁺): 506 [M + H]⁺ |
| 1-45 | 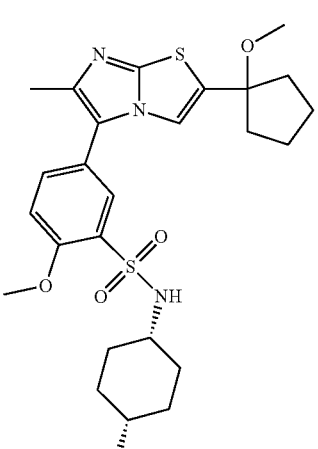 | ¹H-NMR (400 MHz, CDCl₃) δ: 1.30 (1H, d, J = 3.7 Hz), 1.51-1.64 (8H, m), 1.75-1.90 (6H, m), 2.10-2.20 (2H, m), 2.40 (3H, s), 3.14 (3H, s), 3.30 (1H, br), 3.83 (1H, br), 4.06 (3H, s), 4.95 (1H, d, J = 7.3 Hz), 7.16 (1H, d, J = 8.6 Hz), 7.20 (1H, s), 7.58 (1H, dd, J = 8.6, 2.4 Hz), 7.99 (1H, d, J = 2.4 Hz). MS (ESI⁺): 520 [M + H]⁺ |
| 1-46 | 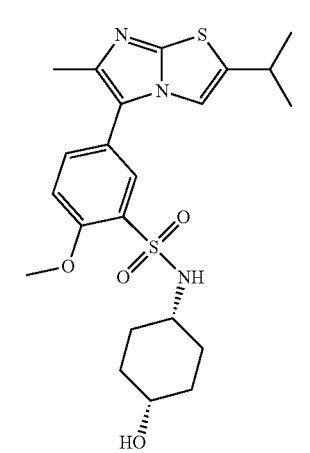 [SMILES: COc1ccc(-c2c(C)nc3sc(C(C)C)cn23)cc1S(=O)(=O)N[C@H]1CC[C@@H](O)CC1] | ¹H-NMR (400 MHz, CDCl₃) δ: 1.31 (1H, d, J = 3.7 Hz), 1.33 (6H, d, J = 6.7 Hz), 1.52-1.67 (8H, m), 2.39 (3H, s), 3.04-3.10 (1H, m), 3.29 (1H, br), 3.83 (1H, br), 4.05 (3H, s), 4.95 (1H, d, J = 7.3 Hz), 7.09 (1H, d, J = 1.2 Hz), 7.15 (1H, d, J = 8.6 Hz), 7.57 (1H, dd, J = 8.3, 2.1 Hz), 7.99 (1H, d, J = 2.4 Hz). MS (ESI⁺): 464 [M + H]⁺ |

TABLE 74-continued

| Example | Structure | Instrumental Data |
| --- | --- | --- |
| 1-47 | 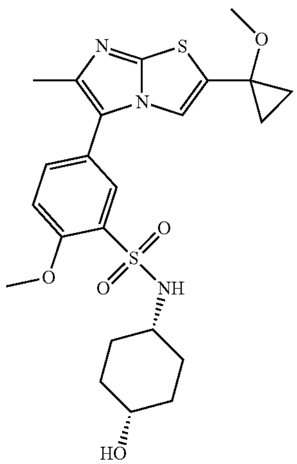 [SMILES: COc1ccc(-c2c(C)nc3sc(C4(OC)CC4)cn23)cc1S(=O)(=O)N[C@H]1CC[C@@H](O)CC1] | ¹H-NMR (400 MHz, CDCl₃) δ: 1.01 (2H, dd, J = 7.6, 5.8 Hz), 1.23 (2H, dd, J = 7.3, 5.4 Hz), 1.29 (1H, d, J = 3.0 Hz), 1.52-1.66 (8H, m), 2.40 (3H, s), 3.29-3.33 (4H, m), 3.84 (1H, br), 4.06 (3H, s), 4.95 (1H, d, J = 7.3 Hz), 7.16 (1H, d, J = 8.5 Hz), 7.23 (1H, s), 7.57 (1H, dd, J = 8.5, 2.4 Hz), 7.98 (1H, d, J = 2.4 Hz). MS (ESI⁺): 492 [M + H]⁺ |
| 1-48 | 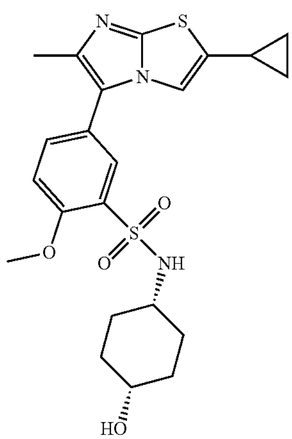 [SMILES: COc1ccc(-c2c(C)nc3sc(C4CC4)cn23)cc1S(=O)(=O)N[C@H]1CC[C@@H](O)CC1] | ¹H-NMR (400 MHz, CDCl₃) δ: 0.72-0.77 (2H, m), 0.97-1.02 (2H, m), 1.33 (1H, d, J = 3.6 Hz), 1.54-1.66 (8H, m), 1.93-2.00 (1H, m), 2.39 (3H, s), 3.29 (1H, br), 3.83 (1H, br), 4.05 (3H, s), 4.96 (1H, d, J = 7.3 Hz), 7.13 (1H, d, J = 1.2 Hz), 7.15 (1H, d, J = 8.5 Hz), 7.56 (1H, dd, J = 8.5, 2.4 Hz), 7.97 (1H, d, J = 2.4 Hz). MS (ESI⁺): 462 [M + H]⁺ |

TABLE 75

| Example | Structure | Instrumental Data |
| --- | --- | --- |
| 1-49 | 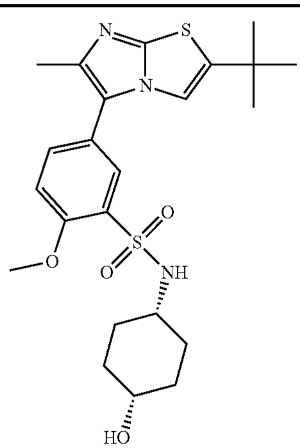 | ¹H-NMR (400 MHz, CDCl₃) δ: 1.30 (1H, d, J = 3.1 Hz), 1.37 (9H, s), 1.53-1.67 (8H, m), 2.39 (3H, s), 3.29 (1H, br), 3.83 (1H, br), 4.06 (3H, s), 4.94 (1H, d, J = 7.9 Hz), 7.04 (1H, s), 7.16 (1H, d, J = 8.6 Hz), 7.58 (1H, dd, J = 8.6, 2.4 Hz), 7.99 (1H, d, J = 2.4 Hz). MS (ESI⁺): 478 [M + H]⁺ |

TABLE 75-continued

| Example | Structure | Instrumental Data |
|---------|-----------|-------------------|
| 1-50 | 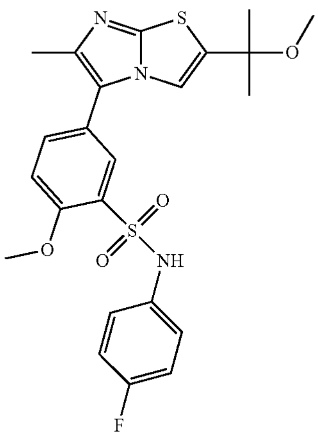 | ¹H-NMR (400 MHz, DMSO-d₆) δ: 1.51 (6H, s), 2.18 (3H, s), 3.08 (3H, s), 3.95 (3H, s), 7.03-7.07 (2H, m), 7.11-7.15 (2H, m), 7.32 (1H, d, J = 8.5 Hz), 7.51 (1H, s), 7.70 (1H, d, J = 2.4 Hz), 7.73 (1H, dd, J = 8.5, 2.4 Hz), 10.14 (1H, brs). MS (ESI⁺): 490 [M + H]⁺ |
| 1-51 | 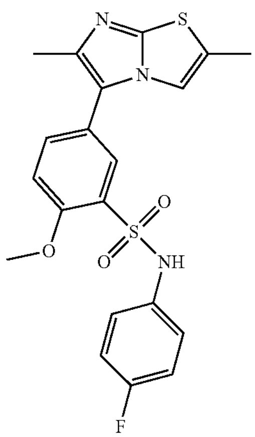 | ¹H-NMR (400 MHz, DMSO-d₆) δ: 2.18 (3H, s), 3.33 (3H, s), 3.94 (3H, s), 7,04-7.08 (2H, m), 7.11-7.15 (2H, m), 7.31 (1H, d, J = 8.5 Hz), 7.41 (1H, d, J = 1.8 Hz) 7.67-7.69 (2H, m), 10.13 (1H, s). MS (ESI⁺): 432 [M + H]⁺ |
| 1-52 | 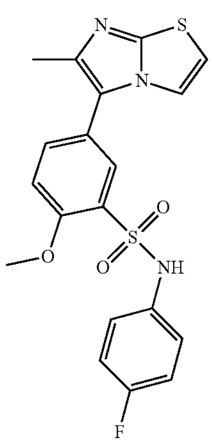 [SMILES: COc1ccc(-c2c(C)nc3sccn23)cc1S(=O)(=O)Nc1ccc(F)cc1] | ¹H-NMR (400 MHz, DMSO-d₆) δ: 2.21 (3H, s), 3.94 (3H, s), 7.04-7.09 (2H, m), 7.12-7.15 (2H, m), 7.27 (1H, d, J = 4.2 Hz), 7.32 (1H, d, J = 8.5 Hz), 7.64 (1H, d, J = 4.2 Hz), 7.69-7.72 (2H, m), 10.14 (1H, s). MS (ESI⁺): 418 [M + H]⁺ |

TABLE 75-continued

| Example | Structure | Instrumental Data |
|---|---|---|
| 1-53 | 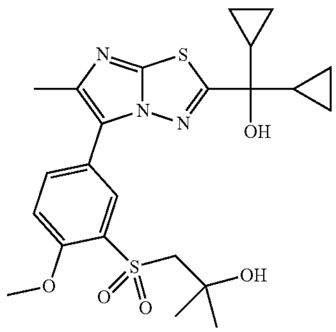 [SMILES: COc1ccc(-c2c(C)nc3sc(C(O)(C4CC4)C4CC4)nn23)cc1S(=O)(=O)CC(C)(C)O] | ¹H-NMR (400 MHz, DMSO-d₆) δ: 0.34-0.41 (2H, m), 0.46-0.62 (6H, m), 1.24 (6H, s), 1.29-1.37 (2H, m), 2.43 (3H, s), 3.56 (2H, s), 4.01 (3H, s), 4.81 (1H, s), 6.01 (1H, s), 7.44 (1H, d, J = 8.8 Hz), 7.97 (1H, dd, J = 8.8, 2.4 Hz), 8.25 (1H, d, J = 2.4 Hz). MS (ESI⁺): 492 [M + H]⁺ |

Reference Examples 51-1 to 51-3

A suitable compound of General Formula (4) and a suitable compound of General Formula (3) were used to perform reactions according to any of methods similar to Example 1-1 and the method described in Step A-2 or similar methods thereto to give the compounds of Reference Examples 51-1 to 51-3 shown below.

TABLE 76

| Reference Example | Structure | Instrumental Data |
|---|---|---|
| 51-1 | 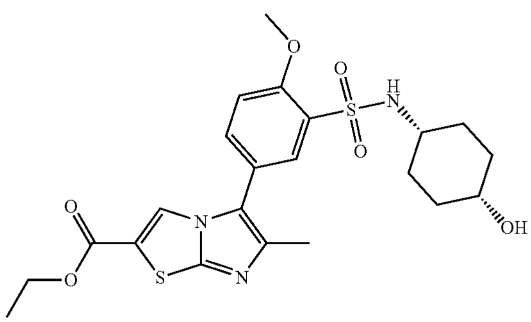 [SMILES: CCOC(=O)c1cn2c(-c3ccc(OC)c(S(=O)(=O)N[C@H]4CC[C@@H](O)CC4)c3)c(C)nc2s1] | ¹H-NMR (400 MHz, CDCl₃) δ: 1.34 (1H, d, J = 3.6 Hz), 1.39 (3H, t, J = 7.3 Hz), 1.53-1.67 (8H, m), 2.42 (3H, s), 3.31 (1H, br), 3.84 (1H, br), 4.07 (3H, s), 4.39 (2H, q, J = 7.3 Hz), 4.97 (1H, d, J = 7.3 Hz), 7.18 (1H, d, J = 8.5 Hz), 7.59 (1H, dd, J = 8.5, 2.4 Hz), 7.99 (1H, d, J = 2.4 Hz), 8.06 (1H, s). MS (FD⁺): 493 [M]⁺ |
| 51-2 | 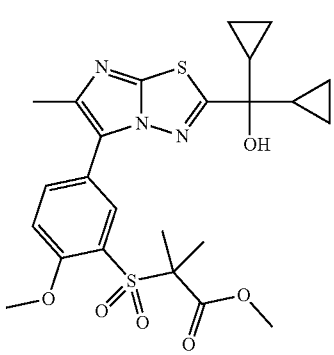 [SMILES: COC(=O)C(C)(C)S(=O)(=O)c1cc(-c2c(C)nc3sc(C(O)(C4CC4)C4CC4)nn23)ccc1OC] | ¹H-NMR (400 MHz, CDCl₃) δ: 0.47-0.52 (2H, m), 0.59-0.69 (6H, m), 1.33-1.40 (2H, m), 1.68 (6H, s), 2.40 (1H, s), 2.52 (3H, s), 3.71 (3H, s), 3.96 (3H, s), 7.15 (1H, d, J = 8.6 Hz), 7.91 (1H, dd, J = 8.6, 2.4 Hz), 8.32 (1H, d, J = 2.4 Hz). MS (ESI⁺): 520 [M + H]⁺ |

TABLE 76-continued

| Reference Example | Structure | Instrumental Data |
|---|---|---|
| 51-3 | 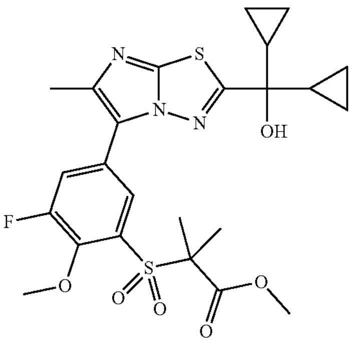 [SMILES: COC(=O)C(C)(C)S(=O)(=O)c1cc(-c2c(C)nc3sc(C(O)(C4CC4)C4CC4)nn23)cc(F)c1OC] | $^1$H-NMR (400 MHz, DMSO-$d_6$) δ: 0.34-0.41 (2H, m), 0.46-0.62 (6H, m), 1.30-1.38 (2H, m), 1.57 (6H, s), 2.48 (3H, s), 3.62 (3H, s), 3.93 (3H, d, J = 1.8 Hz), 6.05 (1H, s), 8.01 (1H, dd, J = 12.7, 2.4 Hz), 8.07-8.09 (1H, m). MS (ESI$^+$): 538 [M + H]$^+$ |

Example 2-1

[Formula 97]

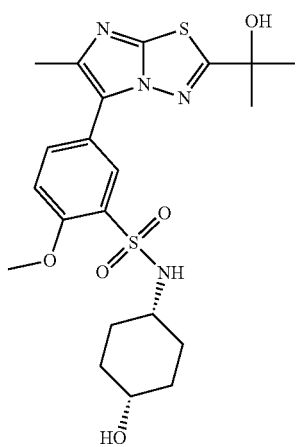

The compound obtained in Reference Example 6-38 (79.6 mg), hexamethyldistannane (107 mg), and tetrakis(triphenylphosphine)palladium (0) (25.2 mg) were suspended in 1,4-dioxane (2 mL), and the suspension was stirred with heating to reflux for 2 hours under an argon atmosphere. The reaction was filtered with Celite, and the solvent in the filtrate was distilled away under reduced pressure. The residue was dissolved in 1,4-dioxane (1 mL), and the compound obtained in Reference Example 26-18 (56.4 mg), tetrakis(triphenylphosphine)palladium (0), (25.2 mg), and copper (I) iodide (8.3 mg) were added to the solution. The mixture was stirred with heating to reflux under an argon atmosphere for 3.5 hours. The solvent in the reaction was distilled away under reduced pressure, and the residue was purified by silica gel column chromatography (ethyl acetate:methanol=20:1) to give the title compound (40.2 mg).

$^1$H-NMR (400 MHz, CDCl$_3$) δ: 1.27-1.30 (1H, m), 1.58-1.67 (8H, m), 1.80 (6H, s), 2.56 (1H, s), 2.74 (3H, s), 3.29-3.36 (1H, m), 3.82-3.87 (1H, m), 4.14 (3H, s), 4.94 (1H, d, J=7.9 Hz), 8.56 (1H, s), 8.70 (1H, s). MS (ESI$^+$): 482 [M+H]$^+$.

Examples 2-2 to 2-98

A suitable compound of General Formula (3) synthesized in reactions using a suitable compound of General Formula (2) according to any of methods similar to Reference Example 50-1 and the method described in Step A-1 or similar methods thereto was directly used as a crude product to perform reactions according to any of methods similar to Example 1-1 or Example 2-1, and the method described in Step A-2 or similar methods thereto to give the compounds of Examples 2-2 to 2-98 shown below.

TABLE 77

| Example | Structure | Instrumental Data |
|---|---|---|
| 2-2 | 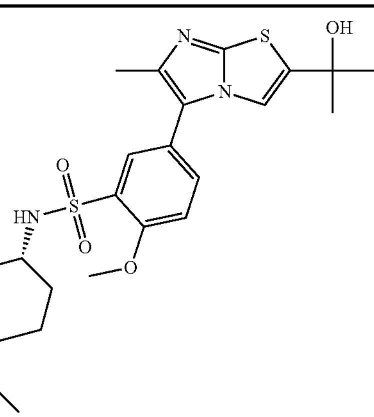 | $^1$H-NMR (400 MHz, DMSO-$d_6$) δ: 1.29-1.40 (4H, m), 1.43-1.54 (8H, m), 1.66-1.76 (2H, m), 2.27 (3H, s), 3.06-3.13 (1H, m), 3.15 (3H, s), 3.18-3.22 (1H, m), 3.96 (3H, s), 5.75 (1H, s), 7.35 (1H, d, J = 8.5 Hz), 7.39 (1H, d, J = 7.3 Hz), 7.52 (1H, s), 7.71 (1H, dd, J = 8.5, 2.4 Hz), 7.74 (1H, d, J =2.4 Hz). MS (ESI$^+$): 494 [M + H]$^+$ |

TABLE 77-continued
| Example | Structure | Instrumental Data |
|---------|-----------|-------------------|
| 2-3 | 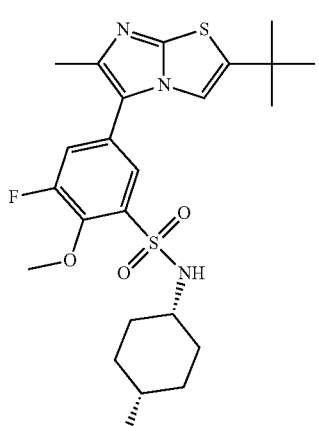 | $^1$H-NMR (400 MHz, DMSO-$d_6$) δ: 1.28-1.44 (13H, m), 1.50-1.70 (4H, m), 2.29 (3H, s), 3.10-3.18 (1H, m), 3.58-3.64 (1H, m), 4.03 (3H, d, J = 2.1 Hz), 4.34 (1H, d, J = 3.0 Hz), 7.54-7.56 (1H, m), 7.56 (1H, s), 7.67 (1H, d, J = 6.7 Hz), 7.75 (1H, dd, J = 12.3, 2.3 Hz). MS (ESI$^+$): 496 [M + H]$^+$ |
| 2-4 | 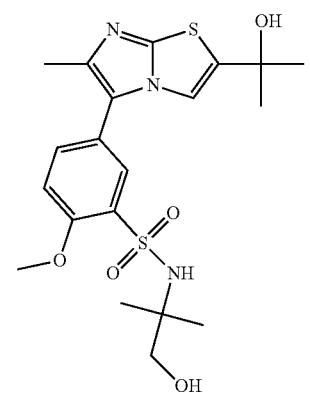 | $^1$H-NMR (400 MHz, DMSO-$d_6$) δ: 1.02 (6H, s), 1.51 (6H, s), 2.27 (3H, s), 3.19 (2H, d, J = 5.5 Hz), 3.97 (3H, s), 4.92 (1H, t, J = 5.5 Hz), 5.75 (1H, s), 6.74 (1H, s), 7.36 (1H, d, J = 8.7 Hz), 7.50 (1H, s), 7.72 (1H, dd, J = 8.7, 2.3 Hz), 7.75 (1H, d, J = 2.3 Hz). MS (ESI$^+$): 454 [M + H]$^+$ |
| 2-5 | 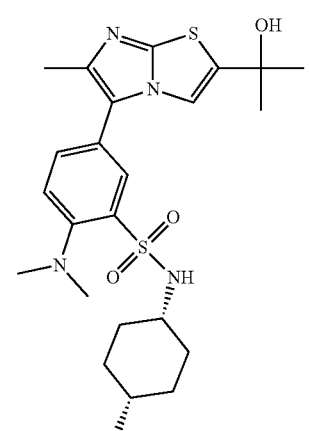 | $^1$H-NMR (400 MHz, DMSO-$d_6$) δ: 1.27-1.38 (4H, m), 1.45-1.64 (10H, m), 2.29 (3H, s), 2.76 (6H, s), 2.96-3.05 (1H, m), 3.54-3.60 (1H, m), 4.34 (1H, d, J = 3.0 Hz), 5.77 (1H, s), 7.13 (1H, d, J = 6.7 Hz), 7.59-7.63 (2H, m), 7.72 (1H, dd, J = 8.3, 2.4 Hz), 7.84 (1H, d, J = 2.4 Hz). MS (ESI$^+$): 493 [M + H]$^+$ |

TABLE 77-continued

| Example | Structure | Instrumental Data |
|---|---|---|
| 2-6 | 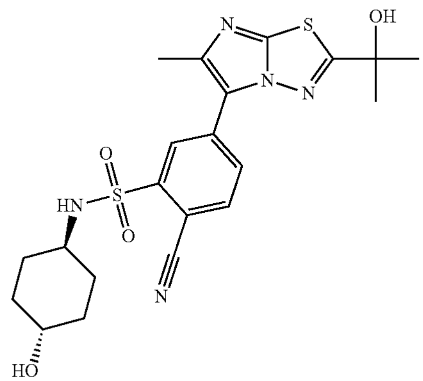 [SMILES: Cc1nc2sc(C(C)(C)O)nn2c1-c1ccc(C#N)c(S(=O)(=O)N[C@H]2CC[C@H](O)CC2)c1] | $^1$H-NMR (400 MHz, DMSO-$d_6$) δ: 1.02-1.15 (2H, m), 1.22-1.34 (2H, m), 1.57-1.78 (10H, m), 2.53 (3H, s), 3.09-3.18 (1H, m), 3.23-3.36 (1H, m), 4.52 (1H, d, J = 4.2 Hz), 6.57 (1H, s), 8.11 (1H, dd, J = 8.2, 1.7 Hz), 8.19 (1H, d, J = 8.2 Hz), 8.48 (1H, d, J = 1.7 Hz). MS (ESI$^+$): 476 [M + H]$^+$ |
| 2-7 | 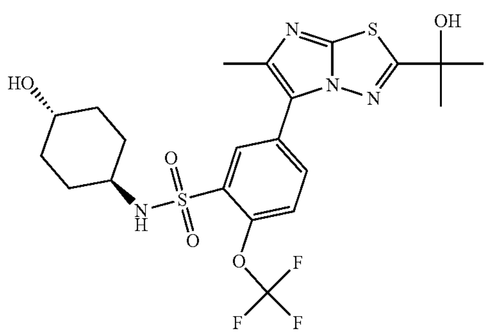 [SMILES: Cc1nc2sc(C(C)(C)O)nn2c1-c1ccc(OC(F)(F)F)c(S(=O)(=O)N[C@H]2CC[C@H](O)CC2)c1] | $^1$H-NMR (400 MHz, DMSO-$d_6$) δ: 1.01-1.12 (2H, m), 1.21-1.33 (2H, m), 1.57-1.67 (8H, m), 1.69-1.78 (2H, m), 2.47 (3H, s), 3.05-3.14 (1H, m), 3.23-3.35 (1H, m), 4.52 (1H, d, J = 4.2 Hz), 6.52 (1H, s), 7.68-7.73 (1H, m), 7.95 (1H, br s), 8.05 (1H, dd, J = 8.6, 2.4 Hz), 8.33 (1H, d, J = 2.4 Hz). MS (ESI$^+$): 535 [M + H]$^+$ |

TABLE 78

| Example | Structure | Instrumental Data |
|---|---|---|
| 2-8 | 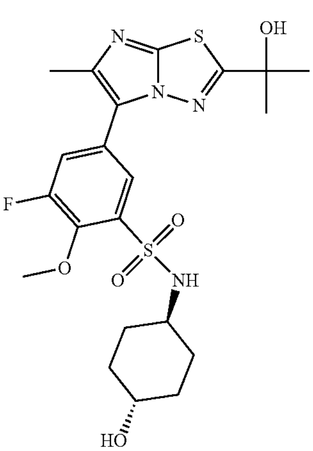 [SMILES: COc1c(F)cc(-c2c(C)nc3sc(C(C)(C)O)nn23)cc1S(=O)(=O)N[C@H]1CC[C@H](O)CC1] | $^1$H-NMR (400 MHz, DMSO-$d_6$) δ: 1.00-1.12 (2H, m), 1.20-1.32 (2H, m), 1.60 (6H, s), 1.61-1.69 (2H, m), 1.69-1.76 (2H, m), 2.44 (3H, s), 2.98-3.08 (1H, m), 3.23-3.35 (1H, m), 4.02 (3H, d, J = 2.1 Hz), 4.50 (1H, d, J = 4.2 Hz), 6.51 (1H, s), 7.61-7.66 (1H, m), 7.84 (1H, dd, J = 12.9, 2.3 Hz), 7.96-7.98 (1H, m). MS (ESI$^+$): 499 [M + H]$^+$ |

TABLE 78-continued

| Example | Structure | Instrumental Data |
|---|---|---|
| 2-9 | 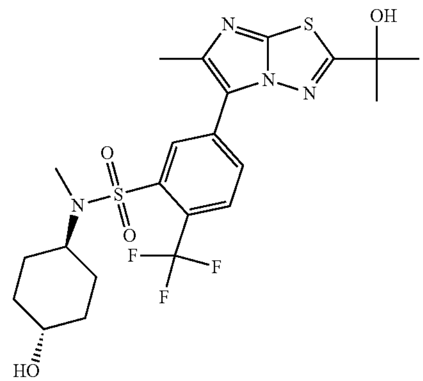 [SMILES: Cc1nc2sc(C(C)(C)O)nn2c1-c1ccc(C(F)(F)F)c(S(=O)(=O)N(C)[C@H]2CC[C@H](O)CC2)c1] | ¹H-NMR (400 MHz, DMSO-d₆) δ: 1.08-1.21 (2H, m), 1.36-1.45 (2H, m), 1.50-1.65 (8H, m), 1.76-1.85 (2H, m), 2.53 (3H, s), 2.81 (3H, s), 3.24-3.35 (1H, m), 3.62-3.73 (1H, m), 4.57 (1H, d, J = 4.5 Hz), 6.58 (1H, s), 8.10-8.16 (2H, m), 8.53-8.55 (1H, m). MS (ESI⁺): 533 [M + H]⁺ |
| 2-10 | 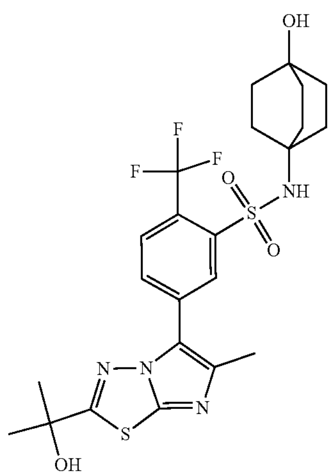 [SMILES: Cc1nc2sc(C(C)(C)O)nn2c1-c1ccc(C(F)(F)F)c(S(=O)(=O)NC23CCC(O)(CC2)CC3)c1] | ¹H-NMR (400 MHz, DMSO-d₆) δ: 1.45-1.53 (6H, m), 1.63 (6H, s), 1.75-1.84 (6H, m), 2.52 (3H, s), 4.30 (1H, s), 6.57 (1H, s), 7.82 (1H, s), 8.05 (1H, d, J = 8.2 Hz), 8.08-8.12 (1H, m), 8.61 (1H, d, J = 1.5 Hz). MS (ESI)⁺: 545 [M + H]⁺ |
| 2-11 | 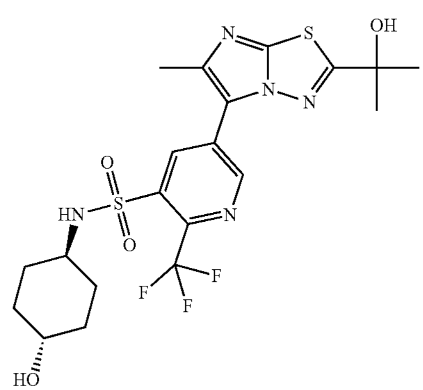 [SMILES: Cc1nc2sc(C(C)(C)O)nn2c1-c1cnc(C(F)(F)F)c(S(=O)(=O)N[C@H]2CC[C@H](O)CC2)c1] | ¹H-NMR (400 MHz, DMSO-d₆) δ: 1.01-1.15 (2H, m), 1.25-1.38 (2H, m), 1.63 (6H, s), 1.65-1.77 (4H, m), 2.57 (3H, s), 3.07-3.17 (1H, m), 3.25-3.39 (1H, m), 4.52 (1H, d, J = 4.2 Hz), 6.59 (1H, s), 8.25-8.28 (1H, m), 8.87 (1H, d, J = 1.8 Hz), 9.25 (1H, d, J = 1.8 Hz). MS (ESI)⁺: 520 [M + H]⁺ |
| 2-12 | 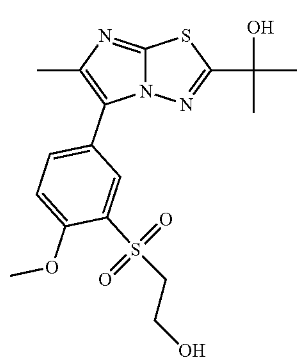 [SMILES: COc1ccc(-c2c(C)nc3sc(C(C)(C)O)nn23)cc1S(=O)(=O)CCO] | ¹H-NMR (400 MHz, DMSO-d₆) δ: 1.59 (6H, s), 2.42 (3H, s), 3.58 (2H, t, J = 5.8 Hz), 3.69 (2H, q, J = 5.8 Hz), 4.00 (3H, s), 4.84 (1H, t, J = 5.8 Hz), 6.46 (1H, s), 7.45 (1H, d, J = 8.7 Hz), 8.00 (1H, dd, J = 8.7, 2.4 Hz), 8.13 (1H, d, J = 2.4 Hz). MS (ESI⁺): 412 [M + H]⁺ |

TABLE 78-continued

| Example | Structure | Instrumental Data |
|---|---|---|
| 2-13 | 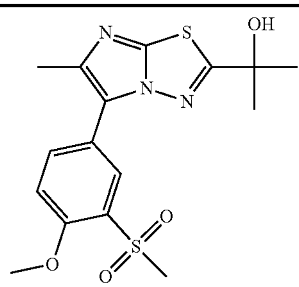 | $^1$H-NMR (400 MHz, DMSO-$d_6$) δ: 1.58 (6H, s), 2.42 (3H, s), 3.30 (3H, s), 4.02 (3H, s), 6.47 (1H, s), 7.47 (1H, d, J = 8.8 Hz), 8.00 (1H, dd, J = 8.8, 2.4 Hz), 8.18 (1H, d, J = 2.4 Hz). MS (ESI$^+$): 382 [M + H]$^+$ |

TABLE 79

| Example | Structure | Instrumental Data |
|---|---|---|
| 2-14 | 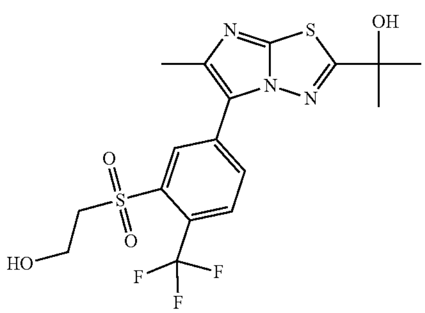 [SMILES: Cc1nc2sc(C(C)(C)O)nn2c1-c1ccc(C(F)(F)F)c(S(=O)(=O)CCO)c1] | $^1$H-NMR (400 MHz, CDCl$_3$) δ: 1.77 (6H, s), 2.62 (3H, s), 2.71 (1H, s), 2.82 (1H, t, J = 6.7 Hz), 3.57-3.59 (2H, m), 4.10 (2H, dd, J = 10.6, 6.4 Hz), 8.01 (1H, d, J = 7.9 Hz), 8.08 (1H, d, J = 7.9 Hz), 8.81 (1H, s). MS (ESI$^+$): 450 [M + H]$^+$ |
| 2-15 | 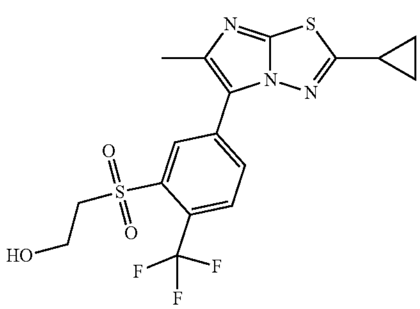 [SMILES: Cc1nc2sc(C3CC3)nn2c1-c1ccc(C(F)(F)F)c(S(=O)(=O)CCO)c1] | $^1$H-NMR (400 MHz, CDCl$_3$) δ: 1.17-1.32 (4H, m), 2.25-2.31 (1H, m), 2.60 (3H, s), 2.72 (1H, t, J = 6.7 Hz), 3.56-3.59 (2H, m), 4.09-4.13 (2H, m), 8.00 (1H, d, J = 8.2 Hz), 8.10 (1H, d, J = 8.2 Hz), 8.76 (1H, d, J = 1.8 Hz). MS (ESI$^+$): 432 [M + H]$^+$ |
| 2-16 | 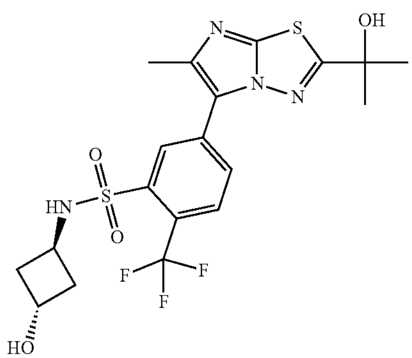 [SMILES: Cc1nc2sc(C(C)(C)O)nn2c1-c1ccc(C(F)(F)F)c(S(=O)(=O)N[C@H]2C[C@H](O)C2)c1] | $^1$H-NMR (400 MHz, DMSO-$d_6$) δ: 1.63 (6H, s), 1.88-1.97 (2H, m), 2.06-2.15 (2H, m), 2.52 (3H, s), 3.84-3.94 (1H, m), 4.11-4.19 (1H, m), 4.93 (1H, d, J = 4.9 Hz), 6.54 (1H, s), 8.09 (1H, d, J = 8.3 Hz), 8.14 (1H, dd, J = 8.3, 1.2 Hz), 8.29 (1H, s), 8.50 (1H, d, J = 1.2 Hz). MS (ESI$^+$): 491 [M + H]$^+$ |

TABLE 79-continued

| Example | Structure | Instrumental Data |
|---|---|---|
| 2-17 | 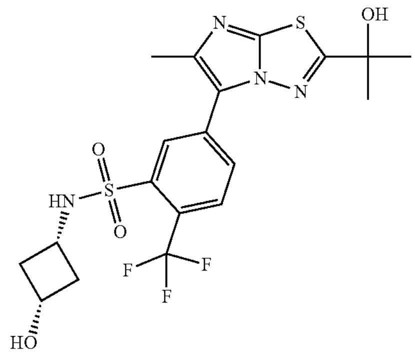 [SMILES: Cc1nc2sc(C(C)(C)O)nn2c1-c1ccc(C(F)(F)F)c(S(=O)(=O)N[C@H]2C[C@@H](O)C2)c1] | ¹H-NMR (400 MHz, DMSO-d₆) δ: 1.62 (6H, s), 1.69-1.79 (2H, m), 2.26-2.35 (2H, m), 2.52 (3H, s), 3.19-3.30 (1H, m), 3.80-3.70 (1H, m), 5.04 (1H, d, J = 5.5 Hz), 6.55 (1H, s), 8.08 (1H, d, J = 8.4 Hz), 8.14 (1H, dd, J = 8.4, 1.3 Hz), 8.25 (1H, s), 8.49 (1H, d, J = 1.3 Hz). MS (ESI⁺): 491 [M + H]⁺ |
| 2-18 | 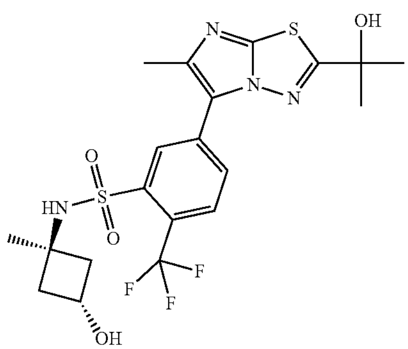 [SMILES: Cc1nc2sc(C(C)(C)O)nn2c1-c1ccc(C(F)(F)F)c(S(=O)(=O)N[C@]2(C)C[C@@H](O)C2)c1] | ¹H-NMR (400 MHz, DMSO-d₆) δ: 1.36 (3H, s), 1.62 (6H, s), 1.69-1.76 (2H, m), 2.52 (3H, s), 2.53-2.58 (2H, m), 3.93-4.02 (1H, m), 4.95 (1H, d, J = 5.8 Hz), 6.55 (1H, s), 8.07 (1H, d, J = 8.5 Hz), 8.09-8.16 (2H, m), 8.62 (1H, d, J = 1.5 Hz). MS (ESI⁺): 505 [M + H]⁺ |
| 2-19 | 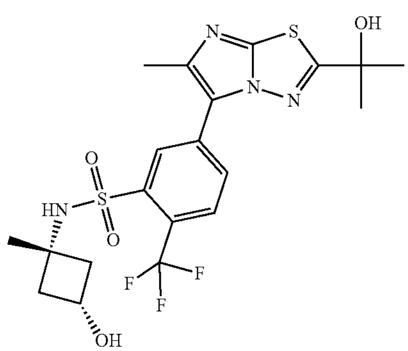 [SMILES: Cc1nc2sc(C(C)(C)O)nn2c1-c1ccc(C(F)(F)F)c(S(=O)(=O)N[C@]2(C)C[C@H](O)C2)c1] | ¹H-NMR (400 MHz, DMSO-d₆) δ: 1.24 (3H, s), 1.62 (6H, s), 1.99-2.07 (2H, m), 2.14-2.22 (2H, m), 2.53 (3H, s), 3.82-3.92 (1H, m), 5.01 (1H, d, J = 6.1 Hz), 6.55 (1H, s), 8.07 (1H, d, J = 8.4 Hz), 8.12 (1H, d, J = 8.4 Hz), 8.20 (1H, s), 8.62 (1H, d, J = 1.5 Hz). MS (ESI⁺): 505 [M + H]⁺ |
| 2-20 | 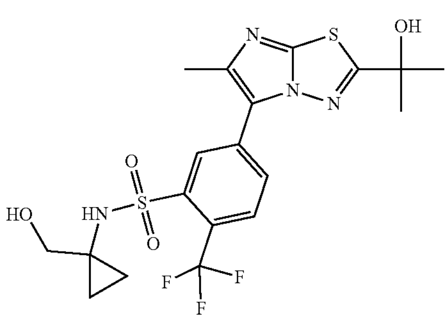 [SMILES: Cc1nc2sc(C(C)(C)O)nn2c1-c1ccc(C(F)(F)F)c(S(=O)(=O)NC2(CO)CC2)c1] | ¹H-NMR (400 MHz, DMSO-d₆) δ: 0.55-0.60 (2H, m), 0.61-0.66 (2H, m), 1.62 (6H, s), 2.52 (3H, s), 3.37 (2H, d, J = 5.6 Hz), 4.66 (1H, t, J = 5.6 Hz), 6.54 (1H, s), 8.06 (1H, d, J = 8.5 Hz), 8.10-8.15 (1H, m), 8.46 (1H, br s), 8.56 (1H, d, J = 1.8 Hz). MS (ESI⁺): 491 [M + H]⁺ |

TABLE 80

| Example | Structure | Instrumental Data |
|---|---|---|
| 2-21 | 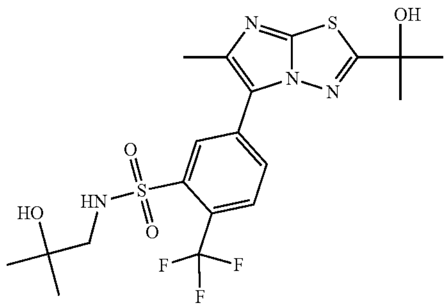 [SMILES: Cc1nc2sc(C(C)(C)O)nn2c1-c1ccc(C(F)(F)F)c(S(=O)(=O)NCC(C)(C)O)c1] | ¹H-NMR (400 MHz, DMSO-d₆) δ: 1.07 (6H, s), 1.62 (6H, s), 2.52 (3H, s), 2.89 (2H, s), 4.49 (1H, s), 6.54 (1H, s), 7.91 (1H, s), 8.07-8.13 (2H, m), 8.44 (1H, s). MS (ESI⁺): 493 [M + H]⁺ |
| 2-22 | 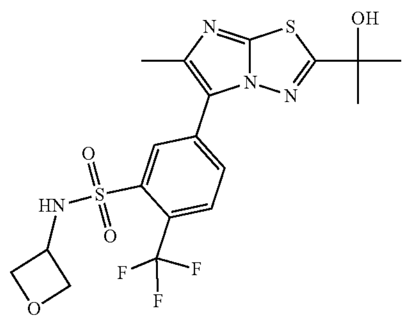 [SMILES: Cc1nc2sc(C(C)(C)O)nn2c1-c1ccc(C(F)(F)F)c(S(=O)(=O)NC2COC2)c1] | ¹H-NMR (400 MHz, DMSO-d₆) δ: 1.63 (6H, s), 2.52 (3H, s), 4.41-4.45 (2H, m), 4.46-4.53 (1H, m), 4.54-4.58 (2H, m), 6.55 (1H, s), 8.09 (1H, d, J = 8.5 Hz), 8.14 (1H, dd, J = 8.5, 1.4 Hz), 8.49 (1H, d, J = 1.4 Hz), 8.94 (1H, br s). MS (ESI⁺): 477 [M + H]⁺ |
| 2-23 | 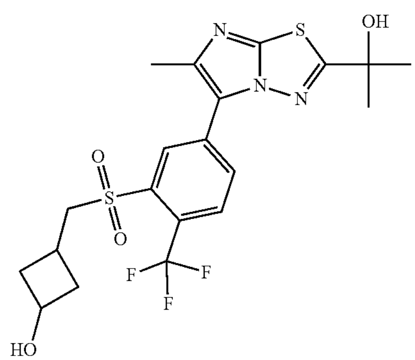 [SMILES: Cc1nc2sc(C(C)(C)O)nn2c1-c1ccc(C(F)(F)F)c(S(=O)(=O)CC2CC(O)C2)c1] | ¹H-NMR (400 MHz, CDCl₃): δ: 1.64-1.77 (3H, m), 1.78 (6H, s), 2.23-2.31 (1H, m), 2.48-2.55 (3H, m), 2.63 (3H, s), 3.45 (2H, d, J = 7.3 Hz), 4.11-4.18 (1H, m), 7.99 (1H, d, J = 8.5 Hz), 8.10 (1H, d, J = 8.5 Hz), 8.76 (1H, s). MS (ESI⁺): 490 [M + H]⁺ |
| 2-24 | 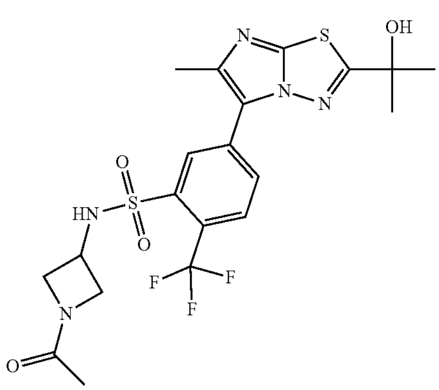 [SMILES: CC(=O)N1CC(NS(=O)(=O)c2cc(-c3c(C)nc4sc(C(C)(C)O)nn34)ccc2C(F)(F)F)C1] | ¹H-NMR (400 MHz, DMSO-d₆) δ: 1.61 (6H, s), 1.67 (3H, s), 2.53 (3H, s), 3.54-3.61 (1H, m), 3.86-3.94 (2H, m), 4.12-4.26 (2H, m), 6.55 (1H, s), 8.11 (1H, d, J = 8.5 Hz), 8.15-8.20 (1H, m), 8.53 (1H, d, J = 1.5 Hz), 8.74 (1H, br s). MS (ESI⁺): 518 [M + H]⁺ |

TABLE 80-continued

| Example | Structure | Instrumental Data |
| --- | --- | --- |
| 2-25 | 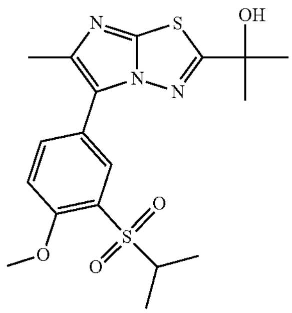 [SMILES: COc1ccc(-c2c(C)nc3sc(C(C)(C)O)nn23)cc1S(=O)(=O)C(C)C] | ¹H-NMR (400 MHz, DMSO-d₆) δ: 1.19 (6H, d, J = 6.7 Hz), 1.58 (6H, s), 2.42 (3H, s), 3.61-3.73 (1H, m), 3.99 (3H, s), 6.46 (1H, s), 7.46 (1H, d, J = 8.8 Hz), 8.01 (1H, dd, J = 8.8, 2.4 Hz), 8.15 (1H, d, J = 2.4 Hz). MS (ESI⁺): 410 [M + H]⁺ |
| 2-26 | 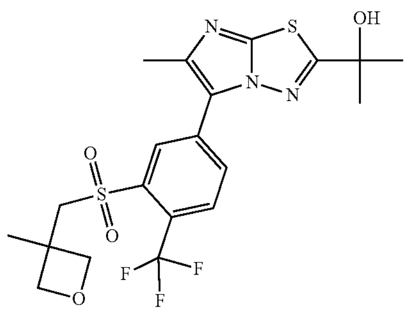 [SMILES: Cc1nc2sc(C(C)(C)O)nn2c1-c1ccc(C(F)(F)F)c(S(=O)(=O)CC2(C)COC2)c1] | ¹H-NMR (400 MHz, CDCl₃) δ: 1.75 (3H, s), 1.78 (6H, s), 2.59 (1H, s), 2.63 (3H, s), 3.69 (2H, s), 4.46 (2H, d, J = 6.7 Hz), 4.69 (2H, d, J = 6.1 Hz), 8.00 (1H, d, J = 7.9 Hz), 8.11 (1H, d, J = 7.9 Hz), 8.81 (1H, s). MS (ESI⁺): 490 [M + H]⁺ |
| 2-27 | 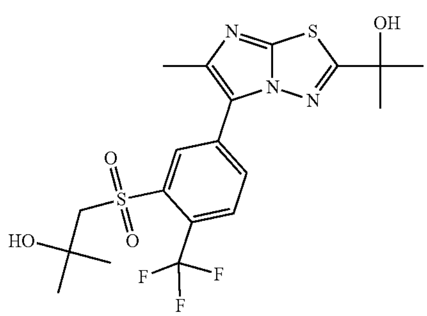 [SMILES: Cc1nc2sc(C(C)(C)O)nn2c1-c1ccc(C(F)(F)F)c(S(=O)(=O)CC(C)(C)O)c1] | ¹H-NMR (400 MHz, CDCl₃) δ: 1.50 (6H, s), 1.77 (6H, s), 2.60 (1H, s), 2.63 (3H, s), 3.51 (2H, s), 3.64 (1H, s), 7.99 (1H, d, J = 8.5 Hz), 8.09 (1H, d, J = 8.5 Hz), 8.84 (1H, s). MS (ESI⁺): 478 [M + H]⁺ |

TABLE 81

| Example | Structure | Instrumental Data |
| --- | --- | --- |
| 2-28 | 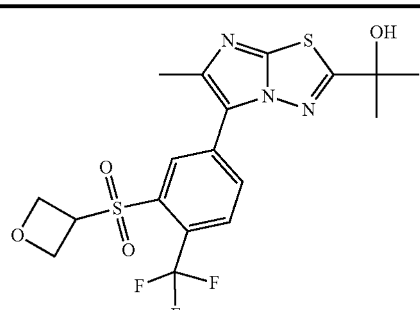 | ¹H-NMR (400 MHz, CDCl₃) δ: 1.78 (6H, s), 2.52 (1H, s), 2.63 (3H, s), 4.76-4.86 (3H, m), 5.07 (2H, t, J = 6.4 Hz), 8.00 (1H, d, J = 7.9 Hz), 8.09 (1H, d, J = 7.9 Hz), 8.85 (1H, d, J = 1.8 Hz). MS (ESI⁺): 462 [M + H]⁺ |

TABLE 81-continued

| Example | Structure | Instrumental Data |
|---|---|---|
| 2-29 | 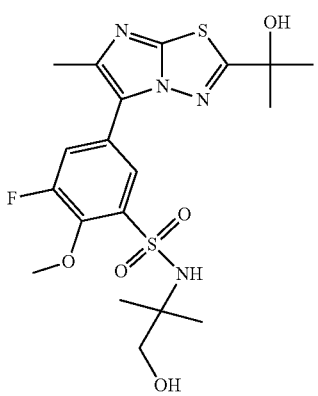 [SMILES: COc1c(F)cc(-c2c(C)nc3sc(C(C)(C)O)nn23)cc1S(=O)(=O)NC(C)(C)CO] | $^1$H-NMR (400 MHz, CDCl$_3$) δ: 1.18 (6H, s), 1.76 (6H, s), 2.28-2.34 (1H, m), 2.55 (3H, s), 2.56-2.60 (1H, m), 3.49 (2H, s), 4.15 (3H, d, J = 2.4 Hz), 5.12 (1H, s), 7.67 (1H, dd, J = 12.4, 2.0 Hz), 8.10 (1H, t, J = 2.0 Hz). MS (ESI$^+$): 473 [M + H]$^+$ |
| 2-30 | 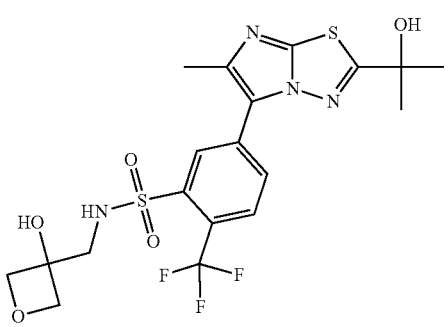 [SMILES: Cc1nc2sc(C(C)(C)O)nn2c1-c1ccc(C(F)(F)F)c(S(=O)(=O)NCC2(O)COC2)c1] | $^1$H-NMR (400 MHz, DMSO-d$_6$) δ: 1.60 (6H, s), 2.52 (3H, s), 3.27 (2H, s), 4.37 (2H, d, J = 6.7 Hz), 4.44 (2H, d, J = 6.7 Hz), 5.95 (1H, br s), 6.53 (1H, s), 8.08-8.14 (2H, m), 8.28-8.50 (2H, m). MS (ESI$^+$): 507 [M + H]$^+$ |
| 2-31 | 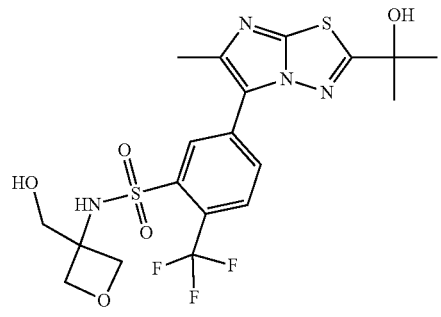 [SMILES: Cc1nc2sc(C(C)(C)O)nn2c1-c1ccc(C(F)(F)F)c(S(=O)(=O)NC2(CO)COC2)c1] | $^1$H-NMR (400 MHz, CDCl$_3$) δ: 1.79 (6H, s), 2.64 (3H, s), 2.96 (1H, s), 4.13 (2H, d, J = 5.1 Hz), 4.40 (2H, d, J = 7.2 Hz), 4.79 (2H, d, J = 7.2 Hz), 5.47 (1H, s), 8.00-8.03 (2H, m), 8.84-8.86 (1H, m). MS (ESI$^+$): 507 [M + H]$^+$ |
| 2-32 | 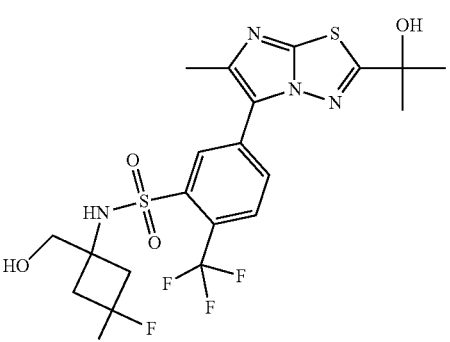 | $^1$H-NMR (400 MHz, DMSO-d$_6$) δ: 1.61 (6H, s), 2.52 (3H, s), 2.66-2.84 (4H, m), 3.42 (2H, br s), 5.19 (1H, br s), 6.54 (1H, s), 8.07 (1H, d, J = 8.2 Hz), 8.11-8.15 (1H, m), 8.56 (1H, br s), 8.63 (1H, d, J = 1.5 Hz). MS (ESI$^+$): 541 [M + H]$^+$ |

TABLE 81-continued

| Example | Structure | Instrumental Data |
|---|---|---|
| 2-33 | 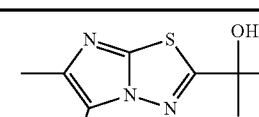 | $^1$H-NMR (400 MHz, DMSO-$d_6$) δ: 1.60 (6H, d, J = 1.8 Hz), 2.52 (3H, s), 3.10 (1H, dd, J = 13.9, 8.2 Hz), 3.25 (1H, dd, J = 14.1, 4.1 Hz), 3.99-4.10 (1H, m), 6.54 (1H, s), 8.09 (1H, d, J = 8.5 Hz), 8.11-8.14 (1H, m), 8.47 (1H, d, J = 1.5 Hz). MS (ESI$^+$): 533 [M + H]$^+$ |
| 2-34 | 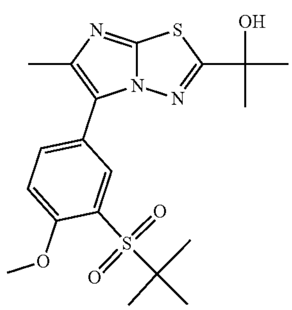 [SMILES: COc1ccc(-c2c(C)nc3sc(C(C)(C)O)nn23)cc1S(=O)(=O)C(C)(C)C] | $^1$H-NMR (400 MHz, DMSO-$d_6$) δ: 1.30 (9H, s), 1.56 (6H, s), 2.41 (3H, s), 3.92 (3H, s), 6.47 (1H, s), 7.44 (1H, d, J = 8.8 Hz), 7.98 (1H, dd, J = 8.8, 2.4 Hz), 8.11 (1H, d, J = 2.4 Hz). MS (ESI$^+$): 424 [M + H]$^+$ |

TABLE 82

| Example | Structure | Instrumental Data |
|---|---|---|
| 2-35 | 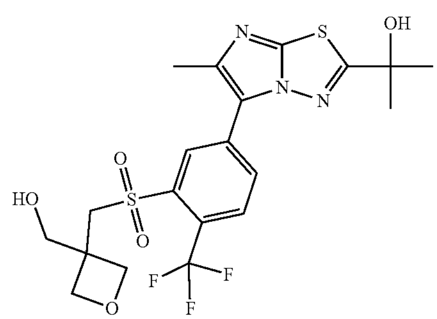 [SMILES: Cc1nc2sc(C(C)(C)O)nn2c1-c1ccc(C(F)(F)F)c(S(=O)(=O)CC2(CO)COC2)c1] | $^1$H-NMR (400 MHz, CDCl$_3$) δ: 1.77 (6H, s), 2.47-2.52 (1H, m), 2.63 (3H, s), 2.65 (1H, s), 3.82 (2H, s), 4.33 (2H, d, J = 6.1 Hz), 4.54 (2H, d, J = 7.3 Hz), 4.66 (2H, d, J = 6.7 Hz), 8.02 (1H, d, J = 8.3 Hz), 8.12 (1H, d, J = 8.3 Hz), 8.82 (1H, s). MS (ESI$^+$): 506 [M + H]$^+$ |
| 2-36 | 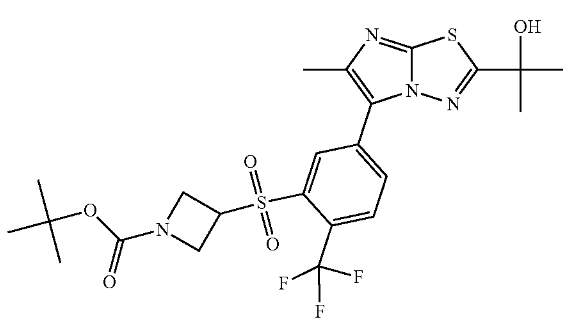 [SMILES: Cc1nc2sc(C(C)(C)O)nn2c1-c1ccc(C(F)(F)F)c(S(=O)(=O)C2CN(C(=O)OC(C)(C)C)C2)c1] | $^1$H-NMR (400 MHz, CDCl$_3$) δ: 1.45 (9H, s), 1.78 (6H, s), 2.61 (3H, s), 3.52 (1H, s), 4.11-4.40 (5H, m), 8.01 (2H, s), 8.86 (1H, s). MS (ESI$^+$) 561 [M + H]$^+$ |

TABLE 82-continued

| Example | Structure | Instrumental Data |
|---|---|---|
| 2-37 | 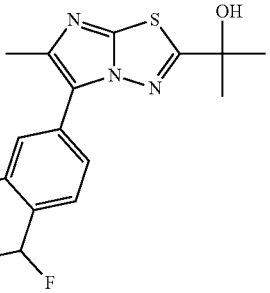 | $^1$H-NMR (400 MHz, CDCl$_3$) δ: 1.49 (6H, s), 1.77 (6H, s), 2.61 (3H, s), 2.70 (1H, s), 3.46 (2H, s), 3.49 (1H, s), 7.63 (1H, t, J = 55.3 Hz), 7.99 (1H, d, J = 7.9 Hz), 8.08 (1H, dd, J = 7.9, 1.8 Hz), 8.61 (1H, s). MS (ESI$^+$): 460 [M + H]$^+$ |
| 2-38 | 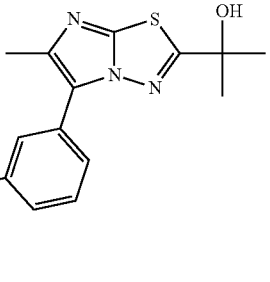 | $^1$H-NMR (400 MHz, CDCl$_3$) δ: 1.47 (6H, s), 1.76 (6H, s), 2.58 (3H, s), 2.67 (1H, s), 3.38 (2H, s), 3.70 (1H, s), 7.68 (1H, t, J = 7.9 Hz), 7.86 (1H, d, J = 7.9 Hz), 7.97 (1H, d, J = 7.9 Hz), 8.38 (1H, s). MS (ESI$^+$): 410 [M + H]$^+$ |
| 2-39 | 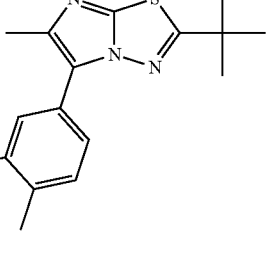 | $^1$H-NMR (400 MHz, CDCl$_3$) δ: 1.48 (6H, s), 1.75 (6H, s), 2.55 (3H, s), 2.59 (1H, s), 2.76 (3H, s), 3.38 (2H, s), 3.78 (1H, s), 7.45 (1H, d, J = 7.9 Hz), 7.85 (1H, dd, J = 7.9, 1.8 Hz), 8.47 (1H, d, J = 1.8 Hz). MS (ESI$^+$): 424 [M + H]$^+$ |
| 2-40 | 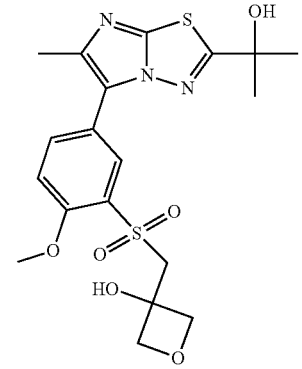 [SMILES: COc1ccc(-c2c(C)nc3sc(C(C)(C)O)nn23)cc1S(=O)(=O)CC1(O)COC1] | $^1$H-NMR (400 MHz, DMSO-d$_6$) δ: 1.58 (6H, s), 2.40 (3H, s), 3.96 (2H, s), 3.99 (3H, s), 4.38 (2H, d, J = 7.2 Hz), 4.67 (2H, d, J = 7.2 Hz), 5.97 (1H, s), 6.47 (1H, s), 7.42 (1H, d, J = 8.9 Hz), 7.96 (1H, dd, J = 8.9, 2.3 Hz), 8.08 (1H, d, J = 2.3 Hz). MS (ESI$^+$): 454 [M + H]$^+$ |

TABLE 82-continued

| Example | Structure | Instrumental Data |
|---|---|---|
| 2-41 | 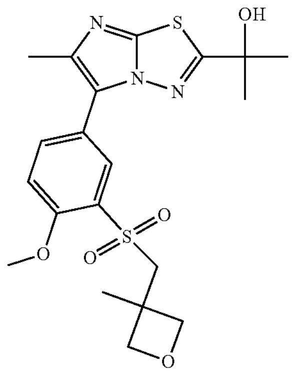 [SMILES: COc1ccc(-c2c(C)nc3sc(C(C)(C)O)nn23)cc1S(=O)(=O)CC1(C)COC1] | ¹H-NMR (400 MHz, DMSO-d₆) δ: 1.47 (3H, s), 1.58 (6H, s), 2.41 (3H, s), 3.88 (2H, s), 4.03 (3H, s), 4.15 (2H, d, J = 5.9 Hz), 4.56 (2H, d, J = 5.9 Hz), 6.48 (1H, s), 7.48 (1H, d, J = 8.8 Hz), 8.00 (1H, dd, J = 8.8, 2.4 Hz), 8.14 (1H, d, J = 2.4 Hz). MS (ESI⁺): 452 [M + H]⁺ |

TABLE 83

| Example | Structure | Instrumental Data |
|---|---|---|
| 2-42 | 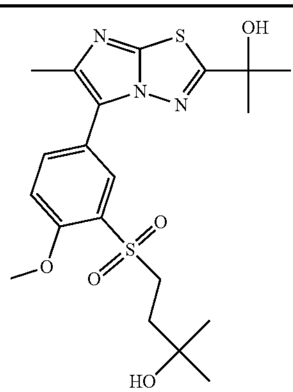 | ¹H-NMR (400 MHz, DMSO-d₆) δ: 1.06 (6H, s), 1.55-1.63 (8H, m), 2.42 (3H, s), 3.40-3.49 (2H, m), 4.00 (3H, s), 4.46 (1H, s), 6.48 (1H, s), 7.47 (1H, d, J = 8.7 Hz), 8.01 (1H, dd, J = 8.7, 2.3 Hz), 8.15 (1H, d, J = 2.3 Hz). MS (ESI⁺): 454 [M + H]⁺ |
| 2-43 | 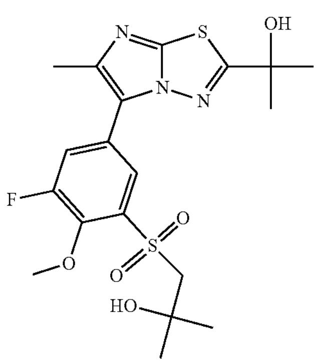 [SMILES: COc1c(F)cc(-c2c(C)nc3sc(C(C)(C)O)nn23)cc1S(=O)(=O)CC(C)(C)O] | ¹H-NMR (400 MHz, DMSO-d₆) δ: 1.27 (6H, s), 1.59 (6H, s), 2.45 (3H, s), 3.62 (2H, s), 4.05 (3H, d, J = 1.8 Hz), 4.81 (1H, s), 6.50 (1H, s), 7.93 (1H, dd, J = 12.7, 2.3 Hz), 8.03 (1H, dd, J = 2.3, 1.1 Hz). MS (ESI⁺): 458 [M + H]⁺ |
| 2-44 | 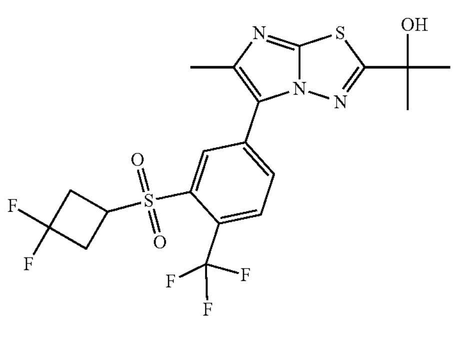 [SMILES: Cc1nc2sc(C(C)(C)O)nn2c1-c1ccc(C(F)(F)F)c(S(=O)(=O)C2CC(F)(F)C2)c1] | ¹H-NMR (400 MHz, CDCl₃) δ: 1.78 (6H, s), 2.55 (1H, s), 2.62 (3H, s), 2.78-2.91 (2H, m), 3.13-3.26 (2H, m), 3.96-4.01 (1H, m), 8.02 (1H, d, J = 8.3 Hz), 8.07 (1H, d, J = 8.3 Hz), 8.79 (1H, s). MS (ESI⁺): 496 [M + H]⁺ |

TABLE 83-continued

| Example | Structure | Instrumental Data |
|---|---|---|
| 2-45 | 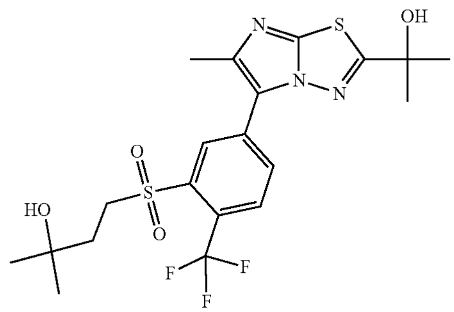 [SMILES: Cc1nc2sc(C(C)(C)O)nn2c1-c1ccc(C(F)(F)F)c(S(=O)(=O)CCC(C)(C)O)c1] | ¹H-NMR (400 MHz, CDCl₃) δ: 1.27 (6H, s), 1.43 (1H, s), 1.80 (6H, s), 1.98-2.02 (2H, m), 2.65 (3H, s), 2.72 (1H, s), 3.47-3.51 (2H, m), 8.03 (1H, d, J = 8.5 Hz), 8.12 (1H, d, J = 8.5 Hz), 8.78 (1H, s). MS (ESI⁺): 492 [M + H]⁺ |
| 2-46 | 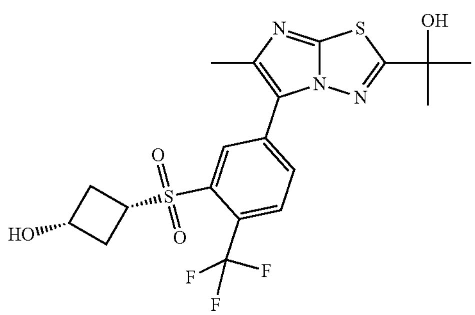 [SMILES: Cc1nc2sc(C(C)(C)O)nn2c1-c1ccc(C(F)(F)F)c(S(=O)(=O)[C@H]2C[C@@H](O)C2)c1] | ¹H-NMR (400 MHz, CDCl₃) δ: 1.78 (6H, s), 2.38 (1H, d, J = 8.6 Hz), 2.49-2.56 (2H, m), 2.62 (3H, s), 2.65-2.69 (2H, m), 2.71 (1H, s), 3.69-3.77 (1H, m), 4.24 (1H, dd, J = 14.7, 7.3 Hz), 7.99 (1H, d, J = 8.6 Hz), 8.05 (1H, d, J = 8.6 Hz), 8.75 (1H, s). MS (ESI⁺): 476 [M + H]⁺ |
| 2-47 | 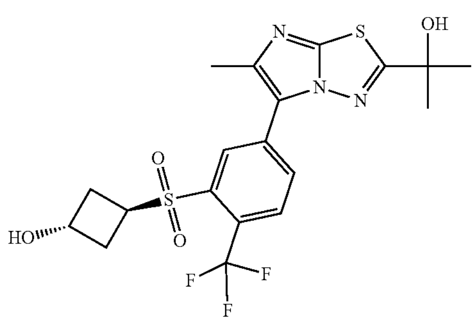 [SMILES: Cc1nc2sc(C(C)(C)O)nn2c1-c1ccc(C(F)(F)F)c(S(=O)(=O)[C@H]2C[C@H](O)C2)c1] | ¹H-NMR (400 MHz, CDCl₃) δ: 1.77 (6H, s), 1.99 (1H, d, J = 4.9 Hz), 2.32-2.40 (2H, m), 2.54 (1H, s), 2.62 (3H, s), 2.88-2.95 (2H, m), 4.07-4.13 (1H, m), 4.73-4.77 (1H, m), 8.00 (1H, d, J = 8.3 Hz), 8.06 (1H, d, J = 8.3 Hz), 8.74 (1H, s). MS (ESI⁺): 476 [M + H]⁺ |
| 2-48 | 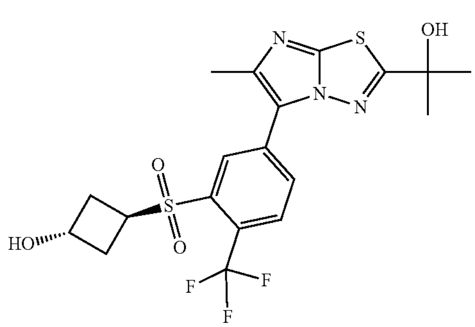 | ¹H-NMR(400 MHz, CDCl₃) δ: 1.38 (3H, s), 1.77 (6H, s), 2.42-2.48 (2H, m), 2.62 (3H, s), 2.64-2.69 (2H, m), 2.88 (1H, s), 2.92 (1H, s), 3.78-3.86 (1H, m), 7.99 (1H, d, J = 8.5 Hz), 8.03 (1H, d, J = 8.5 Hz), 8.79 (1H, d, J = 1.8 Hz). MS (ESI⁺): 490 [M + H]⁺ |

TABLE 84

| Example | Structure | Instrumental Data |
|---|---|---|
| 2-49 | 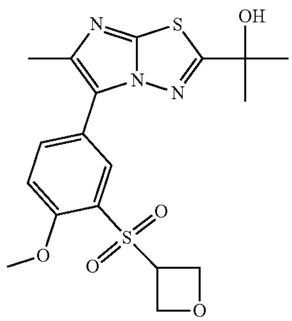 [SMILES: COc1ccc(-c2c(C)nc3sc(C(C)(C)O)nn23)cc1S(=O)(=O)C1COC1] | $^1$H-NMR (400 MHz, DMSO-d$_6$) δ: 1.58 (6H, s), 2.42 (3H, s), 3.96 (3H, s), 4.80 (4H, d, J = 7.3 Hz), 4.96-5.04 (1H, m), 6.48 (1H, s), 7.45 (1H, d, J = 8.9 Hz), 8.01 (1H, dd, J = 8.9, 2.4 Hz), 8.21 (1H, d, J = 2.4 Hz). MS (ESI$^+$): 424 [M + H]$^+$ |
| 2-50 | 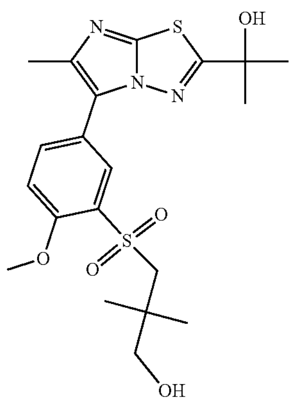 [SMILES: COc1ccc(-c2c(C)nc3sc(C(C)(C)O)nn23)cc1S(=O)(=O)CC(C)(C)CO] | $^1$H-NMR (400 MHz, DMSO-d$_6$) δ: 0.97 (6H, s), 1.58 (6H, s), 2.42 (3H, s), 3.15 (2H, d, J = 5.2 Hz), 3.42 (2H, s), 4.00 (3H, s), 4.77 (1H, t, J = 5.2 Hz), 6.47 (1H, s), 7.45 (1H, d, J = 8.8 Hz), 7.97 (1H, dd, J = 8.8, 2.4 Hz), 8.18 (1H, d, J = 2.4 Hz). MS (ESI$^+$): 454 [M + H]$^+$ |
| 2-51 | 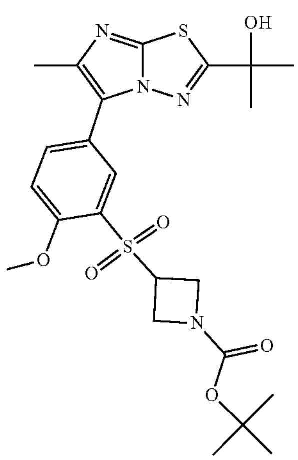 [SMILES: COc1ccc(-c2c(C)nc3sc(C(C)(C)O)nn23)cc1S(=O)(=O)C1CN(C(=O)OC(C)(C)C)C1] | $^1$H-NMR (400 MHz, DMSO-d$_6$) δ: 1.38 (9H, s), 1.58 (6H, s), 2.42 (3H, s), 3.95-4.05 (5H, m), 4.07-4.18 (2H, m), 4.52-4.60 (1H, m), 6.47 (1H, s), 7.47 (1H, d, J = 8.8 Hz), 8.02 (1H, dd, J = 8.8, 2.4 Hz), 8.22 (1H, d, J = 2.4 Hz). MS (ESI$^+$): 523 [M + H]$^+$ |
| 2-52 | 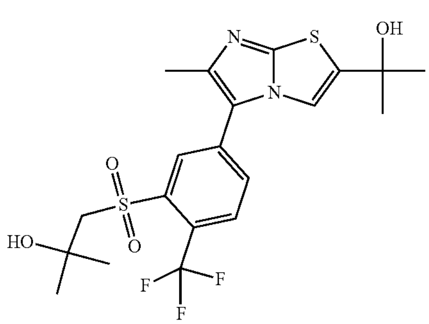 [SMILES: Cc1nc2sc(C(C)(C)O)cn2c1-c1ccc(C(F)(F)F)c(S(=O)(=O)CC(C)(C)O)c1] | $^1$H-NMR (400 MHz, CDCl$_3$) δ: 1.50 (6H, s), 1.68 (6H, s), 2.22 (1H, s), 2.49 (3H, s), 3.43 (1H, s), 3.51 (2H, s), 7.43 (1H, s), 7.79 (1H, dd, J = 8.5, 1.2 Hz), 8.00 (1H, d, J = 8.5 Hz), 8.35 (1H, d, J = 1.2 Hz). MS (ESI$^+$): 477 [M + H]$^+$ |

TABLE 84-continued

| Example | Structure | Instrumental Data |
|---------|-----------|-------------------|
| 2-53 | 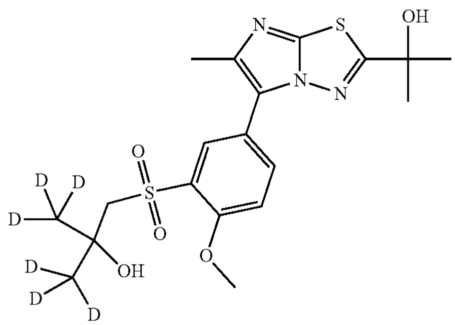 [SMILES: [2H]C([2H])([2H])C(O)(CS(=O)(=O)c1cc(-c2c(C)nc3sc(C(C)(C)O)nn23)ccc1OC)C([2H])([2H])[2H]] | $^1$H-NMR (400 MHz, DMSO-d$_6$) δ: 1.58 (6H, s), 2.41 (3H, s), 3.55 (2H, s), 4.01 (3H, s), 4.78 (1H, s), 6.47 (1H, s), 7.44 (1H, d, J = 8.7 Hz), 7.97 (1H, dd, J = 8.7, 2.2 Hz), 8.16 (1H, d, J = 2.2 Hz). MS (ESI$^+$): 446 [M + H]$^+$ |
| 2-54 | 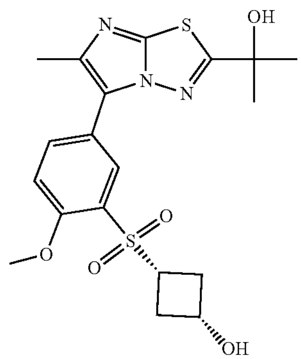 [SMILES: COc1ccc(-c2c(C)nc3sc(C(C)(C)O)nn23)cc1S(=O)(=O)[C@H]1C[C@@H](O)C1] | $^1$H-NMR (400 MHz, CDCl$_3$) δ: 1.75 (6H, s), 2.30 (1H, d, J = 9.7 Hz), 2.42-2.49 (2H, m), 2.52 (3H, s), 2.54 (1H, s), 2.64-2.71 (2H, m), 3.87-3.95 (1H, m), 4.02 (3H, s), 4.19-4.28 (1H, m), 7.15 (1H, d, J = 8.5 Hz), 7.90 (1H, dd, J = 8.5, 2.1 Hz), 8.36 (1H, d, J = 2.1 Hz). MS (ESI$^+$): 438 [M + H]$^+$ |

TABLE 85

| Example | Structure | Instrumental Data |
|---------|-----------|-------------------|
| 2-55 | 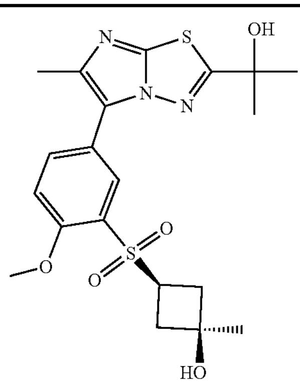 | $^1$H-NMR (400 MHz, CDCl$_3$) δ: 1.38 (3H, s), 1.75 (6H, s), 2.41-2.47 (2H, m), 2.52 (3H, s), 2.56-2.61 (3H, m), 2.83 (1H, s), 3.93-4.01 (1H, m), 4.03 (3H, s), 7.15 (1H, d, J = 8.5 Hz), 7.90 (1H, dd, J = 8.5, 2.4 Hz), 8.37 (1H, d, J = 2.4 Hz). MS (ESI$^+$) 452 [M + H]$^+$ |
| 2-56 | 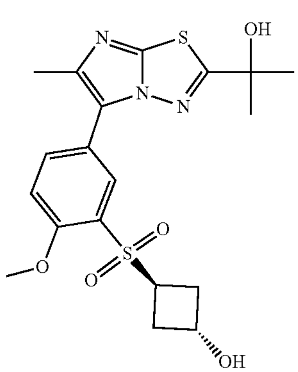 [SMILES: COc1ccc(-c2c(C)nc3sc(C(C)(C)O)nn23)cc1S(=O)(=O)[C@H]1C[C@H](O)C1] | $^1$H-NMR (400 MHz, CDCl$_3$) δ: 1.69 (6H, s), 2.28-2.36 (2H, m), 2.50 (3H, s), 2.73-2.80 (2H, m), 3.31 (1H, s), 4.02 (3H, s), 4.21-4.28 (1H, m), 4.56-4.63 (1H, m), 7.19 (1H, d, J = 9.1 Hz), 7.92 (1H, dd, J = 8.5, 2.4 Hz), 8.31 (1H, d, J = 2.4 Hz). MS (ESI$^+$): 438 [M + H]$^+$ |

TABLE 85-continued

| Example | Structure | Instrumental Data |
|---|---|---|
| 2-57 | 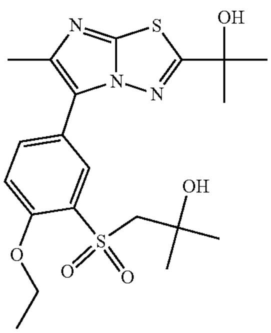 [SMILES: CCOc1ccc(-c2c(C)nc3sc(C(C)(C)O)nn23)cc1S(=O)(=O)CC(C)(C)O] | ¹H-NMR (400 MHz, CDCl₃) δ: 1.44 (6H, s), 1.56-1.57 (3H, m), 1.75 (6H, s), 2.48 (1H, s), 2.52 (3H, s), 3.64 (2H, s), 3.83 (1H, s), 4.30 (2H, q, J = 7.1 Hz), 7.15 (1H, d, J = 8.8 Hz), 7.90 (1H, dd, J = 8.8, 2.4 Hz), 8.36 (1H, d, J = 2.4 Hz). MS (ESI⁺): 454 [M + H]⁺ |
| 2-58 | 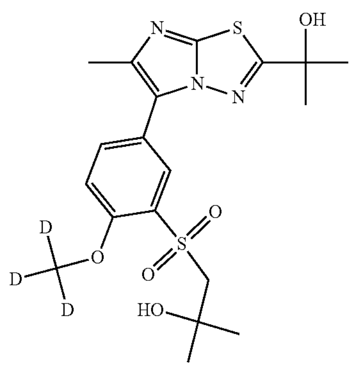 [SMILES: [2H]C([2H])([2H])Oc1ccc(-c2c(C)nc3sc(C(C)(C)O)nn23)cc1S(=O)(=O)CC(C)(C)O] | ¹H-NMR (400 MHz, CDCl₃) δ: 1.43 (6H, s), 1.74 (6H, s), 2.51 (3H, s), 2.56 (1H, s), 3.61 (2H, s), 3.78 (1H, s), 7.17 (1H, d, J = 8.8 Hz), 7.91 (1H, dd, J = 8.8, 2.1 Hz), 8.36 (1H, d, J = 2.1 Hz). MS (ESI⁺): 443 [M + H]⁺ |
| 2-59 | 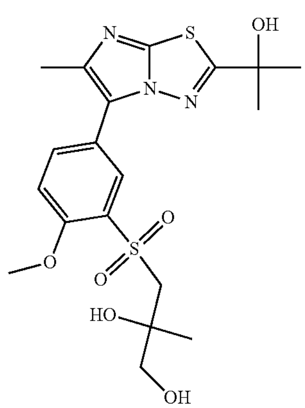 [SMILES: COc1ccc(-c2c(C)nc3sc(C(C)(C)O)nn23)cc1S(=O)(=O)CC(C)(O)CO] | ¹H-NMR (400 MHz, CDCl₃) δ: 1.41 (3H, s), 1.74 (6H, s), 2.52 (3H, s), 2.56 (1H, t, J = 7.0 Hz), 2.60 (1H, s), 3.59-3.69 (3H, m), 3.75-3.80 (2H, m), 4.07 (3H, s), 7.18 (1H, d, J = 8.5 Hz), 7.93 (1H, dd, J = 8.5, 2.4 Hz), 8.35 (1H, d, J = 2.4 Hz). MS (ESI⁺): 456 [M + H]⁺ |
| 2-60 | 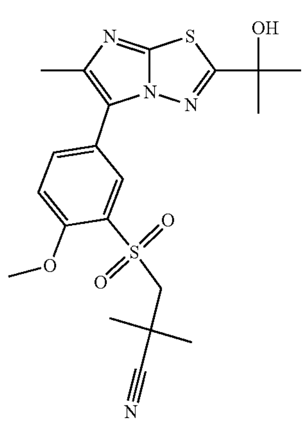 [SMILES: COc1ccc(-c2c(C)nc3sc(C(C)(C)O)nn23)cc1S(=O)(=O)CC(C)(C)C#N] | ¹H-NMR (400 MHz, CDCl₃) δ: 1.61 (6H, s), 1.74 (6H, s), 2.52 (3H, s), 2.53 (1H, s), 3.62 (2H, s), 4.08 (3H, s), 7.19 (1H, d, J = 8.5 Hz), 7.95 (1H, dd, J = 8.5, 2.1 Hz), 8.40 (1H, d, J = 2.1 Hz). MS (ESI⁺): 449 [M + H]⁺ |

TABLE 86
| Example | Structure | Instrumental Data |
|---|---|---|
| 2-61 | 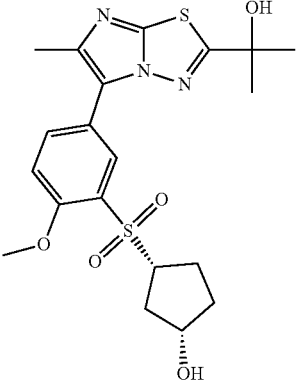 | $^1$H-NMR (400 MHz, CDCl$_3$) δ: 1.40 (1H, d, J = 2.4 Hz), 1.72-1.77 (7H, m), 1.95-2.07 (2H, m), 2.12-2.18 (2H, m), 2.24-2.31 (1H, m), 2.49 (1H, s), 2.52 (3H, s), 4.04 (3H, s), 4.30-4.37 (1H, m), 4.53-4.57 (1H, m), 7.16 (1H, d, J = 8.9 Hz), 7.91 (1H, dd, J = 8.9, 2.1 Hz), 8.33 (1H, d, J = 2.1 Hz). MS (ESI$^+$): 462 [M + H]$^+$ |
| 2-62 | 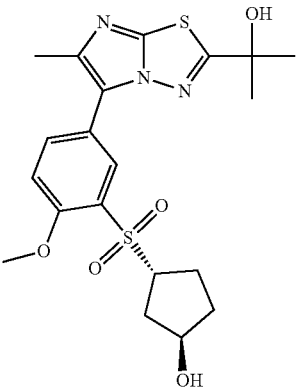 [SMILES: COc1ccc(-c2c(C)nc3sc(C(C)(C)O)nn23)cc1S(=O)(=O)[C@@H]1CC[C@@H](O)C1] | $^1$H-NMR (400 MHz, CDCl$_3$) δ: 1.73 (6H, d, J = 1.8 Hz), 1.81-1.88 (1H, m), 1.96-2.06 (2H, m), 2.16-2.20 (2H, m), 2.29-2.38 (1H, m), 2.53 (3H, s), 3.11 (1H, s), 3.24 (1H, d, J = 9.8 Hz), 4.04 (3H, s), 4.15-4.22 (1H, m), 4.31-4.37 (1H, m), 7.17 (1H, d, J = 8.6 Hz), 7.89 (1H, dd, J = 8.6, 2.4 Hz), 8.42 (1H, d, J = 2.4 Hz). MS (ESI$^+$): 452 [M + H]$^+$ |
| 2-63 | 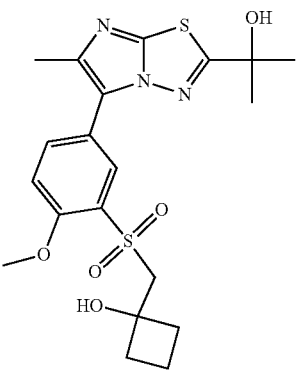 [SMILES: COc1ccc(-c2c(C)nc3sc(C(C)(C)O)nn23)cc1S(=O)(=O)CC1(O)CCC1] | $^1$H-NMR (400 MHz, CDCl$_3$) δ: 1.59-1.67 (1H, m), 1.74 (6H, s), 1.87-1.93 (1H, m), 2.18-2.22 (4H, m), 2.50-2.52 (4H, m), 3.75 (2H, s), 4.05 (1H, s), 4.08 (3H, s), 7.19 (1H, d, J = 8.8 Hz), 7.92 (1H, dd, J = 8.6, 2.1 Hz), 8.34 (1H, d, J = 2.1 Hz). MS (ESI$^+$) 452 [M + H]$^+$ |

TABLE 86-continued

| Example | Structure | Instrumental Data |
|---------|-----------|-------------------|
| 2-64 | 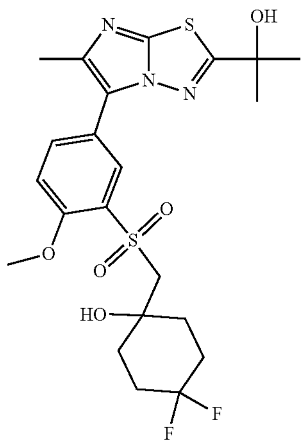 [SMILES: COc1ccc(-c2c(C)nc3sc(C(C)(C)O)nn23)cc1S(=O)(=O)CC1(O)CCC(F)(F)CC1] | ¹H-NMR (400 MHz, CDCl₃) δ: 1.69-1.77 (8H, m), 1.88-1.97 (2H, m), 2.05-2.24 (4H, m), 2.49 (1H, s), 2.52 (3H, s), 3.60 (2H, s), 3.85 (1H, s), 4.07 (3H, s), 7.19 (1H, d, J = 8.5 Hz), 7.94 (1H, dd, J = 8.5, 2.4 Hz), 8.36 (1H, d, J = 2.4 Hz). MS (ESI⁺): 516 [M + H]⁺ |
| 2-65 | 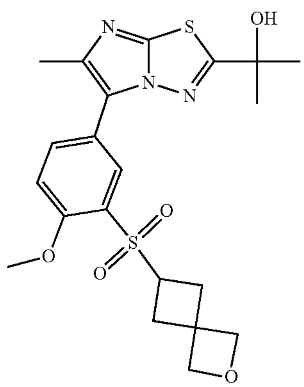 [SMILES: COc1ccc(-c2c(C)nc3sc(C(C)(C)O)nn23)cc1S(=O)(=O)C1CC2(COC2)C1] | ¹H-NMR (400 MHz, CDCl₃) δ: 1.75 (6H, s), 2.51-2.56 (5H, m), 2.73-2.79 (3H, m), 4.01 (3H, s), 4.06-4.14 (1H, m), 4.67 (2H, s), 4.71 (2H, s), 7.14 (1H, d, J = 8.7 Hz), 7.90 (1H, dd, J = 8.7, 2.3 Hz), 8.33 (1H, d, J = 2.3 Hz). MS (ESI⁺): 464 [M + H]⁺ |
| 2-66 | 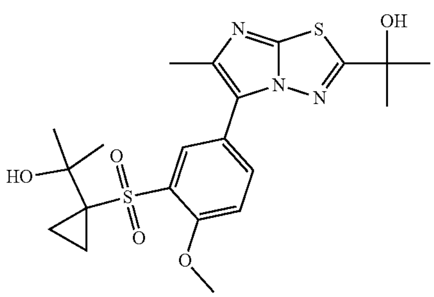 [SMILES: COc1ccc(-c2c(C)nc3sc(C(C)(C)O)nn23)cc1S(=O)(=O)C1(C(C)(C)O)CC1] | ¹H-NMR (400 MHz, CDCl₃) δ: 1.20-1.26 (8H, m), 1.73-1.77 (8H, m), 2.52 (3H, s), 2.58 (1H, s), 2.76 (1H, s), 4.00 (3H, s), 7.13 (1H, d, J = 8.5 Hz), 7.86 (1H, dd, J = 8.5, 2.1 Hz), 8.47 (1H, d, J = 2.1 Hz). MS (ESI⁺): 466 [M + H]⁺ |

TABLE 87

| Example | Structure | Instrumental Data |
|---------|-----------|-------------------|
| 2-67 | 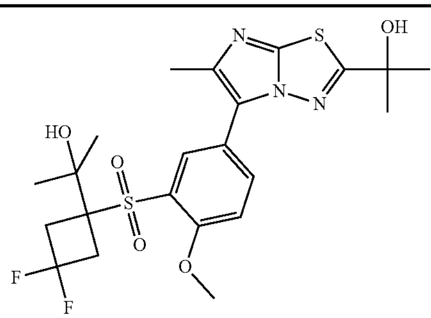 | ¹H-NMR (400 MHz, CDCl₃) δ: 1.46 (6H, s), 1.73 (6H, s), 2.52 (3H, s), 2.53 (1H, s), 2.99 (1H, s), 3.03-3.13 (2H, m), 3.41-3.52 (2H, m), 4.02 (3H, s), 7.18 (1H, d, J = 8.5 Hz), 7.93 (1H, dd, J = 8.5, 2.1 Hz), 8.41 (1H, d, J = 2.1 Hz). MS (ESI⁺): 516 [M + H]⁺ |

TABLE 87-continued

| Example | Structure | Instrumental Data |
|---|---|---|
| 2-68 | 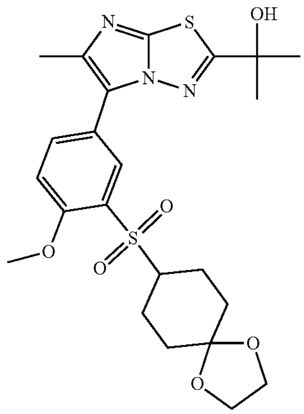 [SMILES: COc1ccc(-c2c(C)nc3sc(C(C)(C)O)nn23)cc1S(=O)(=O)C1CCC2(CC1)OCCO2] | $^1$H-NMR (400 MHz, CDCl$_3$) δ: 1.52-1.60 (2H, m), 1.74 (6H, s), 1.86-2.05 (6H, m), 2.51 (4H, s), 3.42-3.50 (1H, m), 3.93 (4H, s), 4.04 (3H, s), 7.16 (1H, d, J = 8.8 Hz), 7.91 (1H, dd, J = 8.8, 2.4 Hz), 8.32 (1H, d, J = 2.4 Hz). MS (ESI$^+$): 508 [M + H]$^+$ |
| 2-69 | 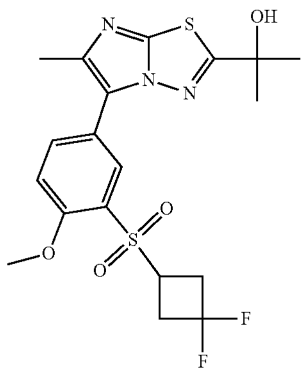 [SMILES: COc1ccc(-c2c(C)nc3sc(C(C)(C)O)nn23)cc1S(=O)(=O)C1CC(F)(F)C1] | $^1$H-NMR (400 MHz, CDCl$_3$) δ: 1.75 (6H, s), 2.52 (4H, s), 2.77-2.88 (2H, m), 3.09-3.22 (2H, m), 4.04 (3H, s), 4.07-4.17 (1H, m), 7.17 (1H, d, J = 8.8 Hz), 7.93 (1H, dd, J = 8.8, 2.4 Hz), 8.36 (1H, d, J = 2.4 Hz). MS (ESI$^+$): 458 [M + H]$^+$ |
| 2-70 | 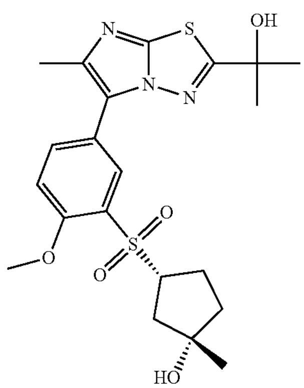 [SMILES: COc1ccc(-c2c(C)nc3sc(C(C)(C)O)nn23)cc1S(=O)(=O)[C@@H]1CC[C@](C)(O)C1] | $^1$H-NMR (400 MHz, CDCl$_3$) δ: 1.36 (3H, s), 1.67-1.71 (1H, m), 1.73 (6H, s), 1.95-2.42 (5H, m), 2.53 (3H, s), 2.82 (1H, s), 3.60 (1H, s), 4.04 (3H, s), 4.20-4.29 (1H, m), 7.17 (1H, d, J = 8.8 Hz), 7.89 (1H, dd, J = 8.8, 2.4 Hz), 8.44 (1H, d, J = 2.4 Hz). MS (ESI$^+$): 466 [M + H]$^+$ |
| 2-71 | 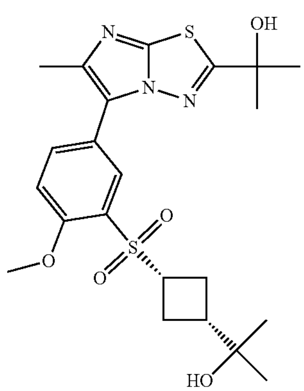 [SMILES: COc1ccc(-c2c(C)nc3sc(C(C)(C)O)nn23)cc1S(=O)(=O)[C@H]1C[C@@H](C(C)(C)O)C1] | $^1$H-NMR (400 MHz, CDCl$_3$) δ: 1.12 (6H, s), 1.66 (1H, s), 1.74 (6H, s), 2.12-2.19 (2H, m), 2.28-2.37 (1H, m), 2.47-2.55 (5H, m), 2.76 (1H, s), 4.02 (3H, s), 4.08-4.17 (1H, m), 7.13 (1H, d, J = 8.8 Hz), 7.87 (1H, dd, J = 8.8, 2.4 Hz), 8.38 (1H, d, J = 2.4 Hz). MS (ESI$^+$): 480 [M + H]$^+$ |

TABLE 87-continued

| Example | Structure | Instrumental Data |
|---|---|---|
| 2-72 | 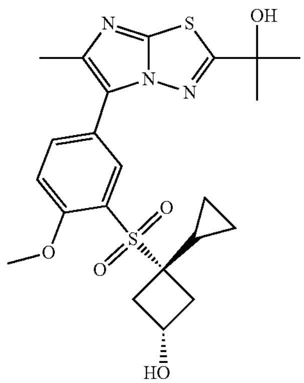 [SMILES: COc1ccc(-c2c(C)nc3sc(C(C)(C)O)nn23)cc1S(=O)(=O)[C@]1(C2CC2)C[C@H](O)C1] | $^1$H-NMR (400 MHz, CDCl$_3$) δ: 0.24 (2H, q, J = 5.7 Hz), 0.41 (2H, q, J = 6.7 Hz), 0.87-0.94 (1H, m), 1.73 (6H, s), 2.27-2.34 (3H, m), 2.51 (3H, s), 2.57 (1H, s), 2.84-2.89 (2H, m), 3.96 (3H, s), 4.11-4.19 (1H, m), 7.11 (1H, d, J = 8.7 Hz), 7.88 (1H, dd, J = 8.7, 2.0 Hz), 8.38 (1H, d, J = 2.0 Hz). MS (ESI$^+$): 478 [M + H]$^+$ |

TABLE 88

| Example | Structure | Instrumental Data |
|---|---|---|
| 2-73 | 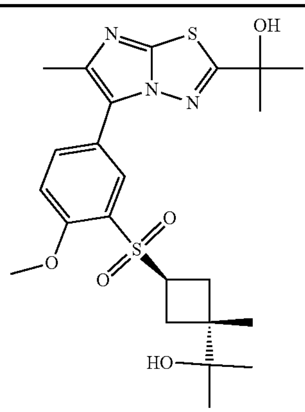 | $^1$H-NMR (400 MHz, CDCl$_3$) δ: 1.15 (6H, s), 1.21 (3H, s), 1.28 (1H, s), 1.74 (6H, s), 2.19-2.24 (2H, m), 2.45-2.50 (2H, m), 2.52 (3H, s), 2.56 (1H, s), 4.00 (3H, s), 4.11-4.18 (1H, m), 7.12 (1H, d, J = 9.1 Hz), 7.86 (1H, dd, J = 9.1, 2.3 Hz), 8.35 (1H, d, J = 2.3 Hz). MS (ESI$^+$): 494 [M + H]$^+$ |
| 2-74 | 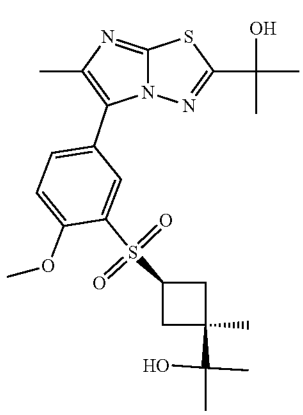 [SMILES: COc1ccc(-c2c(C)nc3sc(C(C)(C)O)nn23)cc1S(=O)(=O)[C@H]1C[C@@](C)(C(C)(C)O)C1] | $^1$H-NMR (400 MHz, CDCl$_3$) δ: 1.09 (6H, s), 1.22 (3H, s), 1.73-1.78 (8H, m), 1.97 (1H, s), 2.52 (3H, s), 2.79-2.85 (3H, m), 4.03 (3H, s), 4.15-4.24 (1H, m), 7.14 (1H, d, J = 8.6 Hz), 7.86 (1H, dd, J = 8.6, 2.4 Hz), 8.40 (1H, d, J = 2.4 Hz). MS (ESI$^+$): 494 [M + H]$^+$ |

TABLE 88-continued

| Example | Structure | Instrumental Data |
|---|---|---|
| 2-75 | 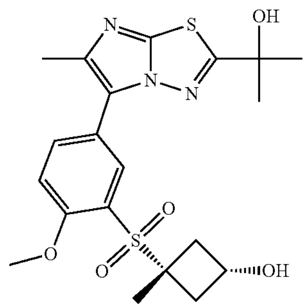 [SMILES: COc1ccc(-c2c(C)nc3sc(C(C)(C)O)nn23)cc1S(=O)(=O)[C@]1(C)C[C@H](O)C1] | $^1$H-NMR (400 MHz, CDCl$_3$) δ: 1.38 (3H, s), 1.73 (6H, s), 2.31 (1H, d, J = 9.1 Hz), 2.42-2.47 (2H, m), 2.51 (3H, s), 2.70 (1H, s), 2.91-2.96 (2H, m), 3.97 (3H, s), 4.30-4.36 (1H, m), 7.13 (1H, d, J = 8.7 Hz), 7.89 (1H, dd, J = 8.7, 2.0 Hz), 8.34 (1H, d, J = 2.0 Hz). MS (ESI$^+$): 452 [M + H]$^+$ |
| 2-76 | 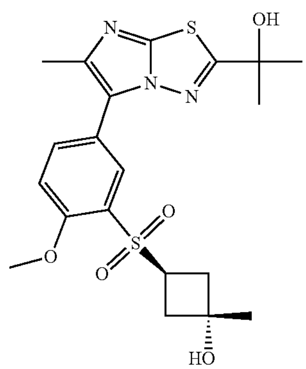 [SMILES: COc1ccc(-c2c(C)nc3sc(C(C)(C)O)nn23)cc1S(=O)(=O)[C@H]1C[C@](C)(O)C1] | $^1$H-NMR (400 MHz, CDCl$_3$) δ: 1.48 (3H, s), 1.66 (1H, s), 1.74 (6H, s), 2.30-2.35 (2H, m), 2.52 (4H, s), 2.61-2.66 (2H, m), 4.02 (3H, s), 4.37-4.46 (1H, m), 7.14 (1H, d, J = 8.6 Hz), 7.89 (1H, dd, J = 8.6, 2.1 Hz), 8.33 (1H, d, J = 2.1 Hz). MS (ESI$^+$): 452 [M + H]$^+$ |
| 2-77 | 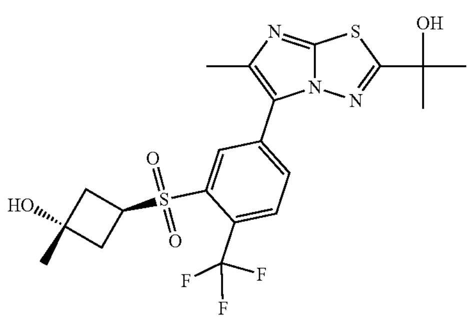 [SMILES: Cc1nc2sc(C(C)(C)O)nn2c1-c1ccc(C(F)(F)F)c(S(=O)(=O)[C@H]2C[C@](C)(O)C2)c1] | $^1$H-NMR (400 MHz, CDCl$_3$) δ: 1.50 (3H, s), 1.67 (1H, s), 1.78 (6H, s), 2.31-2.37 (2H, m), 2.56 (1H, s), 2.62 (3H, s), 2.66-2.72 (2H, m), 4.24-4.32 (1H, m), 7.99 (1H, d, J = 8.0 Hz), 8.06 (1H, d, J = 8.0 Hz), 8.71 (1H, d, J = 1.2 Hz). MS (ESI$^+$): 490 [M + H]$^+$ |
| 2-78 | 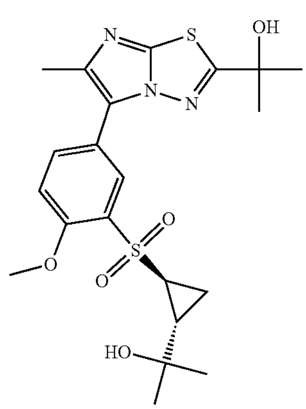 [SMILES: COc1ccc(-c2c(C)nc3sc(C(C)(C)O)nn23)cc1S(=O)(=O)[C@H]1C[C@@H]1C(C)(C)O] | $^1$H-NMR (400 MHz, CDCl$_3$) δ: 1.04 (1H, s), 1.14-1.19 (4H, m), 1.26 (3H, s), 1.37-1.42 (1H, m), 1.74 (6H, s), 1.78-1.83 (1H, m), 2.51 (3H, s), 2.55 (1H, s), 3.03-3.07 (1H, m), 4.06 (3H, s), 7.17 (1H, d, J = 8.9 Hz), 7.89 (1H, dd, J = 8.9, 2.4 Hz), 8.26 (1H, d, J = 2.4 Hz). MS (ESI$^+$): 466 [M + H]$^+$ |

TABLE 89

| Example | Structure | Instrumental Data |
|---------|-----------|-------------------|
| 2-79 | 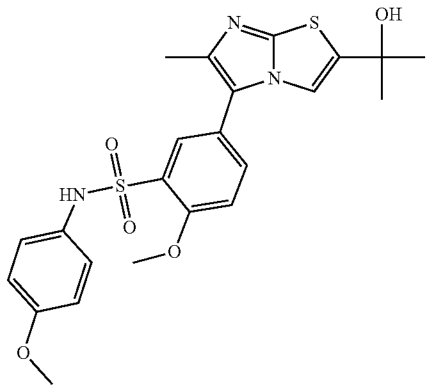 [SMILES: COc1ccc(NS(=O)(=O)c2cc(-c3c(C)nc4sc(C(C)(C)O)cn34)ccc2OC)cc1] | $^1$H-NMR (400 MHz, DMSO-d$_6$) δ: 1.50 (6H, s), 2.17 (3H, s), 3.63 (3H, s), 3.97 (3H, s), 5.74 (1H, s), 6.77 (2H, d, J = 9.1 Hz), 7.03 (2H, d, J = 9.1 Hz), 7.32 (1H, d, J = 8.6 Hz), 7.40 (1H, s), 7.63 (1H, d, J = 2.2 Hz), 7.67 (1H, dd, J = 8.6, 2.2 Hz), 9.79 (1H, s). MS (ESI$^+$): 488 [M + H]$^+$ |
| 2-80 | 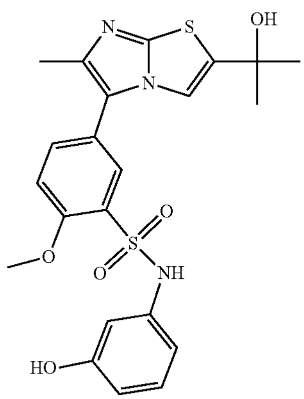 [SMILES: COc1ccc(-c2c(C)nc3sc(C(C)(C)O)cn23)cc1S(=O)(=O)Nc1cccc(O)c1] | $^1$H-NMR (400 MHz, DMSO-d$_6$) δ: 1.50 (6H, s), 2.21 (3H, s), 3.94 (3H, s), 5.74 (1H, s), 6.34 (1H, d, J = 7.3 Hz), 6.54-6.61 (2H, m), 6.95 (1H, t, J = 8.1 Hz), 7.32 (1H, d, J = 8.7 Hz), 7.46 (1H, s), 7.68 (1H, dd, J = 8.7, 2.2 Hz), 7.73 (1H, d, J = 2.2 Hz), 9.38 (1H, s), 10.05 (1H, s). MS (ESI$^+$): 474 [M + H]$^+$ |
| 2-81 | 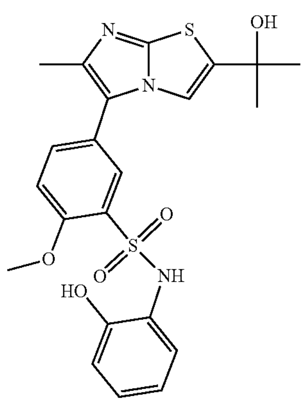 [SMILES: COc1ccc(-c2c(C)nc3sc(C(C)(C)O)cn23)cc1S(=O)(=O)Nc1ccccc1O] | $^1$H-NMR (400 MHz, DMSO-d$_6$) δ: 1.49 (6H, s), 2.16 (3H, s), 3.94 (3H, s), 5.73 (1H, br s), 6.66 (1H, td, J = 7.8, 1.4 Hz), 6.74 (1H, dd, J = 7.8, 1.4 Hz), 6.88 (1H, td, J = 7.8, 1.4 Hz), 7.20 (1H, dd, J = 7.8, 1.4 Hz), 7.34 (1H, d, J = 8.5 Hz), 7.40 (1H, s), 7.65 (1H, d, J = 2.4 Hz), 7.68 (1H, dd, J = 8.5, 2.4 Hz), 8.61 (1H, br s), 9.74 (1H, br s). MS (ESI$^+$): 474 [M + H]$^+$ |
| 2-82 | 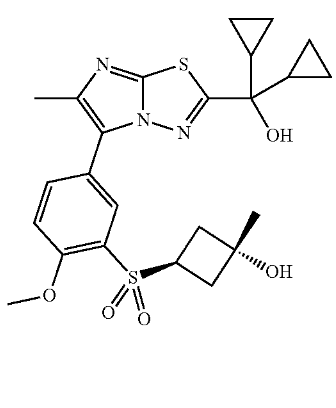 [SMILES: COc1ccc(-c2c(C)nc3sc(C(O)(C4CC4)C4CC4)nn23)cc1S(=O)(=O)[C@H]1C[C@](C)(O)C1] | $^1$H-NMR (400 MHz, CDCl$_3$) δ: 0.50-0.75 (8H, m), 1.37-1.43 (2H, m), 1.51 (3H, s), 1.70 (1H, s), 2.29 (1H, s), 2.32-2.38 (2H, m), 2.55 (3H, s), 2.63-2.69 (2H, m), 4.05 (3H, s), 4.40-4.49 (1H, m), 7.17 (1H, d, J = 8.6 Hz), 7.91 (1H, dd, J = 8.6, 2.4 Hz), 8.41 (1H, d, J = 2.4 Hz). MS (ESI+): 504 [M + H]+. |

TABLE 89-continued

| Example | Structure | Instrumental Data |
|---|---|---|
| 2-83 | 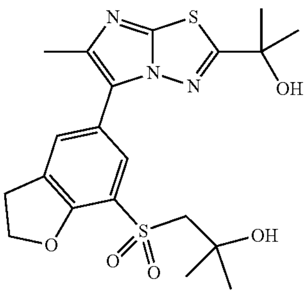 [SMILES: Cc1nc2sc(C(C)(C)O)nn2c1-c1cc2c(c(S(=O)(=O)CC(C)(C)O)c1)OCC2] | ¹H-NMR (400 MHz, CDCl₃) δ: 1.47 (6H, s), 1.76 (6H, s), 2.52 (3H, s), 2.63 (1H, s), 3.42 (2H, t, J = 8.9 Hz), 3.59 (2H, s), 3.69 (1H, s), 4.91 (2H, t, J = 8.6 Hz), 7.75 (1H, s), 8.04 (1H, s). MS (ESI⁺): 452 [M + H]⁺. |
| 2-84 | 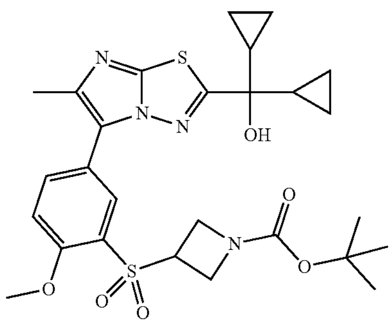 [SMILES: COc1ccc(-c2c(C)nc3sc(C(O)(C4CC4)C4CC4)nn23)cc1S(=O)(=O)C1CN(C(=O)OC(C)(C)C)C1] | ¹H-NMR (400 MHz, CDCl₃) δ: 0.49-0.54 (2H, m), 0.59-0.71 (6H, m), 1.34-1.41 (2H, m), 1.44 (9H, s), 2.34 (1H, s), 2.53 (3H, s), 4.03 (3H, s), 4.08-4.15 (2H, m), 4.31-4.44 (3H, m), 7.16 (1H, d, J = 8.8 Hz), 7.91 (1H, dd, J = 8.8, 2.4 Hz), 8.46 (1H, d, J = 2.4 Hz). MS (ESI⁺): 575 [M + H]⁺ |

TABLE 90

| Example | Structure | Instrumental Data |
|---|---|---|
| 2-85 | 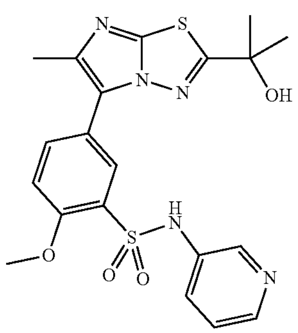 [SMILES: COc1ccc(-c2c(C)nc3sc(C(C)(C)O)nn23)cc1S(=O)(=O)Nc1cccnc1] | ¹H-NMR (400 MHz, DMSO-d₆) δ: 1.56 (6H, s), 2.33 (3H, s), 3.90 (3H, s), 6.42 (1H, s), 7.20 (1H, dd, J = 8.2, 5.1 Hz), 7.32 (1H, d, J = 8.5 Hz), 7.48 (1H, d, J = 7.3 Hz), 7.84 (1H, dd, J = 8.8, 2.1 Hz), 8.12 (1H, d, J = 2.4 Hz), 8.16 (1H, d, J = 3.6 Hz), 8.32 (1H, d, J = 2.4 Hz), 10.39 (1H, s). MS (ESI⁺): 460 [M + H]⁺ |
| 2-86 | 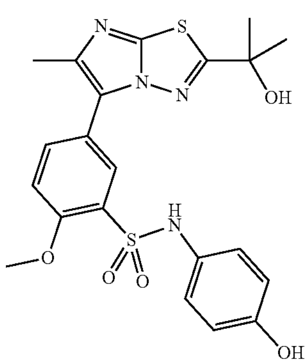 [SMILES: COc1ccc(-c2c(C)nc3sc(C(C)(C)O)nn23)cc1S(=O)(=O)Nc1ccc(O)cc1] | ¹H-NMR (400 MHz, DMSO-d₆) δ: 1.57 (6H, s), 2.32 (3H, s), 3.97 (3H, s), 6.44 (1H, s), 6.53-6.57 (2H, m), 6.88-6.92 (2H, m), 7.33 (1H, d, J = 8.5 Hz), 7.83 (1H, dd, J = 9.1, 2.4 Hz), 7.98 (1H, d, J = 2.4 Hz), 9.20 (1H, s), 9.57 (1H, s). MS (ESI⁺): 475 [M + H]⁺ |

TABLE 90-continued

| Example | Structure | Instrumental Data |
|---|---|---|
| 2-87 | 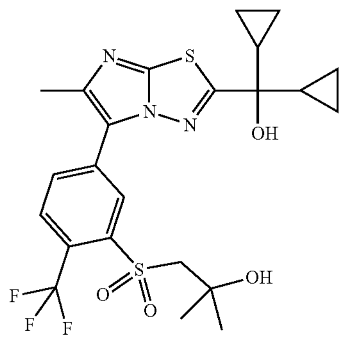 [SMILES: Cc1nc2sc(C(O)(C3CC3)C3CC3)nn2c1-c1ccc(C(F)(F)F)c(S(=O)(=O)CC(C)(C)O)c1] | $^1$H-NMR (400 MHz, CDCl$_3$) δ: 0.50-0.55 (2H, m), 0.62-0.71 (6H, m), 1.38-1.42 (2H, m), 1.50 (6H, s), 2.36 (1H, s), 2.63 (3H, s), 3.50 (2H, s), 3.64 (1H, s), 7.98 (1H, d, J = 8.5 Hz), 8.07 (1H, d, J = 8.5 Hz), 8.89 (1H, d, J = 1.2 Hz). MS (ESI$^+$): 530 [M + H]$^+$ |
| 2-88 | 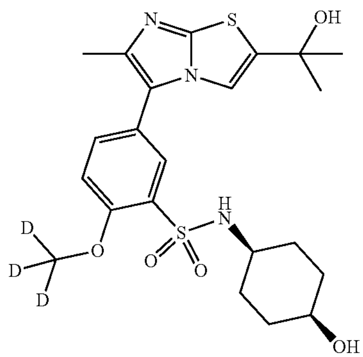 [SMILES: [2H]C([2H])([2H])Oc1ccc(-c2c(C)nc3sc(C(C)(C)O)cn23)cc1S(=O)(=O)N[C@H]1CC[C@@H](O)CC1] | $^1$H-NMR (400 MHz, DMSO-d$_6$) δ: 1.28-1.38 (4H, m), 1.51-1.64 (10H, m), 2.26 (3H, s), 3.03-3.11 (1H, m), 3.57-3.61 (1H, m), 4.32 (1H, d, J = 3.1 Hz), 5.75 (1H, s), 7.32-7.36 (2H, m), 7.51 (1H, s), 7.69-7.74 (2H, m). MS (ESI$^+$): 483 [M + H]$^+$ |
| 2-89 | 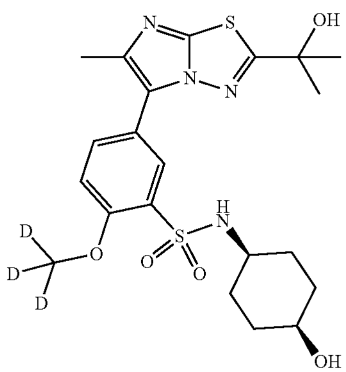 [SMILES: [2H]C([2H])([2H])Oc1ccc(-c2c(C)nc3sc(C(C)(C)O)nn23)cc1S(=O)(=O)N[C@H]1CC[C@@H](O)CC1] | $^1$H-NMR (400 MHz, DMSO-d$_6$) δ: 1.24-1.36 (4H, m), 1.52-1.63 (10H, m), 2.40 (3H, s), 2.99-3.08 (1H, m), 3.56-3.61 (1H, m), 4.31 (1H, d, J = 3.1 Hz), 6.45 (1H, s), 7.28 (1H, d, J = 7.3 Hz), 7.36 (1H, d, J = 8.6 Hz), 7.89 (1H, dd, J = 8.6, 2.4 Hz), 8.10 (1H, d, J = 2.4 Hz). MS (ESI$^+$): 484 [M + H]$^+$ |

TABLE 91

| Example | Structure | Instrumental Data |
|---|---|---|
| 2-90 | 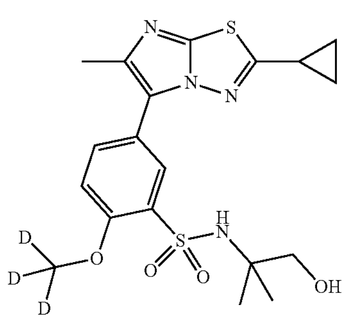 [SMILES: [2H]C([2H])([2H])Oc1ccc(-c2c(C)nc3sc(C4CC4)nn23)cc1S(=O)(=O)NC(C)(C)CO] | $^1$H-NMR (400 MHz, DMSO-d$_6$) δ: 1.02 (6H, s), 1.05-1.09 (2H, m), 1.20-1.25 (2H, m), 2.39 (3H, s), 2.44-2.48 (1H, m), 3.18 (2H, d, J = 6.1 Hz). 4.91 (1H, t, J = 5.8 Hz), 6.67 (1H, s), 7.36 (1H, d, J = 8.6 Hz), 7.86 (1H, dd, J = 8.6, 2.4 Hz), 8.08 (1H, d, J = 1.8 Hz). MS (ESI$^+$): 440 [M + H]$^+$ |

TABLE 91-continued

| Example | Structure | Instrumental Data |
|---|---|---|
| 2-91 | 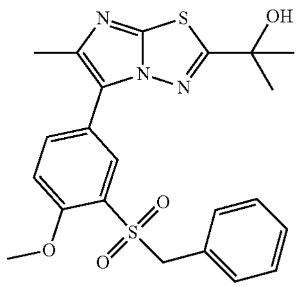 [SMILES: COc1ccc(-c2c(C)nc3sc(C(C)(C)O)nn23)cc1S(=O)(=O)Cc1ccccc1] | ¹H-NMR (400 MHz, DMSO-d₆) δ: 1.55 (6H, s), 2.26 (3H, s), 4.09 (3H, s), 4.76 (2H, s), 6.44 (1H, s), 7.17-7.22 (2H, m), 7.24-7.29 (3H, m), 7.47 (1H, d, J = 8.6 Hz), 7.82 (1H, d, J = 2.4 Hz), 7.96 (1H, dd, J = 9.2, 2.4 Hz). MS (ESI⁺) 458 [M + H]⁺ |
| 2-92 | 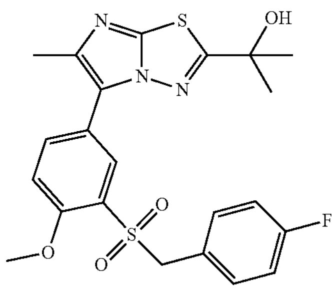 [SMILES: COc1ccc(-c2c(C)nc3sc(C(C)(C)O)nn23)cc1S(=O)(=O)Cc1ccc(F)cc1] | ¹H-NMR (400 MHz, DMSO-d₆) δ: 1.54 (6H, s), 2.27 (3H, s), 4.09 (3H, s), 4.76 (2H, s), 6.44 (1H, s), 7.07-7.13 (2H, m), 7.20-7.26 (2H, m), 7.47 (1H, d, J = 8.5 Hz), 7.82 (1H, d, J = 2.4 Hz), 7.97 (1H, dd, J = 8.5, 2.4 Hz). MS (ESI⁺): 476 [M + H]⁺ |
| 2-93 | 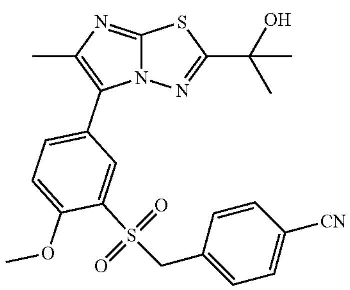 [SMILES: COc1ccc(-c2c(C)nc3sc(C(C)(C)O)nn23)cc1S(=O)(=O)Cc1ccc(C#N)cc1] | ¹H-NMR (400 MHz, DMSO-d₆) δ: 1.54 (6H, s), 2.27 (3H, s), 4.08 (3H, s), 4.91 (2H, s), 6.44 (1H, s), 7.40 (2H, d, J = 8.5 Hz), 7.48 (1H, d, J = 8.5 Hz), 7.76 (2H, d, J = 8.5 Hz), 7.81 (1H, d, J = 2.4 Hz), 7.97 (1H, dd, J = 8.5, 2.4 Hz). MS (ESI⁺): 483 [M + H]⁺ |
| 2-94 | 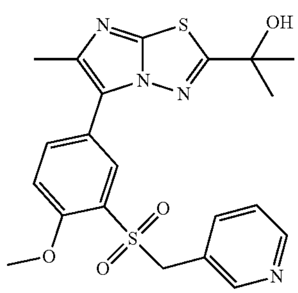 | ¹H-NMR (400 MHz, DMSO-d₆) δ: 1.55 (6H, s), 2.27 (3H, s), 4.09 (3H, s), 4.84 (2H, s), 6.44 (1H, s), 7.31 (1H, dd, J = 7.6, 5.1 Hz), 7.49 (1H, d, J = 8.5 Hz), 7.61-7.65 (1H, m), 7.82 (1H, d, J = 2.4 Hz), 7.98 (1H, dd, J = 9.1, 2.4 Hz), 8.34 (1H, d, J = 1.8 Hz), 8.46 (1H, dd, J = 4.8, 1.2 Hz). MS (ESI⁺): 459 [M + H]⁺ |
| 2-95 | 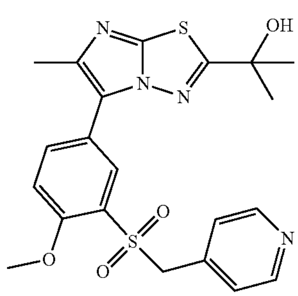 [SMILES: COc1ccc(-c2c(C)nc3sc(C(C)(C)O)nn23)cc1S(=O)(=O)Cc1ccncc1] | ¹H-NMR (400 MHz, DMSO-d₆) δ: 1.55 (6H, s), 2.28 (3H, s), 4.09 (3H, s), 4.85 (2H, s), 6.45 (1H, s), 7.21 (2H, dd, J = 4.2, 1.2 Hz), 7.48 (1H, d, J = 8.5 Hz), 7.85 (1H, d, J = 2.4 Hz), 7.98 (1H, dd, J = 8.5, 2.4 Hz), 8.47 (2H, dd, J = 4.2, 1.8 Hz). MS (ESI⁺): 459 [M + H]⁺ |

TABLE 92
| Example | Structure | Instrumental Data |
|---|---|---|
| 2-96 | 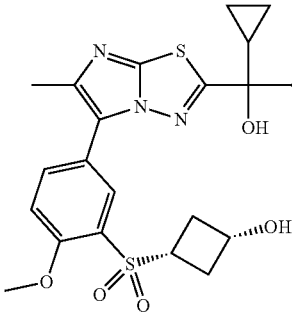 | ¹H-NMR (400 MHz, CDCl₃) δ: 0.48-0.54 (2H, m), 0.59-0.71 (6H, m), 1.34-1.42 (2H, m), 2.26 (1H, s), 2.32 (1H, d, J = 9.1 Hz), 2.42-2.49 (2H, m), 2.53 (3H, s), 2.62-2.71 (2H, m), 3.88-3.96 (1H, m), 4.02 (3H, s), 4.19-4.28 (1H, m), 7.15 (1H, d, J = 8.8 Hz), 7.90 (1H, dd, J = 8.8, 2.4 Hz), 8.41 (1H, d, J = 2.4 Hz).<br>MS (ESI⁺): 490 [M + H]⁺ |
| 2-97 | 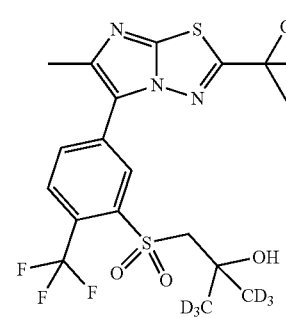 | ¹H-NMR (400 MHz, DMSO-d₆) δ: 1.62 (6H, s), 2.55 (3H, s), 3.55 (2H, s), 4.83 (1H, s), 6.55 (1H, s), 8.12 (1H, d, J = 8.5 Hz), 8.20-8.24 (1H, m), 8.75 (1H, d, J = 1.8 Hz).<br>MS (ESI⁺): 484 [M + H]⁺ |
| 2-98 | 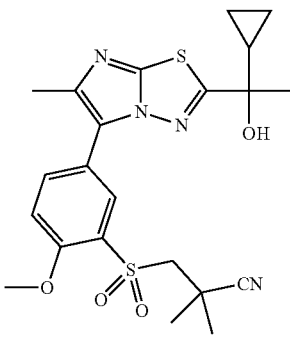 | ¹H-NMR (400 MHz, CDCl₃) δ: 0.48-0.53 (2H, m), 0.58-0.72 (6H, m), 1.33-1.40 (2H, m), 1.61 (6H, s), 2.39 (1H, s), 2.53 (3H, s), 3.63 (2H, s), 4.08 (3H, s), 7.19 (1H, d, J = 8.9 Hz), 7.94 (1H, dd, J = 8.9, 2.4 Hz), 8.46 (1H, d, J = 2.4 Hz).<br>MS (ESI⁺): 501 [M + H]⁺ |

Reference Examples 52-1 to 52-14

A suitable compound of General Formula (3) synthesized in reactions using a suitable compound of General Formula (2) according to any of methods similar to Reference Example 50-1 and the method described in Step A-1 or similar methods thereto was directly used as a crude product to perform reactions according to any of methods similar to Example 1-1 or Example 2-1 and the method described in Step A-2 or similar methods thereto to give the compounds of Reference Examples 52-1 to 52-14 shown below.

TABLE 93

| Reference Example | Structure | Instrumental Data |
|---|---|---|
| 52-1 | 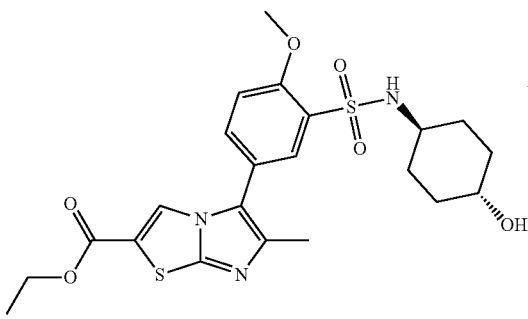 [SMILES: CCOC(=O)c1cn2c(-c3ccc(OC)c(S(=O)(=O)N[C@H]4CC[C@H](O)CC4)c3)c(C)nc2s1] | $^1$H-NMR (400 MHz, DMSO-$d_6$) δ: 1.05-1.11 (2H, m), 1.16-1.26 (2H, m), 1.31 (3H, t, J = 7.3 Hz), 1.59-1.61 (2H, m), 1.71-1.73 (2H, m), 2.31 (3H, s), 2.97-3.02 (1H, m), 3.25-3.32 (1H, m), 3.97 (3H, s), 4.33 (2H, q, J = 7.3 Hz) 4.48 (1H, d, J = 4.2 Hz), 7.35-7.38 (2H, m), 7.80-7.83 (2H, m), 8.37 (1H, s).<br>MS (ESI$^+$): 494 [M + H]$^+$ |
| 52-2 | 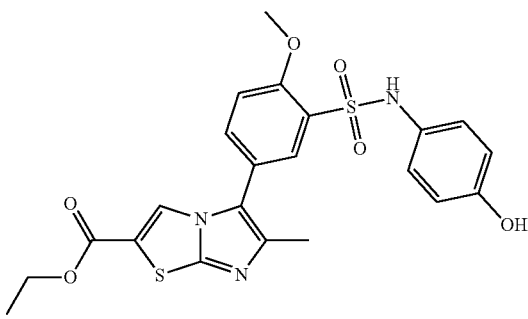 [SMILES: CCOC(=O)c1cn2c(-c3ccc(OC)c(S(=O)(=O)Nc4ccc(O)cc4)c3)c(C)nc2s1] | $^1$H-NMR (400 MHz, CDCl$_3$) δ: 1.40 (3H, t, J = 7.0 Hz), 2.28 (3H, s), 4.12 (3H, s), 4.39 (2H, q, J = 7.1 Hz), 6.68-6.71 (2H, m), 6.92-6.96 (2H, m), 7.16 (1H, d, J = 8.5 Hz), 7.51 (1H, dd, J = 8.5, 2.4 Hz), 7.70 (1H, d, J = 2.4 Hz), 7.77 (1H, s).<br>MS (FD$^+$): 487 [M]$^+$ |
| 52-3 | 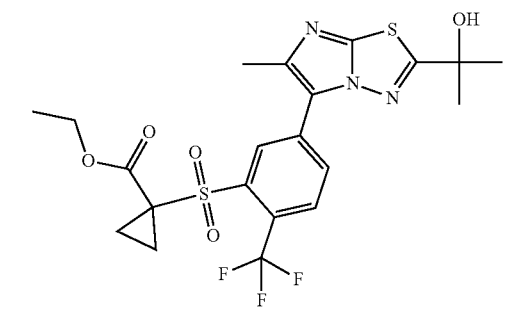 [SMILES: CCOC(=O)C1(S(=O)(=O)c2cc(-c3c(C)nc4sc(C(C)(C)O)nn34)ccc2C(F)(F)F)CC1] | $^1$H-NMR (400 MHz, CDCl$_3$) δ: 0.92 (3H, t, J = 7.2 Hz), 1.77 (6H, s), 1.89 (2H, q, J = 4.4 Hz), 2.13 (2H, q, J = 4.4 Hz), 2.63 (3H, s), 2.77 (1H, s), 4.01 (2H, q, J = 7.2 Hz), 7.97 (1H, d, J = 8.5 Hz), 8.07 (1H, d, J = 8.5 Hz), 8.89 (1H, s).<br>MS (ESI$^+$): 518 [M + H]$^+$ |
| 52-4 | 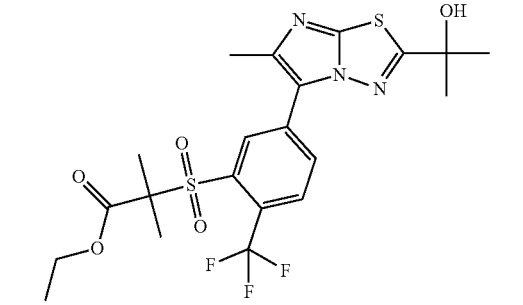 [SMILES: CCOC(=O)C(C)(C)S(=O)(=O)c1cc(-c2c(C)nc3sc(C(C)(C)O)nn23)ccc1C(F)(F)F] | $^1$H-NMR (400 MHz, CDCl$_3$) δ: 1.14 (3H, t, J = 7.2 Hz), 1.73 (6H, s), 1.77 (6H, s), 2.62 (3H, s), 2.72 (1H, s), 4.09 (2H, q, J = 7.2 Hz), 8.00 (1H, d, J = 8.5 Hz), 8.09 (1H, d, J = 8.5 Hz), 8.67 (1H, d, J = 1.8 Hz).<br>MS (ESI$^+$): 520 [M + H]$^+$ |

TABLE 93-continued

| Reference Example | Structure | Instrumental Data |
|---|---|---|
| 52-5 | 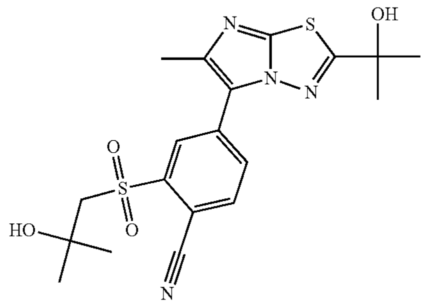 [SMILES: Cc1nc2sc(C(C)(C)O)nn2c1-c1ccc(C#N)c(S(=O)(=O)CC(C)(C)O)c1] | $^1$H-NMR (400 MHz, CDCl$_3$) δ: 1.50 (6H, s), 1.78 (6H, s), 2.60 (1H, s), 2.64 (3H, s), 3.24 (1H, s), 3.64 (2H, s), 7.96 (1H, d, J = 8.2 Hz), 8.11 (1H, dd, J = 8.2, 1.8 Hz), 8.73 (1H, d, J = 1.8 Hz).<br>MS (ESI$^+$): 435 [M + H]$^+$ |
| 52-6 | 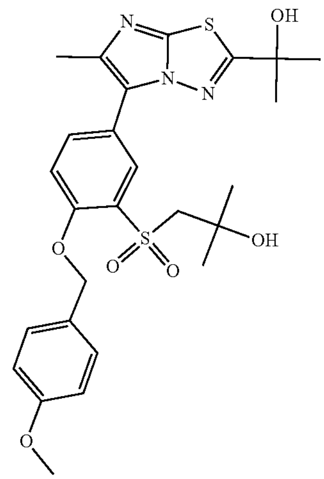 [SMILES: COc1ccc(COc2ccc(-c3c(C)nc4sc(C(C)(C)O)nn34)cc2S(=O)(=O)CC(C)(C)O)cc1] | $^1$H-NMR (400 MHz, CDCl$_3$) δ: 1.35 (6H, s), 1.74 (6H, s), 2.51 (3H, s), 2.58 (1H, s), 3.58 (2H, s), 3.67 (1H, s), 3.83 (3H, s), 5.26 (2H, s), 6.95 (2H, d, J = 8.8 Hz), 7.21 (1H, d, J = 8.5 Hz), 7.45 (2H, d, J = 8.8 Hz), 7.87 (1H, dd, J = 8.5, 2.4 Hz), 8.38 (1H, d, J = 2.4 Hz).<br>MS (ESI$^+$): 546 [M + H]$^+$ |
| 52-7 | 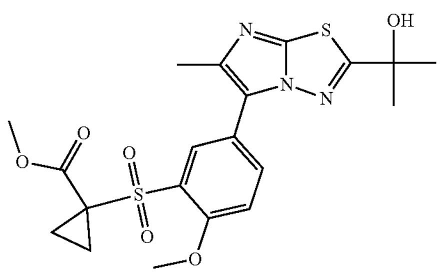 [SMILES: COC(=O)C1(S(=O)(=O)c2cc(-c3c(C)nc4sc(C(C)(C)O)nn34)ccc2OC)CC1] | $^1$H-NMR (400 MHz, DMSO-d$_6$) δ: 1.59 (6H, s), 1.76 (2H, q, J = 4.6 Hz), 1.94 (2H, q, J = 4.6 Hz), 2.44 (3H, s), 3.50 (3H, d, J = 0.6 Hz), 3.95 (3H, s), 6.48 (1H, s), 7.42 (1H, d, J = 8.8 Hz), 8.00 (1H, dd, J = 8.8, 1.5 Hz), 8.29 (1H, d, J = 1.5 Hz).<br>MS (ESI$^+$): 466 [M + H]$^+$ |

TABLE 94

| Reference Example | Structure | Instrumental Data |
|---|---|---|
| 52-8 | 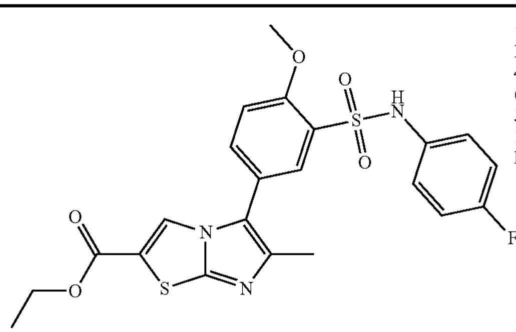 | $^1$H-NMR (400 MHz, DMSO-d$_6$) δ: 1.30 (3H, t, J = 7.2 Hz), 2.22 (3H, s), 3.95 (3H, s), 4.34 (2H, q, J = 7.1 Hz), 7.03-7.09, (2H, m), 7.11-7.17 (2H, m), 7.33 (1H, d, J = 8.6 Hz), 7.75-7.80 (2H, m), 8.27 (1H, s), 10.14 (1H, s).<br>MS (ESI$^+$): 490 [M + H]$^+$ |

TABLE 94-continued

| Reference Example | Structure | Instrumental Data |
|---|---|---|
| 52-9 | 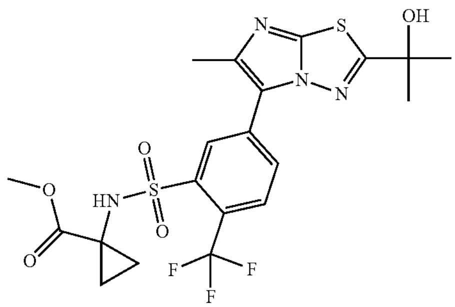 [SMILES: COC(=O)C1(NS(=O)(=O)c2cc(-c3c(C)nc4sc(C(C)(C)O)nn34)ccc2C(F)(F)F)CC1] | $^1$H-NMR (400 MHz, DMSO-d$_6$) δ: 1.22-1.26 (2H, m), 1.32-1.37 (2H, m), 1.62 (6H, s), 2.50-2.51 (3H, m), 3.27 (3H, s), 6.55 (1H, s), 8.09 (1H, d, J = 8.2 Hz), 8.11-8.15 (1H, m), 8.54 (1H, d, J = 1.5 Hz), 8.93 (1H, s).<br>MS (ESI$^+$): 519 [M + H]$^+$ |
| 52-10 | 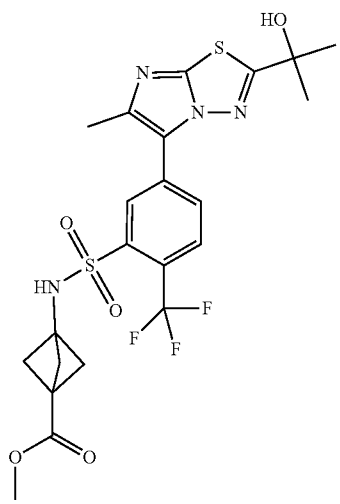 [SMILES: COC(=O)C12CC(NS(=O)(=O)c3cc(-c4c(C)nc5sc(C(C)(C)O)nn45)ccc3C(F)(F)F)(C1)C2] | $^1$H-NMR (400 MHz, DMSO-d$_6$) δ: 1.61 (6H, s), 2.06 (6H, s), 2.53 (3H, s), 3.52 (3H, s), 6.57 (1H, s), 8.09 (1H, d, J = 8.6 Hz), 8.11-8.15 (1H, m), 8.66 (1H, d, J = 1.5 Hz), 9.11 (1H, br s).<br>MS (ESI$^+$): 545 [M + H]$^+$ |
| 52-11 | 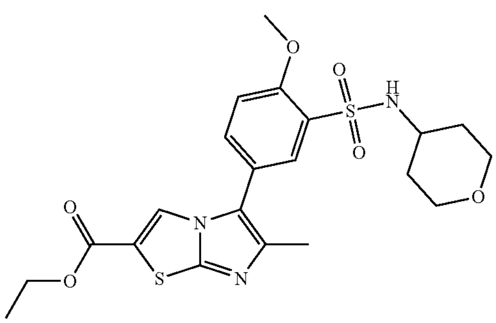 [SMILES: CCOC(=O)c1cn2c(-c3ccc(OC)c(S(=O)(=O)NC4CCOCC4)c3)c(C)nc2s1] | $^1$H-NMR (400 MHz, CDCl$_3$) δ: 1.39 (3H, t, J = 7.0 Hz), 1.49-1.53 (2H, m), 1.73-1.79 (2H, m), 2.42 (3H, s), 3.33-3.44 (3H, m), 3.85-3.90 (2H, m), 4.07 (3H, s), 4.39 (2H, q, J = 7.1 Hz), 4.92 (1H, d, J = 7.3 Hz), 7.19 (1H, d, J = 8.5 Hz), 7.60 (1H, dd, J = 8.5, 2.4 Hz), 7.99 (1H, d, J = 2.4 Hz), 8.06 (1H, s).<br>MS (ESI$^+$): 480 [M + H]$^+$ |
| 52-12 | 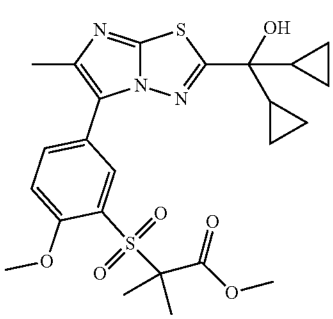 [SMILES: COC(=O)C(C)(C)S(=O)(=O)c1cc(-c2c(C)nc3sc(C(O)(C4CC4)C4CC4)nn23)ccc1OC] | $^1$H-NMR (400 MHz, CDCl$_3$) δ: 0.47-0.52 (2H, m), 0.59-0.69 (6H, m), 1.33-1.40 (2H, m), 1.68 (6H, s), 2.40 (1H, s), 2.52 (3H, s), 3.71 (3H, 5), 3.96 (3H, s), 7.15 (1H, d, J = 8.6 Hz), 7.91 (1H, dd, J = 8.6, 2.4 Hz), 8.32 (1H, d, J = 2.4 Hz).<br>MS (ESI$^+$): 520 [M + H]$^+$ |

TABLE 94-continued

| Reference Example | Structure | Instrumental Data |
|---|---|---|
| 52-13 | 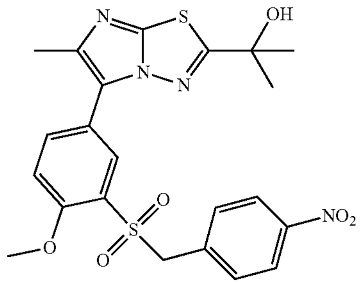 [SMILES: COc1ccc(-c2c(C)nc3sc(C(C)(C)O)nn23)cc1S(=O)(=O)Cc1ccc([N+](=O)[O-])cc1] | $^1$H-NMR (400 MHz, DMSO-$d_6$) δ: 1.51 (6H, s), 2.27 (3H, s), 4.09 (3H, s), 4.99 (2H, s), 6.43 (1H, s), 7.47-7.52 (3H, m), 7.84 (1H, d, J = 1.8 Hz), 7.98 (1H, dd, J = 8.5, 2.4 Hz), 8.13-8.17 (2H, m). MS (ESI$^+$): 503 [M + H]$^+$ |

TABLE 95

| Reference Example | Structure | Instrumental Data |
|---|---|---|
| 52-14 | 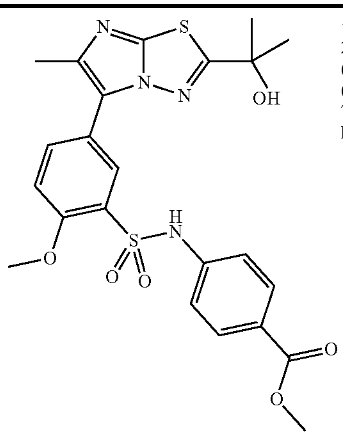 | $^1$H-NMR (400 MHz, CDCl$_3$) δ: 1.74 (6H, s), 2.47 (3H, s), 2.53 (1H, s), 3.84 (3H, s), 4.06 (3H, s), 7.09 (1H, d, J = 8.6 Hz), 7.14-7.18 (3H, m), 7.81 (1H, dd, J = 8.6, 2.4 Hz), 7.86-7.90 (2H, m), 8.28 (1H, d, J = 1.8 Hz). MS (ESI$^+$): 517 [M + H]$^+$ |

Example 3-1

[Formula 98]

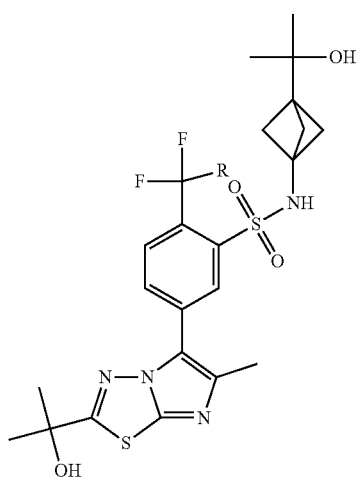

The compound obtained in Reference Example 52-10 (32.7 mg) was dissolved in tetrahydrofuran (0.60 mL) under an argon atmosphere and cooled to 0° C., and 0.95 mol/L methylmagnesium bromide in tetrahydrofuran (0.316 mL) was then added to the mixture dropwise. The mixture was stirred at the same temperature for 1.5 hours and then stirred at room temperature for 3.5 hours. Saturated aqueous ammonium chloride solution (5 mL) and water (5 mL) were added to the reaction mixture, and the mixture was extracted with ethyl acetate (10 mL). The organic layer was washed with saturated brine (10 mL), dried over anhydrous sodium sulfate, and then filtered to remove insoluble residues. The solvent was distilled away under reduced pressure, and the residue was then dissolved in dichloromethane (3 mL) and purified by silica gel column chromatography (ethyl acetate: methanol=99:1 to 90:10) to give the title compound (12.5 mg).

$^1$H-NMR (400 MHz, DMSO-$d_6$) δ: 0.92 (6H, s), 1.61 (6H, s), 1.63 (6H, s), 2.54 (3H, s), 4.07 (1H, s), 6.55 (1H, s), 8.08 (1H, d, J=8.5 Hz), 8.14-8.15 (1H, m), 8.62 (1H, d, J=1.5 Hz), 8.94 (1H, br s). MS (ESI$^+$): 545 [M+H]$^+$.

Examples 3-2 to 3-3

A suitable compound of General Formula (2b) was used to perform reactions according to any of methods similar to Example 3-1 and the method described in Step H-1 or similar methods thereto to give the compounds of Examples 3-2 to 3-3 shown below.

TABLE 96

| Example | Structure | Instrumental Data |
|---|---|---|
| 3-2 | 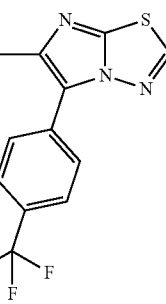 | $^1$H-NMR (400 MHz, DMSO-$d_6$) δ: 0.55-0.59 (2H, m), 0.86-0.91 (2H, m), 1.18 (6H, s), 1.64 (6H, s), 2.48-2.52 (3H, m), 4.26 (1H, s), 6.56 (1H, s), 8.03-8.06 (2H, m), 8.35-8.37 (1H, m), 8.52 (1H, br s). MS (ESI$^+$): 519 [M + H]$^+$ |
| 3-3 | 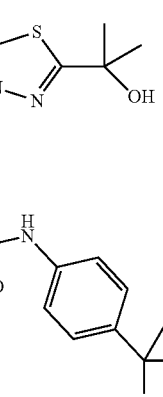 | $^1$H-NMR (400 MHz, DMSO-$d_6$) δ: 1.28 (6H, s), 1.56 (6H, s), 2.32 (3H, s), 3.92 (3H, s), 4.82 (1H, s), 6.43 (1H, s), 7.03 (2H, d, J = 8.6 Hz), 7.24 (2H, d, J = 9.2 Hz), 7.31 (1H, d, J = 9.2 Hz), 7.82 (1H, dd, J = 8.6, 2.4 Hz), 8.09 (1H, d, J = 2.4 Hz), 10.00 (1H, s). MS (ESI$^+$): 517 [M + H]$^+$ |

Example 4-1

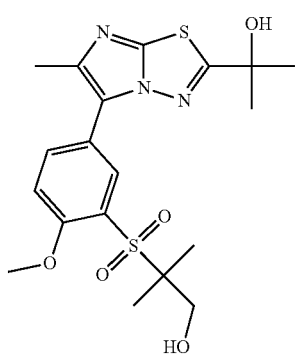

[Formula 99]

Example 1-41 (18.8 mg) was dissolved in tetrahydrofuran (0.400 mL) under an argon atmosphere, and 1.01 mol/L diisobutylaluminum hydride in toluene (0.199 mL) was added to the mixture. The mixture was stirred at room temperature for 5 hours and then left to stand for 14 hours. The reaction was diluted with tetrahydrofuran (0.400 mL), and water (5 mL), (+)-potassium sodium tartrate (100 mg), and ethyl acetate (5 mL) were added to the mixture at room temperature. The mixture was stirred at room temperature for 2 hours. Water (15 mL) and ethyl acetate (15 mL) were added to the mixture, and the mixture was extracted. The organic layer was washed with saturated brine (10 mL), dried over anhydrous sodium sulfate, and filtered to remove insoluble residues. The solvent was distilled away under reduced pressure, and the residue was then dissolved in dichloromethane (3 mL) and purified by silica gel column chromatography (ethyl acetate:methanol=99:1 to 90:10) to give the title compound (14.3 mg).

$^1$H-NMR (400 MHz, DMSO-$d_6$) δ: 1.25 (6H, s), 1.57 (6H, s), 2.41 (3H, s), 3.57 (2H, d, J=5.5 Hz), 3.93 (3H, s), 4.94 (1H, t, J=5.5 Hz), 6.47 (1H, s), 7.43 (1H, d, J=8.7 Hz), 7.97 (1H, dd, J=8.7, 2.1 Hz), 8.10 (1H, d, J=2.1 Hz). MS (ESI$^+$): 440 [M+H]$^+$.

Examples 4-2 to 4-5

A suitable compound of General Formula (2b) was used to perform reactions according to any of methods similar to Example 4-1 and the method described in Step H-2 or similar methods thereto to give the compounds of Examples 4-2 to 4-5 shown below.

TABLE 97

| Example | Structure | Instrumental Data |
|---|---|---|
| 4-2 | 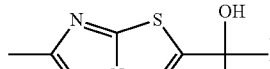 | $^1$H-NMR (400 MHz, CDCl$_3$) δ: 1.17 (2H, dd, J = 7.3, 5.5 Hz), 1.75 (6H, s), 1.81 (2H, dd, J = 6.7, 4.9 Hz), 2.62 (3H, s), 2.89 (1H, t, 4 = 5.8 Hz), 3.35 (1H, s), 3.81 (2H, d, J = 5.5 Hz), 8.00-8.05 (2H, m), 8.81 (1H, s).<br>MS (ESI$^+$): 476 [M + H]$^+$ |
| 4-3 | 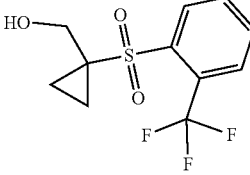 | $^1$H-NMR (400 MHz, CDCl$_3$) δ: 1.43 (6H, s), 1.75 (6H, s), 2.62 (3H, s), 3.37 (1H, t, J = 6.4 Hz), 3.55 (1H, s), 3.89 (2H, d, J = 6.7 Hz), 8.00 (1H, d, J = 8.6 Hz), 8.06 (1H, d, J = 8.6 Hz), 8.71 (1H, d, J = 1.2 Hz).<br>MS (ESI$^+$): 478 [M + H]$^+$ |
| 4-4 | 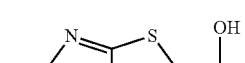 | $^1$H-NMR (400 MHz, DMSO-d$_6$) δ: 1.09 (2H, dd, J = 7.1, 4.6 Hz), 1.43 (2H, dd, J = 7.1, 4.6 Hz), 1.59 (6H, s), 2.42 (3H, s), 3.62 (2H, d, J = 5.8 Hz), 3.94 (3H, s), 4.79 (1H, t, J = 5.8 Hz), 6.47 (1H, s), 7.42 (1H, d, J = 8.7 Hz), 7.96 (1H, dd, J = 8.7, 2.3 Hz), 8.18 (1H, d, J = 2.3 Hz).<br>MS (ESI$^+$): 438 [M + H]$^+$ |
| 4-5 | 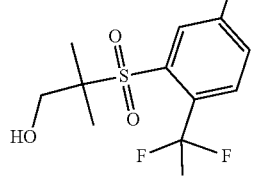 | $^1$H-NMR (400 MHz, DMSO-d$_6$) δ: 0.33-0.41 (2H, m), 0.45-0.62 (6H, m), 1.25 (6H, s), 1.29-1.38 (2H, m), 2.42 (3H, s), 3.56 (2H, d, J = 5.5 Hz), 3.93 (3H, s), 4.93 (1H, t, 3 = 6.1 Hz), 6.01 (1H, s), 7.43 (1H, d, J = 8.6 Hz), 7.98 (1H, dd, J = 8.6, 2.4 Hz), 8.17 (1H, d, J = 2.4 Hz).<br>MS (ESI$^+$): 492 [M + H]$^+$ |

Reference Example 53-1

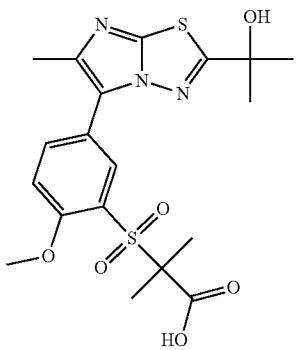

[Formula 100]

The compound obtained in Example 1-41 (199 mg) was suspended in methanol (2.1 mL), and 2 mol/L aqueous sodium hydroxide solution (0.640 mL) was added to the suspension. The mixture was stirred at 50° C. for 2 hours. The solvent was distilled away under reduced pressure, and water (2 mL), 1 mol/L hydrochloric acid (1.28 mL), and water (6 mL) were added followed by collection by filtration. The collected product was dried at 70° C. under reduced pressure to give the title compound (180.9 mg).

$^1$H-NMR (400 MHz, DMSO-$d_6$) δ: 1.50 (6H, s), 1.58 (6H, s), 2.41 (3H, s), 3.89 (3H, s), 6.46 (1H, s), 7.41 (1H, d, J=8.7 Hz), 8.00 (1H, dd, J=8.7, 2.3 Hz), 8.09 (1H, d, J=2.3 Hz), 13.21 (1H, s). MS (ESI$^+$): 454 [M+H]$^+$.

Reference Examples 53-2 to 53-3

A suitable compound of General Formula (2b) was used to perform reactions according to any of methods similar to Reference Example 53-1 and the method described in Step H-3 or similar methods thereto to give the compounds of Examples 53-2 to 53-3 shown below.

TABLE 98

| Reference Example | Structure | Instrumental Data |
|---|---|---|
| 53-2 | (structure) | $^1$H-NMR (400 MHz, DMSO-$d_6$) δ: 0.33-0.41 (2H, m), 0.45-0.62 (6H, m), 1.29-1.38 (2H, m), 1.49 (6H, s), 2.42 (3H, s), 3.89 (3H, s), 6.00 (1H, s), 7.41 (1H, d, J = 8.6 Hz), 8.00 (1H, dd, 4 = 8.6, 2.4 Hz), 8.16 (1H, d, J = 2.4 Hz), 13.21 (1H, br s). MS (ESI$^+$): 506 [M + H]$^+$ |
| 53-3 | (structure) | $^1$H-NMR (400 MHz, DMSO-$d_6$) δ: 0.34-0.42 (2H, m), 0.46-0.62 (6H, m), 1.29-1.38 (2H, m), 1.54 (6H, s). 2.47 (3H, s), 3.95 (3H, d, J = 1.8 Hz), 6.04 (1H, s), 7.99 (1H, dd, J = 12.4, 2.1 Hz), 8.05-8.07 (1H, m), 13.41 (1H, br s). MS (ESI$^+$): 624 [M + H]$^+$ |

Example 5

A suitable compound of General Formula (2b) was used to perform reactions according to any of methods similar to Reference Example 53-1 and the method described in Step H-3 or similar methods thereto to give the compounds of Example 5 shown below.

TABLE 99

| Example | Structure | Instrumental Data |
|---|---|---|
| 5 | 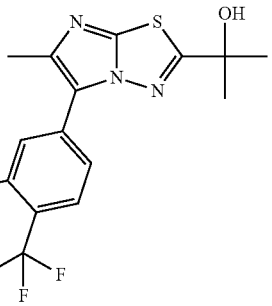 | $^1$H-NMR (400 MHz, DMSO-d$_6$) δ: 1.56 (6H, s), 1.60 (6H, s), 2.54 (3H, s), 6.57 (1H, br), 8.13 (1H, d, J = 8.3 Hz), 8.23 (1H, d, J = 8.3 Hz), 8.64 (1H, s), 13.49 (1H, br).<br>MS (ESI$^+$): 492 [M + H]$^+$ |

Example 6-1

[Formula 101]

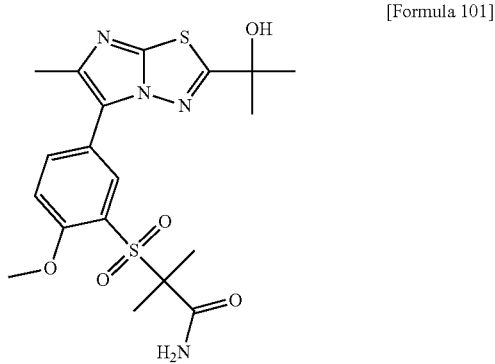 [SMILES: COc1ccc(-c2c(C)nc3sc(C(C)(C)O)nn23)cc1S(=O)(=O)C(C)(C)C(N)=O]

The compound obtained in Reference Example 53-1 (50.0 mg) was dissolved in N,N-dimethylformamide (1.1 mL), and N,N-diisopropylethylamine (0.0576 mL), 1-[bis(dimethylamino)methylene]-1H-1,2,3-triazolo[4,5-b]pyridinium-3-oxid hexafluorophosphate (HATU) (62.9 mg), and ammonium chloride (8.8 mg) were added to the mixture. The mixture was stirred at room temperature for 7.5 hours and left to stand for 15.5 hours. After stirring was resumed, water (10 mL) was added to the mixture and stirred for 1 hour followed by collection by filtration. The collected product was dried at 50° C. under reduced pressure to give the title compound (42.9 mg).

$^1$H-NMR (400 MHz, DMSO-d$_6$) δ: 1.48 (6H, s), 1.58 (6H, s), 2.41 (3H, s), 3.89 (3H, s), 6.46 (1H, s), 7.33 (1H, s), 7.41 (1H, d, J=9.0 Hz), 7.44 (1H, s), 7.99 (1H, dd, J=9.0, 2.4 Hz), 8.05 (1H, d, J=2.4 Hz). MS (ESI$^+$): 453 [M+H]$^+$.

Examples 6-2 to 6-4

A suitable compound of General Formula (2f) was used to perform reactions according to any of methods similar to Example 6-1 and the method described in Step H-4 or similar methods thereto to give the compounds of Examples 6-2 to 6-4 shown below.

TABLE 100

| Example | Structure | Instrumental Data |
|---|---|---|
| 6-2 | 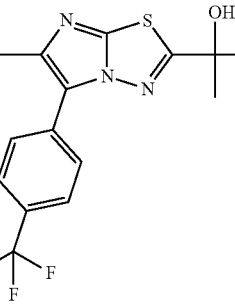 | $^1$H-NMR (400 MHz, CDCl$_3$) δ: 1.68 (6H, s), 1.72 (6H, s), 2.57 (3H, s), 4.66 (1H, s), 6.60 (1H, s), 6.97 (1H, s), 7.94 (1H, d, J = 8.0 Hz), 8.04 (1H, d, J = 8.0 Hz), 8.53 (1H, d, J = 1.8 Hz).<br>MS (ESI$^+$) 491 [M + H]$^+$ |

TABLE 100-continued

| Example | Structure | Instrumental Data |
|---------|-----------|-------------------|
| 6-3 | 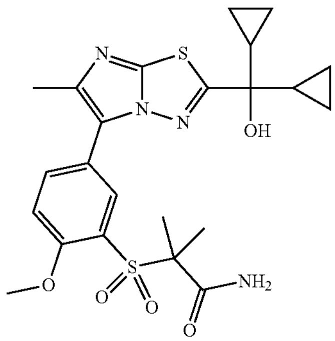 [SMILES: COc1ccc(-c2c(C)nc3sc(C(O)(C4CC4)C4CC4)nn23)cc1S(=O)(=O)C(C)(C)C(N)=O] | $^1$H-NMR (400 MHz, DMSO-d$_6$) δ: 0.34-0.41 (2H, m), 0.45-0.62 (6H, m), 1.30-1.38 (2H, m), 1.47 (6H, s), 2.42 (3H, s), 3.89 (3H, s), 6.00 (1H, s), 7.32 (1H, s), 7.41 (1H, d, J = 9.1 Hz), 7.45 (1H, s), 8.00 (1H, dd, J = 9.1, 2.1 Hz), 8.12 (1H, d, J = 2.1 Hz). MS (ESI$^+$): 505 [M + H]$^+$ |
| 6-4 | 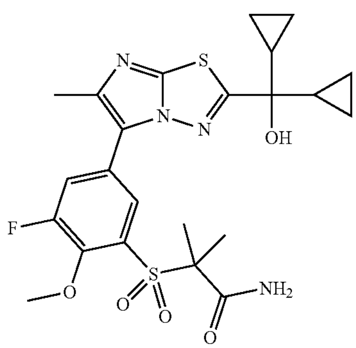 [SMILES: COc1c(F)cc(-c2c(C)nc3sc(C(O)(C4CC4)C4CC4)nn23)cc1S(=O)(=O)C(C)(C)C(N)=O] | $^1$H-NMR (400 MHz, DMSO-d$_6$) δ: 0.35-0.42 (2H, m), 0.47-0.61 (6H, m), 1.30-1.39 (2H, m), 1.52 (6H, s), 2.46 (3H, s), 3.96 (3H, d, J = 2.4 Hz), 6.02 (1H, s), 7.42 (1H, s), 7.52 (1H, s), 7.95-8.01 (2H, m). MS (ESI$^+$): 523 [M + H]$^+$ |

Example 7-1

[Formula 102]

The compound obtained in Example 6-1 (33.9 mg) was suspended in dichloromethane (0.750 mL) under an argon atmosphere, and pyridine (0.0302 mL) and trifluoroacetic anhydride (0.0315 mL) were added to the mixture. The mixture was stirred at room temperature for 7 hours and 30 minutes and left to stand for 15 hours. Dichloromethane (0.750 mL) was added to the mixture, and the mixture was stirred for 1 hour and 30 minutes. Pyridine (0.0302 mL) and trifluoroacetic anhydride (0.0315 mL) were added to the mixture, and the mixture was stirred at room temperature for 5 hours and 30 minutes and left to stand for 17 hours. After stirring for additional 3 hours, saturated aqueous sodium bicarbonate solution (5 mL) and water (10 mL) were added to the mixture. The mixture was extracted with ethyl acetate (15 mL). The organic layer was washed with saturated brine (10 mL), dried over anhydrous sodium sulfate, and filtered to remove insoluble residues. The solvent was distilled away under reduced pressure, and the residue was then dissolved in dichloromethane (4 mL) and purified by silica gel column chromatography (ethyl acetate:methanol=99:1 to 90:10) to give the title compound (14.4 mg).

$^1$H-NMR (400 MHz, DMSO-d$_6$) δ: 1.58 (6H, s), 1.70 (6H, s), 2.43 (3H, s), 3.97 (3H, s), 6.47 (1H, s), 7.54 (1H, d, J=9.0 Hz), 8.12 (1H, dd, J=9.0, 2.3 Hz), 8.21 (1H, d, J=2.3 Hz). MS (ESI$^+$): 435 [M+H]$^+$.

Example 7-2

A suitable compound of General Formula (2e) was used to perform reactions according to any of methods similar to Example 7-1 and the method described in Step H-5 or similar methods thereto to give the compounds of Example 7-2 shown below.

TABLE 101

| Example | Structure | Instrumental Data |
|---|---|---|
| 7-2 | 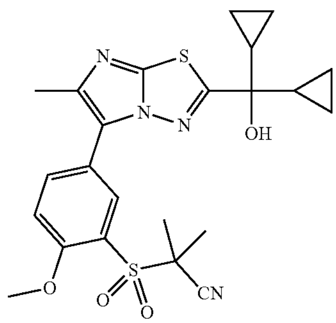 [SMILES: COc1ccc(-c2c(C)nc3sc(C(O)(C4CC4)C4CC4)nn23)cc1S(=O)(=O)C(C)(C)C#N] | $^1$H-NMR (400 MHz, DMSO-$d_6$) δ: 0.33-0.41 (2H, m), 0.45-0.62 (6H, m), 1.30-1.38 (2H, m), 1.70 (6H, s), 2.44 (3H, s), 3.97 (3H, s), 6.00 (1H, s), 7.55 (1H, d, J = 8.5 Hz), 8.12 (1H, dd, J = 9.1, 2.4 Hz), 8.28 (1H, d, J = 2.4 Hz). MS (ESI$^+$) 487 [M + H]$^+$ |

Example 8-1

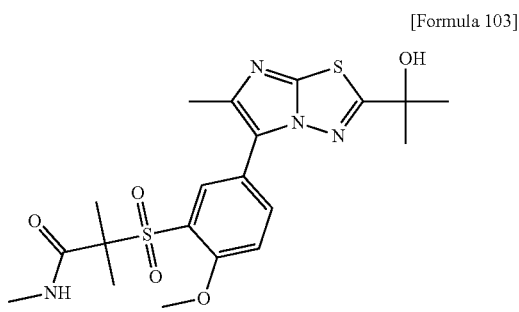 [SMILES: CNC(=O)C(C)(C)S(=O)(=O)c1cc(-c2c(C)nc3sc(C(C)(C)O)nn23)ccc1OC]

[Formula 103]

The compound obtained in Reference Example 53-1 (26.0 mg) was dissolved in N,N-dimethylformamide (0.3 mL), and N,N-diisopropylethylamine (0.0146 mL), 1-[bis(dimethylamino)methylene]-1H-1,2,3-triazolo[4,5-b]pyridinium-3-oxid hexafluorophosphate (HATU) (23.2 mg, 0.0688 mmol), and methylamine (2.0 mol/L in tetrahydrofuran, 0.0573 mL) were added to the mixture. The mixture was stirred at room temperature for 1 hour. The solvent in the reaction was distilled away under reduced pressure, and the residue was purified by silica gel column chromatography (ethyl acetate:methanol=20:1) to give the title compound (15.6 mg).

$^1$H-NMR (400 MHz, CDCl$_3$) δ: 1.60 (6H, s), 1.73 (6H, s), 2.50 (3H, s), 2.60 (1H, s), 2.91 (3H, d, J=4.8 Hz), 3.94 (3H, s), 7.01 (1H, d, J=4.3 Hz), 7.13 (1H, d, J=9.1 Hz), 7.91 (1H, dd, J=9.1, 2.1 Hz), 8.26 (1H, d, J=2.1 Hz). MS (ESI$^+$): 467 [M+H]$^+$.

Examples 8-2 to 8-4

A suitable compound of General Formula (2f) was used to perform reactions according to any of methods similar to Example 8-1 and the method described in Step H-6 or similar methods thereto to give the compounds of Examples 8-2 to 8-4 shown below.

TABLE 102

| Example | Structure | Instrumental Data |
|---|---|---|
| 8-2 | 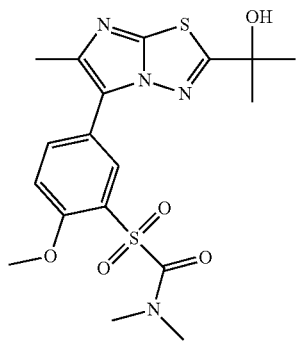 | $^1$H-NMR (400 MHz, CDCl$_3$) δ: 1.72 (6H, s), 1.73 (6H, s), 2.50 (3H, s), 2.64 (1H, s), 2.94-3.47 (6H, m), 3.92 (3H, s), 7.10 (1H, d, J = 8.8 Hz), 7.89 (1H, dd, J = 8.8, 2.0 Hz), 8.23 (1H, d, J = 2.0 Hz) MS (ESI$^+$): 481 [M + H]$^+$ |

TABLE 102-continued

| Example | Structure | Instrumental Data |
|---|---|---|
| 8-3 | 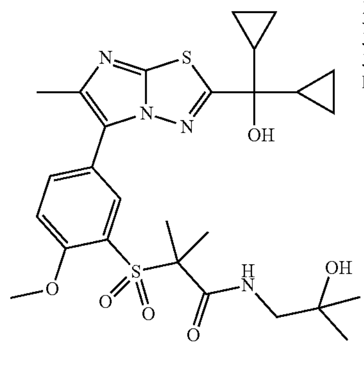 | $^1$H-NMR (400 MHz, DMSO-$d_6$) δ: 0.34-0.41 (2H, m), 0.46-0.62 (6H, m), 1.02 (6H, s), 1.29-1.37 (2H, m), 1.51 (6H, s), 2.42 (3H, s), 3.08 (2H, d, J = 5.4 Hz), 3.90 (3H, s), 4.57 (1H, s), 6.00 (1H, s), 7.43 (1H, d, J = 8.5 Hz), 7.48 (1H, t, J = 5.8 Hz), 8.01 (1H, dd, J = 8.5, 2.4 Hz), 8.14 (1H, d, J = 2.4 Hz). MS (ESI$^+$): 577 [M + H]$^+$ |
| 8-4 | 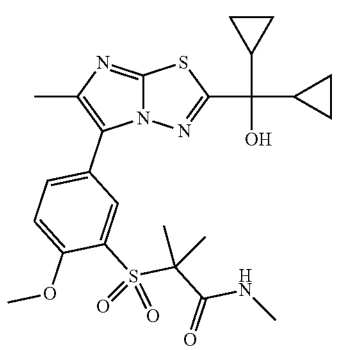 [SMILES: CNC(=O)C(C)(C)S(=O)(=O)c1cc(-c2c(C)nc3sc(C(O)(C4CC4)C4CC4)nn23)ccc1OC] | $^1$H-NMR (400 MHz, DMSO-$d_6$) δ: 0.34-0.41 (2H, m), 0.46-0.61 (6H, m), 1.30-1.38 (2H, m), 1.49 (6H, s), 2.42 (3H, s), 2.60 (3H, d, J = 4.8 Hz), 3.88 (3H, s), 5.99 (1H, s), 7.41 (1H, d, J = 9.1 Hz), 7.88 (1H, q, J = 4.4 Hz), 8.00 (1H, dd, J = 8.5, 2.4 Hz), 8.09 (1H, d, J = 2.4 Hz). MS (ESI$^+$); 519 [M + H]$^+$ |

Reference Example 54-1

[Formula 104]

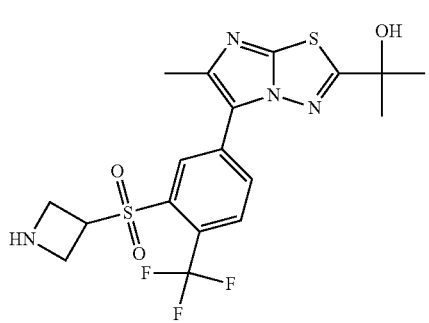

To a solution of the compound obtained in Example 2-36 (26.9 mg) in methylene chloride (1 mL) was added trifluoroacetic acid (0.5 mL) at 0° C., and the mixture was stirred at 0° C. for 1 hour and then stirred at room temperature for 1 hour. The solvent in the reaction mixture was distilled away under reduced pressure followed by addition of saturated aqueous sodium bicarbonate solution, and the mixture was extracted with chloroform/methanol (10:1). The solvent in the organic layer was distilled away under reduced pressure, and the residue was purified by silica gel column chromatography (ethyl acetate:methanol=9:1) to give the title compound (12.9 mg). $^1$H-NMR (400 MHz, CDCl$_3$) δ: 1.77 (6H, s), 2.62 (3H, s), 3.80 (2H, t, J=8.9 Hz), 4.20 (2H, dd, J=9.2, 6.7 Hz), 4.49-4.57 (1H, m), 8.00 (1H, d, J=8.6 Hz), 8.09 (1H, d, J=8.6 Hz), 8.76 (1H, d, J=1.2 Hz). MS (ESI$^+$): 461 [M+H]$^+$.

Reference Examples 54-2 to 54-3

A suitable compound of General Formula (2n) was used to perform reactions according to any of methods similar to Reference Example 54-1 and the method described in Step I-1 or similar methods thereto to give the compounds of Reference Examples 54-2 to 54-3 shown below.

TABLE 103

| Reference Example | Structure | Instrumental Data |
|---|---|---|
| 54-2 | 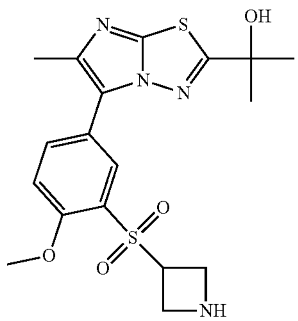 [SMILES: COc1ccc(-c2c(C)nc3sc(C(C)(C)O)nn23)cc1S(=O)(=O)C1CNC1] | $^1$H-NMR (400 MHz, DMSO-$d_6$) δ: 1.59 (6H, s), 2.42 (3H, s), 3.86 (2H, t, J = 9.4 Hz), 3.95-4.02 (5H, m), 4.65-4.74 (1H, m), 6.48 (1H, s), 7.47 (1H, d, J = 8.7 Hz), 8.02 (1H, dd, 1 = 8.7, 2.4 Hz), 8.19 (1H, d, 1 = 2.4 Hz). MS (ESI$^+$): 423 [M + H]$^+$ |
| 54-3 | 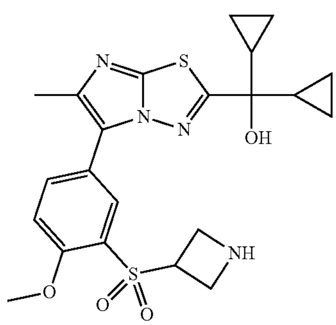 [SMILES: COc1ccc(-c2c(C)nc3sc(C(O)(C4CC4)C4CC4)nn23)cc1S(=O)(=O)C1CNC1] | $^1$H-NMR (400 MHz, CDCl$_3$) δ: 0.48-0.54 (2H, m), 0.59-0.71 (6H, m), 1.34-1.41 (2H, m), 2.53 (3H, s), 2.56 (1H, s), 3.77 (2H, t, J = 8.5 Hz), 3.81-3.84 (1H, m), 4.02 (3H, s), 4.15-4.20 (2H, m), 4.61-4.68 (1H, m), 7.15 (1H, d, J = 8.7 Hz), 7.91 (1H, dd, J = 8.7, 2.3 Hz), 8.41 (1H, d, J = 2.3 Hz). MS (ESI$^+$): 475 [M + H]$^+$ |

Example 9-1

[Formula 105]

To a solution of the compound obtained in Reference Example 54-1 (44.6 mg) and N,N-diisopropylethylamine (0.0329 mL) in methylene chloride (1 mL) was added methane sulfonyl chloride (0.00750 mL) at 0° C., and the mixture was stirred at room temperature for 1 hour. To the reaction mixture were added 2 mol/L aqueous sodium carbonate solution and chloroform/methanol (10:1) at 0° C., and the mixture was stirred for 5 minutes. The resultant insoluble materials were collected by filtration to give the title compound (28.8 mg).

$^1$H-NMR (400 MHz, DMSO-$d_6$) δ: 1.61 (6H, s), 2.54 (3H, s), 3.08 (3H, s), 4.18-4.25 (4H, m), 4.62-4.69 (1H, m), 6.55 (1H, s), 8.20 (1H, d, J=9.2 Hz), 8.25 (1H, d, J=9.2 Hz), 8.74 (1H, d, J=1.8 Hz). MS (ESI$^+$): 539 [M+H]$^+$.

Examples 9-2 to 9-3

A suitable compound of General Formula (2m) was used to perform reactions according to any of methods similar to Example 9-1 and the method described in Step I-3 or similar methods thereto to give the compounds of Examples 9-2 to 9-3 shown below.

TABLE 104

| Example | Structure | Instrumental Data |
|---|---|---|
| 9-2 | 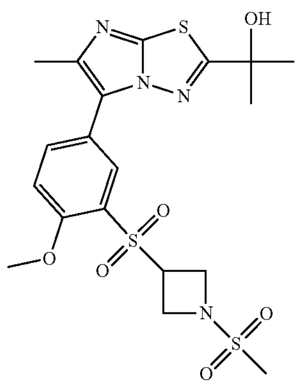 [SMILES: COc1ccc(-c2c(C)nc3sc(C(C)(C)O)nn23)cc1S(=O)(=O)C1CN(S(C)(=O)=O)C1] | $^1$H-NMR (400 MHz, DMSO-$d_6$) δ: 1.58 (6H, s), 2.42 (3H, s), 3.07 (3H, s), 3.99 (3H, s), 4.13-4.21 (4H, m), 4.61-4.70 (1H, m), 6.47 (1H, s), 7.48 (1H, d, J = 8.7 Hz), 8.03 (1H, dd, J = 8.7, 2.3 Hz), 8.22 (1H, d, J = 2.3 Hz). MS (ESI$^+$): 501 [M + H]$^+$ |
| 9-3 | 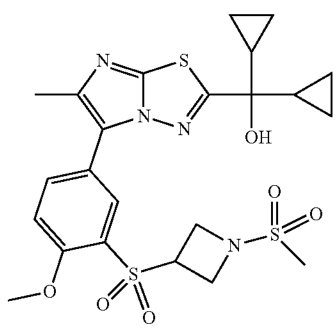 [SMILES: COc1ccc(-c2c(C)nc3sc(C(O)(C4CC4)C4CC4)nn23)cc1S(=O)(=O)C1CN(S(C)(=O)=O)C1] | $^1$H-NMR (400 MHz, CDCl$_3$) δ: 0.48-0.54 (2H, m), 0.59-0.71 (6H, m), 1.34-1.41 (2H, m), 2.54 (3H, 3), 2.99 (3H, s), 4.04 (3H, s), 4.23 (2H, t, J = 9.2 Hz), 4.34 (2H, dd, J = 9.8, 6.1 Hz), 4.43-4.50 (1H, m), 7.18 (1H, d, J = 8.8 Hz), 7.94 (1H, dd, J = 8.8, 2.3 Hz), 8.44 (1H, d, J = 2.3 Hz). MS (ESI$^+$): 553 [M + H]$^+$ |

Example 10-1

[Formula 106]

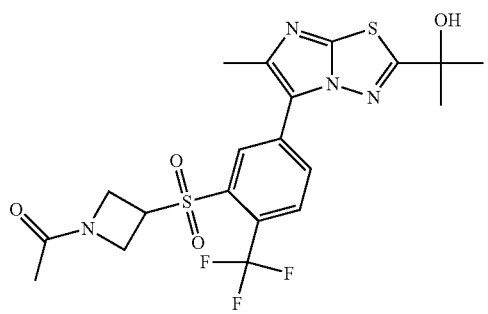

To a solution of the compound obtained in Reference Example 54-1 (37.4 ml) and N,N-diisopropylethylamine (0.0329 mL) in methylene chloride (0.8 mL) was added acetic anhydride (0.00920 mL) at 0° C., and the mixture was stirred at room temperature for 1 hour. To the reaction mixture was added 2 mol/L aqueous sodium carbonate solution, and the mixture was extracted with chloroform/methanol (10:1). The solvent in the organic layer was distilled away under reduced pressure, and the residue was purified by silica gel column chromatography (ethyl acetate:methanol=20:1) to give the title compound (30.5 mg).

$^1$H-NMR (400 MHz, CDCl$_3$) δ: 1.75 (3H, s), 1.79 (3H, s), 1.93 (3H, s), 2.61 (3H, d, J=1.2 Hz), 3.81 (1H, s), 4.08-4.13 (1H, m), 4.28-4.33 (1H, m), 4.40-4.47 (2H, m), 4.67-4.70 (1H, m), 8.01 (2H, s), 8.85 (1H, s). MS (ESI$^+$): 503 [M+H]$^+$.

Examples 10-2 to 10-3

A suitable compound of General Formula (2m) was used to perform reactions according to any of methods similar to Example 10-1 and the method described in Step I-4 or similar methods thereto to give the compounds of Examples 10-2 to 10-3 shown below.

TABLE 105

| Example | Structure | Instrumental Data |
|---|---|---|
| 10-2 | 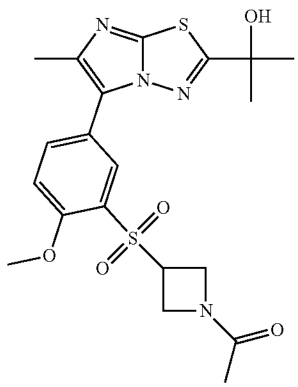 [SMILES: COc1ccc(-c2c(C)nc3sc(C(C)(C)O)nn23)cc1S(=O)(=O)C1CN(C(C)=O)C1] | ¹H-NMR (400 MHz, CDCl₃) δ: 1.75 (6H, s), 1.90 (3H, s), 2.52 (3H, s), 2.75 (1H, s), 4.04 (3H, s), 4.13-4.17 (1H, m), 4.31-4.37 (2H, m), 4.42-4.48 (1H, m), 4.58-4.61 (1H, m), 7.18 (1H, d, J = 8.5 Hz), 7.93 (1H, dd, J = 8.5, 2.4 Hz), 8.40 (1H, d, J = 2.4 Hz). MS (ESI⁺): 465 [M + H]⁺ |
| 10-3 | 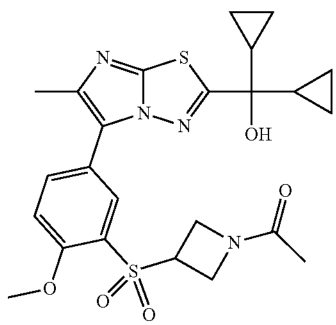 [SMILES: COc1ccc(-c2c(C)nc3sc(C(O)(C4CC4)C4CC4)nn23)cc1S(=O)(=O)C1CN(C(C)=O)C1] | ¹H-NMR (400 MHz, CDCl₃) δ: 0.49-0.54 (2H, m), 0.59-0.70 (6H, m), 1.33-1.40 (2H, m), 1.90 (3H, s), 2.40 (1H, s), 2.54 (3H, s), 4.04 (3H, s), 4.12-4.18 (1H, m), 4.32-4.37 (2H, m), 4.42-4.49 (1H, m), 4.58-4.61 (1H, m), 7.18 (1H, d, J = 8.6 Hz), 7.93 (1H, dd, J = 8.6, 2.4 Hz), 8.45 (1H, d, J = 2.4 Hz). MS (ESI⁺): 517 (M + H)⁺ |

Example 11

[Formula 107]

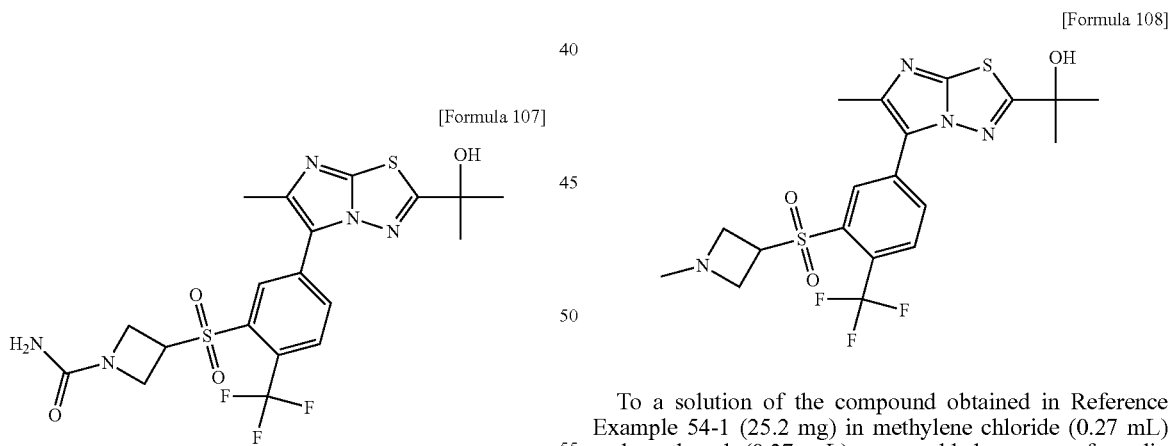

To a solution of the compound obtained in Reference Example 54-1 (20.0 mg) in methylene chloride (0.8 mL) was added isocyanatotrimethylsilane (10.0 mg) at 0° C., and the mixture was stirred at room temperature for 2.5 hours. Water (1 mL) was added to the reaction mixture, and the resultant insoluble materials were collected by filtration to give the title compound (16.3 mg).

¹H-NMR (400 MHz, CDCl₃) δ: 1.62 (6H, s), 2.55 (3H, s), 4.04-4.05 (4H, m), 4.50-4.57 (1H, m), 6.08 (2H, s), 6.54 (1H, s), 8.20 (1H, d, J=9.1 Hz), 8.26 (1H, d, J=9.1 Hz), 8.71 (1H, d, J=1.8 Hz). MS (ESI⁺): 504 [M+H]⁺.

Example 12-1

[Formula 108]

To a solution of the compound obtained in Reference Example 54-1 (25.2 mg) in methylene chloride (0.27 mL) and methanol (0.27 mL) were added aqueous formalin solution (37%, 0.00670 mL) and sodium triacetoxyborohydride (17.4 mg) at 0° C., and the mixture was stirred at room temperature for 1.5 hours. Saturated aqueous sodium bicarbonate solution was added to the reaction, and the mixture was extracted with methylene chloride. The solvent in the organic layer was distilled away under reduced pressure, and the residue was purified by silica gel column chromatography (ethyl acetate) to give the title compound (15.3 mg).

¹H-NMR (400 MHz, CDCl₃) δ: 1.78 (6H, s), 2.38 (3H, s), 2.62 (3H, s), 2.87 (1H, s), 3.56-3.63 (4H, m), 4.25-4.32 (1H, m), 7.99 (1H, d, J=8.6 Hz), 8.07 (1H, d, J=8.6 Hz), 8.75 (1H, d, J=1.8 Hz). MS (ESI⁺): 475 [M+H]⁺.

Example 12-2

A suitable compound of General Formula (2m) was used to perform reactions according to any of methods similar to Example 12-1 and the method described in Step I-6 or similar methods thereto to give the compound of Example 12-2 shown below.

TABLE 106

| Example | Structure | Instrumental Data |
|---|---|---|
| 12-2 | 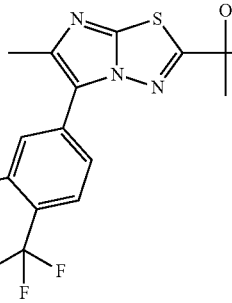 | $^1$H-NMR (400 MHz, CDCl$_3$) δ: 1.78 (6H, s), 2.62 (3H, s), 2.70 (2H, t, J = 5.1 Hz), 3.55 (2H, t, J = 5.1 Hz), 3.67 (4H, dt, J = 18.4, 7.9 Hz), 4.31-4.39 (1H, m), 8.00 (1H, d, J = 8.2 Hz), 8.06 (1H, d, J = 8.2 Hz), 8.79 (1H, d, J = 1.8 Hz). MS (ESI$^+$): 505 [M + H]$^+$ |

Example 13

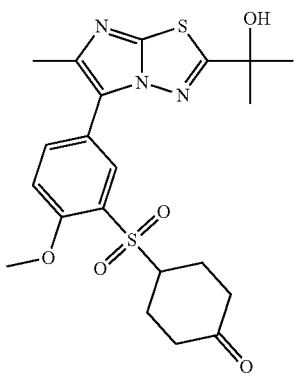

[Formula 109]

To a solution of the compound obtained in Example 2-(138 mg) in acetone (4 mL) was added 3 mol/L hydrochloric acid (2 mL) at 0° C., and the mixture was stirred at room temperature for 5 hours under an argon atmosphere. Saturated aqueous sodium bicarbonate solution was added to the reaction mixture, and the mixture was extracted with chloroform/methanol (10:1). The organic layer was distilled away under reduced pressure, and the residue was purified by silica gel column chromatography (ethyl acetate:methanol=20:1) to give the title compound (126 mg).

$^1$H-NMR (400 MHz, CDCl$_3$) δ: 1.74 (6H, s), 2.12-2.23 (2H, m), 2.28-2.41 (4H, m), 2.45 (1H, s), 2.52 (3H, s), 2.60-2.68 (2H, m), 3.83-3.91 (1H, m), 4.07 (3H, s), 7.20 (1H, d, J=8.8 Hz), 7.94 (1H, dd, J=8.8, 2.4 Hz), 8.36 (1H, d, J=2.4 Hz). MS (ESI$^+$): 464 [M+H]$^+$.

Reference Example 55

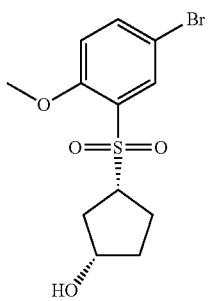

[Formula 110]

To a solution of the compound obtained in Reference Example 35 (123 mg) in methanol in tetrahydrofuran (1:1, 4.2 mL) was added sodium tetrahydroborate (15.9 mg, 0.420 mmol) at 0° C., and the mixture was stirred at room temperature for 30 minutes under an argon atmosphere. Saturated aqueous sodium bicarbonate solution and acetone were added to the reaction mixture, and the mixture was extracted with ethyl acetate. The solvent in the organic layer was distilled away under reduced pressure, and the residue was purified by silica gel column chromatography (ethyl acetate) to give the title compound (128 mg).

$^1$H-NMR (400 MHz, CDCl$_3$) δ: 1.73-1.82 (1H, m), 1.91-1.98 (2H, m), 2.16-2.23 (3H, m), 2.87-2.92 (1H, m), 3.97 (3H, s), 4.09-4.19 (1H, m), 4.33 (1H, s), 6.96 (1H, d, J=9.1 Hz), 7.68-7.71 (1H, m), 8.08-8.09 (1H, m). MS (ESI$^+$): 335 [M+H]$^+$.

Example 14

A suitable compound of General Formula (2r) was used to perform reactions according to any of methods similar to Reference Example 55 and the method described in Step J-2 or similar methods thereto to give a mixture of cis- and trans-isomers of the compound of Example 14 shown below.

TABLE 107

| Example | Structure | Instrumental Data |
|---|---|---|
| 14 | 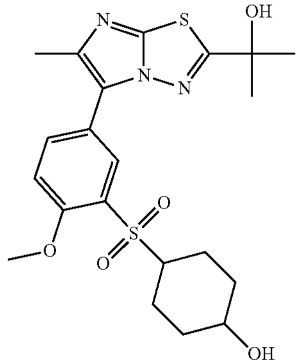 [SMILES: COc1ccc(-c2c(C)nc3sc(C(C)(C)O)nn23)cc1S(=O)(=O)C1CCC(O)CC1] | Main Product<br>$^1$H-NMR (400 MHz, CDCl$_3$) δ: 1.24-2.14 (14H, m), 2.54 (3H, s), 2.66 (1H, s), 3.39-3.47 (1H, m), 3.62-3.69 (1H, m), 4.07 (3H, s), 7.20 (1H, d, J = 8.8 Hz), 7.83 (1H, dd, J = 8.8, 2.1 Hz), 8.25 (1H, d, J = 2.1 Hz).<br>MS (ESI$^+$): 466 [M + H]$^+$ |

Reference Example 56

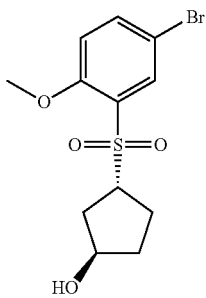

[Formula 111]

To a solution of the compound obtained in Reference Example 55 (78.7 mg), 4-nitrobenzoic acid (47.1 mg), and triphenylphosphine (92.5 mg) in tetrahydrofuran (1.2 mL) was added diisopropyl azodicarboxylate (0.0694 mL) at 0° C., and the mixture was stirred at room temperature for 3 hours under an argon atmosphere. The solvent in the reaction mixture was distilled away under reduced pressure, and the residue was purified by silica gel column chromatography (hexane:ethyl acetate=1:1). The resulting residue was dissolved in methanol (2.4 mL). Potassium carbonate (97.3 mg) was added to the reaction mixture at room temperature, and the mixture was stirred at room temperature for 16 hours. Ethyl acetate was added to the reaction, and the mixture was filtered with Celite. The solvent in the filtrate was distilled away under reduced pressure, and the residue was purified by silica gel column chromatography (ethyl acetate) to give the title compound (63.4 mg).

$^1$H-NMR (400 MHz, CDCl$_3$) δ: 1.43 (1H, s), 1.71-1.77 (1H, m), 1.90-2.05 (2H, m), 2.09-2.15 (2H, m), 2.19-2.26 (1H, m), 3.97 (3H, s), 4.24-4.32 (1H, m), 4.54 (1H, s), 6.94 (1H, d, J=8.6 Hz), 7.68 (1H, dd, J=8.6, 2.4 Hz), 8.06 (1H, d, J=2.4 Hz). MS (CI$^+$): 335 [M+H]$^+$.

Reference Example 57

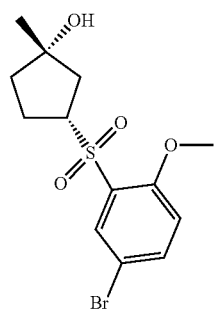

[Formula 112]

To a solution of the compound obtained in Reference Example 35 (72.0 mg) in tetrahydrofuran (2.2 mL) was added methylmagnesium bromide (0.98 mol/L in tetrahydrofuran, 0.331 mL) at 0° C., and the mixture was stirred at 0° C. for 20 minutes under an argon atmosphere and then stirred at room temperature for 17 hours. Saturated aqueous ammonium chloride solution was added to the reaction mixture, and the mixture was extracted with ethyl acetate. The solvent in the organic layer was distilled away under reduced pressure, and the residue was purified by silica gel column chromatography (ethyl acetate) to give the title compound (9.9 mg).

$^1$H-NMR (400 MHz, CDCl$_3$) δ: 1.37 (3H, s), 1.61-1.69 (1H, m), 1.92-2.05 (3H, m), 2.17-2.31 (2H, m), 3.27 (1H, s), 3.97 (3H, s), 4.17-4.25 (1H, m), 6.95 (1H, d, J=8.8 Hz), 7.70 (1H, dd, J=8.8, 2.4 Hz), 8.10 (1H, d, J=2.4 Hz).

Examples 15-1 to 15-2

A suitable compound of General Formula (2r) was used to perform reactions according to any of methods similar to Reference Example 57 and the method described in Step J-4 or similar methods thereto to give the compounds of Examples 15-1 to 15-2 shown below.

TABLE 108

| Example | Structure | Instrumental Data |
|---|---|---|
| 15-1 | 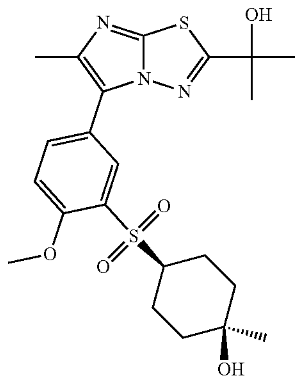 [SMILES: COc1ccc(-c2c(C)nc3sc(C(C)(C)O)nn23)cc1S(=O)(=O)[C@H]1CC[C@@](C)(O)CC1] | $^1$H-NMR (400 MHz, CDCl$_3$) δ: 1.24 (3H, s), 1.39-1.46 (2H, m), 1.74 (6H, s), 1.78-1.87 (4H, m), 1.96-2.06 (2H, m), 2.51 (4H, s), 3.35-3.44 (1H, m), 4.03 (3H, s), 7.16 (1H, d, J = 8.7 Hz), 7.91 (1H, dd, J = 8.7, 2.0 Hz), 8.33 (1H, d, J = 2.0 Hz). MS (ESI$^+$): 480 [M + H]$^+$ |
| 15-2 | 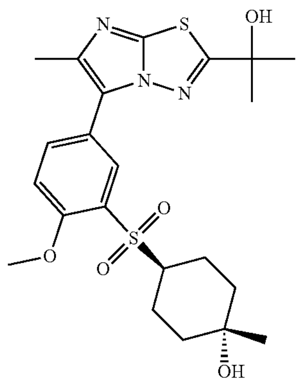 [SMILES: COc1ccc(-c2c(C)nc3sc(C(C)(C)O)nn23)cc1S(=O)(=O)[C@H]1CC[C@](C)(O)CC1] | $^1$H-NMR (400 MHz, CDCl$_3$) δ: 1.29 (3H, s), 1.31 (1H, s), 1.46-1.53 (2H, m), 1.74 (6H, s), 1.78-1.91 (4H, m), 1.99-2.04 (2H, m), 2.45 (1H, s), 2.52 (3H, s), 3.46-3.53 (1H, m), 4.03 (3H, s), 7.17 (1H, d, J = 8.8 Hz), 7.92 (1H, dd, J = 8.8, 2.4 Hz), 8.31 (1H, d, J = 2.4 Hz). MS (ESI$^+$): 480 [M + H]$^+$ |

Example 16

[Formula 113]

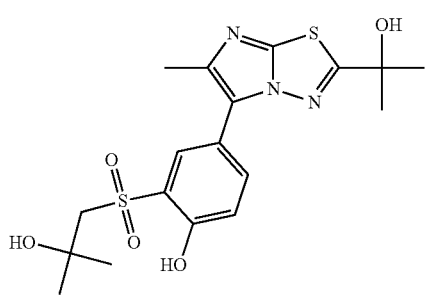

To a solution of the compound obtained in Reference Example 52-6 (44.1 mg) in methylene chloride (0.8 mL) were added trifluoroacetic acid (0.4 mL) and anisole (0.0437 mL) at 0° C., and the mixture was stirred at room temperature for 0.5 hours under an argon atmosphere. The solvent in the reaction mixture was distilled away under reduced pressure, and the residue was purified by silica gel column chromatography (ethyl acetate:methanol=20:1) to give the title compound (30.9 mg).

$^1$H-NMR (400 MHz, CDCl$_3$) δ: 1.44 (6H, s), 1.69 (6H, s), 2.48 (3H, s), 3.61 (2H, s), 7.12 (1H, d, J=8.5 Hz), 7.78 (1H, dd, J=8.5, 2.4 Hz), 8.17 (1H, d, J=2.4 Hz). MS (ESI$^+$): 426 [M+H]$^+$.

Example 17

[Formula 114]

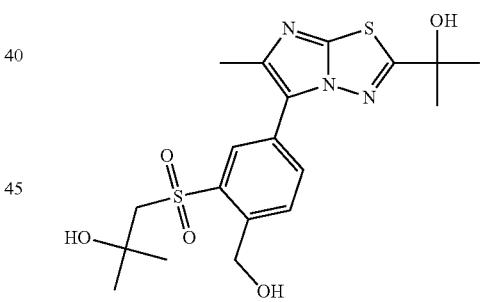

To a solution of the compound obtained in Reference Example 52-5 (53.7 mg) in methylene chloride (1.2 mL) was added diisobutylaluminum hydride (1.0 mol/L in hexane, 0.494 mL) with ice cooling, and the mixture was stirred at room temperature for 2 hours under an argon atmosphere. To the reaction mixture was added 10% aqueous tartaric acid solution with ice cooling, and the mixture was stirred and then extracted with chloroform:methanol (10:1). The solvent in the organic layer was distilled away under reduced pressure, and the residue was passed through silica gel column chromatography (ethyl acetate). The product with impurities was used in the next step. To a solution of a part of the residue (7.3 mg) in methanol (0.2 mL) and methylene chloride (0.4 mL) was added sodium tetrahydroborate (0.63 mg) at 0° C., and the mixture was stirred at room temperature for 7 hours under an argon atmosphere. Saturated aqueous sodium bicarbonate solution was added to the reaction mixture at 0° C., and the mixture was extracted with chloroform:methanol (10:1). The solvent in the organic layer was distilled away under reduced pressure, and the residue was purified by silica gel column chromatography (ethyl acetate) to give the title compound (3.2 mg).

¹H-NMR (400 MHz, CDCl₃) δ: 1.49 (6H, s), 1.75 (6H, s), 2.57 (3H, s), 2.77 (1H, s), 3.02-3.07 (1H, m), 3.52 (2H, s), 3.61 (1H, s), 5.01 (2H, d, J=6.1 Hz), 7.67 (1H, d, J=8.1 Hz), 7.96 (1H, dd, J=8.1, 2.0 Hz), 8.51 (1H, d, J=2.0 Hz). MS (ESI⁺): 440 [M+H]⁺.

Example 18-1

[Formula 115]

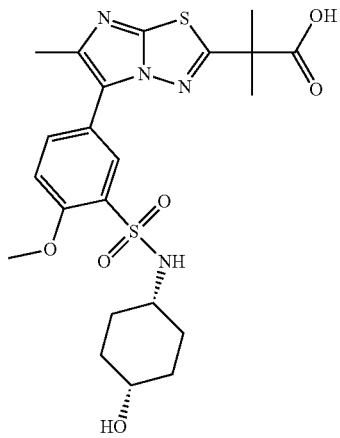

Example 18-2

To a solution of the compound obtained in Example 1-(44.7 mg) in tetrahydrofuran (0.3 mL) and ethanol (0.3 mL) was added aqueous sodium hydroxide solution (2.0 mol/L, 0.3 mL), and the mixture was stirred at 50° C. for 1 hour under an argon atmosphere. The solvent in the reaction was distilled away under reduced pressure, and 10% aqueous citric acid solution was added to the residue at 0° C. The resulting solid was collected by filtration, and the solid was washed with water to give the title compound (33.2 mg).

¹H-NMR (400 MHz, DMSO-d₆) δ: 1.27-1.35 (4H, m), 1.51-1.61 (4H, m), 1.65 (6H, s), 2.42 (3H, s), 3.04 (1H, br), 3.58 (1H, br), 3.96 (3H, s), 4.31 (1H, br), 7.29 (1H, d, J=7.3 Hz), 7.37 (1H, d, J=9.1 Hz), 7.90 (1H, dd, J=8.8, 2.1 Hz), 8.14 (1H, d, J=2.4 Hz). MS (ESI⁺): 509 [M+H]⁺.

Example 18-2

A suitable compound of General Formula (1f) was used to perform reactions according to any of methods similar to Example 18-1 and the method described in Step X-1 or similar methods thereto to give the compound of Example 18-2 shown below.

TABLE 109

| Example | Structure | Instrumental Data |
|---|---|---|
| 18-2 | 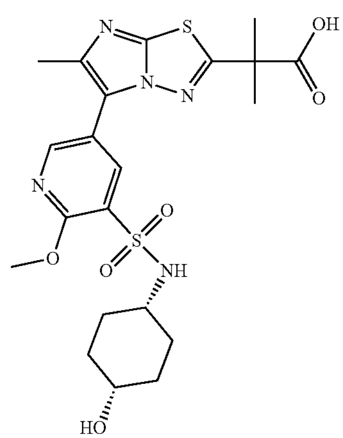 [SMILES: COc1ncc(-c2c(C)nc3sc(C(C)(C)C(=O)O)nn23)cc1S(=O)(=O)N[C@H]1CC[C@@H](O)CC1] | ¹H-NMR (400 MHz, DMSO-d₆) δ: 1.30-1.37 (4H, m), 1.50-1.60 (4H, m), 1.63 (6H, s), 2.43 (3H, s), 3.12 (1H, br), 3.60 (1H, br), 4.06 (3H, s), 4.31-4.34 (1H, m), 7.70 (1H, d, J = 7.3 Hz), 8.47 (1H, d, J = 2.4 Hz), 8.70 (1H, d, J = 2.4 Hz). MS (ESI⁺): 510 [M + H]⁺ |

Example 19

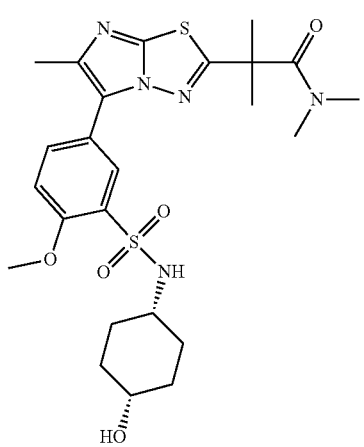

[Formula 116]

The compound obtained in Example 18-1 (19.2 mg) was dissolved in N,N-dimethylformamide (0.2 mL), and N,N-diisopropylethylamine (0.00950 mL), 1-[bis(dimethylamino)methylene]-1H-1,2,3-triazolo[4,5-b]pyridinium-3-oxid hexafluorophosphate (HATU) (17.2 mg), and dimethylamine (2.0 mol/L in tetrahydrofuran, 0.0283 mL) were added to the mixture at 0° C. The mixture was stirred at room temperature for 1 hour. The solvent in the reaction mixture was distilled away under reduced pressure, and the residue was purified by silica gel column chromatography (ethyl acetate:methanol=9:1) to give the title compound (6.5 mg).

$^1$H-NMR (400 MHz, CDCl$_3$) δ: 1.44-1.65 (9H, m), 1.73 (6H, s), 2.53 (3H, s), 2.83-3.02 (6H, m), 3.29 (1H, br), 3.82 (1H, br), 4.05 (3H, s), 4.94 (1H, d, J=7.3 Hz), 7.15 (1H, d, J=8.6 Hz), 7.83 (1H, dd, J=8.9, 2.1 Hz), 8.27 (1H, d, J=1.8 Hz). MS (ESI$^+$): 536 [M+H]$^+$.

Example 20-1

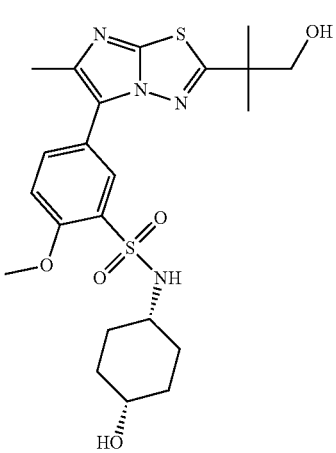

[Formula 117]

The compound obtained in Example 1-22 (30.2 mg) was dissolved in methylene chloride (0.6 mL), and diisobutylaluminum hydride (1.0 mol/L in hexane, 0.282 mL) was added to the solution at 0° C. The mixture was stirred at the same temperature for 1 hour under an argon atmosphere. Water (0.5 mL) was added to the reaction mixture, and the mixture was stirred at room temperature for 20 minutes. Ethyl acetate and anhydrous sodium sulfate were added to the reaction mixture, and the mixture was stirred at room temperature for 30 minutes.

The reaction mixture was filtered with Celite, and the solvent in the filtrate was distilled away under reduced pressure. The residue was purified by silica gel column chromatography (ethyl acetate:methanol=10:1) to give the title compound (21.2 mg).

$^1$H-NMR (400 MHz, CDCl$_3$) δ: 1.28 (1H, d, J=2.4 Hz), 1.47 (6H, s), 1.54-1.67 (8H, m), 2.31 (1H, t, J=6.4 Hz), 2.52 (3H, s), 3.28 (1H, br), 3.79-3.83 (3H, m), 4.05 (3H, s), 4.93 (1H, d, J=7.3 Hz), 7.14 (1H, d, J=8.5 Hz), 7.85 (1H, dd, J=8.5, 2.4 Hz), 8.35 (1H, d, J=1.8 Hz). MS (ESI$^+$): 495 [M+H]$^+$.

Example 20-2

A suitable compound of General Formula (1f) was used to perform reactions according to any of methods similar to Example 20-1 and the method described in Step X-3 or similar methods thereto to give the compound of Example 20-2 shown below.

TABLE 110

| Example | Structure | Instrumental Data |
|---|---|---|
| 20-2 | (structure) | $^1$H-NMR (400 MHz, CDCl$_3$) δ: 1.28 (1H, d, J = 3.0 Hz), 1.47 (6H, s), 1.54-1.68 (8H, m), 2.07-2.11 (1H, m), 2.53 (3H, s), 3.29 (1H, br), 3.80 (2H, d, J = 6.1 Hz), 3.84 (1H, br), 4.17 (3H, s), 4.97 (1H, d, J = 7.9 Hz), 8.61 (1H, d, J = 2.4 Hz), 8.67 (1H, d, J = 2.4 Hz). MS (ESI$^+$): 496 [M + H]$^+$ |

Reference Example 58

[Formula 118]

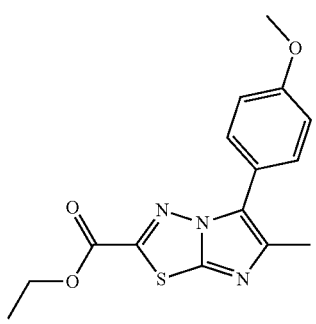

To a solution of 1-bromo-1-(4-methoxyphenyl)propan-2-one (7.12 g) in ethyl methyl ketone (60 mL) was added ethyl 5-amino-1,3,4-thiadiazole-2-carboxylate (5.07 g) at 0° C., and the mixture was stirred at room temperature for 1 hour under an argon atmosphere and heated to reflux for 15 hours. The reaction was cooled to room temperature, and insoluble materials were then filtered off. After an addition of saturated aqueous sodium carbonate solution to the mixture, pH of the solution was adjusted to 10, and the resulting solution was extracted with ethyl acetate. The solvent in the organic layer was distilled away under reduced pressure, and the residue was purified by silica gel column chromatography (hexane:ethyl acetate=2:1) to give the title compound (965 mg).

$^1$H-NMR (400 MHz, CDCl$_3$) δ: 1.45 (3H, t, J=7.1 Hz), 2.52 (3H, s), 3.87 (3H, s), 4.51 (2H, q, J=7.1 Hz), 7.04 (2H, d, J=8.5 Hz), 7.61 (2H, d, J=8.5 Hz). MS (ESI$^+$): 318 [M+H]$^+$.

Reference Example 59-1

[Formula 119]

To a solution of the compound obtained in Reference Example 58 (965 mg) in methylene chloride (15 mL) was added dropwise chlorosulfuric acid (5 mL) at −10° C., and the mixture was stirred at the same temperature for 1 hour under an argon atmosphere. The reaction mixture was added dropwise to ice water (30 mL), and the mixture was extracted with ethyl acetate. A part (126 mg) of the residue (1.22 g) obtained by distilling the solvent in the organic layer away under reduced pressure was dissolved in methylene chloride (1 mL), and the solution was added dropwise to a mixture of cis-3-(aminomethyl)cyclobutan-1-ol hydrochloride (62.7 mg) and aqueous sodium carbonate solution (2.0 mol/L, 1.0 mL) at 0° C. The reaction mixture was stirred at room temperature for 17 hours, and the methylene chloride layer was then purified by silica gel column chromatography (ethyl acetate) to give the title compound (101 mg).

$^1$H-NMR (400 MHz, CDCl$_3$) δ: 1.46 (3H, t, J=7.3 Hz), 1.50-1.55 (2H, m), 1.77 (1H, d, J=6.1 Hz), 1.91-1.95 (1H, m), 2.35-2.42 (2H, m), 2.54 (3H, s), 2.98 (2H, t, J=6.4 Hz), 4.05 (3H, s), 4.10-4.16 (1H, m), 4.52 (2H, q, J=7.3 Hz), 4.91 (1H, t, J=6.1 Hz), 7.20 (1H, d, J=9.0 Hz), 7.94 (1H, dd, J=9.0, 2.0 Hz), 8.16 (1H, d, J=2.0 Hz). MS (ESI$^+$): 481 [M+H]$^+$.

Reference Examples 59-2 to 59-16

A suitable compound of General Formula (24) was used to perform reactions according to any of methods similar to Reference Example 59-1 and the methods described in Step U-3 and Step U-4 or similar methods thereto to give the compounds of Reference Examples 59-2 to 59-16 shown below.

TABLE 111

| Reference Example | Structure | Instrumental Data |
|---|---|---|
| 59-2 | 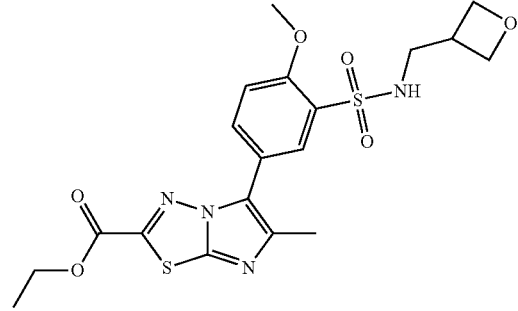 [SMILES: CCOC(=O)c1nn2c(-c3ccc(OC)c(S(=O)(=O)NCC4COC4)c3)c(C)nc2s1] | $^1$H-NMR (400 MHz, CDCl$_3$) δ: 1.46 (3H, t, J = 7.2 Hz), 2.55 (3H, s), 3.11-3.18 (1H, m), 3.26 (2H, t, J = 6.7 Hz), 4.06 (3H, s), 4.33 (2H, t, J = 5.8 Hz), 4.52 (2H, q, J = 7.2 Hz), 4.74 (2H, dd, J = 7.6, 6.4 Hz), 5.06 (1H, t, J = 6.4 Hz), 7.21 (1H, d, J = 8.8 Hz), 7.97 (1H, dd, J = 8.8, 2.1 Hz), 8.19 (1H, d, J = 2.1 Hz). MS (ESI$^+$): 467 [M + H]$^+$ |
| 59-3 | 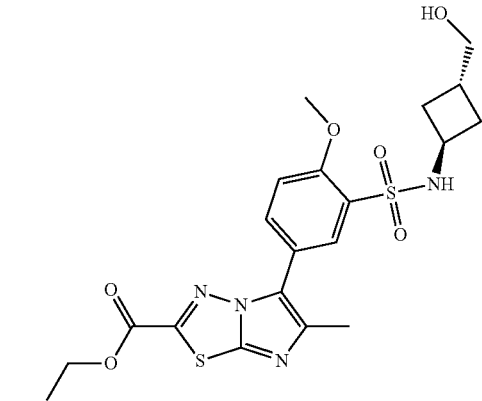 [SMILES: CCOC(=O)c1nn2c(-c3ccc(OC)c(S(=O)(=O)N[C@H]4C[C@H](CO)C4)c3)c(C)nc2s1] | $^1$H-NMR (400 MHz, CDCl$_3$) δ: 1.46 (3H, t, J = 7.2 Hz), 1.93-2.05 (4H, m), 2.28-2.34 (1H, m), 2.54 (3H, s), 3.58 (2H, dd, J = 6.7, 5.4 Hz), 3.88-3.96 (1H, m), 4.07 (3H, s), 4.52 (2H, q, J = 7.2 Hz), 5.08 (1H, d, J = 8.5 Hz), 7.18 (1H, d, J = 8.8 Hz), 7.93 (1H, dd, J = 8.8, 2.4 Hz), 8.15 (1H, d, J = 2.4 Hz). MS (ESI$^+$): 481 [M + H]$^+$ |
| 59-4 | 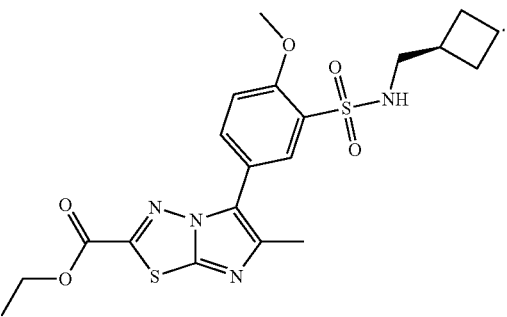 | $^1$H-NMR (400 MHz, CDCl$_3$) δ: 1.46 (3H, t, J = 7.0 Hz), 1.72 (1H, d, J = 5.4 Hz), 1.98-2.11 (4H, m), 2.32-2.38 (1H, m), 2.55 (3H, s), 2.97 (2H, dd, J = 7.6, 6.4 Hz), 4.05 (3H, s), 4.34-4.39 (1H, m), 4.52 (2H, q, J = 7.0 Hz), 4.90 (1H, t, J = 6.1 Hz), 7.20 (1H, d, J = 8.7 Hz), 7.96 (1H, dd, J = 8.7, 2.3 Hz), 8.16 (1H, d, J = 2.3 Hz). MS (ESI$^+$): 481 [M + H]$^+$ |
| 59-5 | 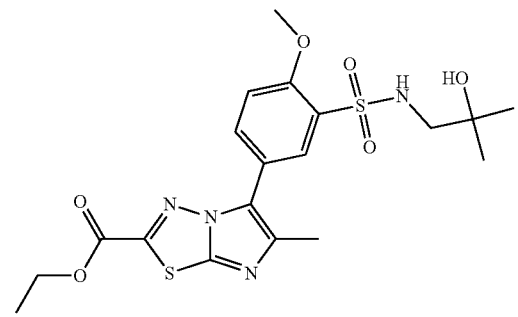 [SMILES: CCOC(=O)c1nn2c(-c3ccc(OC)c(S(=O)(=O)NCC(C)(C)O)c3)c(C)nc2s1] | $^1$H-NMR (400 MHz, CDCl$_3$) δ: 1.26 (6H, s), 1.46 (3H, t, J = 7.2 Hz), 1.63 (1H, s), 2.55 (3H, s), 2.84 (2H, d, J = 6.7 Hz), 4.05 (3H, s), 4.52 (2H, q, J = 7.2 Hz), 5.32 (1H, t, J = 6.7 Hz), 7.20 (1H, d, J = 8.8 Hz), 7.96 (1H, dd, J = 8.8, 2.4 Hz), 8.16 (1H, d, J = 2.4 Hz). MS (ESI$^+$): 469 [M + H]$^+$ |

TABLE 111-continued

| Reference Example | Structure | Instrumental Data |
|---|---|---|
| 59-6 | 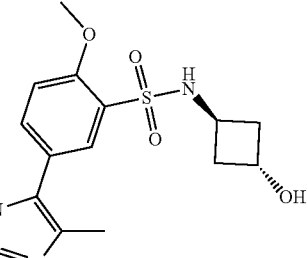 | ¹H-NMR (400 MHz, CDCl₃) δ: 1.46 (3H, t, J = 7.2 Hz), 1.74 (1H, d, J = 3.6 Hz), 2.14-2.25 (4H, m), 2.54 (3H, S), 3.93-3.98 (1H, m), 4.06 (3H, s), 4.45-4.47 (1H, m), 4.52 (2H, q, J = 7.2 Hz), 5.02 (1H, d, J = 6.1 Hz), 7.19 (1H, d, J = 8.5 Hz), 7.94 (1H, dd, J = 8.5, 2.4 Hz), 8.15 (1H, d, J = 2.4 Hz). MS (ESI⁺): 467 [M + H]⁺ |
| 59-7 | 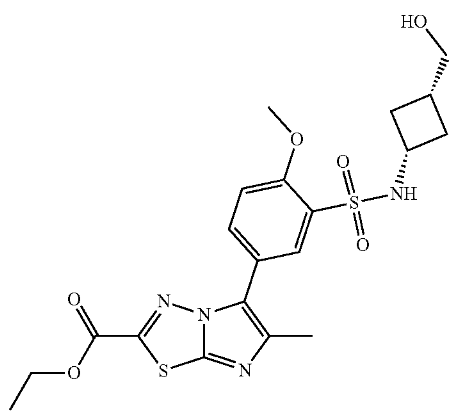 [SMILES: CCOC(=O)c1nn2c(-c3ccc(OC)c(S(=O)(=O)N[C@H]4C[C@@H](CO)C4)c3)c(C)nc2s1] | ¹H-NMR (400 MHz, CDCl₃) δ: 1.31 (1H, t, J = 5.5 Hz), 1.46 (3H, t, J = 7.3 Hz), 1.58-1.66 (2H, m), 2.02-2.12 (1H, m), 2.17-2.24 (2H, m), 2.54 (3H, s), 3.52 (2H, t, J = 4.8 Hz), 3.69-3.77 (1H, m), 4.07 (3H, s), 4.52 (2H, q, J = 7.3 Hz), 5.14 (1H, d, J = 8.5 Hz), 7.18 (1H, d, J = 8.7 Hz), 7.95 (1H, dd, J = 8.7, 2.3 Hz), 8.16 (1H, d, J = 2.3 Hz). MS (ESI⁺): 481 [M + H]⁺ |

TABLE 112

| Reference Example | Structure | Instrumental Data |
|---|---|---|
| 59-8 | 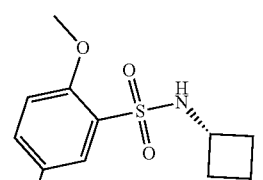 | ¹H-NMR (400 MHz, CDCl₃) δ: 1.46 (3H, t, J = 7.4 Hz), 1.72-1.79 (3H, m), 2.51-2.57 (5H, m), 3.34-3.40 (1H, m), 3.91-3.96 (1H, m), 4.08 (3H, s), 4.52 (2H, q, J = 7.4 Hz), 5.05 (1H, d, J = 9.1 Hz), 7.19 (1H, d, J = 8.7 Hz), 7.96 (1H, dd, J = 8.7, 2.3 Hz), 8.16 (1H, d, J = 2.3 Hz). MS (ESI⁺): 467 [M + H]⁺ |

TABLE 112-continued

| Reference Example | Structure | Instrumental Data |
|---|---|---|
| 59-9 | 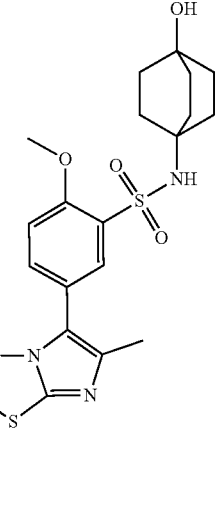 | ¹H-NMR (400 MHz, CDCl₃) δ: 1.46 (3H, t, J = 7.3 Hz), 1.67-1.69 (6H, m), 1.84-1.88 (6H, m), 2.55 (3H, s), 4.05 (3H, s), 4.53 (2H, q, J = 7.2 Hz), 4.81 (1H, s), 7.18 (1H, d, J = 8.7 Hz), 7.95 (1H, dd, J = 8.7, 2.3 Hz), 8.15 (1H, d, J = 2.3 Hz). MS (ESI⁺): 521 [M + H]⁺ |
| 59-10 | 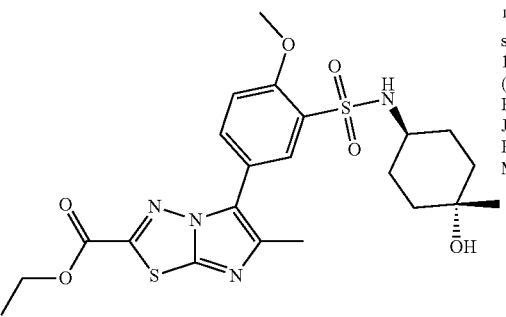 | ¹H-NMR (400 MHz, CDCl₃) δ: 1.24 (3H, s), 1.41-1.50 (7H, m), 1.59-1.65 (2H, m), 1.79-1.87 (2H, m), 2.55 (3H, s), 3.23-3.29 (1H, m), 4.05 (3H, s), 4.52 (2H, q, J = 7.1 Hz), 4.88 (1H, d, J = 6.1 Hz), 7.19 (1H, d, J = 8.8 Hz), 7.97 (1H, dd, J = 8.8, 2.4 Hz), 8.18 (1H, d, J = 2.4 Hz). MS (ESI⁺): 509 [M + H]⁺ |
| 59-11 | 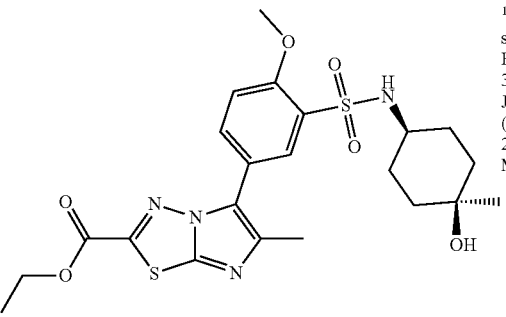 | ¹H-NMR (400 MHz, CDCl₃) δ: 1.17 (3H, s), 1.33-1.39 (2H, m), 1.46 (3H, t, J = 7.1 Hz), 1.51-1.63 (6H, m), 2.55 (3H, s), 3.09-3.21 (1H, m), 4.05 (3H, s), 4.53 (2H, q, J = 7.1 Hz), 4.84 (1H, d, J = 7.9 Hz), 7.18 (1H, d, J = 8.7 Hz), 7.96 (1H, dd, J = 8.7, 2.3 Hz), 8.17 (1H, d, J = 2.3 Hz). MS (ESI⁺): 509 [M + H]⁺ |
| 59-12 | 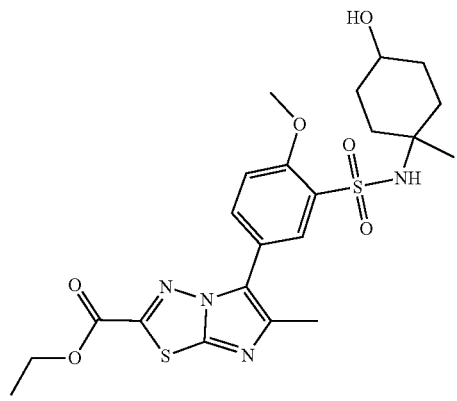 [SMILES: CCOC(=O)c1nn2c(-c3ccc(OC)c(S(=O)(=O)NC4(C)CCC(O)CC4)c3)c(C)nc2s1] | ¹H-NMR (400 MHz, CDCl₃) δ: 1.19 (3H, s), 1.30-1.37 (2H, m), 1.44-1.55 (5H, m), 1.68-1.75 (2H, m), 1.96-2.03 (2H, m), 2.54 (3H, s), 3.60 (1H, br), 4.08 (3H, s), 4.51 (2H, q, J = 7.1 Hz), 4.88 (1H, s), 7.18 (1H, d, J = 8.6 Hz), 7.92 (1H, dd, J = 8.6, 2.4 Hz), 8.18 (1H, d, J = 2.4 Hz). MS (ESI⁺); 509 [M + H]⁺ |

TABLE 112-continued

| Reference Example | Structure | Instrumental Data |
|---|---|---|
| 59-13 | 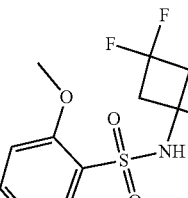 | ¹H-NMR (400 MHz, CDCl₃) δ: 0.96 (3H, t, J = 7.2 Hz), 1.45 (3H, t, J = 7.1 Hz), 1.47-1.50 (4H, m), 2.52 (3H, s), 3.86 (2H, q, J = 7.1 Hz), 4.07 (3H, s), 4.51 (2H, q, J = 7.2 Hz), 5.92 (1H, s), 7.18 (1H, d, J = 8.5 Hz), 7.91 (1H, dd, J = 8.5, 2.4 Hz), 8.11 (1H, d, J = 2.4 Hz). |

TABLE 113

| Reference Example | Structure | Instrumental Data |
|---|---|---|
| 59-14 | 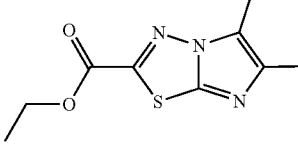 | ¹H-NMR (400 MHz, CDCl₃) δ: 1.45 (3H, t, J = 7.2 Hz), 2.30 (1H, s), 2.54 (3H, s), 2.60-2.69 (2H, m), 2.74-2.86 (2H, m), 3.71 (2H, d, J = 5.4 Hz), 4.08 (3H, s), 4.52 (2H, q, J = 7.2 Hz), 5.66 (1H, s), 7.21 (1H, d, J = 8.8 Hz), 7.93 (1H, dd, J = 8.8, 2.4 Hz), 8.18 (1H, d, J = 1.8 Hz).<br>MS (ESI⁺): 517 [M + H]⁺ |
| 59-15 | 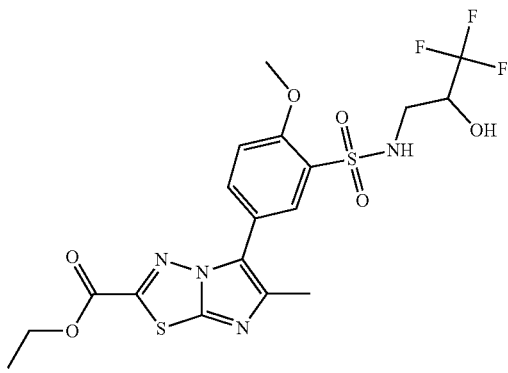 [SMILES: CCOC(=O)c1nn2c(-c3ccc(OC)c(S(=O)(=O)NCC(O)C(F)(F)F)c3)c(C)nc2s1] | ¹H-NMR (400 MHz, CDCl₃) δ: 1.45 (3H, t, J = 7.1 Hz), 1.77 (1H, d, J = 3.0 Hz), 2.53 (3H, s), 3.06-3.13 (1H, m), 3.38-3.44 (1H, m), 4.06 (3H, s), 4.16 (1H, br s), 4.52 (2H, q, J = 7.1 Hz), 5.52-5.56 (1H, m), 7.22 (1H, d, J = 8.7 Hz), 7.95 (1H, dd, J = 8.7, 2.3 Hz), 8.18 (1H, d, J = 2.3 Hz).<br>MS (ESI⁺): 509 [M + H]⁺ |

TABLE 113-continued

| Reference Example | Structure | Instrumental Data |
|---|---|---|
| 59-16 | 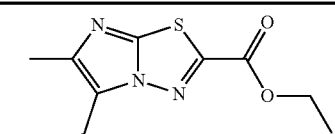 | $^1$H-NMR (400 MHz, CDCl$_3$) δ: 1.47 (3H, t, J = 7.3 Hz), 2.52 (3H, s), 4.06 (3H, s), 4.54 (2H, q, J = 7.3 Hz), 7.15 (1H, d, J = 9.1 Hz), 7.22-7.25 (2H, m), 7.52-7.56 (2H, m), 7.57 (1H, s), 7.89 (1H, dd, J = 9.1, 2.4 Hz), 8.22 (1H, d, J = 2.4 Hz). MS (ESI$^+$): 496 [M − H]$^−$. |

Example 21-1

[Formula 120]

To a solution of the compound obtained in Reference Example 51-1 (43.0 mg) in tetrahydrofuran (0.4 mL) was added a solution of methylmagnesium bromide (0.98 mol/L in tetrahydrofuran, 0.53 mL) at 0° C., and the mixture was stirred at 0° C. for 5 hours. Saturated aqueous ammonium chloride solution was added to the reaction mixture at 0° C., and the mixture was extracted with a mixed solvent of chloroform:methanol (10:1). The solvent in the organic layer was distilled away under reduced pressure, and the residue was purified by silica gel column chromatography (ethyl acetate:methanol=9:1) to give the title compound (16.6 mg).
$^1$H-NMR (400 MHz, CDCl$_3$) δ: 1.31 (1H, d, J=3.1 Hz), 1.51-1.62 (8H, m), 1.66 (6H, s), 2.14 (1H, s), 2.39 (3H, s), 3.29 (1H, br), 3.83 (1H, br), 4.05 (3H, s), 4.95 (1H, d, J=7.3 Hz), 7.15 (1H, d, J=8.6 Hz), 7.26 (1H, s), 7.57 (1H, d, J=8.6 Hz), 7.98 (1H, s). MS (ESI$^+$): 480 [M+H]$^+$.

Examples 21-2 to 21-20

A suitable compound of General Formula (26) was used to perform reactions according to any of methods similar to Example 21-1 and the method described in Step U-5 or similar methods thereto to give the compounds of Examples 21-2 to 21-20 shown below.

TABLE 114

| Example | Structure | Instrumental Data |
|---|---|---|
| 21-2 | 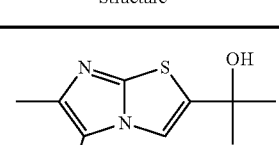 | $^1$H-NMR (400 MHz, DMSO-d$_6$) δ: 1.37-1.56 (10H, m), 2.27 (3H, s), 3.18-3.27 (3H, m), 3.70-3.77 (2H, m), 3.97 (3H, s), 5.75 (1H, s), 7.36 (1H, d, J = 8.5 Hz), 7.52 (1H, s), 7.56 (1H, d, J = 7.9 Hz), 7.72 (1H, dd, J = 8.5. 2.4 Hz), 7.75 (1H, d, J = 2.4 Hz). MS (ESI$^+$): 455 [M + H]$^+$ |

TABLE 114-continued

| Example | Structure | Instrumental Data |
|---------|-----------|-------------------|
| 21-3 | 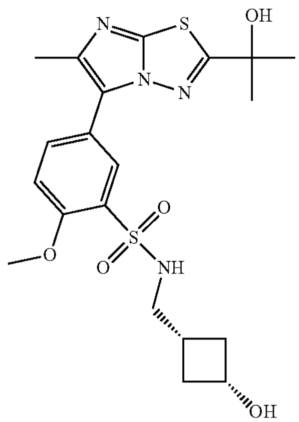 [SMILES: COc1ccc(-c2c(C)nc3sc(C(C)(C)O)nn23)cc1S(=O)(=O)NC[C@H]1C[C@@H](O)C1] | ¹H-NMR (400 MHz, CDCl₃) δ: 1.51-1.56 (2H, m), 1.71 (1H, d, J = 6.1 Hz), 1.75 (6H, s), 1.92-1.97 (1H, m), 2.36-2.42 (2H, m), 2.50 (1H, s), 2.52 (3H, s), 2.96 (2H, t, J = 6.4 Hz), 4.04 (3H, s), 4.10-4.17 (1H, m), 4.90 (1H, t, J = 6.4 Hz), 7.16 (1H, d, J = 8.5 Hz), 7.88 (1H, dd, J = 8.5, 2.4 Hz), 8.29 (1H, d, J = 2.4 Hz).<br>MS (ESI⁺): 467 [M + H]⁺ |
| 21-4 | 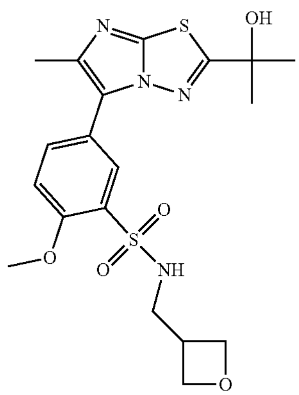 [SMILES: COc1ccc(-c2c(C)nc3sc(C(C)(C)O)nn23)cc1S(=O)(=O)NCC1COC1] | ¹H-NMR (400 MHz, CDCl₃) δ: 1.75 (6H, s), 2.53 (3H, s), 2.55 (1H, s), 3.10-3.17 (1H, m), 3.26 (2H, t, J = 7.0 Hz), 4.05 (3H, s), 4.33 (2H, t, J = 6.1 Hz), 4.73 (2H, dd, J = 7.6, 6.4 Hz), 5.05 (1H, t, J = 6.4 Hz), 7.17 (1H, d, J = 8.8 Hz), 7.89 (1H, dd, J = 8.8, 2.4 Hz), 8.31 (1H, d, J = 2.4 Hz).<br>MS (ESI⁺): 453 [M + H]⁺ |
| 21-5 | 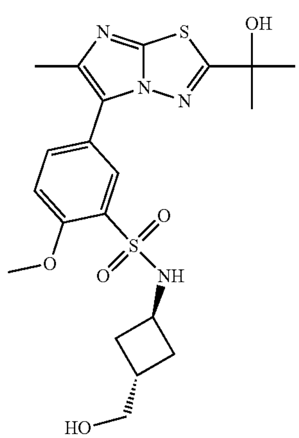 [SMILES: COc1ccc(-c2c(C)nc3sc(C(C)(C)O)nn23)cc1S(=O)(=O)N[C@H]1C[C@H](CO)C1] | ¹H-NMR (400 MHz, CDCl₃) δ: 1.75 (6H, s), 1.97-1.99 (4H, m), 2.27-2.34 (1H, m), 2.52 (3H, s), 2.56 (1H, s), 3.57 (2H, dd, J = 7.0, 5.1 Hz), 3.88-3.92 (1H, m), 4.06 (3H, s), 5.09 (1H, d, J = 9.1 Hz), 7.14 (1H, d, J = 8.8 Hz), 7.86 (1H, dd, J = 8.8, 2.4 Hz), 8.28 (1H, d, J = 2.4 Hz).<br>MS (ESI⁺): 467 [M + H]⁺ |

TABLE 114-continued

| Example | Structure | Instrumental Data |
|---|---|---|
| 21-6 | 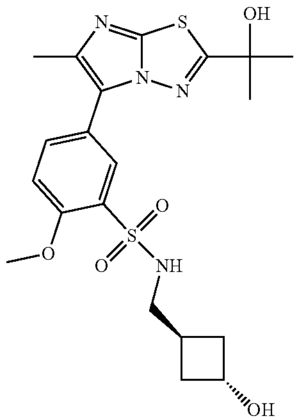 [SMILES: COc1ccc(-c2c(C)nc3sc(C(C)(C)O)nn23)cc1S(=O)(=O)NC[C@H]1C[C@H](O)C1] | $^1$H-NMR (400 MHz, CDCl$_3$) δ: 1.67 (1H, d, J = 5.4 Hz), 1.75 (6H, s), 1.98-2.09 (4H, m), 2.34-2.37 (1H, m), 2.48 (1H, s), 2.53 (3H, s), 2.97 (2H, dd, J = 7.9, 6.1 Hz), 4.04 (3H, s), 4.33-4.38 (1H, m), 4.90 (1H, t, J = 6.4 Hz), 7.16 (1H, d, J = 8.7 Hz), 7.89 (1H, dd, J = 8.7, 2.3 Hz), 8.30 (1H, d, J = 2.3 Hz).<br>MS (ESI$^+$): 467 [M + H]$^+$ |
| 21-7 | 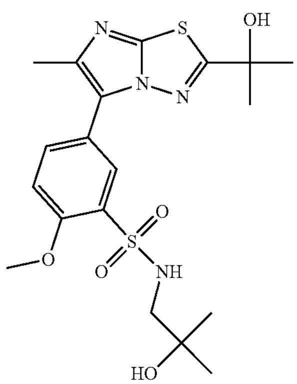 [SMILES: COc1ccc(-c2c(C)nc3sc(C(C)(C)O)nn23)cc1S(=O)(=O)NCC(C)(C)O] | $^1$H-NMR (400 MHz, CDCl$_3$) δ: 1.26 (6H, s), 1.68 (1H, s), 1.75 (6H, s), 2.52 (3H, s), 2.55 (1H, s), 2.84 (2H, d, J = 6.7 Hz), 4.04 (3H, s), 6.31 (1H, t. J = 6.7 Hz), 7.16 (1H, d, J = 8.5 Hz), 7.88 (1H, dd, J = 8.5, 2.1 Hz), 8.29 (1H, d, J = 2.1 Hz).<br>MS (ESI$^+$): 455 [M + H]$^+$ |

TABLE 115

| Example | Structure | Instrumental Data |
|---|---|---|
| 21-8 | 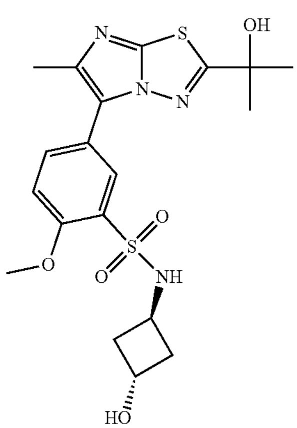 [SMILES: COc1ccc(-c2c(C)nc3sc(C(C)(C)O)nn23)cc1S(=O)(=O)N[C@H]1C[C@H](O)C1] | $^1$H-NMR (400 MHz, CDCl$_3$) δ: 1.70 (6H, s), 2.04-2.22 (4H, m), 2.49 (3H, s), 3.88-3.91 (1H, m), 4.04 (3H, s), 4.35-4.38 (1H, m), 7.17 (1H, d, J = 8.5 Hz), 7.88 (1H, dd, J = 8.5, 2.4 Hz), 8.25 (1H, d, J = 1.8 Hz).<br>MS (ESI$^+$): 453 [M + H]$^+$ |

TABLE 115-continued
| Example | Structure | Instrumental Data |
|---|---|---|
| 21-9 | 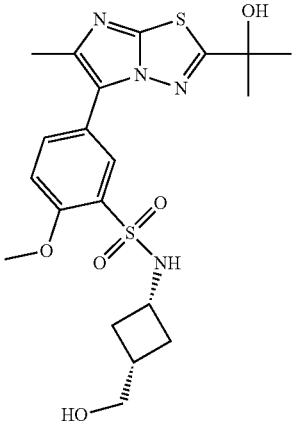 [SMILES: COc1ccc(-c2c(C)nc3sc(C(C)(C)O)nn23)cc1S(=O)(=O)N[C@H]1C[C@@H](CO)C1] | ¹H-NMR (400 MHz, CDCl₃) δ: 1.57-1.65 (2H, m), 1.75 (6H, s), 2.02-2.10 (1H, m), 2.16-2.21 (2H, m), 2.48 (1H, s), 2.52 (3H, s), 3.52 (2H, t, J = 5.4 Hz), 3.67-3.75 (1H, m), 4.06 (3H, s), 5.12 (1H, d, J = 9.1 Hz), 7.14 (1H, d, J = 8.7 Hz), 7.87 (1H, dd, J = 8.7, 2.3 Hz), 8.30 (1H, d, J = 2.3 Hz).<br>MS (ESI⁺): 467 [M + H]⁺ |
| 21-10 | 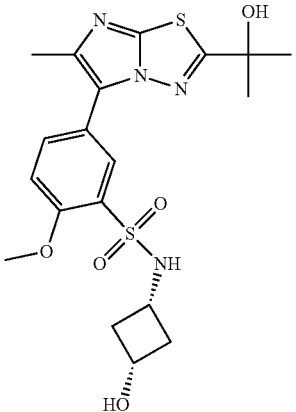 [SMILES: COc1ccc(-c2c(C)nc3sc(C(C)(C)O)nn23)cc1S(=O)(=O)N[C@H]1C[C@@H](O)C1] | ¹H-NMR (400 MHz, CDCl₃) δ: 1.71-1.78 (9H, m), 2.47 (1H, s), 2.49-2.55 (5H, m), 3.34-3.40 (1H, m), 3.91-3.93 (1H, m), 4.07 (3H, s), 5.05 (1H, d, J = 9.1 Hz), 7.15 (1H, d, J = 8.7 Hz), 7.88 (1H, dd, J = 8.7, 2.3 Hz), 8.29 (1H, d, 3 = 2.3 Hz).<br>MS (ESI⁺): 453 [M + H]⁺ |
| 21-11 | 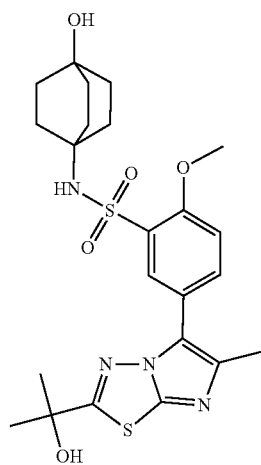 [SMILES: COc1ccc(-c2c(C)nc3sc(C(C)(C)O)nn23)cc1S(=O)(=O)NC12CCC(O)(CC1)CC2] | ¹H-NMR (400 MHz, CDCl₃) δ: 1.64-1.68 (6H, m), 1.75 (6H, s), 1.85-1.89 (6H, m), 2.516 (1H, 8), 2.524 (3H, s), 4.04 (3H, s), 4.81 (1H, s), 7.14 (1H, d, J = 8.5 Hz), 7.84 (1H, dd, J = 8.5, 2.4 Hz), 8.29 (1H, d, J = 2.4 Hz).<br>MS (ESI⁺): 507 [M + H]⁺ |

TABLE 115-continued

| Example | Structure | Instrumental Data |
|---|---|---|
| 21-12 | 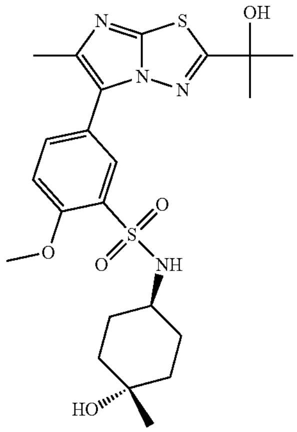 [SMILES: COc1ccc(-c2c(C)nc3sc(C(C)(C)O)nn23)cc1S(=O)(=O)N[C@H]1CC[C@](C)(O)CC1] | ¹H-NMR (400 MHz, CDCl₃) δ: 1.24 (3H, s), 1.41-1.48 (4H, m), 1.58-1.65 (2H, m), 1.75 (6H, s), 1.79-1.85 (2H, m), 2.50 (1H, s), 2.53 (3H, s), 3.25 (1H, s), 4.04 (3H, s), 4.88 (1H, d, J = 6.1 Hz), 7.15 (1H, d, J = 8.5 Hz), 7.88 (1H, dd, J = 8.5, 2.4 Hz), 8.32 (1H, d, J = 2.4 Hz). MS (ESI⁺): 495 [M + H]⁺ |

TABLE 116

| Example | Structure | Instrumental Data |
|---|---|---|
| 21-13 | 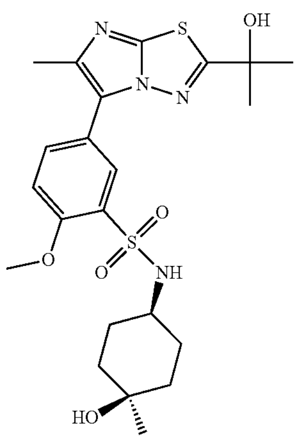 [SMILES: COc1ccc(-c2c(C)nc3sc(C(C)(C)O)nn23)cc1S(=O)(=O)N[C@H]1CC[C@@](C)(O)CC1] | ¹H-NMR (400 MHz, CDCl₃) δ: 1.17 (3H, s), 1.34-1.38 (2H, m), 1.55-1.64 (6H, m), 1.75 (6H, s), 2.47 (1H, s), 2.53 (3H, s), 3.16 (1H, br), 4.04 (3H, s), 4.84 (1H, d, J = 7.9 Hz), 7.14 (1H, d, J = 8.8 Hz), 7.87 (1H, dd, J = 8.8, 2.4 Hz), 8.31 (1H, d, J = 2.4 Hz). MS (ESI⁺): 495 [M + H]⁺ |
| 21-14 | 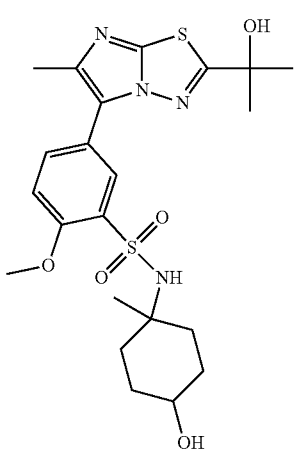 [SMILES: COc1ccc(-c2c(C)nc3sc(C(C)(C)O)nn23)cc1S(=O)(=O)NC1(C)CCC(O)CC1] | ¹H-NMR (400 MHz, CDCl₃) δ: 1.20 (3H, s), 1.31-1.70 (6H, m), 1.74 (6H, s), 1.97-2.00 (2H, m), 2.49 (1H, s), 2.51 (3H, s), 3.60 (1H, br), 4.07 (3H, s), 4.82 (1H, s), 7.14 (1H, d, J = 8.9 Hz), 7.82 (1H, dd, J = 8.9, 2.4 Hz), 8.30 (1H, d, J = 2.4 Hz). MS (ESI⁺); 495 [M + H]⁺ |

TABLE 116-continued
| Example | Structure | Instrumental Data |
|---|---|---|
| 21-15 | 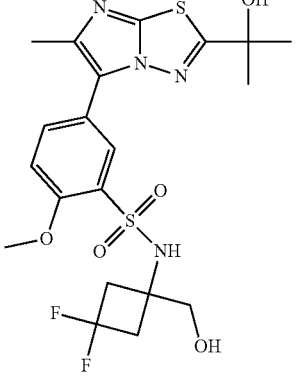 | $^1$H-NMR (400 MHz, CDCl$_3$) δ: 1.74 (6H, s), 2.13 (1H, t, J = 5.4 Hz), 2.52 (3H, s), 2.55 (1H, s), 2.58-2.65 (2H, m), 2.78 (2H, q, J = 14.1 Hz), 3.71 (2H, d, J = 5.4 Hz), 4.07 (3H, s), 5.54 (1H, s), 7.18 (1H, d, J = 8.7 Hz), 7.87 (1H, dd, J = 8.7, 2.0 Hz), 8.31 (1H, d, J = 2.0 Hz).<br>MS (ESI$^+$): 503 [M + H]$^+$ |
| 21-16 | 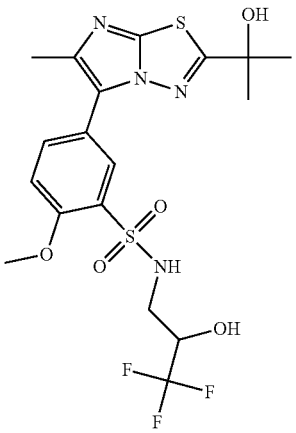 [SMILES: COc1ccc(-c2c(C)nc3sc(C(C)(C)O)nn23)cc1S(=O)(=O)NCC(O)C(F)(F)F] | $^1$H-NMR (400 MHz, CDCl$_3$) δ: 1.74 (6H, d, J = 1.2 Hz), 2.51 (1H, s), 2.52 (3H, s), 3.04-3.14 (2H, m), 3.37-3.44 (1H, m), 4.06 (3H, s), 4.11-4.19 (1H, m), 5.34-5.41 (1H, m), 7.18 (1H, d, J = 8.5 Hz), 7.89 (1H, dd, J = 8.8, 2.1 Hz), 8.32 (1H, d, J = 2.4 Hz).<br>MS (ESI$^+$): 495 [M + H]$^+$ |
| 21-17 | 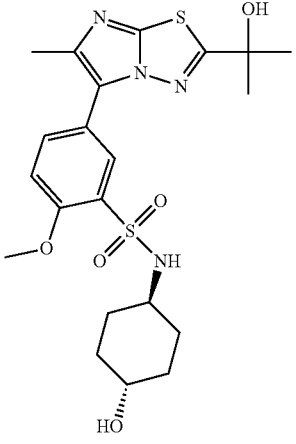 [SMILES: COc1ccc(-c2c(C)nc3sc(C(C)(C)O)nn23)cc1S(=O)(=O)N[C@H]1CC[C@H](O)CC1] | $^1$H-NMR (400 MHz, CDCl$_3$) δ: 1.25-1.31 (4H, m), 1.36 (1H, d, J = 4.8 Hz), 1.66 (6H, s), 1.87-1.94 (4H, m), 2.09 (1H, s), 2.40 (3H, s), 3.13 (1H, br), 3.58 (1H, br), 4.05 (3H, s), 4.79 (1H, d, J = 7.3 Hz), 7.16 (1H, d, J = 8.5 Hz), 7.25 (1H, s), 7.59 (1H, dd, J = 8.8, 2.1 Hz), 7.98 (1H, d, J = 2.4 Hz).<br>MS (ESI$^+$): 480 [M + H]$^+$ |

TABLE 117

| Example | Structure | Instrumental Data |
|---|---|---|
| 21-18 | 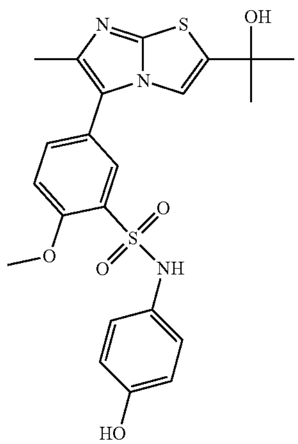 | ¹H-NMR (400 MHz, DMSO-d₆) δ: 1.50 (6H, s), 2.17 (3H, s), 3.98 (3H, d, J = 8.8 Hz), 5.74 (1H, s), 6.57 (2H, d, J = 8.6 Hz), 6.89 (2H, d, J = 8.6 Hz), 7.31 (1H, d, J = 8.6 Hz), 7.39 (1H, s), 7.60 (1H, d, J = 2.4 Hz), 7.65 (1H, d. J = 8.6 Hz), 9.21 (1H, s), 9.61 (1H, s).<br>MS (ESI⁺): 474 [M + H]⁺ |
| 21-19 | 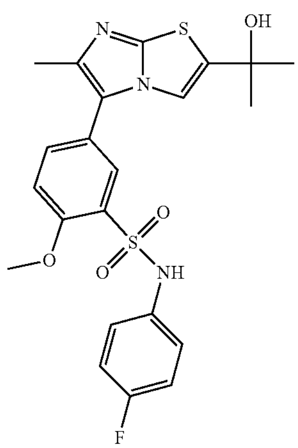 [SMILES: COc1ccc(-c2c(C)nc3sc(C(C)(C)O)cn23)cc1S(=O)(=O)Nc1ccc(F)cc1] | ¹H-NMR (400 MHz, DMSO-d₆) δ: 1.50 (6H, s), 2.18 (3H, s), 3.94 (3H, s), 5.75 (1H, s), 7.02-7.09 (2H, m), 7.10-7.16 (2H, m), 7.32 (1H, d, J = 9.4 Hz), 7.42 (1H, s), 7.66-7.71 (2H, m), 10.14 (1H, s).<br>MS (ESI⁺): 476 [M + H]⁺ |
| 21-20 | 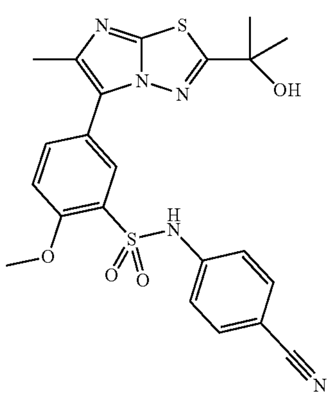 [SMILES: COc1ccc(-c2c(C)nc3sc(C(C)(C)O)nn23)cc1S(=O)(=O)Nc1ccc(C#N)cc1] | ¹H-NMR (400 MHz, CDCl₃) δ: 1.75 (6H, s), 2.49 (3H, s), 2.54 (1H, s), 4.06 (3H, s), 7.12 (1H, d, J = 9.2 Hz), 7.19-7.22 (2H, m), 7.29 (1H, s), 7.49-7.52 (2H, m), 7.85 (1H, dd, J = 8.6, 2.4 Hz), 8.31 (1H, d, J = 1.8 Hz).<br>MS (ESI⁺): 484 [M + H]⁺. |

Example 22

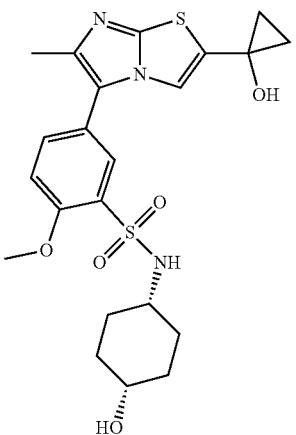

[Formula 121]

To a solution of the compound obtained in Reference Example 51-1 (232 mg) in tetrahydrofuran (9.4 mL) was added dropwise tetraisopropyl orthotitanate (0.209 mL) at 0° C., and the mixture was gradually allowed to rise in temperature from 0° C. to room temperature under an argon atmosphere and stirred for 20 minutes. Ethylmagnesium bromide (1.0 mol/L in tetrahydrofuran, 2.82 mL) was added dropwise to the reaction mixture over 2 hours at 0° C., and the mixture was gradually allowed to rise in temperature from 0° C. to room temperature under an argon atmosphere and stirred for 16 hours. Saturated aqueous ammonium chloride solution was added to the reaction mixture, and the mixture was extracted with ethyl acetate. The solvent in the organic layer was distilled away under reduced pressure, and the residue was purified by silica gel column chromatography (ethyl acetate:methanol=20:1) to give the title compound (26.5 mg).

$^1$H-NMR (400 MHz, CDCl$_3$) δ: 1.04-1.07 (2H, m), 1.30-1.33 (3H, m), 1.53-1.66 (8H, m), 2.39 (3H, s), 2.92 (1H, br), 3.29 (1H, br), 3.83 (1H, br), 4.05 (3H, s), 4.95 (1H, d, J=7.3 Hz), 7.15 (1H, d, J=8.5 Hz), 7.26 (1H, s), 7.55 (1H, dd, J=8.2, 2.1 Hz), 7.96 (1H, d, J=2.4 Hz). MS (ESI$^+$): 478 [M+H]$^+$.

Example 23

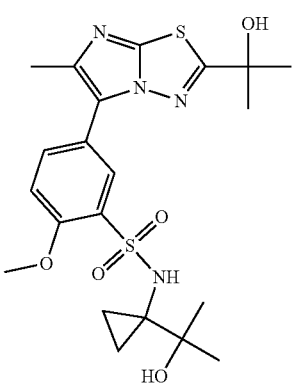

[Formula 122]

To a solution of the compound obtained in Reference Example 59-13 (116 mg) in tetrahydrofuran (2.4 mL) was added methylmagnesium bromide (0.95 mol/L in tetrahydrofuran, 2.4 mL) at 0° C., and the mixture was stirred at room temperature for 9 hours under an argon atmosphere. Saturated aqueous ammonium chloride solution was added to the reaction mixture, and the mixture was extracted with ethyl acetate. The solvent in the organic layer was distilled away under reduced pressure, and the residue was purified by silica gel column chromatography (ethyl acetate:methanol=20:1) to give the title compound (48.4 mg).

$^1$H-NMR (400 MHz, CDCl$_3$) δ: 0.68 (2H, dd, J=6.9, 5.7 Hz), 0.88 (2H, dd, J=6.9, 5.7 Hz), 1.23 (6H, s), 1.74 (6H, s), 2.51 (1H, s), 2.52 (3H, s), 2.70 (1H, s), 4.03 (3H, s), 5.42 (1H, s), 7.13 (1H, d, J=8.6 Hz), 7.84 (1H, dd, J=8.6, 2.4 Hz), 8.27 (1H, d, J=2.4 Hz). MS (ESI$^+$): 481 [M+H]$^+$.

Reference Example 60

[Formula 123]

The compound obtained in Reference Example 6-19 (80.0 mg) and potassium carbonate (35.7 mg) were suspended in N,N-dimethylformamide (2.0 mL) under an argon atmosphere, and iodomethane (0.0186 mL) was added to the mixture. The mixture was stirred at room temperature for 1.5 hours. Water (10 mL) was added to the mixture, and the mixture was extracted with ethyl acetate (10 mL). The organic layer was washed with saturated brine (10 mL), dried over anhydrous sodium sulfate, and filtered to remove insoluble residues. The solvent was distilled away under reduced pressure, and the residue was then dissolved in dichloromethane (4 mL) and purified by silica gel column chromatography (hexane:ethyl acetate=84:16 to 0:100) to give the title compound (80.3 mg).

$^1$H-NMR (400 MHz, CDCl$_3$) δ: 1.34-1.47 (3H, m), 1.50-1.63 (2H, m), 1.66-1.75 (2H, m), 1.99-2.07 (2H, m), 2.77 (3H, s), 3.48-3.57 (1H, m), 3.75-3.84 (1H, m), 7.73 (1H, d, J=8.5 Hz), 7.79-7.83 (1H, m), 8.29 (1H, d, J=1.8 Hz). MS (ESI$^+$): 416 [M+H]$^+$.

Example 24

A suitable compound of General Formula (1m) was used to perform reactions according to any of methods similar to Reference Example 60 and the method described in Step Z-1 or similar methods thereto to give the compound of Example 24 shown below.

TABLE 118

| Example | Structure | Instrumental Data |
|---|---|---|
| 24 | 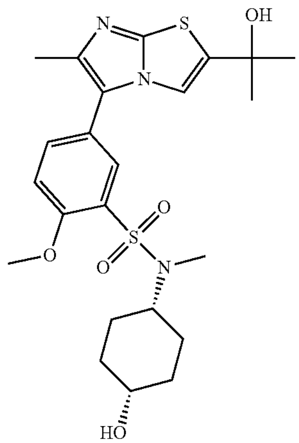 [SMILES: COc1ccc(-c2c(C)nc3sc(C(C)(C)O)cn23)cc1S(=O)(=O)N(C)[C@H]1CC[C@@H](O)CC1] | ¹H-NMR (400 MHz, CDCl₃) δ: 1.19 (1H, d, J = 2.4 Hz), 1.40-1.62 (4H, m), 1.66 (6H, s), 1.82-1.93 (4H, m), 2.08 (1H, s), 2.39 (3H, s), 2.90 (3H, s), 3.75-3.82 (1H, m), 3.99 (3H, s), 4.00-4.03 (1H, m), 7.11 (1H, d, J = 8.6 Hz), 7.25 (1H, s), 7.54 (1H, dd, J = 8.6, 2.1 Hz), 8.01 (1H, d, J = 2.1 Hz). MS (ESI⁺): 494 [M + H]⁺ |

Example 25

[Formula 124]

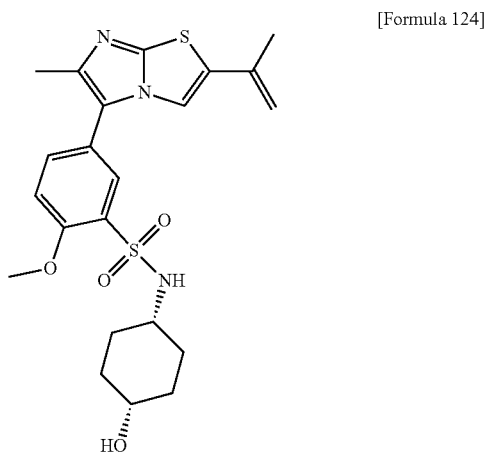 [SMILES: C=C(C)c1cn2c(-c3ccc(OC)c(S(=O)(=O)N[C@H]4CC[C@@H](O)CC4)c3)c(C)nc2s1]

The compound obtained in Reference Example 29 (41.2 mg) was dissolved in dimethylsulfoxide (0.6 mL), and the compound obtained in Reference Example 50-2 (57.5 mg), (2-dicyclohexylphosphino-2',4',6'-triisopropylbiphenyl) aminobiphenyl palladium chloride (10.7 mg), and aqueous sodium carbonate solution (2.0 mol/L, 0.19 mL) were added to the mixture. The mixture was heated with stirring at 90° C. for 1 hour under an argon atmosphere. Ethyl acetate was added to the reaction mixture, and the mixture was filtered with Celite and anhydrous sodium sulfate. The solvent in the filtrate was distilled away under reduced pressure. The residue was purified by silica gel column chromatography (ethyl acetate:methanol=20:1) followed by reversed-phase silica gel column chromatography (methanol:water=4:1) to give the title compound (5.9 mg).

¹H-NMR (400 MHz, CDCl₃) δ: 1.29 (1H, s), 1.56-1.66 (8H, m), 2.09 (3H, s), 2.39 (3H, s), 3.26-3.32 (1H, s), 3.83 (1H, s), 4.06 (3H, s), 4.95 (1H, d, J=7.3 Hz), 5.09 (1H, d, J=1.8 Hz), 5.26 (1H, s), 7.17 (1H, d, J=8.8 Hz), 7.24 (1H, s), 7.58 (1H, dd, J=8.8, 2.4 Hz), 7.99 (1H, d, J=2.4 Hz). MS (ESI⁺): 462 [M+H]⁺.

Example 26

[Formula 125]

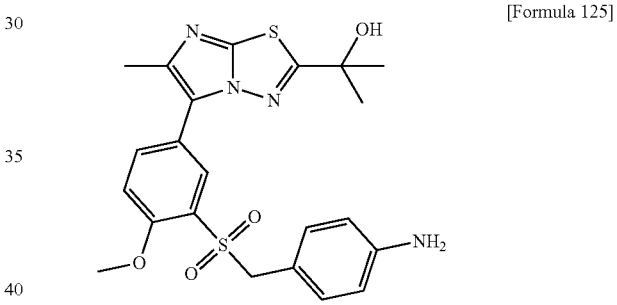

The compound obtained in Reference Example 52-13 (20.0 mg) was suspended in ethanol (0.2 mL) and water (0.2 mL), and saturated aqueous ammonium chloride solution (0.2 mL) and reduced iron (11.1 mg) were added to the mixture. The mixture was stirred at 50° C. for 10 minutes. Tetrahydrofuran (0.2 mL) was added to the mixture, and the mixture was stirred at 50° C. for 1 hour and left to stand at room temperature for 17 hours. The reaction mixture was stirred again at 50° C. for 1 hour, and then diluted with tetrahydrofuran (2 mL) at room temperature. Insoluble materials were filtered off with filter-paper powder, and washed with tetrahydrofuran. Water was added to the filtrate, and the mixture was extracted with ethyl acetate. The organic layer was washed with saturated brine, dried over anhydrous sodium sulfate, and then filtered to remove insoluble residues. The solvent was distilled away under reduced pressure, and the residue was then dissolved in dichloromethane and purified by silica gel column chromatography (ethyl acetate:methanol=99:1 to 90:10) to give the title compound (5.9 mg).

¹H-NMR (400 MHz, DMSO-d₆) δ: 1.56 (6H, s), 2.29 (3H, s), 4.07 (3H, s), 4.50 (2H, s), 5.12 (2H, s), 6.38 (2H, d, J=8.5 Hz), 6.44 (1H, s), 6.80 (2H, d, J=8.5 Hz), 7.44 (1H, d, J=8.5 Hz), 7.83 (1H, d, J=2.4 Hz), 7.95 (1H, dd, J=8.5, 2.4 Hz). MS (ESI⁺): 473 [M+H]⁺.

Example 27-1

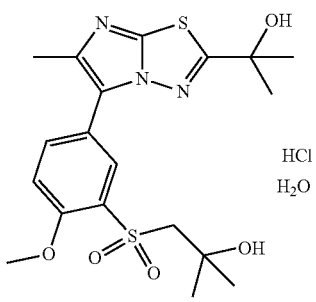

The compound obtained in Example 1-38 (100.0 mg) was suspended in ethyl acetate (1.5 mL), and 1 mol/L hydrogen chloride in ethyl acetate (0.30 mL) was added to the suspension. After stirring at room temperature for 10 minutes, the reaction was collected by filtration, and the collected reaction was washed with ethyl acetate (1 mL). The resulting product was dried at 50° C. under reduced pressure to give the title compound (90.4 mg).

$^1$H-NMR (400 MHz, DMSO-$d_6$) δ: 1.24 (6H, s), 1.59 (6H, s), 2.45 (3H, s), 3.57 (2H, s), 4.02 (3H, s), 7.46 (1H, d, J=8.8 Hz), 7.98 (1H, dd, J=8.8, 2.3 Hz), 8.17 (1H, d, J=2.3 Hz).

Examples 27-2 to 27-10

A suitable compound of General Formula (1) was used to perform reactions according to any of methods similar to Example 27-1 and the method described in Step AK-1 or similar methods thereto to give the compounds of Examples 27-2 to 27-10 shown below.

TABLE 119

| Example | Structure | Instrumental Data |
|---|---|---|
| 27-2 | 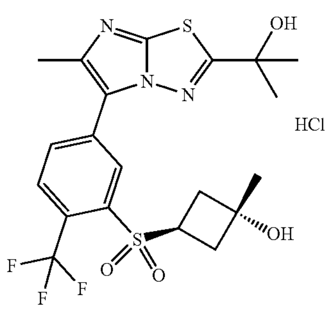 [SMILES: Cc1nc2sc(C(C)(C)O)nn2c1-c1ccc(C(F)(F)F)c(S(=O)(=O)[C@H]2C[C@](C)(O)C2)c1 ; Cl] | $^1$H-NMR (400 MHz, DMSO-$d_6$) δ: 1.31 (3H, s), 1.62 (6H, s), 2.18-2.27 (2H, m), 2.43-2.52 (2H, m), 2.54 (3H, s), 4.15-4.26 (1H, m), 8.14-8.21 (2H, m), 8.68 (1H, s). |
| 27-3 | 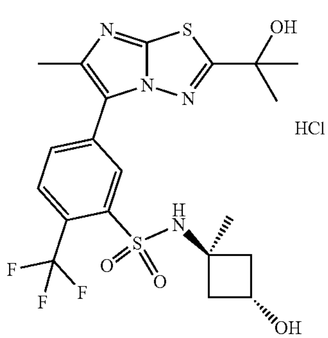 [SMILES: Cc1nc2sc(C(C)(C)O)nn2c1-c1ccc(C(F)(F)F)c(S(=O)(=O)N[C@]2(C)C[C@@H](O)C2)c1 ; Cl] | $^1$H-NMR (400 MHz, DMSO-$d_6$) δ: 1.36 (3H, s), 1.62 (6H, s), 1.69-1.77 (2H, m), 2.52-2.59 (5H, m), 3.93-4.03 (1H, m), 8.08 (1H, d, J = 8.5 Hz), 8.10-8.14 (1H, m), 8.15 (1H, s), 8.62 (1H, s). |
| 27-4 | 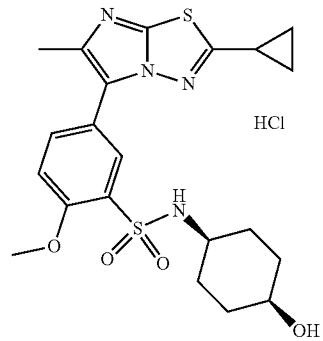 [SMILES: COc1ccc(-c2c(C)nc3sc(C4CC4)nn23)cc1S(=O)(=O)N[C@H]1CC[C@@H](O)CC1 ; Cl] | $^1$H-NMR (400 MHz, DMSO-$d_6$) δ: 0.81-0.88 (2H, m), 1.01-1.08 (2H, m), 1.28-1.39 (4H, m), 1.48-1.66 (4H, m), 2.14-2.23 (1H, m), 2.34 (3H, s), 3.02-3.14 (1H, m), 3.55-3.64 (1H, m), 3.98 (3H. s), 7.37-7.44 (2H, m), 7.76-7.84 (3H, m). |

TABLE 119-continued

| Example | Structure | Instrumental Data |
|---|---|---|
| 27-5 | 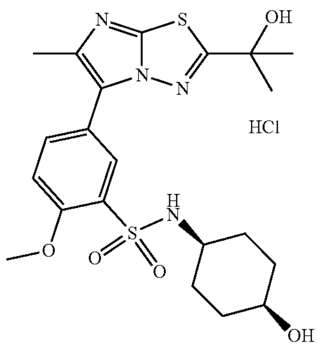 [SMILES: COc1ccc(-c2c(C)nc3sc(C(C)(C)O)nn23)cc1S(=O)(=O)N[C@H]1CC[C@@H](O)CC1 ; Cl] | $^1$H-NMR (400 MHz, DMSO-d$_6$) δ: 1.25-1.36 (4H, m), 1.49-1.66 (10H, m), 2.44 (3H, s), 2.98-3.09 (1H, m), 3.55-3.62 (1H, m), 3.97 (3H, s), 7.33 (1H, d, J = 7.3 Hz), 7.39 (1H, d, J = 9.1 Hz), 7.90 (1H, dd, J = 8.5, 2.4 Hz), 8.11 (1H, d, J = 2.4 Hz). |
| 27-6 | 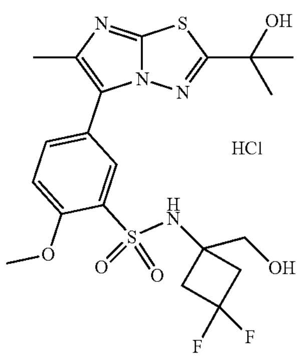 [SMILES: COc1ccc(-c2c(C)nc3sc(C(C)(C)O)nn23)cc1S(=O)(=O)NC1(CO)CC(F)(F)C1 ; Cl] | $^1$H-NMR (400 MHz, DMSO-d$_6$) δ: 1.58 (6H, s), 2.43 (3H, s), 2.70 (4H, t, J = 12.5 Hz), 3.33 (2H, s), 3.97 (3H, s), 7.39 (1H, d, J = 8.6 Hz), 7.86 (1H, s), 7.90 (1H, dd, J = 8.6, 2.4 Hz), 8.10 (1H, d, J = 2.4 Hz). |

TABLE 120

| Example | Structure | Instrumental Data |
|---|---|---|
| 27-7 | 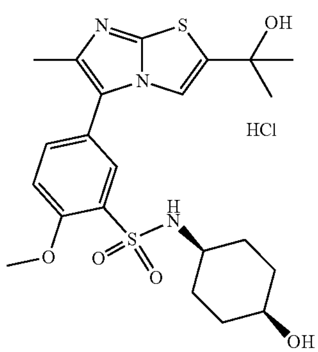 [SMILES: COc1ccc(-c2c(C)nc3sc(C(C)(C)O)cn23)cc1S(=O)(=O)N[C@H]1CC[C@@H](O)CC1 ; Cl] | $^1$H-NMR (400 MHz, DMSO-d$_6$) δ: 1.27-1.39 (4H, m), 1.49-1.67 (10H, m), 2.34 (3H, s). 3.02-3.13 (1H, m), 3.57-3.63 (1H, m), 3.99 (3H, s), 7.39-7.44 (2H, m), 7.78-7.87 (3H, m). |
| 27-8 | 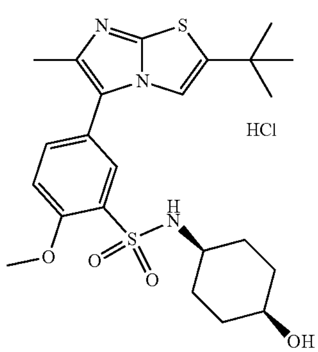 [SMILES: COc1ccc(-c2c(C)nc3sc(C(C)(C)C)cn23)cc1S(=O)(=O)N[C@H]1CC[C@@H](O)CC1 ; Cl] | $^1$H-NMR (400 MHz, DMSO-d$_6$) δ: 1.28-1.41 (13H, m), 1.49-1.67 (4H, m), 2.34 (3H, s), 3.02-3.12 (1H, m), 3.57-3.63 (1H, m), 3.99 (3H, s). 7.39-7.44 (2H, m), 7.69 (1H, s), 7.80-7.85 (2H, m). |

TABLE 120-continued

| Example | Structure | Instrumental Data |
|---|---|---|
| 27-9 | 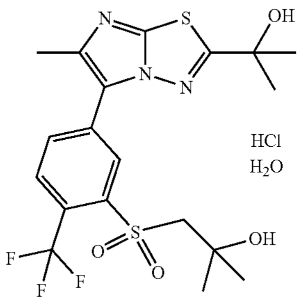 [SMILES: Cc1nc2sc(C(C)(C)O)nn2c1-c1ccc(C(F)(F)F)c(S(=O)(=O)CC(C)(C)O)c1 ; "HClH2O"] | $^1$H-NMR (400 MHz, DMSO-$d_6$) δ: 1.33 (6H, s), 1.62 (6H, s), 2.55 (3H, s), 3.56 (2H, s), 8.13 (1 H, d, J = 7.9 Hz), 8.20-8.24 (1H, m), 8.74 (1H, d, J = 1.8 Hz). |
| 27-10 | 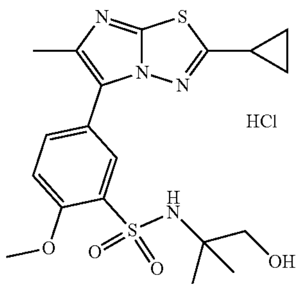 [SMILES: COc1ccc(-c2c(C)nc3sc(C4CC4)nn23)cc1S(=O)(=O)NC(C)(C)CO ; Cl] | $^1$H-NMR (400 MHz, DMSO-$d_6$) δ: 1.02 (6H, s), 1.08-1.12 (2H, m), 1.23-1.29 (2H, m), 2.43 (3H, s), 2.48-2.56 (1H, m), 3.18 (2H, s), 3.98 (3H, s), 6.71 (1H, s), 7.39 (1H, d, J = 8.6 Hz). 7.86 (1H, dd. J = 8.9, 2.1 Hz), 8.09 (1H, d. J = 2.4 Hz). |

Reference Example 61

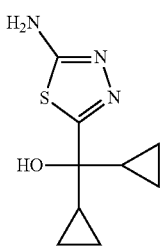

[Formula 127]

To a solution of ethyl 5-amino-1,3,4-thiadiazole-2-carboxylate (2.62 g) in tetrahydrofuran (100 mL) was added cyclopropylmagnesium bromide (0.5 mol/L in tetrahydrofuran, 100 mL) at 0° C., and the mixture was stirred at 0° C. for 4.5 hours under an argon atmosphere. Saturated aqueous ammonium chloride solution was added to the reaction mixture, and the mixture was extracted with ethyl acetate. The solvent in the extracted layer was distilled away under reduced pressure, and the residue was purified by silica gel column chromatography (ethyl acetate) to give the title compound (1.24 g).

$^1$H-NMR (400 MHz, CDCl$_3$) δ: 0.40-0.46 (2H, m), 0.50-0.67 (6H, m), 1.22-1.29 (2H, m), 2.80 (1H, s), 5.07 (1H, s), 5.78 (1H, s). MS (ESI$^+$): 212 [M+H]$^+$.

Test Example 1

Evaluation of inhibitory activity against human rhinovirus infection and replication (by quantitative real-time PCR)

A required amount of a test compound was weighed off and dissolved in dimethyl sulfoxide (DMSO) to yield a 10 mmol/L stock solution. Next, the stock solution was diluted with a medium for viral infection (minimum essential medium (MEM) supplemented with 2% fetal bovine serum, 5% Tryptose phosphate broth, and 30 mmol/L MgCl$_2$) to prepare 100 nmol/L and 1000 nmol/L of test compound solutions. MRC-5 (human fetal lung fibroblast: ATCC) was suspended at a density of 30000 cells/mL in cell culture medium (MEM supplemented with 10% fetal bovine serum), and 625 μL of the suspension per well was seeded into a 24-well cell culture plate and cultured at 37° C. in 5% CO$_2$. After 72 hours, it was confirmed that the plate had become 80% confluent. The plate was washed with 625 μL of phosphate-buffered physiological saline (Ca/Mg-free; PBS-) once, and 625 μL of the test compound solution prepared just before use was immediately added to the plate. After 30 minutes, the medium was removed followed by addition of 187.5 μL of the test compound solution that had been prepared such that the cells were infected with HRV14 (ATCC) at multiplicity of infection (MOI)=0.2. The cells were then cultured at 35° C. in 5% CO$_2$. After additional 2 hours, 625 μL of the test compound solution prepared just before use was added, and the cells were cultured at 35° C. in 5% CO$_2$. After 48 hours, the cells were washed with 625 μL of PBS- once, and total RNA was extracted from the cells using RNeasy (R) plus kit (Qiagen) according to the manufacturer's instruction. Subsequently, cDNA was synthesized using High-Capacity cDNA Reverse Transcription Kit (Thermo Fisher Scientific). Finally, quantitative real-time PCR was performed in 7500 Fast Real-time PCR system (Life technologies) to measure HRV14 and 18s rRNA. The measurement protocol consisted of the initial denaturation phase at 95° C. for 20 seconds followed by 40 cycles of the denaturation step at 95° C. for 3 seconds and the annealing/elongation step at 60° C. for 30 seconds. The primers used were HRV14 forward primer set forth in SEQ ID NO: 1 and HRV14 reverse primer set forth in SEQ ID NO: 2, and the probe is set forth in SEQ ID NO: 3.

18s rRNA was measured using Eukaryotic 18S rRNA Endogenous Control (Applied Biosystems). According to Equation 1, 18s ribosomal RNA was used as an internal standard to normalize the viral load of HRV14:

Viral load of HRV14=The amount of HRV14 in virus-infected cells/the amount of 18s rRNA in virus-infected cells     Equation 1

Inhibitory activity of test compounds was calculated as a percent inhibition (%) according to Equation 2:

Percent inhibition (%)=[the viral load of HRV in virus-infected cells in the absence of the test compound −the viral load of HRV in virus-infected cells in the presence of the test compound]/[the viral load of HRV in virus-infected cells in the absence of the test compound]×100     Equation 2

The results of using 100 nmol/L test compound solutions were shown in the tables below according to Examples. In the tables, percent inhibition was expressed as follows: percent inhibition >80%: +++, 80%≥percent inhibition >50%: ++, and 50%≥percent inhibition:+.

TABLE 121

| Example No. | Percent Inhibition |
|---|---|
| 1-1 | ++ |
| 1-2 | + |
| 1-3 | + |
| 1-4 | +++ |
| 1-5 | ++ |
| 1-6 | +++ |
| 1-7 | +++ |
| 1-8 | ++ |
| 1-9 | +++ |
| 1-10 | +++ |
| 1-11 | + |
| 1-12 | +++ |
| 1-13 | +++ |
| 1-14 | ++ |
| 1-15 | +++ |
| 1-16 | ++ |
| 1-17 | +++ |
| 1-18 | ++ |
| 1-19 | +++ |
| 1-20 | +++ |
| 1-21 | + |
| 1-22 | +++ |
| 1-23 | +++ |
| 1-24 | + |
| 1-25 | +++ |
| 1-26 | +++ |
| 1-27 | + |
| 1-28 | +++ |
| 1-29 | +++ |
| 1-30 | +++ |
| 1-31 | +++ |
| 1-32 | +++ |
| 1-33 | +++ |
| 1-34 | ++ |
| 1-35 | +++ |
| 1-36 | ++ |
| 1-37 | ++ |
| 1-38 | +++ |
| 1-39 | + |
| 1-40 | + |
| 1-41 | ++ |
| 1-42 | + |
| 1-43 | +++ |

TABLE 122

| Example No. | Percent Inhibition |
|---|---|
| 1-44 | + |
| 1-45 | +++ |
| 1-46 | +++ |
| 1-47 | ++ |
| 1-48 | ++ |
| 1-49 | +++ |
| 1-50 | +++ |
| 1-51 | ++ |
| 1-52 | + |
| 1-53 | +++ |
| 2-1 | + |
| 2-2 | + |
| 2-3 | +++ |
| 2-4 | + |
| 2-5 | + |
| 2-6 | + |
| 2-7 | +++ |
| 2-8 | +++ |
| 2-9 | +++ |
| 2-10 | +++ |
| 2-11 | + |
| 2-12 | + |
| 2-13 | + |
| 2-14 | + |
| 2-15 | ++ |
| 2-16 | +++ |
| 2-17 | +++ |
| 2-18 | +++ |
| 2-19 | +++ |
| 2-20 | +++ |
| 2-21 | +++ |
| 2-22 | +++ |
| 2-23 | ++ |
| 2-24 | + |
| 2-25 | + |
| 2-26 | +++ |
| 2-27 | +++ |
| 2-28 | +++ |
| 2-29 | +++ |
| 2-30 | +++ |
| 2-31 | +++ |
| 2-32 | +++ |
| 2-33 | +++ |
| 2-34 | +++ |
| 2-35 | ++ |
| 2-36 | +++ |

TABLE 123

| Example No. | Percent Inhibition |
|---|---|
| 2-37 | ++ |
| 2-38 | + |
| 2-39 | +++ |
| 2-40 | + |
| 2-41 | ++ |
| 2-42 | + |
| 2-43 | ++ |
| 2-44 | +++ |
| 2-45 | + |
| 2-46 | +++ |
| 2-47 | +++ |
| 2-48 | ++ |
| 2-49 | + |
| 2-50 | + |
| 2-51 | +++ |
| 2-52 | + |
| 2-53 | ++ |
| 2-54 | + |
| 2-55 | + |
| 2-56 | + |
| 2-57 | ++ |
| 2-58 | ++ |
| 2-59 | + |
| 2-60 | + |
| 2-61 | ++ |
| 2-62 | + |
| 2-63 | + |
| 2-64 | +++ |
| 2-65 | +++ |
| 2-66 | +++ |
| 2-67 | +++ |

TABLE 123-continued

| Example No. | Percent Inhibition |
|---|---|
| 2-68 | ++ |
| 2-69 | ++ |
| 2-70 | + |
| 2-71 | +++ |
| 2-72 | + |
| 2-73 | +++ |
| 2-74 | + |
| 2-75 | + |
| 2-76 | +++ |
| 2-77 | +++ |
| 2-78 | + |
| 2-79 | ++ |
| 2-80 | + |
| 2-81 | +++ |
| 2-82 | +++ |
| 2-83 | ++ |

TABLE 124

| Example No. | Percent Inhibition |
|---|---|
| 2-84 | +++ |
| 2-85 | + |
| 2-86 | +++ |
| 2-87 | +++ |
| 2-88 | + |
| 2-89 | ++ |
| 2-90 | +++ |
| 2-91 | +++ |
| 2-92 | ++ |
| 2-93 | ++ |
| 2-94 | ++ |
| 2-95 | ++ |
| 2-96 | +++ |
| 2-97 | +++ |
| 2-98 | +++ |
| 3-1 | +++ |
| 3-2 | +++ |
| 3-3 | + |
| 4-1 | +++ |
| 4-2 | +++ |
| 4-3 | +++ |
| 4-4 | ++ |
| 4-5 | +++ |
| 5 | + |
| 6-1 | ++ |
| 6-2 | + |
| 6-3 | +++ |
| 6-4 | +++ |
| 7-1 | +++ |
| 7-2 | +++ |
| 8-1 | ++ |
| 8-2 | + |
| 8-3 | +++ |
| 8-4 | +++ |
| 9-1 | +++ |
| 9-2 | ++ |
| 9-3 | +++ |
| 10-1 | +++ |
| 10-2 | + |
| 10-3 | +++ |
| 11 | + |
| 12-1 | ++ |
| 12-2 | ++ |
| 13 | + |
| 14 | + |
| 15-1 | + |
| 15-2 | ++ |

TABLE 125

| Example No. | Percent Inhibition |
|---|---|
| 16 | + |
| 17 | + |
| 18-1 | ++ |
| 18-2 | + |
| 19 | +++ |
| 20-1 | +++ |
| 20-2 | + |
| 21-1 | + |
| 21-2 | + |
| 21-3 | ++ |
| 21-4 | ++ |
| 21-5 | + |
| 21-6 | + |
| 21-7 | ++ |
| 21-8 | ++ |
| 21-9 | + |
| 21-10 | + |
| 21-11 | + |
| 21-12 | ++ |
| 21-13 | + |
| 21-14 | +++ |
| 21-15 | +++ |
| 21-16 | ++ |
| 21-17 | + |
| 21-18 | ++ |
| 21-19 | ++ |
| 21-20 | + |
| 22 | + |
| 23 | +++ |
| 24 | + |
| 25 | ++ |
| 26 | + |

INDUSTRIAL APPLICABILITY

The compounds of the present invention are useful for a therapeutic or prophylactic agent against picornavirus infections, particularly rhinovirus infections.

SEQUENCE LISTING FREE TEXT

Sequence Listing 1

SEQ ID NO: 1 is a sequence of the forward primer that recognizes a DNA sequence complementary to HRV14 RNA.

Sequence Listing 2

SEQ ID NO: 2 is a sequence of the reverse primer that recognizes a DNA sequence complementary to HRV14 RNA.

Sequence Listing 3

SEQ ID NO: 3 is a sequence of the probe that has a fluorescent dye FAM sequence at its 5' end.

The invention claimed is:

1. A compound represented by Formula (1):

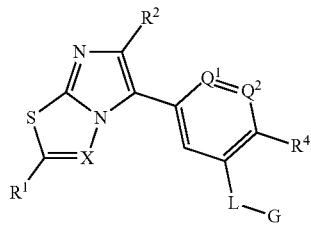

wherein
X represents N or CH;
$Q^1$ represents N or CH;
$Q^2$ represents N or $CR^3$;
L represents —$SO_2$—, —$SO_2C(R^8)_2$—, or —$SO_2NR^8$—;
$R^1$ represents H; a $C_1$-$C_6$ alkyl group, wherein the alkyl group is optionally substituted with one or more substituents selected from the group consisting of a halogen atom, a hydroxy group, a $C_1$-$C_6$ alkyl group, a $C_1$-$C_6$ alkoxy group, a halo$C_1$-$C_6$ alkyl group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)$NR^{10}R^{11}$; a $C_3$-$C_6$ cycloalkyl group, wherein the cycloalkyl group is optionally substituted with one or more substituents selected from the group consisting of a halo$C_1$-$C_6$ alkyl group, a $C_1$-$C_6$ alkoxy group, a hydroxy group, and a cyano group; or a $C_2$-$C_6$ alkenyl group, wherein the alkenyl group is optionally substituted with one or more substituents selected from the group consisting of a halogen atom, a $C_1$-$C_6$ alkoxy group, a cyano group, a carboxy group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)$NR^{10}R^{11}$;

$R^2$ represents a $C_1$-$C_6$ alkyl group;

$R^3$ represents H; a $C_1$-$C_6$ alkyl group, wherein the alkyl group is optionally substituted with one or more substituents selected from the group consisting of a halogen atom, a hydroxy group, a $C_1$-$C_6$ alkoxy group, a halo$C_1$-$C_6$ alkyl group, a cyano group, a $C_3$-$C_{10}$ cycloalkyl group, a 3- to 10-membered heterocycloalkyl group, a $C_3$-$C_{10}$ cycloalkyloxy group, a 3- to 10-membered heterocycloalkyloxy group, —C(O)$R^9$, and —C(O)$NR^{10}R^{11}$; a hydroxy group; a $C_1$-$C_6$ alkoxy group; a halo$C_1$-$C_6$ alkyl group; a cyano group; a $C_3$-$C_{10}$ cycloalkyl group; a 3- to 10-membered heterocycloalkyl group; a $C_3$-$C_{10}$ cycloalkyloxy group; a 3- to 10-membered heterocycloalkyloxy group; —C(O)$R^9$; —C(O)$NR^{10}R^{11}$; or a halogen atom;

$R^4$ represents H, a halogen atom, a $C_1$-$C_6$ alkoxy group, a deuterated $C_1$-$C_6$ alkoxy group, a $C_1$-$C_6$ alkyl group, a halo$C_1$-$C_6$ alkyl group, a halo$C_1$-$C_6$ alkoxy group, a hydroxy$C_1$-$C_6$ alkyl group, a hydroxy group, a cyano group, —C(O)$R^9$, —C(O)$NR^{10}R^{11}$, or $NR^{10}R^{11}$;

when $Q^2$ is $CR^3$, $R^3$ and $R^4$ may be joined together to form a ring;

G represents —R⁵—R⁶—R⁷; a hydroxyC₁-C₆ alkyl group, wherein the hydroxyC₁-C₆ alkyl group is optionally substituted with W¹ and W², wherein W¹ and W² are each independently selected from the group consisting of hydrogen, a C₁-C₆ alkyl group, a deuterated C₁-C₆ alkyl group, a haloC₁-C₆ alkyl group, and a hydroxyC₁-C₆ alkyl group, wherein W¹ and W² may be joined together to form a ring, and the ring formed by W¹ and W² is optionally substituted with one or more halogen atoms; a C₃-C₆ cycloalkyl group, wherein the C₃-C₆ cycloalkyl group is optionally substituted with W³ and W⁴, wherein W³ and W⁴ are each independently selected from the group consisting of hydrogen, a halogen atom, a hydroxy group, a C₁-C₆ alkyl group, a C₁-C₆ acyl group, a hydroxyC₁-C₆ alkyl group, a C₁-C₆ alkoxy group, a C₁-C₆ alkoxycarbonyl group, —SO₂R¹², and an oxo group, and W³ and W⁴ may be joined together to form a ring; a C₅-C₈ bicycloalkyl group, wherein the C₅-C₈ bicycloalkyl group is optionally substituted with W³ and W⁴, wherein W³ and W⁴ are each independently selected from the group consisting of hydrogen, a halogen atom, a hydroxy group, a C₁-C₆ alkyl group, a C₁-C₆ acyl group, a hydroxyC₁-C₆ alkyl group, a C₁-C₆ alkoxy group, a C₁-C₆ alkoxycarbonyl group, —SO₂R¹², and an oxo group, and W³ and W⁴ may be joined together to form a ring; a 3- to 10-membered heterocycloalkyl group, wherein the 3- to 10-membered heterocycloalkyl group is optionally substituted with W³ and W⁴, wherein W³ and W⁴ are each independently selected from the group consisting of hydrogen, a halogen atom, a hydroxy group, a C₁-C₆ alkyl group, a C₁-C₆ acyl group, a hydroxyC₁-C₆ alkyl group, a C₁-C₆ alkoxy group, a C₁-C₆ alkoxycarbonyl group, —SO₂R¹², —C(O)N(R¹³)₂, and an oxo group, and W³ and W⁴ may be joined together to form a ring; a C₁-C₆ alkyl group, wherein the C₁-C₆ alkyl group is optionally substituted with W⁵ and W⁶, wherein W⁵ and W⁶ are each independently selected from the group consisting of H, a cyano group, a hydroxyC₁-C₆ alkyl group, a C₁-C₆ alkyl group, a C₁-C₆ alkoxycarbonyl group, a carboxy group, and —C(O)N(R¹³)₂, and W⁵ and W⁶ may be joined together to form a ring; a phenyl group, wherein the phenyl group is optionally substituted with one or more substituents selected from the group consisting of a halogen atom, a C₁-C₆ alkyl group, a hydroxyC₁-C₆ alkyl group, a C₁-C₆ acyl group, a carboxy group, a hydroxy group, a haloC₁-C₆ alkyl group, a cyano group, a C₃-C₁₀ cycloalkyl group, a 3-, to 10-membered heterocycloalkyl group, —NR¹⁰R¹¹, —C(O)R⁹, —C(O)NR¹⁰R¹¹, a C₁-C₆ alkoxycarbonyl group, —SO₂R¹², and a C₁-C₆ alkoxy group; or a heteroaryl group, wherein the heteroaryl group is optionally substituted with one or more substituents selected from the group consisting of a halogen atom, a C₁-C₆ alkyl group, a hydroxyC₁-C₆ alkyl group, a C₁-C₆ acyl group, a carboxy group, a hydroxy group, a haloC₁-C₆ alkyl group, a cyano group, a C₃-C₁₀ cycloalkyl group, a 3- to 10-membered heterocycloalkyl group, —NR¹⁰R¹¹, —C(O)R⁹, —C(O)NR¹⁰R¹¹, a C₁-C₆ alkoxycarbonyl group, —SO₂R¹², and a C₁-C₆ alkoxy group;

R⁵ represents a hydroxyC₁-C₆ alkylene group, wherein the hydroxyC₁-C₆ alkylene group is optionally substituted with W¹ and W², wherein W¹ and W² are each independently selected from the group consisting of H, a C₁-C₆ alkyl group, a deuterated C₁-C₆ alkyl group, a haloC₁-C₆ alkyl group, and a hydroxyC₁-C₆ alkyl group, and W¹ and W² may be joined together to form a ring, and the ring formed by W¹ and W² is optionally substituted with one or more halogen atoms; a C₃-C₆ cycloalkylene group, wherein the C₃-C₆ cycloalkylene group is optionally substituted with W³ and W⁴, wherein W³ and W⁴ are each independently selected from the group consisting of H, a halogen atom, a hydroxy group, a C₁-C₆ alkyl group, a C₁-C₆ acyl group, a hydroxyC₁-C₆ alkyl group, a C₁-C₆ alkoxy group, a C₁-C₆ alkoxycarbonyl group, —SO₂R¹², and an oxo group, and W³ and W⁴ may be joined together to form a ring; a C₅-C₈ bicycloalkylene group, wherein the C₅-C₈ bicycloalkylene group is optionally substituted with W³ and W⁴, wherein W³ and W⁴ are each independently selected from the group consisting of H, a halogen atom, a hydroxy group, a C₁-C₆ alkyl group, a C₁-C₆ acyl group, a hydroxyC₁-C₆ alkyl group, a C₁-C₆ alkoxy group, a C₁-C₆ alkoxycarbonyl group, —SO₂R¹², and an oxo group, and W³ and W⁴ may be joined together to form a ring; a 3- to 10-membered heterocycloalkylene group, wherein the 3- to 10-membered heterocycloalkylene group is optionally substituted with W³ and W⁴, wherein W³ and W⁴ are each independently selected from the group consisting of H, a halogen atom, a hydroxy group, a C₁-C₆ alkyl group, a C₃-C₁₀ cycloalkyl group, a C₁-C₆ acyl group, a hydroxyC₁-C₆ alkyl group, a C₁-C₆ alkoxy group, a C₁-C₆ alkoxycarbonyl group, —SO₂R¹², —C(O)N(R¹³)₂, and an oxo group, and W³ and W⁴ may be joined together to form a ring; a C₁-C₆ alkylene group, wherein the C₁-C₆ alkylene group is optionally substituted with W⁵ and W⁶, wherein W⁵ and W⁶ are each independently selected from the group consisting of H, a cyano group, a hydroxyC₁-C₆ alkyl group, a C₁-C₆ alkyl group, a C₁-C₆ alkoxycarbonyl group, a carboxy group, and —C(O)N(R¹³)₂, and W⁵ and W⁶ may be joined together to form a ring; a phenylene group, wherein the phenylene group is optionally substituted with one or more substituents selected from the group consisting of a halogen atom, a C₁-C₆ alkyl group, a hydroxyC₁-C₆ alkyl group, a C₁-C₆ acyl group, a carboxy group, a hydroxy group, a haloC₁-C₆ alkyl group, a cyano group, a C₃-C₁₀ cycloalkyl group, a 3- to 10-membered heterocycloalkyl group, —NR¹⁰R¹¹, —C(O)R⁹, —C(O)NR¹⁰R¹¹, a C₁-C₆ alkoxycarbonyl group, —SO₂R¹², and a C₁-C₆ alkoxy group; or a heteroarylene group, wherein the heteroarylene group is optionally substituted with one or more substituents selected from the group consisting of a halogen atom, a C₁-C₆ alkyl group, a hydroxyC₁-C₆ alkyl group, a C₁-C₆ acyl group, a carboxy group, a hydroxy group, a haloC₁-C₆ alkyl group, a cyano group, a C₃-C₁₀ cycloalkyl group, a 3- to 10-membered heterocycloalkyl group, —NR¹⁰R¹¹, —C(O)R⁹, —C(O)NR¹⁰R¹¹, a C₁-C₆ alkoxycarbonyl group, —SO₂R¹², and a C₁-C₆ alkoxy group;

R⁶ represents a bond or a C₃-C₆ cycloalkylene group;
R⁷ represents H or a hydroxy group;
each R⁸ independently represents H or a C₁-C₆ alkyl group;
R⁹ represents H, a hydroxy group, a C₁-C₆ alkyl group, a C₁-C₆ alkoxy group, or a C₃-C₆ cycloalkoxy group;
R¹⁰ represents H or a C₁-C₆ alkyl group;
R¹¹ represents H or a C₁-C₆ alkyl group;
R¹² represents H or a C₁-C₆ alkyl group; and
each R¹³ independently represents H, a C₁-C₆ alkyl group, or a hydroxyC₁-C₆ alkyl group, a pharmacologically acceptable salt of the compound, a hydrate of the compound or a hydrate of the salt.

2. The compound, a pharmacologically acceptable salt of the compound, a hydrate of the compound or a hydrate of the salt according to claim 1, wherein in Formula (1), $Q^1$ is CH, $Q^2$ is $CR^3$, and $R^3$ is $H$.

3. The compound, a pharmacologically acceptable salt of the compound, a hydrate of the compound or a hydrate of the salt according to claim 1, wherein in Formula (1), X is N.

4. The compound, a pharmacologically acceptable salt of the compound, a hydrate of the compound or a hydrate of the salt according to claim 1, wherein in Formula (1), $R^2$ is a methyl group.

5. The compound, a pharmacologically acceptable salt of the compound, a hydrate of the compound or a hydrate of the salt according to claim 1, wherein in Formula (1), X represents N;
$Q^1$ represents CH;
$Q^2$ represents $CR^3$;
L represents $-SO_2-$;
$R^1$ represents a $C_1$-$C_6$ alkyl group, wherein the alkyl group is optionally substituted with one or more substituents selected from the group consisting of a halogen atom, a hydroxy group, a $C_1$-$C_6$ alkoxy group, a halo$C_1$-$C_6$ alkyl group, a cyano group, a 3- to 10-membered heterocycloalkyloxy group, $-C(O)R^9$, and $-C(O)NR^{10}R^{11}$;
$R^2$ represents a methyl group;
$R^3$ represents H;
$R^4$ represents a $C_1$-$C_6$ alkoxy group, a $C_1$-$C_6$ alkyl group, or a halo$C_1$-$C_6$ alkyl group; and
G represents a hydroxy$C_1$-$C_6$ alkyl group, wherein the hydroxy$C_1$-$C_6$ alkyl group is optionally substituted with $W^1$ and $W^2$, wherein $W^1$ and $W^2$ are each independently H or a $C_1$-$C_6$ alkyl group, and $W^1$ and $W^2$ may be joined together to form a ring, and the ring formed by $W^1$ and $W^2$ is optionally substituted with one or more halogen atoms.

6. The compound, a pharmacologically acceptable salt of the compound, a hydrate of the compound or a hydrate of the salt according to claim 5, wherein in Formula (1), $R^4$ is a $C_1$-$C_6$ alkoxy group.

7. The compound, a pharmacologically acceptable salt of the compound, a hydrate of the compound or a hydrate of the salt according to claim 1, wherein in Formula (1), X represents N;
$Q^1$ represents CH;
$Q^2$ represents $CR^3$;
L represents $-SO_2-$, $-SO_2NR^8-$, or $-SO_2C(R^8)_2-$;
$R^1$ represents a $C_1$-$C_6$ alkyl group, wherein the alkyl group is optionally substituted with one or more hydroxy groups or $C_1$-$C_6$ alkoxy groups;
$R^2$ represents a methyl group;
$R^3$ represents H or a halogen atom;
$R^4$ represents a $C_1$-$C_6$ alkoxy group, a $C_1$-$C_6$ alkyl group, a halo$C_1$-$C_6$ alkyl group, or a halo$C_1$-$C_6$ alkoxy group; and
G represents a hydroxy$C_1$-$C_6$ alkyl group, wherein the hydroxy$C_1$-$C_6$ alkyl group is optionally substituted with $W^1$ and $W^2$, wherein $W^1$ and $W^2$ are each independently H or a $C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkyl group, wherein the $C_3$-$C_6$ cycloalkyl group is optionally substituted with $W^3$ and $W^4$, wherein $W^3$ and $W^4$ are each independently selected from the group consisting of H, a hydroxy group, a $C_1$-$C_6$ alkyl group, a $C_1$-$C_6$ acyl group, a hydroxy$C_1$-$C_6$ alkyl group, a $C_1$-$C_6$ alkoxycarbonyl group, and $-SO_2R^{12}$, and $W^3$ and $W^4$ may be joined together to form a ring; a 3- to 10-membered heterocycloalkyl group, wherein the 3- to 10-membered heterocycloalkyl group is optionally substituted with $W^3$ and $W^4$, wherein $W^3$ and $W^4$ are each independently selected from the group consisting of H, a hydroxy group, a $C_1$-$C_6$ alkyl group, a $C_1$-$C_6$ acyl group, a hydroxy$C_1$-$C_6$ alkyl group, a $C_1$-$C_6$ alkoxycarbonyl group, $-SO_2R^{12}$, and $-C(O)N(R^{13})_2$, and $W^3$ and $W^4$ may be joined together to form a ring; a $C_1$-$C_6$ alkyl group, wherein the $C_1$-$C_6$ alkyl group is optionally substituted with $W^5$ and $W^6$, wherein $W^5$ and $W^6$ are each independently selected from the group consisting of H, a cyano group, a hydroxy$C_1$-$C_6$ alkyl group, a $C_1$-$C_6$ alkyl group, a $C_1$-$C_6$ alkoxycarbonyl group, a carboxy group, and $-C(O)N(R^{13})_2$, and $W^5$ and $W^6$ may be joined together to form a ring; or a heteroaryl group, wherein the heteroaryl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, $-NR^{10}R^{11}$, $-C(O)R^9$, $-C(O)NR^{10}R^{11}$, a $C_1$-$C_6$ alkoxycarbonyl group, $-SO_2R^{12}$, and a $C_1$-$C_6$ alkoxy group.

8. The compound, a pharmacologically acceptable salt of the compound, a hydrate of the compound or a hydrate of the salt according to claim 1, wherein in Formula (1), X represents CH;
$Q^1$ represents N or CH;
$Q^2$ represents N or $CR^3$;
L represents $-SO_2-$, $-SO_2NR^8-$, or $-SO_2C(R^8)_2-$;
$R^1$ represents H; a $C_1$-$C_6$ alkyl group, wherein the alkyl group is optionally substituted with one or more substituents selected from the group consisting of a halogen atom, a hydroxy group, a $C_1$-$C_6$ alkoxy group, and a 3- to 10-membered heterocycloalkyloxy group; a $C_3$-$C_6$ cycloalkyl group, wherein the cycloalkyl group is optionally substituted with one or more substituents selected from the group consisting of a $C_1$-$C_6$ alkoxy group and a hydroxy group; or a $C_2$-$C_6$ alkenyl group;
$R^2$ represents a $C_1$-$C_6$ alkyl group;
$R^3$ represents H or a halogen atom;
$R^4$ represents a halogen atom, a $C_1$-$C_6$ alkoxy group, a $C_1$-$C_6$ alkyl group, a halo$C_1$-$C_6$ alkyl group, a halo$C_1$-$C_6$ alkoxy group, a cyano group, or $NR^{10}R^{11}$;
G represents a hydroxy$C_1$-$C_6$ alkyl group, wherein the hydroxy$C_1$-$C_6$ alkyl group is optionally substituted with $W^1$ and $W^2$, wherein $W^1$ and $W^2$ are each independently H or a $C_1$-$C_6$ alkyl group, and $W^1$ and $W^2$ may be joined together to form a ring, and the ring formed by $W^1$ and $W^2$ is optionally substituted with one or more halogen atoms; a $C_3$-$C_6$ cycloalkyl group, wherein the $C_3$-$C_6$ cycloalkyl group is optionally substituted with $W^3$ and $W^4$, wherein $W^3$ and $W^4$ are each independently hydrogen, a hydroxy group, or a $C_1$-$C_6$ alkoxy group, and $W^3$ and $W^4$ may be joined together to form a ring; a 3- to 10-membered heterocycloalkyl group; a phenyl group, wherein the phenyl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —NR$^{10}$R$^{11}$, —C(O)R$^9$, —C(O)NR$^{10}$R$^{11}$, a $C_1$-$C_6$ alkoxycarbonyl group, —SO$_2$R$^{12}$, and a $C_1$-$C_6$ alkoxy group; or a heteroaryl group, wherein the heteroaryl group is optionally substituted with one or more substituents selected from the group consisting of a halogen atom, a $C_1$-$C_6$ alkyl group, a hydroxy$C_1$-$C_6$ alkyl group, a $C_1$-$C_6$ acyl group, a carboxy group, a hydroxy group, a halo$C_1$-$C_6$ alkyl group, a cyano group, a $C_3$-$C_{10}$ cycloalkyl group, a 3- to 10-membered heterocycloalkyl group, —NR$^{10}$R$^{11}$, —C(O)R$^9$, —C(O)NR$^{10}$R$^{11}$, a $C_1$-$C_6$ alkoxycarbonyl group, —SO$_2$R$^{12}$, and a $C_1$-$C_6$ alkoxy group;

R$^8$ represents H or a $C_1$-$C_6$ alkyl group;

R$^{10}$ represents H or a $C_1$-$C_6$ alkyl group; and

R$^{11}$ represents H or a $C_1$-$C_6$ alkyl group.

9. The compound, a pharmacologically acceptable salt of the compound, a hydrate of the compound or a hydrate of the salt according to claim 8, wherein in Formula (1), Q$^1$ is CH, and Q$^2$ is N.

10. The compound, a pharmacologically acceptable salt of the compound, a hydrate of the compound or a hydrate of the salt according to claim 1, wherein the compound represented by Formula (1) is any one of the compounds listed in the following Tables 1 to 11:

TABLE 1

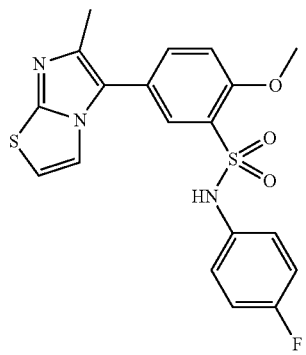 [SMILES: COc1ccc(-c2c(C)nc3sccn23)cc1S(=O)(=O)Nc1ccc(F)cc1]

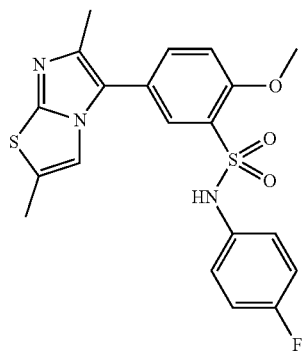 [SMILES: COc1ccc(-c2c(C)nc3sc(C)cn23)cc1S(=O)(=O)Nc1ccc(F)cc1]

TABLE 1-continued

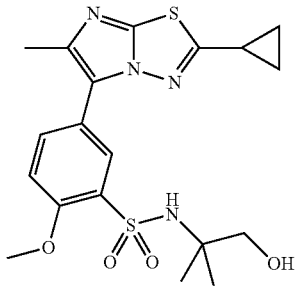 [SMILES: COc1ccc(-c2c(C)nc3sc(C4CC4)nn23)cc1S(=O)(=O)NC(C)(C)CO]

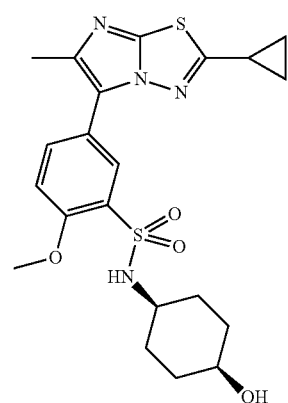

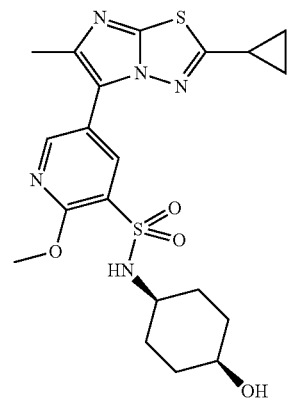 [SMILES: COc1ncc(-c2c(C)nc3sc(C4CC4)nn23)cc1S(=O)(=O)N[C@H]1CC[C@@H](O)CC1]

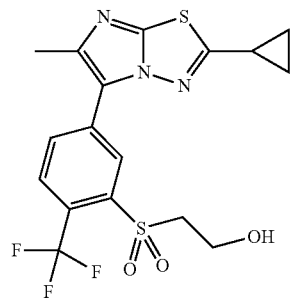 [SMILES: Cc1nc2sc(C3CC3)nn2c1-c1ccc(C(F)(F)F)c(S(=O)(=O)CCO)c1]

TABLE 1-continued
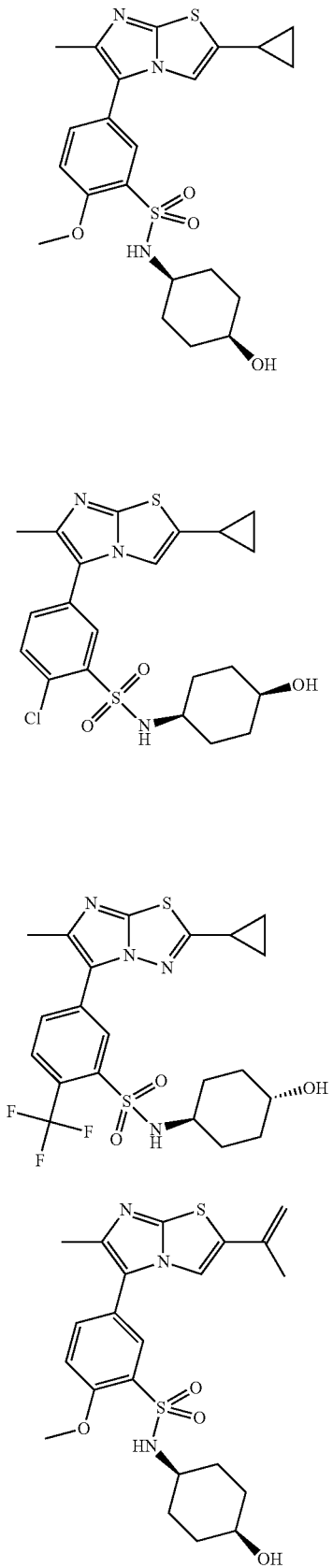
TABLE 1-continued
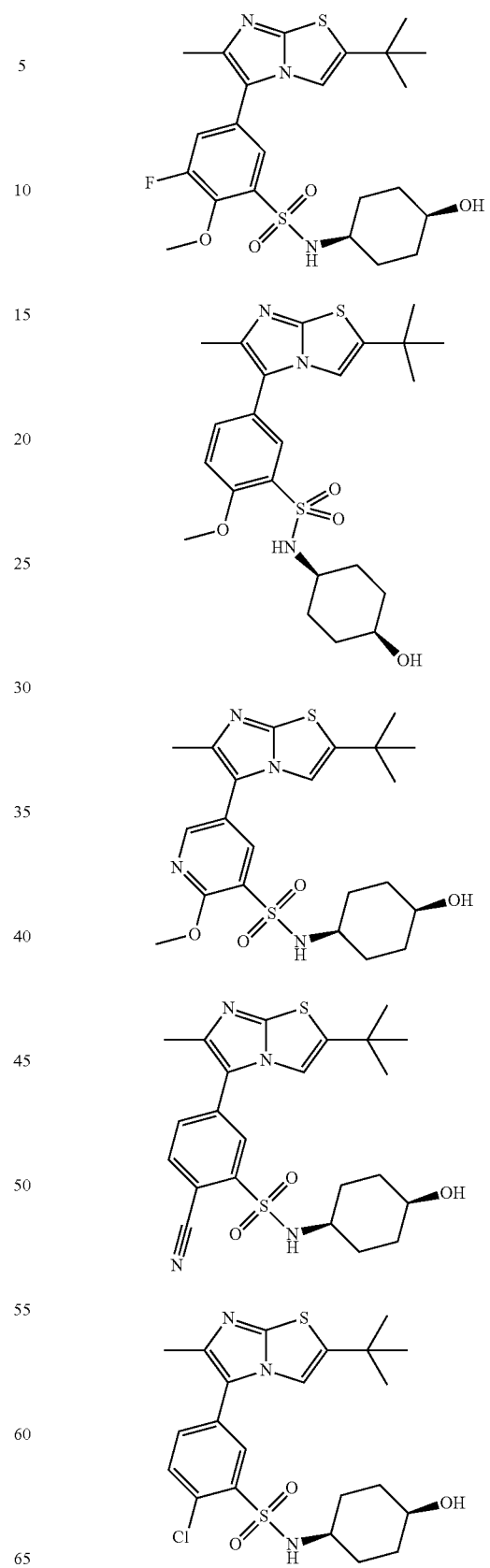

TABLE 1-continued
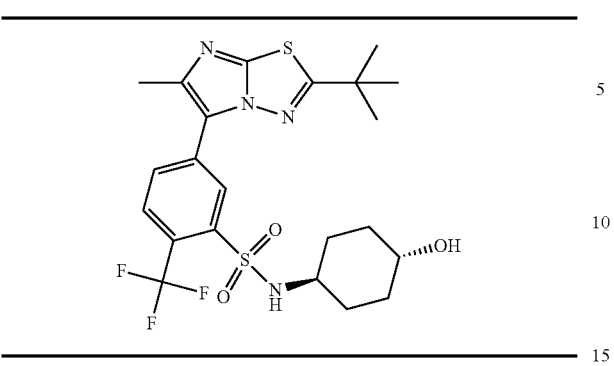
TABLE 2
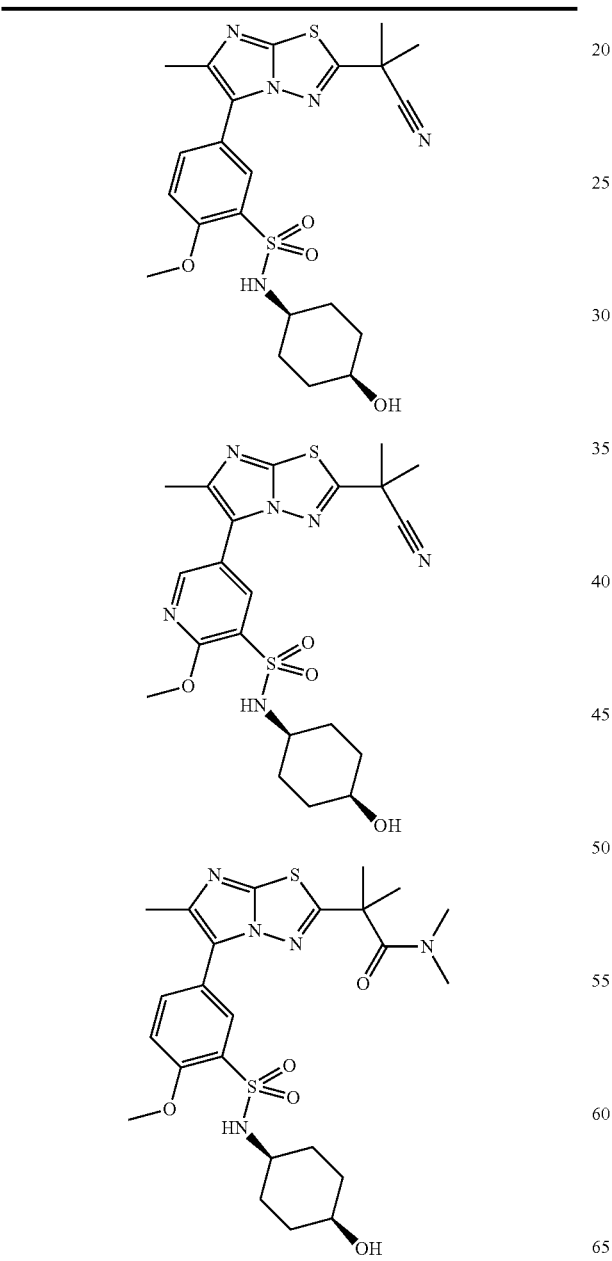
TABLE 2-continued
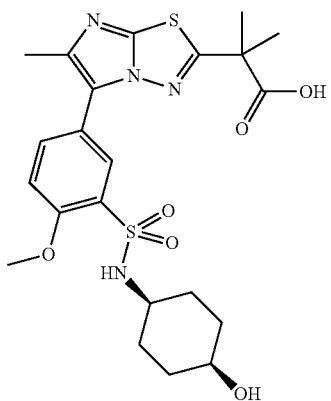 [SMILES: COc1ccc(-c2c(C)nc3sc(C(C)(C)C(=O)O)nn23)cc1S(=O)(=O)N[C@H]1CC[C@@H](O)CC1]
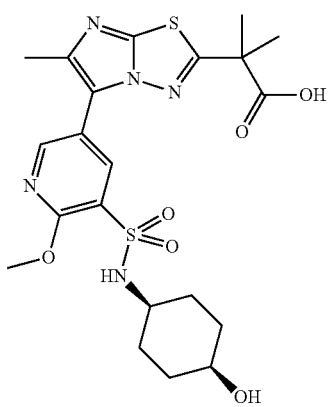
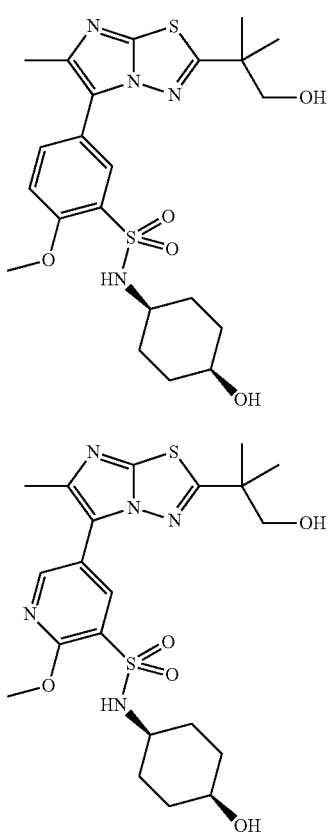

TABLE 2-continued
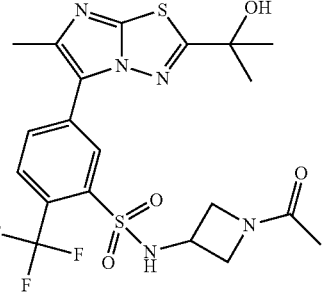
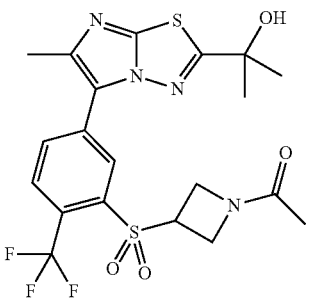 [SMILES: CC(=O)N1CC(S(=O)(=O)c2cc(-c3c(C)nc4sc(C(C)(C)O)nn34)ccc2C(F)(F)F)C1]
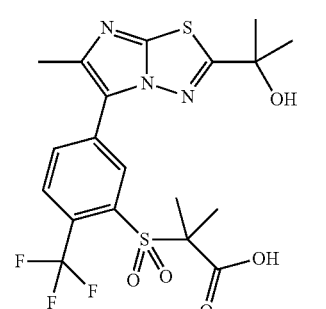
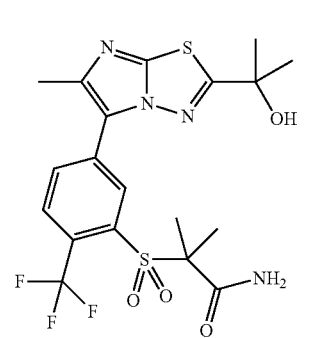 [SMILES: Cc1nc2sc(C(C)(C)O)nn2c1-c1ccc(C(F)(F)F)c(S(=O)(=O)C(C)(C)C(N)=O)c1]
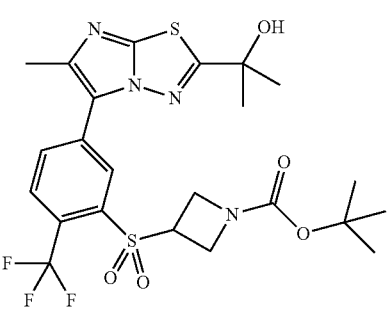 [SMILES: Cc1nc2sc(C(C)(C)O)nn2c1-c1ccc(C(F)(F)F)c(S(=O)(=O)C2CN(C(=O)OC(C)(C)C)C2)c1]
TABLE 2-continued
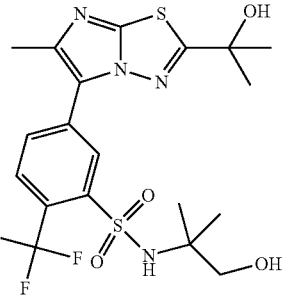
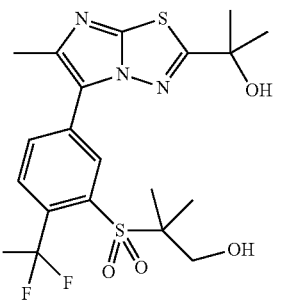

TABLE 2-continued
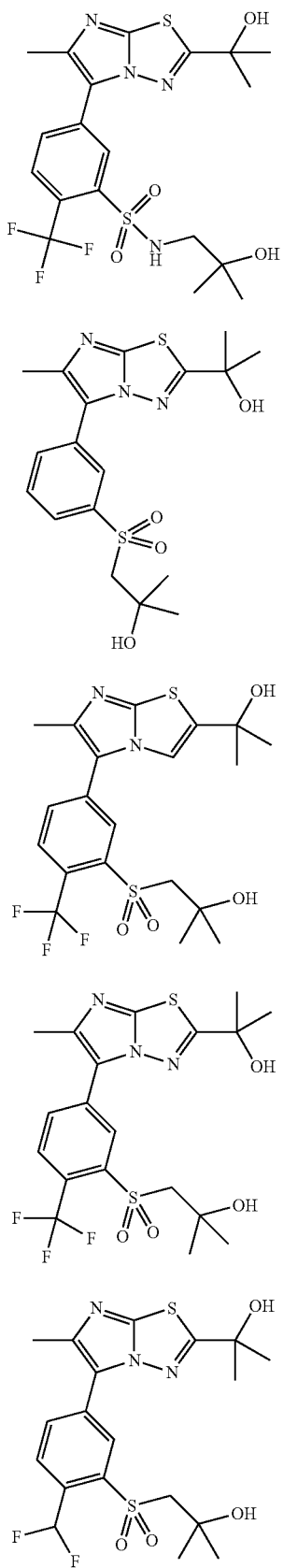
TABLE 2-continued
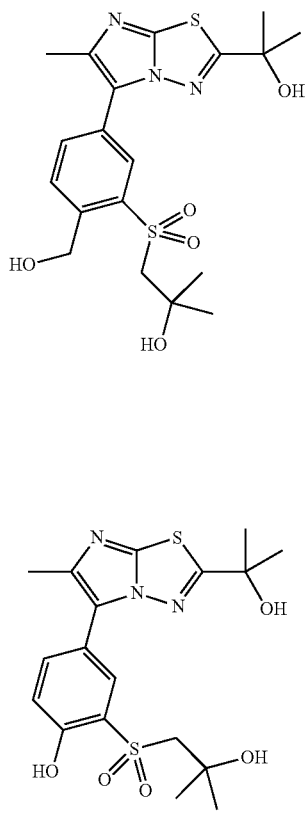
TABLE 3
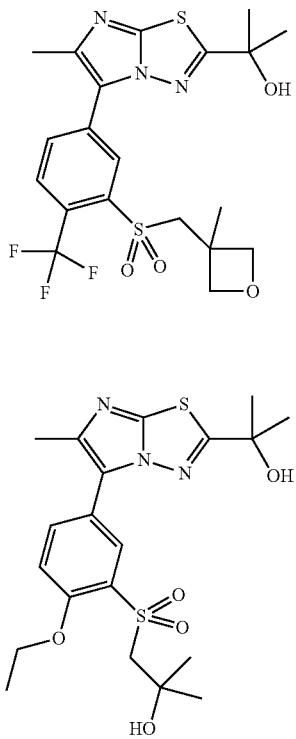

451
TABLE 3-continued
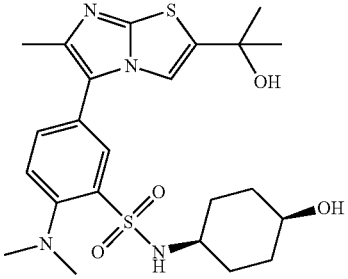 [SMILES: Cc1nc2sc(C(C)(C)O)cn2c1-c1ccc(N(C)C)c(S(=O)(=O)N[C@H]2CC[C@@H](O)CC2)c1]
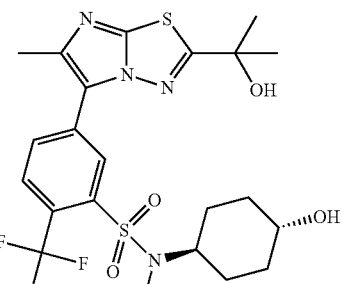
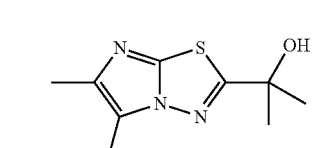
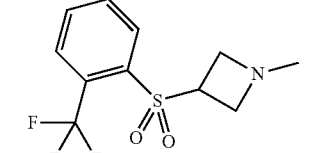
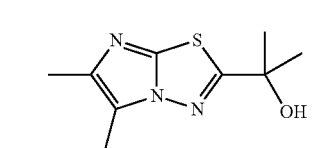
452
TABLE 3-continued
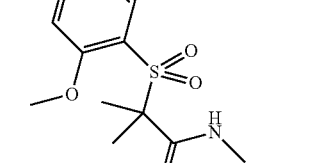
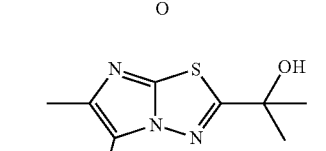
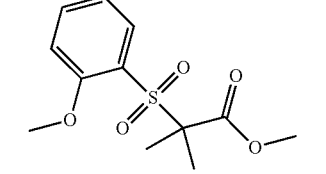
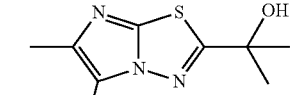

TABLE 3-continued
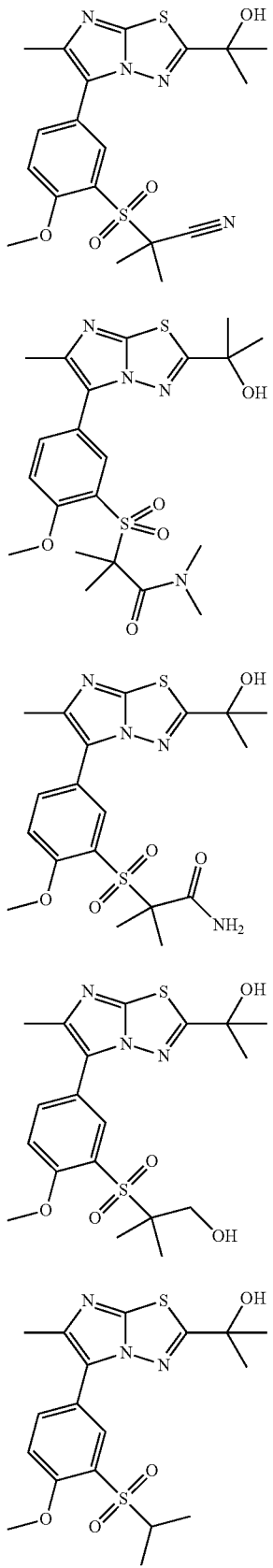
TABLE 3-continued
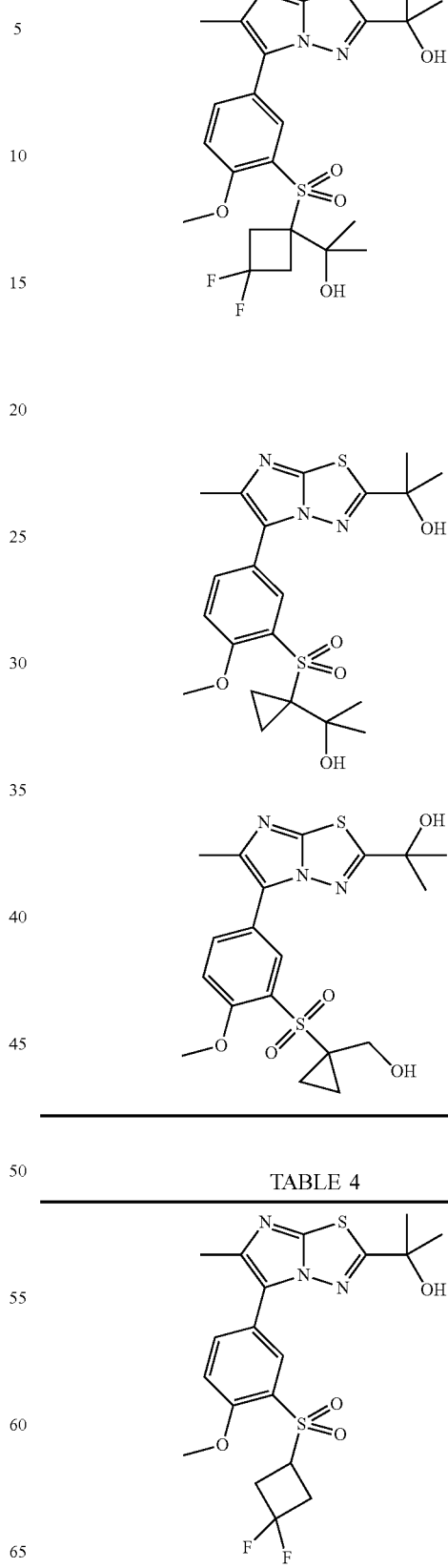
TABLE 4
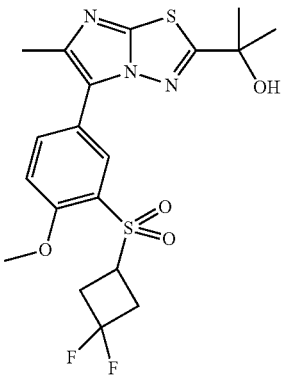 [SMILES: COc1ccc(-c2c(C)nc3sc(C(C)(C)O)nn23)cc1S(=O)(=O)C1CC(F)(F)C1]

TABLE 4-continued
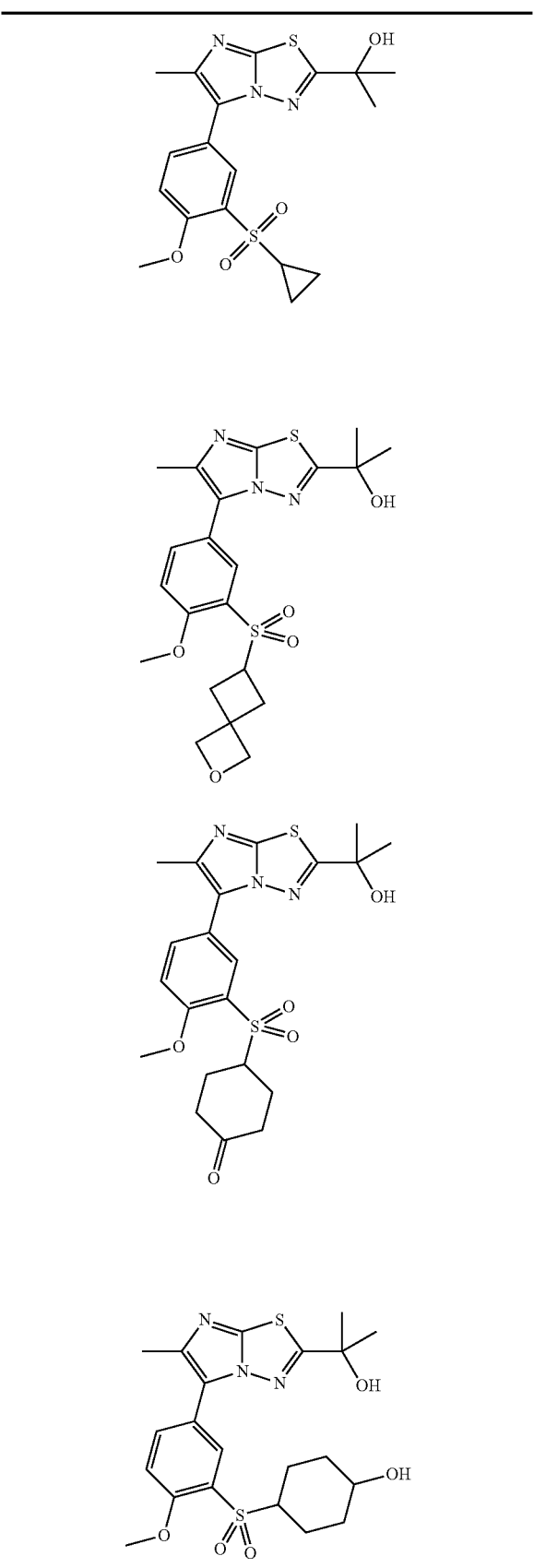
TABLE 4-continued
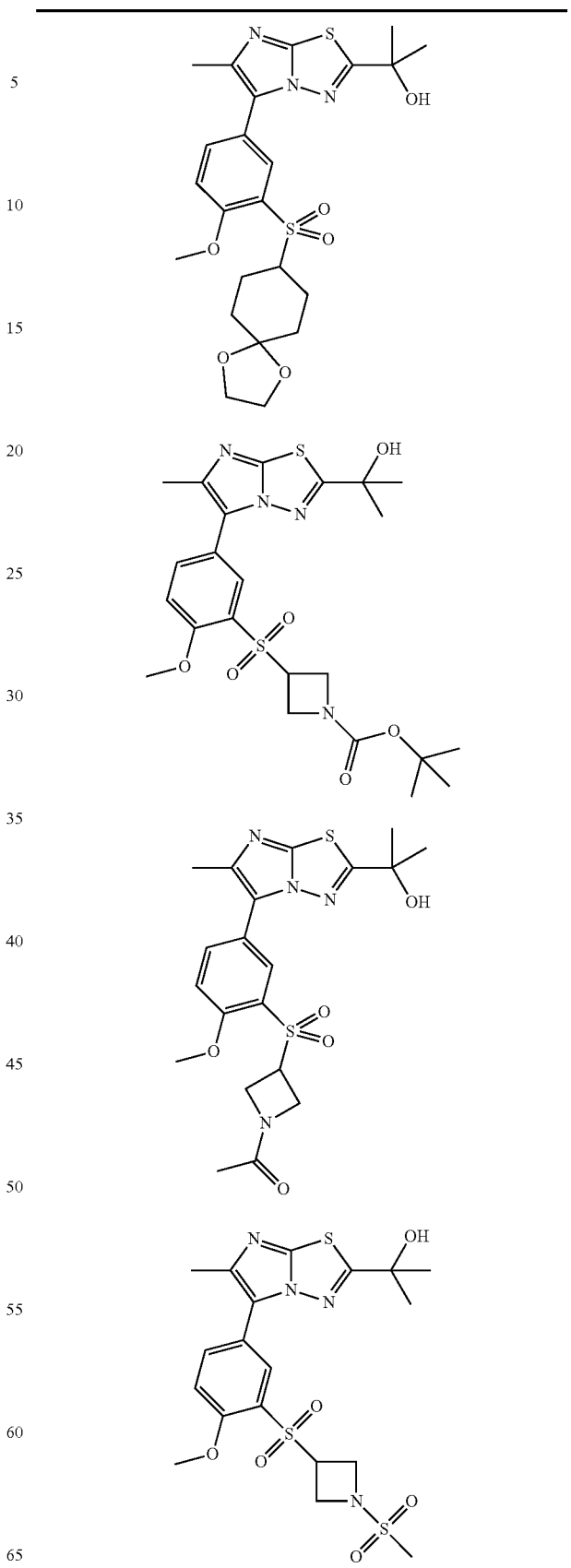

TABLE 4-continued
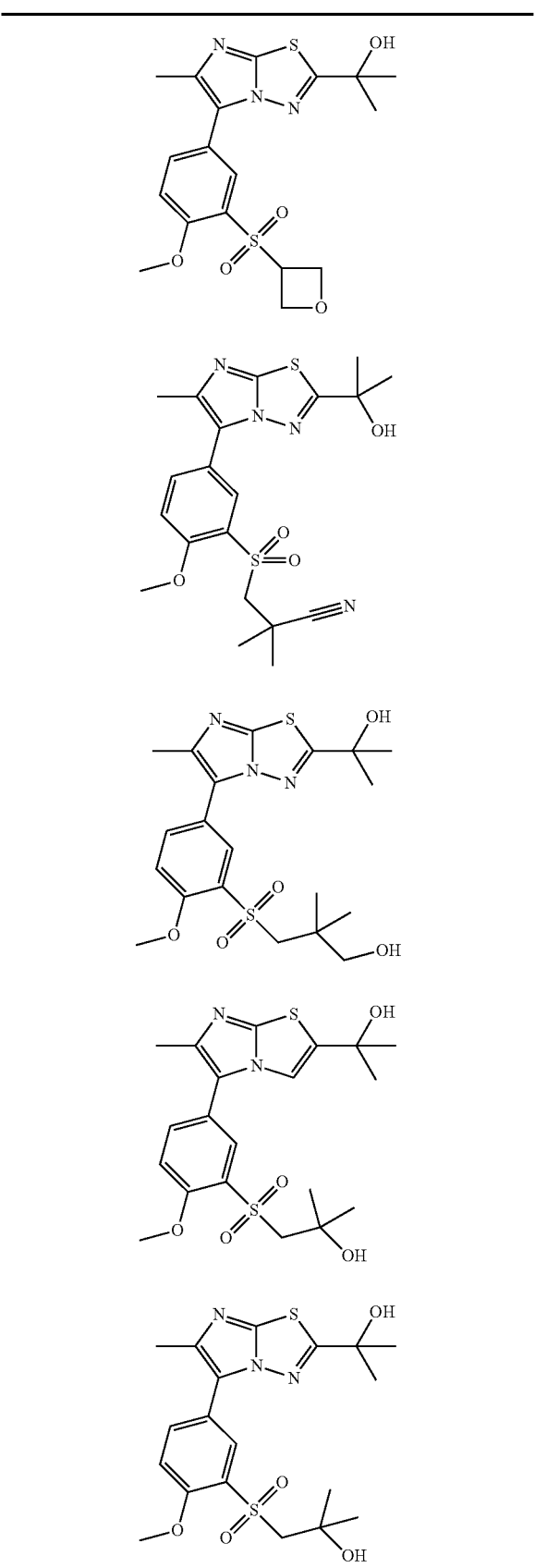
TABLE 4-continued
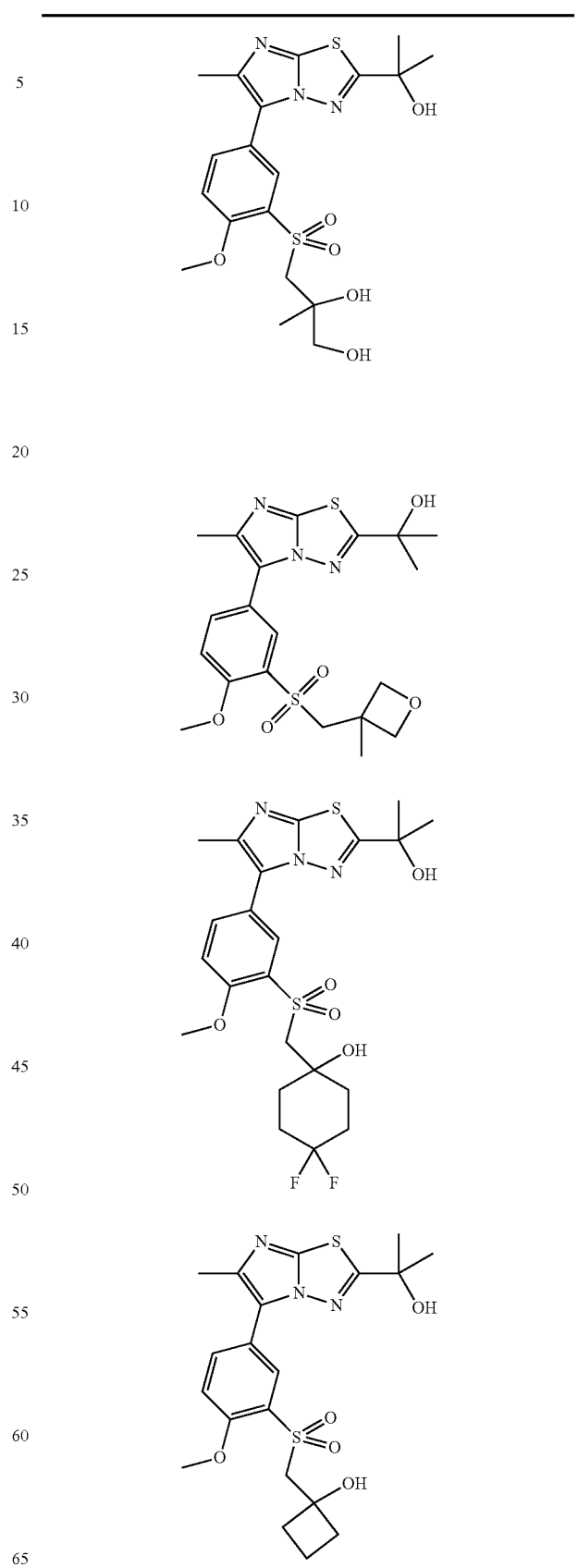

TABLE 4-continued
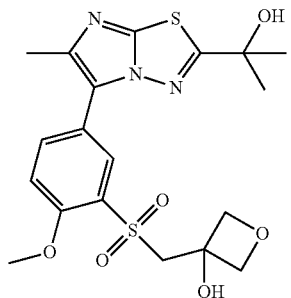 [SMILES: COc1ccc(-c2c(C)nc3sc(C(C)(C)O)nn23)cc1S(=O)(=O)CC1(O)COC1]
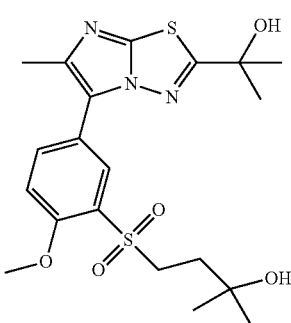
TABLE 5
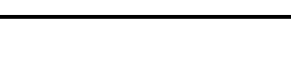
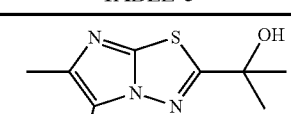
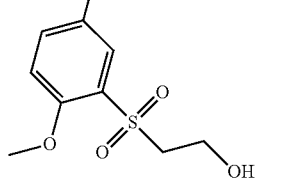
TABLE 5-continued
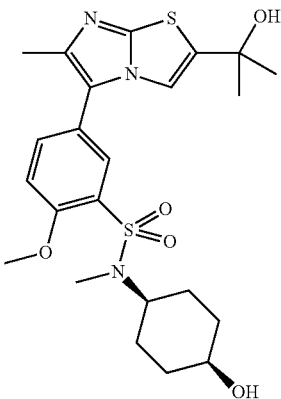 [SMILES: COc1ccc(-c2c(C)nc3sc(C(C)(C)O)cn23)cc1S(=O)(=O)N(C)[C@H]1CC[C@@H](O)CC1]
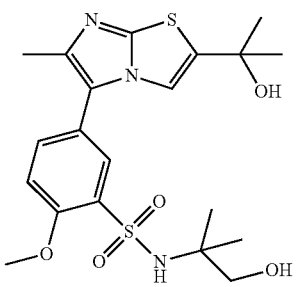 [SMILES: COc1ccc(-c2c(C)nc3sc(C(C)(C)O)cn23)cc1S(=O)(=O)NC(C)(C)CO]
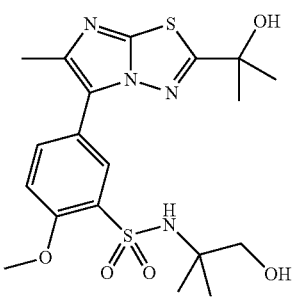 [SMILES: COc1ccc(-c2c(C)nc3sc(C(C)(C)O)nn23)cc1S(=O)(=O)NC(C)(C)CO]
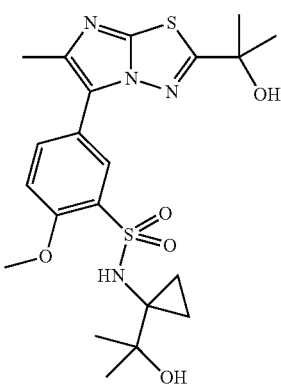 [SMILES: COc1ccc(-c2c(C)nc3sc(C(C)(C)O)nn23)cc1S(=O)(=O)NC1(C(C)(C)O)CC1]

461
TABLE 5-continued
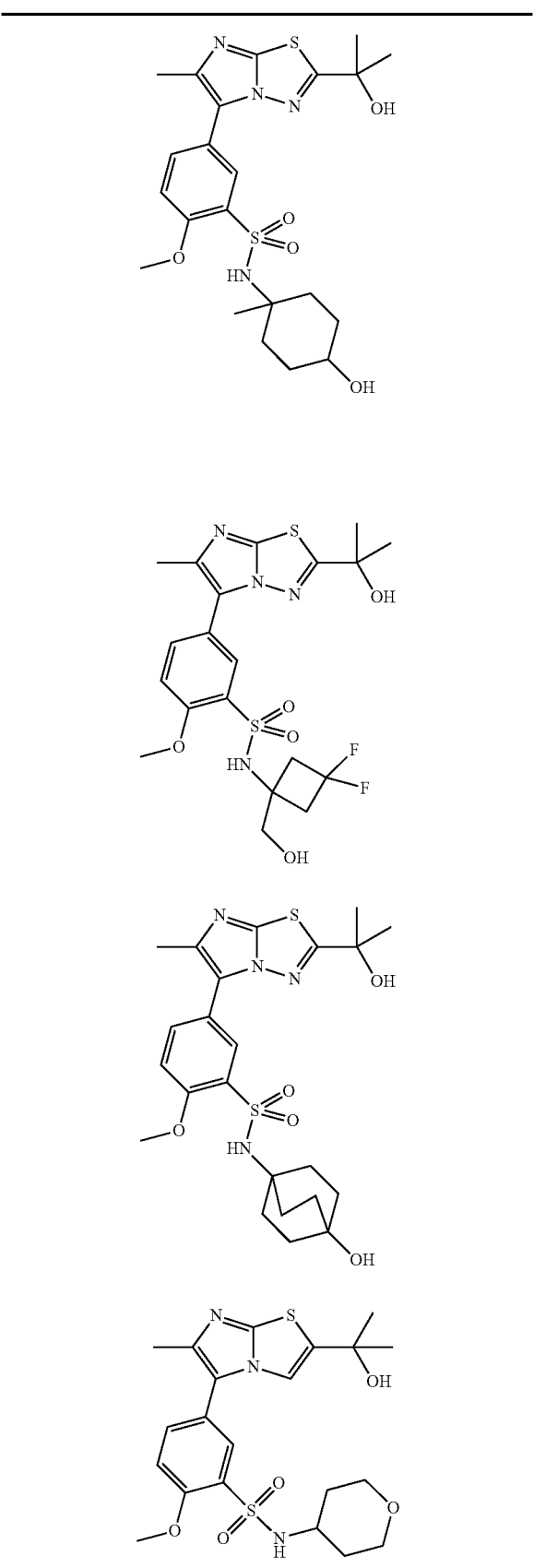
462
TABLE 5-continued
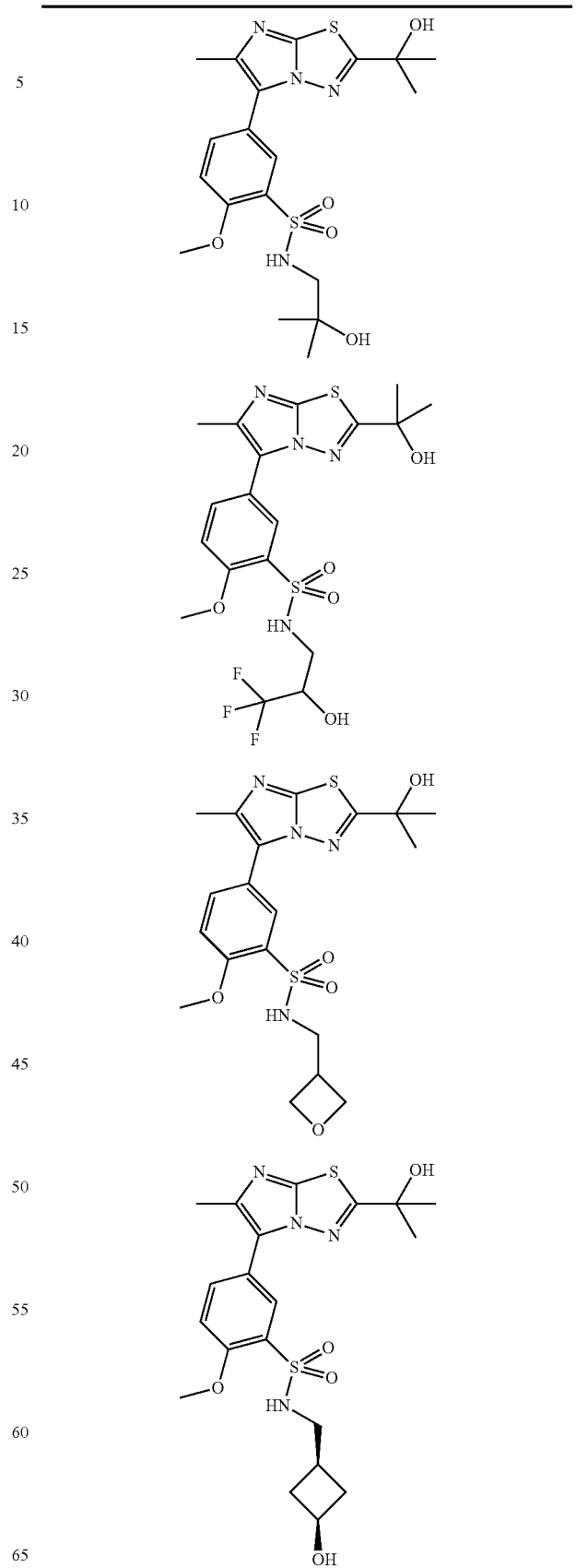

TABLE 5-continued
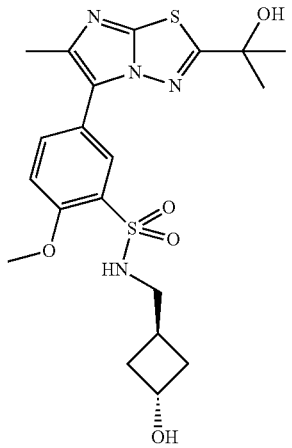 [SMILES: COc1ccc(-c2c(C)nc3sc(C(C)(C)O)nn23)cc1S(=O)(=O)NC[C@H]1C[C@H](O)C1]
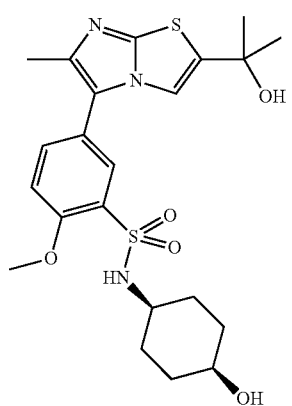 [SMILES: COc1ccc(-c2c(C)nc3sc(C(C)(C)O)cn23)cc1S(=O)(=O)N[C@H]1CC[C@@H](O)CC1]
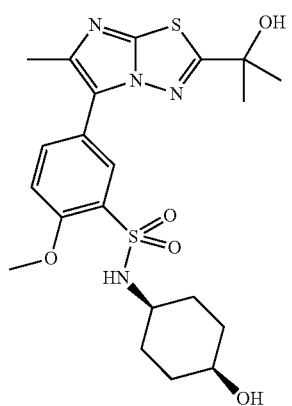
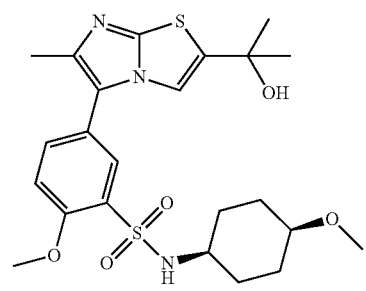
TABLE 5-continued
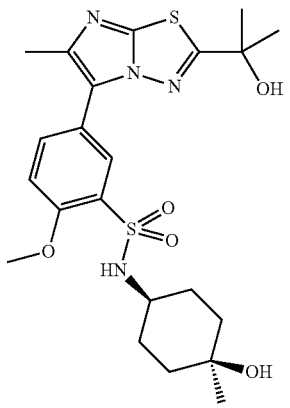 [SMILES: COc1ccc(-c2c(C)nc3sc(C(C)(C)O)nn23)cc1S(=O)(=O)N[C@H]1CC[C@@](C)(O)CC1]
TABLE 6
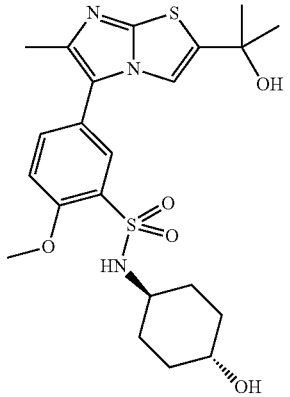 [SMILES: COc1ccc(-c2c(C)nc3sc(C(C)(C)O)cn23)cc1S(=O)(=O)N[C@H]1CC[C@H](O)CC1]
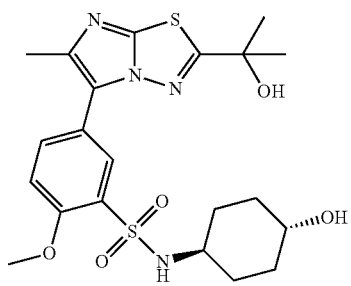
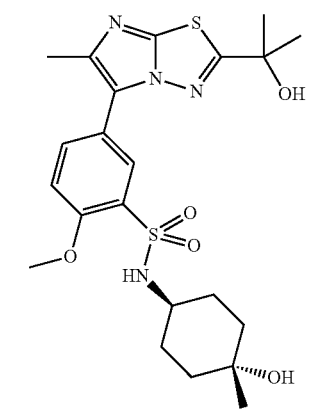 [SMILES: COc1ccc(-c2c(C)nc3sc(C(C)(C)O)nn23)cc1S(=O)(=O)N[C@H]1CC[C@](C)(O)CC1]

TABLE 6-continued
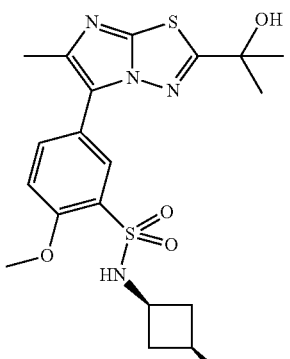
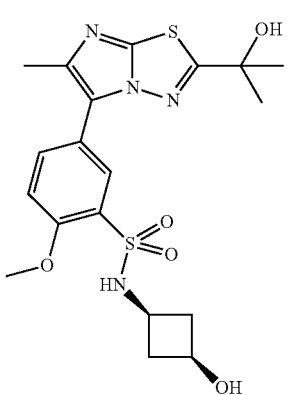 [SMILES: COc1ccc(-c2c(C)nc3sc(C(C)(C)O)nn23)cc1S(=O)(=O)N[C@H]1C[C@@H](O)C1]
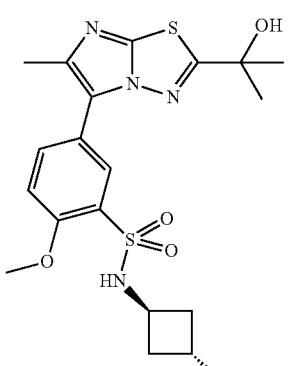
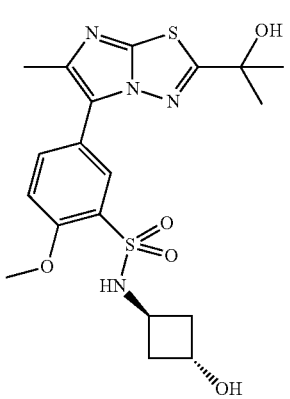 [SMILES: COc1ccc(-c2c(C)nc3sc(C(C)(C)O)nn23)cc1S(=O)(=O)N[C@H]1C[C@H](O)C1]
TABLE 6-continued
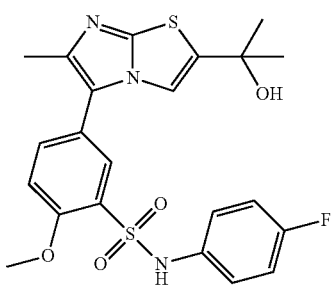 [SMILES: COc1ccc(-c2c(C)nc3sc(C(C)(C)O)cn23)cc1S(=O)(=O)Nc1ccc(F)cc1]
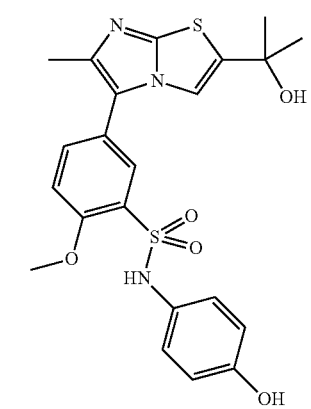 [SMILES: COc1ccc(-c2c(C)nc3sc(C(C)(C)O)cn23)cc1S(=O)(=O)Nc1ccc(O)cc1]
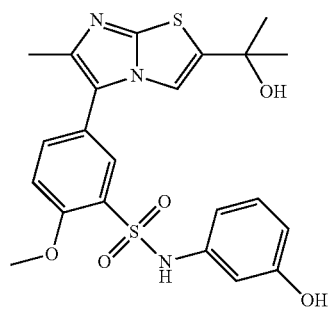 [SMILES: COc1ccc(-c2c(C)nc3sc(C(C)(C)O)cn23)cc1S(=O)(=O)Nc1cccc(O)c1]
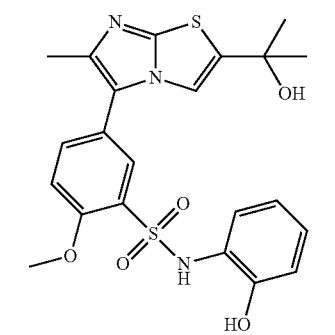 [SMILES: COc1ccc(-c2c(C)nc3sc(C(C)(C)O)cn23)cc1S(=O)(=O)Nc1ccccc1O]

TABLE 6-continued
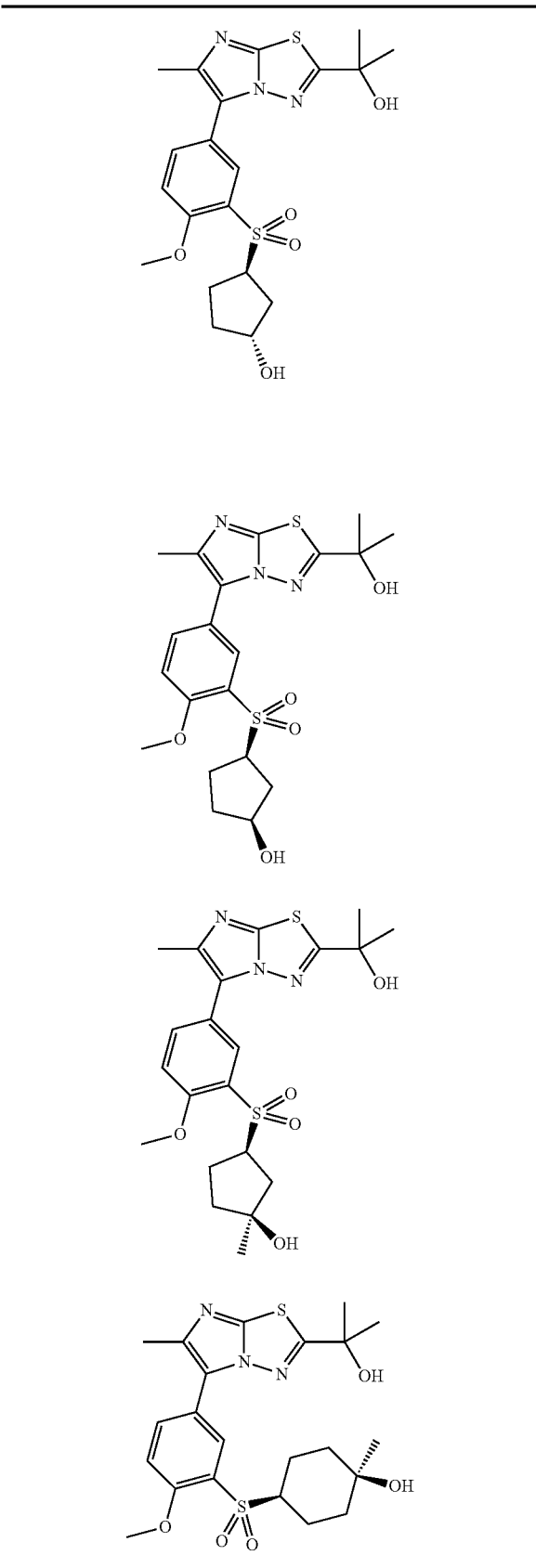
TABLE 6-continued
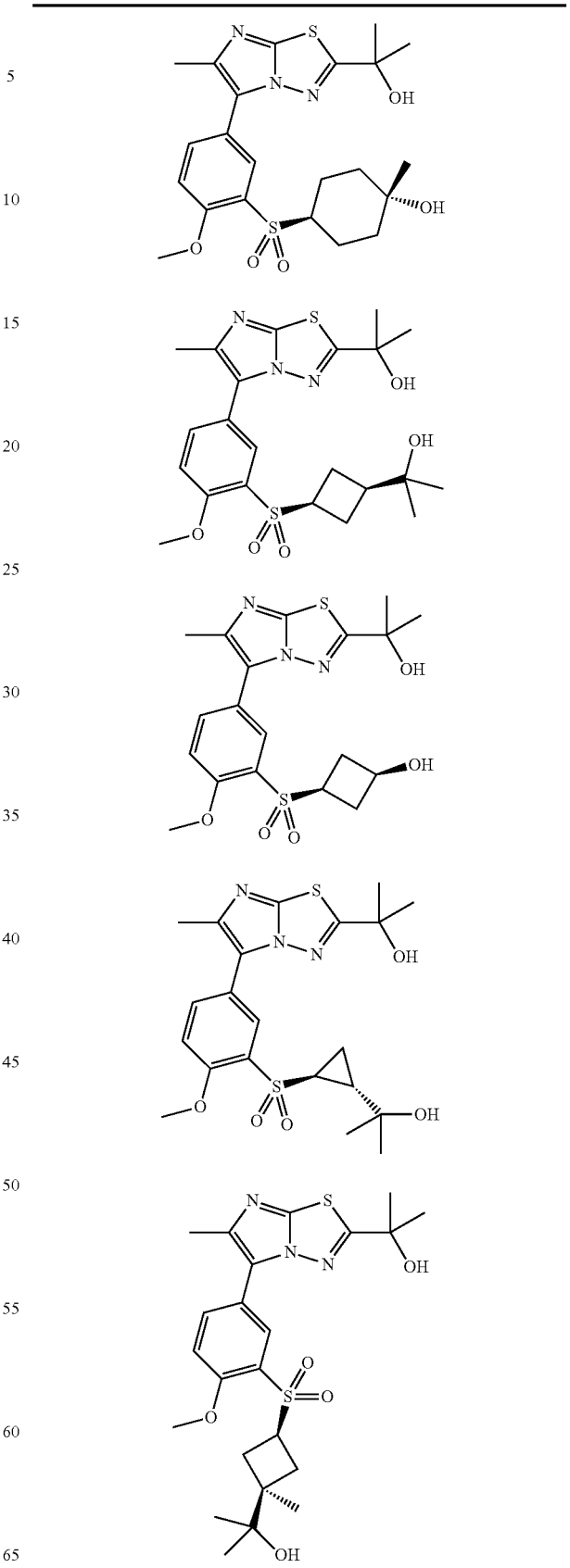

TABLE 7
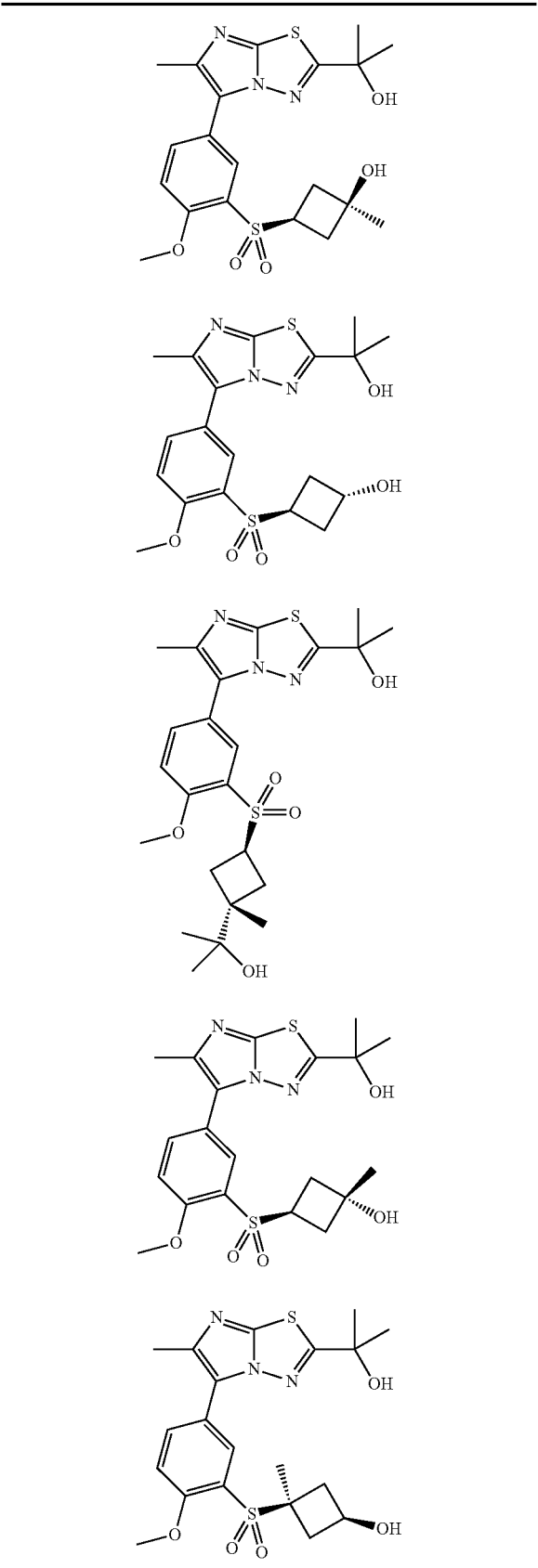
TABLE 7-continued
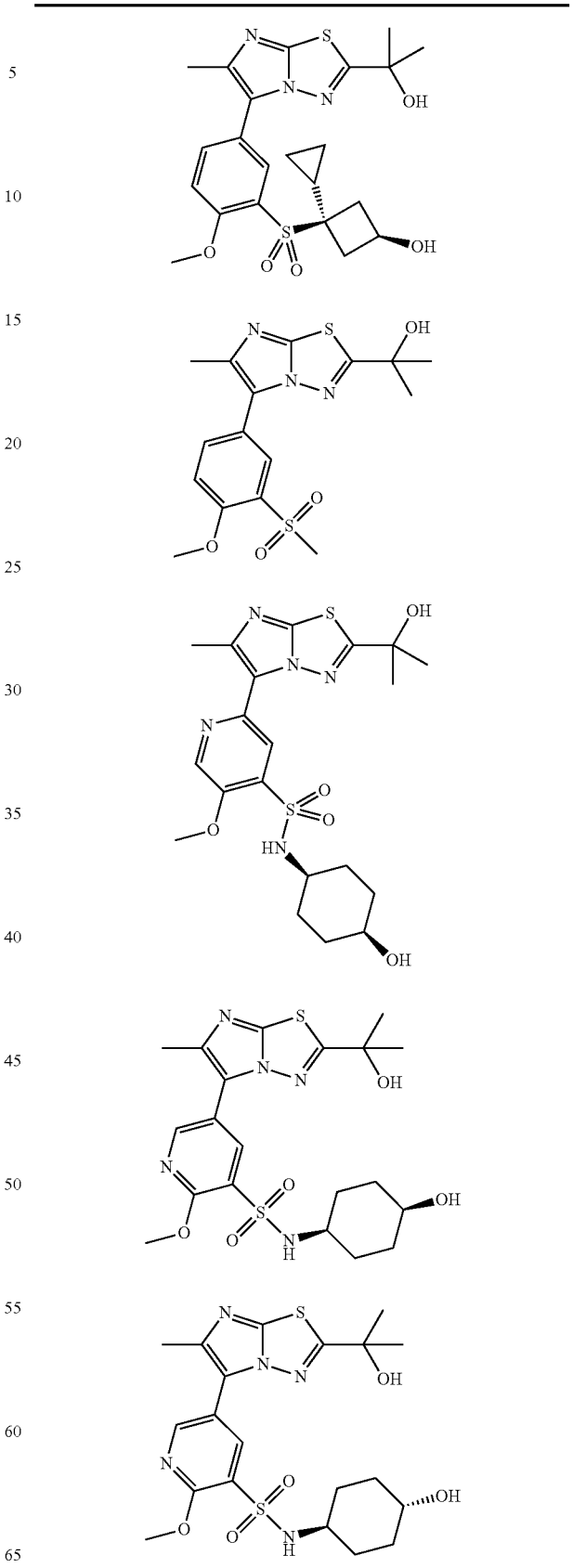

471
TABLE 7-continued
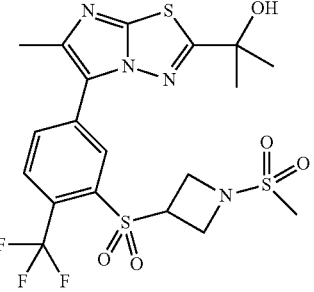
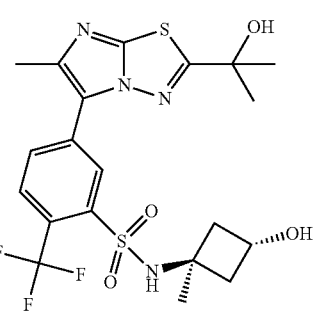
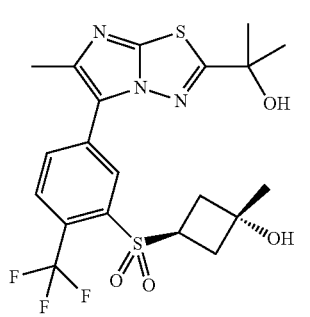
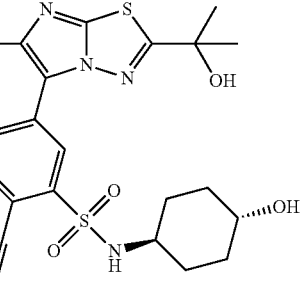
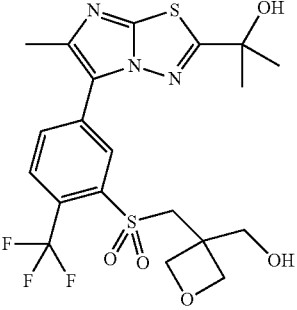
472
TABLE 7-continued
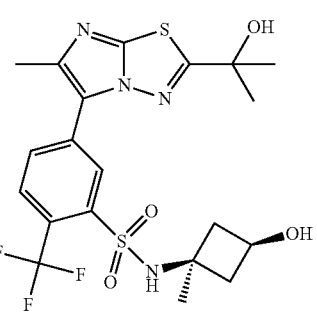
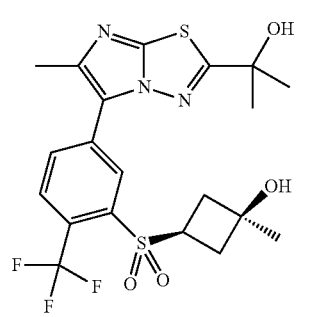 [SMILES: Cc1nc2sc(C(C)(C)O)nn2c1-c1ccc(C(F)(F)F)c(S(=O)(=O)[C@H]2C[C@@](C)(O)C2)c1]
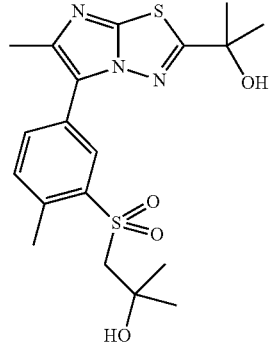 [SMILES: Cc1ccc(-c2c(C)nc3sc(C(C)(C)O)nn23)cc1S(=O)(=O)CC(C)(C)O]
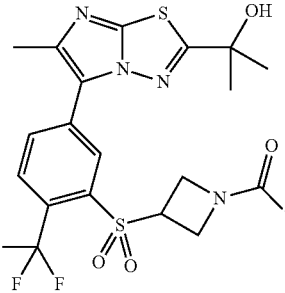
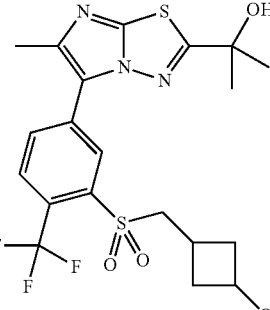

TABLE 7-continued
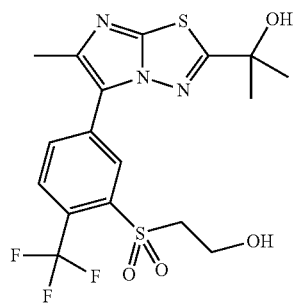 [SMILES: Cc1nc2sc(C(C)(C)O)nn2c1-c1ccc(C(F)(F)F)c(S(=O)(=O)CCO)c1]
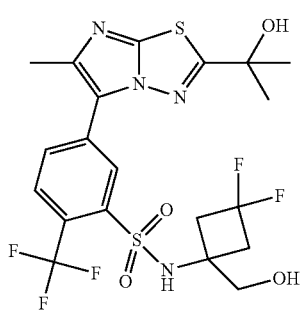 [SMILES: Cc1nc2sc(C(C)(C)O)nn2c1-c1ccc(C(F)(F)F)c(S(=O)(=O)NC2(CO)CC(F)(F)C2)c1]
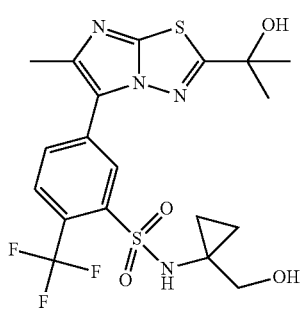 [SMILES: Cc1nc2sc(C(C)(C)O)nn2c1-c1ccc(C(F)(F)F)c(S(=O)(=O)NC2(CO)CC2)c1]
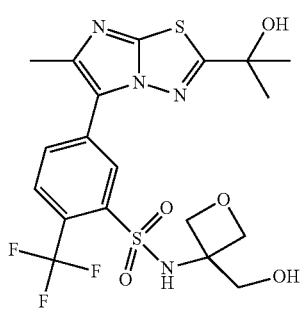 [SMILES: Cc1nc2sc(C(C)(C)O)nn2c1-c1ccc(C(F)(F)F)c(S(=O)(=O)NC2(CO)COC2)c1]
TABLE 8
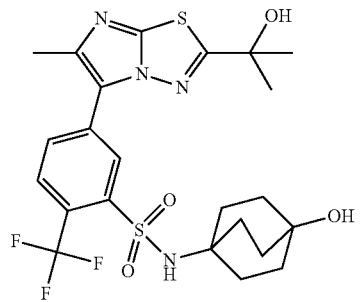 [SMILES: Cc1nc2sc(C(C)(C)O)nn2c1-c1ccc(C(F)(F)F)c(S(=O)(=O)NC23CCC(O)(CC2)CC3)c1]
TABLE 8-continued
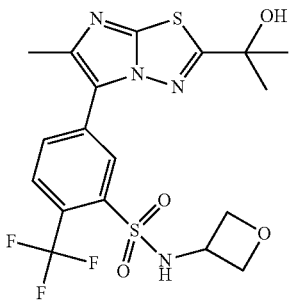 [SMILES: Cc1nc2sc(C(C)(C)O)nn2c1-c1ccc(C(F)(F)F)c(S(=O)(=O)NC2COC2)c1]
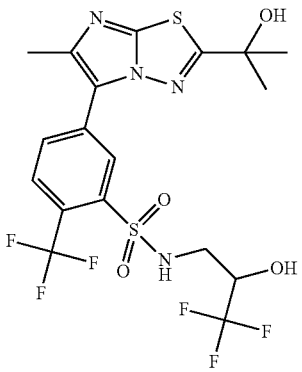 [SMILES: Cc1nc2sc(C(C)(C)O)nn2c1-c1ccc(C(F)(F)F)c(S(=O)(=O)NCC(O)C(F)(F)F)c1]
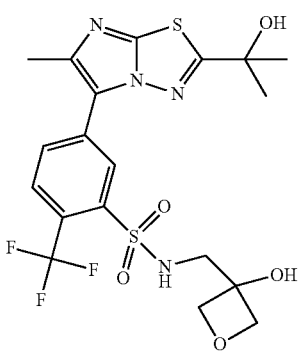 [SMILES: Cc1nc2sc(C(C)(C)O)nn2c1-c1ccc(C(F)(F)F)c(S(=O)(=O)NCC2(O)COC2)c1]
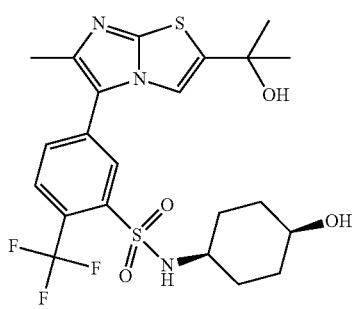 [SMILES: Cc1nc2sc(C(C)(C)O)cn2c1-c1ccc(C(F)(F)F)c(S(=O)(=O)N[C@H]2CC[C@@H](O)CC2)c1]
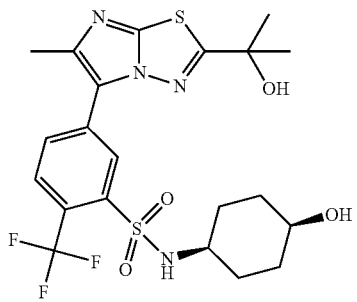 [SMILES: Cc1nc2sc(C(C)(C)O)nn2c1-c1ccc(C(F)(F)F)c(S(=O)(=O)N[C@H]2CC[C@@H](O)CC2)c1]

TABLE 8-continued
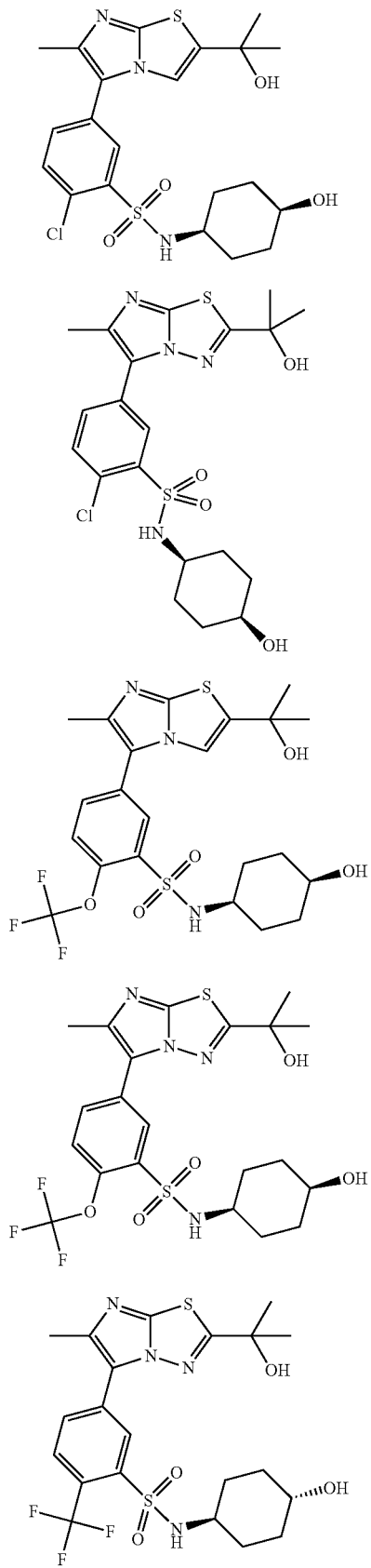
TABLE 8-continued
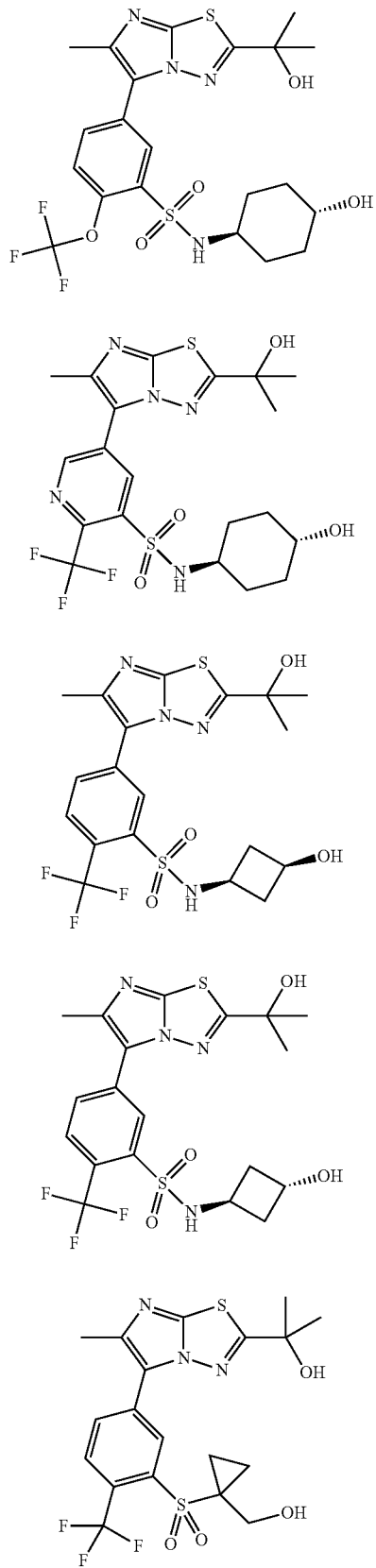

TABLE 8-continued
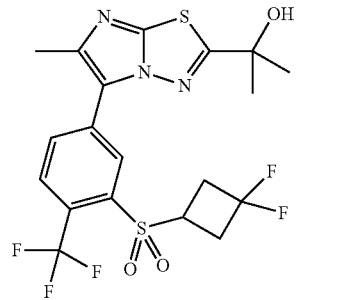 [SMILES: Cc1nc2sc(C(C)(C)O)nn2c1-c1ccc(C(F)(F)F)c(S(=O)(=O)C2CC(F)(F)C2)c1]
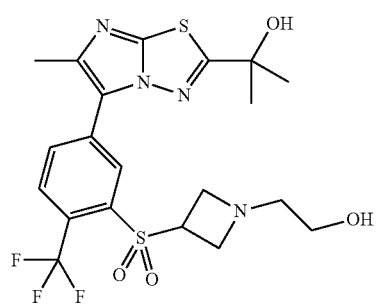 [SMILES: Cc1nc2sc(C(C)(C)O)nn2c1-c1ccc(C(F)(F)F)c(S(=O)(=O)C2CN(CCO)C2)c1]
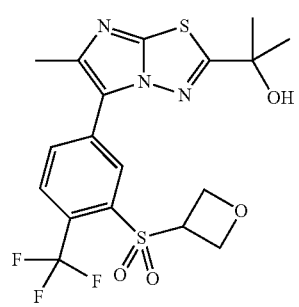 [SMILES: Cc1nc2sc(C(C)(C)O)nn2c1-c1ccc(C(F)(F)F)c(S(=O)(=O)C2COC2)c1]
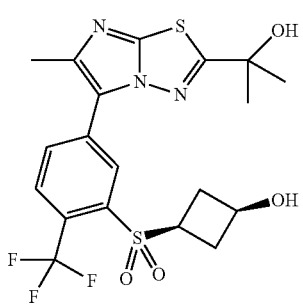 [SMILES: Cc1nc2sc(C(C)(C)O)nn2c1-c1ccc(C(F)(F)F)c(S(=O)(=O)[C@H]2C[C@@H](O)C2)c1]
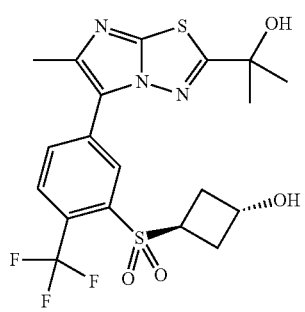 [SMILES: Cc1nc2sc(C(C)(C)O)nn2c1-c1ccc(C(F)(F)F)c(S(=O)(=O)[C@H]2C[C@H](O)C2)c1]
TABLE 8-continued
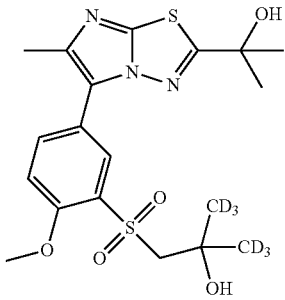 [SMILES: [2H]C([2H])([2H])C(O)(CS(=O)(=O)c1cc(-c2c(C)nc3sc(C(C)(C)O)nn23)ccc1OC)C([2H])([2H])[2H]]
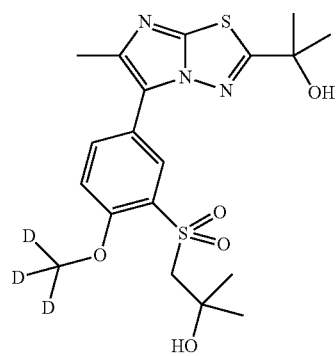 [SMILES: [2H]C([2H])([2H])Oc1ccc(-c2c(C)nc3sc(C(C)(C)O)nn23)cc1S(=O)(=O)CC(C)(C)O]
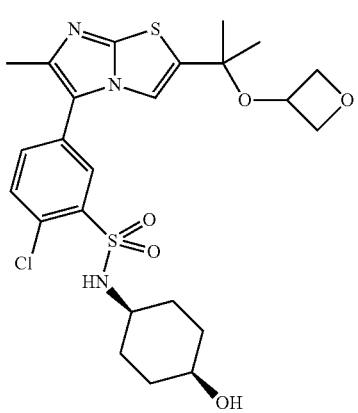 [SMILES: Cc1nc2sc(C(C)(C)OC3COC3)cn2c1-c1ccc(Cl)c(S(=O)(=O)N[C@H]2CC[C@@H](O)CC2)c1]
TABLE 9
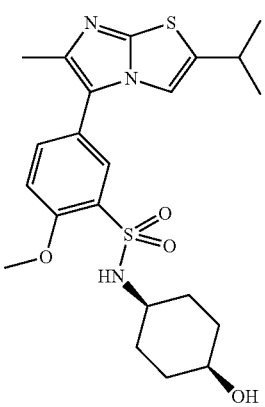

TABLE 9-continued
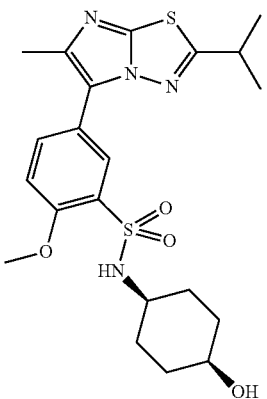
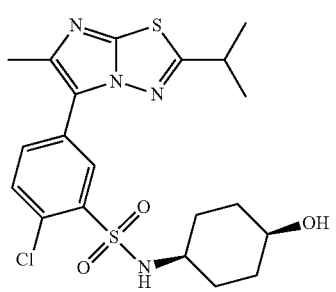 [SMILES: Cc1nc2sc(C(C)C)nn2c1-c1ccc(Cl)c(S(=O)(=O)N[C@H]2CC[C@@H](O)CC2)c1]
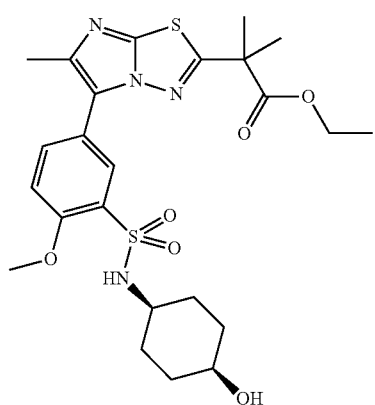 [SMILES: CCOC(=O)C(C)(C)c1nn2c(-c3ccc(OC)c(S(=O)(=O)N[C@H]4CC[C@@H](O)CC4)c3)c(C)nc2s1]
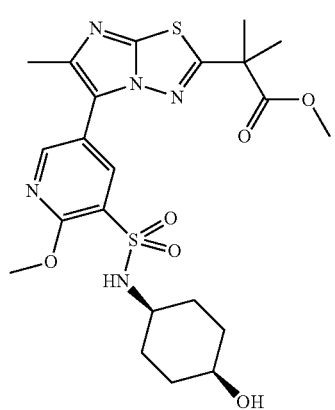
TABLE 9-continued
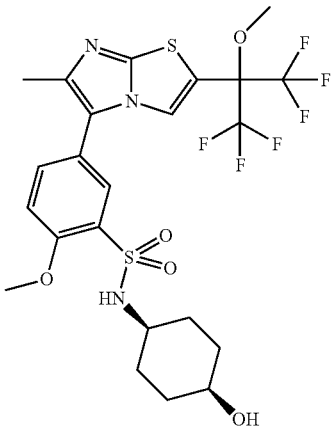 [SMILES: COc1ccc(-c2c(C)nc3sc(C(OC)(C(F)(F)F)C(F)(F)F)cn23)cc1S(=O)(=O)N[C@H]1CC[C@@H](O)CC1]
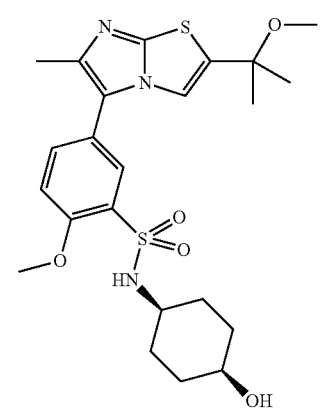
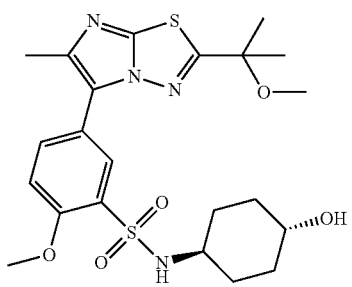 [SMILES: COc1ccc(-c2c(C)nc3sc(C(C)(C)OC)nn23)cc1S(=O)(=O)N[C@H]1CC[C@H](O)CC1]
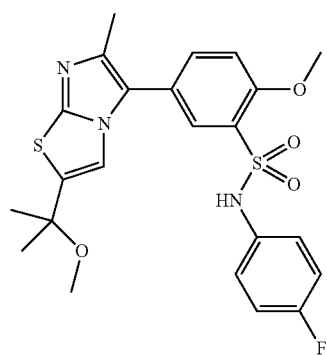 [SMILES: COc1ccc(-c2c(C)nc3sc(C(C)(C)OC)cn23)cc1S(=O)(=O)Nc1ccc(F)cc1]

| | |
|---|---|
| 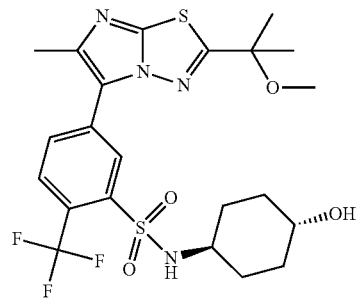 [SMILES: COC(C)(C)c1nn2c(-c3ccc(C(F)(F)F)c(S(=O)(=O)N[C@H]4CC[C@H](O)CC4)c3)c(C)nc2s1] | 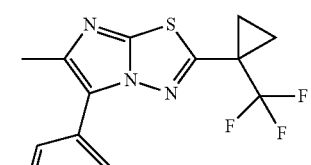 |
| 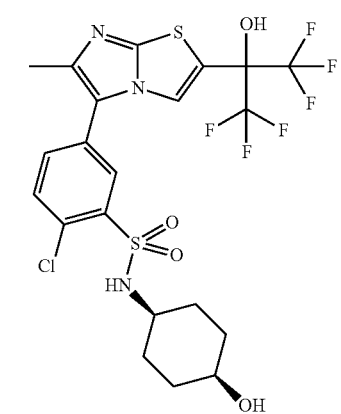 [SMILES: Cc1nc2sc(C(O)(C(F)(F)F)C(F)(F)F)cn2c1-c1ccc(Cl)c(S(=O)(=O)N[C@H]2CC[C@@H](O)CC2)c1] | 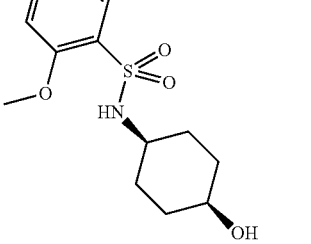 |
| 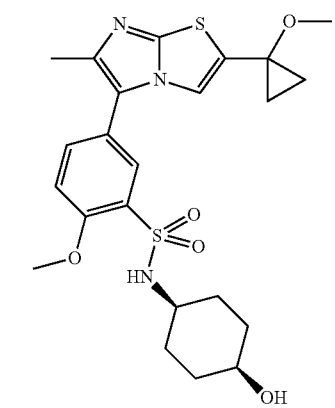 | 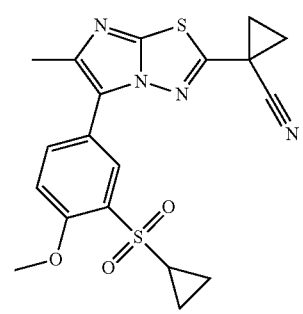 [SMILES: COc1ccc(-c2c(C)nc3sc(C4(C#N)CC4)nn23)cc1S(=O)(=O)C1CC1] |
| 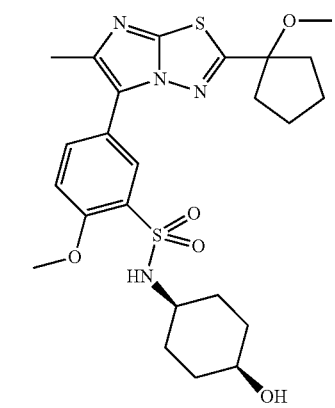 | 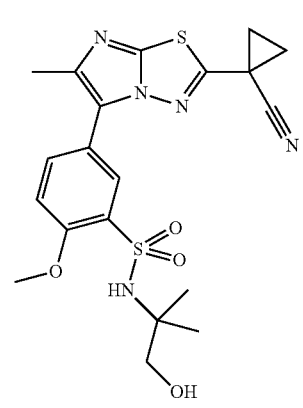 [SMILES: COc1ccc(-c2c(C)nc3sc(C4(C#N)CC4)nn23)cc1S(=O)(=O)NC(C)(C)CO] |

TABLE 9-continued
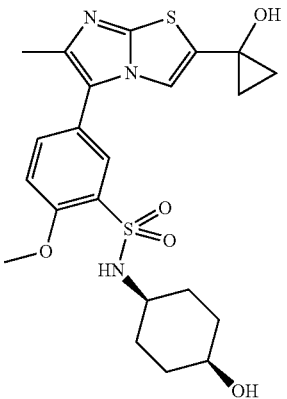 [SMILES: COc1ccc(-c2c(C)nc3sc(C4(O)CC4)cn23)cc1S(=O)(=O)N[C@H]1CC[C@@H](O)CC1]
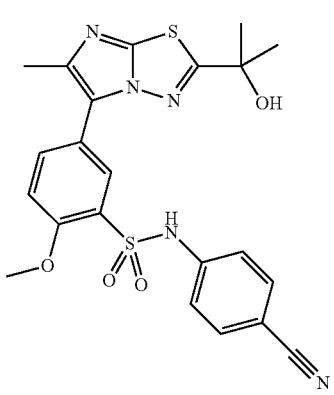 [SMILES: COc1ccc(-c2c(C)nc3sc(C(C)(C)O)nn23)cc1S(=O)(=O)Nc1ccc(C#N)cc1]
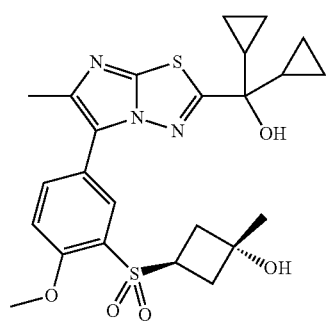 [SMILES: COc1ccc(-c2c(C)nc3sc(C(O)(C4CC4)C4CC4)nn23)cc1S(=O)(=O)[C@H]1C[C@](C)(O)C1]
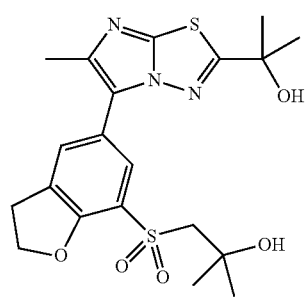 [SMILES: Cc1nc2sc(C(C)(C)O)nn2c1-c1cc2c(c(S(=O)(=O)CC(C)(C)O)c1)OCC2]
TABLE 9-continued
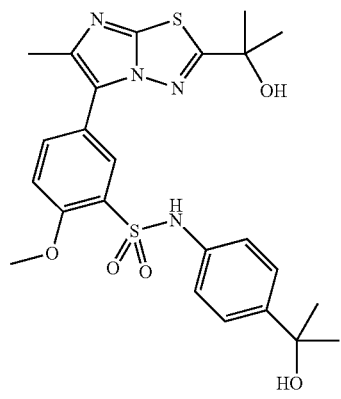 [SMILES: COc1ccc(-c2c(C)nc3sc(C(C)(C)O)nn23)cc1S(=O)(=O)Nc1ccc(C(C)(C)O)cc1]
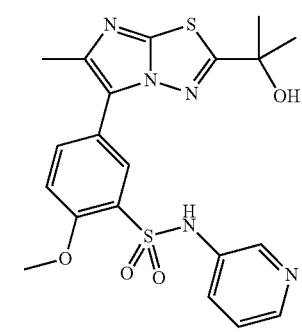 [SMILES: COc1ccc(-c2c(C)nc3sc(C(C)(C)O)nn23)cc1S(=O)(=O)Nc1cccnc1]
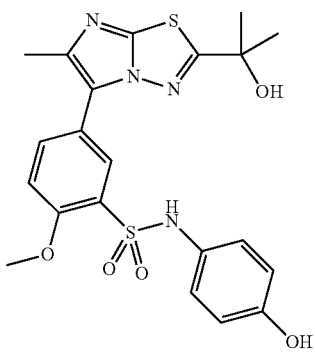 [SMILES: COc1ccc(-c2c(C)nc3sc(C(C)(C)O)nn23)cc1S(=O)(=O)Nc1ccc(O)cc1]
TABLE 10
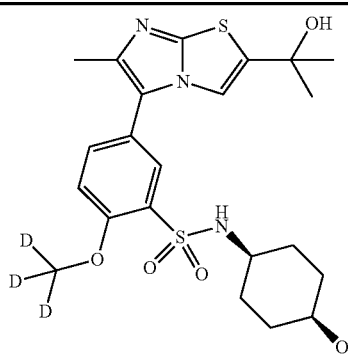

TABLE 10-continued

TABLE 10-continued
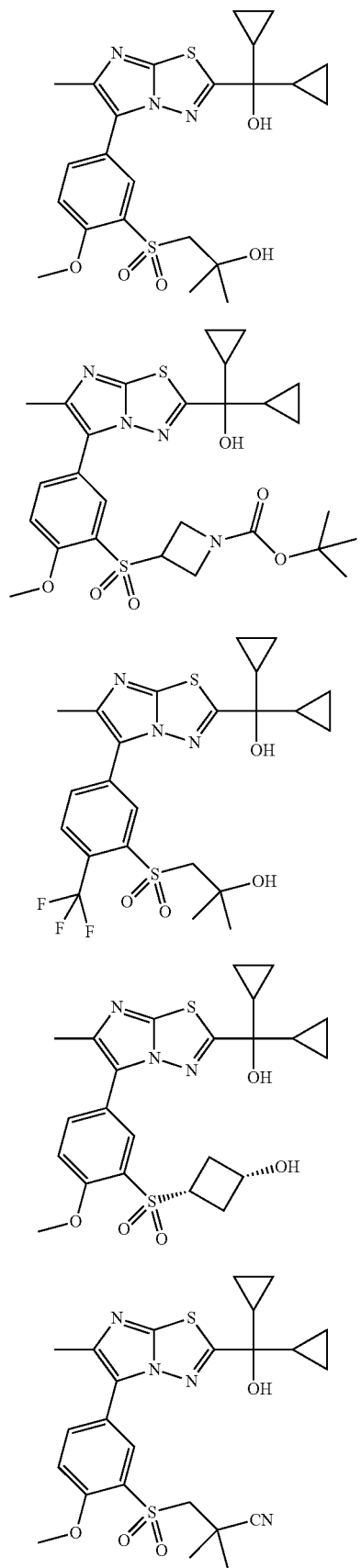
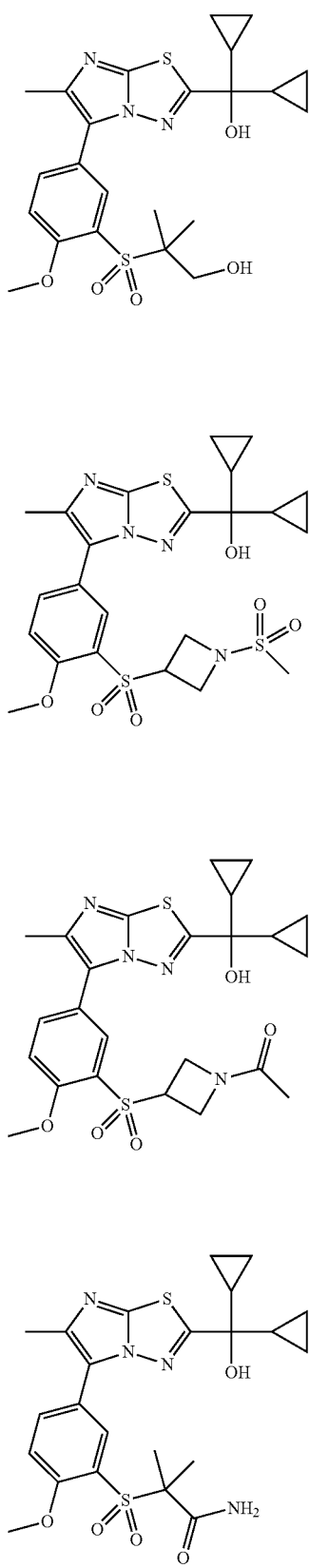

TABLE 10-continued

TABLE 11

TABLE 11-continued

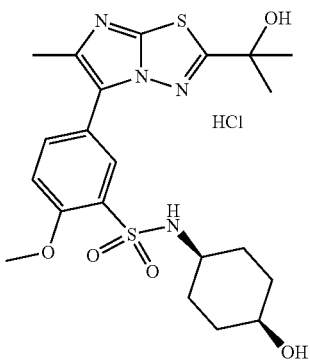 [SMILES: COc1ccc(-c2c(C)nc3sc(C(C)(C)O)nn23)cc1S(=O)(=O)N[C@H]1CC[C@@H](O)CC1 ; Cl]

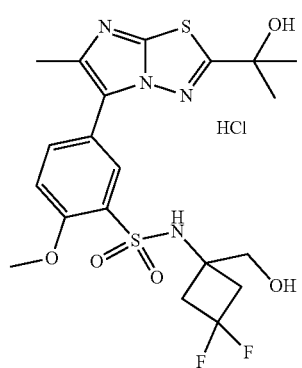 [SMILES: COc1ccc(-c2c(C)nc3sc(C(C)(C)O)nn23)cc1S(=O)(=O)NC1(CO)CC(F)(F)C1 ; Cl]

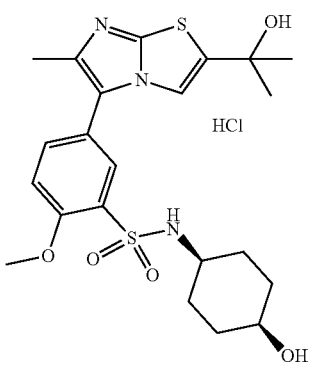 [SMILES: COc1ccc(-c2c(C)nc3sc(C(C)(C)O)cn23)cc1S(=O)(=O)N[C@H]1CC[C@@H](O)CC1 ; Cl]

TABLE 11-continued

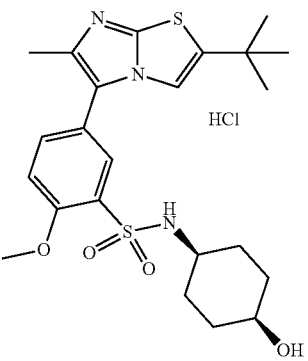 [SMILES: COc1ccc(-c2c(C)nc3sc(C(C)(C)C)cn23)cc1S(=O)(=O)N[C@H]1CC[C@@H](O)CC1 ; Cl]

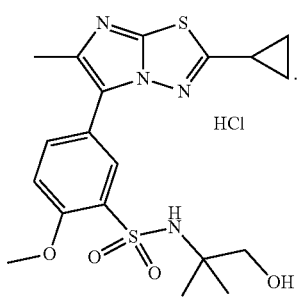 [SMILES: COc1ccc(-c2c(C)nc3sc(C4CC4)nn23)cc1S(=O)(=O)NC(C)(C)CO ; Cl]

11. A pharmaceutical composition comprising the compound, a pharmacologically acceptable salt of the compound, a hydrate of the compound or a hydrate of the salt according to claim 1 as an active ingredient, and a pharmacologically acceptable carrier.

12. An antiviral agent against a virus belonging to the family Picornaviridae, comprising the compound, a pharmacologically acceptable salt of the compound, a hydrate of the compound or a hydrate of the salt according to claim 1 as an active ingredient.

13. A method for treating or preventing a viral infection caused by an enterovirus, a rhinovirus, or a coxsackievirus, comprising administering an effective amount of the compound, a pharmacologically acceptable salt of the compound, a hydrate of the compound or a hydrate of the salt according to claim 1, to a human in need thereof.

14. A method for treating or preventing exacerbation of asthma or COPD, comprising administering an effective amount of the compound, a pharmacologically acceptable salt of the compound, a hydrate of the compound or a hydrate of the salt according to claim 1, to a human in need thereof.

* * * * *